(12) United States Patent
Hjörleifsdottir et al.

(10) Patent No.: US 6,818,425 B2
(45) Date of Patent: Nov. 16, 2004

(54) RNA LIGASE OF BACTERIOPHAGE RM 378

(75) Inventors: Sigridur Hjörleifsdottir, Reykjavik (IS); Gudmundur O. Hreggvidsson, Reykjavik (IS); Olafur H. Fridjonsson, Reykjavik (IS); Arnthor Aevarsson, Hveragerdi (IS); Jakob K. Kristjansson, Reykjavik (IS)

(73) Assignee: Prokaria Ltd., Reykjavik (IS)

( * ) Notice: Subject to any disclaimer, the term of this patent is extended or adjusted under 35 U.S.C. 154(b) by 0 days.

(21) Appl. No.: 10/270,878

(22) Filed: Oct. 11, 2002

(65) Prior Publication Data

US 2003/0082790 A1 May 1, 2003

Related U.S. Application Data

(62) Division of application No. 09/585,858, filed on Jun. 1, 2000, now Pat. No. 6,492,161.
(60) Provisional application No. 60/137,120, filed on Jun. 2, 1999.

(51) Int. Cl.$^7$ ......................... C12N 9/00; C07K 14/005; C07H 21/04
(52) U.S. Cl. ...................... 435/183; 530/350; 536/23.2; 536/23.72; 536/24.1
(58) Field of Search ............................. 435/183, 235.1; 530/350; 536/23.2, 23.72, 24.1; 930/240

(56) References Cited

U.S. PATENT DOCUMENTS

| 5,436,149 A | 7/1995 | Barnes |
| 6,492,161 B1 | 12/2002 | Hjörleifsdottir |

FOREIGN PATENT DOCUMENTS

| WO | WO94 26766 | 11/1994 |

OTHER PUBLICATIONS

Cong et al. Journal of Biological Chemistry. 1993; 268 (10): 7256–7260.*
Shuman et al. PNAS. 1994; 91: 12046–12050.*
Cong et al. Molecular and Cellular Biology. 1995; 15 (11): 6222–6231.*
Blondal et al. Nucleic Acids Research. Dec. 15, 2003; 31 (24): 7247–54.*
Durantel et al. Journal of General Virology. Mar., 1998; 79: 629–637.*
Rand et al. The EMBO Journal. 1984; 3 (2): 397–402.*
Alfredsson, G.A., et al., "*Rhodothermus marinus*, gen. nov., sp. nov., a Thermophilic Halophilic Bacterium from Submarine Hot Springs in Iceland", J. Gen. Microbiol., 134(Pt. 2):299–306 (1988).
Nunes, O.C., et al., "Isolation and Characterization of Rhodothermus Strains from S. Miguel, Azores", Syst. Appl. Microbiol., 15(1):92–97 (1992).
Moreira, L., et al., "Genomic Typing and Fatty Acid Composition of *Rhodothermus marinus*", Syst. Appl. Microbiol., 19(1):83–90 (1996).
Andresson, O.S. and Fridjonsson, O.H., "The Sequence of the Single 16S rRNA Gene of the Thermophilic Eubacterium *Rhodothermus marinus* Reveals a Distant Relationship to the Group Containing Flexibacter, Bacteroides, and Cytophaga Species", J. Bacteriol., 176(19):6165–6169 (1994).
Wang, J. et al., "Crystal Structure of a Pol Family Replication DNA Polymerase from Bacteriophage RB69," Cell, 89(7): 1087–1099 (1997).
Hopfner Karl–Peter et al., "Crystal Structure of a Thermostable Type B DNA Polymerase From *Thermococcus gorgonarius*," Proc. Nat. Acad. of Sci., 96(7): 3600–3605 (1999).
"Exonuclease III (*E. Coli*)," New England Biolabs Catalog, 94 (XP002164084) 1998–1999.
"DNA Polymerase I, Klenow (Exonuclease–Free)," Mol. Bio. Reagents, 88 (XP000606205), (1990).
Pisani, F.M., et al., "Amino Acid Residues Involved in Determining the Processivity of the 3'-5' Exonuclease Activity in a Family B DNA Polymerase from the Thermoacidophilic Archaeon *Sulfolobus solfataricus*," Biochem. 37(42): 15005–15012 (1998).
"DNA polymerase and formulations comprising it—allowing the amplification of sequences up to 35 kilobases and reducing the mutagenicity generated by the PCR process." WPI Acc No. 1995–006692/199501 (Abstract).

* cited by examiner

Primary Examiner—Shanon Foley
(74) Attorney, Agent, or Firm—Hamilton, Brook, Smith & Reynolds, P.C.

(57) ABSTRACT

A novel bacteriophage RM 378 of *Rhodothermus marinus*, the nucleic acids of its genome, nucleic acids comprising nucleotide sequences of open reading frames (ORFs) of its genome, and polypeptides encoded by the nucleic acids, are described.

2 Claims, 83 Drawing Sheets

>RM378 genome sequence, 129908 bases
CGGGTCTGCTTTTCCTTCACGGACCCAATTCTCCGTGAAAGAAATACGAC
ATTCATACTGCACCTCCTGGTTGGTTTAATTAGGGTTAATGTTATACCTT
TTCAGGAACTTCGATCGCTTTAACTCCCTCTGATGAAGCACGGTTTCCAC
CGCGGCAAAAATCACCAGCAGCAGAAACCACGCTCCTATCAGAAGCAGCG
CCGTTTCAAAATAAACCCACTTCATCACAAGCCCCGCCAGTACGAAGGCG
GGCAAAAAACCTGTTATAACGTAAACAGCGCTCATGGTTCACCCCTGAGT
CTGGAGTGCAAAGGCACCTGTAATATCCACCCAACCCTCATGACGAAATA
CCGTCTTCTTGACCACGGTTCCGTCGGGCTGCTGCTCCTCCACCGACACC
CTCTTCGTAAAGGAAAACAGAGGAATGATACAGAAAGCCATCAGAGCATT
GACCAGAAACGGCATGAAGTAGGGCGCGCCTCCAATCATGGCGGCACCCA
GCAAAATATCCTCCGTCTCCCCACTCTTCTTGAAAAACCCGGCGGCAAGA
GCGGCAATCTCCCACGCGCGAGACATCATCTGATCGAAATCAGGAATTTC
CTCGAACGTAAGAAGCTCCTTCACCCGATTCCACTGATCATCAGGAAGGT
TTACAACCCCCGCCTCCATCTGTTCGGGAGTCGGATTGTGCTGGGTGAGA
TTCAGAATCGTCATGGCTTGTACCTCCGTTTGTTTGTTAAGTGATCCACA
GCCAGTATACGCATAAAGCGGAAAAAAGTCAATCGGTATTTTCTTTCTTC
ATCTTAATTTCATTTTTTTCCTTGAGGGAAATATCCGCCGCATACATTTT
TTCGGCTTCCTTCAGCACCTCAGAGACTCTGCTGAAGATCTCCCTGAGCT
GAACCATTGACCACTCCGGATCGTCAAGCACCAGTGGAAGCGCGTAGCCG
TCTTCATACGTTTCATAGTTATCCTCAAACAGATCTTCCAGCAGACGATC
CAGCAGTGCAGGAATTTCATATCGGTAACTCATAACTCCTCCGGCGGTTA
ACTTATCGGTAAACCTTCACGGATGAAGGTCTCATGTGAATGAACACTTT
TGCTCCCGGATACACTTCATCCAGAACCATAAGCGCCACAAGCGAAGCAA
GCGTCATGTACACCCCTGGATACCTCCCACCGTCATATAATCCAGAAAT
CTGATCGTACCCGCCGAAATGGTATCTTCAAGCCCCCCATCCCAGATAAG
ATATTCCACGATGGAGGGAATCTGAACCCTGATCTTTTCCAGCTCCCGCT
CGATATGCATATGCGGATCCGAACTACGCGCTGCTTCCCTGCAGATACCT
TCCGCCAGAACAAGCAACGTTTCATTTCGATTCTGATAAAAATAATTCAG
AGCACCCTCGAACAGCGCTTCAGGATCTGTAGCCGCACGCGGAACGCTTC
TGGAAACGTCTTTCAGAATCTGCATCATGACGCACCTCCATTTTTTCCAA
CATAACCTTCTTATTTCCTTTTCGGTTCCACGCAATCCCAATTACCACTA
TTAATCTCCATCAAGTCAGAAACCCGAATTCAATTTAAAACTTTTCTGTC
TGAAATTCCCTTATAACCCTTAAAACTTAACACTACCCTTTCAACACAAT
CCCAATCACCAGTAAAAACCTACCTGCATTAGATCTACTACTCCCCTTTG
AAGCAAAAAGGAAAAAACCAAAAATCAAAATTCTATAACCCCTACAGGAT
ACGCTCAGCTTTAAGTCGCATATTACCCATTGGGATTTTAGAATTTTAAA
ATTTTGTTTTTCTTTAATCTCCATAGGGTACGCTTAGCATTGAGTCTTAA
TTTACCATTTGAGGGATTTTAATTTAGAAGTTTTTGTTTTTCTTTAATCT
CCATAGGGTACGCTTAGCATTGAGTCTTAATTTACCATTTGAGGGATTTT
AATTTAGAAATTCAAAAATTTAATTTTTTCATAACCTTGAGTGGCTTATT
TACCTGTAGAGCGTCATTCAAAAAACACCCCATTTCAAGAAACCTTCACA
TTGATCTGTCGTTTTACAACATAAAACCTTTAAGTGGTATATGATCAGAA
AGCGTAAAAATCTGAACATATCGGAGCGGATGCGATTCCAAAGGGATTG
GTCTATGATGTTTTAAATCTTGGGTATACCGATAAGCTCAAATCCCGCAT
GATTGCTATACTGAGCATTCTTATCTACCATCGCCACCGGGAAGATCACA
CCTACGAGATTGAAACAGGATCGAAATGCAAGCGCATGGTGGAAGTTAAA
AAAGGGGAGTCCTGGATCAGCATTCCAACGCTTATTGAGCGGGTTTACAA
CACATTTGGAATTAAGCTTACCAGGGAGCAGGTTAAATATGCCCTTCGTT
TGCTTTTACAGCATGGTCTGATTTCGGTAAAGGAAGCAACCGGTGGGGTT
TCGAAAGGTCATTTTGGAAACATTTATACATTCAGAGAAACGGATTTTGA
AGGAGAGTTTGTCGATCCTGTGGATTTTGTGAGGGAAAATAGTGAAAGTG
AAGAAGAAATCTGGTATGCAGATTATACGGAAAGTCGGTATTCGAATCGC
GTAACCGTCAGAGAAGGAGCATTTCATCCGATTATGAAAAGTAGGACACT
TCTAAAAACGCATGTGCTTAGAAATCATCCAGATAGAGAAAAAGCTACGA
AGTTTTACCCGAAAGAGATTGTTGTGGATATCGAAGCGGGTGGATATCGC
GTAGATGAAACAGAGCGGTACAGACGCTTTAGACTCTTCGTGATAAACCG
CGCTGCGAAGTTTGCGAGAAAGTTCAGAGCACGCTACGGGGGGAAAGTTG
ATATATGTTTTACCGGAGGTAGGGGAATTCATCTGCATATTACGGGAAGT
GTGCTCAATGTTCCAATGAACCGCAGTCAATTCGACAGGATTTTGAAAGA
AGCAATTGTTCGTATGCTTAAAGATACGGAACTATGGCGGTTTTTCGATC

FIG. 1A

```
CTTCCACGCTGAATCCTTTTCAGCTTGCCGGGGTTCGCGGAAAACTTCAT
GATAAGGCTCCTTTTGACGACTGGGTGTATGTGAAGCGTACCTATCAAAC
GATTAAGCCGCTCAAAGCCGGAAGTCTGCTTTCGAGTTTTGAGGAGGCGG
CTTTCTGGATTTCGCGTAGCTTCGTCAGAAAAGCGGCTAAAGGCAATCCA
TTTAGAACGTACAGTCTGGTAAAGGAAGGGCTACTGGAAGGGGAGCCGTG
GAGCGATCACCATGCGGAAGAGATACGGCTGCTTTCTGCATGGCATGCG
ATCTTCTGGAAGCCGGATACATGACGGATCAGGTGTTGCTGTTTCTGAAA
GATTGGGATAAGAAAAACAAACCTTCTCTTGGAGATAAGATTATCGCGCA
GAAGGTAAGATCGGCGCGGCGGCTTCTTGCGCGAAAAGGAAAGCTTAAAG
CAAACCCTTCTCTACAGCTTCTCTAATTGTTTTGAAAAAGTGATAGAATC
TTTCCGGGGAAAAGCTGTATCCGATCATGTCGGTGATAACGCTCATCACA
TTGAAAAATCGTTGGACTTCATCCGGATTTCTTCTGTCGATTTTGATAAG
AAGTTCGATTATACGTTTAAACGATTAGGATAATCGTACCACAGAAAGG
AAAGATATGCACCCGACGATCCTTCTTCCTCTTCTTTTTTCATGTAAGAA
CGAATATCTTCATACAGATACCATATATCCACAATGCTTTGAGCGAGTTT
CTCCATAATTCTGGTGGCGGTGTTGCTGAACGTATTGATATACTCACAGG
TAACAACATACATATTCTTTTTGATTTCTTCGATAATTTCAACATGAATA
TTTGTTTCCAGAAGATAAACAGGGAAAGAAATTGAAAGTTTTTCAAGCTG
CACAATTTTATGCAGAAAGGTGTTTTCGCGCACTTCCCAATCCCACAGAC
ATTTCACAGTCAGATATATTTCATTTCTTATAACTTTCTCCAGTTCGACG
AAAATATACGATTTATTTTCTATAAAGCCGGGTAACTCTTCATGAATGAT
GCGGTTTAAGTTGCTGTGTTTTTTCATACGGGTGTTATCTCTCAGCAATT
TTCTTTTAGCATTTGCCACAAATCTCTGATATCTTTCTTCAAAATCTTCT
TTTTTGAATTGGATGTTGGCTTCATTTTGCAATTGTCTGGTTCTTATAGC
AAGCGTCTCAATGAACGTTTTGATTAGAAGTATTGCTCCCTTAGCCATAT
CCTGAATGGTGGAATCGGCGGGTAAATCCACACGAAAGATTTTTCGAGTT
TCTTCGTTTTTGATCAGTGCGACGTTCCATCCCATTCTCTTTTCCATGAA
AAACCTGAGCGCCCAGACCAGATATTCGTAGAAGTTTTCAGTCATTTTAT
TTTAAATATTCCCTTATCTGTATTCCACTTCCGGAGATTCTATATGGATG
TAAAGTATATTTTTTCGTGGTATAAAATTCATCTGAGCGTGCACCGCAAT
TTTCAGGTCGTTCTCGCTCAAATGATGCTCGCCCCACCTGAACGATCCGA
TAAACTGCAGCGTGATATGGTGCGTGATCAAATCCGTAGAAAACTCCAGC
TTATCATCTGTTTCGGGTGGAAGCACATCGGTAGAGGGAAACCGGGATTT
CACATCAAGACGTGCAAGCACCAGATAATGATGGTAATTCTCGACGTTTG
ATGCCGGTGATATGTTTTTGAGTTTGTCGTTTAATGTGCGGATTACTTCT
TTCATTTCCTTTTCGATGGTGGTATCCTCTGATTCTTTTCTGGAGAAAAT
GTTTTTATAAGAGGGTCCTTTTTTGATATGTTCTACCGGGGAAATGGCTT
TAAGCAGTCTGTAGGCATAATGCAACGTGTCGTTTATCATCTTTATGAAT
TTTCTGATCGCAACGCTTACAGGTGTATCCTCAGAGATGCTCAGGTAGAC
CAGATCGGGGTGTTTTCTCAAATGATAATCAGGTGGAGAGAAGCCGGGAT
ATTTTTCCAGATAGTTTTTGATGGTGTTTGTAAGCAGTTCCTGATACGAT
GGCATTTTATTTTAAATAAGTGTTGATAAACAAACAGGCTTTTTTCACAT
ATTCGAACAATTCATCTTTGGAAAGATGGTGTGGTTTGTACTGACGATGC
ATAAACTTATAAGCAATATCAAACAATACCCTACCCTTTTCCTCACTTTC
TTTAATAATATCTATAATGCTGTCTATTTCCTCTTTCAGTTCTCTGTAAA
TGGTTCGGTATCGGTTTATGTCCTGCTCTGTCAGGTGTTCACTATTTTCA
TATTTTATCCCGAATACAGACATAATACCTATTGTTCCTCCGATAAATTC
CAGTGTTCCATTCCGGGTAGAGGCGCTTACAAATGAGTTGCGAATCTTCA
ATGTTTTATCTGAAACGAAACTTTTAAAACTTAAGTCAAGGAGCATTTCT
GTAACAAACAGAGGAGCATTCAGGTGGAAAATTTTTGCAAATTTTGAATT
TTCTCGGGGAAACCATTTAACAAAACCGATTATCATTATACCAAGATGAG
CTTCCTTTGCAAAAACCGGCATAATGTAAAGATGAATTTCGTTTCGAAAT
TCTATTTCGTCTGTGAAGTGGGTGATTAATTTTTATCGATATTATTGTA
GTGTATAGTATCGTCTTTAAGTTCTTTCATTTTTTTCTGAAGTTTCTTTA
ATGCCTGTTGAAACTTCTCCTCAATTTGATCTACAGCTATTTTTTCAACT
CCGATATCTTCTTCGAAGTGTCTGATTTGGTAAGTGATAGTTCTATAGT
CTTTTTAAGCGTATGAACATACATCCGCGTAAATCTCTGGGTAACTGCT
```

FIG. 1B

```
TTTCGGCGGGAATAAGACGCACTTTTACATAAGAAGGTCGTTTCTCTATA
ATTTCTACACTGGAAAATTCCGATCTTTTTTTTAAAATATTCAATGATGT
TCATTGCAAGTAGTGCTTCAACAACGCCTTCCATAGTTTTTTTAGCTAAG
GTTTTTTGTTTACAGTTTTGTAGTTTTCGTTAATTAAGGTGTTTAATGCT
ATTGGTTTTTTTAACTATTCCCCACGAACTATCTGTTTCAATACACGATA
TCTTTCCACCATATCGAGGTTTATAATATCCAGCGCTCTACCTATTTCAT
CAAACATTTCGATCACGCGTTCATCCTGATTGTTTTTGCTGTGTTCGATA
AGGTTTCTGAGTTCAAAAGCTCCCCGTATACCACTGGAATACAGAAATGC
GATTTTTGGAATATCAGGGTGTCCGGGATTAATAAGAGATAGAAAATGTT
CAATGTTTTTTATGAGTTCATGAAGCCGATTATACTGCATGTTGAAATAA
GCGTGGGCTTTTGTCAGCCTGATGTTTTCTTCTATCATGGGGCGCACGTA
AAAACTCCCATGCAGAGCGGTTCCGATATTGGTAAAAACTGTCTCGTGAA
ACAGAATAGCGGAAAGTGCGGCGTTTTTAACCGGATAGAGAGAACTTGCA
CCAATAACCGATATATCAAACAGAGCAGGAAAAAACTCGAAAAGACTCTG
ATCATTAAAGAAAATATGCATTTCGTTTTTTCGATATACCAGATCAGGGT
ATTTATGTGTGGTGTTAAATATTTTCTGTATTTTCTGAACCGTTTCTTTC
TCCTTATTTATTTTTTCTTTAAACTTCTCAATAGCCTGCTGGTACTTATC
ATTTATTTTGCTGTCTACAGAAAACCCGGAATAAATGGTTCGTGTCTTTT
TTATAAAAAACTCGATCAGTTCTTTGAACATGCGCGGCGTTTCTTTTATA
ATCTCTTTTGCGGTTGCGTTTTCACCGATGTCAAGGATTATGGTTACATG
TTTATCGCCGGCGTCTATGTTTACCGGATACTTTTTTTGAAATCTGTAAT
ACTGCTGAATTGCACTTAAAATCTCTTTACGGTATTTTTTCGGAGTCATA
AGGTGTCGGGTTTGATTTTATTAAATCACTCAGGTTTTTAAGTCGTGCAT
GTTTAACCCAGTTTTTTAACCACCCTGTTATTCCACCATATGACTTTTCC
ATCTGATCTTACGATTCCTCCGTATCCCATGCGGCTCAGGATCTCATTGA
TTTTTCCGTTTTGAGGAACGTTGAGTGCACCAAAATAGAGTTCAGTAAGT
TGCTTCATAAAACGGTTTCTATCCTGATTCAGATCTTCTTCTATCATCAT
CTGAATGCGGGTTGGAAATGTATCTACGATCAGGTTTACGACGTAGACTC
TATCGCTGGCTTCCCATCTTGAAAGGAAAAAGGAATCATATCGAAGCAAC
CGGTCAAACGTTTCGTCAACGACGGTTTTGACAAATGTCGCAAGTTTTCG
GGTGAAAACGGCTCCGGTTTGCTCGAAAGTGATAAGCAACCCTTTGAAAA
GCATTTTTCGGAGTGCGGAGAGGCTGTAGGGAACGTCAAAATGAATTCCC
CTTTCGACGAATCCATATGGCGGCTTTCCAAATACCCCCTGAAGTTTCAT
TCGGTGAAGTTCCCAGCCGCTTCCAAGAAATTCGTCAATCTGAAGTTTTT
TAAGTTTTTTGAGATCGGAGGAGTTAAGGTGCACGCCGAAATAGTTAAGT
GCGCCCCGGTGGACGCGAAAAGGGGGAGGTTGTAAAAATCTTTTGGATA
ATCGTTTTCCTTTTTGACGTTGAGAAATTCCTCCGGCTCGATGATATAGT
AGAGGTGATACCCGCGCTCCAAGATTTCCCGAAGGGTTTTTTCGTTTAAC
GGGATTTCGCTCATAAGGAGTCCGTTTCCCTCCACAGAAGACACAATCAG
GTTGAGGGATCAAGCGTTTCGATTTTTTCAAGGAGCTCTTTCATACGGG
TATCTGCAGGGTTATCTGTTCGCGGTTAATCTGCACAACGATTTTGAGAA
GGTGTGTGGCTTCGTCAAAACTCACGTCTATAGTATCTATGTCGTAGGGT
TCGAGGTTGGAGGCAATCAGGTTGAACAGTTCATCATAATCATAATTCTC
GAAAAGAATGTTGCGAATACCGATCCCTCTTTCTGGATCGTAGGGATATT
CCCCCGGCTCGATGAAAAGCAGGAGTTTTATCTTATCGATCAGGAGTTTT
ACCGGGTCATCAGGAAATCTGAAATTCGGTGCAGTGTCGTTCAGATAGAA
CATTTCATTTTTGTTTAAATAAATCCTCGAGGAATCTTCAAATAAAGAGG
GGCGTTAATGGATGAAAGACTGAGGAATATGGTCAATCTTATCGATCTC
AAAAATCAGTATTATGCTTACTCTTTCAAGTTTTTCGACTCCTATCAGAT
CAGCTGGGATAATTACCCGCATCTTAAAGAGTTCGTCATTGAAAACTATC
CCGGCACTTATTTTTCATGCTACGCTCCGGGGATTCTGTACAAGCTTTTC
CTCAAATGGAAGCGGGGTATGATCATTGACGACTATGACCGACACCCGCT
CCGAAAGAAGTTACTTCCTCAGTACAAGAGCACCGCTATGAATACATTG
AGGGAAAATACGGTGTGGTTCCTTTCCCCGGGTTTCTGAAATATCTGAAG
TTCCACTTTGAGGACTTGCGGTTTAAAATGCGCGATCTTGGAATCACCGA
TTTCAAATATGCACTTGCCATTTCTCTTTTTTACAACCGGGTAATGCTCA
GAGATTTTCTGAAAAACTTTACCTGTTATTACATTGCCGAATATGAAGCT
GACGATGTAATCGCACATCTGGCGCGTGAGATTGCACGAAGCAATATCGA
CGTAAACATCGTCTCAACGGATAAAGATTATTACCAGCTATGGGATGAAG
```

FIG. 1C

```
AGGATATAAGAGAAAGGGTTTATATCAATTCTCTTTCATGTAGTGATGTG
AAGACACCCCGCTACGGATTTCTTACCATTAAAGCACTTCTTGGAGACAA
AAGCGATAACATTCCCAAATCTCTGGAAAAAGGAAAAGGCGAAAAGTATC
TTGAAAAGAAAGGATTTGCGGAGGAAGATTACGATAAGGAACTATTCGAG
AATAATCTGAAGGTGATCAGGTTTGGAGACGAATATCTTGGAGAAAGGGA
TAAAAGCTTTATAGAAAATTTTTCTACGGGGGATACTCTGTGGAACTTTT
ATGAATTTTTTACTATGACCCTTTGCATGAACTTTTCCTCAGAAATATA
AGAAAGAGGAGACTATGAAAGTACTCGCATTTACCGATGCACCTACGTTT
CCCACGGGGGTGGGTCATCAGCTTCACAACATTATCAATTACGGGTTTGA
CGCAACCGATCGCTGGGTTGTGGTGCACCCGCCCCGGTCGCCAAGGGCTG
GAGAGACTAAAAACGTCGTTATTGGAAACACTCCAGTCAAGCTTATCAAT
TCTCCGCGAGGATATGCGGATGATCCGGCGTTTGTGATGAAGGTGGTGGA
AGATGAAAAGCCGGATGTGCTTGTAATTTTTACCGATCCGTGGGCTTACC
ACCCCTTTATGCAACAACTTTCTTACTGGATTATCGAGCGGAATCTCCCG
CTGGTATATTATCATGTGTGGGATAATTTTCCGGCTCCTCTGTACAACAT
CCCCTTCTGGCACACCTGCAATGAAGTGATAGGAATTTCGATGAAATCGA
CGATCAACGTGCAGCTTGCGAAGGAGTATGTGGAGGCGTATGAAATCACC
ATGTATCGCGATCCGGAGGTATTCTATCTTCCGCATGCGGTCGAACCCAA
TGTATTCAAACGCATGGATCGCAAGAAGCACGTGAATTTGTGCGGGGAC
TTGTCGGAGATAGGATGTTTGATGACAGCGTGATCTGGCTTTACAACAAT
CGAAATATTTCACGCAAGAATCTGATGGATACCATTTATGCTTTTCTGGT
ATACATGCTCAAAAACTACAGGAAACATCACCTTTTGATTATAAAGTCTG
ACCCGGTTGTACCGGTGGGAACGGATATTCCCGCGTTTCTTGCCGATATT
AATTCGTTTTCCACTACCGGGATATTGACCTTCGGGAACACATTGTTTT
CATTTCCAATGACGAAGTATTTCACAACGGCGGATTTTCAAGGGAGGAAA
TCGCATTGCTTTATAACGGCGCCGATGTGGTGCTGCAGCTTTCATCTAAT
GAGGGGTTCGGGATCGCTTCGCTTGAGGCGTCGCTGTGTGGAGCCCCGGT
GGTTGCTACTATGACGGGTGGTATTGCAGATCAGTACTCCCTCTACGAAA
TGGATTATGAGGTGGCGGATGGAAGTGATGAAGATATAATCTGCAAGATT
TATGAGGAAGTGCACCGTCAGGTGCTCAATCAGTATCTCGATATGCTCCG
TCAAAACGGAAAGGATCCGGAAAGCGCTCCCCGCAAAAATCATATGATGC
GGATGGTGAAACCTTATCGTCATTATCAGGGATCGCCGGCTACTCCCTAC
ATTCTTGACGACAGGGTTCCTATCCGGGACGTATTCCCGAAGTTCGATGA
AGCGCTGGCGCTGAGGAATCGTGAGGATTACGAAAAACTTTATGAAGAAT
CGGTTGAGTACATCACCATGCACTTCGATGTAGAGGTGCTCGGAAAAGAG
TTCAAGAAATCCCTTAGCCGTGCCATTAAGAATAACCAGAAAACCACAAG
ACAGGTTGTCGTGCTATGAAGAAGAAAGTGCTTCTTGTTTCGCCGCTTCG
TTCCGTTAGCGGCTATGGAACCGTAAGTCGCGGAATTTATCGCATTCTGA
AGCGAATGGAAAAGAGGGGTTGATCGATTTTGATGTGATGGTATTGCGG
TGGGGTACGTTTTCGGAAACCACCCACCTTGATGATGAAATCAAGAAGAG
AATTCAGGAGAAGTATGATCAGGTGTACGATGTTGCGATCATGGTTTCTT
CTCCCTACGACTATCGCTACTGGAACAACATCTTCAGAGCGAAACACCTG
CTCTTTTTCAATGCGATGGTGGAAACGAAACCGTTCCATCCGAATCTGTT
CCAGCAGCTTTTCAACTTCATGCTTCAGGTTCCCACCGCGCACCTTGTGT
TTCCTTCTTCCGAAATCAAGAGGATCTGGGAAGAAATCATCAATTCCCAA
CCCATCCATCCGGCAATGGGTGCTGCAGTGCTCTCCCGCATTCATGTAGT
ACCCAACCCGGTAGATGAAGTTTACTATACTTCGAACTTCGGGAATAAAA
ACGTTCGTAAAAATGTGATCGGCGCGATTCGAAAGAAGATTGAGGAAATC
CGTCGATCCTATGAACTGGAGCGGGTGTTTCTGACTTTTGCGCCTATGGG
AGTAGATCGAAAGAACACCAGGGTTTTACCCGAACTTATCGAAATGGTGG
GGCGGGTTGGAATTCTGGCGCTGGCGGGCGGAACAAATTCTTTTATACTT
TACGACTTTCAGCGGCTTATCTGGATGGAAGGTGAGAAAGCCTATAAGCG
GCTTCCGCTTCACCGATCGATCGACGTTACCCCGGAAGAGCTTATGTTCG
TTTTTGGATCGCTGACGGTGGAAGAGCTGAGTGCGGTGATGGATATGGTG
GATGGTGGAATCAACCTTTCGCATGGAGAATCGTGGGATTACCTGTTGCA
CAACATGATGCTACTGGGCAAACCCTGTCTTTACGTCGACTTCTTCCGTC
GGGATTATATCCCTTCGGAGCTTCGTGATCTGCTGGGGGTGGATTTCAAT
ATGGTACCCCTCCCGAAGGTGGTTCCCAACATTCCGCACGATCATCCGTT
CTTCCACCCGCAAACGATGGTGGCGGAACCCAATTTGCAGGATGCAGCGG
```

FIG. 1D

```
AAAAGCTCGACTGGGTGTTGCGGAACTACGGTGAAGTCTCAAAGATGATT
ACCAGCCATAGAGACGCTTTCAAAACCGACGATACGATCTATGAATTTCT
GGTTGACGCACTGGAGTCGATCGAAGAACCACAGGCGGCATAAAAATTTC
ACATTCTGGATAAACCGGGGGAATTCGGGCATTTATCCCGAAAATCCCCC
TTTTTTGTCTCAAAACCGTTTTGGCGGGGTAGATATTTAATATCACCCCG
TGGAAAGTTTAACCCCAAAACAGGAGTGGATATGTCGTACTATACTGAAG
TCGGCGCACCCTACTTTACACGTGAAGAGCAGTTTGTTCGGAATTTGCTG
TTCGACGTAACTTTTAATTCCAAATATTCTTTCTTCGATCTGACGCTGCA
GCGTCGTCTTACCTTTGAGGAAGTGCTGGAAGAGGTGCTGGCGGTGTTTC
ATGCCCGAATCGAGGAAGTCTGCAAACCCATTTATCGCCAGCAGGCGCAC
CAGTACGTGGAGAAGTTCGGCGAGTATTTCCGCCAGCGCAAGCTTTTTCC
CTCGATGCGCCTTGTGCAGTTTTCGCGCATGGTTCCTTACAACCACACCC
GTCTTTACAATTGCTCTTATACTCCCGTTGATTCCATTGATTCGATCGCG
GAGCTTTTCTACCTGATGTTGTGTGGCGTGGGTGTGGGATACAGCGTGGA
GCGTAAATATATCGAACAGCTTCCTGTTGTATATCCCGAAAGTGAGGGGC
AGACAATCACCTATCAGGTGGAGGATTCGATCGAGGGATGGTGCTCGGCG
CTCAAGCGTTATCTCTATGCGCGGTTTACGCCCAACCACCCGAAGATTGT
ATTTGACTATTCTCTTTTGAGACCGGAGGGAAGTGTGATTGGAAAGCGTT
ACAATGCTGCATTTGGTTATACTAAAAACAATCCCATCAAAGAAGCAATC
GAGGCGGTAAAGGGGATTTTCGACAAAGCAGTAGGAAGGAAACTCAAGCC
GATCGAGGTACATGATCTCATTACAACGTTCGGCATGATTATCAATCGTG
CGAACGTGCGCGGAATGGCGGCGATCGTCTTTTTCGATTATGATGATGAA
GAAATGCTTCGCTGCAAGGATTTCACGCGCGGCGAAGTCCCTCAGAACCG
CTGGTATGCCAACAACTCTGTCGTGTTGTATAGAGACGGCGATAAACTTC
GCGGAGTGCGCGGGGAAATCGTCGATCTTCGGGATATTTTCATGGAAGCC
TATTGTGGGAAGTCTGGTGAACCCGGCGTCTTTGTAACCAACGACGAACA
TTATCGCACGAACCCGTGTGGTGAAGCTTCTCTTTATCGCAATTTCTGCA
ACCTTACGGAGATCGCCATTCCCCGTGTTCATCAGAGTGAGATCGCGGAT
GTGTTGAACACAGCTATCTTCATTGGTGTGCTTCAGTCTACGTTTACCGA
CTTTAAGTTCCTTCGCGATGTGTGGAAAGAGCGCACCGAAGAAGACAACT
TGCTTGGCGTTTCGCTGACCGGCATTTACGAAAATCTGGATGCGCTCAAA
GAGTACATGAAGCTTTCTTCGAAAGGTCATGTCAAATTCATGGCGGCTCA
ATTTGCCGGTTGGTTCGGGTTGAACAACCCGGCTCGCATTACGCTGGTCA
AGCCCTCCGGCACGGTGTCGCTGCTTGCCGGGGTTTCTCCGGGTTGCCAC
CCACCCTATTCCGAATATTTTATCCGGAGAAACCGGGTGGATATGAATCA
CATGCTGGTTGAAGTTTTGAAGGATTATCCGTTTATCATTGATGATGAAG
TGTATCCCGATAAGAAAGTGATCGAATTTCCGCTTCGGGCGCAACGCCAC
TTTACGCACGATCCCATGTTTCAGGTGCGTCTTCGCAACCAGATCATGAG
GGGCTGGGTGGAACCCTCGCATAATCGCGGCAAAAACACACACAACGTAT
CGATTACGGTTTATGTAAGAGATGAAGGGGAAGTGGAGATTGTAAGTCGC
GAACTCAAAAATGAGCGAAACATTTCGGGAATCACGATTCTTCCGGTGGT
TGAGAATGGCTATAAACTGGCACCATTCGAAGCAATTCCCAGGGAAAAGT
ATGCCGACATGATGGGCGAAATCCACGTGTACCTTGATAGAATCAAACAC
CAGCTAAACGGCACGCCCGACTCCCCGCGTCTGAAACTGATCTCCGATTC
CGACGTTTTTGAGGGAGAGAAAGGTTGTGCCGGTCTGCAATGCTATTTCG
ACATGTAACATGAAACTCGTACTTAAACACTCCAGAGAAGAGTCTTTCTA
TCCTGAAACAATAAAAACTCTTGATCATCTTAGAGAGAATGGGTGGGAAA
TCGTTCTCCTACAGGATAATCGTTTTAATATCATAGAAGGTTACGATTTC
GATATGGTGATTACCACGTCGAACCCTCAATACAGCTTTGCGGATTTCCA
CAATGAAGCATTGAAATTTGCCAAGCACGGGGAGTGGCTTTTTTATCTTG
ATTTCGATGAATATTTATGTGATAATTTTTGTGAAAGGGTTAAAAAATAT
ATCAACAGAGATGTTCATTGTTACAACATCGCACGCATAAACATTATAAT
TCCTCAGGAGAAAACGGGTGATGTGTGCGGGATGTACGGATGGCGTAGTT
TTAATATCAATATACCTGAGGAAGGGAGTGTAAAAGCGATAAATTTCCCC
GATTACCAGACGCGTCTGGTTCGCGCCGGAACCGGCAAATGGTACGGGAA
CGCCCACGAACGCTTTGTGTGCGATAATGCTTTTAAACACAAAACGTTAC
CGTTTGATGGTGGATATATTATCCACCGTAAATCTTTTGAGAAACAGATT
ACCGATAACGCGCTCTGGTCAACCTATACACCGTGATATATGTTCAGCGT
AATTCTCATACACGGAAACGAGGATCTTATCAATAAAGAACTGATAGATA
```

FIG. 1E

```
ATCTTAATGAATTCAGGGAAGCAGGATGTGAACTCATTTGCTGCAGGAT
GATCGTTTTTCACCGCCCGACTTTTTCAAATTTGATATTGTTATAAAACA
TTCCGTTTCCGAAGGGATGGACCGTCATCGAAATTTTGCCAATCAACATG
CTTCTTTTGAATGGGTGTTGTGGTTGGATTTTGACGAATATCTATTCCCC
GGATTTACAGAACGAGCTCCTGAATACATGAAAAGGGATATATGGGGGTA
TGGATTTTACAGATTGAACATGATCGTTCCACCTGAAAAAACTTCATGGT
TCGTTCAGAATTATGGCTGGTATGAAATGGTTGGGTGGGTTTCAACCATA
TCGATCAGGGGGGTTTCTTATCAGGCTATAAATTACCCGGAGGTTCATTA
TCGTTTTGTTCGAAGAGATTGCGGCAAGTGGGTTGGTAAAGACATGAAT
ACTGGTATTCAGGTGATTTTCGTAAAAAAGCCATATTTCCGGCGGATCGA
GAAACACTTTTCCACGTTAAACCCATTGACAAAGCAATAAGAGACAACTA
TAAATGGAGGGCACTATGATGAACCCCGAAATGAAAGAGATTCTGAAGAA
GCTTATGAAACCCTTCCACCCTGATCGCCATTCCTATCGCGTTACCGGAA
CCTTCCGGACTCGGGAAGGGCGGAACATGGGGGTGGTGGCATTTTACATT
TCATCACGCGACGTGATGGATCGGTTGGATGCGGTGGTGGGACCAGAGAA
CTGGCGAGACGAATATGAAGTGCCGGCTCCGGGGGTGATGAAGTGTGTGC
TTTATTTGCGTATAGGTGGGGAGTGGGTTGGAAAGAGTGATGTGGGGACC
GGCAACATAGAAAACCCTGAAAGTGGATGGAAAGGCGCCGCTTCTGACGC
CTTGAAGCGAGCGGCGGTCAAGTGGGGAATCGGGCGTTATCTCTATGCAC
TTCCCAAATGCTATGTGGAGGTGGATGATAGAAAGCGTATTGTTAATGAA
GAGGCGGTCAAGTCTTTTCTCCATAAGCATGTTACCGAACTGCTGAAGAA
TTATCAGTAACCCAAACCTAAACCCGAAAAATATATGGAAACGATTGTAA
TTTCCCAAAACAATACGACGGAGATGACGGAACCCCCCCAGAACATTTCC
GATTCGGTTAAAAGCGGGTTTATCTATCTTATCGAAAAGTCTCATTTCCT
TGAAAAGAAAAACTTCCTTAAAATCATATCGAACATGGACCCCCGCCGCA
TTTCCAATCCGGAGGTGCGCGTGGTGGCGGAGTACATATATGATTATTTC
AAAAGTCATAGTAATTTCCCTTCTAAAAGAAATCTTTGCCATCACTTTGA
GTGGAGCGAAGATCTGGAAGGAGACCCCGCCGATTATCAGCGTATCATTC
AGTATCTCAAATCTTCTTACATTCGATCCTCTATAACAAAAACGCTTTCA
TATCTTGAGAACGATGACCTTTCCGCGTTGAAAGAAATTGTCAGAGCCAT
TCGGGTGGTGGAGGATAGTGGGGTGTCGCTGGTGGAGGAATTCGATCTTG
CAACCAGCGAGTTTAATGAACTTTTTGTTAAAGAAGAACGCATTCCCACC
CCCTGGGAGAGTGTAAACAAAAATATGGCGGGCGGTCTTGGTCGGGGAGA
GCTTGGAATCGTTATGCTTCCTTCGGGGTGGGGTAAGTCATGGTTCCTTC
TTTCACTTGGTCTTCATGCCTTTCGAACGGGTAAGCGCGTGATTTATTTC
ACTCTGGAGCTTGACCAAAAATATGTGATGAAGCGGTTTTTAAAGATGTT
TGCACCTTATTGCAAAGGACGCGCTTCTTCCTATCGCGACGTTATCAAA
TAATGAAAGAGCTTATGTTTTCTCAGGATAATCTTTTGAAGATTGTTTTC
TGTAATGCGATGGAAGATATTGAGCACTATATTGCGCTGTATAACCCCGA
CGTTGTGCTGATTGACTATGCCGATCTTATTTATGATGTGGAAACCGACA
AAGAGAAAAATTATCTGCTTTTGCAAAAAATTTATAGGAAACTTCGTCTC
ATTGCAAAGGTATATAATACAGCAGTATGGAGCGCCTCTCAGCTTAATCG
CGGTTCCCTTTCAAAGCAAGCCGACGTCGATTTCATTGAGAAATACATTG
CCGATTCATTTGCAAAAGTTGTTGAAATCGACTTCGGGATGGCGTTTATT
CCGGATAGCGAGAACTCAACCCCCGATATTCACGTCGGATTCGGTAAAAT
CTTCAAAAACCGTATGGGTGCGGTAAGAAAGCTGGAATATACAATTAACT
TTGAAAACTATACGGTAGACGTTGCTGTTAAATGACACAAGTTAAGACAA
AAGGGCTTAAAGACATCAGAATAGGTAGAAAGGAGGGTAAGTTCACACAT
GTAAATACAACAAAGAAAGGAAAGAATAAGAAATATTTCAGGGCGGAACA
TGAACGCCTGTTTCTCAACCTTATTCGAGCACTTCAGGTTGGGGATTATG
CCGAAATCAATTCTCTTTTTCCTCTTGTCGAAAAGCAACTCCGATGGATG
GTACGAAAGATAGTGAACCGACTCAATCTCACTTCACTTGTTTCATATTA
TGACCACGGCGAATGGAGCATGATATTGTAAGTTATGTGTTCTCCAAAC
TCGATAACTATTCTCCCGAAAAGGGAAGGGTGTTCAGTTATATCAGTGTT
ATCATAGTCAATTATGCTATCAATTTGAACAATAAAATTTATTATAACCG
GGTGGGGTATCATTCAGATTTCTATGCAGATAATCCTACCACCGAAGACT
ACAAGGGTCTGGATGAAAGGAAGAGTTGAGTTATGAAATAGACGATCAG
ATTAATCTGAAGATTGATTTTGAGCATTTCTGCAATCTGTTTTTAAATGC
TTCCGAAGAAACTTTACTCAAGCATTTTCAGGAAGACGAAGTTTTTATTG
```

FIG. 1F

```
TTAAAAATATTGCGCTTTCTCTGAAATATGATCCGGATATTATCACGACG
CCTTTTCTGGGGGTTGTACATCGGATGATCTGTGAGTTTTGTGGGGTGGA
ATTTTCCCGCTATAAGTTTTCCAAAGTGTTCAAGAAAATGGTTCAACTAT
ACCACGAAGTTTTTAACGGGGGGTAAAGGTTATTTAAATAAAAAATATGT
TTTCGGCTTCTGATTATAAAGGAAACGTAACTTTTAGTTTTCACTTCCCT
TCGCTTCTCACCAATGCCGGATCGCACCCAAATAAGGCATATGTGTATTA
CGACTATATGGGTAGTGATCTGGTGTTCACTTTTTCTCGAATAAGATTCA
GCCTGTCGGCACCCGGCACCTACGATGCTTATTTTGACGCTCATATTCAG
GATGTTGACACCATTACCTTCGATTCAAACGGATACCGTGAGCTTTATTT
CATTTTCAGCGTTTCCTGGGAAGGATCCAACACTTCGGGCACCATTTCGG
GTGCCAATCTTATCAGCGTATCTTCCTTTGTTACTGGATACCCCGAAAAC
AGTTTTCTTGCCTATACGCTTTCCGTTTACTCTGCTTCCGCCACAACCTA
TCTTAACCTTAATGATGCTTACAGAATTTACGTAGGGAACATTTCGGCA
CCCCGCAATGGGAAGTTGGTTTTACCGGTAGTTTCACGGTTTCTGCTACG
CCTTCAATTTCTCACAACCGTTTCAGGATTTTACTTCTTTCTAACTTTGA
TAGTGCACTTAATTACTATATTACTACGTTCAGCGCACCAGCATTCGCCT
CACATTCATTTCAGGTTATCAGGAAAATATATGAAGTTGAGCCACTTTCT
GCTTACACAGTACCGTCTATCGTGTTTTTCTACACGGTTTCAGCTACTAA
CAGCTTCGGGTGGAGCTATTCCAATATAGAAATGGGGTCTCTTTACAGAA
TATCAACTATGTCCATTCTAAGTTATCCTTACCCCTACACGGCACCGGCT
ATAACGTATATCACTTTTTCTGGCGGAATTGTTTCGGATGAAGAATTTAT
TGTAAAGGTGCCCATAACCCTTTCTTATATTAACAACATAATACCGTATT
TCATCGGCAACCCCACTACCACTTCAAACATTGACGATGTGAATGCTACT
GAAGATAAAATTATCCCTACTTCGATAAGTAACTTTAAAACAACCCTTTC
ATTTCAGGTTTTGCTTTTCCGAACACACTCCCTGTTAAAACGGAACAAG
TATCAATTCCCGTTACCTTCAGTCCGGAAACGGGCAACATTTCTATTCCT
GTTTCCATCTCATTTCCTGCGTTTGTAAGAACTGCTGCGGCTACAATGGA
TAATCCGGGCAATTTTTCCACTTCTGTCGGAAATGGTATCGTGGTTAGCG
ATCTTGTGTGTCAGAATACAGGGAATATACCTATTACATTTAGTGGTGTC
AGTCTTGCAATAGACGATGGTAACTGGTATGTGGACACCCCCTCCGTGGG
ATATGGTTTTAACCCGAACAGCGGGTTTTGGTTCGATGTTCACTTTATGC
CTTATGGGGATGTAAACTACAGTCAATCCATTTATTTTACGTTTTCGTTC
AATTATCCAACAAATTATGGAAATATATTGTCAGGTAGTTTTGTTGAATC
CATTTCTTTCCATGCGGTTGCTACAGGAACCGCCCCTTCCGGTCAGGTGG
GTATTACGGTGTCCAACTGGAATGTGGACAACCCTAACACCGTTATGGTT
GGTAAATATGTTACCGGTTCCTTCAGCATCACGGCAAGTGCTACAAACAA
TCAGATCGCTCAGGTTACCCTGACTTCATCAACCCCCAATCTGTATTTCA
CGACGGTTTCAGGTGTTGGTATTAACAATCTTCATGCTACGGCGGTAAAT
TCTCTGGCGCTACAGGTTGCTCCCGGAGCTTCTCTTTCTGTTTATACCCA
GTGGTATATGAATATGGTTTATACGGCTTCGGCTCCTGATGTAACCATAT
CGGTAACGTCTTCTAATGCTACGGAAATGAACGGCGTGCCGGGATTGACG
GAAGTTAAGCGATCGCATTCGCTGACGAACCCTGCTCGATATGCAAATTT
GAATATAGGAATTTTTTCACTCAGTGCTTATGGTCCCTTCTATCAATCAA
CCGCCTCTATTTTGCCGTTCCCTTATTCTTTTAGTCTTGGGGCATCAAC
GTCGTTAGAAATGTTGGTTTGGCTTGGCTTGATTTTTATCCAACGAACAG
CACTCATTCTGAAATGTATGTTAAATTGACCATGTCTCTGACAGGATCGG
CTTTAAATGTTCATAGCGTAGTAACTTCATCGTATTTTTCTGATCCTTCT
AATTTCGAGTGGGAAGTCAACACTTTGCAGCATACTCTGTTCAGCCCCCC
TTATGGATATTTTCTTCATATTAGAATAAGACCGACTCCAAGTGATATTA
ACATAATACCGACTTCAAGTGCATATGGATATGGTACGTTTGTTGTAAGT
TGGAGCATGAGTCTTATTTCCCATATAAATGGGGTAAGCGTGGCTTCTCT
TGGACAGGGGTATTCAAATGCTTTGAGTTTGTGGTTTGATCATACTGTTT
TCTATGAAGCACCATAGTAATTTCTTATCTATACGACACATACTTGATAA
AATTGCCGCTTTCTCCCATTTCAAAATATTTCTGAGCGTAGAAGGAGTA
AAATCCGTGGCGTCTCCAAGCTTTCGAGTGGGGGTGATCAGTGTTGCGTT
GATTTTGACATAGTGGCTTTTGATCATTTTGTTGTGGGGAAAAGCAGGT
TGTAAAGCGCCATCTGGTTTACGTCGTTCAAAAGATGTTCATGCCAGAGA
ATATCGTAAGTGCGGGTAAGCAGCGCAAGAAGATTGGTGTAGTAGTTCCG
TTCTTCCTTAATGGTGTAAAGCGGCGTGCAGGAAATGATGATCGCTTGAA
```

FIG. 1G

```
TTTCCTCACCCGGCTTTAATTCTTTAAGTTTAATAAGGTTTTCAATGGTA
AACCCAAGCGGAATCACTTCTCTTACCCCACCGTCTACATAGGTGTTGTC
TCCGATTTTAACCGGAGGAAAGACCACCGGAATGCTACAAGAAGCAAGAA
TGGATTTGAGAAGAAGTTCCTCTTTTTGCTCTTCCGGGATTTCCTGATCT
TCAAAAAGGTAGTTACCGTCTTTTACAACGATTCCGGTGGATTTGCCGTT
TTGCAAATTCACAGAACAATTGATATAGATTTTATTGAAATTCAGAAGCG
GGAGCACGTTTTTCTCAAGGTATTTCCCAAGAGGGGAAAAATCATACAGA
TAATTTCGTTTGAGAATAAGTGTTTTGAGAAGGGCAAACCACTCAGGCTG
CTGTTTGTAAACCTGTTTCGGGGAAAGAGAAAGCCACATTTGCTTCATGA
GATCGGTACCTTTCGGGGTAAGCGCCGCGCGGGAAGCACACCACACGCCG
TTGATACTTCCCACCGAAGTTCCGGCTACAGCAAGAATTTCGTTGTCTTT
AAGCGCTCCTTCCCTCACCAGACAGGAAATGACGCCCGCCTGAAAAGCAC
CTTTGGCTCCTCCCCCCGACAGGATCAGCAGTTTTTTCATTTTTAATTAA
ATAATGCTCATTTTCCCGATGGAAGCATGGAAATCCACTTCAATTTGGCA
AATCCGTCTTCCGTTTTCCCGTTGATCATATATGCGTAGGCTCCAAAGAC
GTGAGCTATCTTGCAATACTCCTCTTCGTTGTCAATAAAGATTGTATAGT
GGTTGGGTGGAATGATTCCATAGATGAGTTCGTTTACTTTCCCGATTTTT
TTGCCCCCGACAATGCGGTTGGGAAGTGGAAGATTATGTTTTTTCAAATA
CGACTCGATGTTTTCCCGGTGGTTTGCGCTCAGGATGTAAAGGCGGTGAT
AGTTCGGATTTCTTTTTACCAGATCGTAAAGATAGGTGTACAGGTTATGA
AATTTCGTAATCGTTCCGTCGAAGTCTATACACACCGCCACCTTGATTGG
TTTGACAAGAATCCGGGAGAGCAATATATGAGCGGATTTGTGCATAGTCA
TAGACACCTGATCCGGTGAAAGATCGATAATGCGGGGAAATTTGTAAATG
CGGCGGAGACGGTTGGTAAGGTAGCGGATGTATCTATCCATTCCCATGTA
CTTCTCGATAATATCAAGGTATTCCGGATTTTTCCTTACAAACACCTCTT
TCATCAGGTGTTTAATATGAATGGTTTCCCGTCGGGTGAGAAGAAGTTTT
GTTAAACCTCTCACCCGCAACTCTTCGAGAATCTCCGGAGATAAATCTTC
GAACTGGAGATAAAGCGTTTCGTCAATGGTCTGCATATTCATAGTTTACT
CAGGTATTTTTTTGAACATTGTATTAATGGTGTCGATTTTCTTGATGTAA
TCAACGAATTTGACACCAAGTTTTCCTGTAACATTTCCGATAAGAATATT
GGAAGCGTTCAATGCCAGTGCGGGAGTCAGATTTGAAAGTCTTGCAATTT
CAAACAGCCTCCGGAGAATATGGTTTTTATTTTCGATTTCTTCCATCAAA
ATGGCGTCTACGGCGTTGTATTCCACCAACTTTTTATCCGGGTAGACAGG
AATCTCATGATAGAATCTTACGTCGAAATCCACCTTACCTTCTCCTATTT
CCTCTCGCGCAATATAGTCGAGCCGGTAGGACTCCAACTCTTTGTATGCC
ACAAAGGAGCGATAAAGCCGCATGTAATCAAAAAACACAAATTCTACAGG
GGTACGGGGATTGAAATAGAATGGTAGGTTTCGATCGGAAATTTTCCGCA
CCAGCTTCCAGTCCGGAAGCAACTTATCACTAATGACATTCACCTCATGG
ATATGACTACGAATGAGCAGGTAGGGATAATCGAACTGATAACCGTTCCA
TGCGAGCATGAAAGTAAATTTTGGTTTCAGCACATTCCAGAAATACTCGA
GCAATCTTTTTTCCGAAAGGAATGTTCTGTAATGAATTTCAAATGTGTTA
TCCCCTACGCTGGTGGTAAATTTGTTAAAGTTATCGATATGAGCCTCCGG
GTTGGTGATAAGGAGAAGCACTACCACCACCGGTTTTCCATACGGTTTGA
TGGAAATGGAATAAACTGGGTCTCTCCACGGGTCGGGAAAGCTTTTTTTC
GGGGAAATCGTCTCAATATCGATAAAGACGCACTGAGACAAAGCTTCCGG
CGTGATGTGGCTTTTTTGTTCTCTGATGTAATAGGATATAGCCTCAGCCT
CAATCTTCCCTCGATTCTGCTGAGCGATGCGCTTCAAATGTGGGGTACG
GGTGATTGAAATAAGTGTTTTTTCCCCTCGATTAGCTCCACTCCGTAAAT
TTTCATCGATCGGGGGTATACGCTTGCGCTTAGCGTGATCTTCATAATTC
TCCTTCAGGTCTTCTTCGAGGAAATCGTTTAACGATTGAAGCAACTGATA
ATAAGCTTCGCGGGTTTCGAGCATGTCGAATACTTGCCTGTGAAAAAACA
GAAAATCTCTTATCTTGCGCGTGGCTCCGATCAGAAGACGGTGTTTCCGC
TGGAGGATGTTATACCTTATGATATAAGTAATCAGCACCCCACTTACGGT
TGCCGCAATAGCAACCCCCAACCAGAAATATACTTCCTGCATGGTTTCTT
TTTTTCTTCAAAAAAACCTTTCCGTGAAAAAATAGTTTCAACTGGTAACT
GCAAACAAACATAAGGAGAGAGTCATGCTCGACTTTTATCGCTGCTTTGT
CAAAATCTTTCAGAATAGCTACTTCGCCAACCCAACAAAATACCGGTTTG
GCGAAAAGGTCAGAGAAGCAGTGTTCAACTGGGGAGCACGCGTGGCACAC
CACGACATCAATTCGCGAGAAACCGAAATCGTTGCAGATCCGGAGATGGA
```

FIG. 1H

```
TGATTATTTCAGAAGATCATTTTTCTCCGAAAACCCCTATATGCTTGTTA
AAATTACCCATCCCGATGAATCGATGATAAATACGGTAATATGGCAAAGC
AAGCGATATGAAAACTTTTCCCGCGTCTATCAACTCATTCGCACAATTGC
ACAGATGAGAGAAGAAGAAGTCGATAACTACATGAATCAGATCATGCCGT
TTATTGCGTTGAATCTCAATACGATCAATCGCTATATGAACAAAACAAAT
CTTCTCTTTCAAACCCCTTATGATGAGTTATACGGTTTCACTCTGCTTTT
CAAGTCGGTAATTCGCATTGCCGAAGAAGAAAACGAACTGGAGTATCTTG
CGAATAAAGATGTCATTGATAGTTATAATAAGAAGATTGAGGAATTTTTC
AATACCGATGAAATATCGCTACATTTGGATATGTTCTAAAAGATATGCT
GTCTCACTGCATTATTGCCATCGGTATGATCCTGCTGGAAGCGAAGGATA
AAACACACATGAAGTTTTATGAGGAACTTGGTGAGTTTATGGCGGAAATA
GGTAAGGTATACTTAAAAGTGATAGAGGAAGGTGAGAAAGATATGAATGC
GCTGACGCATTTATACCTCTGGTGTATGATTGCCGGTTGTATCATTAACA
TGTTGAACGTCAGGATTCCGGATGAATTGCGGTTGGCTGCTATCATGGTT
GAAGAAACGCTTGCCTCGCACCAACTGCAACCCTTTATTTCGTTAAACTG
AAGAGGGGTATGATACAGAAAACAACCCCGTATAAAAACTACAAAAAGTA
CATGGATCAGCGGGGAGAAGTGCTGAGACCGCACCCCGCAAGAAGGTAT
ATATCCCATTTCTTATTGCGGAATGTGGAACTTATCTATGGAACGACATA
AGAAACATGATGTTTGCGCTTCCGGGGTGGAAAGATGTGGTGAAAAAATA
CGGTGTGGGGGAAAAATCCACCCCGGAGCCTTTCTATGATTTCCTTTCGC
TTTTTATCAAGAATACTACGCTTTACAGTGATTATAGAACCAAACAAACG
CTTTTTCAATCGCGAATAGAGCGCATAAAAATGGAAGAGGAAGTCTGGAA
TCTTTCCAATGCACTGATCAATCTGTTCTTTTATCTGAAAGAGCATTATC
CCTATTATTTCTCAAAAGAGTTTGTCTTTTACTTTGACATTAATTTCTAT
TTCAGGAAGCTCACATTTTATGATATTCTTGCCGGGGAAGATTTGCGGAA
TAAAATCAACGACACATTTCAGAAAATGCTCTCTAAAGGTTACACGGTAC
ACCTTTCAAAAATGAAACCTCAGAGTAGAGAAGATTATCTATGTTTGCGT
TATGCCGAATATATGGAAGCTATTATGGCTCGAGATGAGTTCAAGCAGGA
AATGGATATGAAAGGGAGTGGGAATCTTTTTTATCTTATTGATGGTTTTA
AATGGGGGTTGATAAATAGAAAAGATGAAGTAGAATTTGTTGTACTGGTA
AGGTAAAAACTATATAAATAAAAGGGGTTAGTTTATGGCGAGCTGGACTT
ACGATACCACTTCGCGTATTCTGTCAATTACCGTTAGTGTGGTGGATCTC
GACAATAACGATGTACTGGTTTACACCGGTAGCAATTATCCTACATGGTT
GAGTCCGCCGACCACTTCGTACGTTTCCGGTTCGTTGTCTCCAAAGCAGT
TTGATGTGTATATCAGCGGTAGCACGCTCAACGTTCAGACAGGGTCTTAT
CAGGTTGATTTGCTTGCCATTGAACAGGGTGTGTCGTTCCCGCTCACCTC
TTCGGCAAGCTTCACGATTACGGTTACGGCGGTTAACAAATTTTAGGCA
AGAAGTCTCCATCCTCTACAGGGTGGAGATGAATTGCCTATTGACAAAAT
TCAGTGGTGTATTACAATAAAAGCAAGATGTTTAGAGCATACAAATACAG
GATATATCCTAACAAAAAACAAAAGAACCCTTAGAGAAAACTTTTGGTT
GTGTGGGGTTCTACTGGAACAGGGCATTAGAAATCAAACTCAAAGCTTTA
GGAAATAAAGAGAAAATACCACAGGTCTTGCCCGCCTTAAGGGTGGTAGG
GTCGGAACGACCCGAACTTATGCCTGTGGAGGAGCGGGTAGCTCCGATGA
AGCAGGAAGCTCCATCTTCTACAAGATGGAGTAGTTCACTTCACAGAAAC
TTTATTTCTGTTTTATCGTTTTTTCCGTAAAAAAAAGAAATTATGGTTG
TAAAACTACCGCTGCATGATTTTTACCCTGAAGGTTCACCTTTCAAAACC
GAAAACTTTACGGTAAAAGACCCCACCATTGAAGACGAAGACCGCCTTTT
CAACCCGGATCGCATCAAGGGGGGATATGCTCTGGATGATTTTGTGAGAG
GACTCCTTCCCGAAGAGGCTCAGCGCCAGTACGGAAACATGTTCCTCATT
GACAGGAATTTCATTCTGTATGCCGTCAGGGTGGCAATGTTCGGAGACAC
CATTGAATTTCGGGAAAACATCGAATGTTCTCATTGCGGCGCTTCGCTTC
GGGAGGCTACCATAGACAGCGAGGTTTTTATTCCCGAAAATCGTAAGTTT
GAGTTAAAAGAAGGGGGTTATTTTATCCGTTTTAAGTTGCTTACCGTTTC
AGATCACAATGTTATGAGAAAAGATCCACTCATGAAAAGCAACTTTCTCA
CGCGCACGCTTTATTACGTAATCGATACGATTGAAAAAGAAGAGAGCGAC
ATTACCGACAAATATGCGCTTATCCGTTCTATTCCTATTTCACTTGGCAC
CAAGATCAGAGAGTTTCTGAATACACAATATCCTCGATTTGATATTTTCA
TCAAATGCGGTTCGTGCGAAAGCACCATCCCCTTTGAGATGAACGAATCC
TTTTTTTGGAATAAGTTATGATTCAGAAGAAGAGCTTGAAAAAATCGTGG
```

FIG. 1I

```
TAGAACGGTATGAAGCCCGAAGGAAATTGCTTCTCTTTCTGAAAGAACTG
GATACCTATTCCAGTTTAAAAACGAAAATTTCTATATCAGAACTCCGGGT
AATTGCCTATATGTATACCCAGCAACTGGAAGAGCAGGAAACAGAGTTCA
AGCGTTTTCGGGGACCGCACTGAAGTCAAGCGTGGCGTAGTCAAATTGAA
GGCTAAGCTGCACGTTCACAAGACCCGAAGCATCGGAGAAGTCGAGCGAG
TCGCCGTTGATGTCGGCAACCCAGGCTCCGTGGAAAGTCCATTGTTCAAT
TACGGCACCCTGAGGATCAAGAAGCAGAAGCTGGATATTTTTCTTGTAAA
CATCCTGATAGCCGTCGCGCCCGGTGGTAGGATCGTGGTGTGCAAGTACC
CACTGGTAAACCGCCATCATCCCCGATTCCTCGATTGGATCATAAAGCGT
CAGGTTGATTGGGTTCCAGCTAATTTTTCCCTTATATTTGAAGTAGGTGT
TAATGTGGTGCACTTCGCCGACGGCAAAGCTGAAATTAGGACGCGCCGAA
GCGTAGACCATGTAGGCGGGAATCCCGTCGATCTGCATGAGGAAAAGGCG
TTTCTGCTTGGGTTCAAAACGCCGGAAAAGCATGTTTTCAACAACGCGTG
CCATATCGTTCCTTTTTCTTTAAATATGTATAAATCGTTTTTCAAAAAAA
TGACAGGGAAAAATATTTAAAGTTGACAATTAACAACAAAACCGGAAAAA
ATATGTATAGGGTAAACGTAAAAGAAGTAGACCTTTCGATTACCCCTGAA
GTCGGGACACCGGTCCAAACGGCGCTTGTAGGTGCGTTCGATCTACCGAT
TCCCAGCGAACTTCCGGTATCGGTAACCCCCGATGAATTCCGCCGCGTCG
GATCAACCGAACTCAGTCTCATTGCAGATTCGCTGGTGGGTGGTCAGGAG
GTTACGGTGATCAGACCGCGAGGAGAAACGCAATCGCTGAATGCGGCATT
TGTTGTGGTGGGTGGTTATAATGTAACCCTTGGTGCCTTCAACGTTTTCT
ATCTGATGTTTCTGGGGTATGATCCTCAGAAAGGATATACTGATGTGTCT
TATGTAGATGTGCAATTGGCTGGTACCCCAACGGATACCATTCTGTTCAG
CTACTCGCTGGACGGTTCTTCGACAACGCATTCACTTACCATAAATCTAA
ACGCCCCAGTGTTACGCTACCTTCTAATATCGTACCGCTCTTTTTCTAC
TATGAACCTTATACGGGTTCGATTACGCTCCAGAGTTCCGTTAACTATAG
TGGATTAACACTGAATTATACGGTCAGCAAAGCGACCACTCCTTGGGTGT
ATTTTGCTGAATATGGCACGCCAACATCTTCTCTTACGCTTTATAAAGGA
TTTTATCTGGAAGGAATTGACCTGAACAGCTTTAACAAACAATTTGTTGT
ATCTATCGAAAATATTACGGTAAATAGAGAAAAAGGTCAGGTGCTTTATC
CTTCGTTTGATGTGGTGGTACACTTCCGGGATATTAGGGGGGTCAGTGCC
AATACCGAATATATTCGCTTCCGTCAGGTCAATCTCAACCCTGAATCTCC
GAATTATATCGAGCGCGTAATTGGCAACATGACCTTTGAGTTTGACGGTG
AGCGCATTGTTACAGGCGGTGAATACCCCAATCAGGTACCCTTCCTCCGC
GTGGTGGTCTCTCAGGATATTAAGCAAAACGTCGCCGGGGTTGAAAGTG
GGTTCCGGTTGGATTTGAAGGTATTTATTCTGTAGGCGACTTCACTGTTA
TTGTTAACGAATTGACCAATGTGTCAATCCCGGTTACGGATTCGGCTATT
ATTCCGCCCATGCGGTTTACCCGCATTGAACAGATTACGCTGTCGGGCGG
TGCTTCGTTCAGCGTGATCAGCAATCAACCGTATGGTTTCAATATTCAGG
ATTCTCGTCATAGCTACTGGCTCTCACCTTTCAAAGATGATGAACTGATA
ATCGGAACCGAACTGGTACTTCCGGCTCTGGATGTTTCAACGGAATTCGG
AGTTTCAAGTTGGGAAGAAGCACTTCCTGAATTCAGCTTCCTGATGCCGT
TCCAGGGCGGTTCAGACGGATACATTCGCGTTGATGAAAATGAGCCGGAT
ACAATCGGGCGCGTGAAGATCACTCCGGCATTGCTTGCCAACTATGAAAG
GTTGCTTCCGCTTCTGACGGAAGATCAATTCGATCTGGTGCTCACGCCCT
ATCTGACGTTTGCTGATCATGCCGGAACGGTGAATGCTTTCATCAATCGC
GCCGAAAACAGGTTCCTATATCTGTTTGACATTGCCGGAGATGATGATAC
CGAAAATCTGGCTATTTCGCTTGCTGGATATATCAACTCCAGCTTCGCAA
CTACGTTCTTTCCGTGGGTGCGTCGTCTGACCAATAAGGGAATGCGTACG
GTTCCGGCTTCTCTTGCAGCCTACCGGAGCATTCGCACCACCGATCCGGA
GACGGGTCTGGCTCCGGTGGGAGCGCGGCGCGGCGTGGTAACGGGCGAGC
CGGTGCGTCAGGTGGATTGGGAAGACCTGTACAACAACCGAATCAACCCG
ATCGTTCGCGTCGGAAACGATGTGCTTCTCTTCGGTCAGAAGACGATGCT
CAATGTCAATTCGGCGCTCAATCGAATCAACGTGCGTCGACTCCTGATTG
TTATGCGCAATCGGATTTCTCAGATTCTTTCCAGCTACCTGTTTGAGAAC
AACACCAGTGAAAACCGGCTTCGTGCCGAAGCGCTGGTGCGCCAGTATTT
GGAATCACTCCGTCTCCGGGGCGCTGTAACCGACTATGAGGTGGCGATCG
ATTCGGTTACCACACCGACGGATATCGACAACAACACGCTCCGCGCACGG
GTTACGGTGCAGCCCGCCCGCTCGATCGAATACATCGATATTACCTTTGT
```

FIG. 1J

```
TATCACGCCGACAGGCGTAGAAATCACCTGAGAAATAAACCTTTCAAAAT
ATAAACCCGCCTATCAAAAGGGGCGGGTTTTTTTATTTAAAATAAAATGA
AGTTTAACAACTGGGTTGAGTATACCGACGACGTACTCCGACTTGAGTAT
TACCTTGAGTACGAAATTCGCCGGTGGAGATATCAGTATTGTGATCCGTT
CCCCACTTTTGAAGATTTCAAAGAGGCGGTCAAAAAAGCCCCTCGAATTA
TCGTAACGCCGGAACTTGATAAAATTATAAGAAATCGTTCTCGAACCCGC
ACGTTTGACGAACTGCTTGCATTGATTAAAACTTACCGGGGATATCCGAA
ATTTCGCAATGAAAAGACGCTTCAGGCTATATATGACGGGTTTAAAAACA
ATAAACCCATGAAAATGCCGATCGTGTTGGAGCTTCCCGACGGAACATTA
CGGGTTATGTCTGGAAATACCCGTATGGATGTGGCATTCCAGCTCGGGAT
AAACCCCAAAGTTATTCTGGTGAAGGTTCCTGATAGGTGCCATTAATCCA
CACTTTCCATATCACCATACTGATCTACAATGTAAATCTTGTTGCAGAAT
TCTTTAAATTTATTCAGCGGAACCACTTTGGGGTTGGTGATAGCCCATTC
GTTTACGATAAATGCGTGGAGACGCGATCCCATTTCTTTCAAATCCCTCT
GGATTTGTTCAACTTCATCATCCCATTCCCCATCACTTATCTTATGGATT
CCTCCACTTGGTACGGGTTTGCCAAGATAGTGAAAAATGAAAGGGTGGGA
GGAGTCGTTTTTAAGCCGCTGCAGGATTTTCTGACCTGCTTTCGAGGAAA
CGCTGAACATTTTCTTTTAAATAAGATTCATAATCTTCAATTAGCGGAAA
GTGTTCAAGCTGTTTGAGCAGGGTGTTAACTTCATAGGCAAAACGAAAGC
GGGAGTTCTGGTAGAAGTCTCCGATTGTTACCGGAATTCTGAAATCAGGA
ATGTTTTGATTTCATTGTCTTCAATATTGAAGACGAAATAGCAGTGAAT
GAGCGGGTTTTGAAGCTCTTGCTTGATAACATAACGATCGAACATTTTGA
TATATTTCCAGATCACTTCCCGGTTGTTCAAATAGATTTCTTTTGCCCGA
TTCGGGAGAAACTTTGTTATGAAGAAATCGTCAAGCAGCTCTTCGATCTC
ACTTAGTGCACTGGTCTGCTTGTTAATAAAGCTTTTAATTACTCCGTTGA
AATCCCCAAGCACACATTCGGAGCTATCGTGCATGAGCACACAATAGCCG
AAAAGCGCATCGCTACACACTTCGCGAGCCACGTCGTAAACAATCAGACT
ATGTTCGAGCACGGAATAAAAATATTTTCCTCCGTTTCCCTGATAGCGGC
AAATGTTGGAGAGCCTTGCAGCAACATCTTCAATGGTAATACGGTGAAGG
CTCGGGTGCAATTCGAGTTTCATGGTGTTATGACTGTTTGGTTCACACGA
CACAATCCTTAAAGAGGATAAGGTTAAAAGAGGTTCCCTTCCTTCAATTA
AAATTCAAAAATGTCAATATCAATGTCAAGATCAGTGTCGTCTTCGGTTT
TACGTTTTCGAAGAACATAATCGACGTAATCTATATGGACCACAAAGTAG
GAGGTATCGTAAATCTGAACCAAAATCGCATTGACAAACCGTTCAACATA
CTTTTTGGAGGAAAAGAAAGCATTTATCAAAATATCTAACATCATCTTAT
AATACCTATCGTCTGTGTTCATTACATTTTTAACAAGTACATCTTTAATT
TCATCTAATATAGATTTGTTTTGAGGTATAGTTTTTATTGCTTGATCTGT
GATAGCTTTCAATAATTCATCGTCATTAAGTATTGTTATTACAGTTTTCC
ATAAATTTGTAATCATATTGCTGTTATTTGAAGAGAAAAAGTTGCGTGGG
TCACTTAAATGCAAAACTACACTTGGTATAAATAAACGGTAAGTATTACT
TACATTATCTTTTAATCCATTATCTTTTAATCCCAGAAGAGATTTATAGG
TATCGATAATTATAGAAATTTTGTCAACATCCATTATAATATCTTTGTAT
TTAAGTATATTTTCTCTGGTGGCGTCATTAAAATCTCTTGTCGGGGTACC
AAACAGCGTTTTAATAATCTCATCTTTCAGTTTAGGTATAATCTCATTTA
AAATTTCCTCTCTTTTTGATTCGTATTGTTTACTTTGTTTTCTATAACT
AAAGACGCGAGAAATGTAGAAAAAAGGTCAAATACTGTTTTTTTGGTCTT
TTCATTATTAGGTCTCACCAGATCTTGATATTTATAATCTATAAAAAATT
TCAAATTGTTTTCTATTTTTTTTCTGTTTATGTTAATAAATTTATCTCTG
AGCGTTTTATATACGACTTCGTTTTGAAGATGGAAATCTCCCACAAGATC
TATGGCTGACGAACTTTCTGGTGGTATGAATTGAAGTTTGACGTTCTTCA
CAAGGGGAGAATCCTCTTCATAGTTGGCTTCTGCAATTCTAAACGTTTCG
GAGCTAATTATATCTGAAATAACTTCCAGTTGGGACTCTCTGATAAAGAA
GGAAATAAAATCTTTTATTTTATCTTTCAATTGATTCCAGAGATCGTAAC
CGGGTACGTATTCCTGAAAATCTGTATTCAACCATATATTAAGTACTTTT
CCCACACTTTCTATTCCCTCCTTTATTTCCTTACTATTAACAGATAAACC
AATGACTTTGTTAATAACATTTTGTGCAATAGTTTTAACTATACCCTCAA
TGACTTTTTCATCCAAACTCTGAGAGGGTTGAAGAATATAGATGTTAGAT
ACAAGGTTCTGGAGTAATAGTAGGGCTTCGGGGGAAACATTTTTCATGAA
TTTATCTAAAGTGGAGTAAAGCTCTTCGAGTTCTTTCTTTGCTTTATCAC
```

FIG. 1K

```
TGAGACCGATTATTTCCGCTATTTTAAAGTTAATCTCTTTAATAATGGGC
AAAGGTAGCGAAAGTGTTTCGAGATTTTGATTGAACTGGTTTTTATACTC
TCTGATATCGGTTGATTTGTAAGTAATGACATGGGCAATGACGCCGCTGG
TTTCAATTGTTCCGGTAAATGTGGATACTTTTATTTTATGGTAAAAGTCA
TTTCTCGGGTGTATAAAGAGAATAAAAACATAATCATGTTTATAATTATC
CCAATAGCTATCGTTTTGAGCAATACAGACGGTGGTACTTTTGTTGGTGT
TGGTTTCGGTTAACATTTCTTTGATTCCTTGATAGGATATTTCAGGTAAA
AGTCGAACAAGTACGGCATCGCTATCTTCCATTTCCGGTTTATTATGATA
GACAAGTTCTATGTCCCCGTTCTTGATATATTTTCTGACGGCTTCCATGG
TGTTGTTCCAGCGATCCAGGTAGCGAACCGTATAAGAGGGGAGGTATGTA
TCGATGATCTGCTCGAGATCGATAAAGCTTTTAATAAACTTGAACTTCAT
AGAATGAAGTTCGTCTTTTCTTCCCTCCTGACTCAATTTTTTATTGATAA
CAAAAAGAGCCGCCAGTTTATCTACATTGCTGAGCATGTTATGATAATAA
AAACGATTCTCCACCGGAATATGACTTTCATCCGATCGATTTGTATACAT
TGCTACAATACCCTGTAGAATAAAAACCTGAGCCTGCTCCGGAAGAGGTG
TGTTGTAGGTGGTTTTTGCCGATTGCATAATTCGATCGACAAGTTCTTTT
TTGACCTTATCTTTTACAAAACTGAAAAACATACTTTTAAGCTCTTGCTC
TGTAGCCGTTTCCGGATCAATTTCTATATTGAGTGTGGGGTCTTCGTTTA
TTTTTTGTGCCAGCTTACGTGCAAAATTAATATCGAATTGCATATTTGTA
GACTTTTATTTTAAATAACTTTTCGTTTTCGGGTATAAAAAGGTCTGGTT
TTGCTGGTGGATTCCTCCACCTGAATGTTCAGCGAGAAGTTCGGATCACG
CGGAAATTCCTGATAGTTTTCCATATGCATTAAAATTTTCAGGTCATAGT
TTATTTCCGCCACAAATACCAGTTCATCAGACGACGGGTTGATCATACGA
TCGGAAATTCCTTCTACGACAATATCCCATACCGCCGCATTGTCTTTGGT
AAGGATAAGATCGGGTCTTACGTTTGAGAGAATCTGAGTGATCTCGCTTT
CTTTTGTAAGATAATAAAAAGCACGATAGTTGACTTTATAGGGAACCGGC
ACCCTGTACTGAATGGTGGATTGGTGTTGATTTTCCGTAAAGGTAAGAAA
AGCAGGAAAATTCTGTATAACTTCGATTCCTTCTCGCATGACAACAACGA
AGGGATACTCCACTTTGAACATATCCGTTACCATCGATTTCCTTTGCGCC
TGAGATTTGTCGAAAATAATGCGCGGTTTGGTGCCAAGAGCCTTTTGATA
GATTTCTTTTGCAAAAACTACGGCAAAGTAATCGGCTGTAATAATTTCGT
TCATTCTTCTTCAGGGAATGGAAGTTCTTCTTCACCACCACCCGTTTCTT
CTTCGAATTCTTCGAAGGCTCCGCCAAGATTAAGTTCGCCGCCCAGTTCT
TCTCCGCCTTCCGTTCCGAAATCGAATTCCGTTCTTCCTCTTGGCGATTC
GATCGGGGAGCCGCGCTCGCCAAGGAAGTCGGCGGGGGTTGTTTCCTCAC
CGAATCCGCCCGTGTCGAAAAGACCGCCGCCACCGGCTGCTTCCGCCACT
TCCTCCTGGGCTTGAGATCGTAGGGAATCTGAAGAATGTTACTATAAAT
CCAGTCTTCACGAACCCAGCCTTTGAGGCGTTCGGCAATACCGATTCGCT
GCTCAATCACGGCAAAGCGCTCACCTTCCACAATCGAATTCGAGCGGTTC
ATTACCAGGCGGAAATCCTGATCGGCAAACTCTTTGTTCATGCGCACCAT
GCGTTCGAGTTCTTCCACAAAGAACCCCTGAATGCGTTTGATCGTGTTGT
TGAATTTGATATCCTGAGTAGCCAGTGTGTTTTTAGCATTCACGTCTCCT
TCATAACCAATGAACGCCTTTGGTACCTTGAGTGCGGAGATGAGTCGGTT
GAGCATGTATTCCACATCTTCAGCAAGATCTACTTTGGAACCCTGAAGAA
TATCGATTTCCACCGCACGACGATCTCCGCGCCGGGGAATGAAGTAATCT
TTGAGAATGCTTTCGATAGAAAAGTAGTTATCGATTCCGAGAAATTGATT
CTGATTATTTCTTACCCAATAGTCTCGCTTATACTGCATGGCAATATTGG
TCAGATATTCGTTGATCTTGTCGGGCGGCACGTTTCCGACATCTACGTAA
AACACCCGTCTATCGACACTACGAACCACACGGTAAAGCATGAGCGCATC
TTCCATGAGTCGAAGCTGGTTCCATATCGCTCGAGCACTTTCAAGGTAGC
TTCTACCATAGGGGAAGAAGTTGGTGTCGATTTTGTGAGAAAGTGAATG
ACATCTTCCTCAGGAATATCTTCGTTAAAGTATCCGCTTACAACGTTACG
GTAAACGTCGGTAATAACATAATACCAGGTATCCGTTTCGGGGTTATATC
GCTTTGAGAAAATGTAAGGAGAGACCACCTGAAATTTTTCGATCGTGCCA
TCCGAACCTTTTTCAAGAATATGAAGAAACATATCTCCGTATTTGATCAT
GTTGCGAATGATAGGATAGGCGTTCTTTTCAATATTTATAACATAATCCA
GATAGGAGAGTATTGCTTTTGCAAGCTCAATGTCTTTTGTTACCACATCC
ACAATATTACCGTTTTCGTTGGGAATCGTGCATTCATCTGCAATGATATC
CAGCACCGTGGAAATAAGCGGATCGGTATAATCCATGCGATCGTACATAT
```

FIG. 1L

```
CGTAGAGGAAAAACCGGTTGAATTCTATTCCTCCGTAGAACCTGCTCGCA
TACCCCGCTGTCGCAAACGGGTGGTACATGTTAATCGGAATCATGGAAGA
GCCACCCGCACCGTGCGGCGCTCCCATACCATACATCGGAGAAAGGAAAT
TGGTGAAGTTGACAGCTTCGTTCAGTTTTTTATATTTTTCCAGAGACGGC
ATATTCTCCACTTTTTTGTTAAATAACATTAACCTAATAATGTACCAAAT
AACGAAATGGTTTCGTTTATTTAAAAGAAAATGACCTATCGGGAAGCCAG
AGCACTTTTCAACAAGATCAAAACACTCCCTGATTATAGAAACCGCGTTG
TCATTCGGATGTCTGAAATCAGAGAAGACCCACCTTCAACCCTCGAGGA
CAATATAATACCACACCCCCGGCACTTATGCCTATCCACTTGGCTTCGT
ACTGGACATCGGGGGTGGGGCGAGGATTTTGTCGATTTTATTGCGGGTA
TTATGCTTTTGCCCTACGCTTCACATGCCGAATGGGTACATATCTTTTAC
ATAAAAGACATGGGTTGTTTCTGAATCTTGGGGATAAAGAGGATACAGA
GGAATTCCTGAGAAAGTATGCAGAGAAAAATCCTTTTATAAATACTTTAA
TAGAGCACATTCGCATTTATCAGCCGATAAATGATAATACGCTCTTTCCC
ATTCTAAACCGCTATCTTGTCGGAATGCCTTATGAAAACATATCAAGCGA
AGAGTTTCACCAGAGTTTCAACAGGGTTCTGGAAAAGCTGAAAGAAGGAT
ACATAGACATTTTCAAAGGTGTTTACCAGCATATCACCCCAGATGACGCA
CCTGCTGTTGCTTTCGTGAACGAATTCAGAGATTTTATTTCCAATCTGGG
GGATTATCACACTGGAAAAAATATACTGGAAGTGGCAATAGCCCGAATTG
TGTTCGCCGTTTTCAGACGTCATGAACTTATAGAAATGATCGAAGCAATG
ATCGGTAATGCACCGGGAGAAATTACCTCCTCACGCTTTATCAACTATCT
TCCGGTTTCTGATTCCAGAAGTCTGAGTGCATTTACCCGATGGTTTGCCA
TTACACATCGCCTGTTTTACTATGCTTTCAATAAAGGGGTAATCAGAGAG
CAATATCTTGAAGAATCGGCTACGCTGTTTGTGGATATGATTTTCACCAT
TGCCTTTTCAAAGGAAAAAATAAGAGCTGCTATGGATACAATGTTCAGAA
TGTTAATAGATCAAATCAAAGATAAAGGTATACCCAAATCCTATCGGGTT
TACAGCGAACTTGGTTATTGCGGAATATACGATCCGGGAACCGGCGGTGT
GCATGAAGCCGAACCTGCTCAGGTGGTCTGGTGGGATCCCTCCGTGGTGG
AATACTACGGGCGATTCCCAACATAGGGATGCGAGAACGTAAAATTCAG
AACCTGAAGGATTATATAACCGCCCTTGACGTGGTCAGATTTTTTGTCAA
GGTGTTTATATACAATAAACATTTACTTACACAAGAACCCCGTTTGTTTA
ATCAATCGGCTGAGGATATTGCTTGGCATTTTAAAAGAATATTTTATAAG
AAAGAATTCATTTACCTTTTTGAAAAAGGTTTGCGGATGATTAGTAGATT
TATCAAAACAGGAAATGTAAATCAGTTGATGTCTCTTATTCATGATGTAC
TCATGTTGCACCTTAGAACAGATCTCCTCGCGAGGGTATCTGCAGTTTAT
AGATCATACTCTCTTGAAGATTATTATAACGAAGAACTCAAACATATGAA
GAGGGTGGTAGGTGATATTGCCGATAACATGGTTGCACTTCTTACAAATT
ACGCCGTGGATATTCTGACCGGTAAAGAGCAGGTTAAGGATATAGACAGC
GCATTTTCCCATTATCTCGATCATCTCAGAGAAAAACTTCAAGAATTGTT
AGATAAGTCTGCTTTAGAGTTGCGCGGAAAAGCAGGTACAAAAACACTAT
TGCAAAGATCTTTAGCAGTAGAGTCGGGGATAGAGTCTATTCTTTCAGGA
ATTATCTTCATGAGAAAGTTTCTGGAAGCTTATGATTCGGATAGAGAGAA
GATTGAGGAAGCGTTCAGGGTGGTAAAAGAAAGACTAAGGGATTAAATAC
TGGTAATTGGGATTGTGTGGAATGGGTATTTTTGAAAAGAAGGTGAATCT
GAAAGAGGGGTGGATCCACCTTACAACATTTCCGTAGAAAGAGGCAAAAA
GGGGAGAATGCTATGAAGATCAAAAAGGTAATTATAGCGCTGCTGTTTCT
ACTCACAGCCTTCCAGCTTGGGGGGATTATGGCATTGTATCTTTTTCCGC
GATAAGCGCCTGTAGCTCAACCGGAAAGAGCACCAGCCTTCTAAGCTGGT
GGTTGTGGGTTCGAGTCCCACCGGGCGCTCAGGTGTAATCAGAAACAAAA
AAAGGGAGGGAGTCATGACAGTCATATGGGCAATCTTTTTTATAGTCATG
GTGTTGATGGAAATTCGAACCTTTCGGGTAAAGAGGTATCTGGAAGATCA
CTCCACCCGACAAGGTTCTTATGCAACCGAATGGTATTACCGGGTGGTGA
ATGAAAGGAGGAACGTAAAAACCGGGTTCGCAATGGGATTTGTAAGAA
AAAAAGAGCGCCTTATTATCAAGCGTGATTTCGACGCGCTTAAATTTGAA
GACGCGTTCGATCTTGAGATCGTGTTTCACGTCAACCCCGAAGTTGAAAT
TATTGATCGGGGAGAAGACGTGGTTGTCGTATATGCCCCGCTTGGCATTT
TGGGAAGCGGGGAAACAGTTGAAGAGGCAATGAATAGTTTGCTTCTTCAG
GCTGTAAAGGAATATAAAGAGAGCACTTATGAAGGAGAGCGAGAGATACT
TCGTTCCTTTATAAAGTTGTACACGTCGTTTCTCCCGCCCGACTGGAAAA
```

FIG. 1M

```
GTCGGGTTTGAGTAATAGGGCATTCGTCTGCTCTCATGAGTAACCGATAA
CCAAACAAACGGAGGTAGCCATGAAAGAGGTCAGCGTCACCCATGTCGTC
GTTTGCCCCTTCTGTGGCAAGACGGGCGAAGTCACCATTACGGCGGATGG
GAGTGGTCCCCGCCTCGTGGAAATGGAGCGCATTTGCCCCCACGTAGATA
CTGAATACGACGAAAGAAAGCGGGGGATTTACGTACATTTCAGTGACGGC
GAAAGGGGGACTACGTCTTCCTATACGCCCCCCTTGCGCTGTACGTCCG
GGAGGGCGATCCCCATCTGATCGCCCGTGCGCTCCGCCGGCGGGCTTTA
AGGTACGGGTCGACGGGCGCCACATCATCTTCAAGACACCCGTCTACCCG
TATCCGGTGGACTTGGCGCTTAGGCAGTATATGCTTAACGCCGGGCGCAC
GGTCTCATACAAACACGTGCATCTGTGAAGATTATGTGAGGGGGTTGCGC
GGCGCTTGGCATTTTCGTATATTAGAACTGTCACCAACCAAACAAACCAA
GGAGGTAGCCACGAAAGCGATTGACGTTCTCAAGACATTCCCAGCCCCGG
ACAGCTTCGAGGGCGTCTATTACTGTCCGGAGCATCCAGAGGTTGAAATC
AAAGAAACCGTCCGTTGGACGGAGGTTCCAAACCCCAACCCCGACGCCCG
CAACCCGGTCGCAGTACACCGGGTTGTGGACCGCTGGTGCCCGGTCTGCG
GGAGACCGGCTGTTCTGGGAGCTCGATCCGCATGACGGGTGTTTCGGCGA
TATTCGCAATCTTCGCAACGCCGAAGCAAAGCTTGCCCGCCACATTTTAA
AGTAATTTCCGTTTATATTTACTTATATTTACATAGGGGTTTAGAACAAA
CCGGAAGATATTATGAAGTGGTTTAAACGACTTACGACGCTGGAGATTTC
CCTTCTTATTCCTCTCTTTATTTCCTTGAGCGTTTACTTCTCCACTCAGG
GAGTCGCCAAATTTGTGGCGCTTCCTGTGTGGGTGGTGGCACTGGTAATA
GCGGCTATTGACGTGGCAAAGTTCGTAAGTGTGGGTCTCCTTGTTACCAC
AAGGGGATGGCTGCTCAAAACAATTCTGATTCCGGTCATCCTGTGCGCCG
TCTTTGCCACTTCTTTCAGTTTTTATGCGGCACTTGTTTATTCACACGCG
GAGTCGGTGTCTTCAGAGAAAGTTGAAAACATCACAGAAGCTACCATAAC
TCGTGAAACCGTTCAGCGTCAGATCGCGCGTTATGAGCAGCTTCTTGAGG
AGGTTGACCGTTCTATTGAAAATATGAACAACACAACCACAGAGAGCATC
TGGCAAGAACGTCTCCGCAAGCGAGAGTTGGAGTCGCTGGTGAATCGAAA
GGAGGAGTACCTTGCCGCTATTGACTCTCTTGAAGCCGTTCTTGTAAGCA
GCACGGTGGAATCGAATCAGCGTCAAAATCTATTTTTCCTCAACTATATT
ACTCCCAACTTCTATTTCGTGCTTCTTACGATCATTTTCGATCCGCTTGC
CGTTCTTCTTTACGCGCTGTTTGTGCGCATGCTGAAGCAAAATGCGCGTG
AGGAAGATGAAAAGAAGTGAAAGAGGAAAAAACGGGAGTGGAGGTTGTG
AAACCTAATGAACCCGAAGAGCAGGATTTCGTTTCCAAGCAAGAGGAAGC
GGAGCAGCTGCTGATGGATAAAGTTTTTCAAACCAAACGCTTTGCATTTG
ATCCAACCCGAATGCAACCCCAGAAGGTGGTTATACGGGAAAAAAGGAGG
AGGTGATATGTACATTGTAAAAAAAGTCAGGATATTGAGTGAGACGGCAA
CGGTAATCGTCGAATATTCAGATTACAGGGCAAATGTATGGGTTGGGAAG
GGAATCTCCTGTAGAGCCTTTCTCAAAAGCAAAGAGGTTAGAACAGGGGT
AATCCCTTACCTGACCATTTACAAAAGATACCCCAGAAATGGAAAGCTAC
TGGAAGATTTCTTAAAATCGATGGAACAACAATATGTACAACATACGCGT
CAACACATATAGTGTAGGGCTGCATTCGCACCAAGTTCCGATTCTCAAAG
CAGCCAACGATCCTTCCATTGTTGATCACAACATGTATCTGTACATTACC
GCCCGCCACCCCTTTTTGCGGCTCAAGATAGATTTCACGTTTAACGGCAA
CAAAAGGGTGGCGTCATCGGCAATTATTTCCATGCACAACAGGGGGAAAG
ATCTGATTAAAGAATATAAGCTGTTCGATCTTGATATATACAAACCGACA
ACTGCTTCGTATAAACCCTCAGATAAGACCAAGACTGTAAAGTTGATTTA
TAACTTTTAAATGATAATAGACGTTGGGTGATTATGTATTGTCTTCGATA
TAAAAATAGCAGATATACGTTGTGCCGCCCTTAACGTACATGCGTCGAAAG
TGGCACCCCCTCCTATGTAGACATAGTGATTAAGGGGGTTTTTAAGATA
AAAAAAGGGGCGCTCAGTATCGCGGTTCATCCTGATACACCTGTGGGAGA
CATAAGGTTTGATTGTCTCATGAAGGTTTATGGAAGCGGAGATGTGTTTG
AAATACACTGTTTTAAAATCATTTTTCATTTGAATGATATTAAAAAGAGG
TGTTATCGGAATCTTTTAAAGTTGGTTATAAGTTAGTGTAAATATGTGGG
TTCTAAAACGGCAAGAGCAGGAAATAGGGATAAAGAGTCAGGATACGCCG
ATTCTGGCTCCTATTAATGCTGAGGTGGAAATACACATAGAAAGTATAT
AGGCGGATTTCCGAAGACAAAAGGCTTGTATGCAGAAGTGATCTATGCGT
CAAAATATAACAAACCGGTTGTTTTGCGCAAACCTTAAATGCGAACTAC
GAAATGTACTTATGTTCTATTGGTATTTATAAAAACGTCGGAAGACAGAA
```

FIG. 1N

```
TAACATTATAAACATCTTAAAACTTTATGTAAACCTGTAACACCATGTAC
GTTTTAAAAATTAAAAAATACAGCTTTCATACCGGATTTTACAAAATTCC
GGCAAATGGTATGGTACGGGATCCTGAGAATGGGTATATTGATCTTTGTC
TCAAAACGGAACTCCCGTTATGTGCTTTCTTTGTAAACTATGAGGAAGAA
GATGAACCGCGCGTTTTTGTTATAAAAGAGGCTGGAAAAGATCCTCAGGA
AACTATCGTAGAATTTATTGTAAGTAAAAACTTTCCCATTAATAGGAATT
TCAACATAATCAAACTGATATTTGCGCCATGATGGTTGTTGCCGGTAGAA
ATTACAAGCTGGAATCCAGCGAAATGCTGATTCCCAACGTGGTGGTTACA
TCCAAAAACCGAATCTATAACGTTTCGATATGGGTTATAGACATCGGATA
TTTCTATGCGGGAAATGAACGGGGGTATCTTGGATTAAGATGTGGGGTTG
AAAAAACGTTTACTGGCTTTAAAATTAATGTCTATAAAACCACAAATCGC
GGGAAGTGATATGTATATGATAAGATTGAAATGCCACGATTATCCCAATA
CGGTCAACAGCAAAAAATGGTTAATTACAAAATAACTCTGAAATCAGAA
CACCCATCAAACACACTTACCATTCTGATAAACTGGGTTTCAACCAATAT
CGAAAGATATGGCAACCATATTATGTTTCAGCGTCCCGGTTATTACCTGA
GCGCTACGTTTTGTTTAAAAAACATCTTTATTTCAAAGGCGGTTACCAT
CTACAAAGCTTTCGACTGTAAAAAATGTAAACCGATATGTATCTCATAAG
ACATAGTCTCAAAAATAGGGTTGCCTATCCAGAGGATCCTTACTACAAAC
CACCGGTTTCCACCGGCGGGAAATGGGTTACGCATCTGGGAAAGCTTTGT
AAAATAGAATTTCACGCACTGGTTTTGCAGAAGGAAATGTGGGAAGAGAT
AAGAAGTAGGAACAAATCACTATTCAACGATCGGATTCGCAAAGTACTTT
TGTACGATACTGAAGAAAACCTATTTGCCATATATAAGATAATCTGATGT
TTCTGCTTAAGACAACACCGCGCAATCACAATCCGCGTCAGGTATGGTTG
AAACTACCTGACCAGAGACGGGTGTTTTTTGAGGTTTCCTACAGATTCGT
AGAAATTTCACATGCGACTGGAAACCGTGTTAACAGAATTCTATTACAAC
TCCTGTCGGAATATCATTTTACATTTGTAAAAAAGGCGGACTATGCTGCT
GGTCAAAAACAGCCACATCGATCCCAATGATGGTGAAATGCGGCTAAAAT
ACAGCCGCGTTATGGATGTTAAAATTTATCTTGGGCGTTTGGGAAATAC
CCAAACCCCCGAAGGGTGTCTTATAGTCTGGCACCCTTTGATGAACTGTT
TGAGTTTGCAAGCTGGATGTCACTTTTGATGATAGAAAAGCACATAAACC
GGAAAAAGTAATATGTACGTGTTTAAAGTAAGTTATTTTATGAACGGCGA
GCCGATAGGCATACGTACCCTTTCAAGGTGGGTGCAGGTTGAAATTGCCT
ACTGGGGTAAAGAAGGTACACGTTATAAAAGAGTTACCGGTGGGAGATTT
GAGGAAAATGATTACTGGTACGAAATAGAGATAAAAAAATAGAATGTGTC
ATTATGTATCTTATGAGAATGAATAAAAGTGTACCAATAACACCCATTTC
CGGGAGGGGGAGTACACTGAGCGGGCATAGCGAGATTAGAATAGGAGCCG
CGTGTTTTCGCGCCATGCACTGGACTTATATAATAAGTGTACACATACCG
AACAATCAGTTTAGTGTTTGTTTAATGGAAAAAAGAGAATTAATAAACGT
ATTTTTAGACAAGCATATAAAATGTACGTATTAAGTACAGGTGTTGATGA
TCCACTATTTATGACCGGAACTTCTACACCGGGTGTGATCACTCCCAAAG
AGGGTTTTTATACAACCCAGAAGTTTATTCGTGTGTGGTTTTTTGTACGC
TACTACAGTGTTCCCCCAAAATCCCACAACGTTGTACATTTTACCAGCGC
CAACCATTATAAACTTATAAAAAAATTCTATTATGTATACTATTAAATTA
AACAAAGGGGTTAAAAACAACGAATGTTTTGTGGTTGTCGGAAACGAAAT
TCTCTCCAATGACCCCATTGTAAACTATAATATATTTAGCAAACAGGATG
ATCTGTTCGCATTTACAATTCAATACTGGCATAGCTTAAGAACACTGGGA
CCAGAAGGCACACCACTTGATCTGGAACTGACGTCTAATGCGATAAATCT
TGGAAGGATTTATAACGAAGAAGATGAACCCTTCCCGGATTTCATTTTTG
AAAAACTGATATATAAAGACTTTCAAGAAAGCTCTAAATTTGGGTGGTGA
TGTATATAACAATCAGAAAACAAATCGAATCGGTAGTATACGTAGAACCT
GAATTGCTATATCATATGTTCGTAGAAATGCTGGGATACGATGTGGTAGT
TTATACGCTATATGCCGCCCAATGTACCAAATATCCCGATAATAAAACGG
GGGTGGTTAAGATGTTTAGTAAAAAGAAGGTGTTTTATGTGCTGAAGGTG
ATAAAAGTGAGCAGGAAACCTTCTTTCTGGAAACGTCTTTTAGAATGGGT
AAAAGCTATTATCAGGGGGTGATATGTATTACCTCAAGTTGCCGGTAGCA
AAGCACTCACCCTTTGATTGTATCTGGGTGTTGTTTATGATACATTACTT
TCCTGTAAGTGTTTCTTTAAACACCCCGAACGCTGTATATTTTAACATCA
AAAATTTTAAACTTATTAAGAGAATTTATCAAAGGTTATAATGTGGAACA
ATCAACTTTGGGGTGATCACAATGATTGTACTTAAAACACCGATACTCAG
```

FIG. 10

```
AGTTACTTCGTGGTTAGATATTAGAACCGTTTTGTACGTTGAGGGGATTG
GATTTGTTACCAGAATCCCCTGGATGTGGGATATTATCTTTGAAATTGTT
TACGTTTATAATAAAATTGAGCGTAATGCTTGTTATTATACCAATTACAT
CAATTTCACTTTGAATCTTGATTCAGTAGGCGGTAAAGCGTTTGCTGTGT
TGAAAGGGGTCGCACCAGAACAGGTTTTTTCCATTATTATGGTGGTTAGA
AGATAGAAAGGTGTCATCTTCGTATTGAAAATGCGTGTTGTCGAAAAGAT
TAGAGATCATTATGTACCTTCCGACTATAGATCTTTTATACGTCTTGGTA
ACTATACTTGGTTCTATCTTTTTTATCATGACACCCATGACATACCGTTG
ACACCGGCGCATAATACCTTCCCACAAACGTTTGCCGCCATGCAGACGCT
CACGGTCAAATGCAAGCTGGTCCTCTCTAAGGAGCAGCGAGAAGCACTTG
ACACCACCATGCGAGCGTTTGCCGCCGCGTGCAACGATGCAATCGCCGTC
GGTCGAAGACTGAATACCGCGTCGAACATTCGCATCCACCGCGTCTGCTA
CAGCGACCTCAGAGCAAGGCATGGTCTTACAGCCAACCTTGCCGTCCGTG
CCATTGCCCGAGCAGCAGGCATTCTCAAAGTCAAGAAGCGCCAGTGCAGT
ACAGTACGCCCGACAAGCATCGACTACGACGCCCGCATCTTCTCCTTCCG
AGAAGCCAACAAGCGCCGTGGTCTGGAAGACGCGGCAAGGAGACTACTAC
ATCGGTATCCACATTAACGTAGAGACGCCCCCACCTGAAGATGAGCACGG
GTGGATTGGCGTCGACCTTGGAATCGCGAGCATTGCCACGCTGAGCGACG
GCACGGTGTTCAGCGGCGACCAGATAGAGCGGGTCCGTGCTCGGTATGAA
AGAACCCGCCGCTCCCTCCAGCGAAAAGGCACGAGGGGCGCAAAGCGCGT
CCTGAAACGGCTCTCGGGAAGGGAGCGGCGCTTCCAGCAGGCGATCAACC
ACACCATCAGTCGCCGTATCGTAGACCGGGCTATCGCCGAGGGTAAGGGT
GTCCGGCTCGAAGACCTCAGCGGCATTCGCAAAAGTGTGCGCGTTCGAAA
ATCGCAGCGCAGAAGAATCCACCGCTGGGCGTTCTATGATTTGCGCATTA
AAATCGCGTACAAGTGCGCCCTTGCCGGGGTGCCCTTCGAGCTGATTGAT
CCCCGATATACGTCTCAGCGCTGTCCGGTCTGCGGGCATACCGAGAGGGC
AAACCGCAAGAGCCAGAGCAAGTTTGTCTGCCGCTCGTGCGGATTGGAAG
CGAACGCCGATGTGGTTGGCGCAATTAACATTGCACTCGGGGGCGTTGTC
AACCGTCCCGAAGTAGCGCCCGATGATGTCGAAGCGGTGTTGCATGGTCA
GCGCCGAACTGAGACGGAGGGCAGCTACAAGCCCACGACTGAAGTCGTGG
GTAGTTGATGAATATCCATAGCCATTTATTTAATCAAAAATGCTTCTCGA
AAGCCGAAAAGGAGAATTCCTACAACAGGAAATTCTTCGGTTGTATAAAA
CCTATGGGATCGTCTTCTGGTAAGATTTTCCAGCGCCGAACGCGAAACC
TTCAATCCCGACGCCGACTATTTCACAACGCCTATCGGTACTTACGCCTA
TCCTGTCGGTGCTATCTTCCACATTTCGGAAGACGATGTGGTGATCGATC
CCGACATGTACGGGGTTTCCGAAAGAAAATATATTTATTTTTTGTGGCA
AGTAAAGATGCTTCTTGGCTTAACATATCCTCTCAACATCCGGCGTTTGA
AATTCCCCTTGTTTTGTACAACCAGTTCAGAAATTATGCCGATCTCTATG
ACGTTTCACTGGATGATGTTTTCCGGAATCGAAACAGTATGGAAAGCTAT
CTTACCTACTGGTGCTTTGCCATTGCATCCGTGTTTTCTCCGATCTTAC
AGAGACACTCAAGCAGAACTTGATGGAATTGCTTCGAAAAGATCTTCCCC
GTATGCGGGGATATTATCAGGAGCTTTCAAATATTTGCAGGGAATTTGAC
GTCGATGTTTCAAGATTCTATCATGCACGTAACAATCCCGAAGAATGGCT
CAATTTGCTGATTGCAGAACTTCTTGACCGGCTCAACAGCGGCTTCAGAC
ACATGAAATCAGCCGGGGATGTAAAGCATAAGTATTTCATGTATCCTCTG
ATCGTTTTTATAACATTGCTTCACAACAGGTATGCACCTTATCCGAATTC
CATTGAAGCGGCTTATAATATAGGAGCCAAAAAAGACCCTGTTGTTCTGA
CGGGTTTCCTTCGAAAGGTGGGATATGATGGAATCTGGGATCATGGCACC
GGAGCCATTCACTCCAATGAACCCGCTCAGGTGGTCTGGTGGAAACCCAC
TGCTGCAAGGCTGGTGAACAAAATGGATAACCCTCTTTATGTTTCGCCTT
CCTCCATAGGATTCGGTTATCTTGCGTTTGCCGATGAAGGGGTTGCACCC
TCCAATGAAAACAGAAAAAATATTTATGGAATCTGATTTTAAGTGGTAA
AATGGATGAGTTTATTGAAATCATGGATATGATCATGTACCGTAAGTATC
TTGCAGCGCTTTTCAACGCGTTTTTGAATGAAAGACGGGTGGCTCTCAAA
CACGCTATCGGATTCAAGGCATTCAAGGAATATCTCAAGCAAAATGCAGA
GGAAATCAGAAACTTTTTCAGAGTGAGCAGCAATGCGCCGGTGCAGCTTG
TATGGGACCGGTTCAGAAAAGCATTCAGAATTTCTGAATTACTTCGAAAC
TACGAAGAATTGATTGACCGGCACCCTTATGAGGTGGATGATTTTGCCCA
CAAGCTTCTTGGTAATTTTAACTTTTTGAAAGAACTGATTAAGCCCACCA
```

FIG. 1P

```
GACTATAAAACGCAAAATAATTAAAAAAATGAAAGTTAATTAAAATAAAA
GGAGGTCAAAATGAAGAGGTTGACAAAAGAACAGTTTATTAACAATTTTC
ACGAGCCCAACTCGCTGCATTTGTTCCCATCTATAGAGGATTTCATTAAC
CCTCGACAAGGAGATATTACTCAATCCTACTGTTATGTATTACCTGTTCA
GGATTTAAAAATCGACAACAAAATGGGCATACCGGTAAATTTTGATTTAT
CACAGGCTTTAAATAAGATGATAGGTTCTAAAGGTGAGTTGAACAAAAAT
TTGATCAAACAAAAAAACTCGGCACTTAAGGAATTAAAAAATATATTACA
GAAGTTTCACAAAATTTTACAATCATTAAAATCTAATTTTAATGAAGGGA
TAGCACTGGTTTTTCATTCCTTTTTTTTATGAAAAAGTGCACTCCTTTG
ATCATGCTCGCGCATCGTATGATTATGTAAAAAGCAACCCCAAAAGTGTT
TTAGAGCCACTCAATGAAGCATTAAAATACGATGAAGAAATCGTCGAGGA
AGCTATTAGAGAAACAGTATCAGATTATCTGGAAAGTGGAGACTGGTATG
ATATGATTGAAAATGCAGTCGAAAAGTATTTGAGGGGTTAATTAAAAGAA
AACCATGCTTGATCAGCTTCTTTCTCTTTCCGGGCTTTACTTTGATCAAC
AGCTTTTTGCGGGTTCACCGGGAGAGTTGTTTTTGCGGTTGGTGGCGGAA
GCACTCGATGAAGCGGAGTTCAATGTAAGGAGTCTGCAGAACCGAAGCTA
TCCGCTGACTGTAGAGAATACTGATGATCTGCTGAGACTGGCACACCTGA
ACGGTGTAAGTATTACCCCCTACGTTCAGGGAATTGTCAAAGCAGAACTT
CTTGTTACTTTCCCCATTTCGGTTACCACATCTGTTCCTGACTTGACAAC
ACATGCACCGGAAATTCTCTACATGGATATTCTTGCCGATACGGATTATT
TCTATCTGGATTATACCGATTTCCGCCAGACCGATACCCGTATCATTACC
ACCAGCACCAATCTTATCTACTCAAGAGACGTAGTCTTTCGTCATGGTAG
GGTTGAGCGGAGAAGCTATCCGGTAAGTCAGACGATCCCCTTCATGATGT
TAGAACTTGAGGAAGATGTGGTGGATGTTAAGAACGTTTTCGTGGAATAC
CCTGATGGAAGGCTGGTCAAGTTTTACCGCTCACGTAATCTTCATGAAAA
TCTGGTGGTTGAAAATGCGGTAATTTACAACACCCGCCACATTTACGACG
TGGTGTTTTCCTCGGGGAGAGTGCATTTGCTTTTCGGTAGAAAGATTTCT
CTGGAAGACCCGATTTCACATACCGGCTATACTTTTCCCGCCGGAAGCAC
CATATATGTCGACACGGTTGCAATCGATCCGACTACCCTGAACAGCTTCA
TTCCGGAACTTGAAGCAGATATCAAAACCGTTAAGATCAACAACCGTATT
GGGGCAACCCCTCAGATTCAGGTGCTCACCGAAGGTGGATACACTTCCCG
TCTTAAAGACATCGAATATCTCAAACGGGAACTGCTTGTCGCTCTTCAGA
AAGACGAACTGGAAAGAGAAATCGCAAAATATTTCGATAAATACAGATTC
GTTCGAGAAGATGATATTGTCTATGTGGAAGGAGCCATATACCGCAACGG
TAGATTCACCTTCCACGAAGCCGATCGATTCTATATGCAGAAAGTGGTTT
CCACCTACAACCGCAACATGATCGTCAGGAAAATTCCGATCACCCCCCTC
AAGATCATCATTCGCGCTTCCAACATTCTGAACCCCGGAGAACTGATCAC
TTTCGTAAAAGATTATATCAGAAAACTTCCGATCGGTGGAACGTGGATCA
CAAATGAACTTGTGGGGTTAATAAAAGAAAAATTCAATGTCGTATGTGTG
CTGGAAATTTATTTTGGAGAAACTTATGCCCGAAAGGTTTCGGAAGATAT
TATCATCTACGACGGCGTACTCGACGTTGAAAGTGTAGAAGTCAAACCCG
TACTGGTTTGATGGGGCGCTATGCAAAAACCAAGGGAAGGAAATTTCAGA
ACTTTGTAAAATCGCTGCTTGAATCCACCTTCAAAAATTGGAGCTTCAAG
ACAGCAATCATGGGCGAATCAGGTTCAGATGTCAAGATATTTCCGGAGCA
GATTTTTTCGGTTGAAGTAAAACACCACAAAAACGGATTGATCAGAAAGG
ATGATATGCCTTCTGAAACCGTACTCAAGCAAGCACGCGAGCTTATCCGT
AAGGAAAACAGTCATTTCTGTTTGATCGTTTTGAAGGAGAATTACAAAAC
CCCACAATATTTTGTGCTTTATCGAAACGGAAAGCTGAGAAAGCTGGAAG
ATATATCGGAGCTTAAGGAAATTGTAAAAAGATATAAATGATAGTTACTT
TGAGAGAAAGACCGTATTGGAGATATATTTACCTGTTGAAAATTCCATAG
CGGCGCTTAAGCAAAAACTGGCAAGGTTAGCCGCTGCAAACGAAACCGCA
GGTGGAACGCCTGGACCCCCCATTTTGCTGAACTCCTGAGCAAACTTGCG
CATCATCTTCGTCATGAAAGAATTGAAAGATTTTCCAAGAAGCGCATTTT
CGGTAGCGCTACTGGTATTGCCTATATAAACCCTGTCTCCATGTAGATAC
ATCCGTTCGGTGGAAATCCTCACCTTTCTCTCCGCACCCATTAGCAATTC
TTCCTGCATGGCAAGGTGCAATTTTTTTGCAGCCACAAGGATTCGCTCAC
GTTGCAGCAGGTGCAGTGAATCCGATCTTATTTTAACAACGTAACCGCCA
CTTTCTTCATCCACCGACTCATTCTTGAAAGATATTTTATATGATTTCAG
ATTTACCTGATCGCCGTCTATTTTACCATAGATTCCATACGGGGATTTAT
```

FIG. 1Q

```
CTTCGTCGACAGAAGTGGTTAAATCGTCAGAGACTTCATCACTGTACTTT
CCAAGAAACAGATTTCCCTCTTCGTCAAACCATAGCGCCTGCATTCCCTT
TCCGTTGAGAAAATATTCACCCGGAAACGATCTTATCCGTGCCCGTTTCA
ATTGATTAATCGTAACACCACTTTCATTGTCGTTGGTGGTTTGAAGGTAG
TTTGACATGTTGACGGGGAAGGGGAAATACCAGAGCCTTCCATTGATTTC
CACATAAGCAAGGAGATCACCCACCTCAGGATAAAATCCTATGTGCACGA
AAAATGGATAGGCTACACCAATCACTTCTTCAGAAATGTCTTTGATTCTG
ACCGCCATGTATCTTTCGGGAGTATCGACATCATCTACTTCCAGTACCAA
TCCGAATTTTACCGGAGATGAAAAGAAAGATATTTTGCTGCTTTTGTTAG
AAAAGAATTCCTGAGTGTTGAACCCCATTTTTTATTTTATTTTGTTAGT
TAAACATATAAACTATATAGTTTTCTTTTAAATAAAACACCAAATGATTT
TTAACACTTCATACTATTGAAGATTTTCAGAATACGATCCACGACCTGT
TTCCATTTTCGGTTATCCTTATATTCACCAACAATCTCTCCTGCTATCTC
GAATACCGCTTCTCCAAAATACCACAAATGTTTTTCCAGTTCTACGTGCA
CATGATATTCGTTCCTTTCAATATAGTCTTCAATTAATCGTTTGATAAAA
TGATGTAAAACGTATTCACCTTCGAATCTTTCTTTAACATAAAACACCAC
AATTTCTGCTCCCAGAGATACCGCATCTGTACCTCTTTGACTGATAGGTT
CATCATAACGCATTCCAACCACAATACTCATAAGAACTTCTGAGGGTAAT
GGATGACCTTCATGAGAGTGGAAAAGATAGTGGTTAGTTATTTTAGTCAG
CAGCTTTTTTACCGTCTCTCTATCCAGAAAGTGTGTGTAGTTATTGATTC
TATCTTCAATATAGTCAACGAATTCCAATTGCAGTTTGGTGAATATAAAT
TCTTCTTGGGCGTATAGTTTATCATATACAAAATCTACAAGATCATCATT
TTGTTCATTGTACTGATCAATAATGGAAGTAACAATTTTTTCTATCTTAT
TCTCTATAAATTTATCTACGTTCAATGCGTGTTTTAAACCTTCCTTTATA
ATCTCTAAAATTTCGGGGTCTGATAAATAATCTTCCCACAAATCATCTTT
AAGCATATCTTTATAAACAATGAAGGCAATCGCATCTTTTACCGGTTCGG
GAATGTGTGGAATAAGGTCTTCAGGTTCATTTATGCGTATTGCTCTTTCG
ATCAACAAACGAATATAAAAATCTATAGATTCGGGGGTTTGAATATTAAA
GTCAAGTATCCTATCAAGGTCTGTTCTGTCATCAATGCCATATTTTAGCA
ACAGTCTCTGCTTATAAGATGGAATAGACGGCACCTGTTCCACAATAAAT
TCATAAAGAGGAGAACCCTCTTTAAGATTGATTACAAAAAGGTCTCTCAA
ATAATTAGCAGCCGTCATCTTTACTCGAGCATTGACAAACGCCATTTTTA
TAACGTGGGGTTCATTATAGTTTTGAACAACATTAAAAAGTGAATGGAAA
TGTTCAGTTGATTCGGCTACTATTAGTTTCCCATTTCTGGTTCCCACTAT
CATAAAAGAATAAAACAGGGATGTGAAATATTCCTTGCCGGTTATGCTGT
ATGGAAAATTAGACTTTCGTAGTCCACAAAAAACAAGGGCTACGCCCCTG
TCAACAATTGATTTCAACTTGTTTAATATTTGCGAACCTTTGGTTTTTAT
CTCATTTTGTTTATGAATAATGAAGTTTCTAAGTTGCAAAAATTGATCTT
GGGTGACCCTTGATGAATGCTTATAGATATAATTGAATGTTTCTAATAAG
TGGTGATTCAAGGGAATGCCTTCTTGGGGATGAAAACTAAGTTTTTCTAC
GGGTAAAACATAACACCTTAAAAACAGCCGAATCCCCACTATCGTTTGGTA
AAACATACATGAACCAGTTAATTGAAGAAAAAAAGCTTAACGCCTCTTTG
CTGTGGAAGTTATCCGCAAATTGTTCTCTTGTCAGTATCAGCATATAACC
TAAGCAAAGTTTATTATACAAGGTAAATTTGGATTAAATAATAACCAGAC
TTCTCAGATGTAATTATTCGTCTTTTCCAACCACATCAGAATAAAACGTT
TCTATTTCGTTAAGATCTTTGTTGATCAGAGTTTCAATTTGTTTTTTTCA
GCCCCATGACACACCCTCCATTTTTTGGCATACTAAACAAGGCAAAACCC
AGACAGTTCCATAGCCGCCGACTTATTTAAAGAAAAATAAATGAAAAATG
CTTCAAGTACTGAAAGACACCTATTTAAACAGCGCTTCCCCGCATAACAA
CTATGGAGCCGACGAAATTCTCCGGCTCAATGCCACTTCCAGCATTGCAT
TGCAGTTTGAAAACCCGATTGGAACGGGTTATGAGATTCGCCTGTTTGTT
GCCGACGCGTGGATTCCCCATGTAGAATATCTGGGTGGGGAAGCTATCA
CCGGCTGCTCCTCACCGTTTCGCTCTACAGCTTTTCTATGGATGAAGGAT
ATGGAACCGAAGTAGAACCGCTTATAAGCCAGAGTTTCAACTATGCGTCG
CTGTCAACGCTTCCTTTACCACTGGAAGTTCGCACGGTAAGCGCATTTAT
TCATCTGGCACCGCTCAAGCGGCGTATGGTAAGCATTCCACTTACAAACT
TTTTCAACGCCGGAAACTTTGTTCTTATCGAATCGGCTGAGGAAATGGCG
GTCAACTTTTTCAGCAGACAGACGCGCACGGCTTTCATTCCCTATACTAT
TCCGACAGTATCCTTGCAGCCCCCGGCGCTTTCAGACTTCGTATACGATA
```

FIG. 1R

```
CCCGCATAGACGACTACGGAGTATATCTGCAGGCTTGGGAGCGGAAGATT
CCCATTGCGGTAAGGGGTTATCTCATGCAGACGCTGTCATACATAGACCT
CTCAACCGTATGGTTTGAAGTATACGTGTTCGACATGATCACCGGTGAGG
AACACTATTATACATCGCTGCTTCCCACTCCCGTTGGGAATAACTGGTAC
TATATTGACATGAGCCGTGTCAATATGAAAAGAACCCAGTATGTGAGACT
CAAACCGGTTGGAAGCACCAACGACATTTTCCTTTCCTTCCACAACCGCT
ATCTGAGACTATGAACACCCAACAGATTATAAAACAGGAGCTTGAAAAAT
GTAAAAACGATCCGATTTATTTCATTCGTAAATATGTGAAAATCCAGCAC
CCGATCAAGCGCGTCATACCGTTCGATCTATACCCGATTCAGGAGAAACT
CATTAACTTTTATCATACACACCGATATGTAATCACGGAAAAACCCCGCC
AGATGGGTGTAACGTGGTGTGCAGTGGCGTATGCACTTCATCAGATGATC
TTCAACTCCAACTACAAGGTACTGATTGCAGCCAACAAGGAAGCCACGGC
AAAAAACGTGCTGGAACGTATCAAGTTTGCTTATGAGCAGCTTCCCAGAT
TTCTTCAGATTAAAAAACGTACATGGAATAAAACCTATATCGAATTTTCC
AACTATTCTTCCGCAAGAGCCGTCTCTTCCAAAAGTGATTCTGGACGTTC
GGAAAGTATTACGCTTCTGATTGTGGAAGAAGCCGCGTTCATTTCCAACA
TGGAGGAACTCTGGGCTTCGGTGCAGCAGACGCTTGCCACCGGTGGTAAA
TGTATCGTCAACTCCACCTACAACGGGGTTGGAAACTGGTACGAACGCAC
AATCCGAGCCGCCAAGGAAGGAAAAAGCGAATTCAAGTATTTTGGTATCA
AATGGAGTGATCATCCTGAGCGAGATGAAAAATGGTTTGAGGAGCAAAAA
AGATTGCTTCCCCCACGTGTGTTTGCTCAGGAGATTCTCTGCATTCCTCA
GGGTTCGGGAGAAAACGTCATTCCGTTCCATTTGATCAGAGAAGAAGAAT
TTATCGATCCGTTTGTGGTAAAATACGGTGGAGATTACTGGGAGTGGTAC
CGCAAACCCGGTTATTACTTTATCAGCGTAGACCCTGCTTCGGGTAGAGG
GGAAGATCGATCCGCCGTAGGTGTGCAGGTGCTGTGGGTAGACCCTCAGA
CGCTCACCATTGAACAGGTGGCGGAATTCGCCTCCGATAAAACCTCGCTT
CCCGTCATGCGTCAGGTGATCAAGCAGATTTATGACGAATTCAAACCACA
ACTCATTTTCATCGAGACAAACGGTATCGGCATGGGGCTCTATCAGTTCA
TGGAAGCTTACACGCCCAGTATTGTAGGATACTATACCACACAGCGGAAA
AAGGTGCACGGATCGGACCTTCTGGCAAAACTCTACGAAGACGGTAGATT
GATTCTGAGATCGAAAAGACTCTTGGAGCAGCTTCAGCGCACAACATGGG
TTAAAAACAAAGTGGAAACAGCAGGAAGAAATGACCTTTACATGGCGCTT
ATCAACGGTCTCATGGCTATCGCTACTCACGAAATCATGGAAGCCAACCC
TGAATGGGAAAGATTAACGTAACCTTCAACAGTTATCTTGGGAATAAGG
TAACCCCCAGCACGCTCGACATCAACCAAGAGTTTGGAGGAGAATTTACC
TATATCGCCACACCGAAGGTAAATCCTGATCTGAACAAAAATCTATTAAT
TCAAAAAAAATCCGAAGATTTCATCTGGTATATCTGAAAACGGCTTTCCA
CACAATCCCAATTACCAGTATTTAATATCCCTCTCTGATATACTCCCCCG
TTATTTAAAAGAAAATGCCACTGAGTAGAGACATCATAAATCGAATCAAA
GAGAAACAGGATACTCTCAGAGAGAATATTACCTACAGCGCAAAGCTTCT
CAAGAAGATTACAGAAACCAACCTTCAGAAATTCTTTTCAGAGACGCTTA
CATGGGGGATAAGGGAAGCCAAAAACCTTGTACTGGCACAACTTCCTCCT
GAATACAGAACTCAAAATCTAAACAACCCCACACTTACTCTTCACTGGTT
TACCTTCAATTTCAATCCCTTTGTTTACAAACGCGAAGTTAAAAGCAAAC
TTTATGATTCTCCGACTCCCAAGGTTTATCCTCTTAAAAGCCATGATTAT
GGGTATAGAACGGAGCTTTTGAGTGGGTCTCCGGTTCCTGCTCCCAACCT
TCGCTATATTGTCAGATACAATCCTGAAACCGATCGTCTTGAAGCTCGCA
CGGTGGATATTACCACCGAAGAAGGAATCAGATATGTGTGGGGTGCGTCG
GGTAATATTCCTCAGGATACGCTCGAGTTTACATCGCTACGTGGTCTTGG
TAAAGACGATATGATCGATCTGGCTCAGAGCGGCGTTCCCTATGAGAACT
CGCTGGTGCAGCTTTTCCGAAACAGAGCTTCCATTGGGTTTCAGTATGAT
GAAGACCTTCGCAAACCCATTCAGGTGGATCGTATCAATATGGAAGGATT
TACTCAGAACGAATCGGAGATTATCAATGATTATGTTACGTTCTATTTCA
AGAGCGTAGTGAGCGGCTGGATATGTCAGTTCAGAGCTTTTATCAACAGT
TTTGGTGAATCCACCAACGCTTCATACAACACTCAGGATTATATCTTCAA
CATCATCAAAATGTATTCGTATATCAATGTAGAGACCACCTATAACATTT
CGTTCACCCTGTTTCCTATGAGTAAGCAGGAGCTTTCAAAAATATGGGGT
AAGCTCTCATTTCTCAAAGCACACCTGTTTCCGGCAAAGCGGGTAACACC
CGGCGGCAACTTTGTACCTCCGGTACTTGAAGTAACGCTTGGCAACGTCT
```

FIG. 1S

```
GGAGAAAAAGGAAGGTGCTTCTTACTTCTCTCAATATCTCATTCGGGGAA
GATACCGTATGGGAACTGGATCCAGGTATGCAACTTCCCCAGTGGATCAA
AGTGGATCTGAATTTGATTTTGCTGTACGAACAGAATATTACCACGGAAG
ACTGGCTTCAAAACCGCGTTAAAATGTTCGATTATACGACAAACAAGCCG
CCTTCTACGCTTGCCGCCTCCGACTCCATGATCGATCCCGCAACAGGCGT
GGCACTTGACATTTCGACGTTCAAATACCCGGAACCCGAAAGTTTTAACC
TGAAACTTGCAAAACTCGATATACTTAAAAACCTTGGATAAATTATGAAA
GTATATTCTTTTTCGGGAACGCGACGCGCTCAGAACATAGCCGTACAGGA
ATATGGAGATTACTCCTACTGGCAAGATATGCTGCTTGCAAACGGTATTT
ACTCCGGATCGATCATTCCCCCGTATGTTCCGTCGCTTTCCATTTACACC
CCGGAGGAACTCGAGAACCGTCTGGTAGATAAATACCATATTCCCGATCT
GAAATATTTTTAACCTATGCTGATAAGAAGCCTGCACCCTTCCGTTGTAA
AGTATATCAGACAATTTGCTTCGACATCGACGGTTCAGAAGATTTCCGCA
AGGCTTGTGTTCATGGTGCGCGTGAGAGACGCCGCACCTTTCAGAGCGTA
CAACATTGTCTTAAACAACATAAATTTCTATACCATTGAAAACGAAATCA
CTCCTGATCTCCAGTCGTACTACGATTATCTTCCGGCTCCAGCTATTCTT
TCGGTGGACGTCGATCCGGCTCCTGACGGGATATACGGTATGATGGCGCG
TGCCACCGTCAATGTGCGTTGCTTTTCTCAAACAACTTCGGGAACTGG
AGTGGAGCCTGTTTCCGGGAATTACGGCGCTCATTGAAGTAGTGCGCACA
AACAATGAAATTCCCGTGGATTTATTTCTGATCGCTATGTGCGAAATCC
TTCGCTTCTGAAAGACATTCTTTTTAGCCCGCAATCGGTAATCAAACTCC
ATGAGAGAGATGAAGGCAATAGGATATTTTCCCCGGAATACTTAAAAGA
ACAAATGTTTCGTATAACAACAATACCTTTGACATTACCTTTGAGTTTAG
TAATTTTAGTATAGCTTCCGTATTTTTTTCTCGAAACTACGATATTAAGG
ATGTAGAGACGGCTCGAAAAACGCTGGCTGGTTTCTACAATGAGCGCTGG
AGTACGCTTTCCAGCCACAAGAAAGTCAGATCGGGTCAGGATCTGAACCT
TGACAGAACCTATCAGATGTTCGGTGGGGGGAATAAAGCATTTCCCGCCG
AAAAGGGTATTGAAGTGGGCGTGGGTACTCATTTCGATACAGGCGACAAA
ACTTTCGCCCCTTCGCTTCCTTCCAACACCTTCGAGTCGCTGGAATATAT
TCGTTTTGAAGATTTCCTGAAGGAAATTCTGATTCCCTATATTCGGGACA
CCTACCCGGAAGATGTTCCTCCGGAAATGGCAATTCTACCGATCGACATA
GACAACTCCTATATGTTCATTCATAAACACTTGAGAACCAACAACGTAGA
TATCATTTTCCCAACCGAATACATGGTGTTCGATTCTACGAATATGACGC
CGGATTACATTATGGGATTTTCAGATTATGAGGATCATGCAGAGTGGTTC
GAGAAGAATTTCGGGAAACCTTACACCCGTCACCCGATTGGATCAGTTGG
TAAAGTGGGGAAAGTGATGTTGGCTCGAAAGTATCTTTCCGAACTGATCG
GAGAATTCGAACGCGGCGACGACAAGCCGTTCAGTTTCATTATTGATAGA
ATCATTCAGGATATAATAAAATCCACCTATGGCTTTTCTCAGCTTTTCCT
GATGAAGGTGGGAGAGCAATACGTCATTTATGATAATAGACTTCTGGATG
TAGAGACGCCTGTTCAGCAGGTGGAAAACAAATCCCGTCTTGAACCGGAA
GAAATCAAGATATGGGAACTTCACGACATCAGCTATACGCTGGATATTCC
TGAATATCTTGCGATGGCGGTAATGATGAAGCGTCTTTCAGACTCGCTGA
ATACCTACGTCAACGATCCAGTGGATTTCCTTATTCCCGGTTCCGTTGAG
GATGTGGTGCTGAAGACGCTTACCGGAGAGCGTGTGAAAGGAACCGCGCT
GGAAGATACCACGGAAAGTTCGGATGTGGTTGTTACCAAGGTGAACCTGA
GCGCTGAAGTAATCCGTGCACTCATGAACAATCCCAATTTCAGAGCGCTC
ATGAATGTAATCAAAGAAATGAATCGGGGGCAACTACGAAGCCATTGA
AATAGAACATATTATAGCAAAACACGGAAGTTATGATAACGCTTTTGCGC
TGGCGCGGCTGGCGAACACCCGCTTTGCGCGGGGTAAAGTGTGGTATCGG
GTAAGAGGCGATCAGAAAGAGGAAATTACCGGAGAGCTTGTAAGAAAGGT
CGAACAGGCTTCCAGCTTCAGCGATCTGGTTACGCACCCGTTCGTCGATG
TGCCGAAATCTCAGGTGTCGCTTCCGGTTTCTCCCGGAAGATATACCACC
GCCTGTGGCGCTTACCAGTTTACGGAAACAACATGGCGGTGGATCGAGAG
AGAGTACGCCGATCTGTGGCGGGAGCTTAGTAAGAAAGCGGATGTGGCGG
TGGATTCCGCCGGAAATGAAATGGTGGTTACCGGTCTTCCACCCGCTACG
GTATATGAATATCAGGCGGTTGTCGACACTACCGTTCAGTCTCGAATTGT
GGTTCCTCCCACCCCCGTCAATCAGGATTACATGGTGGCAATTTATCTCA
CGATCATTCTCAACAACGCAAACCTTACCGAAGAAGAGTGGAATCTGTTT
TTGAACGAAGGATTCGGGTTTAAGCGTGAGGAAATAGTTAAAGAAAAACT
```

FIG. 1T

```
TACCACCCATTTTGCTTCCCTCAGAAAAGTCAATCTCAATGCTTCAATCA
GAAGAGACGCGTTTGAGCGCAAAGGAAATGTCAGTACATTTTGAGTATA
AAACATAAGGATCTGAGCGAAACAAAAAGTGTTAAATCTATTACATTTCA
TGTAACGAAGGTTGACGATAGATATGTAGCCTACATTCCCATGCACCTGT
CAACCTATTACAAAGTGCTTCTTTATATGGGCACGCTCCCGGAAAGACAG
CGGGGGAAGGGTGCTCAGTATCTGACCGGTATTACACTCAACATAACGGT
TCCGGGTAATTCGCTCTGGAGGATTTTTGACACGTTCAAAATAGAAGGTA
TTCCCGAAATCTATTATGAAAACGGCTATTTCATTGTAACGAAAATCTCC
CACAACATATCAGGCGGAACATGGACCACCGGGGTTACGGCAAAATACTT
TTACACGGGCAAAACGTAAAAAAAAACTATGAGCAAGTACTTTCTAAAAC
CAACTTCTTACGCTTCCGACGTTTATCTTGCACCACACGTTCCCGAACTG
GAATACGTTCCAAAGGAACTGATAAAAGGGTTTGACATGCTCCTCAACTG
GATCAGTGCACTGGAAACAAATCATCTGTTTTACAGCGCAATCAACTATC
TGGCTAAAGATTACCATGTAAAGAAACACCGCGAATATGTGATCCATTTC
ATTTATCCTAAATTCAATCTTTCGGAAAAGGATTATCCAGAAAAAGATGA
AGATTCCCTTATTATGCTTCCCGATCACCCTTTTGCTCGGCACCGCAAAG
AGGAAATCTTAAAACCATTTAAGGGTAGATATCTTGCGTTTACCGCTTCC
GGAAGATATCAGTTTATTCGATCCACATGGAAACATCTTGTAATGAATTA
TCACACTCAGAAAATTACCGCCTTTTCTTCGCTAAATCAGGATTATCTTG
CGCTGTGTCTTGTAAGGGAAGCCTTAATGCGCGTTAAGGCAACGGGGAAT
AAACGGTATATGAACCTCTGGGAGTATTTTATAGACTACGGATATATTCA
TTTCGATGAATTCATGCACCATAAACAGGTAGTATATGCCCTTTCAATGG
TATGGGAAGCTTTCCAGAAATTTCCTGAGGGGCTTCAGAGTGATGAATTT
ATTAAAGAATATGAAAAGCTCTATCGCTGACGAGTTTCTGTTACATACCC
CGTCGATTTGATCTGCATAATCGCTTCTCTTCTGGTAGAGTCGTACAGGA
TAGAAGTCTCATGATCCATGTAACCCAACTCTCCGGCTTTTTCATGAAGG
ATACCGCTCAGCGTCTGCGCCAGGTTCGAGTTGGGAAGAATACCCGGCGT
GATTTCGATAAGATATTTTCCTCCCTGTTTCGATCCGTTGAGTTTGCCGC
CCCCAAGACCAAATTCCCGCAAAACAGATTTCAACCTTTCGACGTTAATT
TCTTTGCTTTGAGCCGTAACGTATATCGAGATCGTATTCCGCTCTTTTTC
CTGCTGGTATTTGTGGTTGAACACCACTTCGATCTTTTCAGGGGTTTCAA
AAGCAGTTTGCAGTCTGGAGACAAAACGCTCAAGTACCGGAATGCGGAGC
GCGGCTTTTACAAGTTGACGCGTTCCTTCTTCTGGATAATTTTGTGAGA
GCGCTGAATGATGAATGAAAGATGCTGAAGCACTTCCACAGTGAATTCGG
CAATGCTTTCGTCTACTTCGGCAAGCTGATCGTCGGGTAAATTGTCGGCT
TCTTCCAGCGATTGATAAAGTGCGTTAATGTATTGCCTTACTTCATCAGG
GATATAGAAATGCATGACCGGCTCAACTCTGAAAGGTAGCGTGCCGTAAA
AAAGTACGGCATGACCGTTTTCTCTGTTAATTTCGATCATGGTGGTACCG
ATATTCTGTAAATAATTACCTTCAATCGGCACCCTTCTTTTGGACGCCCG
CTCCAGAGGAATCTCCATCTCCTCCTGTTCGATTTCTTCCTCTTCTTCCT
CCTCTTCTTCCTGAGCTAAAACAAGCATGTCATCTTCTTCTTCCTCGACA
TAAGCAGGCTCACCGGTGGTCTTGAAGAATTGGAGCGTAATGATTGCCAC
CTCTTGCGGCTGAGGAAGTCTGATCACACCACCTTCTCCCCACCCCGGCG
GCGGCTCAAAACCCATGCGAATCAGCGCTTGCATTTCCTCCGGGGTTGGA
GCCGGAAGTTCCATACCCCCTTCGGTAATCTGACAGATAATTGAAAGCTC
CGGGGGATTGATGCGCCTTACGTAAACGATGCGATCGTAAGGGCTGTACG
CACCGACGTATTCGTGCTCCTGCAAAGTGGAAAAATAGGAAAGAAATGTC
TGTATTCCCTTTAGCGGATTCATTTTCTTTTAAATATATGCTTCTTCAGG
AACAAGCGAAATGGTGGAGGAGACGTGATTCGGGAAAAATCTTTAAATT
CATAATCATTCCCACGATACAGTAGATATGGAGAGATTCCCCCTACAGGC
AAAGGTGGTGTGGGTTTTCTTGGGGGAGTACCACCGCCGCCGGGTTCATC
TTCATCGTCATCCATATCTTTGTTTCTTTTTCCACCAAACAGATTTTGGC
GGTATTTTGCCTCGAAAATAATTTCAATAATGTAGTAAAGAACAACGCAC
ATGACGATACAGGCGAGCAGAAAAACGCTGACGACAAATATGTACTGCAT
CAGGTACTCCATGTTACAAACCGTTCAAAACAACTTTTACATACGGGTTT
ATAATGGCTTACCTCCGGCACAATTAAATAAGGGTCTTCCAGAGGGTTCA
GGTAACCCATTCCCCTCAAATCCACACTTCCATTCACAAATCGTATGTTG
TATTGCGTTGGATTACCGCACTCACAACGACTGGAAATGTTTATTTTAAT
GGGATTGTATTTTTCTTCGATCTGTTTCCATACCGGAAATTCTCTTCCAA
```

FIG. 1U

```
GATAGTCGGTTCTGAGACCGCTGAGCACCACTTCTATTTTCCACGAAAAA
ATAAATTCGATCTCTTCAGGTGTTGCAAACTGGAATTCATCAACGGCTAT
GAGCGAACACCTACCGGTTTTAAGCTGGAGATATTCGGCTTCATAAATG
TGGGGTTTTGAATGAAGTCGGTAAGATTGTAAACGCAAGAATGGGTAAAT
CCGCTTCGAGATTTCAAGGTAGGGGAATAGCCGTAAATGCTTCCGGGTTT
AAAGACAAGATAATCGTCAAAGTTTTCTAAAAGTTTTATAAGAAAATGAG
TTTTACCCGATGCCATCGCCCCGTTGATGACGGTAACGGAGCGGGTTGAG
CGTTCCTTCAGAAATTTTATAACAGCCTTATCCAGTTCGATATTGTGCAG
GGTGGTATCTCCGGAAAGCGTCTCAGGGAAATCGTACTTCATAGTTGATT
TATTTTTAAGCCGAAGTCTCTGACCACAAGGGGTTTGTCATCGGTTCTAC
CCCAGTTGTCGATCAGGGTAAAATCCTCACCCAGCAGATTGAATTGCCGA
ATCAGCCTTACGGTTTCCCGGATTACAGGATTTTTAAGAACGGTGAAGTA
AAAAGTGTGCCTATCTTCTACGCTTACGTTGTCAAGCGTGAGTCTATTAA
TGGCATTTCCAAATATATCGGCAAAACGCCTATCATAAGCAGAAACCACC
TCGAAACCCTCGAACGTTGCGTCTTCCCGTAAGTAGCGTTTCCGGATAAA
CCCTTCAATCAGAACACTATAAACATCAAAGTCAATATCAGCGACACTTT
CAAAATAGGCTTCATTGACAGGTGCGACAAATTCGGTGATTAGAACCCCA
CCTTCTTTGAAAACCTGAGCGTAGTCGACGGCGATTTCACTTCCTGACCT
ACGCACCACCTCATATTCGGTAATGTTCTGTTTGATTCCATTGTCATTAT
GAGCAATTTTCAAAACCAGTTCGGTGTCGCCTATTCTGAATACTTCTCTC
CCTCTTCCCCTTTTGACGGGTTCAAGGTATTTCTTTTGAGCCAGAAGGTA
AGCCGCGCGAAGCGGGTTTTCACTTCGCTGAAAGTAAGTCAGAATATCCC
GGAGCGTGTCTGTTTCTTTTAAGGTTATCATAGGCTAATCCAGTGTTATA
TCATACATGATTTGTGCGGCAACCACTTCTTTAAAATATTCAACGAAATC
TCTGTCGTCTCTAACGTCCTTTAAATACTTTTCTATTTCCGGTTTTACAT
ATTCAAAAAACTCATCCATAATAACTTGTTTGATAAATAATGTAAAATGA
TCCCCCTCTTCATCCATATTGAGTTTGTTAATGATAACACCATAAGCAAT
TCGTATAAAGGTTTGTACATCTATTACGTGGCGAAGGTCTTTCTGAATAA
GGATATTTTCTATCTTATGCTTTATTGGAAAATATCCGGAAAGAAACCGA
ATCGCTTCCTCAAGATTTTTGCTGACAAAAGCTATAATATCGCTCTGCAG
TTTTCGCAAAATATAATGATAATGTGCATCTTCGATTTTATAATAAGCCG
CATCTCTGAGATAATCGTATATCTGATCCGCGATATTAAGATGATCTATT
GCTTCCTTTATGGCTTTTGCTTTGAAATTTCTGTCAAAGAAAATTGGGTG
TTGCCTTCTTTCCTCTTCTTCAAATTTACGTACAACATATTGTGCGATCG
GATTTAAATGATCTTGCCCGTAATGATAAGCCGCGAATCTTATGACATTT
GACCAGAAATATTCGATTTGGGGAGGAAAAAGCACATTTATTAGACTGGT
TCCACCGTATTCTTCATAAAGAAAAGAGCGAACACACCAGCGGATAATGT
CTTCGTTATTTTTATAATCCGACAGAATCAAATAAACCTGATTGGTGGGA
TCGAAGCCGCCAAGTACATCTCGAGTCAATTTTGAGATTGTCTCTTTCAG
TTCAAAAGAAGGGGTGGTTTCTTTTAGCAGGAATATCATTCCGTCCCCGC
GGGGTATTTTACCTTCGTGGATGTAAAAATAGTAGTACATTTCACGGGTT
ACAATGATATTCCAGAGAGGAGTAGCCACCCATTGATAAACTTCGTCATC
ATACCGCGCCCCTATAAGTATAGAACCCATAAACAGAAAATCTATATCTC
GATACTTTTCATTGAGCGTGCTTACCTCAATAATCACAAAAAAATGGTCT
GTCATGGACTTCAATTTTCTTTCCAATAACACCAATGTTTTTCCTGTTTT
TATCAACGCTTTCCGTGTTTCTTCAAGTAGTTCACCCGCCCATTGGTGCT
GTCTTAATTTTTCTTCAATGAAATTTTTGTAAATCTGTTGGTACATAACA
TTTGACAGGCTTGTTCTGGTAAGATCCTCTGAAGTCAATATGAAATAGTT
GGTGTTGTAATAATATGGGGTGTTTGGGGCAAATTGGTTTTAATAAACT
GTTGACTTAACCCGTTGAACAACGGTTTATTAAGAACAAAGGTATCGGTG
TTTATCGTTTCCATTGGTTTTTATTTAAATAAAAAGAACGTATGAGAGAA
CCTTTTCTGTTTCGAGATCCGACAATCGAAAGCTTTGGAAGCTTTTTATT
GGAATACCTTGACATTCAGGAAGTTCGTGTTAAAACCGAATTTTTCGGCG
GTAAACTGCAAAAACTCAAAGATGGTTATCATTTTCCGGATGTAAAACTT
AAACCCGGTAAAGATGTCGAAAAGTTCCGAACTCTGTGCAACGCATTCGG
GTTTGATGTGGAAATATCCGAAAACGGGATAACGTTCACAAAAAGACAGG
AATATTGTTTTATCGAGGAGGCTCTGAAAAAGGCGACAGAGAAATATCAG
ATTTTCGTTCTTGCACCAATAGAAGTTGATCTTGTTTTTACATGTTGCAA
CCAGATATTTGTCGAATATGAAATATGAGCACTGTTAAAATACCTTTAGC
```

FIG. 1V

```
CGTTAACATATACGACCCCAAGGGCGACGAATGGGAATTTATCTACAGCA
ACTATGCGGTAGAAGTTGTAGGAAGTGAATATCTGGTTCCGGTTGTAACA
CTGAAAACCGGATCGGTTAACTATTTCAGATTCAATGTGCTTCTAACCTA
CTCTCAGACCGGGTCTTTCCCCCTTTATCTGAATTTTCTGAACAAAAACA
CCAATCAGATCAATGTAGTTTACCGAAATATCAGTTACAGTTATATCAGT
TCCAGCAATGTGAACTGGTATCCCACAAGTATATCCGGTCTTCTTGGTTG
GTGGCAAGCATATCATCCGTCACGTGTTAAAGATTACATCATAGACCGCA
CTGAAAACCAGAGCCATCTGGTAAAAATTGAAAGGTATACCTATAATGAT
CAGTGGCTTAACCCTACAACAACATTCGTTTCTCATGAGAGTAATAGGAT
AAAAATGATGCTTCCAATGAATGATTTGATTGATAATCACGGGAATAACT
GGGTGTCAGAACCCCGAAATTCTTATGTAGGATATGTTTCACAATCTCAG
AAATTCCTGTCGAAGGAATACACTTTTTTCTATGTTTTTTCGGTAGTTGA
AAAAAACCCCTATGTAACAGTAAGTGGGGAGCCGCTGATACCGGGTGCTG
CATATCCCGCCCTTTCAACAAGCTATTACTCTATTATTCCCAAGGGTGGC
GAATATCTGGCTGGTTTACATATATTTCGTTCTAAAACTTATAGTTCTGT
AAACGATAAAATGAATACGGCTTCTCTTATGATTCTTTTTACCACCTATC
CCGTTATAAGTAGTTCTACGTTTGCTCCGGAATATAAGGGGGATAATGAA
AACGCTTTTTCCAATACACAATATCGCATACACCCCGCTATAGCGGCTAT
CGGAGAGAAAGATTTAAAGTCTCATTATGTTCCGGGAATAAGAATAGTCT
ATCATACAGAATCTACAATGAACCCGGGAGTTCAGCTTTATGAGCTTTAT
CTTGGTTATAAGAATACCACTTCACTTTATGAACTGGAAGTAACTTCTTC
AGATATAGCACGTTTTGATGTACCTACCATTGTAGGGTACCGCATTAAAC
AAAGTGGTAGCGTTATTTCTTATTCTGTTACTTTGAACAATGAACCGCCG
GTATGGTATGTAATTACGGCAAGCATTCCTTCCATCGATCTTTCTGATCC
GATTTTTACCGATCATAGAAACGAAGCCGGCATTATTATAGGGTCGCTGT
ACGGGTATCTATATGATTATCAGCTTGGAGATGTCGGAAATCTTTCGGCT
ATTTATCGGTGGGGATCCAAGGGTATTTACTTTTATGAAGCACTGTTATA
TACCCGCTCGCTTGACGATGCAGAATACCAGCAAGTGAACGAACACCTTG
TTAAGAAATACCGATTCGGGCTGTAATGGGAAGAATAAATACGACATATT
TTATTTATCTGTATTTCCCGCGTATAGATATAAGCGGTCTTGATAATATA
CATATTGAAATAGAAATATTGGGTGGCTTTAGTTTTACACCCGTTTCTTA
TACCTACAATACATCTGGCTCTTTTATTACAACAGAAACCCCGTTGTCA
GGGTGATGGAAAATCGCACACCGGATATATACCTTCATGTTGTGAGTTTA
AGTGCTTTATATAGTAATTTCGACCCCTCTCTTCATTCTTGGCATATCTG
GCTTGATTTCACAAGGCTTACGGCTTCTAAAACCGACGGTCAACCTGTTT
ATACATCGGATATACAATCCATTCAGAGTGATATATCTATGGAAAACTCC
GGAGGCTATACGTATTATGAAAATATTATGAATGGGCTTCCTATGGTGCG
AACCAACAATACAGGATTGACAAAAACCGGTGGCATTCTGACGGATGATC
CGATCATGGTAGTCGCAGCGGTTTATATCAGCCAATCCGCTACATATTGT
CGTCTTATAAGCTGGGGATATAGTATTAATGAAGCATGGGATGTATATGC
TGAGTTTCTGGCGCGTTGGTAAGATTTATATTTGTCACCGATACGGCGA
CGGCTGGGAGCGGTCCTACTATAACCAGTGACTGGTTCAGTTATCCTCAG
GGGTTTGTACTTGCCGCATGGCAAGAGGATGACGAAACCATGCATTTCCG
GATTATGGATGAAAGCGGAAATGAGTACGATTATCCTGTAATTACCGGAC
GCGGGGGCGGATTTTCAAACTTCAGATTGTTCGATATTTATTATCCAAGT
TACAACTGGGGATTTAATAATTATGTGGGAGAAATCATTGTTCACAATGA
TATATATATGGTTGAAGACGTCTTTCATTATATGGCTTTCAAATGGGTGC
CGGGATTAACCGGAAGGGTGCGGATAAATCGCTTGTGGGAAAATCTTTAT
AAACCTGAATTATATACATCGCTCAATAGTGTTGTACTTATTACAGGCTC
AACATCTTTTACCGGTTCTATTATTAATAACGATCCAATTATTCTAACTT
CAATAAATAACATAGATACACTACAATGGAACCCGCAATTTACCGGATCT
ATTGTCAATAACAACCCAATCATCCTAACCCCGGTAAACAACATAGATAC
ACTACAATGGAACCCGCAATTTACCGGATCTATTGTCAATAACAACCCTG
TTTTGTTAACAACGATAAGTAACGTATTACTTTTGATGTTTAATTAATAA
AAAAACCACGAAAGCTATGCCTTATTATTTCGAGTTTAAAGTTAGAGAAC
TGGATCTTGAACCGGTAAGTGTAACGCTCTCTCCGGCTCCAAGTTGGGTT
TCGGTTTATAAATACAACACCCAGCCTTTTGACCAATTTTACGGAACTTA
TGACATTACAGTGTTTCTGGTAGCAAACCCACCCCCGGGAACACCGGATG
GTACCTATTCGATAGGGCTTACTTTGAGCGACGCGCTGGGCGGAATAACC
```

FIG. 1W

```
ACACATTCAGTCAATTTCATAATCAACACTTCTGGAACCATTACATTTGA
TCCTGTTTCGGTGCCGGGGCTCTGGGGTTGGTGGCAACCCGGAAACTGGC
TTACTCAGAGCAGTGATACTTTCAATGATGTGGCTATATGGTATGACGCT
TCTCCGGGGGCACATCATCTTACACTTGATAGGAGAATTACTATTTTACC
ATGGAATAGTACAGATGCTGGAAGTGCTTATGTCGGATCTTACATAAAAA
CACTTTCGGATAATTCACTTCTGTTTTCATGGAGCCATGTCAATCACCAA
TTTGCCAATATGAATTATTCGTCGGGGGCTGATAACTACAAACCCGAAAA
TGTTTTGATTACAAAAGATACTTCTTTTTACTCCAATCAGTACTCTATTT
TCTTTGTTTATAGAAATCATCTCGACTGGTTTTCTCATCGTATAACCGGA
ATGAGATTAACTATAAATCACTATGAATACTGGGCAACCAATATATGGGA
CTTTGATGTTGAACGGGGTAATAATCATCTTGCAATGCCGGTCTATTCCC
CGGTGGTGATTAACAGAGCGGCGCCTTATACAACCGTCTCTTATGGATCA
TACTGGAATGACGATTATAATCACGGGTTTGTCGGCGGCTGGTTTATTGC
GTTCTGTCTTCCTCCCTATGCCGCTAATCCGTCAGCCAGAGACGCTTATT
ACTATGATGACGGGGCGGACTTACCACCATGAGCGTATTCAACTATGCC
CCCGGCTATTACCAGAATAATGTTCCGCATCAACCTTATATTACCATATT
CAAAGTTAATAAATATGCTTCTCAAACAGATGGGTCTCTCGGTATTCACC
CTATTAAATTGTTTTATTACACCAATGAAGAATATGCGTCTATGTCGCTA
ATTGAAAGAAACAACAGGTTCAGCAGATTTGTCTTTACTAAAGATCAGTG
GAATGCTGTTGGATATATTGTTGAGGAAAATCCCCTTATTTCCAACAGCG
TTGTTATCGGTTATTCCTACACTTACAGCATTTATTTCAACGAAACAACT
TCCGTTACAAAATCTCTGGAAGTAACATTTTATGACATAAATGGCAATTT
CAGACCCCCGACAACTTATGCTTATATTGACGGTTCAGACAACCAGCAGG
CATATATAGACGTATATGGTGGGTTTGGCATAGGAACACGTTTTGCGACA
GCTCAGAGTCAATATTATGCCAACACCGGTACTATAGGATGGAGAACTTA
TAACTTTACACCCGGGGTGTTTTCTCTCTCTTTCAAGGAATGTCTGTTTT
ATACCCGCGCATTATGGAACGAAGCGCCCCAGATCATGGATTATCTTATG
AAAAAACACGGTATCCCGTTTGTAAGCTGATATGCTGGAATTTACCTACA
GTGGTACGTTTTCATACCCGGATAGTCAAACACTTTCCAGTTTTTACTGG
ATTATTAACGCCCCGTCTGGAAGTGTTGTTACTTATTCCGAAATTTTAAA
CCCCCCGCTTAAAGAAATCCCTATTGAAGTAACCATTTCCCTCGATACCA
CAAGTATACCGTCAGGAAATGTAACATGGAGTGTTAACTTTTTTGCATAT
ACAACCACCTCTATTACAGGAGAAGTTTATCTTTATATTTCCAATATCTC
AGGATTGGAACCATATAGCATATCTATCTTTCTGACTTCAAGTTATGAGA
AGAAGGGCTCTGGAGAAATCTCGGGTTGGGTGAATCTTTTTACTGCTAT
TCGCTTTCCACCACTCCGAATGTACGATTTATCAAACACACCATTTCTCT
TCAGAGTATCAGTTTGATACCAGCCGGTGGTAGTATCAAATGGGAAAAAC
CCCCGGAAAAAACTTATTATTCTTTTTCGATTTTCGCCAAAGGGTTTTTC
CTTAGAACAGTTGATTTTGAGGGGTTGACTACAAGTCAGCTTAGCTGGTA
TAATGATATTCCATTTGCTGTTTCAGGAGCCTATCTGTATACCGGATCAG
GATTTCCGCTCATTACTTTTATCAACCAGAGTATGCTTTATCTGGTAACT
TCATCGGGGGACTTCAGTAACTTTGTTTTTAGAGATCTGACAACTAACAC
CGATGTGTTTTCTTTCAGTGTGGAATATCCAACGCTTTCTCTTGCAAGAA
TATATATCACCTACGATGGGAATGATTTGTCATAACATTCAGCAGTACT
GTTAGTGATTATTACTATACCTATAATTTGCCCGGACTCAGTTTTTCTGA
TCATCTACTTATTGGGAATTATCAATCTTTTTCGGGTCATTCCGCATGGA
ACTCTTTTATTGTACTTGACTATAATGCGACAGGAAGTGCGTACCAGACA
ATAAGCAACCTGATATGAGCCATTTTGATGAACTACACGAACATTACAGC
ACCACCACGCTCAGCGTTAACGGGGTAGTGGTAAGTCATAGTTACAGAGC
ATTTCCTTCGCTTAGCTACGTTGAAATTACGCTGTACAACGTACCTGCAC
CTACTGGATCAAATTATTTCTTTGTTTATGATCACGTTTACAATCAAAAC
ATATTTCTTTATGCGCTGAAACCTCAGGATATAGGGAAAGAAATTCTGGA
AACGGTTAGTTTCAGGATTATTGTTGATTGATCATCAATAGATAATAAAT
TCTGGTTTTGTAAGCGTAATATTGATCTCAAACCACCCGTCTTCGATAAA
CAGTGCCCCTGCTCCTGAAAGTGTGTAATTTCCTGTAATTATATTGATTC
TTCTGTTGAAATGGGATGTAGTCAATTCCCATATACTACCACCCGAAACA
AACGTCTCAAATTCTTCTTCCTCTATAACAGGTTGATGTTCTATCTCAAC
CAGACTCATAGAAGCAATTATGGTGCGCCTGTAGTTGAATTCAGATATAT
GATTCATTTCTATTGTGCTGTAGGAAACGAGTCGGAATTGTTGATGTTCG
```

FIG. 1X

```
GGAATGGTGATAACCGAAAGAGATATCCCGTCTACTTTGTGAGAAAAGAA
AATTCTGTTTTGAGCGAAGTTTGAGTAAATAGAGTCGTGGGTTTTGGTAT
ATGTCCCAAGCCCGATATATCTCAAATAATATCTTACCGGATATTCCAGA
CTACCGCTGAAGTTGTAGATTTTATCAAGAATGCGTTCCTGAAGTGCAGC
ATATCGTATTTCACTTGCTGTAAATACATAAGGTATGGTGGTGCGGATAT
ACGGGAATGTAATATAATCCAGTTCAGAGCCGGTAAGTGCTATGATACCT
TTGAAAATCTCATTTGGAAACGTGATATAACTTATAGATAATTGTGTATA
GGTATAAAGATAGGTAAGTCTCCTGTTTTCAAACGTTTCTACAAAGGAAA
TGGTATCCATTGAATGGCTTGCGAAGAAAAAGAGATAATTTTCAATCAGA
TGCTGTAAAGTAGCATTAACAAGAGATTTTGTTAAACGATTAAAATAGAG
GGTTCTGTTGAAATGAAAAGATACATAATCTAACCCGTAATTATTGGTTC
GAAGTGCAATAAGATCAGTGTTTTGCTCAACAGGAGCATTTACAAACCCT
CAAAGCGTTCTAAAAAGGGTATATATTTTCCCCGTCTGAAAAGCCTCTAA
GTTCAATCCGATCGGATCGGTAAGATATCCCCTGAAATATTTTTCATTGC
GCAATTGTGTATTGAAGCTTACGTAATAGCTGAAGGAGTAAAGGGTAGTT
GGATCAACTGTATCGTGAACAGGAGGAACAATCAAATCATAAGTCATGGG
GAGAAAGTCTATTTTTTCAATGCTGATTGGATCATAAAACTCATTTTTCC
ACCCAATGCGGTTGAACACAAGAACGGAGGAACTCCTTCGGTGGAATAA
GTGCCAGCGGGTATGGAACCAGACAAAACGAATTCTGAATAAGTGGGTCT
GTAGGTGTAAAGCCGATAGATGATAGATTGGGAATACTGAGATGTAGTAG
ACTGATGATATACCGAAACGGTGAACGAATGGGTTCCGGATACGAACCCA
CTCATTGTGATATAAAGAACCAATTCTTTGTATTCAGGATTTCCCTGATA
GAAATTATCAATTATGCTGTGCGAAAAAACAAAAGGTGGAAGGGATGATA
CCACTTCCACCTGATTGAGAAATACCCTTCTTACAGGGTAAGAAACTGAA
TAAGTCATGGTTTCATATCATCACTTAAGGATTACAAAGTGGTCAGCATG
AACGTCTGCACGGTTCATAAGCGTGAAGCTACGCGCGGCAAGATACTGTT
CAAGCAGGATAATATCGCGCTCCGTCGGTGATTTGATAATAACCAGTTCG
TAAATGCTACCGACAAGCGGGCGCACGCCGTCGGTACCAATTGTGAGAAT
ATTGATTCCGTCTGGACCCACCGCCACATTGTTCATCAAGGGGATACCGG
AAATCCGGAGCGAACTGTTCCCGCTGAACACACCCACTACCACCTGATCG
CGGGTAGCGAGTGAAAGCGTATATTCCGTGCTGGAGCCTCCGATTCCCCA
GTTGTGGGGCATTTCACAGAAAATATGGGGGTTGACAGAAAGTGTACCAC
CGGAGAACAACCCACCGTTGGCGAAAGAACCCACAATACCGATAGCGAAC
GGCTGCTCGATTTCCAGACCGGTACCTTCGAGACCCATCGACCGAAGCCA
TTCGTTTCCACGGAACACCACCGCCGACAATCCGTTGTATGCATCCCGCA
CGAAAATGGGCTGGTTATCCGGGTTGGATTGTGTGAGGGAGTAAGATAGA
TAAGCCGATGTTGAAACATATGCTGGCACCCACGCATCAACCTTATCGCC
CGTGTTGTAGGAAGCCGTGAGGGTGTTCGCATCAAAGCGAAGCACCACTT
TGGGCACCCAGCTTTCAATGGTTTCCGCCGGATCGACAAAATAGGGGATG
TTATATTTCTTAGCCAGATAGTTTTCAACGTTCTGACGTTCAGCGTTGGT
AAGTTTACGGTCAAACACGCATAGCTCAGCAATATAGCCTCTCAGGTTCC
ACCCTATGAACATATTCGATTCAACACGGTTACCGGTCTTACCTTCCATA
TACCGCACACCGTTGATGTAAATGCGGTCAAGCGGATATTTGGGGTGGGA
AGTAGCAAAGCCAACATCGTTGGTTGTTGGCGAACCAGAGAGACCACTAA
TGTGGTACAGATTGACATATGAACCTGTTTCATTTTCAAGTATCACCGTA
ATGATATTCCAGTCATTCAGGGGTACAAAAGCGTCTGCGGGTTGTGGAAC
AGTATTGTACCCACCGTAAGAGTCCGGTAGTGCGTTGGAGACTCGAGGGT
TGCGATATGAAGAGTTCAAATAAATCCAGTGTTCAACCTGATTTTCTTTT
ACTTCAAGGCGGGGCACAATTACTGAATAACTGTGAACATTATTTTCATC
AACCATTCTGAAATAAGGTACATCCGTATCGTCTGTGTTGTGAGTATCCG
ACTTTGGTTGAGGATCCCACATGGAGAACATCCACAGAAACCTACCCGGA
ATGTTTCCGTAATTTACTGAATTGTTAGGAATGGGATTAGAAGAATTGGT
TGTAATATTGCTGTAATTCGGATGATAAACCCACACCGATCCACTCTGCA
CAAACACCCCAGATGTCGTATCCGGGAGTCTATCCAGTTTGGCAACCATG
ATAATGGTGCGTTCAGTATTCTGAGAATAATCTCCGGTGCCCGGATAGTT
AATACGCATAACCGAACCGGAACCGAAATACCAAGCCGGATAACCGTTGA
CAATATTTTCGACGAAAATAGGTTTGCGGAAATCGTTAACCTGAGTAGCT
TTAAATCCGGAATATGCGGGAACAAGGTTGGGAATTTCGTCAACGTAATC
GCCGGTTTCAAGCTGAGGAGTGGAGCCGTCGGCGCTCATCCAGATTTTGC
```

FIG. 1Y

```
AGTTGGGGACGTCCGACGGCGAAGAATACGCATTGATCGTCTGAACATAA
ATGGGATAAGTGCGAACTGTTTCCGGGGTAACGCCATCGGTAGAGCGTAC
CGTAATGCTGTAGGTGCCCGGCGCTACACCCGACAGATCACCGTATACAC
TCAGAATCCCTTCGGTGCGCCCGTCGGGAAGAATGGACTGGGTAAAATCA
TATCCGGTAACCCAGCTCGGGGCGGCGGAAACCGTAGCAGTAATCGTATT
ACCGTCGTTATCGTAGATATAAATGGAAAACGTTACGGTGTTAGAACTCT
GGTAAGTCGGCATTGTTTATCCCGGTTTTGTTTTAAATATTCTTATTTCA
CTCAAAATAAAAAGTCAAATAGAGATAAGGCACAGAAATACTGCTATAGT
CATTGATGGAGTCTATATAGTCTTTTCCAATATACATGTGTGATAACA
TCTCCGCTATTATAGTCATACATCAAGATGTATTCGGCTACATCGGGAGG
AATGTTGTTCATAAAGAACCCTGAAATGTTATGGAGTAAATATTTCCGT
CAAACTGTTCGTCAATCATACTGACAGTTTGCGTCAGATCCCCCCCCACT
ACCCGTTACAACATACAAACTGAAAGATGAGTGTGTAACGTTAAATTCCG
GATAATAAGAATTAACCGGCACCACTGAAAGAGTTTTTCCATAGAAAATA
TTTCTTACCGCTTCTTTAAAAGCATTCATTATGGTTTCTTTTCGGTAAAA
AGGTTCGGTGTTGTAAGATAGATTGATAAATCCATAGATTTTATCTCTGT
ATAGAGAGTAACTGTAACCTACTCTATAGTTAATTAAGTTGTATTCCTGA
TTTAGTGTATGGTTAACAGGCTGACTGTATACCCATTTGTAAGCAAGCCA
GCGGTGTTTTCATACATGCTGGATATAAGCGGCTTTCGAGAGATCACAG
GCGATGTGTTTCTTTGAGTAGCATTTATCCAGTAATTGATAGGCGATTCC
ACCTTTCTGCTCATGATGTTTGTTCTATTTCCGGCAATGATCGCTCTTCT
TAATGTGTGTTTATTAATCGTTTTGAACAATTGTCGATAGATAGTGCGGG
TCTTGTTTTTGACAGTGTTTCCGGTTCTATGATATGCTATAAGTATCTGT
CGGAGTTGGTTGAGATCAAGGAGAAAATTTTGAGTTTTCTTTACAGAAGT
GAGCAGGACGTTACCCTGAAAACTTGGAAAGAAGTCTCTGGTGGTACGGA
TAACTTCCCGGATTTTTAAAAGTCTCCGGTCAAAATGGGGGATATCATAG
CTTGCATAAATGTTAGTGCCCCTGAAGAACAATCCGATTATTCTATCAAT
GGTTGTTTTATAGTTTAATTTTATTGTGCGTATGGTTAATTTTATCAAAC
GTTGCATCTGATTTGCTATAAGGTTAAGGTACTTTTTAAAACTCAGAAGT
CTGATGGTTACATATGGCTCTAAGGTGGAATAAATGATTTTTCCAACAAA
TCTGACCTGTTTAATAATCTGTTGGTAAAAACGTAGCACATAGTTAACCG
GTGTGTATCCGGTCAAAGTTTTAAAGAAAGTTTTATTCACCAGAGTCGAT
TTAATGAGTGATCTGGTCTTGATGATAGTTTTAATAAAAAAGTTTTTGAT
TGAATTCAACAGACTGTTAAAGGAGGTAGATATATTTAAAACTTTAAAAA
ATTCTTCAGTGCTCCATACAAAAGCGGAAAGCAATTTATTGAAAGTTTTT
AAATTGGGAAATCTCAGTTTTAAAGTGGGGGTGTAGTTGACAGGTGTGTT
TTTTGTTTTCAAGATATACTTGAACTCATTAGAACTAAGAGGTTGGTTGA
CAGCATTATATCCATTGAAAAGCGTAAGTGCGTAGGGGTTGTCGTAGTTG
TTGTCAAGGAAAAGTCGAAGTGCTGTCGGGTCATCATTTTCTATCAACAG
CGGATCATCAATCGGGTCTATATAAGGATCATAGGGAACGGAAAATATAT
CCCTGAAATCGTTTGTCGAAGTATAAATATAAGATAATGTATAGTTAAAG
ATTACCGACTTTGTTTCATATTTGTCAGTTGAATAAAACCTGAACCGTAT
ACTTCCAGTATACCAGTCAGGCGGAAAGGAAGATGCCGTTAAAAGATTGA
GATAGGTTATAGTAGACCCGGAGTGCGATACACCAAACCAGAACTTATTG
GGTGGGGATTGTTGAACGATAAGTGGGCTGAATACTCCTCTTCCTTTGTG
GTCTACTTTAAATCTCATTTTGTTCGTAGGTTATGTCATATTCGTCCAGT
ATCAAAGCGTTGTCAACAAATAGAGAATTTTCATATCCGTGCATGAATGG
AATGGGTTCTCCATCGAGTGATATGTCTTGAATACCAATGAATATGGGAA
AATACAGACTGATCGATATATCCATTACTTCTATAATCGGATAATGATAT
TCGATAGTTATATTGAATACTGTTATTTCAGGGTAATTCAAACTTATGGT
GAAGATAAACCCATATTCCATAAGAGGGTGATATAGATTAATTGAAATGG
TGTTGAAGTTAATGTCAAAATCGAGGGTGGATTCATATTGTGTGCTGAAC
GTTTTGCCGTTTATGTCGCTGAGATCAGGTGAATAAAGATAAATATTAAA
ATCGAGGGGGGTATCTATAATCAAAGCTTCCATATCTATATAATAGAGGT
CTATATCGGCAATCTTTTTTCCTTGATAATACACATCATATTCCAGATCT
TTTGAAAAACTGGTACTGAAAAAATACCGGTAAGTGTCAAACAGATCAAG
AATTATTGAAACTGTGTGTTCGTTTTGGAAGACCAGACTATAACTGACAT
CTGAAACTAACGTCAGACTACTGGTACTTACAGGATATCTGAAATAAATG
TCTCTATAACGTAAATACCTGTCGGCTGATTCGGTATATACTTTTATTAT
```

FIG. 1Z

```
GTAATCTGTATTAATACTCATAATTTATCGATATAAGTTCGTTTCCCTTT
TTAACCAGAATAGTACTGATGGGTACATTTCCGTTCATGAATTCACCAAG
CATATCGATAATAAAATCTACTTCTTCCCTCACTTCCAGCATAAGTGTGG
GGGGTATTTCAAGATAGACAATACCATCTTGATAGGAACCTTTTACATAT
TCACGGTTTTTATACCAATTGATATATCGGCTCATAGAATGTTGAATTTT
CCAATCGTCTTTTTTAAAGGAAAACATTCCTTCATATTTGTTGAAGGGAT
CGTAAACGAAACCGACGTAGTCTTTCATGTTTTTCTTTAAATAAACAGGC
GGTTGTGTTTTTATTCAGAAAAAACTTATTTAAAGAAAAAAGATGTATAC
CGAACTGTTCAAGAAAAGCAACCCGCACAACTCATATTACTATCATTACG
TGCATTTTGACAGTAATTCAAACACACATTCAATCGATGTTCCCGGCGGA
AATGCGCTCAAAAACATTCTTATTGTGGGTAACGCTTCTACCCCTTATTT
TGTCTCTTTTAAAATCTATACATCGCATAGCGGGTTTGTGCCGGTTCCAG
TATCCTACGATTACGAAGCGCTTGGAAACAATGCGCTGATTACCCCTAAT
ATCTCTTCATTTGCAGTTTTTTCCTCTATTCAAACCTCATCGCTTCGCAT
TAGCATTACCAATATCACCCGTTTAGCGGAAGTGTTTACATACTGTTTA
AAGTCGAGTAACGTATGTTTACGAACCTTCTGTAAGCTTTTTGCAGTA
TATCCTCAGTACAGCACCAGCGCGGCTTTTCTCACAGAATTCAATAAATC
ATCGGCGTGGGTGCTCCACAAACTGGGCTACCCGGTGGTATCGGTGGAAT
TGACGAAAGATCAGCTTATGTTTCTCTTTCACGAAGCATGGCAAGAATAC
TCTCAGTATATTTCAGAATTTCTGATTCAGGAAAACTATGATAACGTTTT
AATAAAAAACATTTTCCAGACGGAAGGGGAAATCTTTGAGAAGTTTCCCA
AACCTAACAGTTCGCTTATCATCGAGCTTTCTGATCGCTATGGAATGTAC
GACATGAACACCGAATATGTAATCATTCCACTTACCGCTTCTCAATCGGT
TTATGACTTGAAGAATTACATTACCGCATCCGGAAAAATTCACGTTCAGC
AGGTGCTTGTCAATAGACCGCGCGTTGGTCTTGGTTCTACGCTGTACGGT
AATGCTTTTGTCTTCAACAACTATTCTCCCTTCACCGTAGGATACGGCGC
GGGCTGGAATATCGGTCAGGTGCTCACGCCGCTTTCCTATCTTGCCACCA
CCATGCAGGCTACCGATCTTGCCTACAATATGTATCGCAAGCTCCACTTC
TTTGAAATTGTCTCTGGAAGTATGATTCGCATTTCTCCTGTTCCCGATTC
CAACGACTCCCGGCTTACAATCAGATACAAACTGGAACGGGAAGAAGGTG
ATCTTATTGAAATGTACAATTCAATATTTTATACGAAAACAGGTCTCCTC
GATCTGGAAAAACTAAATGAAAACTCCCTTATTGTGCTTCGGCATATCTT
CCTCATGAAGGTGATCGATACGCTTATTTTCATCCGCAAGAAGTACGACA
ACTACGCACTTCCCAATGCGGAACTTACGCTGAACGTCGACAACCTGAAG
GAACTCAGGGAATCCACCAAGGAAAAGATCGACAAATACAAAGAGTGGCT
TGACAACATGAAACTTCACGCAAGGCTTCAGCGGAAAGGAGAAGAAGCAG
AAGCGCTGGAGCGGGAACTCCAGCGCTATCCTATGGGGTTCCTATTTATG
TAATCTCTCACCTGCAATCACTCAGCGTGCAGGCGCCCATGGGGTGATCT
CCTCTACCGGGCTTTTTGAACGGCGGTGGAATCTTATGTCCCGGTTTGTG
GTGTGCAGTAACTTCCTCAACCTTTCCATAGGTTGTGAGCATGGGGTAA
TCCACCTTTTCATGGCTTCTCCGATTTTTATTGTTGGTTCTTATAGATA
AATAACCCTGTGGCACGCATCGTAAGTGAAAAACCACCCCAACAGCCACC
ACCGGTTCACATAACGGAAAAATTCTTTGCCTTTTTAAACTCTTTCATG
ATTGTTCTTCTTTTGGAAGATTCAGCTTAATGGTGATATAATCCGAGTCG
GGGAATTCTTTTCTTAAATCCTCCAGCGACTCATACACAAAAATCATCCC
GACGGCACCGGTGTTAGCTATCTTAGAAAGTGGATAGACGACTTTCTGAA
CGCCGTTATTGATGACAACCTGCAGGTCATCCAGAAAGTTAAGCTGCATC
GCGACGTAATACACGCGCTCTTCGTTATTGTTGTCGTTCATGGCACACAG
GGTTTTAAGGTTACGCATGGTAGTCTATTTTACAATGTAGGTTTTGTCG
TTATATTCTATCATGTGATAATGCGCCTGATAAATATGGGTTCCTTCCAG
AAATAGGGGCTCGTTACCTTCAAGGTAGACGAACACCATATCTTCGTCTC
CACCCCCTGAGAAAGGCGGATAAAGGGAGTGTGCTGACTCTGGTAGTA
ATACCGATAACAACATCGGGGTTTTTCTCGATAAAATCGAGAATTTCCCG
CTCCTGTTCAGTGGGTTCAAAATGCTTCCATTGATACACCCGGTAGGGGC
GATTCGAAGCGATGTAATAGGGAAGAGAAGCTACATGTCGGTTATAAATA
TCCAGAACAATCTCTTCAATATCAGTATTTTCTTTATTTTTAATTTCTTC
CTCGAGTAGCATGTTAAGATCAAGTATCATGTGAGCCAGCGTGCTGACTT
CTGCTTCATGCATTTTAATACCTTTCTTTTCAAGGATACGAACAATGCCT
TCAGTGTCGAATTTGAGAATCATGGCGCTAATGGGTTTAGTTTTCACTCT
```

FIG. 1A2

```
CTACAAGAAAACGAATAAGATCCTCAACGGTTTTTATCTTTGTAGTATTT
TCAACATACCCGAGACTTTTCAGCAGATCAATTGTTTTCTCTGAAATGAT
CTGACAGTATTTGTCTCTATCTATGTATTTTTAACGATTTCAAGACCCT
CCTCATCATCCTCACGTATGCTAAGTGCGTGGATATTGCGGAGCCTGTTG
ATATGCGTTTTCTTTCCCGCTTTCAGAATATCCCACACGCCGCTCCCATG
TTCGGGGTTAACTTCTTCCAGAGAAAGCGGGAGATTGGTTCTGGAAGGAT
CCAGCATGGTGCAGTAGAACCAGTAGATCTTGTCTCCCATTTGCGGGGT
TTGCATCCTATAATGGAAGCGAAAAGCGCTCCCTTATAATGAATGGGAAG
TGTATGGTCATACATTTTATGAATATCTCAGAGATTGGGACATTCTCCT
TTTTCATCTTCATAACTTCCTCTACATACTCCACATATCTTTCGGCGCTG
TCAGACGAAGATATTTTCATTTGTGATAGAGATCTTCAATAGACCAGAA
ATTCTTTTGAGACACAAAGTTATTGTAGAACGCTATGGTGGCGGAAATGA
CATCGATGTCGGGTTGGCTGATATACTTCAGGTAACCCCTGAAATACTTC
TTGACAATTTCAGGCACCGAAGAGTTGATCACTTCGATTCCCTTCATCTC
TTCTTTACCGTCTACAGTAACCGCAAGTAGCGGTTGATTTCTTTGATAA
GAATGGATTTGAACACGAACTCCTGCTTTAACTCCAGCTTGAAATCTTCT
CTTGCATTAAAGTTATTTTCCATATAGTCATTGATAAAAGAGTTGAGATG
TTCTTGAAGCTCACCGGCTTCCGCCACCGGATCATCCGTAAAAGCTTTGA
CGAAAATGGAGTCGGTATGCGAATAAATGAAGCGATCGCGAATCTGAGAA
ATCACGGAGCGAATAGACATGCGCCCGGCGGCGGTTACACTTTCCGCAAT
GGGAAGGCACCCCATGTACACCGAACGGTTTCCGAAGATACCGTACATGG
AGTTCATCATAATTTTAAGTGCCCATTGACGGAAATGGTGTTCCATGTTG
CCAGTTTCTTTGAAAAGCTTACGTTCTTCCTTACGTCGGGTGAAAATCTC
CCGAATGATAGAAGGAAGCACGCCAACCGGCTCTTTCCTGTAAAACCAGC
AGATACCCGACGGGTTGGGCACCATAATGATATTTCGACTTTTTAAAAAT
TGCCGGAGTTCCTCAAAGCTGTTGATGACAAAGAGGGGTTCACTCCGGTA
AGAAGGGTTCATCCCTGAATCGAAGATGTAGAGGGGAAACCCGAATTCCG
GTTCTTCCTGATCTACCGGAATCACTTTGTTCTCCACCCGCATACACCCG
TAAAACTCCGTTACGAACGTAGCGGGATCGATATTGAATTTGCTGATTAC
AGAGGGGTACAGCGATGTAAAATCAAGATCGAATACGTTGAAGTAAATAT
CGGGGTTGGTAAGTTCAATGTAAGCACCGCGATAACGATACTTGTTGATG
TTCATAGCAGAATACGTTTGTTTTACATTGCGGGATCAAAATGGGTATCT
TTCACCTCGATAAGGTAGGTGTCTTTTAAATCACATTTGTATAATACGCC
ATCGAGTGGAGAAAGATCAATAATTCTCAAAACTTCATCCGTATAGAATT
TTCGCTCGATAAGATTATGCGTTTCCAGACGTTTGCAGTACTCGAAGATA
GCGTCTCCAACAACATAGCTTTCCAGGTGCCAGCAGGCAAGCCCATCATA
ATGATAAAGCCCCCACCAACCATTTGCTCTTTCCCTGACCACTGCAGGGA
TAACCCCCAGATCTTCAAGAAATGCTTCAAGTTTATTTTCATCCATATAA
AGCAAATCGCGTCGCATTATGTTTTTTCCCCGCTCCTCAAGAAACGCATC
AACATACATCCACCCGGTTTCATCCCGGATAAGCTTGCGAAGTGAAGGGT
ATGCCTCAACCGATGTAAACCCGGTCTTCAAATCGGTAATAATATCCCGC
GAAAACCGCATAACGAAATAATAAGGGGTTTCGTAGTCGATAAGTTTTTC
AATAATTTTAATGATTTCGTACTTCATGGCTAAAACGCTACTTCATGGCT
AATACGCTACGGTTAGTTTAAGTGTCGGGTAAACCTTTCCATTAACTAAT
GCCACGCCACCCCCCGTAAATGGATCCGAAAAATCTCTTCTGGAAAGA
AAAGTCGTAATAATTGAGCCCTACGGAAGCGCTGATAAGGTTGTGCGTTT
TTCTAACCTTCAGCGCAAAATCTTCCTGCATGAAACGTCCGGTTTCCGGG
TTGAAAAACGTTACGCGGAGCGTGTTGCCCTTCCACGTGGCATATCTTTC
CGGAAGAAGCCCGTAGAGTTTCATGTCCACCGGCTTCGGACACTCCACCG
TGTCAATCTTCCCCACGGGCGTCTCCCGGTAAATGATCTGTTTGACCGGC
TGGGCAAACTTCCCTTCAACCTTCAATTCTGAAGGAAAAACTCTGTCCGA
AAGTTCCACTCTGACTTCCGGTCTGTAAACGGTGCGGTTGACGTAAAGAT
GTATGTTAACCGCGATCAGGATCAAAAGGAGTGCTTCTTTCCAGTACTTC
ATAAGTCTTCCTCTTCTTGGAATTTGTCTTCTTCGTCTCTGATCATAGCG
TATAGAATGATCAGATAGTTAATTGCGTCAATGATTCTACCTTCGACAGC
ATCCCGCTGGTTTTTAACCCCTCTGATCCAGCGTGCCACCCCTCTTAAAT
GTTTATCCAGAAATACATACAGCACTTCTTCCCTTGAAATACCCAATCGC
TTTGCAGTTTCTTCAAAATTCTGAAATACATTGTCGGTTTCGGCATACTC
CTGTTGGGCTTGGAGTCGGACACGATTTACTTCTCCAATAAGCTCTTTTA
```

FIG. 1B2

```
CAATGCGTTCGAATTTTGTGGTATTCATGGATTTCCTCCATTAAGTTTCT
GGTATTTATCTTATTTAAAGAAAAAGATGAATACTCCCCGCAAAATATTT
CTTAATCCACCCACCTCAAGATCCCTACAGGATATTGAATACCTTTACCT
CACCAACAAACACATCATTACCGGCGCGATAAATAAAGCCGGTATGAGCA
TTGATGAAGCTTGTAATGTGTTGTGGGGGGGATCGTGCTCGAATATAAA
GAAACACACGGCATCAATATTTTTGATAATCTGACTATGGCGGTGGAGTA
TTTCATTAACAGGTACAAGAGGATTTAAAAACCGGGCGCATTTAACTCA
TCATCTTTTCGTTGATAAATTGAATGAGTTCCTGTACGGAAGGATAAAAC
TGTTCCTCGAAAATCTGGTGGTTTGTCTTTATCAATTCTTCAAGTTTATC
CACATCCGCCCCGATCTTTTCAAAAAAGGTACGGGCTTCGGAAAACAGTT
CCCCTCTGGTTTCACATTCGGTATAAACCAGAAGAGGAACCATAACCCGG
TAGAAAAATTCTTCCGGTGCTTCCCTATCAACATACTCTTCAATAAGTTT
CTCTGTAATAGGAACCCCGCACGCCTCAAACACGTCATCCTGCACGGCGA
AGTGAATGACGCCGTTATACAAAAGGTGCCGCAACCGCACCTTCCACATC
AGGGAAGGGTCGGTTACGAACTCATACACCATTTGGAGAGCATTCTCGAG
AGGAACCTCCTTTAACGGAAGCTCCTCAATTTCTTCTTCGATCGGGTAGA
AGACGTTCTCTTCTTTGGAGAACTTACGCTCCGGGGTAATTATAATCCAG
AGCGCTTCTTTGACCTGAGCAGCGTTCAAGTTGCCCATGTTGTACCTCCT
TGTTTTTGTTAGTTACAGATTAAACAATTTGCTGGTTTTCTCGAACTCCT
CGAACCACTGTTTCCGGAGTTCATCCGAACCCTGTATTTCAGGGGCTTG
CTATCTTCTTTAACTTTCGATTCCGGTTCAGGTTGCTCCTGGGTTTCGAG
TTTCAGGGGAATTTCAACTTTCCCTTTGAGTTCTTTGAGCTTGTTCTCAA
TACCCGGCGGAACAATCCGATTTTTGAAGACCAGTTCCACCGCTTTGTTA
ATCACTTCATCAGCGGCTTTACGGGTGCGCTGATAAATGGCATCCTGCTG
AGCCTCTTTGAGTAAATACAAAGCGCGGCGTTTTAGATAATCCTCGCTGG
CGCATCTCTGCATGGTGAACTCCAGCGAACGTCGGTTGTGGATTTCGCTG
TTAGCCATAAGGCTCTCCCACCACATATACTCTTTTTCAGAATTGAGGAT
ATAAGCCCCCTTGAATCTGACATAGGTATCCTCATCAAGCTTGAACCAGT
ATGCATCATAGAAACTGTACCCCCGCAAGGAATCGTCAATAACGTACCCC
GCAAGGGGTTCGACAAAAACAAGCTCCAGATCGGCTACTGATAGTACATC
GATCATATAGTCGCATCCTTTGTTCATAGCGTCTTTGAATTTTTCTCTAA
TCATGGCTTTTTCCTCCTTTGGTTTATCGTTAAACCCACCAACGTCAAAA
AGAGGGAGTTTGTTTTTCGGATGGAGACAGAATTCGGAGTTTTTGGGCAT
ACCCCGCTTCCAGTGTTCCACCCAGCTATGACATACTTCCTCAAACATAT
CGGGGTATGTCTCTCTGAACTTGGGAATTACGTATCGATAGAATTCGATA
TCGTATTTGAATAGCGCATTTCTTATAACCGTAGGATCTTTTTCCATTGT
GCTCTGTACGCGGAGATTTCTATGAAAATCAAGACTCTGGTACAGGAAGA
AAAACGTTGCGTTCACAACAAAAAGATATGCTGTAAACTCGATCCAACTA
AATGCTCTATATTCGGTTGCAACAGGGTAAAATTTGTAAAGCCAGTAGCC
CACGAAACCAAACGCCACAACCTTCAAAGGTTCGTGTACCTTGTTCACAA
CACGCGGGCTGTAAAGCTTAAAACCCGAAAGCACGTTGTACGTGCCGGTA
ACGAACCACCTCCCAATCCAACACAAACCGATAGAACCCGATACAAGAAT
GGTGATCATTGTCTGGCTCATGTGGGCGACGGCTTCGTGGTGCCCGAGCA
TAAACGGGAAACCAATAAACCGCCCGAATATTAGCAAGACCGGGAATGAC
AGAAGGTCCCCGGTTATAATGCAGACGGCGGCAATGAATGCAATCCACGC
AATACCGGCGGCAAACGTAAACGACAGATAAAGGGCGTCGTTAAACGCTT
CCGCCTCCTTGCGCCACAGCTTCAAATTATCTCCATAATAAAACCCCAGA
ACCGGAACCGCTACAAGATAGCGATCCAGCCCCTCCACCACTTCCTTCTT
GCTCAACTCAAGTTCGCCCTTACCCCACTTGAGGAGCTTATCTCGATAAA
GCTTGAAAGCTGTAAGGGCGTACTTTCTTGTTACTCCGGCGTACATGGCT
TTCCGGGTTTGAGTTATCAATCTGCTTATAACATACGCCGGAAATCCAGA
AAAGTCAAGGGGATTACGTTAATTTTTTACGAAGAAGAAGACGTGCTACG
TCGTCAAAGTAAATGGCGGTTTTAGTGGCGTTGAGACGCTTGACTTTGAG
CGGTTTATAAAGTCTGTTCTTGATAAAAAACGAAGCTCTGATAATTTTCC
AGACGTTTACGTAAAAACTACTATTCTTTTCGTAAAAAATGCAGAGGGCG
ATAAAATCGTCAGATTGGGGGTTATAGACAAGCCGGTCATTTTTCTGAAA
CACCCAAGACCTCTCTATTCTGGTGTATCTATATCTGGGTACATCCTCAC
AGGTTTTAACATGTATATATCTACCCTCGCATATCAGATCAGCCGCATAG
GATTTGTCTGAAGTGATAGTCAGATCGGGTGGGGTGCATTCATAACCAAG
```

FIG. 1C2

```
GTTGGTGAGATATTCATAAACGGCGAATTCTCCTATTTTACCAACAAAAT
AATTCCATTTTATTCTTTCGGGGTTGTGCTGGTGGCGCTTTTTGTATTGC
TCAAGCACAATCCCGTCGTTTATCTGATTCTTAGCATATTCCATGCAGAT
GGGCACATACTGATCTACTTTTATCATCTTACCCACCCTTACCCAAGAGC
GATACTTGTGGACGGATTGATAAGGTACATCACCGCCGTTTCACGGTAAA
ACGTTGATTTTGTGTAATGGATCCCAAGCGAAGAGACAAAGGGAGTTCCC
GGATAAGCCATTTGTGTGTTGTATCTATTGACACCGCTTTTCGGAAATGT
ATCTGCTACAATGGAAAAGACCGCACCCTCGCGCTCTGTTGCTATACGGT
CGACTGTAACGGTATCCGGAATTGGAATTTCACCATCGAAAGATTTGAAC
ATACTGAAAGAAAATTGCTCAAAATGAGGGATTGACTGAGTCATCTGAAA
TGCGTAGAAAGGTTTACCTTCAATTACCACTCCCGCGAAGAAATTCTCTC
CGGCAAAAAGCTGACGAAGCAACAAGATAGCGTCGCGGGTTTTGTTTACC
ACCTCAAGCATATCCTGATTGCGGGTTTCAATAACGTGTACATTATCCCC
CTCCGCCAGATTTCTAACGCGGTTGGAAAGATTTCGCTGCAAAACACCA
CGGCGGAATAAGGAGTATCTTCGAGTTTTTGAACAGGGTTTTCGGTAATG
ATATGATCCGGTTGATAAATCGAGCCTTCGAAAGCGTTATCCGTAATGAC
TCCGATATGTCTCAGATTGGATTCCATGTAGGAAAGCGTTGAAACATAAT
AACTGTAACTGATCGTCGATGTGGTAACCTCTGGAAACATGCTGTAGGTG
TGGTTGTCAATGAGCCACATTGAGATAGTACTGTCAGATGTACCTTTCAG
GTAGAAATAAACCGAAGTGGAAATAACAGTAGGCATTACCATCATCATGT
AGCTCATGCTGTAAAGCTGATCTATTCCGGGGAAAAGCAGCGTAATCACT
TTCCCCTGAAGCACCACATTGAACGGAAGCAGCGAAAGACCATTTTCCAA
ATCTCTCATGTAGCAGACGCCGTGGAAATTCAGACTATCTACAACAAAAC
CGGAATTATCAATAACATTTACAGAAACTGAAGTTATAAGCTCGCCGCGA
GATGTATAGACCGGATAGTTAAAAGCCCCGGTTACATAATAGGGGTTGGC
GTTGCTGACGGTAATGGAGAAGGTAATAGAATCGAGAAAGCTATTGGCGG
TAACTTCATAATATTCTCTAATATCCTTATGTTCATTATAGGGAATGAAC
CCGTAAAACGTAAAATAATTATTCAACACAATATCTTCCGGAGGAATGTT
TTGACTTACCGGTATAATGTGTTCCGTGATGTAATACTGATCCCCCAGAA
ACGCGTCATGAATGATCACATCAAACTGATAATCTTTATTTCGTAAATCC
AGCGATTCAGCCAGCGTGTTTAACCATTTAACTTTCATTTTGCGATTGAA
GGCGTGATAGGTAATACGATTGATCTGATCGTGCAGCGCGTCGAACGCAT
CGAGAAGTTTTCCGGTAAGCTGCTCAAGCGTTTGAGACGGGTTCTGAGTT
GTCGGTTCATTCAAAATATTTGTTTCCACAAACTGAAGATCATTGCGGAA
GTAGAAAACATCCATCGATATTCCCGATCATATCCATATAGGTGAGATATG
AAGGATCGAACACTTCTTCAGGAAGTCTTGAAGAAAGGCGATACGGGTTG
GATACGTCGTATTCAGTCGCAGCATAAAGGTGCATATCAAGAAGCACCTG
ATACGGATTGACGCCCGGATAAATTGAAGAAAACGAAGGAAATACTTCTT
CCCAGAAATGTATGGGGAGCAGATAAAAGGTACCCGGAAGCGATGTCGAG
TTGTAGTAGTAATCCAGATATCCCAGCGCGTAACTCTGACGAATGGAGTC
GTCTCTAAAGTAATGGTTGATGTGCGTTACGTCTTCCGAAGCAAACCATT
TAATGAATGGAAGGAAGCTATCGTAGAGTTTATTTTTTATTTCCTTATAT
TTTTCAGCCTTCTCCGGATAAAAACCTGAAAGCGTGGTGATAATCTCATC
ATATTTCCTGAGCAGCGTGATTCCTTTGAACGCCGCCTGAATGAGCGCTT
CTGCTGACCCGAATTTGACAAATCCGGAGAGCAGATGGAAATTGGATTTC
TGCTCCATACTTCCGAAGCTAAAAGACGGGATATAGGTGTTGATTCGATT
GTATTCAATGTATTCCAGTAGATCGACGGGACTCCTATCTTCAAATTCGA
GATGAAACACGTTGTTGGCAAACGCATCTTCCCTACCCCCAATGGCGCTG
AAGGTAACCGTGTCTGTTTCCGTGAGATTTACCGGAATGGATTCCTGCAA
ATCCACCTGACGCACAAGATACACTTCTTTTGTCGAGTGAAGGAGTGATG
AAGTTCCATATACATAAAACGTTTCCTGATAATAAACCGGGGTACCCAGT
TTATGAATATTCCCGTTTACTTTAACCAGAATACTGTAGCTATTCTGGAT
TCGAGCGGTTACTTCAGCGTAATAGTTGAACAGGTCTTCAAAAGTGATAC
TGGTGCTGATGTAGTTTTCAAAAGCTTCGTTAATCTGGTTTTCAAGTTGT
TCTATGGCTTCGACGGCAAATGAAATGGTGAGGAATATCTGATTGAGACC
GGTTTGCGCAGAAAGGTATTCTTTCGAAAGTGGTTCGGCTTCTTCAAGAA
CTTGCTGATAAGCGGAAATTTCATTTTGATAAAAATTATTGAAAAACTCC
TGTACATCGTTGAAACTGACGGTAGAGGTGAGTTCCAGCCGGGAGGTTGT
AAAACTAAACGCCTGCTCTTCTACGTAGCTGTAAGTTCCTAATTTTTTGA
AATAAGCGTAGACGGGATAGGAGTCTACAGAGAAGGTATAAACAAACGGA
AGCGAAATGGTGGGTTTTTCAATTCCTTCAAAAACTTCAGCCGGAACAGA
```

FIG. 1D2

```
GTCAACCACCAGATAGACGTTTCCACTTCTTACATACTTGGAGGTTACTT
TGCCAATAAAATCAACGGAATAAATGATTTCCCCGGCTGAAGAACCGCTG
AAGTGTTCAATGTAAATGTAAGGATTTGTGTAGGAAAGAGAATATGGAGT
AAACCCGGCTACAATTTGAGAACCCGAAATAATTATAAAATCTTGCATTC
CTCTTTTTCTGTTAAATAATAACGCAATAAGTCAAGTGCATCTTTGGGAT
AGAAAGGCTGATAGTCTTTCATGGAATGTGGATATTCGCCCCAGTCTTTG
TAACCGGCGGGAGGAAACAGAAAACCAACTTTACATACGCCGCTATAGAG
TTCCAACACTTTAGAAATTTCTTCAACGCTTACATCCGAATCAAAACAGA
ACACCAGTTCTTTAACCTTTAATTTTTGCACAACGTAGGAATCCGGAATA
CGATTCTTTCCACAGAGTACGCACATTCCCACACCCAACCCATCCGTTGC
ATGGGGAAGCATATCGAACATTCCCTCGAACAGATAAATCTTTCCTTTTC
GAGCCGCTTCGTAGAAATAGACCGGGAGCTTACCCACCATATAGGAAAGA
TACCGAACCTTATCGAAAGGTTGATAGAATTGAACGTTTCCTATGGAATC
ACCGAAGGCAACCCGCTTTTCATCTACCACCTTGAAAAATCCTTTTGACG
ACATATAGCTGAGAAGTTCCGGTTTTACCCGGCGCTCTTCAATGATGTGT
TTGATAACCGGATATTCGATATTTTCCTCTGAAAGAGGGAGCCGCCTTTTT
AAAAAGCGAGCGGTAGTAAAAGTTTTTCTTGACGTTTGTCTGTTCAACAT
CCGTAAAATCGATATCACCCGAATTCTTATAATATGAAATGAGTTCGACA
GGTTTAAATCCGAAAATGCGCTCGAAGTCTCTATAAACGGTGCCTGAAAA
CCCACAACGGAAACAGATGAAAAGAGGGGCGTCTATGGAAAAGTAAAGCG
TGAGTCGGCGGTTGTTTTTATGCGGGGCGCACTTAGGGCACAAACAGGCT
ACTTCTTTACCGCCCCCGGCAACTTTAGCTTCGCTGAAGTATTTGGTGAG
GATTTCTACAATCATGGTTTTTTCTACAAAAACTCTAAGGAATCACAATG
GTTCCCGGTGTAGTAATCACAGGATGATTTAAAGTAATGTTCACATCGGT
TACCGTTATATCCGGCGGAATCGTTGAAATGTCAATCGGGATATCGCAGT
ATTTGCTCTGAGAAATCTCTACGGCTTCGACGGTTACGGAAAAATTGAAA
TCATCGTCGGTATCGAATGCAGCCATGAAAAACTGTTCATCGGTACGTAC
GTTGACAATTTCATACCATCTTCTGGATTCCCCAAGCACCAGATCTCCCG
GTTGTGGAAAATAGTCGAATTCTTTCAGCACATTCCTAAGAAGATGAAGT
CGGAGTTTCCGCACCGATCGCATTCCAACCTCCTCTGAAGCCGGTTCCCC
AACCTCATATTCCACACGACAGGGGATCCGGTACATTTTATATTCTCTAA
TATCTTTCTTAGGAGACTCTCCATACAGATAGTGCAATACGTCGTTTTCG
TCATCTTCCACCGCGTTTTCAATAATACGAACAAAAAGGAAGTTGGCGTT
GAGAATATCCTCAAGCGCTTCAAGGGCAAAATGCTGAAGAAGATTGAGTT
CCCGTCTTCCCCAGAAAAGAGGATTACGCTTTTTATCATTTTTATTTAA
ATAACCCCTTTTCAATTCTCTCCGTTAGAAGCTTCTTTTCCGACTTTTGC
ATTTTCTCTTCGTCGCCGTCAAGGCGGGCAAAAAACCAACTTTTATCATG
ATAATCCATAAGTCGAAGAGCGAACCTTTTGCGAAACTCTCCGGGGTTTT
CTTCCGGAGAAACCTGTTCGGAAATCTCTTTATAAATCGTATCAAAAGAT
GACTCAAGCTGATTTCGCATATCGGTATAAATTTCTTTGAGTTTCATCAC
GGTTTCCTGTTCATCCGGGGTAAGTACAAAATCATCAAGTTTGTTTTCAA
GAAAAAGATCGGCGAGCTTCTCAGGAGTGATTGTAGTTTTAATCCGGTGG
AGCTCCAGATATACCGGGTGCTTGATCTTTGTGCGGTAATAAACACGCGG
GGCAATTTCCTGTACGGCTACAAATCCTTCATATACCACCTCATAACCGT
CTCTCAGGCTTTTGAAAAGCGGTGTAACTTCCTCAAATAGTTCCTGAAGG
CGATTGGCACGAAAAAGAGTATAGTTTTGCTCTTGAGACAGAACAGCCGG
TAGCTTAAGATTTATTTTTCCGCCACTTTCGTTGAAAATGCGTACGGCTT
CTTCGGAGGGACCCACCTCGAAATATCCCTTCTCCGGATCCACCGAACGC
ACACCGATCAGAATGATATTTGGCTCCTCATAAGGAACCACCACTCGCGC
GTCCGGATGAACCATTTCAAATATGTAACAGTATGAGGAGTTCAAATGAT
AGAGAAGGTAAGGCGGATATTTCTTTTCAAAGGTTTCCCAGAACAATTCT
CGATATGTTTTATCCATATGAGTGGTAACCATTCCGTTTTGACAATGGA
TCCATTTGCGTCAATACTCCCAAGAGTGTGAATTTTCCACCCTTCATCAT
AATATAAAACCACACAAGTACCATCCAGCTTTTCAACCAGTTTCATGGGA
AGTTTGAACATGAAACCGGCTTTGCGCTTTTCATTCAGGGGAGACGCGTA
ACGAAGCGTCTGATAATAGTTTACGATTTCCGGCTGGAGTTCTTCCCCCC
AGTTGAAAAATTTGTCAAAGGGATAAGACAGAACTTTCCAACCACTATCC
GTTTTGCGGAGAATCGCCCCGCGACAGGCAAGGTGATATATCTTATCAAA
CTTACAACCAAGGTGATATTTGAACATGTATAGATCACCCCGGTTTTTGC
ACATAATCCCCTCCTTGCGAAGGGATTCGACGGCTACTTCCGGAGACTCA
```

FIG. 1E2

```
AAAGAGTTCAGGTGTTCGATAAGGTACTCAACCGGGTATTTTACGTTCAT
CGATTCCATAGCGTACTATAAGTCTTGTTTTGAGTTTTCGGAAGCGTCGG
TTGATCAGGGAGTTCGTCTACAACTTCATAGTTTCCGGATAGGAAACCGT
AGCAATCACACACCTCCTTCGTAAATCTGTTTACGGGAATTGGTTACAAG
TTTTTCAGCTACGCGCAACATTTTGTTACTCCACTTTTCAACCGGGGTTT
CCACAAGGAAATGACCAATACGGGTATCAAACCGGTTGAAGCCCACATTG
TTGCGCTGAGCCGCGCGGTCTTTATCCAGCGCCGCCACGATCGCCAGCTT
CTGCTGAAGCTCCAGCGCATAACCCCGCTCTTCCTCCGAAATGGTTTTAC
TTTCTTCTTCCTCCTCCCGCTGCTGCTTCTGCTCAGACGTAGTAATCACA
TCGAGCAGAGATACAGGCTTCTCAAGTTCAGTCTTCATACGCTCATGATT
GAGTGCCTTTTCGATAATTTCAATCTTGCGCGTCAGGTAATCGGCAAAGT
TTTCATCCAGCGTATGACGCGCAACAATGTAGTGAATATCCACACATTCG
GCTTCCTGACCAATGCGGTGGAGACGATCTTCCGCCTGCAGGATATTGCC
GGGTACCCAGTCCAATTCCACAAACACGGCGGTCTTAGCACGCGTCAGCG
TAATGCCGACACCAGCCGCCAGAATGCTGCAGAGCACCACGTCCACCTTA
CCACTCTGAAAATCCTCCACCGCCTTTTGACGCTGCACCACATTTTCCTC
GCCGGTAATGCGGGCGTAGGTAATACCTTTAGCTTCAAGCACCTTCTGAA
TGATCTCGAACACATCATGATGGTGTGCAAACACAACCAACCCGTCCACT
TCTTCCTCTTTCACAAGAGAAACAATATAGTCAGCAGCGAACGGGGCTTT
GTGAATGGCATAAAAGCGCCGCATTTCTGCAACGCGCTCAAACATAACCT
TCATTTTTTCATCAAACTCCGCCATTGCCTCAGCCAGATCAGCGCTTTCA
ACCCCAACCCGCTCAAACTCGCGGAGAACGGAAATATAATTTTTGAGATT
CTGGAGATCTTCAGCCAGCTTGAAAATTTCTTCTTCAGCAAACATCTTAT
TAAGTTTTACAGGAACGATTTTACGGCTTTTCGGCGGAAGCTCCTTGAGC
ACATCTTTTTTCAAGCGACGAATCATGATAGTGGAGCGAAGCTTTCCCTG
AAGTTCTTCAAGGTTACTTGCACCACGAAAATCCCAACCATACCCATTAT
AGTAAGCGTTGCAATACCGCTTGGCGTAGCCCCAGAAATTACCAAACACC
TTCGGAGCCGCCATCTCAAGAATGGGATAAAGCTCAATCGGTCTATTGAC
GATAGGAGTACCGGTAAGAAAGAGCACCTTCCCGCCCTGTTCTATGGAAG
ATTTGACAATAGATTTTACAAACCCGGAGCGCTTCGTCTTCGGGTTTTTG
ATATAATGGCATTCGTCTACGATCACAAGATCGTAAGCATAATCCTCTTC
CGAAATGCGGTGGAGAATGTCATAATTGATAATGTAAATCGTGTTTTTCA
GAGAAAAATCGACTTCATTGCCCGTTAACCACAATAATTTCTTTTTCGTGA
ACCACCCAGCGCTTCAATTCCCGCTCCCAGTTGTACTTCAGAGAAGCGGC
ACACACTACCAGCACGCGATCGGGGTTCATTACATTGATAACCCCGGCGC
TCTGAATTGTTTTTCCGGTACCCATTTCGTCTGCAATGAGAGCACCCGGA
TATTCTTTAAAAACTTCGGTAACAAAATGCACCCCCGCCTTCTGAAATGG
GAAATAATCATATCCGGTAGGTGCAGGTACGGCAAAATCGCTGCTGGTGA
CGCTGCTGAGCTCGAGCTTGTGATTTTTTTCTTCCAGGAGAAGGTTGTAC
TGCTGAGCAGCCTTTTCGTCGAAATAACCTTTCAGTTTACTCGCATAATC
GAGAATTGTCGTATACCATACCCTCTTATCCGGATCCCACTTCCACCCGG
CATTTTTGGGGATCAGACGTTCTTCGTAGGTTCCTTTCCACTCGAACCGG
TTGTTGTAAGTAACGTAGCCCATGACCGCCCTGTCTTTGGCTGTCAATCT
GCTGATAATATACGACACTGAACAAGAAAGTCAACCCCTTGACAGAAAT
TTCAATTAGAAGGGAAACGAAAGTTGAACAAACAGGTGATTGAAATGCTT
CCGATAGCGCGTCGGAAGATCAAAGGTGTCGTGGATAAACTTTTCAAATT
CATCTTTTTCACCCTCTAAAACATCATCAAGCCATAGTCTTCGACGTTCA
AGGCTCCCAATAATCGCCTCAATCGGATATGCTTCTATAAAAGCATTACC
GGGATAATCATCTACAACACTCCTCACAACTTCTTCAATGTTTGTTGTAT
CTATCAATCCCCTTTCCGTATAATACACTATATGTGGTTCTTCGTTTGAT
CCGTAATCTGATTCTAAGTATACTATAACTTCATATTCTACTATATCTTT
AACATACTCGATAATACTTTCTATTCCACTTTCAACCATTTCCTCTACTT
TCTCCCCCCACTCTTCATCAAAATGATCTAAAATATCATCCGAGTTGATT
ATTTTTTCTATAAGATCATAGTTTACATTTTCAGGTTTAATTGTGCTGTA
AAAATATTCAAAACAGCCGGTTGTCGACATATTTTTATAAAGAGAAGCAA
CTACATCGGGATATGCTTCGTGTTCCGCCCATTTACCAATATGTTGTTTG
AAAAGAAAATAGGCGATACGATAAGAACCTCTGTTGGCTCTCCTTTTTTC
TATATCTTCTGGCAACTCTATATTAAGATATTCATGAAGGTCTTTAATAC
CCTCCGCTTCCCCCATATGATCAATTGCGATATCTACAAATTGTCTTATG
AGATCGACAACCACCGAAAGATTGATATATTCCTCGAATTTATTCTTCTG
ATAAAGCACAAATACCTGCAGGGTTTCAGCGGGAATATAAACAGTATCAT
AATTATAAGCGAGGACGCTCCTTACACTGTCTAAAGCCATATTAATATAA
TATTCGATTGCATCTTCTGAAGGTGCAAGATTTTCTACCAGATGGGGATA
TTTTTCAGCAATCACATCCAGCATCCGCGCCGCATAAGTAGCATAGGGTT
```

FIG. 1F2

```
CTTCGTCAATCGGTACCATTGTATTATCAGGAAGGTGAAATTCCTTTCCC
TTACCAAATGTAGCGATTGCGTAAACAAGTCCGTCATACGGATTGCTACT
ATCGGCTTCGAAATCTATTCCCGGTTTGATCGCCGAAGGATGAAATACCC
CCACGAACAAGGGATAATAATAGTTGAAATGTTGATCGCCAAGTCCCACA
CACACATGAATATGATTACCAATCATCCCGAGAATACGTCTGTTTTCCAC
CACATTTTGGGGGTGATATATGATCATAGAATTGTCTTCGTAGATAATCA
AATCCGCATATTCTGTGTGCATAAGCTGACGAAACTTCTCCCACAATGCC
AGATAAGAAGCCCCCACCTCTTCCACTTTTCCGGCGCGTTGATATGCCCC
AACGACTTTTCCGGGATCGAGAAGCTGAAGGTTATCCGTAAGATCAAATT
CCCTCAAAACGGAGGGTTGGTGTCGCACCGAAAAATACCAGCGAAATGGC
TCGATGTAAAGAGGGAGATCGATCGGATCGATTTTGTCGCTCATCACCAT
ACGATAAAAATATTCAACCAGCGCATTTGTCGAGATAAGGTTATATTCGG
GATTGTTGCGAAGCGGCTCAAAAATAGACTGAGCAACTTTGTGAAGAATA
TTTCCAAAAAATAAAATACGCTCCCCCGGATCACGGGGAACTTCTCCAAG
ATTTAATTGCTGAGCCAGAAACCTGAGTTTGTTTTCGGGAAGTTTTGCAA
GTAGTTCTTTACCCCTACGGGACCCCGGAGCAGGAAAAGTAAACGCCATT
TTTTTATTTTAAATAACTACGCCCCAAAATCCACATAAAGATAGCAAATT
TTCCAGCTATCCTCCATCGAGATAGTATATTTTTATCCCCCTCTTTTTT
AATCTGATAATCTTCCTTACCGACATAATGTAAAAATTGCCTTATAAGTT
GCCACAACCTATCATATTCCTCCGTTTCATCAGTGCAAGCCAGCTTGTAC
TGATAATCAACGAAGGACATATCGTTTATTTCATCATAAAAATTGTCATT
GCCCCCCACAATGATAACTTCTGGATCAAATACAACCCATTCGATAAAAT
CAAGCATAAACTGGCTTAATTCCGGATTTTTAAGAATATAACGCCAGTTC
CAGCGCGATTCATGATCACATCGATCAAGCCTTTCTATCACCTTATAATC
TTCATTATATCTGGCAAGTAGAAAACGTCTCATTTCGGCAACGTTCATAT
CGTAGCTCAGATTATCTGAAATATCGTTCAACATCTCCCGAAGTGCGTCT
ATAAAGAGACGCTTGATAGGCTCGCGTTCAAACATCAATTCTACAAACTT
CACAACCACACAATCCAGTTCTCTATGATTTTTCAGATAAGCGTCAATGT
ATATATCCGACGCCGCGTTGGCAATCAGATAGCACATCTTAGCCAGCGGC
GTTTTGCAGACAAAAAATTCCCACCCGAAATCGCAAGGGTAAAAATCCTC
CTTCACCTTATCAGGATAACGGCTGATAAGGATGGAGTGGGAAGACGATG
AATTTGTGGAAAGACCGAAACGAATGAATGCTTTCATGACTTCCTCCTTT
GTTTGTCAATGGTTACATAGACAACGTAAAAAACAACGGTAAGAATAAAA
AGAAGTAAAAACTTTATGTTCAACCAGAAGGGATTCTCTCCTCTTAGCAC
CAGCGCTGCAGGGTTTCTCAAGTATAATGAAAGATAAACCAAATACAGCG
CAAGCGCCAGCGAAATAGAGCCTATCAGTATTTTGAACACTTTCATAGTT
TTTTCCAGATGTTGAGAAAAGTTACCGGATCGAACAGTTTTTCCCTCGAC
ACCCTGAAACCCTTTTCTTTCAAATAGGATCCCGGAGCAACAAGTGCTTC
CGGCTCACTCATGTCGATGTAGCAGGAAAAAAGTCCTTCCTGATCGGTAG
TGCTATGTGGAAATTCTCTTTTGAACACCGGGTAAGTTTTAACAAAAAGG
GAATCCACCGAAATGGTGAGTTCTTTCATAAAATACTTCACCGCTTCCAG
TGTCTTGTTTTCTGGAATTGGTATGTTATTATAAGTTTCTCCCCTCCCCA
CTTTCTTAAAACCAAGTAGCAGAAGATGGCTCCCCTCTACCTGAGAAAGC
ATTTGCATCATTTCAATGGTTTCTTCAAAGGGAACGCTCCCCCATACGTG
CTGAGCCACCAGTTGCACATTGGGGGGCTTCTGATTCAGAAGATCGATAT
ACGACTCCACCGATTTCAAACCATGCACGCTGAAACCTATCCCAAAAAGC
CGATTCGGAAAATAATGCCGGTAGAACTTCATAAGCTTTCGGGCAAACGA
AGCATTGAAGGTGGTTACGTTAACATAACCCCGGCTGAACGTTTTGACAA
TGCGATATAACTCTTCCAGAAATCTCCCCTTCAGAAAAAGCAGGGGTCT
CCACCCCCTATGCTGAGTTCGTAGGTACCCATTTCGTTTAACATTCGTGC
GAACCGGATCATGTCACCCGATCACACTCTGATCCCTCCGGGGTGGAGT
TTTCATAACAGAAAGCACACCCAAAATTACACACGTTGGAGGGTTTGACA
TCAACGATATGCGGCACCTGAGTCTTAAACATGATTACCTCTGAGTTTTG
TTTTCGGTGCGTATGTTTTCCACAAAAACTACATAGGCTGAAAATACACC
AAGAATAAAAATCTGAGCAAACCCCACAACCCCGTTTTTGGATTTACTT
CCGCTTTTACTTCAAAAACGATACATATGATTCAAAGGTCTTTGATTTTC
GGAATTTCTTCACAAACTGCTCAAGGGCTTCGTAAACGTCGGGGCGAACC
AAGTTCTTCTCCTTCGTGAACACCACCCGCCTGACTCCCAGTCAACCCC
GAAGTTAAAAAAGTTATTAAGGCTGACACAAAGCGAAGTGAGGGGAAACT
CATATATTTTTACAATTTCCCCATTTCTGTCTATAAGCACCGAATAATAT
CCTCTAAAAGCGTCGCACAGGTTGCGCACAGTCTCCAGAAAATCCGAAAC
CGGCGCAAAGTCTTCAAGCACATAGCAGGTTAGTTGAACGGCTTTTTCTT
CATTCAGGTGCGTTACGGAATACATTACCGGCTTGACTACCATACTTCCT
CCGTTTTTTTGACCGGAAAACCGAATCAAAACACCAGAGTTCCATTCCAC
```

FIG. 1G2

```
ACAATACTAATTACCAGTATTTAATTCCCTGTTATTTCACATACCCTCTG
GATCATTCTGTTTTCTTTCTTATATATTCCATTGTCAGTTGAAACCAAAC
AGATGAGCCATGCCGAACTTCATTACAAACATCAGGAATTCCCGTTTTAA
GGAAGTTCTGACCGAAATGTACCATTGCCATCACGAAAGCGAGTACCACC
TTGAGGGAAATGTTTTAAATCACACGCTTATGGTATTGCAGGTGGTAGAT
AAGATAACCGCTGATCACCGGGAGCAAACTAATCTATCCTTAACCGCCCT
TCTTCATGATAGTGGGAAACCCTATACCCGTGTTGTCGAAAGGGGAAGAG
TAATGTTCCCCGGTCATGAAGGGGTGTCTACGTATATCGCTCCTCTTCTG
CTGTGTGAAGTATTGAGGGATTCCCTCATCACACCAAAAGACGCCATTCA
AATCCTTTACGGCGTCAATTACCATATGTTGCACTGGAAAAATCCAAACC
TTTTTATGCGGCTTTTCACCGAAATGGTTAATTATACCTGTTTATATAAC
TTCTTGAAAAAATTCAATCAGTGTGATCTAAAGGGTAGGGTTTCTACAAA
ACCCCAAAAGCAGGAATTCCCCGTAATCCATTATTTTGAGAATACCCCGA
TCGGTACTGTTGAGCGCCATGTTTATTTTATGATCGGGGTTCCGGGGAGT
GGAAAGAGCACGTTTCTTCAGAAAGTTGGAGAGGGGGCGATTGTATCCCG
TGATGAAATCATGATGGAATACGCCGCTGAAATAGGGATCACAGGAGACT
ACAATACTGTTTTCCGGCAGATTCACAACAACCCTATGCATAAAACCAAG
GTCAACAACCGCTACATGAACGCTTTCCGTAAGGCGGTTGAAGAGAATGA
AAAGGTATTTGTAGACGCAACCAACATGAGTTATAAGAGCCGGAGACGTT
TTTACAATGCGCTTCGGCGGGATATTGCGGAAACCGTGGGTTACCATTAT
ATCGTAATGCTTCCCGATTATTTTACGTGCATTGAACGCGCCGAAAATCG
GGAAGGAAAGTCGATTTCAAGGGAAGTGGTAACCGATATTGCGCGGAGTC
TGCTTCTTCCGTGCAGGGAACATCCCAACAGCATTGATACGACAATTTAT
ATGTCTGATGGGCATGATGAACATGTGTTGAGAGTAGCTTGGTAGTTTTT
AAGATTCGACGATGCTCCCCCTGCTCAAGCGGGGGGATTTTTTATTTAAT
CAAAAAGTGGAACCTTTAGAGAAACTACTTGCCGTTCTCAAAAAGCTTGA
AGCGTTTGAGGAATATCTTTCAAAGATAGATCTTGGAACGCTGGATCAGG
TGATTACCCGGCTTAGAAAGCTCCGGGAATCCAACGAAAAACTGTACAAA
GACTATCTTGAAGAACTTGAAAAGCTTTTCAGCACCAATCAGGAAACGCT
CGAAAAGCTGGTAGACGCCCTTTCGGAGTTTACGGAAGAGGAAAAGGAAA
AACTTGAAAATTTCCTTGAGACGCACCAGAAAGACGCCGCACGACTTCTT
GGATATATTGACGTTTTTGAAGCGTCGTGGAAACACATGAGCGCCGAACA
ACGGGCGGCATTTGAATCCTTTATCGACAGACTCAGAGAACTTCGTAGAA
ACCTCAATCTCGATCGATTCAAGACGGAAACAGCATTCGATGTTTTCGAC
AAAGCACGAAGAGACCTTGGGGTGCCTTATGAATATATCAATCGGTTTGC
ATTAGACTTTATCAGATTTCGCCAGCGATCAGAAATTTTCTTCAAACAGA
TCATGGCATTTTTCACCTATGAAAGGGTGACAAGGTATACCGCTTATGGA
ATGGCAATTAATCTGGTACAGGGGGCGCTTGAACGCTACATTGAAACTAC
TGATGAAGTGATCAGAGTTACCGGTATTTACAACCGGCTGCTTAGGGATC
AGGCGCTTCAGTTTTACCGCGCAAATATTGATCTGAGACGCTTCGGTGTT
CAGCTCCGGGATACTACCCGCTTTATTGCCGAATTTTATGCATTTACGCG
CACGCGCGATCCGTTCGCGTTGATAGCTCAGACAGCAGCGGGTGCTGGAG
ACAACATCGACGGATTCATGCGTCAGATGATTCTCTTGAATCAGCGCCTG
AATATTGACAGCCGCACGCTAACACGTAACATGCTACTTGCAGCTACCAC
GCTGGAAGATAATATCATGCAACATATTCAGCTTATCACTGCTTTTGCAA
ATGAAGCAAATTTGAGCGCTACCGAACTGGTCAGCGATCTTGTTGAAAGT
TATTCAGAATTTGTCGTGCTGCTTGGAAGCGGGGCGCGTCAGATCACGCA
AACTCAGATTGCACTGGCGCGGTGGAATATGTCGCTCAGAGACGGCATGA
ATATTCTGAAAGGTCTCTATCAATCTCAGGAATCGGTGATCGACTCGCTC
ATTCAGATTCAGATTCTCTCGCGCCAGCCGGTTGATTTCGAACGCTTCTT
TGGAGCCATGCTCACCGGCGACATTGAAGGAATCGTCGATCAGCTTGCGG
AAATGGCAATGCAGATGCGGGCATGATGGATGAACTCCCCATTTATCGT
ATGCAGTTTGAGCGGGCACTTGAAGGGTTGGGCTTAACCTCCGAGCAGAT
CGCAACGATTCTTGGAAAGTCCAGAGAGCAGCTTACAGGGTTCGGCACTA
TCGTGGAAGATTTCCGCCGGAAGCTTTCACCTGAAATGCTTATCCAGACT
TTTGATGAACTTCTGAGACCCAACGAATGGGAAGAATTGAAGAATGCCGT
GGATGCATTCTTCGAGACGTTTATGCTTTACGGCGCTGAACTCATTCGCA
ACATGATTCCGGTGCTTAGAATTCTGACACAGGGAATGCAATTGATGTTC
AAGTGGTCTCAGGCTATGACCGATCTTATCGATAAGGTTGGTAGCCTTGG
TGGATTGTTGAAAGACAACGTTCTTGGAGATTTCTTCAAAAGCATTTTCG
CGTTTCTTGGACCCGGTGCCGCGCTTTACGCTATTGCGAATATCGGAAAG
CTTGGAACTGCACTCAAGATGTTATTTGATTTAATCATTTCCATTCCTCG
CCGCATTGGGGGAGGGGTTGTAAACCGTATTGGTTCCTTTTTCAGTCGTC
TTGGAGATGTGTTCAAGAAGTTCTTCGGTAGCCGGGAAATGAAACAGGTT
```

FIG. 1H2

```
GCGGAGGATGCAACTTCAAGAAGAGGAATTCTCCGTCGAATCACCGGTGG
AGTCAAAGATTTTACCAAAAACCTCTTTCAAAGCTTTTCGCTTGGATCGA
TCGTTCGTTTTACAGCAGCGGTGGGGGTGCTGGTTGGTGGTATTTATCTT
TTCGGAAAAGCTGTGAAATCACTTCAGGGAATCGACTGGGGTGAGACTTC
GAAAGGATTGCTTGCCTTCTTTGGAGCGCTTACCACTACGGTAGGGTTGA
TCAGTCTTGGTGGTCTTCTTTCACTTCCCGCACTTCTTACCGGTCTTGCA
GCTTCCATAGGCGCTATTGCCGTGGTGGCGGGCGGTCTCTATCTCACCGG
TGAAGCTATGGGAGTGTTTGCCAGCAACCTTCAGAGACTTGCTTCCACGC
TGGAAACCTACCCCAATCTGACTTCCGGTATATTCCGTCTGGCTGGAGCA
CTTGGTACGCTTGGTGCCGTCGGTACGATTGCTGCTCCGGGCATGCTGGT
TGGAGCTATTACCGAAGCCGTAAGTGCGGCGATCAAACCCGATGTGGCTG
TAAAAGCCATTATCGATCCAGATGTAATTACCGCCGGAGAAAAACTGATC
GCAAACAAACTTGACCGGATTATTGCGCTGCTTACGGAAATGCAAAATAG
AACGGAGCCAAGAGTGGTTACGCTGAATAAGCCGGAAAAGCCGGTTGAAA
AACCAATCTTCAGCACATTTAACTTTTAATCTTCATCCTTTTCTTCTCCC
TTTTTCCAGACCGGATGATACCAGTCGTTTTCTTTCATCAGGTTGATGTA
AAATACATATTTATAATTTTCAAATTTTTCATTCATGCGAAGCTTATAGA
GATAATCATCTTTGAACTTTTGGATAGGTATTCTTCCTCCAACATAAAGC
AGACCACCTTTTCCCACCACAAAGAACATATCTTCGGGGAAACGTTTGAT
CTGAAGCACTTCGATCACATCGTCAATGGTAAAAAACTTGTATGCGGTTT
CTTTGGATGCGTTGTAAATGTAATAATGATGCGCAACGTTGGATTTTCTG
TTATCCGTAATCATAGAAGTTTCTGCTTAAGTAGCTAAATATCACTATTA
AATAACCGGATTTGATATTTAAAGAAAAAGATGAAATTAACCGATCTCAG
AAATAAAGTTACAAACGCATATAACCAGATTTCCAAGCAGAACCGCGAGT
TAATCGCCGCCAAACTTCGTAAAGACTCCAGTGCCACCATTTACTTCGGG
GCTGCTGTCGAAAAACTTGACGACGCTACGATCAAAGAACGTATGATCGA
CGTTTTTGCCACGATCATTGCTCAGGCGTATGATCGCGCGATTTCCTTGC
GCAAAGGAAAACCGACACATCTACCCTCCCCTCAGTCAATGGTACTTACG
CTGGCAAGATTTTACGTGGAAAATGAAGACATTACGCTCAGCAAACTTAA
CGAAATTTCCATTGCGCTGGGCTGGTATATCGCGCTGGTAAACGAACCGA
ATTTGCTTCAAAAATACAACCTCCCCAAACAGATCACGGAACTTGAGCCG
GAGCAGCTTCTGCACACTTACAACCAGATCGCAAGATATTCCGACACCTA
TCAGGTGGAACTGGTAAATCGCTATAAAGAAATTATCGATTTCCTCACGC
AAAACGGTGAAGAGTTCTGGGAAAAAGAATACGGGGTTATTTTCAAACCT
TCCTCTTACGAAATCAACGCCAAAGTGCTTCAGCTTGCCTCCGATCGTCT
TTTTATCTGCACCGCACTTAACCCTATTTTCCACGACACCTATTATCCTT
ACTATGTGCTTGTAGTCAACCCGGCTTACAAGGGAGACGGCAATGTTCAC
TATATCAAAGACGGCGTCAAGGGATATTCAGGTATGGAGTTTTATCTTGC
CACCTTCTCCGACAAACACCCCTACCAGAAGGGATTATTTGCTCAGTTTC
GTAGCCAGTATAATATCGCCACCCCTCTCAGCTTTATCGAAAGCAGACTG
TATCTGGGGATTTATGGAGTTTTTGTGGAAACGTAAAGATCTTCAGCC
GCATATCTCTAAACTCATAAACCTTTACAAACAACACCCCGGCTTATCTTT
TCGATGAGAACGCAATGAAAAGGTTTGTGGAAAATGAGCTTTTCGATTTC
AAAAATATCAACGACTCACCCGGCGCACGCGAAGCCGTAGCTTATTTTTA
TTCCAAGATCGACAACCGTTCTTTTATCGAGGGGCTGACTCCGCTGATCG
GAGCCGCCGTTGAAACGGTTATGGAATCGGGAGAAGACCCCAATTACAAA
AATGTACTTCCGGTGCTGGTAGAGCTTATGGTCAAAAACAACTACGCTAT
GAAAAAGATTGAAGAAGCTGTAATCGAAGCGGTGCATAGAAAAGCGGAAA
ACATTCTCAAATTCACCCCGGAAGACCATATCAGATATATGGCAATTCAT
TTCGCTCATAAAAATATTCCTTCAAATTCTGAAGAAGAAGGAAGAGATTT
TGCCGAACAGATTTATTATAACATAATCAGACCTCAGATTACAGGCACCT
CACCGTATGCTATTATGTTTAAACGTTTTATATATTCAATCATTCTTGCC
GAAATGAAAGGTATTCTCAAAAACAAGATAAATCAGGTGGTTAAAGAAAT
GGAAGAAGAATTCGGGTTTGGAGACATTTCCCTTGCCGATTTCGACTGGG
GGGCGGTGAAGAAGACGAAGATTCGTTCGAAATGGAACTTTAACTGGAA
GTGTACACCGTTTCTCCGACGATATAGAGACGCTGTCCACGAGATGTTCT
TGAAACCTGAAAGGTGGCATTGTAAATGTCGTGATCTTCAACCACTTCTT
CAAGCTTTTTCTTAATATCTCGATAAAGAAATGACTTTTCATCCACGTAG
AAGAAGTACATCCACGTCTGATACTCTTCTCCCCCCATTTTTTCCGAAGA
GTGATCTTCCTGATACAGGTGAAATCCGTAATCCTTTAAAATAGGTATAT
GTTTTTTGATGGCGTCGGATGAAGCCTCGCTTCCGTCATAAAATACCTTG
AGAATCATATTCTCCATTCCGGTGGAAGGAATGACAACTTTCCCTTCTTC
CGTATACGCACCCTGAATGGCAATAAGCAGCAGCCCCGGAGATATTTCAT
CAAAGAACTGGTAGGTATCCTCGACGGCGCGAATATCGGTAATCAATGTA
```

FIG. 112

```
ATCTTGGTTTTACCTTTTTTGACAAGGTTGCGAAGGGCAAAAATGGAAAG
GAAAACAACCGCTTCGAGAACCTGATCCGGAGACAAATCTTCCGATCTTC
TTATGCTTAAGAAATACTCCCGGTGGTAGTCTCTCAGACGAAATCTCAGA
TCTTCCTCTTTCCTCAAAACCCTCGCAATGCGACGGTCTGTTTCAACAAT
GAAGTCGGTATGCGTTATTTTTTCTCCCATTCTCCGTCGAAAAATTCTA
CATCGTAAACAATAAAACCTATCGTGTTGTAGTGGTAGTTGATTTCTACT
TCGATTCCCCATGAACTATCAGGCGCACGAAACAGAAAGTTTCGCGGGGT
AAGCTTCCACTTCTCCAGAACCGCGCTTTGAAAATTGACGAAGTTTCTAA
TGATTTTCCTGAGTGCATTCCTCAGTTCACTCATAAATAGCGATAAAGAG
TTTTCTCAACCGTTTCCAATATCTGAAGCGACTGTTTGGTTCCAAATCGA
GATTCCTGAAGCACTCTTGCACTTTGAAAAGAAGGAACGGCTACAACATC
TATCGCTGTGATAAAGAAGTCGTCAACAATTTCTACCCGTTTTTGCTGGC
GGTAACCTACTTTGGTTTTACCGCTCCCACGAAGGGAAAACCCGAAATTG
ATACCGTTTTCAAGAAGCGATTTGACCAGATTTCCGTAAGGAGTTGGGAG
AATGCGGAATTTTCCGTACACTTTATTTCCTTCCATCCATACGTCTACCC
ACTGCACGGCAAGGCGCTCAAGCGACACGAACCCGATTCGAAATCGTTC
TGGTAGGGGTGATCCAGCTCGCCGTACATCTGACCCTTTTCAATCTCCTG
CTTCATACGCTCCACTGCTTTTTTTACGGCTTCCGGCGTGTAGAGTGTAC
CATTGTCGGAAATGACGTCGGCTTCCATAATCAGAGCCGTATAAGTTTTA
TCGTTAACTTCCATAGCGGTTATTCTTCAGTTTTATTGTTTTCTTCTTCC
TTTTTGTCTTCGGCGTACAGGAAAACGGCTTCCACCGAAGGAAGCATTTC
GCGAAGCCGCGCAAGCACATCGGTAAGCGCAACCAGCTTGGAAACACTTC
CGCGAGAAGCTTCGATCGTGTTGATAAGCTCGCGAATGTAATTGCGATAG
TTTTCATCCAGCGTAATCTTGTCAATGATCTCTTCGATCATTTCACACAA
TTCCTCGCTCACGCGGGCAATATCCTTTTCCAGTTCTTCCGTGATTTTTT
CGGCTTCTTTCACCCTCTTTTCTTCGGGGATTTCATAACTATTCTGATCG
TTTTCCTCCTCCATTAACACCTTTTCCTCTTCATCTTTCTTGTCCTGCTT
GACATCTTTACGGATTTTTTCCACATCACGGCTGGAGTAACCTACCGGCG
CGTCATACCCCGCAATGTCGCCGGTGGTGGTCATCTCCTCGATCTGTTTC
AACGCCGATTCATAAAGGTGCGAGAGGATTGCCGCCACTTTAGCAGGTTT
CCTTGCGCTCAGGAAAGCTCAGCCACACCAGCCGCGCGATAAATGCGGG
GATCGATACGGGTTTCGTAAACTTTTGAAAGCTCTTTTTCTCCAATGATC
TTTTCCAGCGCTTCATGGAAACCGTTGTACTGGCGCTTTTTGCGGTATTC
GTGGACGAAATAGGGAACCCTTTCATATTCCTGATCTATGCAGGCTTCGA
CAATTTTGGTAATGTAATAAACATCGTCAGATTCCACGAAATTCATCAAT
TCACTTGCGGAAGCCGACTCCAGCAATTTCTTGTCTTCCGAAGAAGCCTT
CATGAACTGGAATAGAAGGATTATATCCTTCTGCTTCATAACAACCTTTT
TTTTCTTAAATAAATAAAATCGAAGGAGAATTAAACAACTACGGTATTAT
AACCCCATCCACCGATATAGTTGTAATTGTGGCTGGTTTTATATACGGGT
AACAGTCATGAAATACTCTGTTTCTGATGTGGCGAATTTGTTCTTGTGTC
ATATCACCCGGTATTAGAGTGGAATTCAGATAGGCTGCATCTTTAGTTAT
TGCTATGTGATACAAAAGGGGCGCCATTTCACTGTAAGTGTGTGTATCTC
TAAATATAAGTCTATTATTCAAATAAAATGAAACAGTAAGATCATTACTA
AGAGGGTCCATTTCATAATGAAATTCATGGAACACAAAATAAGACCGGTT
TGGATTATAAAATCCCCATTCAGATACTGTTATACTATGAGTTACTTTCT
TTGTTAAAAATGGGGTAACTATAGTCGAATAAGTTACTCGAATACCCAGA
TTCCCGGAAGATAATGTAGAATAATATATTGAAATAATATTTTCACCACT
TAAAATTCTACCTATGTAACTAACATCTACATTGAACACCGAAGAGTCAT
CTGCATAACCGTCAAGAAATATTGTCTGAAATAAATGGAATTTTTCTTTT
TTACCATTTATAAAAAGTTCGATATTGTTTACAGTTCCCCAATAATCCAA
ATCGTAAAAAAGACTAAAAGAATAATTGGGGAAATGACTCTGATACGCCG
CTTGACTACCACCAGCATAGCTATCTGCAATATAAAATTGATTCCATCTA
CTTATAGCTCCATAATTGATATTTGCCCTGGCAATAAAAGCATTATGACC
AAAATCATAGAAAAAGAAGAATTAAAAAACTTTGTTCTAACTGATTGGG
TACCATTTATTCCATCTGTATATTCGGTTACTATATAATAGCCCGAACCC
GTTTCAATAGTGGGGTGATCTGTTTTGATTAAATAATATACATCTCTGAC
GCTCATACTCCCTTTATATCCCCCAGCTACCAGATATTGATTGGAAACTG
AAACCGTCAACCAGTCGGGTAAAAAGGGTGTAACATCAACACCATTTATA
GCCGAAACATAAGTGTTCAAGACACTGATGTTATCTTGATCCGGGTCAAA
TAACGAAAATGAAATGGTAACATAGCCGTTTGCATCCGGGTATATAAAA
TCTGGTATGCCATAACTTAAATGTTTTTTATTAAATATTACAAGCTGTAA
ATGAAGACTGCAGCCGCAACCGAAGAAGTAAACCTGTCAAGTCTGAACAA
TTCGTAAATAAATTTAATATTATCACTTCCGGCAACTCCGCTGTATGAAA
ACACCCCCTGTCTGCGTGTGATGATATTGTCGGTAAGCATATAAACATAC
```

FIG. 1J2

```
ATGCTGTTGGTAACATAAGGAGGGAAACCATCTGGATTGATCCAATTGAC
AACATAGCTATGGGTTTCTCCCGGAGCAATTGATGAAGAGGGATAAGTGT
ACACCGTAGAGTTAGTAACAAACTCAAAATAAGATGTACTGTTATACGTA
TCGGGTGTGGAACCGCTCAATGTATAAAATAGAGAAAAAGTGTTGTTAAT
ATGAGACATAATTGAAAGGGTAAACGAAAATGTATACGGTTGTGTCGAAA
GAGTCCCCATTAAAGACGGATAATCAACAGATCGACTGCTCAGTATGTTG
AATGACTTACCTTCATATAACAGCATATTGTACTTATACTTATGATAATA
ATATTTTCGAATCATAGAGACTGTAGGAGCCGGGAGAGAAGTACTAAAAA
CAGCGATTTCGTAAAATTTAAAAGCAGGGTCTCCAGCATGATCTCTCATA
AGCAATCTGTTAATATCTCGCCTTGTGTCTGTATTATACTTTTCACCAAC
AAAAACTCCGTTGATATAAAATGATGTTGTAGAATTGTTATGAGACACTT
CAAAAAGAAGAGGATAAGATAATACATCTGAGTAAGAAAACTCCAGACCA
TAGCCACTACACGTATATGCGGTGCTCCCAACAGAAGAACCGCTATCAAG
ACTGAAAAGCACTACATTTAGTTTATTGTTGTTGTTTACAAACCCTGTTC
CTATAAAGCGGTTGTTGTCTGTACTGGTATTTAACATCATCACATCCATA
AACTGGGAAATGCTATGTAGCATTGCAGGAGCAAAAACCATAAAAACATG
GAATGGTGAATCTGGGTTATTGTCTAACAGATTAACACTAAATGTGTTGT
TATAATTATAACTATTTATATGGCTGGCAAGATAAGAATAGCCTTTGTCC
CAGTAATAATGCCAACCTTGCCCTGTTGAATATAAAGATACATGGCGATT
ACCCGTTAAAGACGGTAAAACAGAAATGGTTGGGGTATATCCACTTTGTG
TTATAGTTATATACTCGACACTCCAAATTTCACTTAAACTACTCAAAGAA
ACAATTTCAAAATTGGAAGTAAAAAGAGACAGATTATAAAACTTTACGTT
ATTATCAAAATACACATAAACACCCATATCATACACACTTTCAAGGGAAA
AAGACGGGTGTGTATGGTCAAAAGATATTGTAACATCAATGACACTTCTG
GTGCCGATGTAATATAAAGAACTGGTAACAACCGTAAACCAGGGCGGTGT
AACAGAAAAAGATATATTATTTTCTTTCAATATGGAAGCACTTACTGAAA
AGGGTATTCCATAATCATCTTTCACTGAAAAGGTGATAATGATGGAGTTA
CTGCTTATTATGTAATCTCTGTTCATCTCATTCTTTAAAATTTAAACCTT
AAATAATCAAGATCAACTTCGGGGGTTGTGGTTGGATAACTTTTATTGGC
TGCTTTAAGCTCCCATTTAAACCCGGCATTAGAAAATGGTGGAACTTGAG
AATATGTATCAAACGGATAATTTGCCGCCTTGAGTTCCCATTTAAACCCG
GCATTAGAAAATGGTGGAACTTGAGAATATGTATCAAACGGATAATTTGC
CGCCTTGAGTTCCCATTTAAACCCGGCATTAGAAAATGGTGGAACTTGAG
AATATGTATCATATCGTATTTCAGATGATACAAGTTGGGTGTTAAGAGCA
GCGGAAGGGGTTAACCCTAAACTCTGGAAGGAATTTTTCATAGAAGAATT
GCTATTAGTCAGATAAACGTTACTAACAGGCACATAATTTACCACCGGAG
CAATCTGTCTGACAAATTTTGATACCGCTCCAATAAACGACACGCTTACA
CTCGATTTGGGAGATTTGAAAAGTCCCCATGCACTTCCGGTTACCGCTGA
AAAGAAAAGGAGATTGACCGGCTCATTCCAGACGTTTTCCCAATCGACTT
CCAGCGCACCCATTTGAGGAGATGAGTAGAAAGTCAGATTGTTACCCGTA
CTTTTGAGAACAACGTTTGCTCCGGATGACGTCAGATAGAAATACTGAGT
AGATGTAGAGACATATACTGAGAAGTAAGAAAGATAACTTACCGTCAGAA
ATCCTGAATTAATTGGGTTGAAGAAATAGGGTGATGTGGTTGTATAACTG
GCATATTTCAAATAAGGTGTATTATCCGTGTAATACAGAACACTTGTCGA
ATAATTCAAATCCATGAAAATGCTTGCCGTTCCGAAAAAGTCGGAGAAGG
TGACTAAATAGGGTGATTTCGAACCATGTATGTTCCATTATCAGCCGAA
ACGATAAAAACAGATTTTGTTATATCGTAAAGTAATGCGTTGAATGTGGT
GCTACCCTGATTGGAAAATGTTATATAATCTTCAATATATCCGCCGCCAA
GGAAAAGACGTTTGATTGAGACGGTTTCGGTGCTGGATGTCGTGTAATAA
TCCAACCAGAACACATCATATCCCCATGCAGCTACCCCACCGTATTGAAT
GCTGGTGGTGGTAACCTGTTTATAACTTCCACTGGAATCCAGGAGTCCCA
CTTCTCCGGAAGATCCATCGTGCAGATTGAGAAAGAGTGCGGGAGATTGA
TCGTAAAAGAATCCAAGCGATACGATTATATCCGAAGGGGTAGTAATATC
CGGGAAGTAAAGAGAGATATTCGGGTCTGTAGTTGTAATGTTCGGGAAAT
ACAGTTCTATATTAACGTCGGATGTAGTAATCGGAGGCGGTTCACTTGGG
GATGGGGGCGGAGGAGGAACATACGAATAAGAGGGGATCAGAATCTTCTG
CACGAAAACATAAGCTTCATCCAGCTTGATCGGTTGAGAAAACTTCGATA
CAAACACCACGTCCCCATTCTGATTCATTCCATAGATTCCGCTGACATAA
GGAGAAACCCCCGCAACAGCCGTGGGATTGGTGGTAAAGTTTTTGGCTAC
AAATTCGCAACGAGAAGCTTCAGAGGCTGCAATTCATAAAGCGTAAGGC
TAAAGAAAAGCGGGGAAATAGCCGGTACTTTCTTTCCCACAACCACAAAC
GATTCATTTCGAACAAGGATAAAATCCGGGTGATCATAATAACTGTCATT
CACAAGCGAGATAGGATTTCCTCCATACGTAATGGAATGTATGTGATAGT
ACTGTCGCTTGATTCTCACAATTTCAAAAGTGAGCGCATCAAAATCGATA
```

FIG. 1K2

```
TTCAGCTTACGAAAAAGATCGATAAAAAGCGCACGAATCTGAGCTTTGAG
TTGATCATCCGGGGCAATTTCCAGTTTTATATTATCATTTTCGTAGCTAC
CGGGAGAAGGGAAACCAACAACTTCGGTGAATACTTTTATATCGGTTTTA
TAAAAATCCTTCGCTCTCATTTTATACTTGATGTTCTTCTCTATTAAATA
AGAAAAGTTTATTCAGGGGCTACCTTTGATAATATTCCCTGTACACCCAG
CCGGTAAACCCAAGGTCCAGAAGTTTGGGAATATCCCCTTCTCTTCCCCA
CTGCTTTTTCTGAAATACATCCCCCACGTTCAGATCAAAACTCATAACCG
GATCCTGTAAATCTTCAATGTAACGGCTGGCGAAACCGTTATCTCTGATC
CTCAAAATTTCTTCATCGGTTATCTGATCATGAGGAAGATCATAAAGCTC
TATCAGCTTACGACAGGATTGAATATAGCGGTTATCTTCATAAAAATTAG
GCGGATGTGGGTTAATCCAGCCGGATAAAATATCGGAATAAACCTTACCG
GCAATCAGTTCGTGAGCTTTGTTTTTCATATCGGGTTCGAGAATATCCAG
AAGTATATAAAGCTCTTGATAGGTTTTAACCGGCTCATAATACCTGAGTA
TGGAAGCGATCGCCATTCTGGTTTTTGTGTTCTCATAAAAAGCATGGAGT
TCCGGTAGAATATACTCCGCCGAAGAATGTCTTATTATATCCACTTCCGC
CATATTCTGAGCCATACCCTTTTGATTGTATGCAATTTTTATAACATAAG
GAGTTCCAACTATGCGATAAACCTTACGAGAAGAACCACCTCCTATATAC
TCCACAGAAGGCAATTCATCCATCAAAGCTTTAAGTGCTCTGAAGGAAAG
ATGATTGTTCAGCAACTCTTCAAAATACTCAAATAAATCCTGATCTAACG
ATATGTTGTAACCGTAAACAATTTTCTCTTTCATTACTTCTTCTTATTGT
TTTTCTCCGTTCGCTTAAGATAAGCGCGAGCCGATTTGAAAACCCGTTTA
TTACTGGTATTTGCTGCAAAATTGATCATTTTCATAGCCCGATCTCTACC
CACTTTTCTGATAAGGGCACGCGCCAGCGATTCACCCGACTTGTACACAT
CATCAATATCTTTGTCTTTGGGGATTCCAAGCACTTCATGCATTTTCCCG
CGCTTGACTTTACCGCTTTTGAATGCTTATTGAATCCACTTTTCTTCCTT
TTTAGCCTCAGCCAGTTTACGTTTCTTGAGTTCCTTGATATACTTCAGAG
CGCGGTCATAAATATTGTGTTCAGGGTTGACGTTGGCGGCAAAAACCAAC
ATCCCCACGGCTTCTTTGTACGAAACTTTCTTCAGGAGATCACGCACCAA
TTTGCGGTGATCTTTGTAATGATCGACAATATCTTCATCTTCGGGGATTC
CAAGCACTTCCTTCATGTGCCCGGCTTCACGCTTGACCTTGCTCACCCAG
TCTTTTTCCCGCGCTTCTGCAACGGTTTCCCCACCTTCATCCAGAAGTGC
AATAGCTTCCGTATAGAAGAAAGAATCCCCCTCCGTTCTTCCAGAACGC
GCAACGCTTCTTTCAGAAGCTCCTTGTGTTCAATATGCATACGCTTTGCC
ATTTTCAACAAATCTTTGACAAAAGACCGGGCATCATAACCGTAATACTT
GGCGACAGAAACGACGGAAGGAACTCCAAGATACTTACGCAACTTCATTG
CTATGCGTTCAGCCGTTGCCTCTGGATTACCCATCTTTTGAATGAGTTCT
TCGCGGGTGACATTTTCGGTCAGCAGTTTCTGGCGAAATTCGTTAAGCTT
GGTTCTGGTCTCCTGCAAAAGCCGCGCAACACGGAGAATTTCCTTTCGGT
TCATATCTTATTCTCCTTTTCTTTTAATTAAAGAAAAATAAAGACTCTAT
GAAAACAGAAGACAGAAAAAAACTTGCTCAGGAAATCCTCGACAAAATCG
TAAACAAAGCCATGCAGCTTGAAACGTTGATTGACGATGAATACAACTAT
CTCAACAGAACCAGTGTGCTGGTTGAAGAGGAGAGCAATCTGATGTCGGC
AAAGGCTCGAATGCTTGAGCTACATATTAAGATTCTCGACACGCTGCAGA
AAGTGTATAAAGATCTGAAAGAAGGGATTCAGGAAGAAGACGAAACGGAA
AAGATTCTCATGGAGATTATCAATCAGAGCAAGGCTAACCTGTGAAAACA
GGTAGTTCATTCAATTTTTTAGCTATATTGATTCCCTGAGCTATCACCTG
ATCCATGTTGTAATAGTTATAAGTAGCCAGTCTACCCACCAGTATAATCC
CATGGCACTCCAGTTCGTTCTTCATAGAAGCCGCCTTTCTCTGTAGGTT
TTCTTGTTAATCGGATAGGCTTTGAACGAATTTTCCTGAGGATGTTGAGA
GGGATACTCTATGGTATAAACCCTGTCAAGATTCAGCCTGGAGTGATCGA
TAACGCGGGTAAAGGGTTCTCTATCAGAGGAAAGATGAAATCCGATGGAT
TCGAGCGTACTCCACTCTTTCAGTTTGCGAAGCACATAGGGATCGGAAGA
TATACCTTCAAGTTTTTCTCTGGTTTCAATTCTGAGATGAATGTAAGGGA
GATGTTCTTCTTTACCTGTTACTCTCTGGTAAAGCCTATCAAGGTCCCCG
GTATAAATAAAAGGGTTATTTTTATGTCGTTTAGATGATCAAGCGCGTC
TTCGGAATAAACTATATTGACTACCGGCACATAATTTCTGATATAATCAA
TCATCCGTATAATCATTTTCCAGTAACCATCAACCGGGAGCGCCACCATT
TTATCGTCAAAATAAGAGTGATATCTTTTCCAGTCGGTAAAGAAGGGAAC
GCGGGAAGCTACCGTTTTACCATCTCTTCATCCCAGTAATCTCCCCACA
CCTTTTTTGAGTAAGGGGCATACCAGTTTTCATAGACGAAAGATTTAAGC
GGTTCCGGGAGATTGCCTACCGGAATTTTCTGTTAAGAAGTTCTTCTTC
CAGCTCAATTTCTCCAAGATACAGCCGCACCCAGAAAAGAGATGAAGGAA
TAAATGAACATATATCATTTTCGGTAACAGCATAGGCATTGTAACTGATA
GAGTAAAAGGAAGAGAATCGCGACACAAATTTGATCACTTCGGGGGAATT
```

FIG. 1L2

```
GGTATGAAAGATATGAACCCCGTATCGGTGATATTTTTCCCCCGGTCAA
AATCCCAGACGTTCCCACCGGGGTGGTTGCGCTTTTCAAAAAAAGTAATC
TCTTCAAATCTGAAGCCACGATCAAGGAGAGAAATAACGGTGCTGAGTGC
CGCAAGACCTGTTCCCCCTACAAACAACCGTTTCATAATTTTCTGACCTC
CGGGTCTCTTAGCACTTGAGGAAACATACCCTGTACCTGCTTTCCGACAA
AATAATCCATGTTGACGCGCCGAACGGAGAATATCCGAGAAGGTCTGTAC
ATATGTGCGTGAGATAAATACGGAAGCGTGGCATATCTCCACTTGAACGC
ATGTGCCACATGGATTAAAAAAGTTTCCGTGTGGGTTGGAAGATAATCGT
AATACTTTCTCAGAGATTCGAGATAATACCTGTTAATAACGTGCCCCCCG
TCAAGATGCATGAAAACGCCGCGCTTGTGCAGTTTGTTTGAAGTCAAATA
ATTGTAGACATAATCGGCATATTCATTAAAAAGCTTTACATCGAAATAAT
CGAGAAAATGTTCTTCTCTGATAACAATCTCTCTCCAGTCTTTTTTTGCG
AAAGTCTCCACATAACATGCGGCGGCGTAAATGTAATATCCCTCAGGGGT
TTTTAACCTTTCATCGGCAAGATGATCGGGAAGCTCAATTCGCTCATACG
GATCTTTGAAAGGTGTTTCGTTTTGATAGGGAACAACCCCGTAAGGTTCT
ACCATGTTGGAGCAAATCATAAAATATTTATCGAAACACCCCTCCTCGAA
TGCTTTATCCAACCCTTTCAGATATGCCGGGGGAATATAAACATCGTCGT
GCACAAACACCCCGGCTTCTACACCAAGAAGACCAAGTGCGTCAATAAAT
GCAGCAAACTGAGAGTACTGAATTTCATCTACAAGAAAAACATTAAGTTT
GTGATGTTCCAGTTGATTTTTAAGCCACGATCTCCAAACTTCTTTATCTT
TTACCGGTTGAAGGTTGAAATGCTGGAGCAATTTATAATCCGGGTGAAAG
CGCATTTCCGGATAAACAAAAATATAAAAATAATCCCGAAGGTGTGAAAT
GTGTGGGTAAATATTTTTAAGCCACACTTCGGGAATTTCCCCGAGCGTTA
TCATTACAAAGGCGATTTCCCCGCGATAAAAGAAGGGTTCGGGGAAGAA
GAAATCTTCTCAACCTTCATTGTTTTCCGCAATTTTAATTACAACCCGGT
TTTCTTCAAAGTTAAGCTCGAATTCCTTTTCCGACGCATTGATTCCAAGT
TCTTCCAGTTCCTTTTGAAGTTCCCCCATGATCTTCATGCGCTCCCGCTT
GGCTTTAAGCGCATGCTCGAATACGTTCACATCGCCTTCATCGACGATTT
CCACCAGCATATCAAAGACAAGCACCGCCATTTCAATGTAGGCGTTGCGG
AGTTGCATTTCACGAAGTGCAAGGGATTTGAGCTGGTCAACCTTCTCTTT
GTCTTCTACGACAATGGTATTTTCAGAGCGTGTAACGGTAGGTTCACCCA
CTTTAATGAAATCTTTCCCTTTCATGGCTTTTTTTGATGAAAAAACGATC
GGGTCAAGAAAGGTTTCAGAAGGTGTTAAGCGGATATTCTTCAGACGCC
TGAGCTTCCGAAGCCGCATCGTAATCGCCAACCGTAATATAAATATCCTC
AATTCCAAAAAATTGGGGCGGATAGCGAAATTCATAAAGCGTAAGTTCAG
ACGGCGTTACAACAATATCAAATATCCACACCACCACCTTCATCATTTCCA
AGAATAATCGCTTTGCAGTTGATCTTATCCGATTCGGTAAAGAAAGGTTT
GCTTCTGAGAACAAATCTTCTCCCTACCGCAACAAAAAGGTTGGTGCCGC
TTTCCGGGTAAAAATCGACGTCGTTGTCTTCAGAATCAACGATGGTAAAC
ACATTGGGTTGAATATAAAGCGTATAAGATTTGTTGACTCCATAAGCGGT
TTGTGGTTCGATGATAAAGTTCTGAGGATACTGTGTTTCATAGAGGATAT
TTACGTTTACGATCATCGGCATGAAATCCCTTCGATCCCCTTCATCCGTT
TCATACAGCGTAACCAGATGAAATTTGCTGTCAAAAATATTCCCCACTTC
GCGAGGTTGACGAATGATAGAAACAGTTGGGGAGTATACATTATAAACCA
CTTCGTCATCTGAAAGGGCGAATTTTCCCATCGTACGAAGATAATCGGCA
ATGGAGATTTTCTGGCGAATGAGCTTTGCAATCAAACGCTGACCGTATTC
TGTAAGAGACGCCGTAACAAGCATATCAGAATTCCACCTTCAGTTTAATC
ACGTATTCATCTTCGTTGGTCTTACGAAGCGGAGAGGAAAGTCTTCCAAG
CGCCACAAGCTGATTGTTCTGATCATAGATTCCAACGGTGGTAATATAAG
TACCCTGATCAGGATACAAAATGCGTCCGGAAGTGGGATCGTAGAATGTG
GGATTGAGCGAGTAATTGAATTCGCCAGCCTTTACGCGACAGAAAATAAC
CATAGAGTGAATGTTATCCACCATTGAAAGCGTCATGTCAAGAATAAGGT
TGGCGATGTTTTCATGAAGTTTCGCAACGCCACCGACCGGAGGATTGCTG
TCAATCGGGAATCCGGTTGGATCCAGCATGTAAAGCGAAGTGCTGTATCC
CCCCGATCCAACCCCAAGCGAATGAGAGACAAAATCGCCGCATGCATCCA
GATCGATCAGAAGCAGCGCCGACTGAGGGAATACGATTCCAAACACCTTC
TGAGTTATGGAGTGGGTTACAGGAACCGCCTTTCCACTCTGAAGTGAACC
CGACACCAGATAGTAGAACGGCTGCACCTGGGTGCGGATCGGAGTAGCGA
GGTTGGTTTCGCCGCTGTTGTCAACCAGAGACAGGGTTGCGCGGTTTGAT
CCGTCGGTGAAAGACAGGTTAATCTGGAAATTACCAACATCAATTGTATC
GGCAAAATTATGGAAGGAGACTACCATGAAGTTCTTAAGTTCACTGAATC
CGGCACCGGGATTTGCGGGATCACGGGAACAGTAATAACATCAGAAGCC
AGATTGGTTTTGAATTGATTGATAAAAGCCAGATAATGCTTTCGAGTAAT
TTCATTAGTTCCACCGCCATAGTTCCCTTTGGAAGCAAACGCCACGGAAA
```

FIG. 1M2

```
ACTCCGGATCGGTGGTAAGCGATCCTTTGAAGATATTCACATAGTAATCG
TTGTAATGATCGGGTTGCGAAGAATAAGTTACAAAATCGTTTCGTGCAAT
AACTCCGCTTTTATCCCAGAACCCCGGAACGGCTACATTTCTCGTGCTGT
ACACCACGTCGTCAATTTGCTTGAAGACAAACCCCTGAGGCTGCGGAGCC
GTCTCAGCTTCCGTAGCGATGTTGTTGACAACGTTTCGTATAGTTTCGAG
CTCTTCCGTAGTGATAGACAGATTCGATTGCAGATAGTTCAGAAATCCCT
GCAAAATCTGTCGCTTGGAATAATCGGTAACCGTTCCAAGTAGCGTGGTA
ATGTAGGAAATAAGTTGCTCTCTCATAATCTTATGTAATCAGTTTTACTT
TCAGTTCAGCTTGTGCACCACTTTCGTTGCCCCTGATAAGCACAATGGTT
TCGGTGTTGGGCGTAGCCGTTTGCGCCGGTTCGATCACAAACTTGCGCCC
GGAAATCGCTTTATAGTCGGGGTTGCTTGTCGGGAAGGGGAACGGCGCCT
GTGTCGACGGTTCAGCAACAGAAATGTTTAGCTGTTTGCTATCATAAAGC
AATGAATAACCAAGAATCTTATCAAGTGCAACCACAAACTTTGTACTTGG
GATGAAGAGATATCGGCGAAGGTTATCTGTAGAAGTAACCCTGAGCACGA
TTTCACTCTGATCCAGAAGCAAATGGGAATTTCGTTGACAATGATATTC
GGATCGCCTACCACACTGAAAAGATGATAGCGCGGCACTTCAAACGGCTT
GGGTTCTACCAGCGAATAGCTCAGAATTTGCGGAGGGTTACCCGCGCTTG
CAGAAAACACATATTCATAATCGATTCCGTCGTCAGAAAGTGCAAAGTAG
GCAATATCGAAACTACCGGACGCAAACAACCTTCTACCGTATGCCGTGAG
CGTGGCTACGGAATATACCGTGTTTTCTGATTTGGTGGGGATAAACATTT
TTTTCTTTAAATAAAGTTTTCAGTTACCCACTACAAGTTTTAAAAGCTCA
ACCAGTATCGAAGGGTCTACAATAGCCAGCGCAATGAAGGGAAAAAGTGG
CAAAATCAACCCGACAATAAATCCGGTGAGTAGCAATTTGATGAACAGTT
GTTGTTGATCTTTTCTGTTCTGCAATGCATTGTCATAAGCGCCCTGCAAT
AGATCACGATATTTTCACCCACCTCCGTTTTATCTTTAAGAGACTCGAT
TTGAACGCTCAGTCGATTCAATATATCTTCTATATCATCAAGTTTTTCTC
TAATGTTGTTTCTATCCTGTACAACGGTTCTGAGCACATCTTTAATATCT
TTAATCATTTCAATGATGTTCGATAGAATGAAACGTATCTGATAATCTCT
GTCAAACTGTTCTTCGTTCATCCCTGTTTTTAAATTAAATAAAAAAGGGG
AGACGACACGTAGTACATCTCCCCCATAAAATTATTTTTTATGCGAATTA
AGGCGTGCGCTTTTCCAGAAGATACATCGTAAGAACATCGCCATTTACAG
CAAGCAGTTTGGTACCTTCCCGGTTGGGGAAAGGATTGATCCGGTTGAAA
TCAATGCGGCGCATTTCCTGACGACTATCCTTTTCAAAATGGTTTCTCAG
GAAATTCAGAGCATTTAGCGTATAATACATGTCATTTTCTTTCCAGTAGT
GCGCAATGATCTTGCGTTTGTGGTTCAGCACGAAATCCTTTTCGCGGTGG
AATTCCGGAACGGAATAAATGACATTATCCACCAGCGAGCAGTAATCGGC
AAGATCCTGAAGATGAGCATATTCAGTTGAAAGAATATCAGGAACCTCGC
TGGGAATGTACGTGTCATAATCCCCGTAAACAATTCCCCGGATATTAGCC
GCATTGTAAGTCGAAGACTCGACAAAATGCGTTTTCAACCGCTTGTCTGA
GTAATCCTTGGAAAACAGAAATATCCGGCTTGGATTTTCAGGATCGTCGA
ACATTAAAAGCTTTTCAGCCTTAACAAACCACTCATATTCCGACTTGAAT
ACCGGCTTGAAATAGAACACGGTGCGGAATTGAGTGGAACGTCGAGAGCG
TCTTGGTTTTGCCAACGTACCCATAGTCTTTCTCCTATTTTTTTTTGTT
TGGTTTTAAATACATTCTGTGTAACAATAAAAATTCATAAAGGTTTCAAA
GATTTTTACAATTTCTTATTTAAAGAAAAATGCCCGCAAAATCAAGAAAA
CAACAGAGATATATATTCTATCTCAGAAACAAATATGGATCACCGGAAAA
AACCCCCAAGAAATACAAATGGATATGGCACAAAGATTGGGAGAAACTGG
AGGAAGCCAAACGTAAAAAGAAAAAGAAGAAAAGACGTAAAAATAAACGC
TCTTACCTGAAGCCGGATTCCTATTATAAGAAACCATACGGTTATTACGG
AATCTGGTATTACCATTATGATGACGGTGTGGATGATGGGGAGATGCGG
GTGATGGTGGAAGTGGTGCTGGTGTGGGTGAAGCTAAAGGTGCAAAACCT
GCTAAGAAATCTAAAAAAGAAGTGCTCCGCGATCTTGAGGTCAAACTGCA
CGACTTCAACAAGGAGTTGAAAAAACTCCTCGAGAATCTCGGATTCTAAA
AAAAGAAAGCCGGGGAATCAACCCCGGCATTTTTTGTTTCACCAAGGTAA
ATCGTTATTATCCGTCTGACACGACTCAATCAATTCCTCTTCTTCCGGTT
CTTCTTCTTCATAACTGTAAAACCATATATGAAAGTAATATCCCCGCCCT
TCTTCCCACTCTCGCATTTGCTGCTCTTCGAACACGTCTTGCAAAAAACG
CTTTGTCAAACTCATGGCTCCCTCCTATTTTGGTTGACAAATCGATTCT
ACTGGTAATATACGCATTGATCAGAGAAAAGTCAAATGAAGAATCTGTTA
AACAGAGATATATCCGCACTCAGCGGAAGTGTAGATGTCAACCTCAGATA
CAATCTTATAAAGTTTTTTCATTAGCACCACAAAGTCTTCTTCCGGAAGC
TCTAATAGCAATTCCTCATTATATTTGAGAAGGGGAAGCATAGCTTTACT
TCCGCTACCCACCGAATAATAGGGATCACGAATGAACATTGTCGTGAAAT
TGTCGGATACCACAAACACCCCGTGCTGACTGATTCCCATAATTTTCCCG
```

FIG. 1N2

```
TTCATATCCCCATTATCATTCAGAAGATTCAACCCCTTCAGATGATCTCT
CCACTTGTACGTAAACGTCTCTACAATCGTGTTTTTGCTGTAGGATTCTC
TGTTAAAGATAAGCGGCGAGGAAAATTTTGCAAAGGCGTTCTGATAGATT
ACCCTTCCGACAAAACCAAGCGGAATTCGATCCACCAGTTCGGACGGCGT
CTGAATATCCAGAAAAGCGGCTTTGGGGTCATCCCTGACCACCAGCATGC
CGTCCATTGTGGTGGTATAGTCAAAAAAAACATACCGCTTATCGGCTCTG
TCAATGGCTACTACCGTGCTCATGATTATTTAAGGGTTTGCGTTAAGGTG
TCTTTCAAATGATACACAATGTCTCTAATCTCAGCAGGTATAAGTTCTCT
GATGGTAAAAAATTCGTCAGGAAATATTATCTGTCTCAGATTAATATATC
CTATTCGGTTGTGATAGCGAACTCCGTTCCCCACCGCTACCACAATATGC
TCGAAAGGTGAGCGGTGTCCGTTTTTGTAAAGTCTTCTTGCAAGTTTTAA
ATTTTTATCTAAGTCGGATTCATCAGAAGCATAGGAAACGCGGGCTATAC
GCGCCACCGATGTAACCAGTAGTTTGGAATTCAATTCCTCCGGTGAAATA
ACTCCCTGAAGAGGATCGACAATATCTCCGGGATTGGCTTCGAAAGCCGG
GGAGTTGTCGTAGATATAGCGAATCAGGAGCGCTATTTTCGGAATTCGG
GTTGTGCGTCGGAAGCGCAACGAAGTCTGAAAAAGTTGTCAAGCGAATAC
GGATCGGCAATGGAAGCGATGACATCTGTATATGCATAGGGTGAAAGTAT
TCGATTAGCGTGTTGCTTGTGTACATTGAGTTTCTCGAGCACAAAATGCA
ACCCCGCTGATGTATATAACCCGGTATACCAACACCACCTTGCCAGCACA
TCTTTCCACCCTCCTATTTTTTATCGGAAAACATTGCCCCTGAGTTTTC
CACAAAATCATCTGGAACAAAGGGGTTTTCAAGTACACGCTTCCGGTATT
TTTTCAAGGAAATGGCTCTTGTAGAAGCGGCATTCCTCGAAAAGGCGCGA
TGTGTATTAAATTCAGCCAGTATGACTGTGGGAATTTGAAAGCGAAAGCA
GAAGAAGATATCGTTATTCGTCTTCGTTTTGATCAGATACCACACCATTG
CTTTCTGAGTTTTTTCCATTTAAAACCGATCCATTTAAACAAAGTTTCAT
TTCTCTGATTTCATCTTTCAGGGTTTCAGAAAGGTGTAATATTTCATCCC
ACTCGCGAGTATTGCGCTCAAAAATCTCAACTCCACTGGAAACATCACTC
ATCATTTTTTTCCTCCTTGTGTTTAATGTTGTGGTAAATCTATAATTTGC
GGGTGTTGCCAGAAGCGCATTTCATAGATACCCCACTTTCTTTTAAATAA
AAGAAAAATAACTTTTTTTAAAAAATTATTTACCCCGGTCGTCAAGTCTT
CCAATATCCGGCTCTTTATAGGGATGAATGCGATATTTCTTCTGGAAAAA
CTCCTTCCACTCCGGCGATTTTTCAAATACGACATCCAGATTGTCGATAA
GTGCCTTTGCCACCATGTGTTTGCAGATTCTCCCCCGGTAGTAATGATCC
GGGCACGTACATTTGAATGTGCGGGTGTCAAAATTGACGCGCGTTACGTA
TTTTTTGTAGGAGCCGCTTTCGAGAGTATCACGGGCGCGTTCAAGCAGCG
TTCTCCCCTGTTTGTCTTTCTGAGTCTGACACCATTTGAGAAAAGAGAGG
AGTTGTTTATATCGCTTATCGAACGTTTCAAGCCGCTTGCGCTCGCGTTC
TTCAATAGAGCGCTTGAGTTCTTCAGCCTTTTGCTGTCTCTCTTTTATAC
TTGGCGGCGGCATACGCTCAGATGTTTAAAATTCTCCGAAGCAGACTTTC
GATCTGATCTTCGGTAAAATCTCTTTTGGATATATAAAGCACAAGATTGC
GCTCCGTGTTGTTTTTCGGTGGGGTGTTTCCTTTGAGAAGGTTTCTGAAA
TATTCGATGAACTCTTTTTTAAGCTCTTTTTCCGACTTTCCGGTTTTATT
CTGCACAAGTGTTTTTTCGGTGGAAGTAGCCTCTTCTTCGTTGACGGCGA
CATTATATATAGAGAGCATGAGAAACATCTCTACCGCCGGATCGGTAGCA
TGACGTGCAGCCATATCGGCACTTCGGCGCTGAATGGCTTCATATAGCAG
TGATTCCTCGCGGGTCATTCTTTTCTGTTAAATAAATGTGAATCCGTAGG
AAAGGGAAAACATCAGGGGAAAGCACACATATAAGAACCAGAACCCAGAA
CAAAAAATAGGAGGAAGGTTATGGGTAAGATCGATGTTTCGAACATCAAA
ACCGCCGTTGCCATCTCCCAGAAAGCCAATGTTCCTCTTTATCTGTGGGG
TGGTGTGGGAATCTCCAAAACCCAACAAATCTATCAGTATGCCACCAGCA
CCAATCAAAAATGTGCTGTCGTTACGGGGTTGGCAATAGATCCAACCGAC
GTAGTGGGTCATTACATTGCCGACTTCAATAAACGTATCACCTACCAGAC
CAAACCCTATCTTTATGAACTCTTCGGTGAGGAAGAGCGGGGAATCATCT
TCCTTGACGAATTCAACAACTCAGAAAGTGATGTGATGGGGGTGTTTCTA
AAGCTTCTCGACGAAAAGAGGCTTGGAAGCTACAAACTCCCTGATGGAAT
TCACATCATTGCAGCCGGTAATCCCCCCGAACTGGCTCCAAATGCTTCCT
CGCTTCCGCTTGCCGTCGCTACTCGATTTGCCCATCTTTATGTGGAAGCG
GATTTCATCTCCCTTAAGAGATGGTTGAAAGGAGCGGAAGATGAAGAGGA
TTATGTAAAGATTTTCAATCTTGAAGTCGGGGAAGATGTTGTTCAGCAGG
TGTTCGATATTTTCGTTGACTACTGCATTGAAAACGGTCTTTTCCCGGCT
TCAGAAGATTCTCGTAGTTGCGAGTGGGAGGGGAGCCTGAATTACCGCAC
ATTGCACTATGCAGCAAAAATCGGGGCTGTATACAAAGTTGCTTACAAAA
ATGTATCAAATCAATCGACACTGTATAATGTAACTGTAGAAATGATCCAC
GGTCTGGTTGGAACCATCGCTTCCAACCTGATGGAACATCTTGAAAACAA
```

FIG. 102

```
GTGGCTTCCATCGGCAAAAGAGATTCTCGAAAACTATGATATTGTGCTCA
AGCATCGAGACGCCTATGCCGCCCTTGCCTACAACCTTATGAGCGGCATT
CAGGAAGAAGACTATCCGAGGTTGGTGGATTTCATGCAATGGTTAGAAAA
GAAAAACGAACTTGTAATGCTTGCGGCGATAGTGGAATCTTTCCAGTCGT
TCATTCCGAAGAAAGGTTTCTGACAAGCCGGTTCGAATACTACAACCAG
ATTTTCAAAATCATTAATCGATCGCTGGACGTCTATAAGAAAGTCAAACC
CACAAACAACAAGTGATTGATTATGGAACCGATTGTCGAAAAAAGCTCT
ATGAACTGATTAACTGCATTGTAAAAAATCATACCCCACTCGCCATGATT
CTTTCCCGAATCAAAGTGCGGGTAGGGGTAGGGATAAATACACACTGGG
ACTCTGCAAAGAACGGGAAATCATTCTCAGCCGGTGTCTCTTTGATGATG
AAATCGTTTATCCCAAACTTGTATTTATCAAAGACCCCGACACCGGCGAG
ATCGTAGACTATGATATTGAAGACTATGTTGCCAAAATCGATGATGAAGG
GCGGTATCATACCCTGCTGGAAGAAATCATTCATGCCGGTCTCATGCACC
CCATGCGTGTAGACCGGTTTCAGAAAACATATCAGGAGCTTTTTGAAAAG
AACAAGCGGCTGGTGAATTTTCTGTACCTTTGTCTTGAGGTTGAGCGTCA
TGCAATACATACCGCTGTAGCCAACATCGATCTACTTAAGCCCGTGTTCA
AAGACAACACGCGGGATGAAAAGATTGTGGAATTCATTAAAGTTATTCAA
CATGATCATCCCGATCAAAAGCTGTTTGGGTTTACTTTTGAAAGACTGTT
TTTGAAGTATCTCAACGATTTTGAGGGAGGTAAAATTGCAGCCCCCGCAA
TTTACGATCTGATGGAATACGACGGGAATACCGTTCCCGACAAGTTCATA
GAAGCAATCGAAAAATCTCTTCATAAAGGGAAAAAGTATGGAAATCAGAC
ACTGGATGAAATCTTTGAAATCCGGCGTGTGGATCAAAAGGGGTTGCAAT
TGACGCAACTCCTGAAGCAGATTTGCTTCCGCAGGGCACGTAAAAAACCC
TCGCTGCACGTGCTCGACAAAAAGCGGAAGCACTACGAACCGCTCAGGTT
TGGGAAAATCAAAGAAAAAACTTCAAATATCGCCATTATTCTGGATGTGT
CGGGAAGTATGCTTCGTGATTTCAAAAAGCATCGCCTGATTGACATCGCG
ACAAGTATGATCGTGGAAACTTTCAAAAACGCACCCAATATCGATGTATA
CATCCGACATACCGAAATCAAGGATAAAGCGAAGATCCGCACCCTGTTTT
CCCGTTTCAAAGGGGCGGTGGAACCGATATGTCTAACATCTATAAACAA
CTGAAAGATCGATACCAGAAAATACTGGTTGTTACCGACGGGGAGACACC
CTTCCCCGAACCAAAAGACTACCGCCCTCAGGATACTTTTATCATCATTA
ATGATGAAATGCCCGAAATTCCCAATTACATCAAAACCCTGAAGGTGAAA
CTATGAACGAAAAAGCGTTCCAGTTCCGCAATCTTCTAAAGGAAGTGATC
GGCATGCGAATCCTCGAGCGATTCAACCACATAGAACCTGAAGGAAAAAC
GAAATGGGTAATTTTATCCGCCTACATTCTAATAGTGGAAGAAGAAAATG
CACCCCAGATCTGCAAGGAACTTGTTCGAAACAATACAGAGATAGATCCT
CTGGAATTTGTCAGATCTTTCAAAGAAGAACTTATAAACATGATCGAAAA
TCAAAATTATCGAAATGAATTTGAGAAATACGTTGCAAACTACGCGATAG
AAAACGAAATCAATTACAGAAACATGATAGCAAACTTTTTCTGATATAAA
AAGGAAAACCCCGGTTCATCACCGGGGGCTTCCTCAGCGTCTCTATTCCCT
ATCGGGTAAGTTCCGCCATTACGGCTGCAGGAGCTTCACATACAGCAGAC
CATAGAACTCTGGACGCACCACCTCCAGAGCGTAGCGGGTCATCAGACCA
CGCCGGTAAGAGAAGTTAACGGGATCGACGATCGTCGGCGTGAACAGCAG
CGGCACATACGGAGCGTAAACCGCACCCGTTTGCCACGGCGTGTTCAGAT
CTTGATTACCCATGATGATCACCGGCTGGTTCTGATAGATGTTCTTGTAC
AGGCGGTAGCGTCCCTGCACCATACCTACATAGAAGATACCGGTACCACC
ATCGCGGTTGTCGTTACCCGGCGTAAAGCCCGGCATCGACTCCAGCAGCG
CAGCCACCTGTGGGCTGGTAACAAGGAAGTTGGCACCCGCAACCGCCGTC
TTCTGCTGAATGCGGTTGCTGACCTTGTTCAGTTCGATCATCAGGGTAGC
CAACCATTCCTGCTTCGAGCCGTAGAAGTTGCCGGCAACAAAGTTACCCG
ACGTTCATCGTAGTATTCACCGACCACTTCCGACCAGAAGCCATAGTTG
TCAGTGCGCCGGGCATGCGCCATGATCGTCGACAGGATTTCCAGATCGAT
CTCACGGGCAATATACTGAGACATGAGCGTAACGATTTCGTTTTCAAGAT
CGACGCCCTTATGATAGGCGGCGAGATCCTGCATCGCTTCCGGCGTCCAG
GCGGCACGCAGCTTACGGGTCTTGGTAGCCACCGGACGGCTCCGAAGCTC
AAGGTTGATCTCCGGAATATCCAGCGACTGGAATCCGGGATCCGGATAGT
CAGGATCCGTCGACTGGTCTTCGAAGTCGTTTCGAGCATCGATGTAGTAG
ACCAGATCAAGGTCTTGAGTCGACGGAGTACCACCGGCAACGGTCGCAAA
GTCAGAGCCGGTTACGAAGAACAACCGCGCGTACAGCGCCGAACCGACGG
CACCGACGATCCGGTTGTAGCGCGGAAGCGGGTAAGCGACCGTGTTTTCA
GGATCACCGGAAGCGTCGTCATATTGCCAGAAGCGCACCGTATTCACATC
GGCGACACCGGGAAGCGACGCAACCGGCACATCCACATAGTACACCGCAC
CGCTCGAGACCAGTGAAGCAATGCCGGTGTCAAAACCGACATCCCGCATC
GTCGCCTGCTGGGCGGTAGCCAGATCCACGGTGATCGTGGTCTCATACTC
```

FIG. 1P2

```
CCGACGCGACAGGCGAGCGTTTTCATCATACAGACCGCCCGTAGCCGTGT
CGGTGGTCAGACCGGTACCACCGTAGACCGAGCCGTTTCCGGGAAGCTCA
GGCGACTTGAAATCCAGATAGAAGACCAGACCTGTTGGGAGCGACAGCGG
CTGCACCGACACCAGATCCGTCGCACACGCAGGTTGGCGAACACACGGCGCA
CAATCGGAAGTGCCAGATTCCAGCCGTCAACCTCCGTGGTCTGGGTGGTC
TCCATCAGGTGCTTCTTAGCCTCGCGGTACTGGTTCTCCAGCAGGGTAGC
GAGCGTATGCCGCTCCCAGTCGTTACGGCAACCCTCCAGAAGCGGTTGCC
ACTTCTCGATAAGTTGTTCGTTAATTTTCGGTTGGCTCATTTTACTCTTA
TTTTTTTTTGTTTTAAATCTCTAAAAACATTCGGTATTTAACCGAATTA
GAGTCCGGCAAGACGCTTAATGCGCTCCAGATCCAACAGCGGATCCTCAA
CCGAACCCGACGTGCGGGATTCGGCGACAGGTTTCACCACACGGGTTTCC
TGCAGCTTGCGCTTGATCCGCTCACGAATGCGCTGGCGGGTAACTTCGTC
AATGACGGGCTTCTTCACCCGGCTTTCCCGCATACGGCGCGGCGTCGGAC
ACGAAGCAGCTTCCGCCATTTCCTCCGTCTCCTCACCAGCCACCTTGCGA
AGCAGTTCGATAGCCTCCTCTACGCGCTCAAGAAGCGTGTGCAAAAGATC
CATTTCTTCACGCACATGCTCCTCGCTTTCGACGGCACCCTTGATGTCAA
CATCAATATCGAGTTCTTCGTCGTCCGAAAGATCGGCATCCTTTAACTCG
ATTTCGGCTTCCAGCTCGCCGTCTTCGTCGACGTCTTCAACATCGATTTT
GATGTCTTCGTCATCCAGATCCAGTTCCAGATCCTCCTCATCGAGATCCA
GTTCCAGATCTTCGTCTTCGTGTTCGGCTTCGGTAATCCGACGCTTCATT
TTGTGTTTAGCTTCTCGCATTTCTTCCTGTTGTTTAGTTTCCCAGGCTTT
TTGCAACGTTTGCGCGACTTCTTCGGCAAACGAAGCAAGCGTGTCATCGT
CAGTTTCATCAACCTTCGCTTCCGTCAGGGGATTACCTTCAGGCTCTTCC
ACCTGCTCAAGCTCTTCTTCGAGTTCCTTCAAAGCCTCCCGAATTTCTTC
GGTGATCGAGTGAATGGAAGCTTCCTGAAGATGCCTCTTCTGCTTTTCCT
GACGAAGCGACTCAAGGTAACCCACAAAGTCTTTAAATTCCTGCATAACT
CAAATTTAAATATATTTAATCGCCATTCATTTTAAAAAATGGCACCTGCT
ACGTGGGAATATTAAACCCCACATCAAATTTAAATATATATTTTCCGCA
CGAAATAAAAAAAAGGGAGAGAAACTGATCTCTCCCCCAGGGGTAACATG
TATTTTATAACTTGTGAACTACCACCACCTATAGATGTGGATGGCTTCGT
GGTCAAGGTAGCTCTTGCTACCAGATTCCCCACGCTCAAAGGGCTGTTCC
ATCCCCGAATTTGCCAATTATTGGCTAATTAAATCACTTTCTTCTTCACA
AGCGCCTCGCGCAATCTATGGCGTGCTCTGTTGATTCGAGATTTGACGGT
TCCGATAGGAATGTTGTTTTTCTCAGCCAGCGCCTGCATGGCACATTTTT
CCTTCAACTCCATGTACTGTTTCATTATATTGTAAAACGGGTTATCGCCT
TTTTCAAGTTCTTCCTGAATCACCTCCACCGCACGTTTCAATTCATACTG
CTCATCAAGCAGCGGCTCTCCGGATTCAATTTCTACAGGGGTATCCCGAT
CTCCAAATGTAATTTCTTCCATGTAAATCCTGGGACCACGTCGAGAATTG
TATCGATAACGGGTAATTACAACGGATTTGAATACAGTGTAAATATACGT
AGCGAAAGAAGCTCCTTCAACCACGCTATAGGAATCAAATCTAAGAAGCC
TTAGAAACGTATCCTGCACCATATCCTCGATTTCATGCTCCGACTTTGTA
TATTTCTTTCCGAAATTTTTGAGCCGCTCAGCATACCTACTGTAAAGCAC
TTCATAACGGATTTCGAGCGGAACGTTCTGAAGGAAAAGTTCTTCGTCGG
TCATCTGATAGTATTTACGCTTATCCATAACTTCTCCTCTGTTTTAAAGG
TTGAAAATGATTTCGTAGCCGTCAATGCGGTCATCAGTTATGAGCTTGTC
ATAAAGATCGTCAATCTTTTCTATGTTGTCATAAATCATGAGCATTTCAT
CAATATCATGCACAACAACAGAAATGTAATAACCGTTTTCTTCATCAAAA
CAGAGTTCGGCGTAGCTTTTATGAAGATCCCCCACACATTTTTTGATATT
CTCTACAAATACTTCTACAGGATAATATCTAACCAGACAAAAATCGAGAT
GCGGAAGCACACTGTTCATTATCTGCTCCAGCCACCTCTTCATTAGAAATC
AGCAGTTCATAATCGTCAATGGTATTTACATTGTAGACAAGATGGTTGTT
GGATGTAATAGTAGGAATGACTTCGTGAGTTGGGTTGAAATATGTGTTTA
CCAGATCTTGAACGGAATCGAGCGCGTCGCGATAATCAATTTTAGTCTCC
ATAGCCATATCCTAAAAGGTTGGTTGATATATACCGGTTATGGAAAATAA
AAAAGGGGAGAGAGGGTGTTTCCTTTCCCACACCCTCTCTCCGCGTTTAT
AGGGAAAGTCGTCATCGAAGTAGCCCTCAATCTCCTCCATCGAATGAGAT
TCTTTTTCGGGAGAGATTCACCTTTTTCTTGGGGGGATTACAAAATTCCT
CTTCCGCGGGATCAAAGCCCCTAATGGAGAATCTCTTCCTGGCGGGAGCG
GGTTCATGCTTCCCCAATCATTGTTATTTCCCAGACAAACACATGGACG
TCTCTTCCACCAACAAAACGAACTTCTCCCGAATCGGCGGAGATGTTCGG
GAGTTCACCGCGAACCCGGATCAGGGATCCCACCCCGGCTTTCCGCACAA
GATCGGAAGGTCCCGTTGTAAAAGTAAATGTTGAACCACTCGGTGCTTTC
TTGCTGACCGTCCCACCGACGGACCGCCAGCCGTACGGTGGTATAACTGT
TTCCGCTA
```

FIG. 1Q2

| 1 Locus | 2 start | 3 stop | 4 nt | 6 aa | 5 dir | 7 confidenc | 8 Partial %ident | 9 putative protein | 10 protein (genbank) | 11 aa | 12 Match organism | 13 identity vs. match |
|---|---|---|---|---|---|---|---|---|---|---|---|---|
| Transc.fact. | | | | | | | | | | | | |
| 1 | 133 | 744 | 611 | 204 | 1 | 4 | | | | | | |
| 2 | 290 | 715 | 425 | 142 | -3 | 5 | | | | | | |
| 3 | 1086 | 1505 | 419 | 140 | 3 | 5 | | | | | | |
| 3.1 | 2091 | 3476 | 1385 | 462 | 3 | 1 | | | | | | |
| 4 | 3446 | 4396 | 950 | 317 | -3 | 5 | | | | | | |
| 5 | 3490 | 3885 | 395 | 132 | 3 | 5 | | | | | | |
| 6 | 4415 | 5056 | 641 | 214 | -3 | 5 | | | | | | |
| repl | 5056 | 5823 | 767 | 256 | -2 | 5 | 45% | "Rec N" | | | | |
| 7 | 6064 | 6948 | 884 | 295 | -2 | 4 | | "replicase" | | | | |
| 58=61? | 7004 | 7846 | 842 | 281 | -3 | 5 | | | | | | |
| das=rnh | 8212 | 9168 | 956 | 319 | -1 | 5 | 24% | "helicase-primase" "RNAseH" | gi:4490554 | 305 | Herpes-virus T4 | |
| 8 | 9111 | 9683 | 572 | 191 | -1 | 1 | | | | | | |
| 9 | 9165 | 10619 | 1454 | 485 | 3 | 5 | 27% | "Unknown" | gi:2447052 | 289 | Chlorella virus | 74/268 |
| 10 | 10489 | 11094 | 605 | 202 | -2 | 5 | | | | | | |
| 11 | 10616 | 11893 | 1277 | 426 | 2 | 5 | | | | | | |
| 12 | 11992 | 13671 | 1679 | 560 | 2 | 5 | | | | | | |
| GP50-myco | 12026 | 14008 | 1982 | 661 | -2 | 3 | 24% | "Ribonucleotide | gi:465365 | 682 | Mycob.-phage | 146/603 |
| 13 | 13977 | 14636 | 659 | 220 | 3 | 5 | 26% | "glucosyltransferase" | | | | |
| a-gt | 14640 | 15269 | 629 | 210 | 3 | 5 | | | | | | |
| 14 | 15254 | 15760 | 506 | 169 | 3 | 5 | | | | | | |
| 15 | 15403 | 16041 | 638 | 213 | 1 | 3 | 23% | "T4-primas-helicase" | P04530 | | T4 | 55/237 |
| GP41 | 15785 | 17035 | 1250 | 417 | -1 | 5 | 42% | "DNA-polymerase??" | | | diverse | 19/42 |
| dnapol? | 17032 | 17826 | 794 | 265 | 2 | 4 | | | | | | |
| 16 | 17847 | 20267 | 2420 | 807 | 1 | 5 | 45% | "unknown" | | | Aquiex | |
| 17 | 20254 | 20619 | 365 | 122 | 3 | 5 | | | | | | |
| ExoU | 20276 | 21241 | 965 | 322 | -3 | 3 | 27% | "Polymerase**" | gi:3511205 | | diverse | 67/245 |
| 18 | 21255 | 21989 | 734 | 245 | -1 | 5 | | | | | | |
| 19 | 21351 | 21719 | 368 | 123 | 3 | 3 | | | | | | |
| GP43a=pol(exo) | 21993 | 23042 | 1049 | 350 | -1 | 1 | 19% | "Capsid-protein??" | | | | |
| 20 | 22497 | 22955 | 458 | 153 | 3 | 5 | 35% | "Tail-sheath protein" | CAA32952 | 184 | T4 | 23/117 |
| 21 | 23375 | 24301 | 926 | 309 | 2 | 4 | 34% | "Tail sheath-protein" | P13332 | 659 | T4 Tomato-virus | 84/185 |
| Capsid? | 24310 | 25056 | 746 | 249 | 1 | 4 | | | | | | |
| 22 | 25794 | 26471 | 677 | 226 | 3 | 5 | | | | | | |
| GP3 | 26647 | 27153 | 506 | 169 | -2 | 1 | | | | | | |
| GP18 | 27253 | 29481 | 2228 | 743 | 1 | 2 | | | | | | |
| 22.1 | 30258 | 30920 | 662 | 221 | -1 | 4 | | | | | | |
| 23 | 30997 | 33342 | 2345 | 782 | -2 | 5 | | | | | | |
| 24 | 33362 | 33955 | 593 | 198 | -3 | 5 | | | | | | |

FIG. 2A

| Label | Start | End | Len1 | Len2 | % | Name | Accession | Num | Organism | Ratio |
|---|---|---|---|---|---|---|---|---|---|---|
| 25 | 33724 | 34224 | 500 | 167 | 1 5 | | | | | |
| GP20 | 33948 | 35576 | 1628 | 543 | -1 1 | | | | | |
| 26 | 35631 | 37496 | 1865 | 622 | 3 5 | | | | | |
| 27 | 38627 | 39085 | 458 | 153 | 2 5 | | | | | |
| 28 | 39213 | 40106 | 893 | 298 | 3 5 | | | | | |
| Transpos. | 44821 | 45708 | 887 | 296 | 1 3 33% | "Tail-tube-protein" | P13334 | | T4 | 45/135 |
| 29 | 44882 | 45646 | 764 | 255 | -3 5 | | | | | |
| 30 | 45740 | 47158 | 1418 | 473 | 2 5 | | | | | |
| 31 | 47211 | 47630 | 419 | 140 | 1 5 | | | | | |
| 32 | 47805 | 49211 | 1406 | 469 | 3 5 | | | | | |
| 33 | 49594 | 50577 | 983 | 328 | -2 5 | | | | | |
| 34 | 50661 | 52241 | 1580 | 527 | -1 1 30% | "Transposase" | gi3676289 | 348 | Ifi-virus | 77/252 |
| 35 | 52498 | 53364 | 866 | 289 | 3 5 | | | | | |
| GP17 | 53361 | 54887 | 1526 | 509 | -1 5 26% | "Unknown" "T4-DNA-packaging-" | P17312 | | Chlorella- T4 | 121/459 |
| 36 | 53475 | 54128 | 653 | 218 | 2 5 | | | | | |
| 37 | 54965 | 56341 | 1376 | 459 | 2 5 | | | | | |
| 38 | 56567 | 59419 | 2852 | 951 | -2 5 | | | | | |
| 39 | 56710 | 57381 | 671 | 224 | -2 5 | | | | | |
| 40 | 57381 | 58959 | 872 | 291 | 2 5 | | | | | |
| e | 58087 | 60130 | 701 | 234 | -3 1 37% | "Unknown" | | | | |
| 41 | 59429 | 61324 | 1202 | 401 | -1 5 | "Lyzozyme" | gi:3337264 | 165 | P2-phage | 37/99 |
| tk | 60122 | 62339 | 692 | 231 | -2 5 22-28% | "Thymidine kinase" | | | diverse | |
| 42 | 61647 | 63030 | 692 | 231 | -2 5 | | | | | |
| 43 | 62338 | 64413 | 1379 | 460 | 1 5 | | | | | |
| 44 | 63034 | 66276 | 1451 | 484 | 3 5 | | | | | |
| 45 | 64825 | 67547 | 1271 | 424 | -1 5 | | | | | |
| 46 | 66276 | 66992 | 488 | 163 | 1 5 | | | | | |
| 47 | 66504 | 69180 | 1613 | 538 | 2 5 | | | | | |
| 48 | 67567 | 70168 | 986 | 329 | -3 5 | | | | | |
| 49 | 69182 | 71959 | 1523 | 508 | -3 5 | | | | | |
| 50 | 70436 | 74014 | 2042 | 681 | 1 5 | | | | | |
| 51 | 71972 | 74106 | 734 | 245 | -1 5 | | | | | |
| 52 | 73372 | 75965 | 1706 | 569 | -3 5 | | | | | |
| 53 | 74259 | 76672 | 713 | 238 | -2 5 | | | | | |
| 54 | 75959 | 76977 | 317 | 106 | 3 4 | | | | | |
| GP13 | 76660 | 78503 | 1088 | 363 | -1 1 39% | "Neck-protein" | P11110 | 309 | T4 | 13/39 |
| GP43b=dnapol | 77415 | 81152 | 1568 | 523 | 3 5 25% | "polymerase" | | | diverse | |
| 55 | 79584 | 80381 | 602 | 201 | 3 5 | | | | | |
| 56 | 79779 | 80846 | 398 | 133 | 3 5 | | | | | |
| 57 | 80448 | 82251 | 503 | 168 | -2 5 | | | | | |
| 58 | 81748 | 85047 | 1583 | 528 | -2 3 | | | | | |

FIG. 2B

| | | | | | | | | |
|---|---|---|---|---|---|---|---|---|
| 59 | 86099 | 88750 | 2651 | 884 | -3 | 5 | | |
| 60 | 88731 | 89663 | 932 | 311 | -1 | 5 | | |
| GP63=malg? | 89687 | 90292 | 605 | 202 | -3 | 2 | | |
| Helicase | 90291 | 91607 | 1316 | 439 | -1 | 1 | | |
| 62 | 91704 | 93671 | 1967 | 656 | -1 | 5 | "RNA-ligase" | 374 T4 | 20/152 |
| 63 | 91812 | 93722 | 1910 | 637 | 3 | 5 | "helicase" | 866 diverse | 142/460 |
| 64 | 93758 | 95551 | 1793 | 598 | -3 | 3 | | |
| capsid | 94693 | 95415 | 722 | 241 | -1 | 5 | | |
| 65 | 95565 | 96335 | 770 | 257 | -1 | 5 | "capsid-p??" | 230 Chlorella virus |
| 65.1 | 96545 | 97384 | 839 | 280 | -3 | 3 | | |
| 65.2 | 98061 | 99146 | 1085 | 362 | 3 | 5 | | |
| 66 | 99163 | 101880 | 2717 | 906 | 1 | 5 | "Minor tail protein" | 837 T4 | 24/71 |
| 67 | 10228 | 103895 | 1613 | 538 | 3 | 5 | | |
| GP21 | 10389 | 104784 | 893 | 298 | -2 | 3 | | |
| 68 | 10478 | 105316 | 533 | 178 | -3 | 5 | "Prohead-core" | P=6807 |
| capsid? | 10531 | 106187 | 869 | 290 | -1 | 1 | "RNA-enzyme" | 212 T4 | 41/139 |
| 69 | 10624 | 107365 | 1124 | 375 | -3 | 5 | "Capsid-protein" | |
| 70 | 10739 | 108928 | 1538 | 513 | -3 | 5 | | |
| 71 | 10893 | 110918 | 1985 | 662 | -1 | 5 | | |
| kinase? | 11012 | 110948 | 827 | 276 | 3 | 3 | | |
| 72 | 11097 | 111736 | 764 | 255 | 3 | 5 | "Kinase" | 380 diverse |
| UDP-gal-mut | 11221 | 112683 | 467 | 156 | -3 | 1 | | |
| 73 | 11298 | 114139 | 1151 | 384 | 1 | 5 | "UDP-gal.-pyranose" | gi:2621401 Met.thermoaut | 100/379 |
| 74 | 11310 | 113487 | 383 | 128 | -1 | 1 | | |
| 74.1 | 11413 | 115169 | 1037 | 346 | 3 | 5 | | |
| 75 | 11462 | 115049 | 425 | 142 | 3 | 5 | | |
| 76 | 11553 | 116165 | 626 | 209 | 3 | 5 | | |
| 77 | 11556 | 116273 | 707 | 236 | -1 | 5 | | |
| 78 | 11627 | 117529 | 1250 | 417 | -3 | 5 | | |
| 79 | 11696 | 117495 | 533 | 178 | -1 | 5 | | |
| 80 | 11753 | 118149 | 617 | 206 | -2 | 5 | | |
| 81 | 11864 | 119273 | 626 | 209 | -1 | 5 | | |
| td | 12010 | 120676 | 575 | 192 | -3 | 5 | "Thymidylate synthetase" | gi:279686 |
| 82 | 12067 | 121568 | 893 | 298 | -3 | 5 | | |
| 83 | 12182 | 122266 | 437 | 146 | -1 | 5 | | |
| Transcr-reg. | 12187 | 122319 | 443 | 148 | 1 | 3 | | |
| 84 | 12272 | 123868 | 1145 | 382 | 2 | 5 | | |
| 85 | 12369 | 124311 | 617 | 206 | -2 | 3 | | |
| GP23 | 12387 | 125158 | 1283 | 428 | 2 | 5 | "Capsid-protein" | CAA25911 | 521 |
| 86 | 12556 | 127139 | 1571 | 524 | -1 | 5 | | |
| | 12611 | 126668 | 551 | 184 | 3 | 1 | | |

FIG. 2C

```
              20        40
DPOL_VACCC  : ------------------------QNATMDEFLNISWFYISN-GISPDGCYSLD :  29
DPOL_VACCV  : ------------------------QNATMDEFLNISWFYISN-GISPDGCYSLD :  29
DPOL_VARV/  : ------------------------QNATMDEFLNISWFYISN-GISPDGCYSLD :  29
DPOL_FOWPV  : ------------------------EKQYLQEYLDITWFYLLN-NITPDGCYKID :  29
DPOD_BOVIN  : ----------------------PSFAPYEANVDFEIRFMVDT-DIVGCNWLELP :  31
DPOD_HUMAN  : ----------------------PSFAPYEANVDFEIRFMVDT-DIVGCNWLELP :  31
DPOD_CANAL  : ----------------------IDPCITYDNINYLLRLMIDC-KITGMSWITLP :  31
DPOD_YEAST  : ----------------------SNGTTTYDNIAYTLRLMVDC-GIVGMSWITLP :  31
DPOD_SCHPO  : ----------------------VGVTTFESNTQYLLRFMIDC-DVVGMNWIHLP :  31
DPOD_PLAFK  : ---------------------IGCIVYEANLPFILRYIIDH-KITGSSWINCK :  31
DPOL_CHVN2  : -----------------------EYQIYESSVDPIIRIFHLR-NINPADWMHVS :  30
DPOL_CHVP1  : ------------------------YQIYESSVDPIIRVFHLR-NINPADWIRVS :  29
DPOL_EBV/2  : -----------------------GCRIFEANVDATRRFVLDN-DFVTFGWYSCR :  30
DPOL_HSVSA  : -----------------------GCEVFETNVDAIRRFVIDN-DFSTFGWYTCK :  30
DPOL_HSV11  : ---------------------PAIKKYEGGVDATTRFILDNPGFVTFGWYRLK :  32
DPOL_HSV21  : ---------------------PAIRKYEGGVDATTRFILDNPGFVTFGWYRLK :  32
DPOL_HSVEB  : ---------------------PEITKFEGSVDVTTRLLLDNENFTSFGWYRLR :  32
DPOL_VZVD/  : ---------------------PELKKYEGRVDATTRFLMDNPGFVSFGWYQLK :  32
DPOL_HCMVA  : -----------------------GFPVYEVRVDPLTRLVIDR-RITTFGWCSVN :  30
DPOL_MCMVS  : -----------------------GRKVYELGVDPLARFLIDR-KIPSFGWCLAR :  30
DPOL_HSV6U  : -----------------------GFVVYEIDVDVLTRFFVDN-GFLSFGWYNVK :  30
DPOA_HUMAN  : ------------------------SHVFGTNTSSLELFLMNR-KIKGPCWLEVK :  29
DPOA_MOUSE  : ------------------------SHVFGTNTSSLELFLMNR-KIKGPCWLEVK :  29
DPOA_DROME  : ------------------------AHIFGATTNALERFLLDR-KIKGPCWLQVT :  29
DPOA_SCHPO  : ------------------------SHVFGTNTALFEQFVLSR-RVMGPCWLKIQ :  29
DPOA_YEAST  : ------------------------YHVFGGNSNIFESFVIQN-RIMGPCWLDIK :  29
DPOA_TRYBB  : ------------------------QVVVGASRSLLELFLIKK-RLMGPSYLEIE :  29
DPOL_NPVAC  : ------------------------NAACLDKFLHNVNRVHMQT-PFVEGAYMRFK :  30
DPOL_NPVLD  : ------------------------DKNCLDGYLADVNRVHMQT-SLLEGQYVRFK :  30
DPOZ_YEAST  : ----------------------NKVPSMGNKKTESQISMHTPHSKFLYKFASDVS :  33
DPOL_PYRFU  : -----------------------FKIEHDRTFRPYIYALLRDDSKIEEVKKITGE :  32
DPO1_SULSO  : ------------------------FNNYMYDIGLIPGMPYVVKN-GKLESVYLSLD :  31
DPO2_ECOLI  : ------------------------AQHILQGEQGFRLTPLALKDFHRQPVYGLYCR :  32
DPol_Dtok   : MILDADYITEDGKPVIRVFKKEKGEFKIDYDRDFEPYIYALLKDDSAIEDIKKITAE :  57
RM378       : -------------------------MKITLSASVYPRSMKIYGVELIEGKKHLFQS :  31
RB69        : MKEFYLTVEQIGDSIFERYIDSNGRERTREVE-YKPSLFAHCPESQAT--------- :  47
```

DPOL_VACCC  : ----------EQYLTKINNGC-YHCDDPRNCFAKKIPRFDIP--------------- :  60
DPOL_VACCV  : ----------EQYLTKINNGC-YHCDDPRNCFAKKIPRFDIP--------------- :  60
DPOL_VARV/  : ----------DQYLTKINNGC-YHCGDPRNCFAKEIPRFDIP--------------- :  60
DPOL_FOWPV  : ----------IEHLTPIKKDC-YHCDDVSKVFIQEIPIFEVK--------------- :  60
DPOD_BOVIN  : --------AGKYILRP-EGKA-TLCQLEADVLWSDVISHPPEGEW------------ :  66
DPOD_HUMAN  : --------AGKYALRL-KEKA-TQCQLEADVLWSDVVSHPPEGPW------------ :  66
DPOD_CANAL  : --------RDKYKIVN--NKI-STCQIECSIDYRDLISHPPEGEW------------ :  65
DPOD_YEAST  : --------KGKYSMIEPNNRV-SSCQLEVSINYRNLIAHPAEGDW------------ :  67
DPOD_SCHPO  : --------ASKYQFRY-QNRV-SNCQIEAWINYKDLISLPAEGQW------------ :  66
DPOD_PLAFK  : --------KGHYYIRNKNKKI-SNCTFEIDISYEHVEPITLENEY------------ :  67
DPOL_CHVN2  : --------KAFPVETR----I-SNSDIEVETSFQHLGPS----DL------------ :  58
DPOL_CHVP1  : --------KAYPAQTR----I-SNSDIEVETSFQHLGPV----ED------------ :  57
DPOL_EBV/2  : --------R--AIPRLQHRD--SYAELEYDCEVGDLSVRRED--------------- :  60
DPOL_HSVSA  : --------S--ACPRITNRD--SHTDIEFDCGYYDLEFHADR--------------- :  60
DPOL_HSV11  : PG----RNNTLAQPAAPMAFG-TSSDVEFNCTADNLAIEGGM--------------- :  69
DPOL_HSV21  : PG----RGNAPAQPRPPTAFG-TSSDVEFNCTADNLAVEGAM--------------- :  69
DPOL_HSVEB  : PG----THGERVQLRPVERHV-TSSDVEINCTPDNLEPIPDE--------------- :  69
DPOL_VZVD/  : PG----VDGERVRVRPASRQL-TLSDVEIDCMSDNLQAIPND--------------- :  69
DPOL_HCMVA  : --------R--YDWRQQGRA--STCDIEVDCDVSDLVAVPDD--------------- :  60
DPOL_MCMVS  : --------R--YSVRAAGYV--SRAQLEIDCDVADILPIEEQ---------  ---  :  60
DPOL_HSV6U  : --------K--YIPQDMGKG--SNLEVEINCHVSDLVSLED---------------- :  59
DPOA_HUMAN  : ----------KSTALNQP-V-SWCKVEAMALKPDLVNVIKD-------VSPPPLV :  65
DPOA_MOUSE  : ----------NPQLLNQP-I-SWCKFEVMALKPDLVNVIKD-------VSPPPLV :  65
DPOA_DROME  : ----------GFKVSPTP-M-SWCNTEVTLTEPKNVELVQDKGK----PAPPPPLT :  69
DPOA_SCHPO  : ----------QPNFDAVKNA-SWCRVEIGCSSPQNISVSFEKNEI---TSKTPPMT :  71
DPOA_YEAST  : ----------GADFNSIRNA-SHCAVEVSVDKPQNITPTTTKT--------MPNLR :  66
DPOA_TRYBB  : ----------HLVTAMDR-V-SHCKTEFLVPSPKDIKVYNSS-------KPPPPFT :  66
DPOL_NPVAC  : KT----QRCQNNYVGGSTTRMFNLQHFNEDFELVDEMTLTSG-------------- :  68
DPOL_NPVLD  : NA----HACRDYRLSHTAK---DVHEFESMLERVQVSALSHE-------------- :  65
DPOZ_YEAST  : ----------GKQKRKKSSVHDSLTHLTLEIHANTRSDKIPD--------------- :  65
DPOL_PYRFU  : RH---GKIVRIVDVEKVEKKFLGKPITVWKLYLEHPQDVPTIREKV-REHPAVVDIF :  85
DPO1_SULSO  : ----------EKDVEEIKKAFADSDEMTRQMAVDWLPIFET---------------- :  62
DPO2_ECOLI  : ----------AHRQLMNYEKRLREGGVTVYEADVRPPERYLMER------FITSPVWV :  74
DPol_Dtok   : RHG---TTVRVTRAERVKKKFLGRPVEVWKLYFTHPQDVPAIRDKIREHPAVVDIYE : 111
RM378       : -------------------------------PVPPHLKRI------AQQNR :  45
RB69        : ---------------KYFDIY--GKPCTRKLFANMRDASQWIKRMEDI---GLEAL :  83
```

FIG. 3B

```
                         120            140            160
DPOL_VACCC  : ----------------------RSYLFLDIECHFDKKFPSVFINPISHTSYCYID :  93
DPOL_VACCV  : ----------------------RSYLFLDIECHFDKKFPSVFINPISHTSYCYID :  93
DPOL_VARV/  : ----------------------RSYLFLDIECHFDKKFPSVFINPISHTSYCYID :  93
DPOL_FOWPV  : ----------------------FTYLLFDIECQFDKKFPSVFVNPISHISCWIID :  93
DPOD_BOVIN  : ------------------QRIAPLRVLSFDIECAGRKG----IFPEPE--RDPVIQ :  98
DPOD_HUMAN  : ------------------QRIAPLRVLSFDIECAGRKG----IFPEPE--RDPVIQ :  98
DPOD_CANAL  : ------------------LKMAPLRILSFDIECAGRKG----VFPEAE--HDPVIQ :  97
DPOD_YEAST  : ------------------SHTAPLRIMSFDIECAGRIG----VFPEPE--YDPVIQ :  99
DPOD_SCHPO  : ------------------SKMAPLRIMSFDIECAGRKG----VFPDPS--IDPVIQ :  98
DPOD_PLAFK  : ------------------QQIPKLRILSFDIECIKLDGK---GPPEAK--NDPIIQ : 100
DPOL_CHVN2  : ------------------KEVPPLIIASWDIETYSKDR----KFPLAENPADYCIQ :  92
DPOL_CHVP1  : ------------------KTVPPLVIASWDIETYSKDR----KFPLAENPTDYCIQ :  91
DPOL_EBV/2  : ------------------SSWPSYQALAFDIECLG-----EEGFPTATNEADLILQ :  93
DPOL_HSVSA  : ------------------TEWPPYNIMSFDIECIG-----EKGFPCAKNEGDLIIQ :  93
DPOL_HSV11  : ------------------SDLPAYKLMCFDIECKAGGE-DELAFPVAGHPEDLVIQ : 106
DPOL_HSV21  : ------------------CDLPAYKLMCFDIECKAGGE-DELAFPVAERPEDLVIQ : 106
DPOL_HSVEB  : ------------------AAWPDYKLMCFDIECKAGTG-NEMAFPVATNQEDLVIQ : 106
DPOL_VZVD/  : ------------------DSWPDYKLLCFDIECKSGGS-NELAFPDATHLEDLVIQ : 106
DPOL_HCMVA  : ------------------SSWPRYRCLSFDIECMSG----EGGFPCAEKSDDIVIQ :  94
DPOL_MCMVS  : ------------------SNWPFYRCLSFDIECMSG----TGAFPAAENVDDIIIQ :  94
DPOL_HSV6U  : ------------------VNWPLYGCWSFDIECLGQ----NGNFPDAENLGDIVIQ :  93
DPOA_HUMAN  : VMAFSMKTMQNAKNHQNEIIAMAALVHHSFALDKAAPKPP-------FQSHFCVVSK : 115
DPOA_MOUSE  : VMSFSMKTMQNVQNHQHEIIAMAALVHHSFALDKAPPEPP-------FQTHFCVVSK : 115
DPOA_DROME  : LLSLNVRTSMNPKTSRNEICMISMLTHNRFHIDRPAPQPA-------FNRHMCALTR : 119
DPOA_SCHPO  : VMSLAFRTLINKEQNKQEVVMISARIFENVDIEKGLPAND-------MPSYSFSLIR : 121
DPOA_YEAST  : CLSLSIQTLMNPKENKQEIVSITLSAYRNISLDSPIPENI-------KPDDLCTLVR : 116
DPOA_TRYBB  : VASIQLHAQLDSDGVKNEVIAASIALYGDVSIDGE-RKPN--------ITECFTGVR : 114
DPOL_NPVAC  : ---------------------IMPVLSCYDIETHSD------GHNMSKASVDCIMS :  97
DPOL_NPVLD  : ---------------------ILPVVACYDIETHSD------GQRFSAPDADFIIS :  94
DPOZ_YEAST  : ----------------PAIDEVSMIWCLEEETFPL------------DLDIAYE :  92
DPOL_PYRFU  : EYDIPFAKRYLIDKGLIPMEGEEELKILAFDIETLYHE-----------GEEFGKGP : 131
DPO1_SULSO  : ------------------EIPKIKRVAIDIEVYTPVKG---RIPDSQKAEFPIIS :  96
DPO2_ECOLI  : EGDMHNGTIVNARLKPHPDYR-PPLKWVSIDIETTRHG------ELYCIGLEGCGQR : 124
DPol_Dtok   : YDIPFAKRYLIDRGLIPMEGDEE-LRMLAFDIETLYHE----------GEEFGEGP : 156
RM378       : GKIEAEAISYYIREQKSHITPEALSQCVFIDIETISPKK-------SFPDPWRDPVY :  95
RB69        : GMDDFKLAYLSDTYNYEIKYDHTKIRVANFDIEVTSPDG--------FPEPSQAKHP : 132
                                    Exo I
```

FIG. 3C

```
                              180              200              220
DPOL_VACCC  : LSGKRLLFT---------LINEEMLTEQEIQ---EAVDRGCLRIQSLMEMD------ : 132
DPOL_VACCV  : LSGKRLLFT---------LINEEMLTEQEIQ---EAVDRGCLRIQSLMEMD------ : 132
DPOL_VARV/  : LSGKRLLFT---------LINEEMLTEQEIQ---EAVDRGCLRIQSLMEMD------ : 132
DPOL_FOWPV  : KVT-EYKFT---------LINTDILPDKEP------------SILHHKDFS------ : 122
DPOD_BOVIN  : ICSLGLRWG---------EPEP-FLR--------------LALTLRPCAPIL---- : 126
DPOD_HUMAN  : ICSLGLRWG---------EPEP-FLR--------------LALTLRPCAPIL---- : 126
DPOD_CANAL  : IANVVQKSG---------ESKP-FVR--------------NVFTVNTCSSII---- : 125
DPOD_YEAST  : IANVVSIAG---------AKKP-FIR--------------NVFTLNTCSPIT---- : 127
DPOD_SCHPO  : IASIVTQYG---------DSTP-FVR--------------NVFCVDTCSQIV---- : 126
DPOD_PLAFK  : ISSILYFQG---------EPIDNCTK--------------FIFTLLECASIP---- : 129
DPOL_CHVN2  : IATTFQKYG---------EPEP-YRR--------------VVVCYKQTASVE---- : 120
DPOL_CHVP1  : IATTFQKYG---------EPEP-YRR--------------VVVCYKQTAPVE---- : 119
DPOL_EBV/2  : ISCVLWSTG---------EEAGRYRR-------------ILLTLGTCEDIEG---- : 123
DPOL_HSVSA  : ISCVFWHAG---------ALD-TTRN-------------MLLSLGTCSAVEN---- : 122
DPOL_HSV11  : ISCLLYDLS---------TTA-LEHV-------------LLFSLGSCDLPESHLN-E : 139
DPOL_HSV21  : ISCLLYDLS---------TTA-LEHI-------------LLFSLGSCDLPESHLS-D : 139
DPOL_HSVEB  : ISCLLYSLA---------TQN-HEHT-------------LLFSLGSCDISEEYSF-A : 139
DPOL_VZVD/  : ISCLLYSIP---------RQS-LEHI-------------LLFSLGSCDLPQRYVQ-E : 139
DPOL_HCMVA  : ISCVCYETGGNTAVDQGIPNGNDGRGCTSEGVIFGHSGLHLFTIGTCGQVG------ : 145
DPOL_MCMVS  : ISCVCFGVG------EMVHHAYDVHADLSTPAVPEN---HLFTIGPCAPI------- : 135
DPOL_HSV6U  : ISVISFDTE---------G-DRDER--------------HLFTLGTCEKI------ : 119
DPOA_HUMAN  : PKDCIFPYA---------FKEVIEK------------------------------- : 131
DPOA_MOUSE  : PKDCIFPCD---------FKEVISK------------------------------- : 131
DPOA_DROME  : PAVVSWPLD---------LNFEMAKY------------------------------ : 136
DPOA_SCHPO  : PLKQIFPNG---------FEKLARQH------------------------------ : 138
DPOA_YEAST  : PPQSTSFPL---------GLAALAKQK----------------------------- : 134
DPOA_TRYBB  : QLSPDAPLPLDLETYCLSK------------------------------------- : 133
DPOL_NPVAC  : IGFVVYKND---------EYAKFCFMYH-----------KLPTQIPETYDD----- : 128
DPOL_NPVLD  : IAVVVRRDA---------ADTRICLFYSP----------DDPVDLSSSSSSPPA-A : 130
DPOZ_YEAST  : GIMIVHKASEDS------------T--------------FPTKIQHCIN------- : 115
DPOL_PYRFU  : IIMISYADE---------NEAKVITWKN---------------------------- : 150
DPO1_SULSO  : IALAGSDGLK---------KVLVLNR-------------NDVNEGSVKLDG----- : 125
DPO2_ECOLI  : IVYMLGPEN---------GDASS--------------------------------- : 138
DPol_Dtok   : ILMISYADE---------EGARVITWK-------------------NIDLPY---- : 180
RM378       : SISIKPYGKP---------VVVVLLLIT------------NPEAHIDNFN-----KFTT : 128
RB69        : IDAITHYDSIDDR------FYVFDLLN------SPYGNVEEWSIEIAAKLQEQGGDE : 177
```

FIG. 3D

```
                             240         260         280
DPOL_VACCC  : --------YERELVLCSEIVLLRIAKQLLELTFDYVVTFNGHNFDLRYITNR----- : 176
DPOL_VACCV  : --------YERELVLCSEIVLLRIAKQLLELTFDYVVTFNGHNFDLRYITNR----- : 176
DPOL_VARV/  : --------YERELVLCSEIVLLQIAKQLLELTFDYIVTFNGHNFDLRYITNR----- : 176
DPOL_FOWPV  : --------PKDRITYCTEIVMLLIMKKILEHRFDFVITFNGNNFDIRYISGR----- : 166
DPOD_BOVIN  : --------GAKVQSYEREEDLLQAWSTFIRIMDPDVITGYNIQNFDLPYLISR---- : 171
DPOD_HUMAN  : --------GAKVQSYEKEEDLLQAWSTFIRIMDPDVITGYNIQNFDLPYLISR---- : 171
DPOD_CANAL  : --------GSQIFEHQREEDMLMHWKEFITKVDPDVIIGYNTANFDIPYVLNR---- : 170
DPOD_YEAST  : --------GSMIFSHATEEEMLSNWRNFIIKVDPDVIIGYNTTNFDIPYLLNR---- : 172
DPOD_SCHPO  : --------GTQVYEFQNQAEMLSSWSKFVRDVDPDVLIGYNICNFDIPYLLDR---- : 171
DPOD_PLAFK  : --------GSNVIWFNDEKTLLEAWNEFIIRIDPDFLTGYNIINFDLPYILNR---- : 174
DPOL_CHVN2  : --------GVEIISCAEEADVMNTWMTILQDEITDVSIGYNLWQYDLRYIHGRSMMCV : 170
DPOL_CHVP1  : --------GVEIISCLEESDVMNTWMKILQDEKTDVSIGYNTWQYDLRYVHGRTQMCV : 169
DPOL_EBV/2  : --------VEVYEFPSELDMLYAFFQLIRDLSVEIVTGYNVANFDWPYILDR----- : 167
DPOL_HSVSA  : --------TEVYEFPSEIDMLHGFFSLIRDFNVEIITGYNISNFDLPYLIDR----- : 166
DPOL_HSV11  : LAARGLPTPVVLEFDSEFEMLLAFMTLVKQYGPEFVTGYNIINFDWPFLLAK----- : 191
DPOL_HSV21  : LASRGLPAPVVLEFDSEFEMLLAFMTFVKQYGPEFVTGYNIINFDWPFVLTK----- : 191
DPOL_HSVEB  : CVQRGEPRPTVLEFDSEYELLVAFLTFLKQYSPEFATGYNIVNFDWAYIVNK----- : 191
DPOL_VZVD/  : MKDAGLPEPTVLEFDSEFELLIAFMTLVKQYAPEFATGYNIVNFDWAFIMEK----- : 191
DPOL_HCMVA  : ------PDVDVYEFPSEYELLLGFMLFFQRYAPAFVTGYNINSFDLKYILTR----- : 191
DPOL_MCMVS  : ------PDVKIYTFPSEYEMLRGFFIFLSWYSPEFITGYNINGFDIKYILTR----- : 181
DPOL_HSV6U  : ------DGVHIYEFASEFELLLGFFIFLRIESPEFITGYNINNFDLKYLCIR----- : 165
DPOA_HUMAN  : ------KNVKVEVAATERTLLGFFLAKVHKIDPDIIVGHNIYGFELEVLLQR----- : 177
DPOA_MOUSE  : ------KNMKVEIAATERTLIGFFLAKVHKIDPDILVGHNICSFELEVLLQR----- : 177
DPOA_DROME  : ------KSTTVHKHDSERALLSWFLAQYQKIDADLIVTFDSMDCQLNVITDQ----- : 182
DPOA_SCHPO  : ------KS-SIFCERSEVSLLNNFLNKVRTYDPDVYFGHDFEMCYS-VLLSR----- : 182
DPOA_YEAST  : ------LPGRVRLFNNEKAMLSCFCAMLKVEDPDVIIGHRLQNVYLDVLAHR----- : 180
DPOA_TRYBB  : ------RMPGVHRFINERALLTWFAETLAALDPDIIVGHNIIGYTVETLLNR----- : 179
DPOL_NPVAC  : ------DTYVVMFQNEIDMITAFFDMIKITNPDVILDFNGDVFDLPYILGR----- : 173
DPOL_NPVLD  : ------PDTAAVHFRAERDMIAAFFQLLPLLNADVVLDFNGDKFDLPFLTGR---- : 176
DPOZ_YEAST  : ----EIPVMFYESEFEMFEALTDLVLLLDPDILSGFEIHNFSWGYIIER-------C : 161
DPOL_PYRFU  : -----IDLPYVEVVSSEREMIKRFLRIIREKDPDIIVTYNGDSFDPYLAKR----- : 197
DPO1_SULSO  : --------ISVERFNTEYELLGRFFDILLEYP--IVLTFNGDDFDLPYIYFR----- : 167
DPO2_ECOLI  : ------LDFELEYVASRPQLLEKLNAWFANYDPDVIIGWNVVQFDLRMLQKH----- : 184
DPol_Dtok   : ---------VESVSTEKEMIKRFLKVIQEKDPDVLITYNGDNFDFAYLKKR----- : 222
RM378       : SVGDNTFEIHYRTFLSEKRLLEYFWNVLKPKFT-FMLAWNGYQFDYPYLLIR----- : 179
RB69        : VPSEIIDKIIYMPFDNEKELLMEYLNFWQQKTPVILTGWNVESFDIPYVYNR---- : 229

Exo II
```

FIG. 3E

```
                       300          320          340
DPOL_VACCC  : LELLTGE----KIIFRSPDKKEAVHLCIYERNQSSHKG-----VGGMAN--------  : 216
DPOL_VACCV  : LELLTGE----KIIFRSPDKKEAVYLCIYERNQSSHKG-----VGGMAN--------  : 216
DPOL_VARV/  : LELLTGE----KIIFRSPDKKEAVHLCIYERNQSSHKG-----VGGMAN--------  : 216
DPOL_FOWPV  : LEILEKS----FIYFSLPDATETVKLKIFER-FVTG--------GTFTN--------  : 202
DPOD_BOVIN  : --AQTLK----VPGFPLLGRVIGLRSNIRESS--FQ-------SRQTG--------R : 205
DPOD_HUMAN  : --AQTLK----VQTFPFLGRVAGLCSNIRDSS--FQ-------SKQTG--------R : 205
DPOD_CANAL  : --AKALG----LNDFPFFGRLKRVKQEIKDAV--FS-------SRAYG--------T : 204
DPOD_YEAST  : --AKALK----VNDFPYFGRLKTVKQEIKESV--FS-------SKAYG--------T : 206
DPOD_SCHPO  : --AKSLR----IHNFPLLGRIHNFFSVAKETS--FS-------SKAYG--------T : 205
DPOD_PLAFK  : --GTALN----LKKLKFLGRIKNVASTVKDSS--FS-------SKQFG--------T : 208
DPOL_CHVN2  : DDITGED----NVRLKNLGRLLVGGGEVIERD--LS-------SNAFG--------Q : 206
DPOL_CHVP1  : DDMTGED----KVKLSNLGRLLSGGGEVVERD--LS-------SNAFG--------Q : 205
DPOL_EBV/2  : --ARHIY----SINPASLGKIR--AGGVCEVRRPHDAG-----KGFLR--------  : 202
DPOL_HSVSA  : --ATQIY----NIKLSDYSRVK--TGSIFQVHTPKDTG-----NGFMR--------  : 201
DPOL_HSV11  : --LTDIY----KVPLDGYGRMN--GRGVFRVW---DIG-----QSHFQ--------  : 223
DPOL_HSV21  : --LTEIY----KVPLDGYGRMN--GRGVFRVW---DIG-----QSHFQ--------  : 223
DPOL_HSVEB  : --VTSVY----NIKLDGYGKFN--KGGLFKVW---DIA-----TNHFQ--------  : 223
DPOL_VZVD/  : --LNSIY----SLKLDGYGSIN--RGGLFKIW---DVG-----KSGFQ--------  : 223
DPOL_HCMVA  : --LEYLY----KVDSQRFCKLPTAQGGRFFLHSP-AVGFKRQYAAAFPSASHNNPAS : 241
DPOL_MCMVS  : --AEKLY----KMDVGQFTKLR--RGGRMFVFSP-EKG-----KAGFG--------T : 216
DPOL_HSV6U  : --MDKIY----HYDIGCFSKLK---NGKIGISVP-HEQ----YRKGFL--------  : 199
DPOA_HUMAN  : --INVCK----APHWSKIGRLK--RSNM-PKLGGRS---------GFG--------  : 207
DPOA_MOUSE  : --INECK----VPYWSKIGRLR--RSNM-PKLGSRS---------GFG--------  : 207
DPOA_DROME  : --IVALK----IPQWSRMGRLR--LS---QSFGKR----------------------  : 206
DPOA_SCHPO  : --LKERK----IHNWSSIGRLR--RSEWPRSFNRSS--------QQFV--------  : 214
DPOA_YEAST  : --MHDLN----IPTFSSIGRRL--RRTWPEKFGRGNSN-----MNHFF--------  : 215
DPOA_TRYBB  : --YQELN----IVRWSTIGRLD--VRRFPRIQGNNFN--------LAI--------  : 211
DPOL_NPVAC  : --LNKTK--------MLLKRYDLPAAAPTTKLFINKLG------------------  : 201
DPOL_NPVLD  : --ANKLCGPAEAARATKIARYDLSPVNVVTQQSYDKFS-----------------  : 212
DPOZ_YEAST  : QKIH------QFDIVRELARVKCQIKTKLS-----------DTWG----------Y : 190
DPOL_PYRFU  : --AEKLG------IKLTIGRDG--SEPKMQRIG-----------------------  : 220
DPO1_SULSO  : --ALKLG------YFPEEIPIDVAGKDEAKYLAG----------------------  : 193
DPO2_ECOLI  : --AERYR------LPLRLGRDN--SELEWREHG-----------FKN---------  : 210
DPol_Dtok   : --SEMLG------VKFILGRDG--SEPKIQRMG-----------------------  : 245
RM378       : SHIHEVN----VISDKLLPDWKLVRKISDRNLP-----------------------  : 208
RB69        : --IKNIFG---ESTAKRLS--P--HRKTRVKVIEN-------------------MY : 257
```

FIG. 3F

```
                       360            380              40
DPOL_VACCC : TTFHVNNNNGTIFFDLYSFIQKSEK---LDSYKLDSISKNAFSCMGKVLNRGVREMT : 270
DPOL_VACCV : TTFHVNNNNGTIFFDLYSFIQKSEK---LDSYKLDSISKNAFSCMGKVLNRGVREMT : 270
DPOL_VARV/ : TTFHVNNNNGTIFFDLYSFIQKSEK---LDSYKLDSISKNAFSCMGKVLNRGVREMT : 270
DPOL_FOWPV : KTYHINNNNGVMFFDLYAFIQKTER---LDSYKLDSISKNIFNCNVAIKEIDDTILT : 256
DPOD_BOVIN : RDSKVVSMVGRVQMDMLQVLLREYK---LRSYTLNAVSFHFLGE----QKEDVQHSI : 255
DPOD_HUMAN : RDTKVVSMVGRVQMDMLQVLLREYK---LRSHTLNAVSFHFLGE----QKEDVQHSI : 255
DPOD_CANAL : RENKVVNIDGRMQLDLLQFIQREYK---LRSYTLNSVSAHFLGE----QKEDVQHSI : 254
DPOD_YEAST : RETKNVNIDGRLQLDLLQFIQREYK---LRSYTLNAVSAHFLGE----QKEDVHYSI : 256
DPOD_SCHPO : RESKTTSIPGRLQLDMLQVMQRDFK---LRSYSLNAVCSQFLGE----QKEDVHYSI : 255
DPOD_PLAFK : HETKEINIFGRIQFDVYDLIKRDYK---LKSYTLNYVSFEFLKE----QKEDVHYSI : 258
DPOL_CHVN2 : NKFFLLDMPGVMQIDLLQWFRKNRN---LESYSLNNVSKLYLGD----QKNDLPAMQ : 256
DPOL_CHVP1 : NKFFLLDMPGVMQIDLLQWFRKNRN---LESYSLNNVSKLYLGD----QKNDLPAMQ : 255
DPOL_EBV/2 : -ANTKVRITGLIPIDMYAVCRDKLS---LSDYKLDTVARHLLGA----KKEDVHYKE : 251
DPOL_HSVSA : -SVSKIKISGIIAIDMYIVCKDKLS---LSNYKLDTVANHCIGA----KKEDVSYKD : 250
DPOL_HSV11 : -KRSKIKVNGMVNIDMYGIITDKIK---LSSYKLNAVAEAVLKD----KKKDLSYRD : 272
DPOL_HSV21 : -KRSKIKVNGMVNIDMYGIITDKVK---LSSYKLNAVAEAVLKD----KKKDLSYRD : 272
DPOL_HSVEB : -KKSKVKINGLTSLDMYSVATEKLK---LPSYKLDAVVGDVLGE----HKIDLPYKE : 272
DPOL_VZVD/ : -RRSKVKINGLISLDMYAIATEKLK---LSSYKLDSVAREALNE----SKRDLPYKD : 272
DPOL_HCMVA : TAATKVYIAGSVVIDMYPVCMAKTN---SPNYKLNTMAELYLRQ----RKDDLSYKD : 291
DPOL_MCMVS : SNTVKVFWSGTVVLDMYPVCTAKAS---SPNYKLDTMAEIYLKK----KKDDLSYKE : 266
DPOL_HSV6U : QAQTKVFTSGVLYLDMYPVYSSKIT---AQNYKLDTIAKICLQQ----EKEQLSYKE : 249
DPOA_HUMAN : ---ERNATCGRMICDVEISAKELIR---CKSYHLSELVQQILKT----ERVVIPMEN : 254
DPOA_MOUSE : ---ERNATCGRMICDVEISAKELIH---CKSYHLSELVQQILKT----ERIVIPTEN : 254
DPOA_DROME : ---LLEHFVGRMVCDVKRSAEECIR---ARSYDLQTLCKQVLKLK-ESERMEVNADD : 256
DPOA_SCHPO : ---EKQIIAGRLMCDLSNDFGRSMI-K-AQSWSLSEIVLKELDI----KRQDINQEK : 262
DPOA_YEAST : ---ISDICSGRLICDIANEMGQSLTPK-CQSWDLSEMYQVTCEK----EHKPLDIDY : 264
DPOA_TRYBB : ---EKEACVGRLVVDTYLLAREYYKSTNYKLLSLSTQMEIKGITD-NRGHFEPGSTV : 264
DPOL_NPVAC : NKVDTYYFNYYIHIDLYKFFSSDSNQHKVENFQLNTISSYYLGE----NKIDLPWTE : 254
DPOL_NPVLD : NKLHSHYLTYYIHIDLYQFLSTDSEHNDLENFQLNTVAEHYLKK----RLPHFSFES : 265
DPOZ_YEAST : AHSSGIMITGRHMINIWRALRSDVN---LTQYTIESAAFNILHK----RLPHFSFES : 240
DPOL_PYRFU : -DMTAVEVKGRIHFDLYHVITRTIN---LPTYTLEAVYEAIFGK----PKEKVYADE : 269
DPO1_SULSO : ---LHIDLYKFFFNKAVRNYAFEGK---YNEYNLDAVAKALLGT------SKVKVDT : 238
DPO2_ECOLI : -GVFFAQAKGRLIIDGIEALKSAFWN--FSSFSLETVAQELLGEG---KSIDNPWDR : 261
DPol_Dtok  : -DRFAVEVKGRIHFDLYPVIRRTI---NLPTYTLETVYEPVFGQ----PKEKVYAEE : 294
RM378      : FYFNPRTPVEFVFFDYMRLYRSFVAYKELESYRLDYIAREEIGE----GKVDFDVRF : 261
RB69       : GSREIITLFGISVLDYIDLYKKFSFT-NQPSYSLDYISEFELNV-GKLKYDGPISKL : 312
```

DPOL_VACCC  : FIGDDTTDAKGKAAAFAKVLTTGNYVTVDEDIICKVIRK--DIWENGFKVVLLCPT-  : 324
DPOL_VACCV  : FIGDDTTDAKGKAAAFAKVLTTGNYVTVDEDIICKVIRK--DIWENGFKVVLLCPT-  : 324
DPOL_VARV/  : FIGDDTTDAKGKAAVFAKVLTTGNYVTVDD-IICKVIHK--DIWENGFKVVLSCPT-  : 323
DPOL_FOWPV  : LEATVKDNSKDKLSIFSRVLETGNYITIGDNNVSKIVYK--DINQDSFIIKVISNRD  : 311
DPOD_BOVIN  : ITDLQNGNDQT-------RRRLAVYCLKDAFLPLRLLER--LMVLVNAMEMARVTG-  : 302
DPOD_HUMAN  : ITDLQNGNDQT-------RRRLAVYCLKDAYLPLRLLER--LMVLVNAVEMARVTG-  : 302
DPOD_CANAL  : TTDLQNGTKET-------RRRLAVYCLKDAFLPLRLLDK--LMCLVNYTEMARVTG-  : 301
DPOD_YEAST  : ISDLQNGDSET-------RRRLAVYCLKDAYLPLRLMEK--LMALVNYTEMARVTG-  : 303
DPOD_SCHPO  : ITDLQNGTADS-------RRRLAIYCLKDAYLPQRLMDK--LMCFVNYTEMARVTG-  : 302
DPOD_PLAFK  : MNDLQNESPES-------RKRIATYCIKDGVLPLRLIDK--LLFIYNYVEMARVTG-  : 305
DPOL_CHVN2  : IFEKFEGGADD-------RAIIAAYARKDTDLPLKLLKK--MAILEDITEMANAVK-  : 303
DPOL_CHVP1  : IFEKFEGNAED-------RAIIAAYAAKDTDLPLKLLKK--MAILEDLTEMANAVK-  : 302
DPOL_EBV/2  : IPRLFAAGPEG-------RRRLGMYCVQDSALVMDLLNH--FVIHVEVAEIAKIAH-  : 298
DPOL_HSVSA  : IMPLFMSGPEG-------RAKIGLYCVIDSVLVMKLLKF--FMIHVEISEIAKLAK-  : 297
DPOL_HSV11  : IPAYYAAGPAQ-------RGVIGEYCIQDSLLVGQLFFK--FLPHLELSAVARLAG-  : 319
DPOL_HSV21  : IPAYYASGPAQ-------RGVIGEYCVQDSLLVCQLFFK--FLPHLELSAVARLAG-  : 319
DPOL_HSVEB  : IPSYYAGGPDR-------RGVIGEYCIQDSRLVGKLFFK--YLPHLELSAVAKLAR-  : 319
DPOL_VZVD/  : IPGYYASGPNT-------RGIIGEYCIQDSALVGKLFFK--YLPHLELSAVARLAR-  : 319
DPOL_HCMVA  : IPRCFVANAEG-------RAQVGRYCLQDAVLVRDLFNT--INFHYEAGAIARLAK-  : 338
DPOL_MCMVS  : IPVQFSAGDEG-------RAPGGKYCLQDAVLVRELFEM--LAFHFEAAAIARLAR-  : 313
DPOL_HSV6U  : IPKKFISGPSG-------RAVVGKYCLQDSVLVVRLFKQ--INYHFEVAEVARLAH-  : 296
DPOA_HUMAN  : IQNMYSESSQ--------LLYLLEHTWKDAKFILQIMCE--LNVLPLALQITNIAG-  : 300
DPOA_MOUSE  : IRNMYSESSY--------LLYLLEHIWKDARFILQIMCE--LNVLPLALQITNIAG-  : 300
DPOA_DROME  : LLEMYEKGES--------ITKLISLTMQDNSYLLRLMCE--LNIMPLALQITNICG-  : 302
DPOA_SCHPO  : ALQSWTDTAHG-------LLDYLVHCEIDTFFIAAVAFK--IQMLQLSKNLTNIAG-  : 309
DPOA_YEAST  : QNPQYQNDVNS-------MTMALQENITNCMISAEVSYR--IQLLTLTKQLTNLAG-  : 311
DPOA_TRYBB  : LVKDSMMSSEA-------LCPILLQLLNCAVLSFNVASF--LDVIPLTKRLTLLAG-  : 311
DPOL_NPVAC  : MVKMYNTRRLD--------VIAKYNVQDCMLPIKLFVK--LKMADSVYSQCILHR-  : 299
DPOL_NPVLD  : MLQMYGEKRLS--------RIVEYNVQDCVLPVELFLK--LETADYMYTQCMLLY-  : 310
DPOZ_YEAST  : LTNMWNAKKST-----TELKTVLNYWLSRAQINIQLLRK--QDYIARNIEQARLIG-  : 289
DPOL_PYRFU  : IAKAWESGEN--------LERVAKYSMEDAKATYELG----KEFLPMEIQLSRLVG-  : 313
DPO1_SULSO  : LISFLDVEK-----------LIEYNFRDAEITLQLTTFNNDLTMKLIVLFSRISR-  : 282
DPO2_ECOLI  : MDEIDRRFAED-------KPALATYNLKDCELVTQIFHK--TEIMPFLLERATVNG-  : 308
DPol_Dtok   : IARAWESGEG--------LERVARYSMEDAKATYELGK----EFFPMEAQLSRLVG-  : 338
RM378       : YHFIPVYPDK----------KLVEYNAVDAILMEEIENK--NHILPTLFEIARLSN-  : 305
RB69        : RE------SN--------HQRYISYNIIDVYRVLQIDA--KRQFINLSLDMGYYAK-  : 352

Exo III
```

FIG. 3H

```
                         460            480            500
DPOL_VACCC  : -LPNDTYKLSFGKDDVDLAQMYKDYNLNIALDMARYCIHDACLCQYLWEYYG-----  :  375
DPOL_VACCV  : -LPNDTYKLSFGKDDVDLAQMYKDYNLNIALDMARYCIHDACLCQYLWEYYG-----  :  375
DPOL_VARV/  : -LTNDTYKLSFGKDDVDLAQMYKDYNLNIALDMARYCIHDACLCQYLWEYYG-----  :  374
DPOL_FOWPV  : YEIGSVHNISFGKDDVDLKDMYKNYNLEIALDMERYCIHDACLCKYIWDYYR-----  :  363
DPOD_BOVIN  : --------VPLGYLLSRGQQVKVVSQLLRQAMRQGLLMPVVK---------------  :  336
DPOD_HUMAN  : --------VPLSYLLSRGQQVKVVSQLLRQAMHEGLLMPVVK---------------  :  336
DPOD_CANAL  : --------VPFSYLLSRGQQIKVISQLFRKCLQEDIVIPNLK---------------  :  335
DPOD_YEAST  : --------VPFSYLLARGQQIKVVSQLFRKCLEIDTVIPNMQ---------------  :  337
DPOD_SCHPO  : --------VPFNFLLARGQQIKVISQLFCKALQHDLVVPNIR---------------  :  336
DPOD_PLAFK  : --------TPFVYLLTRGQQIKVTSQLYRKCKELNYVIPSTY---------------  :  339
DPOL_CHVN2  : --------VPVDYINFRGQQVRAFSCLVGKARQMNYAIPDDK---------------  :  337
DPOL_CHVP1  : --------VPVDYINFRGQQIRAFSCLVGKARQMNYAIPDDK---------------  :  336
DPOL_EBV/2  : --------IPCRRVLDDGQQIRVFSCLLAAAQKENFILPMPS---------------  :  332
DPOL_HSVSA  : --------IPTRRVLTDGQQIRVFSCLLAAARAENYILPVSN---------------  :  331
DPOL_HSV11  : --------INITRTTYDGQQIRVFTCLLRLADQKGFILPDTQGR---FRGAGGEAPK  :  365
DPOL_HSV21  : --------INTTRTTYDGQQIRVFTCLLRLAGQKGFILPDTQGR---FRGLDKEAPK  :  365
DPOL_HSVEB  : --------ITLTRVIFDGQQIRVYTCLLKLARERNFILPDNRRR---FDSQADAASE  :  365
DPOL_VZVD/  : --------ITLTKAIYDGQQVRIYTCLLGLASSRGFILPDGG-----YP--------  :  355
DPOL_HCMVA  : --------IPLRRVIFDGQQIRIYTSLLDECACRDFILPNHYSKGTTVPETNSVAVS  :  387
DPOL_MCMVS  : --------IPLRKVIFDGQQIRIYTCLLEECSGRDMILPNMPSLG----------H  :  351
DPOL_HSV6U  : --------VTARCVVFEGQQKKIFPCILTEAKRRNMILP------------------  :  327
DPOA_HUMAN  : --------NIMSRTLMGGRSERNEFLLLHAFYENNYIVPDKQIF-------------  :  336
DPOA_MOUSE  : --------NIMSRTLMGGRSERNEFLLLHAFYENNYIVPDKKPV-------------  :  338
DPOA_DROME  : --------NTMTRTLQGGRSERNEFLLLHASTEKNYIVPDKKPV-------------  :  338
DPOA_SCHPO  : --------NSWARTLTGTRAERNEYILLHEFKKNGYIVPDKQQS-------------  :  345
DPOA_YEAST  : --------NAWAQTLGGTRAGRNEYILLHEFSRNGFIVPDKE-G-------------  :  346
DPOA_TRYBB  : --------NLWSRTLYGARSERIEYLLLHAFHNLKFVTPDKK---------------  :  345
DPOL_NPVAC  : --------LCTDDVICNISHLISVACFYAAITNTRINESTGK---------------  :  333
DPOL_NPVLD  : --------LCTDDLLRNISHKITVAYFHLALTNTVARRPD-----------------  :  342
DPOZ_YEAST  : --------IDFHSVYYRGSQFKVESFLIRICKSESFILLSPG---------------  :  323
DPOL_PYRFU  : --------QPLWDVSRSSTGNLVEWFLLRKAYERNEVAPNKP---------------  :  347
DPO1_SULSO  : --------LGIEELTRTEISTWVKNLYYWEHRKRNWLIPLKEEILAK----------  :  321
DPO2_ECOLI  : --------LPVDRHGGSVAAFGHLYFPRMHRAGYVAPNLG-----------------  :  340
DPol_Dtok   : --------QSLWDVSRSSTGNLVEWFLLRKAYERNDVAPNKP---------------  :  372
RM378       : -LTPALALNASNILIGNVTGKLGVKFV-DYIKKIDTINTMFK---------------  :  345
RB69        : --------IQIQSV--FSPIKTWDAIIFNSLKEQNKVIPQGR---------------  :  384
```

FIG. 31

```
                         520            540            560
DPOL_VACCC : ---------------------------------VETKTDA--GASTYVLPQSMVF  : 395
DPOL_VACCV : ---------------------------------VETKTDA--GASTYVLPQSMVF  : 395
DPOL_VARV/ : ---------------------------------VETKTDA--GASTYVLPQSMVF  : 394
DPOL_FOWPV : ---------------------------------VPSKINA--ASSTYLLPQSLAL  : 383
DPOD_BOVIN : --------------------------T-------E--G--GED-------       : 342
DPOD_HUMAN : --------------------------S-------E--G--GED-------       : 342
DPOD_CANAL : --------------------------S-------E--GS-NEE-------       : 342
DPOD_YEAST : --------------------------S-------Q--AS-DDQ-------       : 344
DPOD_SCHPO : --------------------------V-------N--GT-DEQ-------       : 343
DPOD_PLAFK : ------------------------M---------K--VNTNEK-------       : 347
DPOL_CHVN2 : ------------------------M---------W--TV-DGK-------       : 344
DPOL_CHVP1 : ------------------------A---------W--AT-EGK-------       : 343
DPOL_EBV/2 : ---------------------------AS-DRD-------------           : 337
DPOL_HSVSA : ---------------------------DV-NAD-------------           : 336
DPOL_HSV11 : RPAAAREDEERP------------------EEEGEDEDE--REEGGGEREP-EG   : 398
DPOL_HSV21 : RPAVPRGEGERPGDGNG---------------DEDKDDDED--GDEDGDERE--EV : 402
DPOL_HSVEB : TSELAMDSQSHAFDSTD---------------EPDGVDGTP--DAAGSGATSENGG : 404
DPOL_VZVD/ : ---ATFEYKDVIPDVGD---------------VEEEMDEDE--SVSPTGTSS---- : 387
DPOL_HCMVA : PNAAIISTAAVPGDAGSVAAMFQMSPPLQSAPSSQDGVSPGS--GSNSSSSVGV--- : 439
DPOL_MCMVS : GAAAAIEEAAAGGE-G------------------DETSEGE--NSNNSR-------  : 379
DPOL_HSV6U : ----------------------------------SMVS--S--HNRQG-------  : 337
DPOA_HUMAN : ------------------------------RKPQQKL--GDEDEEIDGD---     : 353
DPOA_MOUSE : ------------------------------RKPQQKL--GDEDEEIDGD---     : 353
DPOA_DROME : ------------------------------SK-RSGA--GDTDRTLSGA---     : 354
DPOA_SCHPO : -------------------------------IRRHAEA--FGAEDGLQ-----    : 360
DPOA_YEAST : -------------------------------NRSRAQK--QRQNEENA-----    : 361
DPOA_TRYBB : ---------------------------------KRDLKR--GREDDDDE-----   : 359
DPOL_NPVAC : ------------------------EEPDPYFFNKNDLSIIS--GQFKADKAAAG-- : 361
DPOL_NPVLD : ------------------------PTPDPYFFNKYDLSVTS--GASAPSTSRPANA : 372
DPOZ_YEAST : ----------------------------------------KKDVRKQK-----    : 331
DPOL_PYRFU : -----------------------------------SE--EEYQRRLR-----     : 357
DPO1_SULSO : ---------------------------------SSNIRT--SALIKGK------   : 334
DPO2_ECOLI : ---------------------------------E--VPPHAS-------        : 347
DPol_Dtok  : -----------------------------DE-------RELARRTES----      : 383
RM378      : ---------------------------------KIPEMN--INKYR--------   : 356
RB69       : ---------------------------------------S--HPVQP-------   : 390
                        End of ORF056e-|-Beginning of ORF632e
```

FIG. 3J

```
                       580         .        600         .        620
DPOL_VACCC  : EYRASTVIKGPLLKLLLETKTILVRSETKQKFPYEGGKVFAPKQKMFSNNVLIFDYN : 452
DPOL_VACCV  : EYRASTVIKGPLLKLLLETKTILVRSETKQKFPYEGGKVFAPKQKMFSNNVLIFDYN : 452
DPOL_VARV/  : GYKASTVIKGPLLKLLLETKTILVRSETKQKFPYEGGKVFAPKQKMFSNNVLIFDYN : 451
DPOL_FOWPV  : EYRASTLIKGPLLKLLLEERVIYTRKITKVRYPYIGGKVFLPSQKTFENNVMIFDYN : 440
DPOD_BOVIN  : ----------------------------------YTGATVIEPLKGYYDVPIATLDFS : 366
DPOD_HUMAN  : ----------------------------------YTGATVIEPLKGYYDVPIATLDFS : 366
DPOD_CANAL  : ----------------------------------YEGATVIEPERGYYDVPIATLDFS : 366
DPOD_YEAST  : ----------------------------------YEGATVIEPIRGYYDVPIATLDFN : 368
DPOD_SCHPO  : ----------------------------------YEGATVIEPIKGYYDTPIATLDFS : 367
DPOD_PLAFK  : ----------------------------------YEGATVLEPIKGYYIEPISTLDFA : 371
DPOL_CHVN2  : ----------------------------------YEGATVLDAKKGAYFTSIAALDFA : 368
DPOL_CHVP1  : ----------------------------------YEGATVLDAKKGAYFTPIAALDFA : 367
DPOL_EBV/2  : --------G-------------------------YQGATVIQPLSGFYNSPVLVVDFA : 362
DPOL_HSVSA  : --------G-------------------------FQGATVINPIPGFYNNAVLVVDFA : 361
DPOL_HSV11  : ARETAGRHVG------------------------YQGARVLDPTSGFHVNPVVVFDFA : 432
DPOL_HSV21  : ARETGGRHVG------------------------YQGARVLDPTSGFHVDPVVVFDFA : 436
DPOL_HSVEB  : CKPGVGRAVG------------------------YQGAKVLDPVSGFHVDPVVVFDFA : 438
DPOL_VZVD/  : -----GRNVG------------------------YKGARVFDPDTGFYIDPVVVLDFA : 416
DPOL_HCMVA  : ------FSVGSGSSGGVGVSNDNHGAGGTAAVSYQGATVFEPEVGYYNDPVAVFDFA : 490
DPOL_MCMVS  : --------TVG-----------------------YQGATVLEPECGFHHVPVCVFDFA : 406
DPOL_HSV6U  : ---------IG-----------------------YKGATVLEPKTGYYAVPTVVFDFQ : 363
DPOA_HUMAN  : ----TNKYKKG-----------------------RKKGAYAGGLVLDPKVGFYDKFILLLDFN : 389
DPOA_MOUSE  : ----TNKYKKG-----------------------RKKATYAGGLVLDPKVGFYDKFILLLDFN : 389
DPOA_DROME  : ----DATMQT------------------------KKKAAYAGGLVLEPMRGLYEKYVLLMDLN : 389
DPOA_SCHPO  : ----EESLGK------------------------KKDKYKGGLVFEPQKGLYETCILVMDFN : 394
DPOA_YEAST  : ----DAPVNS------------------------KKAKYQGGLVFEPEKGLHKNYVLVMDFN : 395
DPOA_TRYBB  : ---------GK-----------------------RKTKYQGGMVLEPKSGLYSEYILLLDFN : 389
DPOL_NPVAC  : ----ISNLKRKLIPLKNIPKDAINLGPANQTVKYKGGKVLKPRAGIYKN-AFSLDFN : 413
DPOL_NPVLD  : --IDLSQLKRTPVDAARIPPSAVKLCSTRQSCTYKGGKVLSPKPGFNRW-VATLDFN : 426
DPOZ_YEAST  : -----------------------------ALECVPLVMEPESAFYKSPLIVLDFQ : 357
DPOL_PYRFU  : ---------ES-----------------------YTGGFVKEPEKGLWEN-IVYLDFR : 382
DPO1_SULSO  : ---------G------------------------YKGAVVIDPPAGIFFN-ITVLDFA : 358
DPO2_ECOLI  : ----------------------------------PGGYVMDSRPGLYDS-VLVLDYK : 369
DPol_Dtok   : ----------------------------------YAGGYVKEPEKGLWEN-IVYLDYK : 406
RM378       : ----------------------------------YRGAYIELTNPDIYFN-VFDLDFT : 379
RB69        : ----------------------------------YPGAFVKEPIPNRYKY-VMSFDLT : 413
                                                                  *
```

FIG. 3K

```
                         640            .       660           .      680
DPOL_VACCC : SLYPNVCIFGNLSPE-TLVGVVVSTNRLEE----EINNQLLLQKYPPPRYITVH---  :  501
DPOL_VACCV : SLYPNVCIFGNLSPE-TLVGVVVSTNRLEE----EINNQLLLQKYPPPRYITVH---  :  501
DPOL_VARV/ : SLYPNVCIFGNLSPE-TLVGVVVSSNRLEE----EINNQLLLQKYPPPRYITVH---  :  500
DPOL_FOWPV : SLYPNVCIYGNLSPE-KLVCILLNSNKLES----EINMRTIKSKYPYPEYVCVS---  :  489
DPOD_BOVIN : SLYPSIMMAHNLCYT-TLLRP---GAAQKL----GLT-EDQFIKTP----------  :  403
DPOD_HUMAN : SLYPSIMMAHNLCYT-TLLRP---GTAQKL----GLT-EDQFIRTP----------  :  403
DPOD_CANAL : SLYPSIMMAHNLCYT-TLLNK---NSIKAF----GLT-EDDYTKTP----------  :  403
DPOD_YEAST : SLYPSIMMAHNLCYT-TLCNK---ATVERL----NLKIDEDYVITP----------  :  406
DPOD_SCHPO : SLYPSIMQAHNLCYT-TLLDS---NTAELL----KLKQDVDYSVTP----------  :  405
DPOD_PLAFK : SLYPSIMIAHNLCYS-TLIKS---NHEVSD----LQNDDITTIQGK----------  :  409
DPOL_CHVN2 : SLYPSIIRAHNMSPE-TLVMD---KRFENL----PGIEYYBIETGL----------  :  406
DPOL_CHVP1 : SLYPSIIRAHNMSPE-TLVME---KRFENV----PGVEYYBIETGL----------  :  405
DPOL_EBV/2 : SLYPSIIQAHNLCYS-TMITPGEEHRLAGL----RPGEDYESFRLT----------  :  403
DPOL_HSVSA : SLYPSIIQAHNLCYS-TLIPHHALHNYPHL----KSS-DYETFMLS----------  :  401
DPOL_HSV11 : SLYPSIIQAHNLCFS-TLSLR--ADAVAHL----EAGKDYLEIEVG----------  :  471
DPOL_HSV21 : SLYPSIIQAHNLCFS-TLSLR--PEAVAHL----EADRDYLEIEVG----------  :  475
DPOL_HSVEB : SLYPSIIQAHNLCFT-TLALD--EVDLAGL----QPSVDYSTFEVG----------  :  477
DPOL_VZVD/ : SLYPSIIQAHNLCFT-TLTLN--FETVKRL----NPS-DYATFTVG----------  :  454
DPOL_HCMVA : SLYPSIIMAHNLCYS-TLLVP---GGEYPV----DPA-DVYSVTLEN---------  :  528
DPOL_MCMVS : SLYPSIIMSNNLCYS-TLLVE---GS-PEV----PEK-DVLRVEIG----------  :  442
DPOL_HSV6U : SLYPSIMMAHNLCYS-TLVLDE--RQIAGL----SES-DILTVKLG----------  :  401
DPOA_HUMAN : SLYPSIIQEFNICFT-TVQRVA--SEAQKV----TEDGEQEQIP------------  :  426
DPOA_MOUSE : SLYPSIIQEFNICFT-TVQRVT--SEVQKA----TEDEEQEQIP------------  :  426
DPOA_DROME : SLYPSIIQEYNICFN-PVQ---------QP-------VDADELP-----------  :  416
DPOA_SCHPO : SLYPSIIQEYNICFT-TVDRS--------P----SNSDSDDQIP------------  :  425
DPOA_YEAST : SLYPSIIQEFNICFT-TVDR--------------NKEDIDELP-------------  :  423
DPOA_TRYBB : SLYPSLIQEFNVCYT-TIDR---------D----ENTVSAEVPPPESL--------  :  423
DPOL_NPVAC : SLYLTIMIAICACLS-NLILCE----------------------------------  :  434
DPOL_NPVLD : ALYPTIMMWEGVCMSSNVFIAS----------------------------------  :  448
DPOZ_YEAST : SLYPSIMIGYNYCYSTMIGRVREINLTENN----LGVSKFSLPRNILALLKNDV---  :  407
DPOL_PYRFU : ALYPSIIITHNVSPD-TLN---------L----EGCKNYDIAP------------  :  411
DPO1_SULSO : SLYPSIIRTWNLSYE-TVDIQQ-------C----KKPYEVKDETG-----------  :  391
DPO2_ECOLI : SLYPSIIRTFLIDPVGLVEG--------------MAQPDPEHSTEG----------  :  401
DPol_Dtok  : SLYPSIIITHNVSPD-TLNR--------------EGCREYDVAP------------  :  435
RM378      : SLYPSVISKFNIDPATFVTEFYGCMRVENK----VIPVDQEEPEFGFPLYIFDSGMN :  432
RB69       : SLYPSIIRQVNISPETIAGTFKVAPLHDYINAVAERPSDVYSCSPNGMMYYKDRDGV :  470
             **
             motif A
```

FIG. 3L

```
                            700            720            740
DPOL_VACCC  : ----------CEPRLPNLISEIAIFDRSIE------------GTIPRLLRTFLAE : 534
DPOL_VACCV  : ----------CEPRLPNLISEIAIFDRSIE------------GTIPRLLRTFLAE : 534
DPOL_VARV/  : ----------CEPRLPNLISEIAIFDRSIE------------GTIPRLLRTFLAE : 533
DPOL_FOWPV  : ----------CESRLSDYYSEIIVYDRREK------------GIIPKLLEMFIGK : 522
DPOD_BOVIN  : ---------------TGDEFVKAS----VRK-----------GLLPQILENLLSA : 428
DPOD_HUMAN  : ---------------TGDEFVKTS----VRK-----------GLLPQILENLLSA : 428
DPOD_CANAL  : ---------------NGDYFVHSN----LRK-----------GILPTILDELLTA : 428
DPOD_YEAST  : ---------------NGDYFVTTK----RRR-----------GILPIILDELISA : 431
DPOD_SCHPO  : ---------------NGDYFVKPH----VRK-----------GLLPIILADLLNA : 430
DPOD_PLAFK  : ---------------NNLKFVKKN----VKK-----------GILPLIVEELIEA : 434
DPOL_CHVN2  : ---------------GTFKYPQKNDETGEGQ-----------GVVPALLDDLAKF : 435
DPOL_CHVP1  : ---------------GKFKYAQKNDETGEGQ-----------GVVPALLDDLAKF : 434
DPOL_EBV/2  : ---------------GGVYHFVKKH----VHE----------SFLASLLTSWLAK : 429
DPOL_HSVSA  : ---------------SGPIHFVKKH----IQA----------SLLSRLLTVWLSK : 427
DPOL_HSV11  : ---------------GRRLFFVKAH----VRE----------SLLSILLRDWLAM : 497
DPOL_HSV21  : ---------------GRRLFFVKAH----VRE----------SLLSILLRDWLAM : 501
DPOL_HSVEB  : ---------------DQKLFFVHAH----IRE----------SLLGILLRDWLAM : 503
DPOL_VZVD/  : ---------------GKRLFFVRSN----VRE----------SLLGVLLKDWLAM : 480
DPOL_HCMVA  : ---------------GVTHRFVRAS----VRV----------SVLSELLNKWVSQ : 554
DPOL_MCMVS  : ---------------DQCHRFVREN----VHR----------SLLAELLVRWLTQ : 468
DPOL_HSV6U  : ---------------DETHRFVKPC----IRE----------SVLGSLLKDWLAK : 427
DPOA_HUMAN  : ----------------ELPDPS---LEM--------------GILPREIRKLVER : 448
DPOA_MOUSE  : ----------------ELPDPN---LEM--------------GILPREIRKLVER : 448
DPOA_DROME  : ----------------TLPDSK---TEP--------------GILPLQLKRLVES : 438
DPOA_SCHPO  : ----------------DTPSAS---ANQ--------------GIFPRLIANLVER : 447
DPOA_YEAST  : ----------------SVPPSE---VDQ--------------GVLPRLLANLVDR : 445
DPOA_TRYBB  : ----------ICLSCRAAGLPSPC---LHK------------CILPKVIRGLVDS : 453
DPOL_NPVAC  : --------------DGNVYLNHN-----SR------------AIVVKLLLKLLSE : 458
DPOL_NPVLD  : --------------DGNVYLDKN-----VN------------AVNPKLLKTLSEM : 472
DPOZ_YEAST  : ----------TIAPNGVVYAKTS----VRK------------STLSKMLTDILDV : 436
DPOL_PYRFU  : --------------QVGHKFCKDIP-----------------GFIPSLLGHLLEE : 435
DPO1_SULSO  : ----------EVLHIVCMD-----RP----------------GITAVITGLLRDF : 415
DPO2_ECOLI  : ----------------FLDAWFS--REK--------------HCLPEIVTNIWHG : 424
DPol_Dtok   : --------------QVGHRFCKDFP-----------------GFIPSLLGDLLEE : 459
RM378       : PSYRSEPLFVINSFEELRQFLKSRNIIMVPNPSGICWFYRKEPVGVLPSIIREIFTR : 489
RB69        : VPTEITKVFNQRKEHKGYMLAAQRNGEIIKEALHN-PNLSVDEPLDVDYRFDFSDEI : 526
```

FIG. 3M

```
                          760            780           8
DPOL_VACCC  : RARYKKMLKQAT---SSTEKAIYDSM--------QYTYKIVANSVYGLMGFRNS-A : 578
DPOL_VACCV  : RARYKKMLKQAT---SSTEKAIYDSM--------QYTYKIVANSVYGLMGFRNS-A : 578
DPOL_VARV/  : RARYKKMLKQAT---SSTEKAIYDSM--------QYTYKIIANSVYGLMGFRNS-A : 577
DPOL_FOWPV  : RKEYKNLLKTAS---TTIESTLYDSL--------QYIYKIIANSVYGLMGFSNS-T : 566
DPOD_BOVIN  : RKRAKAELAKET---DPLRRQVLDGR--------QLALKVSANSVYGFTGAQVG-R : 472
DPOD_HUMAN  : RKRAKAELAKET---DPLRRQVLDGR--------QLALKVSANSVYGFTGAQVG-K : 472
DPOD_CANAL  : RKKAKADLKKET---DPFKKDVLNGR--------QLALKISANSVYGFTGATVG-K : 472
DPOD_YEAST  : RKRAKKDLRDEK---DPFKRDVLNGR--------QLALKISANSVYGFTGATVG-K : 475
DPOD_SCHPO  : RKKAKADLKKET---DPFKKAVLDGR--------QLALKVSANSVYGFTGATNG-R : 474
DPOD_PLAFK  : RKKVKLLIKNEK---NNITKMVLNGR--------QLALKISANSVYGYTGASSGGQ : 479
DPOL_CHVN2  : RKQAKKHMAEAKKNDDEFREALYDAQ--------QRSYKIVMNSVYGFLGASRG-F : 482
DPOL_CHVP1  : RKLAKKHMAEAKRNGDDFKEALYDAQ--------QRSFKVVMNSVYGFLGASKG-F : 481
DPOL_EBV/2  : RKAIKKLLAACE---DPRQRTILDKQ--------QLAIKCTCNAVYGFTGVANG-L : 473
DPOL_HSVSA  : RKAIRQKLAECE---DLDTKTILDKQ--------QLAIKVTCNAVYGFTGVASG-L : 471
DPOL_HSV11  : RKQIRSRIPQS----SPEEAVLLDKQ--------QAAIKVVCNSVYGFTGVQHG-L : 540
DPOL_HSV21  : RKQIRSRIPQS----PPEEAVLLDKQ--------QAAIKVVCNSVYGFTGVQHG-L : 544
DPOL_HSVEB  : RKAVRARIPTS----TPEEAVLLDKQ--------QSAIKVICNSVYGFTGVANG-L : 546
DPOL_VZVD/  : RKAIRARIPGS----SSDEAVLLDKQ--------QAAIKVVCNSVYGFTGVAQG-F : 523
DPOL_HCMVA  : RRAVRECMRECQ---DPVRRMLLDKE--------QMALKVTCNAFYGFTGVVNG-M : 598
DPOL_MCMVS  : RKLVREAMKQCT---NEMQRMIMDKQ--------QLALKVTCNAFYGFTGVAAG-M : 512
DPOL_HSV6U  : RREVKAEMQNCS---DPMMKLLLDKK--------QLALKTTCNSVYGVTGAAHG-L : 471
DPOA_HUMAN  : RKQVKQLMKQQDL--NPDLILQYDIR--------QKALKLTANSMYGCLGFSYS-R : 493
DPOA_MOUSE  : RKQVKQLMKQQDL--NPDLVLQYDIR--------QKALKLTANSMYGCLGFSYS-R : 493
DPOA_DROME  : RKEVKKLMAAPDL--SPELQMQYHIR--------QMALKLTANSMYGCLGFAHS-R : 483
DPOA_SCHPO  : RRQIKGLLKDNSA--TPTQRLQWDIQ--------QQALKLTANSMYGCLGYTKS-R : 492
DPOA_YEAST  : RREVKKVMK-TET--DPHKRVQCDIR--------QQALKLTANSMYGCLGYVNS-R : 489
DPOA_TRYBB  : RREIKRMMK-SEK--DPGNLAMLEIR--------QLALKLTANSMYGCLGFEYS-R : 497
DPOL_NPVAC  : RCKFKKNRDNQSE--SAFLYDLYDQK--------QNSVKRTANSIYGYYGIFYK-- : 502
DPOL_NPVLD  : RVRYKGLRDQCEY--NSFYYKLYDKI--------QNALKRIANSIYGYYGIFFK-- : 516
DPOZ_YEAST  : RVMIKKTMNEIGDD-NTTLKRLLNNK--------QLALKLLANVTYGYTSASFSGR : 483
DPOL_PYRFU  : RQKIKTKMKETQ---DPIEKILLDYR--------QKAIKLLANSFYGYYGYAKA-R : 479
DPO1_SULSO  : RVKIYKKKAKNPNN-SEEQKLLYDVV--------QRAMKVFINATYGVFGAETFP- : 461
DPO2_ECOLI  : RDEAKRQGNKP--------------L--------SQALKIIMNAFYGVLGTTAC-R : 457
DPol_Dtok   : RQKVKKKMKAT---VDPIERKLLDYR--------QRAIKILANSYYGYYAYANA-R : 503
RM378       : RKEERKLFKET-----GNMEHHFR----------QWALKIMMNSMYGIFGNRSV-Y : 529
RB69        : KEKIKKLSAKS------LNEMLFRAQRTEVAGMTAQINRKLLINSLYGALGNVWF-R : 576
                                                *   *  **
                                                    motif B
```

FIG. 3N

```
                    00        .        820         .         840        .
DPOL_VACCC  :  LYSYASAKSCTSIGRRMILYLESVLNGAELSNGML--RFANPLSNP-------FYMD  :  626
DPOL_VACCV  :  LYSYASAKSCTSIGRRMILYLESVLNGAELSNGML--RFANPLSNP-------FYMD  :  626
DPOL_VARV/  :  LYSYASAKSCTSIGRRMILYLESVLNGAELSNGML--RFANPLSNP-------FYMD  :  625
DPOL_FOWPV  :  LYSYSSAKTCTTIGRNMITYLDSIMNGAVWENDKL--ILADFPRN--------IFSG  :  613
DPOD_BOVIN  :  LPCLEISQSVTGFGRQMIEKTKQLVETKYTV------ENGYS---------------  :  508
DPOD_HUMAN  :  LPCLEISQSVTGFGRQMIEKTKQLVESKYTV------ENGYS---------------  :  508
DPOD_CANAL  :  LPCLAISSSVTAFGREMIEKTKNEVQEYYSK------KNGHP---------------  :  508
DPOD_YEAST  :  LPCLAISSSVTAYGRTMILKTKTAVQEKYCI------KNGYK---------------  :  511
DPOD_SCHPO  :  LPCLAISSSVTSYGRQMIEKTKDVVEKRYRI------ENGYS---------------  :  510
DPOD_PLAFK  :  LPCLEVAVSITTLGRSMIEKTKERVESFYCK------SNGYE---------------  :  515
DPOL_CHVN2  :  IPCVPIAASVTATGRKMIEHTAKRVTELLP----------G----------------  :  513
DPOL_CHVP1  :  IPCVPIAASVTATGRKMIEHTAKRAVELLP----------G----------------  :  512
DPOL_EBV/2  :  FPCLSIAETVTLQGRTMLERAKAFVEA--LSPANL--QALAPSP-------------  :  513
DPOL_HSVSA  :  LPCTSIAETVTLQGRTMLEKSKIFIEA--MTPDTL--QEIVP---------------  :  509
DPOL_HSV11  :  LPCLHVAATVTTIGREMLLATREYVHARWAAFEQL--LADFPEA-------------  :  582
DPOL_HSV21  :  LPCIHVAATVTTIGREMLLATRAYVHARWAEFDQL--LADFPEA-------------  :  586
DPOL_HSVEB  :  LPCLRIAATVTTIGRDMLLKTRDYVHSRWATRELL--EDNFPGA-------------  :  588
DPOL_VZVD/  :  LPCLYVAATVTTIGRQMLLSTRDYIHNNWAAFERF--ITAFPDI-------------  :  565
DPOL_HCMVA  :  MPCLPIAASITRIGRDMLERTARFIKDNFSEPCFL--HNFFNQEDYVVGTREGDSEE  :  653
DPOL_MCMVS  :  LPCLPIAASITKIGRDMLLATAGHIEDRCNRPDFL--RTVLGLP-------------  :  554
DPOL_HSV6U  :  LPCVAIAASVTCLGREMLCSTVDYVNSKMQSEQFF--CEEFGLT-------------  :  513
DPOA_HUMAN  :  FYAKPLAALVTYKGREILMHTKEMVQKMN----------------------------  :  522
DPOA_MOUSE  :  FYAKPLAALVTYKGREILMHTKDMVQKMN----------------------------  :  522
DPOA_DROME  :  FFAQHLAALVTHKGRD-LTNTQQLVQKMN----------------------------  :  511
DPOA_SCHPO  :  FYARPLAVLITYKGREALMNTKELADQMG----------------------------  :  521
DPOA_YEAST  :  FYAKPLAMLVTNKGREILMNTRQLAESMN----------------------------  :  518
DPOA_TRYBB  :  FYAQPLAELVTRQGRLALQNTVELIPQISPS--------------------------  :  528
DPOL_NPVAC  :  ----VLANYITRVGRNQLRLAISLIEGLSNDPEIL--EKFNLG--------------  :  539
DPOL_NPVLD  :  ----PLANYITKMGRGKLEVVGKVEAMSDDPRIL--REFGLS---------------  :  553
DPOZ_YEAST  :  MPCSDLADSIVQTGRETLEKAIDIIEKDETWN-------------------------  :  509
DPOL_PYRFU  :  WYCKECAESVTAWGRKYIELVWKELEEKFG---------------------------  :  490
DPO1_SULSO  :  LYAPRVAESVTALGRYVITSTVKKAREE-G---------------------------  :  486
DPO2_ECOLI  :  FFDPRLASSITMRGHQIMRQTKALIEAQG----------------------------  :  486
DPol_Dtok   :  WYCRECAESVTAWGRQYIETTMREIEEKFG---------------------------  :  533
RM378       :  MGCLPIAESVTAAGRMSIRSVISQIRDR-----------------------------  :  557
RB69        :  YYDLRNATAITTFGQMALQWIERKVNEYLNEVCG---TEG-----------------  :  613
                                 *
```

FIG. 30

```
             860         880         900
DPOL_VACCC : DRDINPIVKTSLP--IDYRFRFRSVYGDTDSVFTEIDSQD-------VDKSIEIAKE : 674
DPOL_VACCV : DRDINPIVKTSLP--IDYRFRFRSVYGDTDSVFTEIDSQD-------VDKSIEIAKE : 674
DPOL_VARV/ : DRDINPIVKTSLP--IDYRFRFRSVYGDTDSVFTEIDSQD-------VDKSIEIAKE : 673
DPOL_FOWPV : ETMPNKELEVPN---MNESFKFRSVYGDTDSIFSEISTKD-------IEKTAKIAKH : 660
DPOD_BOVIN : --------TS----------AKVVYGDTDSVMCRFGVSS-------VAEAMALGRE : 539
DPOD_HUMAN : --------TS----------AKVVYGDTDSVMCRFGVSS-------VAEAMALGRE : 539
DPOD_CANAL : --------YD----------AKVIYGDTDSVMVKFGYQD-------LETCMKLGEE : 539
DPOD_YEAST : --------HD----------AVVVYGDTDSVMVKFGTTD-------LKEAMDLGTE : 542
DPOD_SCHPO : --------HD----------AVVIYGDTDSVMVKFGVKT-------LPEAMKLGEE : 541
DPOD_PLAFK : --------HN----------STVIYGDTDSVMVKFGTNN-------IEEAMTLGKD : 546
DPOL_CHVN2 : --------------------SEVIYGDTDSVMIRMKLPDDKIHD--MDEQFKMAKW : 547
DPOL_CHVP1 : --------------------SEVIYGDTDSVMVKMKLPDDKVHD--MDEQFKMAKW : 546
DPOL_EBV/2 : ----DAWAPLN------PEGQLRVIYGDTDSLFIECRGFS-------ESETLRFADA : 553
DPOL_HSVSA : -----HIVKHE------PDAKFRVIYGDTDSLFVECVGYS-------VDTVVKFGDF : 548
DPOL_HSV11 : ----AD-MRAP------GPYSMRIIYGDTDSIFVLCRGLT-------AAGLTAVGDK : 621
DPOL_HSV21 : ----AG-MRAP------GPYSMRIIYGDTDSIFVLCRGLT-------GEALVAMGDK : 625
DPOL_HSVEB : ----IG-FRNH------KPYSVRVIYGDTDSVFIKFVGLT-------YEGVSELGDA : 627
DPOL_VZVD/ : ----ESSVLSQ------KAYEVKVIYGDTDSVFIRFKGVS-------VEGIAKIGEK : 605
DPOL_HCMVA : SSALPEGLETSSGGSNERRVEARVIYGDTDSVFVRFRGLT-------PQALVARGPS : 703
DPOL_MCMVS : ----PEAIDP-------EALRVKIIYGDTDSVFAAFYGID-------KEALLKAVGA : 593
DPOL_HSV6U : ----SSDFTG--------DLEVEVIYGDTDSIFMSVRNMV-------NQSLRRIAPM : 551
DPOA_HUMAN : --------------------LEVIYGDTDSIMINTNSTN------LEEVFKLGNK  : 551
DPOA_MOUSE : --------------------LEVIYGDTDSIMINTNSTN------LEEVFKLGNK  : 551
DPOA_DROME : --------------------YDVVYGDTDSLMINTNITD-------YDQVYKIGHN : 540
DPOA_SCHPO : --------------------LQVIYGDTDSVMLNTNVTD-------KNHALRIGNE : 550
DPOA_YEAST : --------------------LLVVYGDTDSVMIDTGCDN-------YADAIKIGLG : 547
DPOA_TRYBB : --------------------IRVIYGDTDSVMIQTGIKDD------IVKVRNLGFE : 558
DPOL_NPVAC : -----------------SITFKVVYGDTDSTFVLPTFNYNEISN--ETDTLK--QI : 574
DPOL_NPVLD : ------------------KINFSVIYGDTDSCFIRVLFDEAEWRR--TAARPRSAPS : 590
DPOZ_YEAST : --------------------AKVVYGDTDSLFVYLPGKT-------AIEAFSIGHA : 544
DPOL_PYRFU : --------------------FKVLYIDTDGLYATIPGGE-------SEEIKKKALE : 538
DPO1_SULSO : --------------------LTVLYGDTDSLFLLNPPKN--------SLENIIKWV : 518
DPO2_ECOLI : --------------------YDVIYGDTDSTFVWLKGAHS------EEEAAKIGRA : 516
DPol_Dtok  : --------------------FKVLYADTDGFFATIPGAD-------AETVKNKAKE : 562
RM378      : ---------------------FIYSHTDSIFVKAFTDDP------VAEAGELQEH  : 585
RB69       : --------------------EAFVLYGDTDSIYVSADKIIDKVGESKFRDTNHWVDF : 650
                                 *  **
                                motif C
```

FIG. 3P

```
                       920           940           960
DPOL_VACCC  : LERLINNR--V----------LFN----NFKIEFEAVYKNLIMQ--------SKKK : 706
DPOL_VACCV  : LERLINNR--V----------LFN----NFKIEFEAVYKNLIMQ--------SKKK : 706
DPOL_VARV/  : LERLINSR--V----------LFN----NFKIEFEAVYKNLIMQ--------SKKK : 705
DPOL_FOWPV  : LEHIINTK--I----------LHA----NFKIEFEAIYTQLILQ--------SKKK : 692
DPOD_BOVIN  : AADWVS-G--H----------FPS----PIRLEFEKVYFPYLLI--------SKKR : 570
DPOD_HUMAN  : AADWVS-G--H----------FPS----PIRLEFEKVYFPYLLI--------SKKR : 570
DPOD_CANAL  : AANYVS-T--K----------FKN----PIKLEFEKVYFPYLLI--------NKKR : 570
DPOD_YEAST  : AAKYVS-T--L----------FKH----PINLEFEKAYFPYLLI--------NKKR : 573
DPOD_SCHPO  : AANYVS-D--Q----------FPN----PINWSFS--TFPYLLI--------SKKR : 570
DPOD_PLAFK  : AAERIS-K--E----------FLS----PIKLEFEKVYCPYLLL--------NKKR : 577
DPOL_CHVN2  : LAGEIT-K--D----------FKA----PNDLEFEKIYYPYILY--------SKKR : 578
DPOL_CHVP1  : LAGEIT-K--D----------FRA----PNDLEFEKIYYPYILY--------SKKR : 577
DPOL_EBV/2  : LAAHTTRS--L----------FVA----PISLEAEKTFSCLMLI--------TKKR : 585
DPOL_HSVSA  : LAAFTSEK--L----------FNA----PIKLESEKTFQCLLLL--------AKKR : 580
DPOL_HSV11  : MASHISRA--L----------FLP----PIKLECEKTFTKLLLI--------AKKK : 653
DPOL_HSV21  : MASHISRA--L----------FLP----PIKLECEKTFTKLLLI--------AKKK : 657
DPOL_HSVEB  : MSRQISAD--L----------FRA----PIKLECEKTFQRLLLI--------TKKK : 659
DPOL_VZVD/  : MAHIISTA--L----------FCP----PIKLECEKTFIKLLLI--------TKKK : 637
DPOL_HCMVA  : LAHYVTAC--L----------FVE----PVKLEFEKVFVSLMMI--------CKKR : 735
DPOL_MCMVS  : LAANVTNA--L----------FKE----PVRLEFEKMFVSLMMI--------CKKR : 625
DPOL_HSV6U  : IAKHITDR--L----------FKS----PIKLEFEKILCPLILI--------CKKR : 583
DPOA_HUMAN  : VKSEVN----K----------LYK----LLEIDIDGVFKSLLLL--------KKKK : 581
DPOA_MOUSE  : VKSEVN----K----------LYK----LLEIDIDAVFKSLLLL--------KKKK : 581
DPOA_DROME  : IKQSVN----K----------LYK----QLELDIDGVFGCLLLL--------KKKK : 570
DPOA_SCHPO  : FKEKVN----E----------RYS----KLEIDIDNVYQRMLLH--------AKKK : 580
DPOA_YEAST  : FKRLVN----E----------RYR----LLEIDIDNVFKKLLLH--------AKKK : 577
DPOA_TRYBB  : IKGKVN----Q----------RYQ----SLELDIDGVFRAMLLI--------RKKK : 588
DPOL_NPVAC  : CTHVETRVNNS----------FTD----GYKMAFENLMKVLILL--------KKKK : 608
DPOL_NPVLD  : CRTTCAKRSTT----------LWC----GYKMSLENIMLSLILL--------KKKK : 624
DPOZ_YEAST  : MAERVTQN-------------NPK----PIFLKFEKVYHPSILI--------SKKR : 575
DPOL_PYRFU  : FVKYIN---SK----------LPG----LLELEYEGFYKRGFFV--------TKKR : 569
DPO1_SULSO  : KTTFN----------------------LDLEVDKTYKFVAFSG-------LKKN : 543
DPO2_ECOLI  : LVQHVNAWWAETLQK------QRLTS----ALELEYETHFCRFLMPTIRGADTGSKKR : 564
DPol_Dtok   : FLNYIN---PR----------LPG----LLELEYEGFYRRGFFV--------TKKK : 593
RM378       : LNSFINDYMENN---------FNAREDFKLELKQEFVFKSILIK--------EINR : 624
RB69        : LDKFARERMEPAIDRGFREMCEYMNNKQHLMFMDREAIAGPPLGSKGIGGFWTGKKR : 707
```

FIG. 3Q

```
              980              1000             1020
DPOL_VACCC  : YTTMKYSASSNSKSVPERINKGTSETRRDVSKFHKNMIKTYKTRLSE-MLSEGRMNS : 762
DPOL_VACCV  : YTTMKYSASSNSKSVPERINKGTSETRRDVSKFHKNMIKTYKTRLSE-MLSEGRMNS : 762
DPOL_VARV/  : YTTMKYSASSNSKSVPERINKGTSETRRDVSKFHKNMIKIYKTRLSE-MLSEGRMNS : 761
DPOL_FOWPV  : YTTIKYLANYKPGDKPIRVNKGTSETRRDVALFHKHMIQRYKDMLMK-LLMQSKGQ- : 747
DPOD_BOVIN  : YAGLLFSS--RPDAHDRMDCKGLEAVRRDNCPLVANLVTASLRRLLI-DRDPSGAVA : 624
DPOD_HUMAN  : YAGLLFSS--RPDAHDRMDCKGLEAVRRDNCPLVANLVTASLRRLLI-DRDPEGAVA : 624
DPOD_CANAL  : YAGLYWT---RPEKFDKMDTKGIETVRRDNCQLVQNVITKVLEFILE-ERDVPKAQR : 623
DPOD_YEAST  : YAGLFWT---NPDKFDKLDQKGLASVRRDSCSLVSIVMNKVLKKILI-ERNVDGALA : 626
DPOD_SCHPO  : YAGLFWT---RTDTYDKMDSKGIETVRRDNCPLVSYVIDTALRKMLI-DQDVEGAQL : 623
DPOD_PLAFK  : YAGLLYT---NPNKHDKMDCKGIETVRRDFCILIQQMMETVLNKLLI-EKNLNSAIE : 630
DPOL_CHVN2  : YAAIKFE---DPDEKGKVDVKGLALVRRDFSPITREILKESLDTILF-KKDTPTAVT : 631
DPOL_CHVP1  : YAAVKFE---EPDEKGKVDVKGLALVRRDFSPITRDILKESLDTILY-KKDTPTAVS : 630
DPOL_EBV/2  : YVGVLTD-------G-KTLMKGVELVRKTACKFVQTRCRRVLDLVLA-DARVKEAAS : 633
DPOL_HSVSA  : YIGILSN-------D-KLLMKGVDLVRKTACKFVQNTSSKILNLILK-DPEVKAAAQ : 628
DPOL_HSV11  : YIGVIYG-------G-KMLIKGVDLVRKNNCAFINRTSRALVDLLFY-DDTVSGAAA : 701
DPOL_HSV21  : YIGVICG-------G-KMLIKGVDLVRKNNCAFINRTSRALVDLLFY-DDTVSGAAA : 705
DPOL_HSVEB  : YIGVING-------G-KMLMKGVDLVRKNNCSFINLYARHLVDLLLY-DEDVATAAA : 707
DPOL_VZVD/  : YIGVIYG-------G-KVLMKGVDLVRKNNCQFINDYARKLVELLLY-DDTVSRAAA : 685
DPOL_HCMVA  : YIGKVEG-------ASGLSMKGVDLVRKTACEFVKGVTRDVLSLLFE-DREVSEAAV : 784
DPOL_MCMVS  : YIGKVHG-------SQNLSMKGVDLVRRTACGFVKAVVSDVLHMVFN-DETVSEGTM : 674
DPOL_HSV6U  : YIGRQDD-------S-LLIFKGVDLVRKTSCDFVKGVVKDIVDLLFF-DEEVQTAVE : 631
DPOA_HUMAN  : YAALVVEPTSDGNYVTKQELKGLDIVRRDWCDLAKDTGNFVIGQILS-DQSRDTIVE : 637
DPOA_MOUSE  : YAALVVEPTSDGNYITKQELKGLDIVRRDWCDLAKDTGNFVIGQILS-DQSRDTIVE : 637
DPOA_DROME  : YAAIKLSKDSKGNLRREQEHKGLDIVRRDWSQLAVMVGKAVLDEVLS-EKPLEEKLD : 626
DPOA_SCHPO  : YAALQLDS----QGKPNLDVKGLDMKRREFCTLAKEASKFCLDQILS-GELTETVIE : 632
DPOA_YEAST  : YAALTVNLDKNGNGTTVLEVKGLDMKRREFCPLSRDVSIHVLNTILS-DKDPEEALQ : 633
DPOA_TRYBB  : YAALSVVDWQGEGKVYKREVKGLDMVRRDWCPLSQHVSDAVLKRILN-AEGGEDILD : 644
DPOL_NPVAC  : YCYLNSE--------NKIVYKGWLVKKDMPVFMRIAFRTAVEQILR-HLDMDKCLQ  : 655
DPOL_NPVLD  : YCYLNNE--------QRTKYKGWLIKRDMPLFMRKAFRATVDSFS--AATRRVRAR  : 670
DPOZ_YEAST  : YVGFSYES--PSQTLPIFDAKGIETVRRDGIPAQQKIIEKCIRLLFQ-TKDLSKIKK : 629
DPOL_PYRFU  : YAVIDEE-------GKVITRGLEIVRRDWSEIAKETQARVLETILK-HGDVEEAVR  : 617
DPO1_SULSO  : YFGVYQD-------GKVDIKGMLVKKRNTPEFVKKVFNEVKELMIS-INSPNDVKE  : 591
DPO2_ECOLI  : YAGLIQE-----GDKQRMVFKGLETVRTDWTPLAQQFQQELYLRIFR-NEPYQEYVR : 615
DPol_Dtok   : YAVIDEE-------DKITTRGLEIVRRDWSEIAKETQARVLEAILK-HGDVEEAVR  : 641
RM378       : YFAVTVD-------G-KEEMKGIEVINSSVPEIVKKYFRGYLKYISQPDIDVISATI : 673
RB69        : YALNVWDMEGTRYAEPKLKIMGLETQKSSTPKAVQKALKECIRRMLQ--EGEESLQE : 762
                                  *
```

FIG. 3R

```
                             1040            1060           1080
DPOL_VACCC  : NQVCID-----------------ILRSLETDLRSEFDSRSSPLELFMLSRMHHSN- : 800
DPOL_VACCV  : NQVCID-----------------ILRSLETDLRSEFDSRSSPLELFMLSRMHHSN- : 800
DPOL_VARV/  : NQVCID-----------------ILRSLETDLRSEFDSRSSPLELFMLSRMHHLN- : 799
DPOL_FOWPV  : QEITRL-----------------ILQSLETDMISEFTHN-REFEKYLLSRKHHNN- : 784
DPOD_BOVIN  : HAQDV----------IS-------------DLLCN-RIDISQLVITKELTRAAA-- : 654
DPOD_HUMAN  : HAQDV----------IS-------------DLLCN-RIDISQLVITKELTRAAS-- : 654
DPOD_CANAL  : FVKQT----------IA-------------DLLQN-RIDLSQLVITKAYSKHD--- : 652
DPOD_YEAST  : FVRET----------IN-------------DILHN-RVDISKLIISKTLAPN---- : 654
DPOD_SCHPO  : FTKKV----------IS-------------DLLQN-KIDMSQHVITKALSKTD--- : 652
DPOD_PLAFK  : YTKSK----------IK-------------ELLTN-NIDMSLLVVTKSLGKTD--- : 659
DPOL_CHVN2  : ETVEC----------IR-------------KVLDN-EYPMEKFTMSKTLKTG---- : 659
DPOL_CHVP1  : ETLER----------IR-------------KVLDN-EYPMEKFMMSKLLKTG---- : 658
DPOL_EBV/2  : LLSHRPFQESFTQGLPVGFLPVIDILNQAYTDLREG-RVPMGELCFSTELSRKLSA- : 688
DPOL_HSVSA  : LLSTKDPDYAFREGLPDGFLKVIDILNESHKNLRTG-QVPVEELTFSTELSRPISS- : 683
DPOL_HSV11  : ALAERPAEWLARPLPEGLQAFGAVLVDAHRRITDP-ERDIQDFVLTAELSRHPRA- : 756
DPOL_HSV21  : ALAERPAEWLARPLPEGLQAFGAVLVDAHRRITDP-ERDIQDFVLTAELSRHPRA- : 760
DPOL_HSVEB  : EVTDVPPAEWVGRPLPSGFDKFGRVLVEAYNRITAP-NLDVREFVMTAELSRSPES- : 762
DPOL_VZVD/  : EASCVSIAEWNRRAMPSGMAGFGRIIADAHRQITSP-KLDINKFVMTAELSRPPSA- : 740
DPOL_HCMVA  : RLSRLSLDEVKKYGVPRGFWRILRRLVQARDDLYLH-RVRVEDLVLSSVLSKDISL- : 839
DPOL_MCMVS  : KLSRMTFDDLKKNGIPCEFGPVVSRLCRARDDLHLK-KVPVPELTLSSVLSQELSC- : 729
DPOL_HSV6U  : EFSHMTQTQLREQGVPVGIHKILRRLCEAREELFQN-RADVRHLMLSSVLSKEMAA- : 686
DPOA_HUMAN  : NIQKR------------------LIEIGENVLNG SVPVSQFEINKALTKDPQD- : 672
DPOA_MOUSE  : NIQKR------------------LIEIGENVLNG-SVPVSQFEINKALTKDPQD- : 672
DPOA_DROME  : AVHAQ------------------LEKIKTQIAEG-VVPLPLFVITKQLTRTPQD- : 661
DPOA_SCHPO  : NIHSY------------------LMDFSEKMRNG-KFPANKFIIFNRLGKNPED- : 667
DPOA_YEAST  : EVYDY------------------LEDIRIKVETN-NIRIDKYKINMKLSKDPKA- : 668
DPOA_TRYBB  : FVIKY------------------MKGVAQDVRSGNVYPLEEFVISKSLTKEPES- : 680
DPOL_NPVAC  : SLQTS------------------FYEYYDEFAKS-K-SLTDYSFSMTYNDNPGK- : 689
DPOL_NPVLD  : PARRE------------------MLRYYREFGAP-RENLVDYCFSMSYNETSTT- : 705
DPOZ_YEAST  : YLQN-------------------EFFKIQIG-KVSAQDFCFAKEVKLGAYK- : 660
DPOL_PYRFU  : IVKEV------------------IQKLANYEIPPEKLAIYEQITRPLHE- : 648
DPO1_SULSO  : IKRKIVD----------------VVKGSYEKLKNKGYNLDELAFKVMLSKPLDA- : 629
DPO2_ECOLI  : ETID-------------------KLMAG-ELD-ARLVYRKRLRRPLSE- : 642
DPol_Dtok   : IVKEVT-----------------EKLSRHEVPPEKLVIYEQITRDLRS- : 672
RM378       : AFYNN------------------FVSQKNFWSIEDLYHKMKISSSDSAERYVEY : 709
RB69        : YFKEF------------------EKEFRQLNYISIASVSSANNIAKYDVGG : 795
```

DPOL_VACCC  : YKS----------ADNPNMYLVTEYNKNN-----PETIELGERYYFAYICPAN---- : 838
DPOL_VACCV  : YKS----------ADNPNMYLVTEYNKNN-----PETIELGERYYFAYICPAN---- : 838
DPOL_VARV/  : YKS----------ADNPNMYLVTEYNKNN-----PETIELGERYYFAYICPAN---- : 837
DPOL_FOWPV  : YKS----------ATHSNFELVKRYNLEN-----TEKIEIGERYYYIYICDIS---- : 822
DPOD_BOVIN  : DYA----------GKQAHVELAERMRKRDP----GSAPSLGDRVPYVIISA------ : 691
DPOD_HUMAN  : DYA----------GKQAHVELAERMRKRDP----GSAPSLGDRVPYVIISA------ : 691
DPOD_CANAL  : -YS----------AKQAHVELAERMRKRDP----GSAPTLGDRVAYVIIKT------ : 688
DPOD_YEAST  : -YT----------NPQPHAVLAERMKRRE-----GVGPNVGDRVDYVIIG------- : 688
DPOD_SCHPO  : -YA----------AKMAHVELAERMRKRDA----GSAPAIGDRVAYVIIKG------ : 688
DPOD_PLAFK  : -YE----------TRLPHVELAKKLKQRDS----ATAPNVGDRVSYIIVKG------ : 695
DPOL_CHVN2  : YKN----------ECQPHLHVSNKIFERT-----GFPVPSGARVPFVYIED------ : 695
DPOL_CHVP1  : YKN----------ECQPHLHVANKIYERT-----GFPVPSGARVPFVYIED------ : 694
DPOL_EBV/2  : YKS----------TQMPHLAVYQKFVERN-----EELPQIHDRIQYVFVEPK----- : 725
DPOL_HSVSA  : YKT----------ENLPHLTVYKKIITRH-----EEPPQVHDRIPYVFV-------- : 717
DPOL_HSV11  : YTN----------KRLAHLTVYYKLMARR-----AQVPSIKDRIPYVIVAQTREVEE : 798
DPOL_HSV21  : YTN----------KRLAHLTVYYKLMARR-----AQVPSIKDRIPYVIVAQTREVEE : 802
DPOL_HSVEB  : YTN----------KRLPHLTVYFKLAMRN-----EELPSVKERIPYVIVAQTEAAER : 804
DPOL_VZVD/  : YIN----------RRLAHLTVYYKLVMRQ-----GQIPNVRERIPYVIVAPTDEVEA : 782
DPOL_HCMVA  : YRQ----------SNLPHIAVIKRLAARS-----EELPSVGDRVFYVLTAPGVRTAP : 881
DPOL_MCMVS  : YKQ----------KNLPHLAVIRRLAARK-----EELPAVGDRVEYVLTLP------ : 765
DPOL_HSV6U  : YKQ----------PNLAHLSVIRRLAQRK-----EEIPNVCDRIMYVLIAP------ : 722
DPOA_HUMAN  : YPDK---------KSLPHVHVALWINSQG-----GRKVKAGDTVSYVICQDGSN--- : 712
DPOA_MOUSE  : YPDR---------KSLPHVHVALWINSQG-----GRKVKAGDTVSYVICQDGSN--- : 712
DPOA_DROME  : YRNS---------ASLPHVQVALRMNRER-----NRRYKKGDMVDLCDCLDGTT--- : 701
DPOA_SCHPO  : YPNG---------KTMPFVQVALKKKAR------GENVRVGDVIPFIIAGSDAD--- : 706
DPOA_YEAST  : YPGG---------KNMPAVQVALRMRKA------GRVVKAGSVITFVITKQDEI--- : 707
DPOA_TRYBB  : YHG----------TGYPHAVVALRMKQR------KEGVRVGDLIPYVICEGDE---- : 717
DPOL_NPVAC  : KRKSTDDN-EGPSPKRRVITVARHCREILVNKGTDFVPGNGDRIPYLLIDIEG---- : 741
DPOL_NPVLD  : AKRRKEED----PARKPVITIAKHCRELLANPGVDFLPGNGDRIQYVLVDVKE---- : 754
DPOZ_YEAST  : SEK----------TAPAGAVVVKRRINEDH-----RAEPQYKERIPYLVVKG----- : 697
DPOL_PYRFU  : YKAIG--------PHVAVAKKLAAKG------VKIKPGMVIGYIVLRGDG---- : 684
DPO1_SULSO  : YKK----------NTPQHVKAALQLRPFG------VNVLPRDIIYYVKVRS------ : 664
DPO2_ECOLI  : YQR----------NVPPHVRAARLADEEN------Q--KRGRPLQYQNRGT------ : 675
DPol_Dtok   : YRATG--------PHVAVAKRLAARG------IKIRPGTVISYIVLKG------ : 706
RM378       : VEE----------VMKMKKENVPISEIFIKMYDHTLPIHYKGALFASIIG--CKPP : 753
RB69        : FPGP----------KCPFHIRGILTYNRAIKGNIDAPQVVEGEKVYVLPLR---EGN : 839
```

FIG. 3T

```
                                       1160              1180                 1
DPOL_VACCC  : ------------------------VPWTKKLVN-----------------IKT : 850
DPOL_VACCV  : ------------------------VPWTKKLVN-----------------IKT : 850
DPOL_VARV/  : ------------------------VPWTKKLVN-----------------IKT : 849
DPOL_FOWPV  : ------------------------LPWQKKLCN-----------------ILS : 834
DPOD_BOVIN  : ----------------------------AK--------------------GVAA : 697
DPOD_HUMAN  : ----------------------------AK--------------------GVAA : 697
DPOD_CANAL  : ----------------------------G---------------------GDKN : 693
DPOD_YEAST  : ----------------------------G---------------------NDKL : 693
DPOD_SCHPO  : ----------------------------AQ--------------------GDQF : 694
DPOD_PLAFK  : ----------------------------VK--------------------GQAQ : 701
DPOL_CHVN2  : --------------------------KKNL--------------------DTKQ : 703
DPOL_CHVP1  : --------------------------KKNP--------------------DIKQ : 702
DPOL_EBV/2  : --------------------------GGVKG-------------------ARK  : 733
DPOL_HSVSA  : --------------------------GKTT--------------------SCI  : 724
DPOL_HSV11  : TVARLAALRELDAAAPGDEPAPPAALPSPAKRPRETP---SPADPPGGASKPRKLLV : 852
DPOL_HSV21  : TVARLAALRELDAAAPGDEPAPPAALPSPAKRPRETP---SHADPPGGASKPRKLLV : 856
DPOL_HSVEB  : EAGVVNSMR----------G--TAQNPVVTKTARP-----QPK-------RKLLV : 835
DPOL_VZVD/  : DAKSVALLR----------G--DPLQNTAGKRCG------EAK-------RKLII : 812
DPOL_HCMVA  : QGSSDNGDSVTAGVVSRSDAIDGTDDDADGGGVEESNRRGGEPAKKRARKPPSAVCN : 938
DPOL_MCMVS  : -----------------DGCKKN------------    ------VPN : 774
DPOL_HSVGU  : ------------------SIGNKQ------------------THN : 731
DPOA_HUMAN  : -------------------LTASQ------------------R  : 718
DPOA_MOUSE  : -------------------LTATQ------------------R  : 718
DPOA_DROME  : -------------------NAAMQ------------------R  : 707
DPOA_SCHPO  : -------------------GHPAD------------------R  : 712
DPOA_YEAST  : -------------------DNAADTPA----------LSVAER : 721
DPOA_TRYBB  : -------------------HIDD-------------------KV : 722
DPOL_NPVAC  : ------------------------------------------KV : 743
DPOL_NPVLD  : ------------------------------------------KI : 756
DPOZ_YEAST  : ------------------KQGQ--------------------LLR : 704
DPOL_PYRFU  : ------------------P-----------------------I  : 686
DPO1_SULSO  : --------------------------------------------:
DPO2_ECOLI  : ------------------------------------------IKY : 678
DPol_Dtok   : ------------------PG--------     ----RV : 710
RM378       : QMGDKIYWFYCTMLDPSRTNLPLSLEEVNPEHGSGVWDILKAGKKTHINRLRNIHAL : 810
RB69        : PFGDKCIAWPSG----------------------------------TEIT : 855
```

FIG. 3U

```
                         200          1220         1240
DPOL_VACCC  : YETIIDRSFKLGSDQRIFYEVYFK-RLTSEIVNLLDNKVLCIS-------------- : 892
DPOL_VACCV  : YETIIDRSFKLGSDQRIFYEVYFK-RLTSEIVNLLDNKVLCIS-------------- : 892
DPOL_VARV/  : YETIIDRSFKLGSDQRIFYEVYFK-RLTSEIVNLLDNKVLCIS-------------- : 891
DPOL_FOWPV  : YEVIADSKFYLPKDKRIFYEIYFK-RIASEVVNLLTDKTQC---------------- : 874
DPOD_BOVIN  : YMKSEDPLFVLEHSLPIDTQYYLEQQLAKPLLRIFEPILGE---------------- : 738
DPOD_HUMAN  : YMKSEDPLFVLEHSLPIDTQYYLEQQLAKPLLRIFEPILGE---------------- : 738
DPOD_CANAL  : YEKSEDPLYVLENSLPIDVKYYLDQQLTKPLERIFIPILGE---------------- : 734
DPOD_YEAST  : YNRAEDPLFVLENNIQVDSRYYLTNQLQNPIISIVAPIIGD---------------- : 734
DPOD_SCHPO  : YMRSEDPIYVLENNIPIDAKYYLENQLSKPLLRIFEPILGE---------------- : 735
DPOD_PLAFK  : YERAEDPLYVLDNNLAIDYNHYLD-AIKSPLSRIFEVIMQN---------------- : 741
DPOL_CHVN2  : SFRAEDPTFAQENDLIVDRLFYIEHQLMKPICSLFEPLLDD---------------- : 744
DPOL_CHVP1  : SFKAEDPTFAQDNGLIVDRLFYIEHQLLKPICSLFEPLLDD---------------- : 743
DPOL_EBV/2  : TEMAEDPAYAERHGVPVAVDHYFD-KLLQGAANILQCLFDN---------------- : 773
DPOL_HSVSA  : SNMAEDPTYTVQNNIPIAVDLYFD-KLIHGVANIIQCLFKD---------------- : 764
DPOL_HSV11  : SELAEDPAYAIAHGVALNTDYYFS-HLLGAACVTFKALFGN---------------- : 892
DPOL_HSV21  : SELAEDPGYAIARGVPLNTDYYFS-HLLGAACVTFKALFGN---------------- : 896
DPOL_HSVEB  : SDLAEDPTYVSENDVPLNTDYYFS-HLLGTISVTFKALFGN---------------- : 875
DPOL_VZVD/  : SDLAEDPIHVTSHGLSLNIDYYFS-HLIGTASVTFKALFGN---------------- : 852
DPOL_HCMVA  : YEVAEDPSYVREHGVPIHADKYFE-QVLKAVTNVLSPVFPG---------------- : 978
DPOL_MCMVS  : YEIAEDPRHVVEAKLSINAEKYYE-QVVKAVTNTLMPVFPR---------------- : 814
DPOL_HSV6U  : YELAEDPNYVIEHKIPIHAEKYFD-QIIKAVTNAISPIFPK---------------- : 771
DPOA_HUMAN  : AYAPEQLQKQDN--LTIDTQYYLAQQIHPVVARICEPIDGI---------------- : 757
DPOA_MOUSE  : AYAPEQLQKLDN--LAIDTQYYLAQQIHPVVARICEPIDGI---------------- : 757
DPOA_DROME  : AYHLDELKTSEDKKLQLDTNYYLGHQIHPVVTRMVEVLEGT---------------- : 748
DPOA_SCHPO  : AYSPQEIMNTNST-LVIDYNYYLSHQILPPIERVIAPIEGT---------------- : 752
DPOA_YEAST  : AHALNEVMIKSNN-LIPDPQYYLEKQIFAPVERLLERIDSF---------------- : 761
DPOA_TRYBB  : AYHIDEVRRSDG--LSVDVEWYLSSQLYPPVMRLCEHIQGF---------------- : 761
DPOL_NPVAC  : TEKAYPLRLFDP--VKMRISWIKHMGILCTFMNELLEIFGD---------------- : 782
DPOL_NPVLD  : TQKAFPLKLFDPDSPTLQISWLKHMNILCTFMNELIQVFGN---------------- : 797
DPOZ_YEAST  : ERCVSPEEFLEGENLELDSEYYINKILIPPLDRLFNLIGIN---------------- : 745
DPOL_PYRFU  : SNRAILAEEYDPKKHKYDAEYYIENQVLPAVLRILEGFGYR---------------- : 727
DPO1_SULSO  : --KDGVKPVQLAKVTEIDAEKYLE-ALRSTFEQILRAFGVS---------------- : 702
DPO2_ECOLI  : VWTTNGPEPLDYQRSPLDYEHYLTRQLQPVAEGILPFIEDN---------------- : 719
DPol_Dtok   : GDRAIPFDEFDPAKHRYDAEYYIENQVLPAVERILRAFGYRKEDLRYQKTKQAGLGA : 767
RM378       : SIREDDEEGLEIVKKYIDRDKYCQIISEKTIDLLKSLGYVENTTKIKTVEDLIRFLV : 867
RB69        : DLIKDDVLHWMDYTVLLEKTFIKPLEGFTSAAKLDYEKKASLF-------------- : 898
```

FIG. 3V

|  |  | 1260 |  |  |
|---|---|---|---|---|
| DPOL_VACCC | : | ------ | : | - |
| DPOL_VACCV | : | ------ | : | - |
| DPOL_VARV/ | : | ------ | : | - |
| DPOL_FOWPV | : | ------ | : | - |
| DPOD_BOVIN | : | ------ | : | - |
| DPOD_HUMAN | : | ------ | : | - |
| DPOD_CANAL | : | ------ | : | - |
| DPOD_YEAST | : | ------ | : | - |
| DPOD_SCHPO | : | ------ | : | - |
| DPOD_PLAFK | : | ------ | : | - |
| DPOL_CHVN2 | : | ------ | : | - |
| DPOL_CHVP1 | : | ------ | : | - |
| DPOL_EBV/2 | : | ------ | : | - |
| DPOL_HSVSA | : | ------ | : | - |
| DPOL_HSV11 | : | ------ | : | - |
| DPOL_HSV21 | : | ------ | : | - |
| DPOL_HSVEB | : | ------ | : | - |
| DPOL_VZVD/ | : | ------ | : | - |
| DPOL_HCMVA | : | ------ | : | - |
| DPOL_MCMVS | : | ------ | : | - |
| DPOL_HSV6U | : | ------ | : | - |
| DPOA_HUMAN | : | ------ | : | - |
| DPOA_MOUSE | : | ------ | : | - |
| DPOA_DROME | : | ------ | : | - |
| DPOA_SCHPO | : | ------ | : | - |
| DPOA_YEAST | : | ------ | : | - |
| DPOA_TRYBB | : | ------ | : | - |
| DPOL_NPVAC | : | ------ | : | - |
| DPOL_NPVLD | : | ------ | : | - |
| DPOZ_YEAST | : | ------ | : | - |
| DPOL_PYRFU | : | ------ | : | - |
| DPO1_SULSO | : | ------ | : | - |
| DPO2_ECOLI | : | ------ | : | - |
| DPol_Dtok | : | WLKPKT | : | 773 |
| RM378 | : | ESEN-- | : | 871 |
| RB69 | : | ------ | : | - |

FIG. 3W

```
                           20              40
T4-RNAlig  : MQELFNNLMELCKDSQRKFFYSDDVSASG-RTYRIFSYN-----YASYS---DWLLP : 48
ACNV-RNAli : ---MLHVSRLLANGGVKNLCDKFKVKIKNYTEHDLMVLN-----YESFER--DRDHP : 47
ORF-739f   : -MSMNVKYPVEYLIEHLNSFESPEVAVESLRKEGIMCKNRGDLYMFKYHLGCKFDKl : 56
                                *                *

60              80             100
T4-RNAlig  : DALECRGIMFEMDGEKPVRIASRPMEKFFNLNENPFTMNI---------DLNDVDY : 95
ACNV-RNAli : VVVECRGLILNS---RTYAVVSRSFDRFFNFQELLQNIGG-----------EDAHH : 89
ORF-739f   : YHLACRGAILRKT-DSGWKVLSYPFDKFFNWGEELQPEIVNYYQTLRYASPLNEKRK : 112
                ***              *     ***   *

120             140             160
T4-RNAlig  : ---------ILTKEDGSLVSTYLDGDEILFKSKGSIKSE------------QALMA : 130
ACNV-RNAli : KLFQSKENFKFYEKIDGSLIKIYKYNGEWHASTRGSAFAENLCVSD---VTFKRLVL : 143
ORF-739f   : AGFMFKLPMKLVEKLDGTCVVLYYDEG-WKIHTLGSIDANGSIVKNGMVTTHMDKTY : 168
                   * **        *                    **

KX(D/N)G 180             200            220
T4-RNAlig  : NGILMNINHHRLRDRLKELAEDGFTANFEFVAPTNRIVLAYQEMK-IILLNVR---- : 182
ACNV-RNAli : QALQLDEAHNQFQALCNEYLDCASTHMFELTSKHNRIVTVYDEQPTLWYLASR---- : 196
ORF-739f   : RELFWETFEKKYPPYLLYHLNSSYCYIFEMVHPDARVVVPYEEPN-IILIGVRSVDP : 224
                                ** *     * * * *  *

240             260            280
T4-RNAlig  : ---------------ENETGEYISYDDIYKDATLRPYLVERYEIDSPKWIEEAKNA : 223
ACNV-RNAli : ----------------NNETGDYFYCSNLPFCKYPKCYEFT----SVQECVEHAAQL : 233
ORF-739f   : EKGYFEVGPSEEAVRIFNESGGKINLKLPAVLSQEQNYTLFRANRLQELFEEVTPLF : 281
                             ** *                  *         *

300            320            340
T4-RNAlig  : ENIEGYVAVMK-----------DGSHFKIKSDWYVSLHSTKSSLDNPEKLFKTIID : 268
ACNV-RNAli : KNLEEGFVVYDK---------NNAPLCKIKSDVYLNMHKNQSRAENPTKLAQLVIN : 280
ORF-739f   : KSLRDGYEVVYEGFVAVQEIAPRVYYRTKIKHPVYLELHRIKTTIT-PEKLADLFLE : 337
                 *                      ***   *  *        * **

360            380             40
T4-RNAlig  : GASDDLKAMYADDEYSYRKIEAFETTYLKYLDRALFLVLDCHNKHCGKDRKTYAMEA : 325
ACNV RNAli : GEHDDFLALFPHLKSVIKPYVDARNTFTNESTINIMVSGLTLNQQR-FNELVQTLPW : 336
ORF-739f   : NKLDDF-VLTPDEQETVMKLKEIYTDMRNQLESSFDTIYKEISEQVSPEENPGEFRK : 393
                **

0             420             440
T4-RNAlig  : QGVAKGAGMDHLFGIIMSLYQGYDSQEKVMCEIEQNFLKNYKKF---------IPEG : 373
ACNV-RNAli : KCLAYRCRKAQTIDVESEFLKLTEPEKIKMIKNIIKFVSTKQALNNKLAPTIKLPSS : 393
ORF-739f   : R-FALR--LMDYHDKS-WFFARLDGDEEKMQKSEKKLLTERIEKG-------LFK- : 437
                          *                 *

T4-RNAlig  : Y : 374
ACNV-RNAli : K : 394
ORF-739f   : - : -
```

FIG. 4

```
                         20            .         40         .
Ecoli-polI  : --------MVQIPQNP-----LILVDGSSYLYR----AYHAFPPLTNSACEPTGAMY  :  40
Taq-polI    : ---MRGMLPLFEPKGR-----VLLVDGHHLAYR----TFHALKGLTTSRGEPVQAVY     :  45
ORF_1218a   : MKRLRNMVNLIDLKNQYYAYSFKFFDSYQISWD----NYPHLKEFVIENYPGTYFSC     :  53
T4-RNaseH   : ----MDLEMMLDEDYKEG---ICLIDFSQIALSTALVNFPDKEKINLSMVRHLILNS     :  50
T7-gp6exo   : -MALLDLKQFYELREGCDDKGILVMDGDWLVFQAMS-AAEFDASWEEEIWHRCCDHA     :  55
                                                *

60            .         80         .         100         .
Ecoli-polI  : GVLNMLRSLIMQYKP------THAAVVFDAKGKTFRDELFE-HYKSHR---------     :  81
Taq-polI    : GFAKSLLKALKEDG-------DAVIVVFDAKAPSFRHEAYG-GYKAGR---------     :  85
ORF_1218a   : YAPGILYKLFLKWK-------RGMIIDDYDRHPLRKKLLP-QYKEHRYEYIEGKYG     : 101
T4-RNaseH   : IKFNVKKAKTLGYT-------KIVLCIDNAKSGYWRRDFAY-YYKKNR-----GKAR     :  94
T7-gp6exo   : KARQILEDSIKSYETRKKAWAGAPIVLAFTDSVNWRKELVDPNYKANR------K     : 104
                                                *           **    *

120           .         140        .         160         .
Ecoli-polI  : -PPMP---DDLRAQIEPLHAMVKAMGLPLLA------------------------V    : 109
Taq-polI    : -APTP---EDFPRQLALIKELVDLLGLARLE------------------------V    : 113
ORF_1218a   : VVPFPGFLKYLKFHFEDLRFKMRDLGITDFKYALAISLFYNRVMLRDFLKNFTCYYI   : 158
T4-RNaseH   : EESTWDWEGYFESSHKVIDELKAYMPYIVMD------------------------I    : 126
T7-gp6exo   : AVKKP------VGYFEFLDALFEREEFYCIR------------------------E    : 130

180           .         200        .         220
Ecoli-polI  : SCVEADDVIGTLAREAEKA-GRPVLISTGDKDMAQLVTPNITLINTMTNTILGPEEV  : 165
Taq-polI    : PGYEADDVLASLAKKAEKE-GYEVRILTADKDLYQLLSDRIHVLHPEG-YLITPAWL  : 168
ORF_1218a   : AEYEADDVIAHLAREIARS-NIDVNIVSTDKDYYQLWDEEDIRERVYINSLSCSDVK  : 214
T4-RNaseH   : DKYEADDHIAVLVKKFSLE-GHKILIISSDGDFTQLHKYP--NVKQWS--PMHKKWV  : 178
T7-gp6exo   : PMLEGDDVMGVIASNPSAFGARKAVIISCDKDFKTIPNCDFLWCTTGN--------I  : 179
                 * **                *  **           *  *  *

.     240           .         260        .         280
Ecoli-polI  : VNKYGVPPELIIDFLALMGDSSDNIPGVPGVGEKTAQALLQGLGG--LDTLYAEPEK  : 220
Taq-polI    : WEKYGLRPDQWADYRALTGDESDNLPGVKGIGEKTARKLLEEWGS--LEALLKNLDR  : 223
ORF_1218a   : TPRYG-----FLTIKALLGDKSDNIP--KSLEKGKGEKYLEKKG-------FAEEDY  : 257
T4-RNaseH   : KIKSG-SAEIDCMTKILKGDKKDNVASVKVRSDFWFTRVEGERTPSMKTSIVEAIAN  : 234
T7-gp6exo   : LTQTEESADWWHLFQTIKGDITDGYSGIAGWGDTAEDFLNNPFITEPKTSVLKSGKN  : 236
                                         **   *

300           .         320        .         340
Ecoli-polI  : IAGLSFRGAKTMAAKLEQNKEVAYLSYQLATIKTDVELELTCEQLEVQQPAAEELLG  : 277
Taq-polI    : LK----P---AIREKILAHMDDLKLSWDLAKVRTDLPLEVDFAK--RREPDRERLRA  : 271
ORF_1218a   : DK---------ELFENNLKVIRFGDEYLGERDKSFIENFSTG--------DTLWN    : 295
T4-RNaseH   : DR--------EQAKVLLTESEYNRYKENLVLIDFDYIPDNIASN-------IVNYYN  : 276
T7-gp6exo   : KG------------QEVTKWVKRDPEPHETLWDCIKSIGAKAG-------MTEED    : 272

.    360         .
Ecoli-polI  : LFKKYEFKRWTADVEAGKWLQAK------  : 300
Taq-polI    : FLERLEFGSLLHEFGLLESPKALEEAPWP  : 300
ORF_1218a   : FYEFFYYDPLHELFLRNIRKRRL------  : 318
T4-RNaseH   : SYKLPPRGKIYSYFVKAGLSKLTNSINEF  : 305
T7-gp6exo   : IIKQGQMARILRFNEYNFIDKEIYLWRP-  : 300
```

FIG. 5

```
                             20              40
DnaB_Ecoli  : VLDATVARIEQLFQQP-HDGVTGVNTGYDDLNKKTAG-LQPSDLIIVAARPSMGKTT :  55
DnaB-Hinfl  : VLESTIEKIDILSKLENHSGVTGVTTGFTDLDKKTAG-LQPSDLIIVAARPSMGKTT :  56
DnaB-Ctrac  : ALQERQEAFQASAHDSSSPMLSGFPTHFLDLDKMISG-FSPSNLIILAARPAMGKTA :  56
DnaB-Bstea  : ILVQTYDNIEMLHNRD--GEITGIPTGFTELDRMTSG-FQRSDLIIVAARPSVGKTA :  54
DnaB-Hpylo  : VLESAMDLITENQRKG-SLEVTGIPTGFVQLDNYTSG-FNKGSLVIIGARPSMGKTS :  55
DnaB-Mgeni  : EIANQEEALIKKVHRG-ELIISGLSSGFLKLDQLTSG-WKPGELIVIAARPGRGKTA :  55
DnaB-Bburg  : IAERVHNEIYERSMKK-KEANFGIPSGFRKVDSLIGG-FRNSDFIIVGARPSIGKTA :  55
T4-gp41     : YVGHDWMDDYEARWLSYMNKARKVPPKLRILNKITKGGAETGTLNVLMAGVNVGKSL :  57
T7-gp4      : VVSALSLRERIREHLSSEESVGLLFSGCTGINDKTLG-ARGGEVIMVTSGSGMGKST :  56
ORF1293b    : VSLVEEFDLATSEFNELFVKEERIPTPWESVNKNMAGGLGRGELGIVMLPSGWGKSW :  57
                                                   *          **
                                                        motif H1

60              80             100
DnaB_Ecoli  : FAMNLVENAAMLQD---KPVLIFSLEMPSEQIMMRSLASLSRVDQTKIRTGQ-LDDE : 108
DnaB-Hinfl  : FAMNLCENAAMASE---KPVLVFSLEMPAEQIMMRMIASLARVDQTKIRTGQNLDEI : 110
DnaB-Ctrac  : LALNIVENFCFDSR---LPVGIFSLEMTVDQLIHRIICSRSEVEAKKISVGD-ISGR : 109
DnaB-Bstea  : FALNIAQNVATKTN---ENVAIFSLEMSAQQLVMRMLCAEGNINAQNLRTGK-LTPE : 107
DnaB-Hpylo  : LMMNMVLS-ALNDD---RGVAVFSLEMSAEQLALRALSDLTSINMHDLESGR-LDDD : 107
DnaB-Mgeni  : LLINFMASAAKQIDPKTDVVLFFSLEMRNREIYQRHLMHESQTSYTLTNRQR--INN : 110
DnaB-Bburg  : FALNIASYIALRKEEK-KKVGFFSLEMTADALIKRIISSQSCIDSFKVQNSI-LSGQ : 110
T4-gp41     : GLCSLAAD-YLQLG---HNVLYISMEMAEEVCAKRIDANMLDVSLDDIDDGH-ISYA : 109
T7-gp4      : FVRQQALQWGTAMG---KKVGLAMLEESVEETAEDLIGLHNRVRLRQSDSLK-REII : 109
ORF1293b    : FLVSLGLH-AFRTG---KRVIYFTLELDQKYVMKRFLKMFAPYCKGRASSYR----D : 106
                              *    *
                                motif H1a 120             140             160
DnaB_Ecoli  : DWARISGTMGILLEKRNIYIDDSSG--LTPTEVRSRARRIAR-EH-GGIGLIMIDYL : 161
DnaB-Hinfl  : EWNKIASVVGMFKQKNNLFIDDSSG--LTPTDVRSRARRVYR-EN-GGLSMIMVDYL : 163
DnaB-Ctrac  : DFQRVVSVVREMEEHT-LLIDDYPG--LKITDLRARARRMK--ES-YDIQFLVIDYL : 160
DnaB-Bstea  : DWGKLTMAMGSLSNAG-IYIDDTPS--IRVSDIRAKCRRLKQ-ES--GLGMIVIDYL : 158
DnaB-Hpylo  : QWENLAKCFDHLSQKK-LFFYDKSY--VRIEQIRLQLRKLKS-QH-KELGIAFIDYL : 159
DnaB-Mgeni  : VFEELMEASSRIKNLP-IKLFDYSS--LTLQEIRNQITEVSK-TS--NVRLVIIDYL : 161
DnaB-Bburg  : EIKSLNDIINEISDSE-LYIEDTPN--ISLLTLATQARKLKR-FY--GIDIIFVDYI : 161
T4-gp41     : EYKGKMEKWREKSTLGRLIVKQYPTGGADANTFRSLLNELKLKKN-FVPTIIIVDYL : 165
T7-gp4      : ENGKFDQWFDELFGNDTFHLYDS----FAEAETDRLLAKLAYMRSGLGCDVIILDHI : 162
ORF1293b    : VYQIMKELMFSQDNLLKIVFCN------AMEDIEHYIALYN------PDVVLIDYA : 150
                                                                     *
                                motif H2

180             200             220
DnaB_Ecoli  : QLMRVP---ALSDNRTLEIAEISRSLKALAKELNVPVVALSQLNR---SLEQRADKR : 212
DnaB-Hinfl  : QLMRAP---AFSDNRTLEIAEISRSLKALAKELQVPVVALSQLNR---TLEQRGDKR : 214
DnaB-Ctrac  : QLISSSGNLRNSDSRNQEISEISRMLKNLARELNIPILCLSQLSR---KVEDRANHR : 214
DnaB-Bstea  : QLIQGSG--RSKENRQQEVSEISRSLKALARELEVPVIALSQLSR---SVFQRQDKR : 210
DnaB-Hpylo  : QLMSGS---KATKERHEQIAEISRELKTLARELEIPIIALVQLNR---SLENRDDKR : 210
DnaB-Mgeni  : QLVNALKN-NYGLTRQQEVTMISQSLKAFAKEFNTPIIAAAQLSR---RIEERKDSR : 214
DnaB-Bburg  : SLISFET---KNLPRHEQVASISKSLKELARELEIPIVALSQLTR---DTEGRE--- : 209
T4-gp41     : GICKSCRIRVYSENSYTTVKAIAEELRALAVETETVLWTAAQVGK---QAWDSSD-- : 217
T7 gp4      : SIVVSAS---GESDERKMIDNLMTKLKGFAKSTGVVLVVICHLKNPDKGKAHEEGRP : 216
ORF1293b    : DLIYDVET--DKEKNYLLLQKIYRKLRLIAKVYNTAVWSASQLNRG--SLSKQADVD : 203
                          *  *
                                motif H3
```

FIG. 6A

```
                       240          260          280
DnaB_Ecoli  : PVNSDLRESGSIEQDADLIMFIYRDEVYHENSDLK--------------------- : 247
DnaB-Hinfl  : PVNSDLRESGSIEQDADLIMFIYRDEVYNDNSEDK--------------------- : 249
DnaB-Ctrac  : PLMSDLRESGSIEQDADQIMFLLRREYYDPN-DKP--------------------- : 248
DnaB-Bstea  : PMMSDIRESGSIEQDADIVAFLYRDDYYNKDSENK--------------------- : 245
DnaB-Hpylo  : PILSDIKDSGGIEQDADIVLFLYRGYIYQMRAEDNKIDKLKKEGKIEEAQELYLKVN : 267
DnaB-Mgeni  : PILSDLRESGSIEQDADMVLFIHRTNDDKKEQEEENTN------------------ : 252
DnaB-Bburg  : PNLASLRESGALEQDADIVILLHRDKDFKFESSAEIEP------------------ : 247
T4-gp41     : VNMSDIAESAGLPATADFMLAVIETEELAAAEQQLIKQIKSRYGDKNKWNKFLMG-- : 272
T7-gp4      : VSITDLRGSGALRQLSDTIIALERNQQGDMPNLVLVR------------------- : 253
ORF1293b    : FIEKYIADSFAKVVEIDFGMAFIPDSENSTPDIHVG-------------------- : 239
                  *     *
                 motif H4

300          320          340
DnaB_Ecoli  : -----------GIAEIIIGKQRNGPIGTVRLTFNGQWSRFDNYAGP-QYDDE---- : 287
DnaB-Hinfl  : -----------CVAEIIIGKQRNGPIGRVRLKFNGQFSRFDNLAEQREYRDDY--- : 291
DnaB-Ctrac  : -----------GTAELIVAKNRHGSIGSVQLVFEKDFARFRNYAGC-EFPG----- : 287
DnaB-Bstea  : -----------NIIEIIIAKQRNGPVGTVQLAFIKEYNKFVNLERR--FDEAQIPP : 288
DnaB-Hpylo  : EERRIHKQNGSIEEAEIIVAKNRNGATGTVYTRFNAPFTRYEDMPIDSHLEEGQETK : 324
DnaB-Mgeni  : -----------LFEVELILEKNRNGPNGKVKLNFRSDTSSFISQYSP-SFDDQYS-- : 295
DnaB-Bburg  : -----------IETKVIVAKHRNGPTGRADILFLPHITKFVNKDHQY--------- : 283
T4-gp41     : ----------VQKGNQKWVEIEQDSTPTEVNEVAGSQQIQAEQNRYQRNESTRAQLDA : 320
T7-gp4      : --------------ILKCRFTGDTGIAGYMEYNKETGWLEPSSYSGEEESHSESTDW : 296
ORF1293b    : --------------FGKIFKNRMGAVRKLEYTINFENYTVDVAVK----------- : 270

DnaB_Ecoli  : --------  :   -
DnaB-Hinfl  : --------  :   -
DnaB-Ctrac  : --------  :   -
DnaB-Bstea  : GA------  : 290
DnaB-Hpylo  : VDYDIVTT  : 332
DnaB-Mgeni  : --------  :   -
DnaB-Bburg  : --------  :   -
T4 gp41     : LANELKF-  : 327
T7-gp4      : SNDTDF--  : 302
ORF1293b    : --------  :   -
```

FIG. 6B

```
  ---------|---------|---------|---------|---------|---------|---
1 attttctgttttttcacaggcaagtattcgacatgctcgaaacccgcgaagcttattatcagt 63

---|---------|---------|---------|---------|---------|------
64 tgcttcaatcgttaaacgatttcctcgaagaagacctgaaggagaattatgaagatcacgcta 126
                                                M  K  I  T  L    5

---|---------|---------|---------|---------|---------|--------
127 agcgcaagcgtataccccgatcgatgaaaatttacggagtggagctaatcgaggggaaaaaa 189
  6  S  A  S  V  Y  P  R  S  M  K  I  Y  G  V  E  L  I  E  G  K  K   26

|---------|---------|---------|---------|---------|---------|--
190 cacttatttcaatcacccgtaccccacatttgaagcgcatcgctcagcagaatcgagggaag 252
 27  H  L  F  Q  S  P  V  P  P  H  L  K  R  I  A  Q  Q  N  R  G  K   47

--|---------|---------|---------|---------|---------|-----
253 attgaggctgaggctatatcctattacatcagagaacaaaaaagccacatcacgccggaagct 315
 48  I  E  A  E  A  I  S  Y  Y  I  R  E  Q  K  S  H  I  T  P  E  A   68

----|---------|---------|---------|---------|---------|--------
316 ttgtctcagtgcgtctttatcgatattgagacgatttccccgaaaaaaagctttcccgacccg 378
 69  L  S  Q  C  V  F  I  D  I  E  T  I  S  P  K  K  S  F  P  D  P   89

-|---------|---------|---------|---------|---------|---------|-
379 tggagagacccagtttattccatttccatcaaaccgtatggaaaaccggtggtggtagtgctt 441
 90  W  R  D  P  V  Y  S  I  S  I  K  P  Y  G  K  P  V  V  V  L    110

-|---------|---------|---------|---------|---------|----
442 ctccttatcaccaacccggaggctcatatcgataactttaacaaatttaccaccagcgtaggg 504
111  L  L  I  T  N  P  E  A  H  I  D  N  F  N  K  F  T  T  S  V  G   131

---|---------|---------|-------  |---------|---------|-------
505 gataacacatttgaaattcattacagaacattcctttcggaaaaaagattgctcgagtatttc 567
132  D  N  T  F  E  I  H  Y  R  T  F  L  S  E  K  R  L  L  E  Y  F   152

--|---------|---------|---------|---------|---------|---------|
568 tggaatgtgctgaaaccaaaatttactttcatgctcgcatggaacggttatcagttcgattat 630
153  W  N  V  L  K  P  K  F  T  F  M  L  A  W  N  G  Y  Q  F  D  Y   173

----|---------|---------|---------|---------|---------|---
631 ccctacctgctcattcgtagtcatatccatgaggtgaatgtcattagtgataagttgcttccg 693
174  P  Y  L  L  I  R  S  H  I  H  E  V  N  V  I  S  D  K  L  L  P   194

---|---------|---------|---------|---------|---------|------
694 gactggaagctggtgcggaaaatttccgatcgaaacctaccattctatttcaatccccgtacc 756
195  D  W  K  L  V  R  K  I  S  D  R  N  L  P  F  Y  F  N  P  R  T   215

---|---------|---------|----  ----|---------|---------
757 cctgtagaatttgtgttttttgattacatgcggctttatcgctcctttgtggcatacaaagag 819
216  P  V  E  F  V  F  F  D  Y  M  R  L  Y  R  S  F  V  A  Y  K  E   236

|---------|---------|---------|---------|---------|---------|--
820 ttggagtcctaccggctcgactatattgcgcgagaggaaataggagaaggtaaggtggatttc 882
237  L  E  S  Y  R  L  D  Y  I  A  R  E  E  I  G  E  G  K  V  D  F   257

-------|---------|---------|---------|---------|---------|-----
883 gacgtaagattctatcatgagattcctgtctacccggataaaaagttggtggaatacaacgcc 945
258  D  V  R  F  Y  H  E  I  P  V  Y  P  D  K  K  L  V  E  Y  N  A   278
```

FIG. 7A

```
          ----|----------|----------|----------|----------|---------|--------
     946  gtagacgccattttgatggaagaaatcgaaaataaaaaccatattctcccgacgctgtttgaa  1008
     279  V  D  A  I  L  M  E  E  I  E  N  K  N  H  I  L  P  T  L  F  E    299

-|----------|----------|----------|----------|----------|---------|-
    1009  attgcaagactttcaaatctgactcccgcactggcattgaacgcttccaatattcttatcgga  1071
     300  I  A  R  L  S  N  L  T  P  A  L  A  L  N  A  S  N  I  L  I  G    320

--------|----------|----------|----------|----------|----------|----
    1072  aatgttacaggaaaacttggtgtcaaattcgttgattacatcaagaaaatcgacaccattaat  1134
     321  N  V  T  G  K  L  G  V  K  F  V  D  Y  I  K  K  I  D  T  I  N    341

-----|----------|----------|----------|----------|----------|-------
    1135  acaatgttcaaaaaaatacctgagtaaactatgaatatgcagaccattgacgaaacgctttat  1197
     342  T  M  F  K  K  I  P  E  *  350
```

FIG. 7B

```
           ---------|---------|---------|---------|---------|---------|---
    1 ctatacggatgaagttttgagaattattgatctttctccactcgatggcgtattatacaaatg 63

------|---------|-----    --|---------|---------|---------|------
   64 tgatttaaaagacacctaccttatcgaggtgaaagatacccatttgatcccgcaatgtaaaa 126

---|---------|---------|---------|---------|---------|---------
  127 caaacgtattctgctatgaacatcaacaagtatcgttatcgcggtgcttacattgaacttacc 189
                   M  N  I  N  K  Y  R  Y  R  G  A  Y  I  E  L  T    16

|---------|---------|---------|---------|---------|---------|--
  190 aaccccgatatttacttcaacgtattcgatcttgatttacatcgctgtacccctctgtaatc 252
   17  N  P  D  I  Y  F  N  V  F  D  L  D  F  T  S  L  Y  P  S  V  I   37

----  |---------|---------|---------|---------|---------|-----
  253 agcaaattcaatatcgatcccgctacgttcgtaacggagttttacgggtgtatgcgggtggag 315
   38  S  K  F  N  I  D  P  A  T  F  V  T  E  F  Y  G  C  M  R  V  E   58

----|---------|---------|---------|---------|---------|--------
  316 aacaaagtgattccggtagatcaggaagaaccggaattcgggtttcccctctacatcttcgat 378
   59  N  K  V  I  P  V  D  Q  E  E  P  E  F  G  F  P  L  Y  I  F  D   79

-|---------|---------|---------|---------|---------|---------|-
  379 tcagggatgaacccttcttaccggagtgaacccctctttgtcatcaacagctttgaggaactc 441
   80  S  G  M  N  P  S  Y  R  S  E  P  L  F  V  I  N  S  F  E  E  L  100

--------|---------|---------|---------|---------|---------|----
  442 cggcaattttaaaaagtcgaaatatcattatggtgcccaacccgtcgggtatctgctggttt 504
  101  R  Q  F  L  K  S  R  N  I  I  M  V  P  N  P  S  G  I  C  W  F  121

-----|---------|---------   |---------|---------|---------|------
  505 tacaggaaagagccggttggcgtgcttccttctatcattcgggagattttcacccgacgtaag 567
  122  Y  R  K  E  P  V  G  V  L  P  S  I  I  R  E  I  F  T  R  R  K  142

--|---------|---------|---------|---------|---------|---------|
  568 gaagaacgtaagcttttcaaagaaactggcaacatggaacaccatttccgtcaatgggcactt 630
  143  E  E  R  K  L  F  K  E  T  G  N  M  E  H  H  F  R  Q  W  A  L  163

---------|---------|---------|---------|---------|---------|---
  631 aaaattatgatgaactccatgtacggtatcttcggaaaccgttcggtgtacatggggtgcctt 693
  164  K  I  M  M  N  S  M  Y  G  I  F  G  N  R  S  V  Y  M  G  C  L  184

------|---------|---------|---------|---------|---------|------
  694 cccattgcggaaagtgtaaccgccgccgggcgcatgtctattcgctccgtgatttctcagatt 756
  185  P  I  A  E  S  V  T  A  A  G  R  M  S  I  R  S  V  I  S  Q  I  205

---|---------|---------|---------|---------|---------|---------
  757 cgcgatcgcttcatttattcgcataccgactccatttcgtcaaagcttttacggatgatccg 819
  206  R  D  R  F  I  Y  S  H  T  D  S  I  F  V  K  A  F  T  D  D  P  226

|---------|---------|---------|---------|---------|---------|--
  820 gtggcggaagccggtgagcttcaagaacatctcaactcttttatcaatgactatatggaaaat 882
  227  V  A  E  A  G  E  L  Q  E  H  L  N  S  F  I  N  D  Y  M  E  N  247

-------|---------|---------|---------|---------|---------|-----
  883 aactttaatgcaagagaagatttcaagctggagttaaagcaggagttcgtgttcaaatccatt 945
  248  N  F  N  A  R  E  D  F  K  L  E  L  K  Q  E  F  V  F  K  S  I  268
```

FIG. 8A

```
         ----|---------|---------|---------|---------|---------|--------
     946 cttatcaaagaaatcaaccgctactttgcggttactgtagacggtaaagaagagatgaaggga 1008
     269  L  I  K  E  I  N  R  Y  F  A  V  T  V  D  G  K  E  E  M  K  G  289

-|---------|---------|---------|---------|---------|---------|-
    1009 atcgaagtgatcaactcttcggtgcctgaaattgtcaagaagtatttcaggggttacctgaag 1071
     290  I  E  V  I  N  S  S  V  P  E  I  V  K  K  Y  F  R  G  Y  L  K  310

---------|---------|---------|---------|---------|---------|----
    1072 tatatcagccaacccgacatcgatgtcatttccgccaccatagcgttctacaataactttgtg 1134
     311  Y  I  S  Q  P  D  I  D  V  I  S  A  T  I  A  F  Y  N  N  F  V  331

-----|---------|---------|---------|---------|---------|-------
    1135 tctcaaaagaatttctggtctattgaagatctctatcacaaaatgaaaatatcttcgtctgac 1197
     332  S  Q  K  N  F  W  S  I  E  D  L  Y  H  K  M  K  I  S  S  S  D  352

--|---------|---------|---------|---------|---------|---------|
    1198 agcgccgaaagatatgtggagtatgtagaggaagttatgaagatgaaaaaggagaatgtccca 1260
     353  S  A  E  R  Y  V  E  Y  V  E  E  V  M  K  M  K  K  E  N  V  P  373

---------|---------|---------|---------|---------|---------|---
    1261 atctctgagatattcataaaaatgtatgaccatacacttcccattcattataagggagcgctt 1323
     374  I  S  E  I  F  I  K  M  Y  D  H  T  L  P  I  H  Y  K  G  A  L  394

------|---------|---------|---------|---------|---------|------
    1324 ttcgcttccattataggatgcaaaccccgcaaatgggagacaagatctactggttctactgc 1386
     395  F  A  S  I  I  G  C  K  P  P  Q  M  G  D  K  I  Y  W  F  Y  C  415

---|---------|---------|---------|---------|---------|---------
    1387 accatgctggatccttccagaaccaatctcccgctttctctggaagaagttaaccccgaacat 1449
     416  T  M  L  D  P  S  R  T  N  L  P  L  S  L  E  E  V  N  P  E  H  436

|---------|---------|---------|---------|---------|---------|--
    1450 gggagcggcgtgtgggatattctgaaagcgggaaagaaaacgcatatcaacaggctccgcaat 1512
     437  G  S  G  V  W  D  I  L  K  A  G  K  K  T  H  I  N  R  L  R  N  457

-------|---------|---------|---------|---------|---------|-----
    1513 atccacgcacttagcatacgtgaggatgatgaggagggtcttgaaatcgttaaaaaatacata 1575
     458  I  H  A  L  S  I  R  E  D  D  E  E  G  L  E  I  V  K  K  Y  I  478

----|---------|---------|---------|---------|---------|--------
    1576 gatagagacaaatactgtcagatcatttcagagaaaacaattgatctgctgaaaagtctcggg 1638
     479  D  R  D  K  Y  C  Q  I  I  S  E  K  T  I  D  L  L  K  S  L  G  499

-|---------|---------|---------|---------|---------|---------|-
    1639 tatgttgaaaatactacaaagataaaaaccgttgaggatcttattcgttttcttgtagagagt 1701
     500  Y  V  E  N  T  T  K  I  K  T  V  E  D  L  I  R  F  L  V  E  S  520

--------|---------|---------|---------|---------|---------|----
    1702 gaaaactaaacccattagcgccatgattctcaaattcgacactgaaggcattgttcgtatcct 1764
     521  E  N  *  523
```

FIG. 8B

```
        ---------|----------|---------|----------|---------|--------|---
   1 ccggtttgatacccgtattggtcatttccttgtggaaacccccggttgaaaagtggagtaacaa 63

------|----------|---------|---------|---------|---------|------
  64 aatgttgcgcgtagctgaaaaacttgtaaccaattcccgtaaacagatttacgaaggaggtgt 126

---|----------|---------|---------|---------|---------|---------
 127 gtgattgctacggtttcctatccggaaactatgaagttgtagacgaactccctgatcaaccga 189

|---------|----------|---------|---------|---------|---------|--
 190 cgcttccgaaaactcaaaacaagacttatagtacgctatggaatcgatgaacgtaaaataccc 252
                                           M   N   V   K   Y   P   6

--------|----------|---------|---------|---------|---------|-----
 253 ggttgagtaccttatcgaacacctgaactcttttgagtctccggaagtagccgtcgaatccct 315
   7  V  E  Y  L  I  E  H  L  N  S  F  E  S  P  E  V  A  V  E  S  L   28

----|----------|---------|---------|---------|---------|--------
 316 tcgcaaggaggggattatgtgcaaaaaccggggtgatctatacatgttcaaatatcaccttgg 378
  29  R  K  E  G  I  M  C  K  N  R  G  D  L  Y  M  F  K  Y  H  L  G   49

-|----------|---------|---------|---------|---------|----------|-
 379 ttgtaagtttgataagatatatcaccttgcctgtcgcggggcgattctccgcaaaacggatag 441
  50  C  K  F  D  K  I  Y  H  L  A  C  R  G  A  I  L  R  K  T  D  S   70

--------|----------|---------|---------|---------|---------|----
 442 tggttggaaagttctgtcttatccctttgacaaattttttcaactgggggggaagaactccagcc 504
  71  G  W  K  V  L  S  Y  P  F  D  K  F  F  N  W  G  E  E  L  Q  P   91

-----|----------|---------|---------|---------|---------|-------
 505 ggaaatcgtaaactattatcagacgcttcgttacgcgtctcccctgaatgaaaagcgcaaagc 567
  92  E  I  V  N  Y  Y  Q  T  L  R  Y  A  S  P  L  N  E  K  R  K  A   112

--|----------|---------|---------|---------|---------|---------|
 568 cggtttcatgttcaaacttcccatgaaactggttgaaaagctggatggtacttgtgtggtttt 630
 113  G  F  M  F  K  L  P  M  K  L  V  E  K  L  D  G  T  C  V  V  L   133

----------|----------|---------|---------|---------|---------|---
 631 atattatgatgaagggtggaaaattcacactcttgggagtattgacgcaaatggatccattgt 693
 134  Y  Y  D  E  G  W  K  I  H  T  L  G  S  I  D  A  N  G  S  I  V   154

------|----------|---------|---------|---------|---------|------
 694 caaaaacggaatggttaccactcatatggataaaacatatcgagaattgttctgggaaacctt 756
 155  K  N  G  M  V  T  T  H  M  D  K  T  Y  R  E  L  F  W  E  T  F   175

---|----------|---------|---------|---------|---------|---------
 757 tgaaaagaaatatccgccttaccttctctatcatttgaactcctcatactgttacatatttga 819
 176  E  K  K  Y  P  P  Y  L  L  Y  H  L  N  S  S  Y  C  Y  I  F  E   196

|----------|---------|---------|---------|---------|---------|--
 820 aatggttcatccggacgcgcgagtggtggttccttatgaggagccaaatatcattctgatcgg 882
 197  M  V  H  P  D  A  R  V  V  V  P  Y  E  E  P  N  I  I  L  I  G   217

-------|----------|---------|---------|---------|---------|-----
 883 tgtgcgttcggtggatccggagaagggatatttcgaggtgggtccctccgaagaagccgtacg 945
 218  V  R  S  V  D  P  E  K  G  Y  F  E  V  G  P  S  E  E  A  V  R   238
```

FIG. 9A

```
           ----|---------|---------|---------|---------|---------|--------
     946 cattttcaacgaaagtggcggaaaaataaatcttaagctaccggctgttctgtctcaagagca 1008
     239  I  F  N  E  S  G  G  K  I  N  L  K  L  P  A  V  L  S  Q  E  Q  259

-|---------|---------|---------|---------|---------|---------|-
    1009 aaactatactcttttccgtgccaatcgccttcaggaactatttgaggaagttacaccgctttt 1071
     260  N  Y  T  L  F  R  A  N  R  L  Q  E  L  F  E  E  V  T  P  L  F  280

---------|---------|---------|---------|---------|---------|----
    1072 caaaagcctgagagacggttatgaggtggtatatgaaggatttgtagccgtacaggaaattgc 1134
     281  K  S  L  R  D  G  Y  E  V  V  Y  E  G  F  V  A  V  Q  E  I  A  301

-----|---------|---------|---------|---------|---------|-------
    1135 cccgcgtgtttattaccgcacaaagatcaagcacccggtatatctggagctccaccggattaa 1197
      P   R  V  Y  Y  R  T  K  I  K  H  P  V  Y  L  E  L  H  R  I  K  322

--|---------|---------|---------|---------|---------|---------|
    1198 aactacaatcactcctgagaagctcgccgatcttttcttgaaaacaaacttgatgattttgt 1260
     323  T  T  I  T  P  E  K  L  A  D  L  F  L  E  N  K  L  D  D  F  V  343

---------|---------|---------|---------|---------|---------|---
    1261 acttaccccggatgaacaggaaaccgtgatgaaactcaaagaaatttataccgatatgcgaaa 1323
     344  L  T  P  D  E  Q  E  T  V  M  K  L  K  E  I  Y  T  D  M  R  N  364

------|---------|---------|---------|---------|---------|------
    1324 tcagcttgagtcatcttttgatacgatttataaagagatttccgaacaggtttctccggaaga 1386
     365  Q  L  E  S  S  F  D  T  I  Y  K  E  I  S  E  Q  V  S  P  E  E  385

---|---------|---------|---------|---------|---------|---------
    1387 aaaccccggagagtttcgcaaaaggttcgctcttcgacttatggattatcatgataaaagttg 1449
     386  N  P  G  E  F  R  K  R  F  A  L  R  L  M  D  Y  H  D  K  S  W  406

|---------|---------|---------|---------|---------|---------|--
    1450 gttttttgcccgccttgacggcgacgaagagaaaatgcaaaagtcggaaaagaagcttctaac 1512
     407  F  F  A  R  L  D  G  D  E  E  K  M  Q  K  S  E  K  K  L  L  T  427

-------|---------|---------|---------|---------|---------|-----
    1513 ggagagaattgaaaaggggttatttaaataaaaatgataaaaaagcgtaatcctcttttctgg 1575
     428   E  R  I  E  K  G  L  F  K  *  437

----|---------|---------|---------|--------
     576 ggaagacgggaactcaatcttcttcagcattttgcccttgaagc 1619
```

FIG. 9B

```
  1 gcttcgtcaaaactcacgtctatagtatctatgtcgtagggttcgaggttggaggcaatcagg  63

64 ttgaacagttcatcataatcataattctcgaaaagaatgttgcgaataccgatccctctttct 126

127 ggatcgtagggatattcccccggctcgatgaaaagcaggagttttatcttatcgatcaggagt 189

190 tttaccgggtcatcaggaaatctgaaattcggtgcagtgtcgttcagatagaacatttcattt 252

253 ttgtttaaataaatcctcgaggaatcttcaaataaagagggcgttaatggatgaaaagactg 315
                                            M  K  R  L    4

316 aggaatatggtcaatcttatcgatctcaaaaatcagtattatgcttactctttcaagtttttc 378
  5  R  N  M  V  N  L  I  D  L  K  N  Q  Y  Y  A  Y  S  F  K  F  F   25

379 gactcctatcagatcagctgggataattacccgcatcttaaagagttcgtcattgaaaactat 441
 26  D  S  Y  Q  I  S  W  D  N  Y  P  H  L  K  E  F  V  I  E  N  Y   46

442 cccggcacttattttcatgctacgctccggggattctgtacaagcttttcctcaaatggaag 504
 47  P  G  T  Y  F  S  C  Y  A  P  G  I  L  Y  K  L  F  L  K  W  K   67

505 cggggtatgatcattgacgactatgaccgacacccgctccgaaagaagttacttcctcagtac 567
 68  R  G  M  I  I  D  D  Y  D  R  H  P  L  R  K  K  L  L  P  Q  Y   88

568 aaagagcaccgctatgaatacattgagggaaaatacggtgtggttccttttccccgggtttctg 630
 89  K  E  H  R  Y  E  Y  I  E  G  K  Y  G  V  V  P  F  P  G  F  L  109

631 aaatatctgaagttccactttgaggacttgcggtttaaaatgcgcgatcttggaatcaccgat 693
110  K  Y  L  K  F  H  F  E  D  L  R  F  K  M  R  D  L  G  I  T  D  130

694 ttcaaatatgcacttgccatttctcttttttacaaccgggtaatgctcagagattttctgaaa 756
131  F  K  Y  A  L  A  I  S  L  F  Y  N  R  V  M  L  R  D  F  L  K  151

757 aactttacctgttattacattgccgaatatgaagctgacgatgtaatcgcacatctggcgcgt 819
152  N  F  T  C  Y  Y  I  A  E  Y  E  A  D  D  V  I  A  H  L  A  R  172

820 gagattgcacgaagcaatatcgacgtaaacatcgtctcaacggataaagattattaccagcta 882
173  E  I  A  R  S  N  I  D  V  N  I  V  S  T  D  K  D  Y  Y  Q  L  193

883 tgggatgaagaggatataagagaaagggtttatatcaattctctttcatgtagtgatgtgaag 945
194  W  D  E  E  D  I  R  E  R  V  Y  I  N  S  L  S  C  S  D  V  K  214
```

FIG. 10A

```
      ----|----------|---------|----------|---------|---------|--------
 946 acaccccgctacggatttcttaccattaaagcacttcttggagacaaaagcgataacattccc 1008
 215 T   P   R   Y   G   F   L   T   I   K   A   L   L   G   D   K   S   D   N   I   P   235

-|----------|---------|---------|---------|---------|---------|-
1009 aaatctctggaaaaaggaaaaggcgaaaagtatcttgaaaagaaaggatttgcggaggaagat 1071
 236 K   S   L   E   K   G   K   G   E   K   Y   L   E   K   K   G   F   A   E   E   D   256

--------|----------|----------|----------|----------|----------|----
1072 tacgataaggaactattcgagaataatctgaaggtgatcaggtttggagacgaatatcttgga 1134
 257 Y   D   K   E   L   F   E   N   N   L   K   V   I   R   F   G   D   E   Y   L   G   277

----|----------|---   ----|----------|----------|----------|-------
1135 gaaagggataaaagctttatagaaaattttctacgggggatactctgtggaacttttatgaa 1197
 278 E   R   D   K   S   F   I   E   N   F   S   T   G   D   T   L   W   N   F   Y   E   298

--|----------|----------|----------|----------|----------|----------|
1198 ttttttactatgaccctttgcatgaacttttcctcagaaatataagaaagaggagactatga 1260
 299 F   F   Y   Y   D   P   L   H   E   L   F   L   R   N   I   R   K   R   R   L   *    319

----------|----------|----------|----------|----------|----------|---
1261 aagtactcgcatttaccgatgcacctacgtttcccacgggggtgggtcatcagcttcacaaca 1323

------|----------|----------|----------|----------|----------|------
1324 ttatcaattacgggtttgacgcaaccgatcgctgggttgtggtgcacccgccccggtcgccaa 1386

---|----------|----------|----------|----------|----------|
1387 gggctggagagactaaaaacgtcgttattggaaacactccagtcaagcttatca 1440
```

FIG. 10B

```
         ---------|---------|---------|---------|---------|---------|---
     1   acttcccaaatgctatgtggaggtggatgatagaaagcgtattgttaatgaagaggcggtcaa   63

------|---------|---------|---------|---------|---------|------
    64   gtcttttctccataagcatgttaccgaactgctgaagaattatcagtaacccaaacctaaacc  126

---|---------|---------|---------|---------|---------|---------
   127   cgaaaaatatatggaaacgattgtaatttcccaaaacaatacgacggagatgacggaacccc   189
                       M  E  T  I  V  I  S  Q  N  N  T  T  E  M  T  E  P  P    18

|---------|---------|---------|---------|---------|---------|--
   190   ccagaacatttccgattcggttaaaagcgggtttatctatcttatcgaaaagtctcatttcct  252
    19   Q  N  I  S  D  S  V  K  S  G  F  I  Y  L  I  E  K  S  H  F  L    39

--------|---------|---------|---------|---------|---------|-----
   253   tgaaaagaaaaacttccttaaaatcatatcgaacatggaccccgccgcatttccaatccgga   315
    40   E  K  K  N  F  L  K  I  I  S  N  M  D  P  R  R  I  S  N  P  E    60

----|---------|---------|---------|---------|---------|--------
   316   ggtgcgcgtggtggcggagtacatatatgattatttcaaaagtcatagtaatttcccttctaa  378
    61   V  R  V  V  A  E  Y  I  Y  D  Y  F  K  S  H  S  N  F  P  S  K    81

-|---------|---------|---------|---------|---------|---------|-
   379   aagaaatctttgccatcactttgagtggagcgaagatctggaaggagaccccgccgattatca  441
    82   R  N  L  C  H  H  F  E  W  S  E  D  L  E  G  D  P  A  D  Y  Q   102

--------|---------|---------|---------|---------|---------|----
   442   gcgtatcattcagtatctcaaatcttcttacattcgatcctctataacaaaaacgctttcata  504
   103   R  I  I  Q  Y  L  K  S  S  Y  I  R  S  S  I  T  K  T  L  S  Y   123

-----|---------|---------|---------|---------|---------|-------
   505   tcttgagaaggatgacctttccgcgttgaaagaaattgtcagagccattcgggtggtggagga  567
   124   L  E  K  D  D  L  S  A  L  K  E  I  V  R  A  I  R  V  V  E  D   144

--|---------|---------|---------|---------|---------|---------|
   568   tagtggggtgtcgctggtggaggaattcgatcttgcaaccagcgagtttaatgaacttttgt   630
   145   S  G  V  S  L  V  E  E  F  D  L  A  T  S  E  F  N  E  L  F  V   165

---------|---------|---------|---------|---------|---------|---
   631   taaagaagaacgcattcccacccctgggagagtgtaaacaaaaatatggcgggcggtcttgg   693
   166   K  E  E  R  I  P  T  P  W  E  S  V  N  K  N  M  A  G  G  L  G   186

------|---------|---------|---------|---------|---------|------
   694   tcggggagagcttggaatcgttatgcttccttcggggtggggtaagtcatggttccttgtttc  756
   187   R  G  E  L  G  I  V  M  L  P  S  G  W  G  K  S  W  F  L  V  S   207

---|---------|---------|---------|---------|---------|---------
   757   acttggtcttcatgcctttcgaacgggtaagcgcgtgatttatttcactctggagcttgacca  819
   208   L  G  L  H  A  F  R  T  G  K  R  V  I  Y  F  T  L  E  L  D  Q   228

|---------|---------|---------|---------|---------|---------|--
   820   aaaatatgtgatgaagcggttttaaagatgtttgcaccttattgcaaaggacgcgcttcttc   882
   229   K  Y  V  M  K  R  F  L  K  M  F  A  P  Y  C  K  G  R  A  S  S   249

--------|---------|---------|---------|---------|---------|-----
   883   ctatcgcgacgtttatcaaataatgaaagagcttatgttttctcaggataatcttttgragat  945
   250   Y  R  D  V  Y  Q  I  M  K  E  L  M  F  S  Q  D  N  L  L  K  I   270
```

FIG. 11A

```
         ----|---------|---------|---------|---------|---------|--------
    946  tgttttctgtaatgcgatggaagatattgagcactatattgcgctgtataacccccgacgttgt 1008
    271  V  F  C  N  A  M  E  D  I  E  H  Y  I  A  L  Y  N  P  D  V  V   291

-|---------|----------|---------|---------|----------|---------|-
   1009  gctgattgactatgccgatcttatttatgatgtggaaaccgacaaagagaaaaattatctgct 1071
    292  L  I  D  Y  A  D  L  I  Y  D  V  E  T  D  K  E  K  N  Y  L  L   312

--------|---------|---------|---------|---------|---------|----
   1072  tttgcaaaaaatttataggaaacttcgtctcattgcaaaggtatataatacagcagtatggag 1134
    313  L  Q  K  I  Y  R  K  L  R  L  I  A  K  V  Y  N  T  A  V  W  S   333

-----|---------|---------|---------|---------|---------|-------
   1135  cgcctctcagcttaatcgcggttccctttcaaagcaagccgacgtcgatttcattgagaaata 1197
    334  A  S  Q  L  N  R  G  S  L  S  K  Q  A  D  V  D  F  I  E  K  Y   354

--|---------|---------    ----|---------|---------|---------|
   1198  cattgccgattcatttgcaaaagttkttgaaatcgacttcgggatggcgtttattccggatag 1260
    355  I  A  D  S  F  A  K  V  V  E  I  D  F  G  M  A  F  I  P  D  S   375

---------|---------|---------|---------|---------|---------|---
   1261  cgagaactcaaccccgatattcacgtcggattcggtaaaatcttcaaaaaccgtatgggtgc 1323
    376  E  N  S  T  P  D  I  H  V  G  F  G  K  I  F  K  N  R  M  G  A   396

------|---------|---------|---------|---------|---------|------
   1324  ggtaagaaagctggaatatacaattaactttgaaaactatacggtagacgttgctgttaaatg 1386
    397  V  K  K  L  E  Y  T  I  N  F  E  N  Y  T  V  D  V  A  V  K  *   417

---|---------|---------|---------|---------|---------|---------
   1387  acacaagttaagacaaaagggcttaaagacatcagaataggtagaaaggagggtaagttcaca 1449

|---------|---------|---------|---------|---------|--------
   1450  catgtaaatacaacaaagaaaggaaagaataagaaatatttcagggcggaacatgaacg 1508
```

FIG. 11B

RNA LIGASE OF BACTERIOPHAGE RM 378

RELATED APPLICATIONS

This application is a Divisional of U.S. application Ser. No. 09/585,858, filed Jun. 1, 2000, now U.S. Pat. No. 6,492,161 B1, which claims the benefit of U.S. Provisional Application No. 60/137,120, filed Jun. 2, 1999, now abandoned, the entire teachings of which are incorporated herein by reference. Five separate divisional applications are being filed concurrently herewith.

BACKGROUND OF THE INVENTION

The use of thermophilic enzymes has revolutionized the field of recombinant DNA technology. Polymerases (DNA and RNA), ligases, exonucleases, reverse transcriptases, polynucleotide kinases and lysozymes, as well as many other thermophilic enzymes, are of great importance in the research industry today. In addition, thermophilic enzymes are also used in commercial settings (e.g., proteases and lipases used in washing powder, hydrolidic enzymes used in bleaching). Identification of new thermophilic enzymes will facilitate continued DNA research as well as assist in improving commercial enzyme-based products.

SUMMARY OF THE INVENTION

This invention pertains to a novel bacteriophage of *Rhodothermus marinus*, bacteriophage RM 378, which can be isolated from its native environment or can be recombinantly produced. The invention additionally pertains to the nucleic acids of the genome of bacteriophage RM 378 as deposited, as well as to the nucleic acids of a portion of the genome of bacteriophage RM 378 as shown in FIG. 1; to isolated nucleic acid molecules containing a nucleotide sequence of an open reading frame (or more than one open reading frame) of the genome of bacteriophage RM 378, such as an open reading frame as set forth in FIG. 2; to isolated nucleic acid molecules encoding a polypeptide obtainable from bacteriophage RM 378 or an active derivative or fragment of the polypeptide (e.g., a DNA polymerase, such as a DNA polymerase lacking exonuclease domains; a 3'–5' exonuclease, such as a 3'–5' exonuclease lacking DNA polymerase domain; a 5'–3' exonuclease (RNase H); a DNA helicase; or an RNA ligase); to DNA constructs containing the isolated nucleic acid molecule operatively linked to a regulatory sequence; and also to host cells comprising the DNA constructs. The invention further pertains to isolated polypeptides encoded by these nucleic acids, as well as active derivatives or fragments of the polypeptides.

Because the host organism of the RM 378 bacteriophage is a thermophile, the enzymes and proteins of the RM 378 bacteriophage are expected to be significantly more thermostable than those of other (e.g., mesophilic) bacteriophages, such as the T4 bacteriophage of *Escherichia coli*. The enhanced stability of the enzymes and proteins of RM 378 bacteriophage allows their use under temperature conditions which would be prohibitive for other enzymes, thereby increasing the range of conditions which can be employed not only in DNA research but also in commercial settings.

BRIEF DESCRIPTION OF THE DRAWINGS

FIGS. 1A–1Q2 are a depiction of the nucleic acid sequence (SEQ ID NO:1) of the genome of bacteriophage RM 378.

FIGS. 2A–2C delineate the open reading frames (ORFs) in the genome of bacteriophage RM 378.

FIGS. 3A–3W depict a sequence alignment of the predicted gene products of ORF056e and ORF632e and sequences of DNA polymerases of family B. The sequence marked RM378 (SEQ ID NO:36) is the combined sequences of the gene products of ORF056e and ORF632e in bacteriophage RM378. The end of one sequence and the beginning of another is indicated. Other sequences are: Vaccinia virus (strain Copenhagen) DNA polymerase (DPOL_VACCC) (SEQ ID NO:2); Vaccinia virus (strain WR) DNA polymerase (DPOL_VACCV) (SEQ ID NO:3); Variola virus DNA polymerase (DPOL_VARV) (SEQ ID NO:4); Fowlpox virus DNA polymerase (DPOL_FOWPV) (SEQ ID NO:5); *Bos taurus* (Bovine) DNA polymerase delta catalytic chain (DPOD_BOVIN) (SEQ ID NO:6); Human DNA polymerase delta catalytic chain (DPOD_HUMAN) (SEQ ID NO:7); *Candida albicans* (Yeast) DNA polymerase delta large chain (DPOD_CANAL) (SEQ ID NO:8); *Saccharomyces cerevisiae* DNA polymerase delta large chain (DPOD_YEAST) (SEQ ID NO:9); *Schizosaccharomyces pombe* DNA polymerase delta large chain (DPOD_SCHPO) (SEQ ID NO:10); *Plasmodium falciparum* DNA polymerase delta catalytic chain (DPOD_PLAFK) (SEQ ID NO:11); Chlorella virus NY-2A DNA polymerase (DPOL_CHVN2) (SEQ ID NO:12); *Paramecium bursaria chlorella* virus 1 DNA polymerase (DPOL_CHVP1) (SEQ ID NO:13); Epstein-barr virus (strain B95-8) DNA polymerase (DPOL_EBV) (SEQ ID NO:14); Herpesvirus saimiri (strain 11) DNA polymerase (DPOL_HSVSA) (SEQ ID NO:15); Herpes *simplex* virus (type 1/strain 17) DNA polymerase (DPOL_HSV11) (SEQ ID NO:16); Herpes *simplex* virus (type 2/strain 186) DNA polymerase (DPOL_HSV21) (SEQ ID NO:17); Equine herpesvirus type 1 (strain Ab4p) (EHV-1) DNA polymerase (DPOL_HSVEB) (SEQ ID NO:18); *Varicella-zoster* virus (strain Dumas) (VZV) DNA polymerase (DPOL_VZVD) (SEQ ID NO:19); Human cytomegalovirus (strain AD169) DNA polymerase (DPOL_HCMVA) (SEQ ID NO:20); Murine cytomegalovirus (strain Smith) DNA polymerase (DPOL_MCMVS) (SEQ ID NO:21); Herpes *simplex* virus (type 6/strain Uganda-1102) DNA polymerase (DPOL_HSV6U) (SEQ ID NO:22); Human DNA polymerase alpha catalytic subunit (DPOA_HUMAN) (SEQ ID NO:23); Mouse DNA polymerase alpha catalytic subunit (DPOA_MOUSE) (SEQ ID NO:24); *Drosophila melanogaster* DNA polymerase alpha catalytic subunit (DPOA_DROME) (SEQ ID NO:25); *Schizosaccharomyces pombe* DNA polymerase alpha catalytic subunit (DPOA_SCHPO) (SEQ ID NO:26); *Saccharomyces cerevisiae* DNA polymerase alpha catalytic subunit (DPOA_YEAST) (SEQ ID NO:27); *Trypanosoma brucei* DNA polymerase alpha catalytic subunit (DPOA_TRYBB) (SEQ ID NO:28); *Autographa californica* nuclear polyhedrosis virus DNA polymerase (DPOL_NPVAC) (SEQ ID NO:29); *Lymantria dispar* multicapsid nuclear polyhedrosis virus DNA polymerase (DPOL_NPVLD) (SEQ ID NO:30); *Saccharomyces cerevisiae* DNA polymerase zeta catalytic subunit (DPOZ_YEAST) (SEQ ID NO:31); *Pyrococcus woesei* DNA polymerase (DPOL_PYRFU) (SEQ ID NO:32);. *Sulfolobus solfataricus* DNA polymerase I (DPO1_SULSO) (SEQ ID NO:33); *Escherichia coli* DNA polymerase II (DPO2_ECOLI) (SEQ ID NO:34); *Desilforococcus* strain Tok DNA polymerase (Dpol_Dtok) (SEQ ID NO:35); and bacteriophage RB69 DNA polymerase (RB69) (SEQ ID NO:37). Most of the sequences are partial as found in the Protein Families Data Base of Alignments and HMMs (Sanger Institute), family DNA_pol_B, accession no. PF00136.

FIG. 4 depicts a sequence alignment of the predicted gene product of ORF739f from bacteriophage RM378 (ORF- 739f) (SEQ ID NO:40), *Autographa californica* nucleopolyhedrovirus putative bifunctional polynucleotide kinase and RNA ligase (ACNV-RNAlig) (SEQ ID NO:38); and bacteriophage T4 RNA ligase (T4-RNAlig) (SEQ ID NO:39).

FIG. 5 depicts a sequence alignment of the predicted gene product of ORF1218a from bacteriophage RM378 (ORF-1218a) (SEQ ID NO:43) with proteins or domains with 5'–3' exonuclease activity, including: *Escherichia coli* DNA polymerase I (*Ecoli*-polI) (SEQ ID NO:41), *Thermus aquaticus* DNA polymerase I (Taq-polI) (SEQ ID NO:42), bacteriophage T4 ribonuclease H (T4-RNaseH) (SEQ ID NO:44) and bacteriophage T7 gene6 exonuclease (T7-gp6exo) (SEQ ID NO:45). Conservation of acidic residues mainly clustered at the proposed active site are seen.

FIGS. 6A–6B depict a sequence alignment of the predicted gene product of ORF1293b (SEQ ID NO:55) from bacteriophage RM378 (ORF1293b) with sequences of replicative DNA helicases of the DnaB family, including: *Escherichia coli* (DnaB-*Ecoli*) (SEQ ID NO:46), *Haemophilus influenza* (DnaB-Hinflu) (SEQ ID NO:47), *Chlamydomonas trachomatis* (DnaB-Ctracho) (SEQ ID NO:48), *Bacillus stearothermophilus* (DnaB-Bstearo) (SEQ ID NO:49), *Halobacter pylori* (DnaB-Hpylor) (SEQ ID NO:50), *Mycoplasma genitalium* (DnaB-Mgenital) (SEQ ID NO:51), *Borrelia burgdorferi* (DnaB-Bburgdor) (SEQ ID NO:52), bacteriophage T4 gene 41 (T4-gp41) (SEQ ID NO:53), bacteriophage T7 gene 4 (T7-gp4) (SEQ ID NO:54) (from the Protein Families Data Base of Alignments and HMMS (Sanger Institute), family DnaB, accession no. PF00772). The sequences have been truncated at the N-termini, and conserved sequence motifs are indicated.

FIGS. 7A–7B depict the nucleic acid sequence of open reading frame ORF 056e (nucleotides 21993–23042 of the genome) (SEQ ID NO:56) with flanking sequences, and the putative encoded polypeptide (SEQ ID NO:57) which displays amino acid sequence similarity to polymerase 3'–5' exonucleases.

FIGS. 8A–8B depict the nucleic acid sequence of open reading frame ORF 632e (nucleotides 79584–81152 of the genome) (SEQ ID NO:58) with flanking sequences, and the putative encoded polypeptide (SEQ ID NO:59) which displays amino acid sequence similarity to polymerases.

FIGS. 9A–9B depict the nucleic acid sequence of open reading frame ORF 739f (nucleotides 90291–91607 of the genome) (SEQ ID NO:60) with flanking sequences, and the putative encoded polypeptide (SEQ ID NO:40) which displays amino acid sequence similarity to RNA ligase.

FIGS. 10A–10B depict the nucleic acid sequence of open reading frame ORF 1218a (nucleotides 8212–9168 of the genome) (SEQ ID NO:61) with flanking sequences, and the putative encoded polypeptide (SEQ ID NO:43) which displays amino acid sequence similarity to 5'–3' exonuclease of DNA polymerase I and T4 RNase H.

FIGS. 11A–11B depict the nucleic acid sequence of open reading frame ORF 1293b (nucleotides 15785–17035 of the genome) (SEQ ID NO:62) with flanking sequences, and the putative encoded polypeptide (SEQ ID NO:55) which displays amino acid sequence similarity to T4 DNA helicase.

DETAILED DESCRIPTION OF THE INVENTION

The present invention relates to a bacteriophage, the nucleic acid sequence of the bacteriophage genome as well as portions of the nucleic acid sequence of the bacteriophage genome (e.g., a portion containing an open reading frame), and proteins encoded by the nucleic acid sequences, as well as nucleic acid constructs comprising portions of the nucleic acid sequence of the bacteriophage genome, and host cells comprising such nucleic acid constructs. As described herein, Applicants have isolated and characterized a novel bacteriophage active against the slightly halophilic, thermophilic eubacterium *Rhodothermus marinus*. The bacteriophage, RM 378, is a member of the *Myoviridae* family, with an A2 morphology. RM 378, which is completely stable up to about 65° C., appears to consist of approximately 16 proteins with one major protein of molecular weight of 61,000 daltons. RM 378 can be replicated in *Rhodothermus marinus* species ITI 378.

Rhodothermus Marinus ITI 378

Accordingly, one embodiment of the invention is the bacterium, *Rhodothermus marinus* species ITI 378. *Rhodothermus marinus*, and particularly species ITI 378, can be cultured in a suitable medium, such as medium 162 for *Thermus* as described by Degryse et al. (*Arch. Microbiol.* 117:189–196 (1978)), with ⅒ buffer and with 1% NaCl. *Rhodothermus marinus* species ITI 378 can be used in replication of bacteriophage RM 378, as described herein, or in replication or identification of other bacteriophages, particularly thermophilic bacteriophages. *Rhodothermus marinus* species ITI 378 can also used in the study of the relationship between the bacteriophages and their host cells (e.g., between bacteriophage RM 378 and *Rhodothermus marinus* species ITI 378).

Bacteriophage RM 378

Another embodiment of the invention is isolated RM 378 bacteriophage. "Isolated" RM 378 bacteriophage refers to bacteriophage that has been separated, partially or totally, from its native environment (e.g., separated from *Rhodothermus marinus* host cells) ("native bacteriophage"), and also refers to bacteriophage that has been chemically synthesized or recombinantly produced ("recombinant bacteriophage"). A bacteriophage that has been "recombinantly produced" refers to a bacteriophage that has been manufactured using recombinant DNA technology, such as by inserting the bacteriophage genome into an appropriate host cell (e.g., by introducing the genome itself into a host cell, or by incorporating the genome into a vector, which is then introduced into the host cell).

Isolated bacteriophage RM 378 can be used in the study of the relationship between the bacteriophages and their host cells (e.g., *Rhodothermus marinus*, such as *Rhodothermus marinus* species ITI 378). Isolated bacteriophage RM 378 can also be used as a vector to deliver nucleic acids to a host cell; that is, the bacteriophage can be modified to deliver nucleic acids comprising a gene from an organism other than the bacteriophage (a "foreign" gene). For example, nucleic acids encoding a polypeptide (e.g., an enzyme or pharmaceutical peptide) can be inserted into the genome of bacteriophage RM 378, using standard techniques. The resultant modified bacteriophage can be then used to infect host cells, and the protein encoded by the foreign nucleic acids can then be produced.

Bacteriophage RM 378 can be produced by inoculating appropriate host cells with the bacteriophage. Representative host cells in which the bacteriophage can replicate include *Rhodothermus marinus*, particularly species isolated in a location that is geographically similar to the location where bacteriophage RM 378 was isolated (e.g., northwest Iceland). In a preferred embodiment, the host cell is *Rhodothermus marinus* species ITI 378. The host cells are cultured in a suitable medium (e.g., medium 162 for *Thermus* as described by Degryse et al., *Arch. Microbiol.* 117:189–196 (1978), with ⅒ buffer and with 1% NaCl). In addition, the host cells are cultured under conditions suitable for replication of the bacteriophage. For example, in a preferred embodiment, the host cells are cultured at a temperature of at least approximately 50° C. In a more preferred embodiment, the host cells are cultured at a temperature between about 50° C. and about 80° C. The bacteriophage can also be stored in a cell lysate at about 4° C.

Nucleic Acids of the Invention

Another embodiment of the invention pertains to isolated nucleic acid sequences obtainable from the genome of bacteriophage RM 378. As described herein, approximately 130 kB of the genome of bacteriophage RM 378 have been sequenced. The sequence of this 130 kB is set forth in FIG. 1. There are at least approximately 200 open reading frames (ORFs) in the sequence; of these, at least approximately 120 putatively encode a polypeptide of 100 amino acids in length or longer. These 120 are set forth in FIG. 2. FIG. 2 sets forth the locus of each ORF; the start and stop nucleotides in the sequence of each ORF; the number of nucleotides in the ORF, and the expected number of amino acids encoded therein; the direction of the ORF; the identity of the putative protein encoded therein; the protein identified by a BLAST search as being the closest match to the putative protein; the percentage identity at the amino acid level of the putative protein (based on partial sequence similarity; the overall similarity is lower); the organism from which the closest matching protein is derived; and other information relating to the ORFs.

The invention thus pertains to isolated nucleic acid sequence of the genome ("isolated genomic DNA") of the bacteriophage RM 378 that has been deposited with the Deutsche Sammlung Von Mikroorganismen und Zellkulturen GmbH (DSMZ) as described below. The invention also pertains to isolated nucleic acid sequence of the genome of bacteriophage RM 378 as is shown in FIG. 1 (SEQ ID NO:1).

The invention additionally pertains to isolated nucleic acid molecules comprising the nucleotide sequences of each of the ORFs described above or fragments thereof, as well as nucleic acid molecules comprising nucleotide sequences of more than one of the ORFs described above or fragments of more than one of the ORFs. The nucleic acid molecules of the invention can be DNA, or can also be RNA, for example, mRNA. DNA molecules can be double-stranded or single-stranded; single stranded RNA or DNA can be either the coding, or sense, strand or the non-coding, or antisense, strand. Preferably, the nucleic acid molecule comprises at least about 100 nucleotides, more preferably at least about 150 nucleotides, and even more preferably at least about 200 nucleotides. The nucleotide sequence can be only that which encodes at least a fragment of the amino acid sequence of a polypeptide; alternatively, the nucleotide sequence can include at least a fragment of a coding sequence along with additional non-coding sequences such as non-coding 3' and 5' sequences (including regulatory sequences, for example).

In certain preferred embodiments, the nucleotide sequence comprises one of the following ORFs: ORF 056e, 632e, 739f, 1218a, 1293b. For example, the nucleotide sequence can consist essentially of one of the ORFs and its flanking sequences, such as are shown in FIGS. 7–11 (e.g., ORF 056e (SEQ ID NO:56), 632e (SEQ ID NO:58), 739f (SEQ ID NO:60), 1218a (SEQ ID NO:61), 1293b (SEQ ID NO:62)).

Additionally, the nucleotide sequence(s) can be fused to a marker sequence, for example, a sequence which encodes a polypeptide to assist in isolation or purification of the polypeptide. Representative sequences include, but are not limited to, those which encode a glutathione-S-transferase (GST) fusion protein. In one embodiment, the nucleotide sequence contains a single ORF in its entirety (e.g., encoding a polypeptide, as described below); or contains a nucleotide sequence encoding an active derivative or active fragment of the polypeptide; or encodes a polypeptide which has substantial sequence identity to the polypeptides described herein. In a preferred embodiment, the nucleic acid encodes a polymerase (e.g., DNA polymerase); DNA polymerase accessory protein; dsDNA binding protein; deoxyriboncleotide-3-phosphatase; DNA topoisomerase; DNA helicase; an exonuclease (e.g., 3'–5' exonuclease, 5'–3' exonuclease (RNase H)); RNA ligase; site-specific RNase inhibitor of protease; endonuclease; exonuclease; mobility nuclease; reverse transcriptase; single-stranded binding protein; endolysin; lysozyme; helicase; alpha-glucosyltransferase; or thymidine kinase, as described herein. In a particularly preferred embodiment, the nucleic acid encodes a DNA polymerase, 3'–5' exonuclease, 5'–3 exonuclease (RNase H), DNA helicase or RNA ligase. In another particularly preferred embodiment, the nucleic acid encodes a DNA polymerase that lacks exonuclease domains, or a 3'–5' exonuclease that lacks DNA polymerase domain, as described below.

The nucleic acid molecules of the invention are "isolated;" as used herein, an "isolated" nucleic acid molecule or nucleotide sequence is intended to mean a nucleic acid molecule or nucleotide sequence which is not flanked by nucleotide sequences which normally (in nature) flank the gene or nucleotide sequence (as in genomic sequences) and/or has been completely or partially purified from other transcribed sequences (e.g., as in an RNA library). For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Thus, an isolated nucleic acid molecule or nucleotide sequence can include a nucleic acid molecule or nucleotide sequence which is synthesized chemically or by recombinant means. Therefore, recombinant DNA contained in a vector are included in the definition of "isolated" as used herein. Also, isolated nucleotide sequences include recombinant DNA molecules in heterologous organisms, as well as partially or substantially purified DNA molecules in solution. In vivo and in vitro RNA transcripts of the DNA molecules of the present invention are also encompassed by "isolated" nucleotide sequences.

The present invention also pertains to nucleotide sequences which are not necessarily found in nature but which encode the polypeptides described below. Thus, DNA molecules which comprise a sequence which is different from the naturally-occurring nucleotide sequence but which, due to the degeneracy of the genetic code, encode the polypeptides of the present invention are the subject of this invention. The invention also encompasses variations of the nucleotide sequences of the invention, such as those encoding active fragments or active derivatives of the polypeptides as described below. Such variations can be naturally-occurring, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations are silent or conserved; that is, they do not alter the characteristics or activity of the encoded polypeptide.

The invention described herein also relates to fragments of the isolated nucleic acid molecules described herein. The term "fragment" is intended to encompass a portion of a nucleotide sequence described herein which is from at least about 25 contiguous nucleotides to at least about 50 contiguous nucleotides or longer in length; such fragments are useful as probes and also as primers. Particularly preferred primers and probes selectively hybridize to the nucleic acid molecule encoding the polypeptides described herein. For example, fragments which encode polypeptides that retain activity, as described below, are particularly useful.

The invention also pertains to nucleic acid molecules which hybridize under high stringency hybridization conditions, such as for selective hybridization, to a nucleotide sequence described herein (e.g., nucleic acid molecules which specifically hybridize to a nucleotide sequence encoding polypeptides described herein, and, optionally, have an activity of the polypeptide). Hybridization probes are oligonucleotides which bind in a base-specific manner to a complementary strand of nucleic acid. Suitable probes include polypeptide nucleic acids, as described in (Nielsen et al., Science 254, 1497–1500 (1991)).

Such nucleic acid molecules can be detected and/or isolated by specific hybridization (e.g., under high stringency conditions). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 60%, 75%, 85%, 95%). For example, certain high stringency conditions can be used which distinguish perfectly complementary nucleic acids from those of less complementarity.

"High stringency conditions", "moderate stringency conditions" and "low stringency conditions" for nucleic acid hybridizations are explained on pages 2.10.1–2.10.16 and pages 6.3.1–6 in Current Protocols in Molecular Biology (Ausubel, F. M. et al., "Current Protocols in Molecular Biology", John Wiley & Sons, (1998)) the teachings of which are hereby incorporated by reference. The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions can be determined empirically.

By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, Methods in Enzymology, 200:546–556 (1991). Also, in, Ausubel, et al., "Current Protocols in Molecular Biology", John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 min at room temperature; a moderate stringency wash can comprise washing in a prewarmed solution (42° C.) solution containing 0.2×SSC/0.1% SDS for 15 min at 42° C.; and a high stringency wash can comprise washing in prewarmed (68° C.) solution containing 0.1×SSC/0.1% SDS for 15 min at 68° C. Furthermore, washes can be performed repeatedly or sequentially to obtain a desired result as known in the art.

Equivalent conditions can be determined by varying one or more of the parameters given as an example, as known in the art, while maintaining a similar degree of identity or similarity between the target nucleic acid molecule and the primer or probe used. Hybridizable nucleic acid molecules are useful as probes and primers, e.g., for diagnostic applications.

Such hybridizable nucleotide sequences are useful as probes and primers for diagnostic applications. As used herein, the term "primer" refers to a single-stranded oligonucleotide which acts as a point of initiation of template-directed DNA synthesis under appropriate conditions (e.g., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

The invention also pertains to nucleotide sequences which have a substantial identity with the nucleotide sequences described herein; particularly preferred are nucleotide sequences which have at least about 10%, preferably at least about 20%, more preferably at least about 30%, more preferably at least about 40%, even more preferably at least about 50%, yet more preferably at least about 70%, still more preferably at least about 80%, and even more preferably at least about 90% identity, with nucleotide sequences described herein. Particularly preferred in this instance are nucleotide sequences encoding polypeptides having an activity of a polypeptide described herein. For example, in one embodiment, the nucleotide sequence encodes a DNA polymerase, 3'–5' exonuclease, 5'–3' exonuclease (RNase H), DNA helicase, or RNA ligase, as described below. In a preferred embodiment, the nucleotide encodes a DNA polymerase lacking exonuclease domains, or a 3'–5' exonuclease lacking DNA polymerase domain, as described below.

To determine the percent identity of two nucleotide sequences, the sequences are aligned for optimal comparison purposes (e.g., gaps can be introduced in the sequence of a first nucleotide sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent identity between two sequences can be accomplished using a mathematical algorithm. A preferred, non-limiting example of a mathematical algorithm utilized for the comparison of two sequences is the algorithm of Karlin et al., *Proc. Natl. Acad. Sci. USA*, 90:5873–5877 (1993). Such an algorithm is incorporated into the NBLAST program which can be used to identify sequences having the desired identity to nucleotide sequences of the invention. To obtain gapped alignments for comparison purposes, Gapped BLAST can be utilized as described in Altschul et al., *Nucleic Acids Res*, 25:3389–3402 (1997). When utilizing BLAST and Gapped BLAST programs, the default parameters of the respective programs (e.g., NBLAST) can be used. See the programs provided by National Center for Biotechnology Information, National Library of Medicine, National Institutes of Health. In one embodiment, parameters for sequence comparison can be set at W=12. Parameters can also be varied (e.g., W=5 or W=20). The value "W" determines how many continuous nucleotides must be identical for the program to identify two sequences as containing regions of identity.

The invention also provides expression vectors containing a nucleic acid sequence encoding a polypeptide described herein (or an active derivative or fragment thereof), operably linked to at least one regulatory sequence. Many expression vectors are commercially available, and other suitable vectors can be readily prepared by the skilled artisan. "Operably linked" is intended to mean that the nucleotide sequence is linked to a regulatory sequence in a manner which allows expression of the nucleic acid sequence. Regulatory sequences are art-recognized and are selected to produce the polypeptide or active derivative or fragment thereof. Accordingly, the term "regulatory sequence" includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to bacteriophage RM 378 can be employed. It should be understood that the design of the expression vector may depend on such factors as the choice of the host cell to be transformed and/or the type of polypeptide desired to be expressed. For instance, the polypeptides of the present invention can be produced by ligating the cloned gene, or a portion thereof, into a vector suitable for expression in an appropriate host cell (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance. Thus, prokaryotic and eukaryotic host cells transformed by the described expression vectors are also provided by this invention. For instance, cells which can be transformed with the vectors of the present invention include, but are not limited to, bacterial cells such as *Rhodothermus marinus, E. coli* (e.g., *E. coli* K12 strains), *Streptomyces, Pseudomonas, Bacillus, Serratia marcescens* and *Salmonella typhimurium*,. The host cells can be transformed by the described vectors by various methods (e.g., electroporation, transfection using calcium chloride, rubidium chloride, calcium phosphate, DEAE-dextran, or other substances; microprojectile bombardment; lipofection, infection where the vector is an infectious agent such as a retroviral genome, and other methods), depending on the type of cellular host. The nucleic acid molecules of the present invention can be produced, for example, by replication in such a host cell, as described above. Alternatively, the nucleic acid molecules can also be produced by chemical synthesis.

The isolated nucleic acid molecules and vectors of the invention are useful in the manufacture of the encoded polypeptide, as probes for isolating homologous sequences (e.g., from other bacteriophage species), as well as for detecting the presence of the bacteriophage in a culture of host cells.

The nucleotide sequences of the nucleic acid molecules described herein (e.g., a nucleic acid molecule comprising any of the open reading frames shown in FIG. 2, such as a nucleic acid molecule comprising the open reading frames depicted in FIGS. 7–11 (SEQ ID NO:56, 58, 60, 61 and 62, respectively)) can be amplified by methods known in the art. For example, this can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabelled and used as a probe for screening a library or other suitable vector to identify homologous nucleotide sequences. Corresponding clones can be isolated, DNA can be obtained following in vivo excision, and the cloned insert can be sequenced in either or both orientations by art recognized methods, to identify the correct reading frame encoding a protein of the appropriate molecular weight. For example, the direct analysis of the nucleotide sequence of homologous nucleic acid molecules of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)). Using these or similar methods, the protein(s) and the DNA encoding the protein can be isolated, sequenced and further characterized.

Polypeptides of the Invention

The invention additionally relates to isolated polypeptides obtainable from the bacteriophage RM 378. The term, "polypeptide," as used herein, includes proteins, enzymes, peptides, and gene products encoded by nucleic acids described herein. In one embodiment, the invention pertains to the polypeptides encoded by the ORFs as described above. In addition, as described in detail below, bacteriophage RM 378 is similar to the well-known *E. coli* bacteriophage T4. Thus, it is expected that bacteriophage RM 378 comprises additional polypeptides that are homologous to those found in bacteriophage T4.

For example, representative proteins expected to be encoded by genes of bacteriophage RM 378 include the following: DNA topoisomerase; exonuclease (e.g., 3'–5' exonuclease, 5'–3' exonuclease (RNase H)); helicase; enzymes related to DNA or RNA synthesis (e.g., dCTPase, dUTPase, dCDPase, dUDPase, GTPase, dGTPase, ATPase, dATPase); transposase; reverse transcriptase; polymerase (e.g., DNA polymerase, RNA polymerase); DNA polymerase accessory protein; DNA packaging protein; DNA topoisomerase; RNA polymerase binding protein; RNA polymerase sigma factor; site-specific RNase inhibitor of protease; recombinant protein; alpha-glucosyltransferase; mobility nuclease; endonuclease (e.g., endonuclease II, endonuclease V, endonuclease VII); inhibitor of Lon protease; thymidine kinase; site-specific RNase; N-glycosidase; endolysin; lysozyme; dNMP kinase; DNA ligase; deoxyribonucleotide-3'-phosphatase; ssDNA binding protein; dsDNA binding protein; and RNA ligase.

In a particularly preferred embodiment, the polypeptide is polymerase (e.g., DNA polymerase); DNA polymerase accessory protein; dsDNA binding protein; deoxyriboncleotide-3-phosphatase; DNA topoisomerase; RNA ligase; site-specific RNase inhibitor of protease; endonuclease; exonuclease (e.g., 3'–5' exonuclease, 5'–3' exonuclease (RNase H)); nobility nuclease; reverse transcriptase; single-stranded binding protein; enolysin; lysozyme; helicase; alpha-glucosyltransferase; or thymidine kinase. In an especially preferred embodiment, the polypeptide is a DNA polymerase, a 3'–5' exonuclease, a 5'–3' exonuclease (RNase H), a DNA helicase, or an RNA ligase, such as those shown in FIGS. 7–11 (e.g., for a DNA polymerase, SEQ ID NO:58; a 3'–5' exonuclease, SEQ ID NO:56; a 5'–3' exonuclease (RNase H) (SEQ ID NO:61); a DNA helicase (SEQ ID NO:62), or an RNA ligase (SEQ ID NO:60)). In a most preferred embodiment, the polypeptide is a DNA polymerase that lacks exonuclease domains, or a 3'–5' exonuclease that lacks DNA polymerase domain, as described in the examples below. As used herein, the term, "lacking exonuclease domains," indicates that the polypeptide does not contain an amino acid domain (e.g., a consecutive or closely spaced series of amino acids) homologous to domains where such exonuclease activity resides in other similar polymerases (such as polymerases in the same family); it does not refer to the presence of a non-functional domain homologous to domains where exonuclease activity resides. Similarly, the term, "lacking DNA polymerase domain," indicates that the polypeptide does not contain an amino acid domain (e.g., a consecutive or closely spaced series of amino acids) homologous to domains where such DNA polymerase activity resides in other similar exonucleases (such as exonucleases in the same family); it does not refer to the presence of a non-functional domain homologous to domains where DNA polymerase activity resides.

These polypeptides can be used in a similar manner as the homologous polypeptides from bacteriophage T4; for example, polymerases and ligases of bacteriophage RM 378 can be used for amplification or manipulation of DNA and RNA sequences. The polymerases and ligases of bacteriophage RM 378, however, are expected to be much more thermostable than those of bacteriophage T4, because of the thermophilic nature of the host of bacteriophage RM 378 (in contrast with the mesophilic nature of *E. coli*, the host of bacteriophage T4).

The polypeptides of the invention can be partially or substantially purified (e.g., purified to homogeneity), and/or are substantially free of other polypeptides. According to the invention, the amino acid sequence of the polypeptide can be that of the naturally-occurring polypeptide or can comprise alterations therein. Polypeptides comprising alterations are referred to herein as "derivatives" of the native polypeptide. Such alterations include conservative or non-conservative amino acid substitutions, additions and deletions of one or more amino acids; however, such alterations should preserve at least one activity of the polypeptide, i.e., the altered or mutant polypeptide should be an active derivative of the naturally-occurring polypeptide. For example, the mutation(s) can preferably preserve the three dimensional configuration of the binding site of the native polypeptide, or can preferably preserve the activity of the polypeptide (e.g., if the polypeptide is a DNA polymerase, any mutations preferably preserve the ability of the enzyme to catalyze combination of nucleotide triphosphates to form a nucleic acid strand complementary to a nucleic acid template strand). The presence or absence of activity or activities of the polypeptide can be determined by various standard functional assays including, but not limited to, assays for binding activity or enzymatic activity.

Additionally included in the invention are active fragments of the polypeptides described herein, as well as fragments of the active derivatives described above. An "active fragment," as referred to herein, is a portion of polypeptide (or a portion of an active derivative) that retains the polypeptide's activity, as described above.

Appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (*Science* 247:1306–1310(1990)). For example, conservative amino acid replacements can be those that take place within a family of amino acids that are related in their side chains. Genetically encoded amino acids are generally divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan and tyrosine are sometimes classified jointly as aromatic amino acids. For example, it is reasonable to expect that an isolated replacement of a leucine with an isoleucine or valine, an aspartate with a glutamate, a threonine with a serine or a similar conservative replacement of an amino acid with a structurally related amino acid will not have a major effect on activity or functionality.

The polypeptides of the invention can also be fusion polypeptides comprising all or a portion (e.g., an active fragment) of the native bacteriophage RM 378 polypeptide amino acid sequence fused to an additional component, with optional linker sequences. Additional components, such as radioisotopes and antigenic tags, can be selected to assist in the isolation or purification of the polypeptide or to extend the half life of the polypeptide; for example, a hexahistidine tag would permit ready purification by nickel chromatography. The fusion protein can contain, e.g., a glutathione-S-transferase (GST), thioredoxin (TRX) or maltose binding protein (MBP) component to facilitate purification; kits for expression and purification of such fusion proteins are commercially available. The polypeptides of the invention can also be tagged with an epitope and subsequently purified using antibody specific to the epitope using art recognized methods. Additionally, all or a portion of the polypeptide can be fused to carrier molecules, such as immunoglobulins, for many purposes, including increasing the valency of protein binding sites. For example, the polypeptide or a portion thereof can be linked to the Fc portion of an immunoglobulin; for example, such a fusion could be to the Fc portion of an IgG molecule to create a bivalent form of the protein.

Also included in the invention are polypeptides which are at least about 90% identical (i.e., polypeptides which have substantial sequence identity) to the polypeptides described herein. However, polypeptides exhibiting lower levels of identity are also useful, particular if they exhibit high, e.g., at least about 90%, identity over one or more particular domains of the polypeptide. For example, polypeptides sharing high degrees of identity over domains necessary for particular activities, such as binding or enzymatic activity, are included herein. Thus, polypeptides which are at least about 10%, preferably at least about 20%, more preferably at least about 30%, more preferably at least about 40%, even more preferably at least about 50%, yet more preferably at least about 70%, still more preferably at least about 80%, and even more preferably at least about 90% identity, are encompassed by the invention.

Polypeptides described herein can be isolated from naturally-occurring sources (e.g., isolated from host cells infected with bacteriophage RM 378). Alternatively, the polypeptides can be chemically synthesized or recombinantly produced. For example, PCR primers can be designed to amplify the ORFs from the start codon to stop codon, using DNA of RM378 or related bacteriophages or respective recombinant clones as a template. The primers can contain suitable restriction sites for an efficient cloning into a suitable expression vector. The PCR product can be digested with the appropriate restriction enzyme and ligated between the corresponding restriction sites in the vector (the same restriction sites, or restriction sites producing the same cohesive ends or blunt end restriction sites).

Polypeptides of the present invention can be used as a molecular weight marker on SDS-PAGE gels or on molecular sieve gel filtration columns using art-recognized methods. They are particularly useful for molecular weight markers for analysis of proteins from thermophilic organisms, as they will behave similarly (e.g., they will not denature as proteins from mesophilic organisms would).

The polypeptides of the present invention can be isolated or purified (e.g., to homogeneity) from cell culture (e.g., from culture of host cells infected with bacteriophage RM 378) by a variety of processes. These include, but are not limited to, anion or cation exchange chromatography, ethanol precipitation, affinity chromatography and high performance liquid chromatography (HPLC). The particular method used will depend upon the properties of the polypeptide; appropriate methods will be readily apparent to those skilled in the art. For example, with respect to protein or polypeptide identification, bands identified by gel analysis can be isolated and purified by HPLC, and the resulting purified protein can be sequenced. Alternatively, the purified protein can be enzymatically digested by methods known in the art to produce polypeptide fragments which can be sequenced. The sequencing can be performed, for example, by the methods of Wilm et al. (*Nature* 379(6564):466–469 (1996)). The protein maybe isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice*, 2nd Edition, Springer-Verlag, New York (1987); and Deutscher (ed), *Guide to Protein Purification, Methods in Enzymology*, Vol. 182 (1990).

The following Examples are offered for the purpose of illustrating the present invention and are not to be construed to limit the scope of this invention. The teachings of all references cited are hereby incorporated herein by reference in their entirety.

EXAMPLE 1

Isolation, Purification and Characterization of Bacteriophage

A. Materials and Methods

Bacterial Strains and Growth Media

The thermophilic, slightly halophilic eubacterium, *Rhodothermus marinus* was first isolated from shallow water submarine hot springs in Isafjardardjup in northwest Iceland (Alfredsson, G. A. et al., *J. Gen. Microbiol.* 134:299–306 (1988)). Since then *Rhodothermus* has also been isolated from two other areas in Iceland (Petursdottir et al., in prep.), from the Azores and the Bay of Naples in Italy (Nunes, O. C. et al, *Syst. Appl. Microbiol.* 15:92–97 (1992); Moreira, L. et al., *Syst. Appl. Microbiol.* 19:83–90 (1996)). Rhodothermus is distantly related to the group containing *Flexibacter, Bacterioides* and *Cytophaga* species (Anderson, O. S. and Fridjonsson, O. H., *J. Bacteriol.* 176:6165–6169 (1994)).

Strain ITI 378 (originally R-21) is one of the first *Rhodothermus* strains isolated from submarine hot springs in Isafjardardjup in northwest Iceland. The strain was grown at 65° C. in medium 162 for *Thermus* (Degryse et al., *Arch. Microbiol.* 117:189–196 (1978)), with $\frac{1}{10}$ the buffer and with 1% NaCl. Strain ITI 378 is phenotypically and phylogenetically similar (over 99% similarity in 16s rRNA sequence) to type strain DSM 4252.

Bacteriophage Isolation

A water sample with some sand and mud was collected from a hot spring (62° C.) appearing at low tide in Isafjardardjup at the same site as the bacterium was originally isolated. The same kind of samples were collected from the Blue Lagoon and the Salt factory on Reykjanes in southwest Iceland.

After mixing a sample in a Waring blender, the sample was filtered through a Buchner funnel, followed by centrifugation, before filtering the water through a 0.45 $\mu$m membrane. After centrifuging again, the sample was filtered through a sterile 0.2 $\mu$m membrane. This filtrate was used for infecting 18 different *Rhodothermus* strains (8 from Isafjardardjup in northwest Iceland, and 10 from Reykjanes in southwest Iceland). The sample (4 ml) was mixed with 5 ml of soft agar A (the above growth medium with 2% agar) and 1 ml of overnight culture of different *Rhodothermus* strains. After pouring the sample onto a thin layer agar plate, the plates were incubated for 1–2 days at 65° C. A single, well-isolated plaque was stabbed with a sterile Pasteur pipette and dissolved in 100 $\mu$l of 10 mM $MgCl_2$ solution (forming the plaque solution).

The bacteriophage is sensitive to freezing; it can be stored in a cell lysate at 4° C. (e.g., as described below under "Liquid Lysate").

Plate Lysate

Overnight culture (0.9 ml) was mixed with 100 µl of the plaque solution and incubated for 15 minutes at 65° C. before adding 3 ml of soft agar B (same as A, but 1% agar and 10 mM $MgCl_2$). After mixing and pouring onto thin layer agar plates, the plates were incubated for 1–2 days at 65° C. To nearly totally lysed plates was added 1 ml of 10 mM $MgCl_2$, and after incubating at 4° C. for a few hours, the top layer was scraped off and put into a sterile tube. After adding 100 µl chloroform and mixing it, the sample was centrifuged and the supernatant collected. The sample was centrifuged again and filtered through a 0.2 µm filter; the filtrate was stored at 4° C. This lysate was used for testing host specificity.

Liquid Lysate

Liquid cultures were infected when they had reached an absorbance of 0.5 at 600 nm (expected to contain $2.5 \times 10^8$ cells/ml). The phage ratio was 0.1 pfu/cell culture. The cultures were incubated at high shaking (300 rpm) and growth was followed by measuring absorbance at 600 nm. When lysis had occurred, chloroform was added to the cultures (10 µl/ml) and shaking continued for 1 hour. Cell debris was removed by centrifugation and titer estimation was performed on the supernatant. large-scale purification from 300 ml culture was undertaken for DNA isolation and for protein composition analysis, as well as for electron microcopy.

Bacteriophage Purification

For electron microscopy, the bacteriophages were precipitated using PEG 8000 (Sambrook, J. et al., Molecular Cloning, Cold Spring Harbor Laboratory Press, Cold Spring Harbor, N.Y., 1989) and resuspended in SM buffer (Sambrook, J. et al., Molecular Cloning, Cold Spring Harbor Laboratory Press, Cold Spring Harbor, N.Y., 1989) before loading on the top of CsCl (0.75 g/ml). This sample was centrifuged for 23 hours at 38,000 rpm in TY-64 rotor (Sorvall Ultracentrifuge). The layer of bacteriophage was collected using a syringe.

Protein Determination and DNA Isolation

Purified bacteriophage supernatant with a titer of approximately $10^{13}$ pfu/ml was boiled for 5 minutes in SDS and β-mercaptoethanol loading puffer according to the method of Laemmli (Laemmli, U. K., *Nature* 227:680–685 (1970)) using 10% polyacrylamide gel, and stained with Coomassie brilliant blue. Bio-Rad pre-stained low molecular weight standards (7.7–204 kDa) were used as size markers. Bacteriophage DNA was isolated from a purified phage lysate containing approximately $10^{13}$ pfu/ml using the Qiagen lambda kit (Catolog No. 12543, Qiagen) according to manufacturer's instructions.

Temperature and Chloroform Sensitivity

Bacteriophage RM 378 at approximately $10^{11}$ pfu/ml was incubated for 30 minutes over a temperature range of 50–96° C. before the remaining bacteriophage titer was determined. The bacteriophage lysate at approximately $10^{11}$ pfu/ml was mixed with an equal volume of chloroform, and incubated at room temperature. After 30 minutes, the remaining viable bacteriophage were titrated with strain ITI 378 as a host.

Determination of G+C Content

The mole percent guanine plus cytosine content of the bacteriophage was determined by CSM with HPLC according to Mesbah (Mesbah, M. U. et al., *Int. J. Syst. Bacteriol.* 39:159–167 (1989)).

Estimation of Genome Size

Bacteriophage DNA was digested individually with a variety of restriction endonucleases, and the fragments separated by electrophoresis on 0.5–0.8% (w/v) agarose gel. Pulsed-field gel electrophoresis (PFGE) was also used for size estimation. Pulsed Field Certified Agarose from BioRad (Catalog No. 162-0137, Bio Rad) (1%) was used for the gel, and low-melt agarose (Catalog No. 162-0017, Bio Rad) (1%) for filling the wells when using marker plugs. Samples of 1.0 and 0.5 µg DNA were used and Bio Rad low range marker (#350) as well as λ-ladder (Catalog No. 170-3635, Bio Rad) was employed. The running buffer was 0.5×TBE (Sambrook, J. et al., Molecular Cloning, Cold Spring Harbor Laboratory Press, Cold Spring Harbor, N.Y., 1989). Bio Rad Pulsed Field Electrophoresis system (CHEF-DRIII) was used with an initial switch time of 60 seconds, final switch time of 60 seconds, 6 V/cm angle of 120° and 21 hour run time. Gels were stained with ethidium bromide and washed in distilled water for 3 hours before photographing under a UV light illuminator.

Electron Microscopy

The bacteriophage was stained with 2.5% phosphotungstic acid and the grids examined with a Philips EM 300 electron microscope. Bacteriophage samples from CsCl purification, as well as directly from a liquid lysed culture with titer of $10^{13}$ pfu/ml, were used for microscopy studies.

DNA Sequencing and Genome Analysis

The phage genome was sequenced using the "shot gun sequencing" technique (see, e.g., Fleischmann, R. D. et al., *Science* 269:496–512 (1995)). The sequences were aligned (Ewing, B., et al., *Genome Research* 8:175–185 (1998)); Ewing, B. and Green, P., *Genome Research* 8:186–194 (1998)). The consensus sequence of 130,480 bp was visualized with the program XBB-Tools (Sicheritz-Ponten, T., Department of Molecular Evolution, Uppsala, Sweden) for open reading frames (ORFs).

B. Results

Bacteriophage Isolation

The phage sample from the southwest area of Iceland, prepared as described above, infected 4 strains of *Rhodothermus*, all from Reykjanes in southwest Iceland. The phage sample from the northwest area of Iceland, prepared as described above, infected 7 strains of *Rhodothermus*, all from Isafjardardjup in northwest Iceland. Bacteriophages were isolated from two of the strains infected with the sample from the southwest, and from all 7 of the strains infected with the sample from the northwest. Of these, one of the bacteriophages from the sample from the northwest was isolated from strain ITI 378 and designated RM 378. The titer of this bacteriophage was estimated; in liquid culture it repeatedly gave titers of $5-8 \times 10^{13}$ pfu/ml.

Attempts to isolate the bacteriophages from *Rhodothermus* by subjecting it to stress such as ultraviolet (UV) exposure did not succeed. Because such stress would have excised a prophage from the chromosome and have initiated a lytic response, the failed attempts suggest that *Rhodothermus* did not contain prophages.

Bacteriophage Morphology

Bacteriophage RM 378 is a tailed phage with a moderately elongated head. It is a T4-like phage, resembling the T4 phage of *Escherichia coli* both in morphology and genome size, and has a double-stranded DNA genome. RM 378 belongs to the *Myoviridae* family and has the A2 morphology (Ackermann, H. W., *Arch. Virol.* 124:201–209 (1992)). The bacteriophage head measures 85 nm on one side and 95 nm on the other. The tail is 150 nm in length, with a clear right-handed spiral to the tail sheath. The head/tail ratio is 0.63 and the total length is 245 nm.

Host Specificity and Infection

RM 378 concentrated bacteriophage was tested against 9 different *Rhodothermus* strains from the two different areas (Isafjardardjup in northwest Iceland, and Reykjanes in southwest Iceland). It infected 5 strains from the northwest, but no strains from the southwest. Thus, the bacteriophage infected only strains of *Rhodothermus* from the same geographical area from which the bacteriophage was isolated. It did not infect any of the 6 *Thermus* strains that were tested.

Growth of bacteria was followed at 65° C. in a liquid. Uninfected culture was used as control, and growth was followed until the control culture had reached stationary phase. Cell lysis started 9 hours after infection of the culture, and stationary phase in the control was reached about 14 hours after infection.

Stability of the Bacteriophage

Bacteriophage RM 378 was stable to 30 minutes exposure to chloroform, indicating that it probably does not contain lipids. Heat stability of the phage was tested at 50° C.–96° C. by incubating the phage concentrate for 30 minutes, followed by estimation of titer. There was no change of the titer up to 65° C., but at 70° C. and 80° C. a 100-fold drop in pfu/ml was measured. Linear decrease of the titer was observed up to 96° C., where it was 10,000 times lower after 30 minutes than in the starting solution. After 3 months of storage at 4° C. the titer dropped 100-fold (down to $10^{11}$ pfu/ml). After 27 months of storage the titer had fallen from $10^{11}$ pfu/ml to $10^5$ pfu/ml in a CsCl-purified sample.

Composition of Bacteriophage RM 378

Purified bacteriophage was subjected to SDS-PAGE analysis for examination of its protein composition. The phage was composed of at least 16 proteins with apparent molecular weights from 23–150 kDa. The five main bands were at 92, 61, 52, 50 and 26 kDa, and were in a ratio of 0.14:0.45:0.21:0.13:0.06. The major protein band of 61 kDa accounted for about 20% of the total protein; the five main bands together represented about 50% of total proteins.

The average G+C mol % of the RM 378 phage was 42.0±0.1. The DNA was digested with a variety of restriction enzymes (HindIII, XhoI, ClaI, AluI, NotI, SacI, PstI, BamHI, SmaI, SpeI, EcoRV). Three of the enzymes (NotI, SmaI, SpeI) did not cleave RM 378, and the rest resulted in multiple fragments. Because the addition of the fragment sizes resulted in a variable amount for the total genome size, the phage DNA was also run on PFGE, which estimated the size of the DNA to be about 150 kb.

Characteristics of the Bacteriophage

The RM 378 bacteriophage is a virulent bacteriophage following a lytic cycle of infection. Very high titer lysates of up to $10^{13}$ pfu/ml could be obtained, which indicated a large burst size of more than 100. Because no bacteriophages have been reported against this bacterial genus, RM 378 represents a new species.

Genome Analysis and Comparison to T4 Bacteriophage

The nucleic acid sequence of RM 378 is set forth in FIG. 1. The nucleic acid sequence of RM 378 contains at least 200 open reading frames (ORFs); see, for example, the ORFs described in FIG. 2. Of these, five were identified in more detail, as described in Example 2, including the ORFs expected to encode DNA polymerase, 3'–5' exonuclease, 5'–3' exonuclease, RNA ligase and DNA helicase.

RM 378 belongs in the T-even family, in that it is similar to bacteriophage T4 of *Escherichia coli*. Bacteriophage T4 of *E. coli* is a well-studied phage which, together with T2 and T6, belongs to the family of bacteriophages known as T-even phages. T-even phages are nearly identical not only in structure and composition, but also in properties. Several enzymes isolated from bacteriophage T4 are used in the field of recombinant DNA technology as well as in other commercial applications. For example, T4 DNA polymerase, T4 DNA ligase and T4 RNA ligase are frequently used in the research industry today.

The genome of RM 378 was aligned in a consensus sequence, and the open reading frames (ORFs) were analyzed and compared to the T4 bacteriophage genome. The overall genome arrangement seemed to be different and the overall similarity to known proteins was low. However, despite this apparently high genetic divergence, several structural and morphological features were highly conserved. Furthermore, homologs to proteins in T4 were identified in the RM 378 bacteriophage. These similarities are set forth in Table 1, below.

In view of the similarities between bacteriophage T4 and bacteriophage RM 378, it is reasonable to expect that bacteriophage RM 378 comprises genes that are homologous to those found in bacteriophage T4, and that these genes in bacteriophage RM 378 encode proteins and enzymes that correlate to those proteins and enzymes found in bacteriophage T4.

EXAMPLE 2

Detailed Analysis of Five Open Reading Frames (ORFs)

A. Selection of Reading Frames for Analysis

Five open reading frames (ORFs) of the numerous ORFs described above in the genome of bacteriophage RM378, have been further characterized and the corresponding genes cloned and expressed. The genes include a DNA polymerase, 3'–5' exonuclease, 5'–3'-exonuclease (RNase H), replicative DNA helicase and RNA ligase. These genes were chosen as examples of the many valuable genes encoded by the bacteriophage genome. The corresponding polypeptide products of these genes are mainly components of the bacteriophage replication machinery and can be utilized in various molecular biology applications as evident by the current use of homologous counterparts from other sources. The sequences of the five ORFs show low similarity to sequences in public databases indicative of distant relationship to known proteins; however, probable homology to known sequences can be established by comparison with families of sequences showing overall sequence similarity as well as conservation of shorter regions, sequence motifs and functionally important residues, in some cases aided by three-dimensional structural information. The limited sequence similarity or these sequences to publicly available sequences suggests that these gene products have functional properties very different from corresponding proteins currently in use in molecular biology applications. Together with the presumed thermostability, the properties of these gene products render them valuable in various applications in molecular biology.

DNA Polymerase

DNA polymerases have evolved to accommodate the varied tasks required for replication and repair. DNA replication involves 1) local melting of the DNA duplex at an origin of the replication, 2) synthesis of a primer and Okazaki fragment, 3) DNA melting and unwinding at the replication fork, 4) extension of the primer on the leading strand and discontinuous synthesis of primers followed by extension of the lagging strand, 5) removal of RNA primers and 6) sealing of nicks. (Perler et al., *Adv Protein Chem* 48:377–435 (1996)).

The different types of DNA polymerases have been grouped into Families A, B, C and X corresponding to similarity with *E. coli* pol I, II and III and pol b respectively (Braithwaite, D. K. and Ito, J., *Nucleic Acids Res.* 21:787–802 (1993)). Each of these Families contains conserved sequence regions (Perler et al., *Adv Protein Chem.* 48:377–435 (1996); Blanco L., et al., *Gene* 100:27–38 (1991); Morrison A. et al., *Proc Natl Acad Sci USA.* 88:9473–9477 (1991)). Family B DNA polymerasese are also called Pol α Family DNA polymerases.

The DNA polymerases of family B type include bacteriophage T4 and bacteriophage RB69 DNA polymerase as well as archaeal polymerases and *E. coli* polymerase II. Polymerases of this type normally have two activities, the polymerase activity and the proofreading 3'–5' exonuclease activity, found in different domains within the same polypeptide with the exonuclease domain being N-terminal to the polymerase domain (Steitz, T. A., *J Biol Chem* 274:17395–8 (1999); Kornberg, A. and Baker, T. A., DNA Replication, Freeman, N.Y. (1992); Brautigam, C. A. and Steitz, T. A., *Curr.Opin.Struct.Biol.* 8:45–63 (1998) ). Polymerases of family B have an overall domain architecture different from polymerases of family A and do not have a 5'–3' exonuclease activity which is normally found in polymerases in family A. The determined structure of RB69 DNA polymerase is a representative structure of family B type polymerase and shows clearly the modular organization of the enzyme with separate domains (Wang, J. et al., *Cell* 89:1087–99 (1997), Protein data bank (PDB) accession code 1WAJ). The structure of the archaeal DNA polymerase from *Desulfurococcus* strain Tok was shown to have the same overall structure (Zhao, Y. et al., *Structure Fold Des* 7:1189–99 (1999), PDB accession code 1QQC). The alignment of polymerases in this family indicates the presence of several conserved region in the sequences with characteristic sequence motifs both belonging to both the exonuclease domain and the polymerase domain (Hopfner, K. P. et al., *Proc Natl Acad Sci USA* 96:3600–3605 (1999)).

Exonucleases

Besides the basic polymerization function, DNA polymerases may contain 5'–3' and a 3'–5' exonuclease activity. The 3'–5' exonuclease activity is required for proofreading. In general the family B polymerases have 3'–5' exonuclease activity, but not 5'–3' exonuclease activity. If both exonucleases are present, the 5'–3' exonuclease domain is at the N-terminal followed by the 3'–5' exonuclease domain and the C-terminal polymerase domain. The structure of the polymerases can be defined further in terms of domain structure. The polymerase domain is thus composed of a number of smaller domains, often referred to as the palm, fingers and thumb, and although these parts are not homologous across families, they do show analogous structural features (Steitz, T. A., *J Biol Chem* 274:17395–8 (1999); Kornberg, A. & Baker, T. A., DNA Replication, Freeman, N.Y. (1992); Brautigam, C. A. & Steitz, T. A., *Curr.Opin.Struct.Biol.* 8:45–63 (1998)).

RNase H (Ribonuclease H), e.g. from bacteriophage T4, removes the RNA primers that initiate lagging strand fragments, during DNA replication of duplex DNA. The enzyme has a 5'–3' exonuclease activity on double-stranded DNA and RNA-DNA duplexes. Further, T4 RNase H has a flap endonuclease activity that cuts preferentially on either side of the junction between single and double-stranded DNA in flap and fork DNA structures. Besides replication, T4 RNase H also plays a role in DNA repair and recombination. (Bhagwat, M., et al., *J. Biol. Chem.* 272:28531–28538 (1997); Bhagwat, M., et al. *J. Biol. Chem.* 272:28523–28530 (1997)).

T4 RNase H shows sequence similarity to other enzymes with a demonstrated role in removing RNA primers, including phage T7 gene 6 exonuclease, the 5'–3' nuclease domain of *E. coli* DNA polymerase I, and human FEN-1 (flap endonuclease). These enzymes have 5'–3'-exonuclease activity on both RNA-DNA and DNA-DNA duplexes and most of them have a flap endonuclease activity that removes the 5-ssDNA tail of flap or fork structures. The T4 enzyme homologous to members of the RAD2 family of prokaryotic and eukaryotic replication and repair nucleases (Mueser T. C., et al., *Cell.* 85:1101–1112 (1996)).

RNase H is a part of the reverse transcriptase complex of various retroviruses. The HIV-1 RT associated ribonuclease H displays both endonuclease and 3'–5' exonuclease activity (Ben-Artzi, H., et al., *Nucleic Acids Res.* 20:5115–5118 (1992); Schatz, O., et al., *EMBO J.* 4:1171–1176 (1990)).

In molecular biology, RNase H is applied to the replacement synthesis of the second strand of cDNA. The enzyme produces nicks and gaps in the mRNA strand of the cDNA:mRNA hybrid, creating a series of RNA primers that are used by the corresponding DNA polymerase during the synthesis of the second strand of cDNA (Sambrook, J., et al., Molecular cloning: a laboratory manual, 2nd ed. Cold Spring Harbour Laboratory Press (1989)). The RNase H of *E. coli* can promote the formation and cleavage of RNA-DNA hybrid between an RNA site and a base paired strand of a stable hairpin or duplex DNA at temperature below their Tm (Li. J., and R. M. Wartell, *Biochemistry* 37:5154–5161 (1998); Shibahara, S., et al., *Nucleic Acids Res.* 15:4403–4415 (1987)). Thus, the enzyme has been used for site-directed cleavage of RNA using chimeric DNA splints (presence of complementary chimeric oligonucleotides) (Inoue, H., et al., *Nucleic Acids Symp Ser.* 19:135–138 (1988)) or oligoribonucleotide capable of forming a stem and loop structure (Hosaka H., et al., *J. Biol. Chem.* 269: 20090–20094 (1994)).

DNA Helicase

DNA helicases use energy derived from hydrolysis of nucleoside triphosphate to catalyze the disruption of the hydrogen bonds that hold the two strands of double-stranded DNA together. The reaction results in the formation of the single-stranded DNA required as a template or reaction intermediate in DNA replication, repair or recombination (Matson, S. W., et al., *BioEssays.* 16:13–21 (1993)).

The bacteriophage T4 Gp41 is a highly processive replicative helicase (similar to the DNA B protein of *E. coli*) and has been shown to form hexamer in the presence of ATP (Dong, F., and P. H. von Hippel, *J. Biol. Chem.* 271:19625–19631 (1996)). The enzyme facilitates the unwinding of DNA helix ahead of the advancing DNA polymerase and accelerates the movement of the replication fork. It has been suggested that gp41 interacts with the polymerase holoenzyme at the replication fork (Schrock R. D. and B. Alberts, *J. Biol. Chem.* 271:16678–16682 (1996)). Gp41 has a 5'–3' polarity and requires a single stranded region on the 5' side of the duplex to be unwound. The ATP-activated helicase binds to a single gp61 primase molecule on appropriate DNA template (Morris, P. D., and K. D. Raney, *Biochemistry.* 38:5164–5171 (1999)) to reconstitute a stable primosome (Richardson, R. W. and N. G. Nossal, *J. Biol. Chem.* 264:4725–4731 (1989)). Although the gp41 alone does not form a stable complex with DNA template, this helicase by itself can carry out moderately processive ATP-driven translocation along single strand DNA (Dong, F., and P. H. von Hippel. *J. Biol. Chem.* 271:19625–19631 (1996)). The T4 gene 59 protein accelerates the loading of gp41 onto DNA, when it is covered with 32 protein (the T4 single strand binding protein), and stimulates the helicase activity to catalyze replication fork movement through a DNA double helix, even through a promoter-bound RNA polymerase molecule (Barry, J., and B. Alberts. *J. Biol. Chem.* 269:33063–33068 (1994); Tarumi, K., and T. Yonesaki, *J Biol Chem.* 270:2614–2619 (1995)). The T4 gp41 helicase has also been disclosed to participate in DNA recombination. Following exonuclease nicking of ds DNA and further expansion into a gap, gp41 creates a free 3' end, which is required as a substrate by recombination proteins (RecA like) (Tarumi, K., and T. Yonesaki. *J Biol Chem.* 270:2614–2619 (1995)).

RNA Ligase

RNA ligase is abundant in T4-infected cells and has been purified in high yields. Bacteriophage T4 RNA ligase catalyzes the ATP-dependent ligation of a 5'-phosphoryl-terminated nucleic acid donor (i.e. RNA or DNA) to a 3'-hydroxyl-terminated nucleic acid acceptor. The reaction can be either intramolecular or intermolecular, i.e., the enzyme catalyzes the formation of circular DNA/RNA, linear DNA/RNA dimers, and RNA-DNA or DNA-RNA block co-polymers. The use of a 5'-phosphate, 3'-hydroxyl terminated acceptor and a 5'-phosphate, 3'-phosphate terminated donor limits the reaction to a unique product. Thus, the enzyme can be an important tool in the synthesis of DNA of defined sequence (Marie I., et al., *Biochemistry* 19:635–642 (1980), Sugion, A. et al., *J. Biol. Chem.* 252:1732–1738 (1977)).

The practical use of T4 RNA ligase has been demonstrated in many ways. Various ligation-anchored PCR amplification methods have been developed, where an anchor of defined sequence is directly ligated to single strand DNA (following primer extension, e.g. first strand cDNA). The PCR resultant product is amplified by using primers specific for both the DNA of interest and the anchor (Apte, A. N., and P. D. Siebert, *BioTechniques*. 15:890–893 (1993); Troutt, A. B., et al., *Proc. Natl. Acad. Sci. USA*. 89: 9823–9825 (1992); Zhang, X. H., and V. L. Chiang, *Nucleic Acids Res.* 24:990–991(1996)). Furthermore, T4 RNA ligase has been used in fluorescence-, isotope- or biotin-labeling of the 5'-end of single stranded DNA/RNA molecules (Kinoshita Y., et al., *Nucleic Acid Res.* 25: 3747–3748 (1997)), synthesis of circular hammer head ribozymes (Wang, L., and D. E. Ruffner. *Nucleic Acids Res* 26: 2502–2504 (1998)), synthesis of dinucleoside polyphosphates (Atencia, E. A., et al. *Eur. J. Biochem.* 261: 802–811 (1999)), and for the production of composite primers (Kaluz, S., et al., *BioTechniques*. 19: 182–186 (1995)).

B. DNA Polymerase Activity and 3'–5' Exonuclease Activity are Found in Gene Products of Separate Genes in the Phage RM378 Genome The predicted gene products of two open reading frames (ORF056e and ORF632e), which are widely separated in the genome of phage RM378, both showed similarity to family B type polymerases as shown below.

Identification of the ORF056e Gene Product as 3'–5' Exonuclease

The predicted gene product of ORF056e (locus GP43a) was run against a sequence database (NCBI nr) in a similarity search using BLAST (Altschul, S. F. et al., *J. Mol. Biol.* 215:403–410 (1990)) (Table 2). Out of 64 hits with E value lower (better) than 1, all sequences were of DNA polymerases of family B type including DNA polymerase from bacteriophage RB69, archaeal DNA polymerases and *E. coli* polymerase II. Importantly, all these sequences are DNA polymerase sequences having the sequence characteristics of the DNA polymerase domain as well as the 3'–5' exonuclease domain and are considerably longer (excluding partial sequences) than the predicted gene product of ORF056e which has a length of 349 residues. The similarity is restricted to the N-terminal halves of these sequences corresponding to the part of the protein where the 3'–5' proofreading exonuclease domain is located.

Table 2 lists the 20 sequences with strongest similarity to the ORF056e sequence together with the length and E-value according to BLAST search. The sequence identity with the ORF056e sequence ranges from 21 to 27%. Of the 64 sequences identified in the sequence database, 34 are of viral origin and 15 of archaeal origin. Out of the twenty top scoring sequences, 16 are of viral origin.

Identification of the ORF632e Gene Product as DNA Polymerase

The sequence similarity program BLAST (Altschul, S. F. et al., *J. Mol. Biol.* 215:403–410 (1990)) was also used to identify potential homologues of the ORF632e (locus GP43b) gene product. The 100 sequences in the sequence database (NCBI nr) with the strongest similarity to the ORF632e sequence were all defined as DNA polymerase sequences. These sequences all had an E value lower than 10–5 and are considerably longer (excluding partial sequences) than the predicted gene product of ORF632e which has a length of 522 residues (Table 3). Sequence alignments between the ORF632e sequence and the sequences identified in the database shows that the similarity is restricted to a domain with the DNA polymerase activity as characterized by conserved sequence motifs such as DxxSLYPS (Hopfner, K. P. et al., *Proc Natl Acad Sci USA* 96:3600–3605 (1999)). In these sequences this domain is always preceded by a long N-terminal region where the 3'–5' exonuclease activity normally is found. The corresponding N-terminal region is lacking in ORF362e which consists only of the DNA polymerase domain (family B type polymerases). The sequence motif DXXSLYPS (SEQ ID NO:63) in the ORF632e sequence is found very close to its N-terminus unlike its location in all the 100 analyzed sequences in the public database.

Table 3 lists the 20 sequences with strongest similarity to the ORF632e sequence together with the length and E-value according to a BLAST search. The sequence identity with the ORF632e sequence rages from 23 to 28% within aligned regions of 300 to 428 residues. The majority of these 20 sequences are of archaeal DNA polymerases of family B type.

The results of the similarity searches indicated that gene products of ORF056e and ORF632e correspond to the exonuclease domain and the polymerase domain of family B type polymerases, respectively. Partial alignment of sequences of a number of members of this family was obtained from the Protein Families Data Bases of Alignments and HMMs (Sanger Institute), accession number PF00136). The sequences of ORF056e and ORF632e could be combined as one continuous polypeptide and aligned to the previous set of sequences. The coordinates of the three-dimensional structures of DNA polymerases from bacteriophage RB69 (PDB ID 1WAJ), the archaea *Thermococcus gorgonarius* (PDB ID 1TGO) and the archaea *Desulfurococcus* strain Tok (PDB ID 1QQc) were structurally aligned and the sequence alignment produced from the structural alignment. The corresponding sequences were added to the previous alignment and the alignment adjusted, guided by the alignment from the structural superposition, mainly in regions which are less conserved. The resulting alignment, shown in FIG. 3, strongly supports the previous interpretation that 3'–5' proofreading activity and DNA polymerase activity are found in two proteins encoded by separate genes in bacteriophage RM378. As seen in the alignment (FIG. 3), the major conserved regions in this protein family in the 5'–3' exonuclease domain and in the polymerase domain are also conserved in the gene products of ORF056e and ORF632e, respectively. As defined by Hopfner et al. (Hopfner, K. P. et al., *Proc Natl Acad Sci USA* 96:3600–3605 (1999)), this includes regions exo I, -II and -III in the exonuclease domain and motifs A, -B and -C in the polymerase protein. Motif A corresponds to the DxxSLYPS motif mentioned above and includes an aspartic acid residue, involved in coordinating one of the two Mg2+ ions which are essential for the polymerase activity, and a tyrosine residue which stacks it side chain against an incoming nucleotide in the polymerase reaction. Another aspartic residue which also acts as Mg2+ ion ligand (motif C), and is essential for the catalytic mechanism, is also found in the sequence of ORF632e (D215). Inspection of the three-dimensional structure of bacteriophage RM69 DNA polymerase (PDB ID 1WAJ), with respect to the alignment, shows that the end of the ORF056e sequence and the beginning of the ORF632e sequence are found between the 3'–5' exonuclease domain and the DNA polymerase domain.

The polymerase activity encoded by bacteriophage RM378 thus resides in an enzyme which is relatively short corresponding only to the polymerase domain of other members in this family and unlike those relatives does not have an 3'–5' exonuclease domain. The 3'–5' exonuclease is found as another protein encoded by a separate gene elsewhere in the genome. The natural form of DNA polymerase from *Thermus aquaticus* (Taq) also lacks the proofreading 3'–5' exonuclease activity but this polymerase differs from the polymerase of RM378 in several aspects: i) it belong to a different family of polymerase (family A) which have a different general architecture, ii) the lack of 3'–5' exonuclease activity is due to a non-functional domain since it still contains a structural domain homologous to a domain where this activity resides in other polymerase in this family, and iii) naturally occurring Taq has 5'–3' exonuclease activity besides its polymerase activity (Kim, Y. et al., *Nature* 376:612–616 (1995)). Thus, the current protein is the only known example of a DNA polymerase which by nature lacks proofreading activity and the corresponding structural domain present in other polymerases of this type, and therefore represents the discovery of a unique compact type of DNA polymerase found in nature lacking both 3'–5' and 5'–3' exonuclease activity.

C. ORF739f Encodes an RNA Ligase

Several sequences of RNA ligases in a protein sequence database showed similarity to the ORF739f sequence (locus GP63) as identified in a similarity search using BLAST (Altschul, S. F. et al., *J. Mol Biol*. 215:403–410 (1990)). The top scoring sequences found in the BLAST search are show in Table 4. Only 3 sequences showed a score with E-avlue below 1.0. The two most significant and extensive similarities were found to the sequences of RNA ligases from *Autographa californica* nucleopolyhedrovirus and bacteriophage T4. The similarity to the third sequence, that of a DNA helicase, is much less extensive and has considerable higher E-value. The sequence identity between the ORF739f sequence and the two RNA ligase sequences is 23% over regions of 314 and 381 residues. A sequence alignment of these three sequences is shown in FIG. 4.

The site of covalent reaction with ATP (adenylation) has been located at residue K99 in bacteriophage T4 RNA ligase (Thogersen H C, et al., *Eur J Biochem* 147:325–9 (1985); Heaphy, S., Singh, M. and Gait, M. J., *Biochemistry* 26:1688–96 (1999)). A corresponding Lysine residue (K126) is also found in the sequence of ORF739f. An aspartic residue close to the adenylation site in T4 RNA ligase has also been implied as important for the catalytic mechanism (Heaphy, S., Singh, M. and Gait, M. J., *Biochemistry* 26:1688–96 (1999)). This residue is also conserved in ORF739f (D128). It has been suggested that the motif KX(D/N)G may be a signature element for covalent catalysis in nucleotidyl transfer (Cong, P., and Shuman, S., *J Biol Chem* 268:7256–60 (1993)). The conservation of these active site residues supports the interpretation of ORF739f gene product as RNA ligase having catalytic mechanism in common with other RNA ligases and involving covalent reaction with ATP.

Table 4 shows sequences with strongest similarity (E-value cutoff of 1.0) to the ORF739f sequence together with their length and E-value according to BLAST search.

D. Orf 1218a Encodes a Gene Product with 5'–3' Exonuclease Activity

A BLAST search (Altschul, S. F. et al., *J. Mol. Biol.* 215:403–410 (1990)) identified about 60 sequences in the database (NCBI nr) with significant similarity (corresponding to E-value lower than 1) to the sequence of the predicted gene product of ORF 1218a (locus DAS). Almost all the identified sequences are of DNA polymerase I from bacterial species (DNA polymerase family A) and the similarity is restricted to the N-terminal halves of these sequences and the ORF 1218a sequence is much shorter, 318 residues, compared to the identified sequences which usually are between 800 and 900 residues (Table 5).

Structural and functional studies of DNA polymerases of this type (family A) have defined the different structural domains and how these correlate with the different activities of the enzyme. Polymerases of this type normally have a polymerase activity located in a C-terminal domain and two exonuclease activities, a 3'–5' exonuclease proofreading activity in a central domain and a 5'–3 exonuclease activity in an N-terminal domain (Kornberg, A. and Baker, T. A., DNA Replication, Freeman, N.Y. (1992); Brautigam, C. A. and Steitz, T. A., *Curr. Opin. Struct. Biol.* 8:45–63 (1998)). The sequence of ORF 1218a corresponds to the 5'–3' exonuclease domain of these polymerases.

The 5'–3' exonuclease domain of DNA polymerase I belongs to a large family of proteins which also include ribonuclease H (RNase H) including bacteriophage T4 RNase H. The analysis of the structure of bacteriophage T4 RNase H revealed the conservation of a several acidic residues in this family of proteins. These residues are clustered at the active site, some of which help coordinate two functionally important Mg2+ ions (Mueser, T. C.,et al., *Cell* 85:1101–12 (1996)). The corresponding alignment shown in FIG. 5, including the sequence of the ORF 1218a gene product, shows that these acidic residues (possibly with the exception of one) are also found in the gene product of ORF1218a thus further supporting its proposed activity as 5'–3' exonuclease.

The 5'–3' exonuclease of polymerase I and RNase H both remove RNA primers that have been formed during replication but T4 DNA polymerases and other polymerases of the same type (family B), including the identified polymerase of phage RM378 identified here (see above), lack the 5'–3' exonuclease activity. T4 RNase H (305 residues) and the ORF1218a gene product (318 residues) are of similar size with conserved regions scattered throughout most of the sequences (FIG. 5). These proteins are likely to have a very similar structure given the structural similarity between T4 RNase H and 5'–3' exonuclease domain of polymerase I (Mueser, T. C., et al., *Cell* 85:1101–12 (1996)). The gene product of ORF1218a probably has a function analogous to the function of RNase H in bacteriophage T4.

Table 5 sets forth the 21 sequences with strongest similarity to the ORF1218a sequence together with the length and E-value according to BLAST search. The sequence identity with the ORF1218a sequence ranges from 31 to 41% within aligned regions of 82 to 145 residues.

E. A Replicative DNA Helicase is Part of the Replication Machinery of Phage RM378

Several sequences of replicative DNA helicases were identified in a similarity search using BLAST (Altschul, S. F., et al., *J. Mol. Biol.* 215:403–410 (1990)) with the ORF1293b (locus GP41) sequence as query sequence. 15 sequences had an E-value lower than 1.0 with the sequence of bacteriophage T4 replicative DNA helicase (product of gene 41, accession number P04530) having by far the lowest E-value. Some of the sequences found in the similarity search are hypothetical proteins and some are defined as RAD4 repair protein homologues. However, the most extensive similarity was found with the replicative helicase sequences, with sequence identity of 20–23% spanning 210–295 residues, and these sequences are all of length similar to the length of the ORF1293b gene product (416 residues). Table 6 shows the identified sequences of the similarity search.

The replicative DNA helicases with similarity to the ORF1293b sequence are of the same protein family often named after the corresponding helicase in *E. coli* encoded by the DnaB gene (e.g. DnaB-like helicases). The Protein Families Data Base of Alignments and HMMs (Sanger Institute), holds 37 sequences in this family (family DnaB, accession number PF00772;) and the alignment of these sequences shows clearly several regions with conserved sequence motifs. One of this motif is characteristic for ATPases and GTPases (Walker A motif, P-loop) and forms a loop that is involved in binding the phosphates of the nucleotide (Sawaya, M. R. et al., *Cell* 99:167–77 (1999)). The replicative helicases bind single stranded DNA (at the replication fork) and translocate in the 5'–3' direction with ATP (GTP) driven translocation (Matson, S. W., et al., *BioEssays* 16:13–22 (1993)). The significant similarity found in the BLAST search to sequences other than helicase sequences is partly due to the presence of an ATP/GTP binding sequence motif in these sequences.

FIG. 6 shows the sequence alignment of some members of the DnaB protein family together with the sequence of ORF1293b. Sawaya et al. have shown how several conserved motifs and functionally important residues of the DnaB family relate to the crystal structure of the helicase domain of the T7 helicase-primase (Sawaya, M. R. et al., Cell 99:167–77 (1999)). The alignment in FIG. 6 shows how these conserved motifs are present in the ORF1293b sequence thereby supporting its role as replicative helicase.

The bacteriophage T4 replicative helicase sequence was indicated as most closely related to the ORF1293b sequence in the similarity search. The structure and function of the corresponding helicases may be very similar in these two bacteriophages and, together with the similarity of numerous other components of these phages, may be indicative of other similarities of their replication machinery. T4 replicative helicase is known to be an essential protein in the phage replication and interact with other proteins at the replication fork such as the primase to form the primosome (Nossal, N. G., *FASEB J.* 6:871–8 (1992)). Similarly, the helicase encoded by ORF1293b may have an essential function in bacteriophage RM378. Other homologues of components of the T4 replication system have been detected as well as shown above and still others may also be expected to be encoded by the bacteriophage genome.

Table 6 sets forth sequences with strongest similarity (E-value cutoff of 1.0) to the ORF1293b sequence together with the length and E-value according to BLAST search.

F. Subcloning of Selected ORFs from RM378

Plasmids were designated pSH1, pGK1, pOL6, pJB1 and pJB2, were generated for the genes encoding the 3'–5' exonuclease, the DNA polymerase, the RNA-ligase gene, the RNaseH gene and the helicase gene, respectively. The correct insertion of the ORFs into the expression vector was verified by DNA sequencing, and the expression of the genes was verified by SDS gel electrophoresis of respective host strain crude extracts.

*E. coli* strain JM109 [supE44Δ(lac-proAB), hsdR17, recA1, endA1, gyrA96, thi-1, relA1 (F'traD36, proAB, lacIqZΔM15)] (Viera and Messing, *Gene*, 19:259–268 (1982)) and strain XL10-Gold [TetrΔ (mcrA)183 Δ(mcrCB-hsdSMR-mrr)173 endA1 supE44 thi-1 recA1 gyrA96 relA1 lac Hte (F' proAB lacIqZΔM15 Tn10 (Tetr) Amy Camr)] (Stratagene) were used as hosts for expression plasmids.

Restriction enzyme digestions, plasmid preparations, and other in vitro manipulation of DNA were performed using standard protocols (Sambrook et al., Molecular Cloning 2nd Ed. Cold Spring Harbor Press, 1989).

The PCR amplification of the nucleic acids sequence containing the open reading frame (ORF) 056e, which displayed similarity to 3'–5' exonuclease domain of family B polymerase genes was as follows. The forward primer exo-f: CACGAGCTC ATG AAG ATC ACG CTA AGC GCA AGC (SEQ ID NO:64), spanning the start codon (underlined) and containing restriction enzyme site, was used with the reverse primer exo-r: ACAGGTACC TTA CTC AGG TAT TTT TTT GAA CAT (SEQ ID NO:65), containing restriction site and spanning the stop codon (underlined, reverse complement) [codon 350 of ORF 056E shown in FIG. 7]. The PCR amplification was performed with 0.5 U of Dynazyme DNA polymerase (Finnzyme), 10 ng of RM378 phage DNA, a 1 μM concentration of each synthetic primer, a 0.2 mM concentration of each deoxynucleoside triphosphate, and 1.5 mM MgCl$_2$ in the buffer recommended by the manufacturer. A total of 30 cycles were performed. Each cycle consisted of denaturing at 94° C. for 50 s, annealing at 50° C. for 40 s, and extension at 72° C. for 90 s. The PCR products were digested with Kpn I and Sac I and ligated into Kpn I and Sac I digested pTrcHis A (Invitrogen) to produce pSH1. Epicurian Coli XL10-Gold (Stratagene) were transformed with pSH1 and used for induction of protein expression, although any host strain carrying a lac repressor could be used.

The PCR amplification of the nucleic acids sequence containing ORF 632e, which exhibited similarity to DNA polymerase domain of family B polymerase genes was similar as described above for the putative 3'–5' exonuclease gene except that other PCR-primers were used. The forward primer pol-f. CACGAGCTC ATGAACATCAACAAGTATCGTTAT (SEQ ID NO:66), spanning the start codon (underlined) and containing restriction enzyme sites was used with the reverse primer pol-r: ACAGGTACCTTAGTTTTCACTCTCTACAAG (SEQ ID NO:67), containing restriction site and spanning the stop codon (underlined reverse complement) [codon 523 of ORF 632e shown in FIG. 8]. The PCR products were digested with Kpn I and Sac I and ligated into Kpn I and Sac I digested pTrcHis A (Invitrogen) to produce pGK1. Epicurian Coli XL10-Gold (Stratagene) were transformed with pGK1 and used for induction of protein expression. The expressed protein was observed with Anti-Xpress Antibody (Invitrogen) after Western Blot.

The PCR amplification of the nucleic acid sequence containing ORF 739f, (which displayed similarity to the T4

RNA ligase gene) was similar to the procedure described above for the putative 3'–5' exonuclease gene. The forward primer Rlig-f: GGG AAT TCT TAT GAA CGT AAA ATA CCC G (SEQ ID NO:68), spanning the start codon (underlined) and containing restriction enzyme sites was used with the reverse primer Rlig-r: GGA GAT CTT ATT TAA ATA ACC CCT TTT C (SEQ ID NO:69), containing restriction site and spanning the stop codon (underlined reverse complement) [codon 437 of the ORF shown in FIG. 9]. The PCR products were digested with EcoRI and BglII. Subsequently the amplified products were cloned into EcoRI and BamHI digested pBTac1 (Amann et al., *Gene* 25:167–178 (1983)) to produce pOL6. Cells of *E. coli* strain JM109 were transformed with pOL6 and used for induction of protein expression, although any host strain carrying a lac repressor could be used.

The PCR amplification of the nucleic acid sequence containing ORF 1218a, (which displayed similarity to the T4 RNaseH gene) was similar to the procedure described above for the putative 3'–5' exonuclease gene except that other PCR-primers were used. The forward primer RnH-f: GGGAATTCTT ATG AAA AGA CTG AGG AAT AT (SEQ ID NO:70), spanning the start codon (underlined) and containing restriction enzyme sites was used with the reverse primer RnH-r: GGA GAT CTC ATA GTC TCC TCT TTC TT (SEQ ID NO:71), containing restriction site and spanning the stop codon (underlined reverse complement) [codon 319 of the ORF shown in FIG. 10]. The PCR products were digested with EcoRI and BglII and ligated into EcoRI and BamHI digested pBTac1 (Amann et al. *Gene* 25:167–178. 1983) to produce pJB1. As for the RNA ligase clone, cells of *E. coli* strain JM109 were transformed with pJB1 and used for induction of protein expression.

The PCR amplification of the nucleic acid sequence containing ORF 1293b, which displayed similarity to the dnaB like helicase genes was as described above for the putative 3'–5' exonuclease gene except other PCR-primers were used. The forward primer HelI-f: GGGCAATTGTT ATG GAA ACG ATT GTA ATT TC (SEQ ID NO:72), spanning the start codon (underlined) and containing restriction enzyme sites was used with the reverse primer HelI-r: CGGGATCC TCA TTT AAC AGC AAC GTC (SEQ ID NO:73), containing restriction site and spanning the stop codon (underlined reverse complement) [codon 417 of the ORF shown in FIG. 11]. The PCR products were digested with EcoRI and BglII and ligated into EcoRI and BamHI digested pBTac1 (Amann et al. *Gene* 25:167–178 (1983)) to produce pJB2. Cells of *E. coli* strain JM109 were transformed with pJB2 and used for induction of protein expression.

Deposit of Biological Material

A deposit of *Rhodothermus marinus* strain ITI 378, and a deposit *Rhodothermus marinus* strain ITI 378 infected with bacteriophage RM 378, was made at the following depository under the terms of the Budapest Treaty:

Deutsche Sammlung Von Mikroorganismen und Zellkulturen GmbH (DSMZ)

Mascheroder Weg 1b

D-38124 Braunschweig, Germany.

The deposit of *Rhodothermus marinus* strain ITI 378 received accession number DSM 12830, with an accession date of May 28, 1999. The infected strain (*Rhodothermus marinus* strain ITI 378 infected with bacteriophage RM 378) received accession number DSM 12831, with an accession date of May 31, 1999.

During the pendency of this application, access to the deposits described herein will be afforded to the Commissioner upon request. All restrictions upon the availability to the public of the deposited material will be irrevocably removed upon granting of a patent on this application, except for the requirements specified in 37 C.F.R. 1.808(b) and 1.806. The deposits will be maintained in a public depository for a period of at least 30 years from the date of deposit or for the enforceable life of the patent or for a period of five years after the date of the most recent request for the furnishing of a sample of the biological material, whichever is longer. The deposits will be replaced if they should become nonviable or nonreplicable.

TABLE 1

Comparison of Structural Features of T4 and RM 378

| Feature | T4 | RM 378 |
|---|---|---|
| Phage type | T-even, A2 morphology | T-even, A2 morphology |
| Family | Myoviridae | Myoviridae |
| Genome size | 168,900 bases | ca 130,480 bases |
| Number of ORFs | ca 300 | >200 |
| Characteristic structural proteins | GP3, GP13, GP17, GP18, GP20, GP21, GP23 | Putative homologs of the same were identified |
| Arrangement of structural proteins | All of the above genes are on the same strand and clustered in a region covering 35 kb | All of the above genes were dispersed over the whole genome and found on both strands |
| Representative enzymes | lysozyme and thymidine kinase (on same strand) | lysozyme and thymidine kinase (on different strands) |

TABLE 2

| Source: | Accession #: | Definition: | Length: | E-value*: |
|---|---|---|---|---|
| *Spodoptera litura* nucleopolyhedrovirus | AAC33750.1 | DNA polymerase | 603 (partial) | 9e–08 |
| *Spodoptera littoralis* nucleopolyhedrovirus | AAF61904.1 | DNA polymerase | 998 | 9e–08 |
| *Sulfurisphaera ohwakuensis* | O50607 | DNA POLYMERASE I (DNA POLYMERASE B1) | 872 | 3e–07 |
| *Xestia c-nigrum* granulovirus | AAC06350.1 | DNA polymerase | 1098 | 4e–07 |
| *Lymantria dispar* nucleopolyhedrovirus | T30431 | DNA-directed DNA polymerase | 1014 | 5e–07 |
| *Lymantria dispar* nucleopolyhedrovirus | P30318 | DNA POLYMERASE | 1013 | 5e–07 |

TABLE 2-continued

| Source: | Accession #: | Definition: | Length: | E-value*: |
|---|---|---|---|---|
| *Buzura suppressaria* nucleopolyhedrovirus | AAC33747.1 | DNA polymerase | 647 (partial) | 8e–07 |
| *Sulfolobus acidocaldarius* | P95690 | DNA POLYMERASE I | 875 | 4e–06 |
| Bacteriophage RB69 | Q38087 | DNA POLYMERASE | 903 | 5e–06 |
| *Spodoptera exigua* nucleopolyhedrovirus | AAC33749.1 | DNA polymerase | 636 (partial) | 2e–04 |
| *Spodoptera exigua* nucleopolyhedrovirus | AAF33622.1 | DNA polymerase | 1063 | 2e–04 |
| *Mamestra brassicae* nucleopolyhedrovirus | AAC33746.1 | DNA polymerase | 628 (partial) | 9e–04 |
| *Melanoplus sanguinipes* entomopoxvirus | AAC97837.1 | putative DNA polymerase | 1079 | 9e–04 |
| *Orgyia anartoides* nucleopolyhedrovirus | AAC33748.1 | DNA polymerase | 658 | 0.003 |
| *Sulfolobus solfataricus* | AAB53090.1 | DNA polymerase | 882 | 0.003 |
| *Sulfolobus solfataricus* | P26811 | DNA POLYMERASE I | 882 | 0.003 |
| Human herpesvirus 7 | AAC40752.1 | catalytic subunit of replicative DNA polymerase | 1013 | 0.004 |
| Human herpesvirus 7 | AAC40752.1 | catalytic subunit of replicative DNA polymerase | 1013 | 0.004 |
| *Methanococcus voltae* | P52025 | DNA POLYMERASE | 824 | 0.010 |
| *Bombyx mori* nuclear polyhedrosis virus | P41712 | DNA POLYMERASE | 986 | 0.013 |
| *Bombyx mori* nuclear polyhedrosis virus | BAA03756.1 | DNA polymerase | 986 | 0.051 |

*An E-value of 1 assigned to a hit can be interpreted as meaning that in a database of the current size one might expect to see 1 match with a similar score simply by chance.

TABLE 3

| Source: | Accession #: | Definition: | Length: | E-value*: |
|---|---|---|---|---|
| *Aeropyrum pernix* | O93745 | DNA POLYMERASE I | 959 | 4e–20 |
| *Aeropyrum pernix* | BAA75662.1 | DNA polymerase | 923 | 4e–20 |
| *Aeropyrum pernix* | BAA75663.1 | DNA polymerase II | 772 | 7e–14 |
| *Aeropyrum pernix* | O93746 | DNA POLYMERASE II | 784 | 7e–14 |
| *Pyrodictium occultum* | BAA07579.1 | DNA polymerase | 914 | 2e–16 |
| *Pyrodictium occultum* | A56277 | DNA-directed DNA polymerase | 879 | 2e–16 |
| *Pyrodictium occultum* | B56277 | DNA-directed DNA polymerase | 803 | 6e–11 |
| *Sulfolobus acidocaldarius* | P95690 | DNA POLYMERASE I | 875 | 5e–16 |
| *Archaeoglobus fulgidus* | O29753 | DNA POLYMERASE | 781 | 1e–14 |
| Chlorella virus NY2A | P30320 | DNA POLYMERASE | 913 | 3e–14 |
| *Thermococcus gorgonarius* | P56689 | DNA POLYMERASE | 773 | 4e–14 |
| *Paramecium bursaria* Chlorella virus 1 | A42543 | DNA-directed DNA polymerase | 913 | 9e–14 |
| *Paramecium bursaria* Chlorella virus 1 | P30321 | DNA POLYMERASE | 913 | 4e–13 |
| *Pyrobaculum islandicum* | AAF27815.1 | family B DNA polymerase | 785 | 9e–14 |
| Homo sapiens | P09884 | DNA POLYMERASE ALPHA CATALYTIC SUBUNIT | 1462 | 1e–13 |
| Homo sapiens | NP_002682.1 | polymerase (DNA directed), delta 1, catalytic subunit | 1107 | 6e–07 |
| Homo sapiens | S35455 | DNA-directed DNA polymerase delta1 | 107 | 9e–07 |
| Chlorella virus K2 | BAA35142.1 | DNA polymerase | 913 | 3e–13 |
| *Sulfolobus solfataricus* | AAB53090.1 | DNA polymerase | 882 | 3e–13 |
| *Sulfolobus solfataricus* | P26811 | DNA POLYMERASE I | 882 | 3e–13 |

*An E-value of 1 assigned to a hit can be interpreted as meaning that in a database of the current size one might expect to see 1 match with a similar score simply by chance.

TABLE 4

| Source: | Accession #: | Definition: | Length: | E-value*: |
|---|---|---|---|---|
| *Autographa californica* nucleopolyhedrovirus | P41476 | PUTATIVE BIFUNCTIONAL POLYNUCLEOTIDE KINASE/RNA LIGASE | 694 | 3e−07 |
| Coliphage T4 | P00971 | RNA LIGASE | 374 | 0.002 |
| *Aquifex aeolicus* | D70476 | DNA helicase | 530 | 0.25 |

*An E-value of 1 assigned to a hit can be interpreted as meaning that in a database of the current size one might expect to see 1 match with a similar score simply by chance.

TABLE 5

| Source: | Accession #: | Definition: | Length: | E-value*: |
|---|---|---|---|---|
| *Streptococcus pneumoniae* | P13252 | DNA POLYMERASE I | 877 | 2e−08 |
| *Lactococcus lactis* subsp. *cremoris* | O32801 | DNA POLYMERASE I | 877 | 2e−06 |
| *Bacillus stearothermophilus* | AAB52611.1 | DNA polymerase I | 876 | 1e−05 |
| *Bacillus stearothermophilus* | AAB62092.1 | DNA polymerase I | 877 | 2e−05 |
| *Bacillus stearothermophilus* | S70368 | DNA polymerase I | 876 | 2e−05 |
| *Bacillus stearothermophilus* | P52026 | DNA POLYMERASE I | 876 | 2e−05 |
| *Bacillus stearothermophilus* | JC4286 | DNA-directed DNA polymerase | 879 | 4e−05 |
| *Bacillus stearothermophilus* | AAA85558.1 | DNA polymerase | 954 | 4e−05 |
| *Thermus thermophilus* | 2113329A | DNA polymerase | 834 | 3e−05 |
| *Thermus thermophilus* | P52028 | DNA POLYMERASE I | 834 | 3e−05 |
| *Thermus thermophilus* | BAA85001.1 | DNA polymerase | 834 | 3e−05 |
| *Bacillus subtilis* | O34996 | DNA POLYMERASE I | 880 | 4e−05 |
| *Bacillus caldotenax* | Q04957 | DNA POLYMERASE I | 877 | 4e−05 |
| *Deinococcus radiodurans* | A40597 | DNA-directed DNA polymerase | 921 | 4e−05 |
| *Deinococcus radiodurans* | P52027 | DNA POLYMERASE I | 956 | 4e−05 |
| *Aquifex aeolicus* | D70440 | DNA polymerase I 3′–5′ exo domain | 289 | 7e−05 |
| *Thermus filiformis* | O52225 | DNA POLYMERASE I | 833 | 7e−05 |
| *Anaerocellum thermophilum* | Q59156 | DNA POLYMERASE I | 850 | 3e−04 |
| *Rickettsia felis* | CAB56067.1 | DNA polymerase I | 922 | 3e−04 |
| Rhodothermus sp. 'ITI 518' | AAC98908.1 | DNA polymerase type I | 924 | 4e−04 |
| *Thermus aquaticus* | P19821 | DNA POLYMERASE I | 832 | 4e−04 |

*An E-value of 1 assigned to a hit can be interpreted as meaning that in a database of the current size one might expect to see 1 match with a similar score simply by chance.

TABLE 6

| Source: | Accession #: | Definition: | Length: | E-value*: |
|---|---|---|---|---|
| coliphage T4 | P04530 | PRIMASE-HELICASE (PROTEIN GP41) | 475 | 3e−06 |
| *Campylobacter jejuni* | CAB75198.1 | replicative DNA helicase | 458 | 0.003 |
| *Listeria monocytogenes* | Q48761 | DNA REPAIR PROTEIN RADA HOMOLOG | 452 | 0.003 |
| *Listeria monocytogenes* | AAC33293.1 | RadA homolog | 457 | 0.016 |
| *Mycoplasma arthritidis* bacteriophage MAV1 | AAC33767.1 | putative replication protein | 276 | .007 |
| *Aeropyrum pernix* | B72665 | hypothetical protein | 726 | 0.016 |
| *Porphyra purpurea* | P51333 | PROBABLE REPLICATIVE DNA HELICASE | 568 | 0.027 |
| *Escherichia coli* | P03005 | REPLICATIVE DNA HELICASE | 471 | 0.047 |
| *Saccharomyces cerevisiae* | NP_011861.1 | SH3 domain | 452 | 0.047 |

TABLE 6-continued

| Source: | Accession #: | Definition: | Length: | E-value*: |
|---|---|---|---|---|
| *Chlamydia trachomatis* | O84300 | DNA REPAIR PROTEIN RADA HOMOLOG | 454 | 0.14 |
| *Haemophilus influenzae* | P45256 | REPLICATIVE DNA HELICASE | 504 | 0.14 |
| *Caenorhabditis elegans* | T16375 | hypothetical protein | 566 | 0.18 |
| *Pyrococcus horikoshii* | E71133 | hypothetical protein | 483 | 0.18 |
| *Cyanidium caldarium* | AAF12980.1 | unknown; replication helicase subunit | 489 | 0.53 |
| *Rickettsia prowazekii* | Q9ZD04 | DNA REPAIR PROTEIN RADA HOMOLOG | 448 | 0.69 |

*An E-value of 1 assigned to a hit can be interpreted as meaning that in a database of the current size one might expect to see 1 match with a similar score simply by chance.

While this invention has been particularly shown and described with references to preferred embodiments thereof, it will be understood by those skilled in the art that various changes in form and details may be made therein without departing from the spirit and scope of the invention as defined by the appended claims.

```

What is claimed is:

1. An isolated polypeptide encoded by a nucleic acid molecule comprising a nucleotide sequence of an open reading of the nucleotide sequence; wherein the open reading frame is ORF 739f (locus GP63) as set forth in FIG. 2 (SEQ ID NO:1) and encodes an RNA ligase.

2. An isolated polypeptide or a fragment thereof; wherein the polypeptide or fragment thereof is an RNA ligase obtainable from *Rhodothermus marinus* strain ITI378 infected with bacteriophage RM378, which is deposited in the Deutsche Sammlung Von Microorganismen and Zellkulturen GmbH (DSMZ), accession number DSM 12831.

* * * * *

                           SEQUENCE LISTING

<160> NUMBER OF SEQ ID NOS: 73

<210> SEQ ID NO 1
<211> LENGTH: 129908
<212> TYPE: DNA
<213> ORGANISM: Bacteriophage RM378

<400> SEQUENCE: 1
cgggtctgct tttccttcac ggacccaatt ctccgtgaaa gaaatacgac attcatactg      60
cacctcctgg ttggtttaat tagggttaat gttatacctt ttcaggaact tcgatcgctt     120
taactccctc tgatgaagca cggtttccac cgcggcaaaa atcaccagca gcagaaacca     180
cgctcctatc agaagcagcg ccgtttcaaa ataaacccac ttcatcacaa gccccgccag     240
tacgaaggcg ggcaaaaaac ctgttataac gtaaacagcg ctcatggttc accccctgagt    300 ctggagtgca aaggcacctg taatatccac ccaaccctca tgacgaaata ccgtcttctt     360
gaccacggtt ccgtcgggct gctgctcctc caccgacacc ctcttcgtaa aggaaaacag     420
aggaatgata cagaaagcca tcagagcatt gaccagaaac ggcatgaagt agggcgcgcc     480
tccaatcatg gcggcaccca gcaaaatatc ctccgtctcc ccactcttct tgaaaaaccc     540
ggcggcaaga gcggcaatct cccacgcgcg agacatcatc tgatcgaaat caggaatttc     600
ctcgaacgta agaagctcct tcacccgatt ccactgatca tcaggaaggt ttacaacccc     660
cgcctccatc tgttcgggag tcggattgtg ctgggtgaga ttcagaatcg tcatggcttg     720
tacctccgtt tgtttgttaa gtgatccaca gccagtatac gcataaagcg gaaaaaagtc     780
aatcggtatt ttctttcttc atcttaattt catttttttc cttgagggaa atatccgccg     840
catacatttt ttcggcttcc ttcagcacct cagagactct gctgaagatc tccctgagct     900
gaaccattga ccactccgga tcgtcaagca ccagtggaag cgcgtagccg tcttcatacg     960
tttcatagtt atcctcaaac agatcttcca gcagacgatc cagcagtgca ggaatttcat    1020
atcggtaact cataactcct ccggcggtta acttatcggt aaaccttcac ggatgaaggt    1080
ctcatgtgaa tgaacacttt tgctcccgga tacacttcat ccagaaccat aagcgccaca    1140
agcgaagcaa gcgtcatgta cacccctgg atacctccca ccgtcatata atccagaaat     1200
```

-continued

```
ctgatcgtac cgccgaaat ggtatcttca agccccccat cccagataag atattccacg    1260
atggagggaa tctgaaccct gatcttttcc agctcccgct cgatatggat atgcggatcc    1320
gaactacgcg ctgcttccct gcagatacct tccgccagaa caagcaacgt ttcatttcga    1380
ttctgataaa aataattcag agcaccctcg aacagcgctt caggatctgt agccgcacgc    1440
ggaacgcttc tggaaacgtc tttcagaatc tgcatcatga cgcacctcca ttttttccaa    1500
cataaccttc ttatttcctt tcggttcca cgcaatccca attaccacta ttaatctcca    1560
tcaagtcaga aacccgaatt caatttaaaa cttttctgtc tgaaattccc ttataaccct    1620
taaaacttaa cactacccct tcaacacaat cccaatcacc agtaaaaacc tacctgcatt    1680
agatctacta ctccccttg aagcaaaaag gaaaaaacca aaatcaaaa ttctataacc    1740 cctacaggat acgctcagct ttaagtcgca tattacccat tgggatttta gaattttaaa    1800
attttgtttt tctttaatct ccatagggta cgcttagcat tgagtcttaa tttaccattt    1860
gagggatttt aatttagaag ttttgtttt tctttaatct ccatagggta cgcttagcat    1920
tgagtcttaa tttaccattt gagggatttt aatttagaaa ttcaaaaatt taatttttc    1980 ataaccttga gtggcttatt tacctgtaga gcgtcattca aaaacacccc catttcaaga    2040
aaccttcaca ttgatctgtc gttttacaac ataaaacctt taagtggtat atgatcagaa    2100
agcgtaaaaa atctgaacat atcggagcgg atgcgattcc aaagggattg gtctatgatg    2160
ttttaaatct tgggtatacc gataagctca atcccgcat gattgctata ctgagcattc    2220
ttatctacca tcgccaccgg gaagatcaca cctacgagat tgaaacagga tcgaaatgca    2280
agcgcatggt ggaagttaaa aaagggagt cctggatcag cattccaacg cttattgagc    2340
gggtttacaa cacatttgga attaagctta ccagggagca ggttaaatat gcccttcgtt    2400
tgcttttaca gcatggtctg atttcggtaa aggaagcaac cggtggggtt tcgaaaggtc    2460
attttggaaa catttataca ttcagagaaa cggattttga aggagagttt gtcgatcctg    2520 tggatttttgt gagggaaaat agtgaaagtg aagaagaaat ctggtatgca gattatacgg    2580
aaagtcggta ttcgaatcgc gtaaccgtca gagaaggagc atttcatccg attatgaaaa    2640
gtaggacact tctaaaaacg catgtgctta gaaatcatcc agatagagaa aaagctacga    2700
agttttaccc gaaagagatt gttgtggata tcgaagcggg tggatatcgc gtagatgaaa    2760
cagagcggta cagacgcttt agactcttcg tgataaaccg cgctgcgaag tttgcgagaa    2820
agttcagagc acgctacggg gggaaagttg atatatgttt taccggaggt aggggaattc    2880
atctgcatat tacgggaagt gtgctcaatg ttccaatgaa ccgcagtcaa ttcgacagga    2940
ttttgaaaga agcaattgtt cgtatgctta agatacgga actatggcgg ttttcgatc    3000 cttccacgct gaatccttt cagcttgccg gggttcgcgg aaaacttcat gataaggctc    3060
cttttgacga ctgggtgtat gtgaagcgta cctatcaaac gattaagccg ctcaaagccg    3120
gaagtctgct ttcgagtttt gaggaggcgg ctttctggat ttcgcgtagc ttcgtcagaa    3180
aagcggctaa aggcaatcca tttagaacgt acagtctggt aaaggaaggg ctactggaag    3240
gggagccgtg gagcgatcac catgcgggaa gagatacggc tgcttctgc atggcatgcg    3300 atcttctgga agccggatac atgacggatc aggtgttgct gtttctgaaa gattgggata    3360
agaaaaacaa accttctctt ggagataaga ttatcgcgca gaaggtaaga tcggcgcggc    3420
ggcttcttgc gcgaaaagga agcttaaag caaaccctc tctacagctt ctctaattgt    3480
tttgaaaaag tgatagaatc tttccgggga aaagctgtat ccgatcatgt cggtgataac    3540
gctcatcaca ttgaaaaatc gttggacttc atccggattt cttctgtcga ttttgataag    3600
```

-continued

```
aagttcgatt atacgtttaa acgatttagg ataatcgtac cacagaaagg aaagatatgc    3660
acccgacgat ccttcttcct cttcttttt catgtaagaa cgaatatctt catacagata    3720
ccatatatcc acaatgcttt gagcgagttt ctccataatt ctggtggcgg tgttgctgaa    3780
cgtattgata tactcacagg taacaacata catattcttt ttgatttctt cgataatttc    3840
aacatgaata tttgtttcca gaagataaac agggaaagaa attgaaagtt tttcaagctg    3900
cacaatttta tgcagaaagg tgttttcgcg cacttcccaa tcccacagac atttcacagt    3960
cagatatatt tcatttctta taactttctc cagttcgacg aaaatatacg atttattttc    4020
tataaagccg ggtaactctt catgaatgat gcggtttaag ttgctgtgtt ttttcatacg    4080
ggtgttatct ctcagcaatt ttcttttagc atttgccaca aatctctgat atctttcttc    4140
aaaatcttct tttttgaatt ggatgttggc ttcattttgc aattgtctgg ttcttatagc    4200
aagcgtctca atgaacgttt tgattagaag tattgctccc ttagccatat cctgaatggt    4260
ggaatcggcg ggtaaatcca cacgaaagat ttttcgagtt tcttcgtttt tgatcagtgc    4320
gacgttccat cccattctct tttccatgaa aaacctgagc gcccagacca gatattcgta    4380
gaagttttca gtcatttat tttaaatatt cccttatctg tattccactt ccggagattc    4440
tatatggatg taaagtatat tttttcgtgg tataaaattc atctgagcgt gcaccgcaat    4500
tttcaggtcg ttctcgctca atgatgctc gccccacctg aacgatccga taaactgcag    4560
cgtgatatgg tgcgtgatca aatccgtaga aaactccagc ttatcatctg tttcgggtgg    4620
aagcacatcg gtagagggaa accgggattt cacatcaaga cgtgcaagca ccagataatg    4680
atggtaattc tcgacgtttg atgccggtga tatgttttg agtttgtcgt ttaatgtgcg    4740
gattacttct ttcatttcct tttcgatggt ggtatcctct gattcttttc tggagaaaat    4800
gtttttataa gagggtcctt ttttgatatg ttctaccggg gaaatggctt taagcagtct    4860
gtaggcataa tgcaacgtgt cgtttatcat ctttatgaat tttctgatcg caacgcttac    4920
aggtgtatcc tcagagatgc tcaggtagac cagatcgggg tgttttctca aatgataatc    4980
aggtggagag aagccgggat attttttccag atagttttg atggtgtttg taagcagttc    5040
ctgatacgat ggcattttat tttaaataag tgttgataaa caaacaggct ttttttcacat    5100 attcgaacaa ttcatctttg gaagatggt gtggtttgta ctgacgatgc ataaacttat    5160
aagcaatatc aaacaatacc ctaccctttt cctcactttc tttaataata tctataatgc    5220
tgtctatttc ctcttttcagt tctctgtaaa tggttcggta tcggtttatg tcctgctctg    5280
tcaggtgttc actatttca tattttatcc cgaatacaga cataatacct attgttcctc    5340
cgataaattc cagtgttcca ttccgggtag aggcgcttac aaatgagttg cgaatcttca    5400
atgttttatc tgaaacgaaa ctttttaaaac ttaagtcaag gagcatttct gtaacaaaca    5460
gaggagcatt caggtggaaa atttttgcaa attttgaatt ttctcgggga aaccattaa    5520 caaaaccgat tatcattata ccaagatgag cttcctttgc aaaaaccggc ataatgtaaa    5580
gatgaatttc gtttcgaaat tctatttcgt ctgtgaagtg ggtgattaat ttttttatcga    5640 tattattgta gtgtatagta tcgtctttaa gttctttcat ttttttctga agtttcttta    5700
atgcctgttg aaacttctcc tcaatttgat ctacagctat ttttttcaact ccgatatctt    5760 cttcgaagtg tctgattttg gtaagtgata gttctatagt cttttttaagc gtatgaacat    5820 acatccgcgt aaaatctctg ggtaactgct tttcggcggg aataagacgc acttttacat    5880
aagaaggtcg tttctctata atttctacac tggaaaattc cgatcttttt tttaaaatat    5940
```

-continued

```
tcaatgatgt tcattgcaag tagtgcttca acaacgcctt ccatagtttt tttagctaag    6000
gttttttgtt tacagttttg tagttttcgt taattaaggt gtttaatgct attggttttt    6060
ttaactattc cccacgaact atctgtttca atacacgata tctttccacc atatcgaggt    6120
ttataatatc cagcgctcta cctatttcat caaacatttc gatcacgcgt tcatcctgat    6180 tgttttttgct gtgttcgata aggtttctga gttcaaaagc tccccgtata ccactggaat    6240
acagaaatgc gattttttgga atatcagggt gtccgggatt aataagagat agaaaatgtt    6300
caatgttttt tatgagttca tgaaggcgat tatactgcat gttgaaataa gcgtgggctt    6360
ttgtcagcct gatgttttct tctatcatgg ggcgcacgta aaactccca tgcagagcgg    6420 ttccgatatt ggtaaaaact gtctcgtgaa acagaatagc ggaaagtgcg gcgtttttaa    6480
ccggatagag agaacttgca ccaataaccg atatatcaaa cagagcagga aaaaactcga    6540
aaagactctg atcattaaag aaaatatgca tttcgttttt tcgatatacc agatcagggt    6600
atttatgtgt ggtgttaaat attttctgta ttttctgaac cgtttctttc tccttattta    6660 ttttttctt aaacttctca atagcctgct ggtacttatc atttattttg ctgtctacag    6720
aaaacccgga ataaatggtt cgtgtctttt ttataaaaaa ctcgatcagt tctttgaaca    6780
tgcgcggcgt ttcttttata atctcttttg cggttgcgtt ttcaccgatg tcaaggatta    6840
tggttacatg tttatcgccg gcgtctatgt ttaccggata ctttttttga aatctgtaat    6900
actgctgaat tgcacttaaa atctctttac ggtatttttt cggagtcata aggtgtcggg    6960
tttgatttta ttaaatcact caggtttta agtcgtgcat gtttaaccca gtttttaac    7020 caccctgtta ttccaccata tgactttttcc atctgatctt acgattcctc cgtatcccat    7080
gcggctcagg atctcattga ttttttccgtt ttgaggaacg ttgagtgcac caaaatagag    7140
ttcagtaagt tgcttcataa aacggtttct atcctgattc agatcttctt ctatcatcat    7200
ctgaatgcgg gttggaaatg tatctacgat caggtttacg acgtagactc tatcgctggc    7260
ttcccatctt gaaaggaaaa aggaatcata tcgaagcaac cggtcaaacg tttcgtcaac    7320
gacggttttg acaaatgtcg caagttttcg ggtgaaaacg gctccggttt gctcgaaagt    7380
gataagcaac cctttgaaaa gcattttttcg gagtgcggag aggctgtagg gaacgtcaaa    7440
atgaattccc ctttcgacga atccatatgg cggctttcca ataccccct gaagtttcat    7500 tcggtgaagt tcccagccgc ttccaagaaa ttcgtcaatc tgaagttttt taagtttttt    7560
gagatcggag gagttaaggt gcacgccgaa atagttaagt gcgcccccgg tggacgcgaa    7620
aagggggagg ttgtaaaaat cttttggata atcgttttcc ttttttgacgt tgagaaattc    7680 ctccggctcg atgatatagt agaggtgata cccgcgctcc aagatttccc gaagggtttt    7740
ttcgtttaac gggatttcgc tcataaggag tccgtttccc tccacagaag acacaatcag    7800
gtttgaggga tcaagcgttt cgatttttttc aaggagctct ttcatacggg tatctgcagg    7860
gttatctgtt cgcggttaat ctgcacaacg attttgagaa ggtgtgtggc ttcgtcaaaa    7920
ctcacgtcta tagtatctat gtcgtagggt tcgaggttgg aggcaatcag gttgaacagt    7980
tcatcataat cataattctc gaaagaatg ttgcgaatac cgatccctct ttctggatcg    8040
tagggatatt ccccggctc gatgaaaagc aggagtttta tcttatcgat caggagtttt    8100
accgggtcat caggaaatct gaaattcggt gcagtgtcgt tcagatagaa catttcattt    8160
ttgtttaaat aaatcctcga ggaatcttca aataaagagg ggcgttaatg gatgaaagaa    8220
ctgaggaata tggtcaatct tatcgatctc aaaaatcagt attatgctta ctctttcaag    8280
tttttcgact cctatcagat cagctgggat aattacccgc atcttaaaga gttcgtcatt    8340
```

```
gaaaactatc ccggcactta tttttcatgc tacgctccgg ggattctgta caagcttttc   8400
ctcaaatgga agcggggtat gatcattgac gactatgacc gacacccgct ccgaaagaag   8460
ttacttcctc agtacaaaga gcaccgctat gaatacattg agggaaaata cggtgtggtt   8520 cctttcccg ggtttctgaa atatctgaag ttccactttg aggacttgcg gtttaaaatg   8580
cgcgatcttg gaatcaccga tttcaaatat gcacttgcca tttctctttt ttacaaccgg   8640
gtaatgctca gagattttct gaaaaacttt acctgttatt acattgccga atatgaagct   8700
gacgatgtaa tcgcacatct ggcgcgtgag attgcacgaa gcaatatcga cgtaaacatc   8760
gtctcaacgg ataaagatta ttaccagcta tgggatgaag aggatataag agaaagggtt   8820
tatatcaatt ctctttcatg tagtgatgtg aagacacccc gctacggatt tcttaccatt   8880
aaagcacttc ttggagacaa aagcgataac attcccaaat ctctggaaaa aggaaaaggc   8940
gaaaagtatc ttgaaaagaa aggatttgcg gaggaagatt acgataagga actattcgag   9000
aataatctga aggtgatcag gtttggagac gaatatcttg gagaaaggga taaaagcttt   9060
atagaaaatt tttctacggg ggatactctg tggaactttt atgaattttt ttactatgac   9120
cctttgcatg aacttttcct cagaaatata agaaagagga gactatgaaa gtactcgcat   9180
ttaccgatgc acctacgttt cccacggggg tgggtcatca gcttcacaac attatcaatt   9240
acgggtttga cgcaaccgat cgctggggtt gtggtgcaccc gccccggtcg ccaagggctg   9300
gagagactaa aaacgtcgtt attggaaaca ctccagtcaa gcttatcaat tctccgcgag   9360
gatatgcgga tgatccggcg tttgtgatga aggtggtgga agatgaaaag ccggatgtgc   9420
ttgtaatttt taccgatccg tgggcttacc acccctttat gcaacaactt tcttactgga   9480
ttatcgagcg gaatctcccg ctggtatatt atcatgtgtg ggataatttt ccggctcctc   9540
tgtacaacat ccccttctgg cacacctgca atgaagtgat aggaatttcg atgaaatcga   9600
cgatcaacgt gcagcttgcg aaggagtatg tggaggcgta tgaaatcacc atgtatcgcg   9660
atccggaggt attctatctt ccgcatgcgg tcgaacccaa tgtattcaaa cgcatggatc   9720
gcaagaaagc acgtgaattt gtgcggggac ttgtcggaga taggatgttt gatgacagcg   9780
tgatctggct ttacaacaat cgaaatattt cacgcaagaa tctgatggat accatttatg   9840 ctttttctggt atacatgctc aaaaactaca ggaaacatca ccttttgatt ataaagtctg   9900
acccggttgt accggtggga acggatattc ccgcgtttct tgccgatatt aattcgtttt   9960
tccactaccg ggatattgac cttcgggaac acattgtttt catttccaat gacgaagtat  10020
ttcacaacgg cggattttca agggaggaaa tcgcattgct ttataacggc gccgatgtgg  10080
tgctgcagct ttcatctaat gagggggttcg ggatcgcttc gcttgaggcg tcgctgtgtg  10140
gagccccggt ggttgctact atgacggtg gtattgcaga tcagtactcc ctctacgaaa  10200
tggattatga ggtggcggat ggaagtgatg aagatataat ctgcaagatt tatgaggaag  10260
tgcaccgtca ggtgctcaat cagtatctcg atatgctccg tcaaaacgga aaggatccgg  10320
aaagcgctcc ccgcaaaaat catatgatgc ggatggtgaa accttatcgt cattatcagg  10380
gatcgccggc tactccctac attcttgacg acagggttcc tatccgggac gtattcccga  10440
agttcgatga agcgctggcg ctgaggaatc gtgaggatta cgaaaaactt tatgaagaat  10500
cggttgagta catcaccatg cacttcgatg tagaggtgct cggaaaagag ttcaagaaat  10560
cccttagccg tgccattaag aataaccaga aaaccacaag acaggttgtc gtgctatgaa  10620
gaagaaagtg cttcttgttt cgccgcttcg ttccgttagc ggctatggaa ccgtaagtcg  10680
```

```
cggaatttat cgcattctga agcgaatgga aaaagagggg ttgatcgatt ttgatgtgat   10740
ggtattgcgg tggggtacgt tttcggaaac cacccacctt gatgatgaaa tcaagaagag   10800
aattcaggag aagtatgatc aggtgtacga tgttgcgatc atggtttctt ctccctacga   10860
ctatcgctac tggaacaaca tcttcagagc gaaacacctg ctcttttca atgcgatggt    10920 ggaaacgaaa ccgttccatc cgaatctgtt ccagcagctt ttcaacttca tgcttcaggt   10980
tcccaccgcg caccttgtgt ttccttcttc cgaaatcaag aggatctggg aagaaatcat   11040
caattcccaa cccatccatc cggcaatggg tgctgcagtg ctctcccgca ttcatgtagt   11100
acccaacccg gtagatgaag tttactatac ttcgaacttc gggaataaaa acgttcgtaa   11160
aaatgtgatc ggcgcgattc gaaagaagat tgaggaaatc cgtcgatcct atgaactgga   11220
gcgggtgttt ctgactttg cgcctatggg agtagatcga aagaacacca gggttttacc     11280
cgaacttatc gaaatggtgg ggcgggttgg aattctggcg ctggcgggcg aacaaattc    11340 ttttatactt tacgactttc agcggcttat ctggatggaa ggtgagaaag cctataagcg    11400
gcttccgctt caccgatcga tcgacgttac cccggaagag cttatgttcg ttttttggatc  11460 gctgacggtg gaagagctga gtgcggtgat ggatatggtg gatggtggaa tcaacctttc    11520
gcatggagaa tcgtgggatt acctgttgca caacatgatg ctactgggca aaccctgtct    11580
ttacgtcgac ttcttccgtc gggattatat ccccttcggag cttcgtgatg tgctgggggt   11640
ggatttcaat atggtacccc tcccgaaggt ggttcccaac attccgcacg atcatccgtt    11700
cttccacccg caaacgatgg tggcggaacc caatttgcag gatgcagcgg aaaagctcga    11760
ctgggtgttg cggaactacg gtgaagtctc aaagatgatt accagccata gagacgcttt   11820
caaaaccgac gatacgatct atgaatttct ggttgacgca ctggagtcga tcgaagaacc   11880
acaggcggca taaaaatttc acattctgga taaaccgggg gaattcgggc atttatcccg    11940
aaaatccccc ttttttgtct caaaaccgtt ttggcgggt agatatttaa tatcaccccg    12000
tggaaagttt aaccccaaaa caggagtgga tatgtcgtac tatactgaag tcggcgcacc    12060
ctactttaca cgtgaagagc agtttgttcg gaatttgctg ttcgacgtaa ctttttaattc    12120 caaatattct ttcttcgatc tgacgctgca gcgtcgtctt acctttgagg aagtgctgga    12180
agaggtgctg gcggtgtttc atgcccgaat cgaggaagtc tgcaaaccca tttatcgcca    12240
gcaggcgcac cagtacgtgg agaagttcgg cgagtatttc cgccagcgca agcttttttcc  12300 ctcgatgcgc cttgtgcagt tttcgcgcat ggttccttac aaccacaccc gtctttacaa   12360
ttgctcttat actcccgttg attccattga ttcgatcgcg gagcttttct acctgatgtt    12420
gtgtggcgtg ggtgtgggat acagcgtgga gcgtaaatat atcgaacagc ttcctgttgt   12480
atatcccgaa agtgaggggc agacaatcac ctatcaggtg gaggattcga tcgagggatg   12540
gtgctcggcg ctcaagcgtt atctctatgc gcggtttacg cccaaccacc cgaagattgt   12600
atttgactat tctcttttga gaccggaggg aagtgtgatt ggaaagcgtt acaatgctgc   12660
atttggttat actaaaaaca atcccatcaa agaagcaatc gaggcggtaa agggggatttt   12720 cgacaaagca gtaggaagga aactcaagcc gatcgaggta catgatctca ttacaacgtt   12780
cggcatgatt atcaatcgtg cgaacgtgcg cggaatggcg gcgatcgtct ttttcgatta   12840
tgatgatgaa gaaatgcttc gctgcaagga tttcacgcgc ggcgaagtcc ctcagaaccg    12900
ctggtatgcc aacaactctg tcgtgttgta tagagacggc gataaacttc gcggagtgcg    12960
cggggaaatc gtcgatcttc gggatatttt catggaagcc tattgtggga agtctggtga   13020
acccggcgtc tttgtaacca acgacgaaca ttatcgcacg aacccgtgtg gtgaagcttc   13080
```

```
tctttatcgc aatttctgca accttacgga gatcgccatt ccccgtgttc atcagagtga    13140
gatcgcggat gtgttgaaca cagctatctt cattggtgtg cttcagtcta cgtttaccga    13200
ctttaagttc cttcgcgatg tgtggaaaga gcgcaccgaa aagacaact tgcttggcgt     13260
ttcgctgacc ggcatttacg aaaatctgga tgcgctcaaa gagtacatga agctttcttc    13320
gaaaggtcat gtcaaattca tggcggctca atttgccggt tggttcgggt tgaacaaccc    13380
ggctcgcatt acgctggtca agccctccgg cacggtgtcg ctgcttgccg gggtttctcc    13440
gggttgccac ccaccctatt ccgaatattt tatccggaga aaccgggtgg atatgaatca    13500
catgctggtt gaagttttga aggattatcc gtttatcatt gatgatgaag tgtatcccga    13560
taagaaagtg atcgaatttc cgcttcgggc gcaacgccac tttacgcacg atcccatgtt    13620
tcaggtgcgt cttcgcaacc agatcatgag gggctgggtg aaccctcgc ataatcgcgg     13680
caaaaacaca cacaacgtat cgattacggt ttatgtaaga gatgaagggg aagtggagat    13740
tgtaagtcgc gaactcaaaa atgagcgaaa catttcggga atcacgattc ttccggtggt    13800
tgagaatggc tataaactgg caccattcga agcaattccc agggaaaagt atgccgacat    13860
gatgggcgaa atccacgtgt accttgatag aatcaaacac cagctaaacg gcacgcccga    13920
ctccccgcgt ctgaaactga tctccgattc cgacgttttt gagggagaga aaggttgtgc    13980
cggtctgcaa tgctatttcg acatgtaaca tgaaactcgt acttaaacac tccagagaag    14040
agtctttcta tcctgaaaca ataaaaactc ttgatcatct tagagagaat gggtgggaaa    14100
tcgttctcct acaggataat cgttttaata tcatagaagg ttacgatttc gatatggtga    14160
ttaccacgtc gaaccctcaa tacagctttg cggatttcca caatgaagca ttgaaatttg    14220
ccaagcacgg ggagtggctt ttttatcttg atttcgatga atatttatgt gataatttt      14280
gtgaaagggt taaaaaatat atcaacagag atgttcattg ttacaacatc gcacgcataa    14340
acattataat tcctcaggag aaaacgggtg atgtgtgcgg gatgtacgga tggcgtagtt    14400
ttaatatcaa tatacctgag gaagggagtg taaaagcgat aaatttcccc gattaccaga    14460
cgcgtctggt tcgcgccgga accggcaaat ggtacgggaa cgcccacgaa cgctttgtgt    14520
gcgataatgc ttttaaacac aaaacgttac cgtttgatgg tggatatatt atccaccgta    14580
aatcttttga gaaacagatt accgataacg cgctctggtc aacctataca ccgtgatata    14640
tgttcagcgt aattctcata cacggaaacg aggatcttat caataaagaa ctgatagata    14700
atcttaatga attcagggaa gcaggatgtg aactcatttt gctgcaggat gatcgttttt    14760
caccgcccga cttttttcaaa tttgatattg ttataaaaca ttccgtttcc gaagggatgg    14820
accgtcatcg aaattttgcc aatcaacatg cttcttttga atgggtgttg tggttggatt    14880
ttgacgaata tctattcccc ggatttacag aacgagctcc tgaatacatg aaaagggata    14940
tatgggggta tggattttac agattgaaca tgatcgttcc acctgaaaaa acttcatggt    15000
tcgttcagaa ttatggctgg tatgaaatgg ttgggtgggt ttcaaccata tcgatcaggg    15060
gggtttctta tcaggctata aattacccgg aggttcatta tcgttttgtt cgaagagatt    15120
gcggcaagtg ggttggtaaa agacatgaat actggtattc aggtgatttt cgtaaaaaag    15180
ccatatttcc ggcggatcga gaaacacttt tccacgttaa acccattgac aaagcaataa    15240
gagacaacta taaatggagg gcactatgat gaaccccgaa atgaaagaga ttctgaagaa    15300
gcttatgaaa cccttccacc ctgatcgcca ttcctatcgc gttaccgaaa ccttccggac    15360
tcgggaaggg cggaacatgg gggtggtggc attttacatt tcatcacgcg acgtgatgga    15420
```

-continued

```
tcggttggat gcggtggtgg gaccagagaa ctggcgagac gaatatgaag tgccggctcc   15480
gggggtgatg aagtgtgtgc tttatttgcg tataggtggg gagtgggttg gaaagagtga   15540
tgtggggacc ggcaacatag aaaaccctga agtggatgg aaaggcgccg cttctgacgc    15600
cttgaagcga gcggcggtca agtggggaat cgggcgttat ctctatgcac ttcccaaatg   15660
ctatgtggag gtggatgata gaaagcgtat tgttaatgaa gaggcggtca agtcttttct   15720
ccataagcat gttaccgaac tgctgaagaa ttatcagtaa cccaaaccta aacccgaaaa   15780
atatatggaa acgattgtaa tttcccaaaa caatacgacg gagatgacgg aaccccccca   15840
gaacatttcc gattcggtta aaagcgggtt tatctatctt atcgaaaagt ctcatttcct   15900
tgaaaagaaa aacttcctta aaatcatatc gaacatggac cccgccgca tttccaatcc    15960
ggaggtgcgc gtggtggcgg agtacatata tgattatttc aaaagtcata gtaatttccc   16020
ttctaaaaga aatctttgcc atcactttga gtggagcgaa gatctggaag gagacccgc    16080
cgattatcag cgtatcattc agtatctcaa atcttcttac attcgatcct ctataacaaa   16140
aacgctttca tatcttgaga aggatgacct ttccgcgttg aaagaaattg tcagagccat   16200
tcgggtggtg gaggatagtg gggtgtcgct ggtggaggaa ttcgatcttg caaccagcga   16260
gtttaatgaa cttttttgtta aagaagaacg cattcccacc ccctgggaga gtgtaaacaa   16320
aaatatggcg ggcggtcttg gtcggggaga gcttggaatc gttatgcttc cttcggggtg   16380
gggtaagtca tggttccttg tttcacttgg tcttcatgcc tttcgaacgg gtaagcgcgt   16440
gatttatttc actctggagc ttgaccaaaa atatgtgatg aagcggtttt taaagatgtt   16500
tgcaccttat tgcaaaggac gcgcttcttc ctatcgcgac gtttatcaaa taatgaaaga   16560
gcttatgttt tctcaggata atcttttgaa gattgttttc tgtaatgcga tggaagatat   16620
tgagcactat attgcgctgt ataaccccga cgttgtgctg attgactatg ccgatcttat   16680
ttatgatgtg gaaaccgaca aagagaaaaa ttatctgctt ttgcaaaaaa tttataggaa   16740
acttcgtctc attgcaaagg tatataatac agcagtatgg agcgcctctc agcttaatcg   16800
cggttcccct tcaaagcaag ccgacgtcga tttcattgag aaatacattg ccgattcatt   16860
tgcaaaagtt gttgaaatcg acttcgggat ggcgtttatt ccggatagcg agaactcaac   16920
ccccgatatt cacgtcggat tcggtaaaat cttcaaaaac cgtatgggtg cggtaagaaa   16980
gctggaatat acaattaact tgaaaaacta tacggtagac gttgctgtta aatgacacaa   17040
gttaagacaa aagggcttaa agacatcaga ataggtagaa aggagggtaa gttcacacat   17100
gtaaatacaa caaagaaagg aaagaataag aaatatttca gggcggaaca tgaacgcctg   17160
tttctcaacc ttattcgagc acttcaggtt ggggattatg ccgaaatcaa ttctctttt    17220
cctcttgtcg aaaagcaact ccgatggatg gtacgaaaga tagtgaaccg actcaatctc   17280
acttcacttg tttcatatta tgaccacggc gaatgggagc atgatattgt aagttatgtg   17340
ttctccaaac tcgataacta ttctcccgaa aagggaaggg tgttcagtta tcagtgtt     17400
atcatagtca attatgctat caatttgaac aataaaattt attataaccg ggtgggtat    17460
cattcagatt tctatgcaga taatcctacc accgaagact acaagggtct ggatgaaaag   17520
gaagagttga gttatgaaat agacgatcag attaatctga agattgattt tgagcatttc   17580
tgcaatctgt ttttaaatgc ttccgaagaa actttactca agcattttca ggaagacgaa   17640
gttttttattg ttaaaaatat tgcgctttct ctgaaatatg atccggatat tatcacgacg   17700
cctttttctgg gggttgtaca tcggatgatc tgtgagtttt gtggggtgga attttcccgc   17760
tataagttt ccaaagtgtt caagaaaatg gttcaactat accacgaagt ttttaacggg    17820
```

```
gggtaaaggt tatttaaata aaaaatatgt tttcggcttc tgattataaa ggaaacgtaa    17880
cttttagttt tcacttccct tcgcttctca ccaatgccgg atcgcaccca ataaggcat    17940 atgtgtatta cgactatatg ggtagtgatc tggtgttcac tttttctcga ataagattca   18000
gcctgtcggc acccggcacc tacgatgctt attttgacgc tcatattcag gatgttgaca   18060
ccattacctt cgattcaaac ggataccgtg agctttattt cattttcagc gtttcctggg   18120
aaggatccaa cacttcgggc accatttcgg gtgccaatct tatcagcgta tcttcctttg   18180
ttactggata ccccgaaaac agttttcttg cctatacgct ttccgtttac tctgcttccg   18240
ccacaaccta tcttaacctt aatgatgctt acagaattta cgtagggaac attttcggca   18300
ccccgcaatg ggaagttggt tttaccggta gtttcacggt ttctgctacg ccttcaattt   18360
ctcacaaccg tttcaggatt ttacttcttt ctaactttga tagtgcactt aattactata   18420
ttactacgtt cagcgcacca gcattcgcct cacattcatt tcaggttatc aggaaaatat   18480
atgaagttga gccactttct gcttacacag taccgtctat cgtgtttttc tacacggttt   18540
cagctactaa cagcttcggg tggagctatt ccaatataga aatggggtct ctttacagaa   18600
tatcaactat gtccattcta agttatcctt acccctacac ggcaccggct ataacgtata   18660
tcactttttc tggcggaatt gttttcggatg aagaatttat tgtaaaggtg cccataaccc   18720
tttcttatat taacaacata ataccgtatt tcatcggcaa ccccactacc acttcaaaca   18780
ttgacgatgt gaatgctact gaagataaaa ttatccctac ttcgataagt aactttaaaa   18840
caaccctttc atttcaggtt tttgcttttc cgaacacact ccctgttaaa acggaacaag   18900
tatcaattcc cgttaccttc agtccggaaa cgggcaacat ttctattcct gtttccatct   18960
catttcctgc gtttgtaaga actgctgcgg ctacaatgga taatccgggc aattttttcca  19020 cttctgtcgg aaatggtatc gtggttagcg atcttgtgtg tcagaataca gggaatatac    19080
ctattacatt tagtggtgtc agtcttgcaa tagacgatgg taactggtat gtggacaccc   19140
cctccgtggg atatggtttt aacccgaaca gcgggttttg gttcgatgtt cactttatgc   19200
cttatgggga tgtaaactac agtcaatcca tttatttac gttttcgttc aattatccaa   19260
caaattatgg aaatatattg tcaggtagtt ttgttgaatc catttctttc catgcggttg   19320
ctacaggaac cgcccttcc ggtcaggtgg gtattacggt gtccaactgg aatgtggaca   19380
accctaacac cgttatggtt ggtaaatatg ttaccggttc cttcagcatc acggcaagtg   19440
ctacaaacaa tcagatcgct caggttaccc tgacttcatc aaccccccaat ctgtatttca   19500 cgacggtttc aggtgttggt attaacaatc ttcatgctac ggcggtaaat tctctggcgc   19560
tacaggttgc tcccggagct tctctttctg tttatacccca gtggtatatg aatatggttt   19620
atacggcttc ggctcctgat gtaaccatat cggtaacgtc ttctaatgct acggaaatga   19680
acggcgtgcc gggattgacg gaagttaagc gatcgcattc gctgacgaac cctgctcgat   19740
atgcaaattt gaatatagga attttttcac tcagtgctta tggtccccttc tatcaatcaa   19800 ccgcctctat tttgccgttc ccttattctt ttagtcttgg gggcatcaac gtcgttagaa   19860
atgttggttt ggcttggctt gattttatc caacgaacag cactcattct gaaatgtatg   19920
ttaaattgac catgtctctg acaggatcgg ctttaaatgt tcatagcgta gtaacttcat   19980 cgtattttc tgatccttct aatttcgagt gggaagtcaa cactttgcag catactctgt   20040 tcagccccc ttatggatat tttcttcata ttagaataag accgactcca agtgatatta   20100
acataatacc gacttcaagt gcatatggat atggtacgtt tgttgtaagt tggagcatga   20160
```

```
gtcttatttc ccatataaat ggggtaagcg tggcttctct tggacagggg tattcaaatg    20220
ctttgagttt gtggtttgat catactgttt tctatgaagc accatagtaa tttcttatct    20280
atacgacaca tacttgataa aattgccgct ttctcccatt tcaaaatatt ttctgagcgt    20340
agaaggagta aaatccgtgg cgtctccaag ctttcgagtg ggggtgatca gtgttgcgtt    20400
gattttgaca tagtggcttt tgatcatttt gttgtggggg aaaagcaggt tgtaaagcgc    20460
catctggttt acgtcgttca aaagatgttc atgccagaga atatcgtaag tgcgggtaag    20520
cagcgcaaga agattggtgt agtagttccg ttcttcctta atggtgtaaa gcggcgtgca    20580
ggaaatgatg atcgcttgaa tttcctcacc cggctttaat tctttaagtt taataaggtt    20640
ttcaatggta aacccaagcg gaatcacttc tcttacccca ccgtctacat aggtgttgtc    20700
tccgatttta accggaggaa agaccagcgg aatgctacaa gaagcaagaa tggatttgag    20760
aagaagttcc tcttttttgct cttccgggat ttcctgatct tcaaaaaggt agttaccgtc    20820
ttttacaacg attccggtgg atttgccgtt ttgcaaattc acagaacaat tgatatagat    20880
tttattgaaa ttcagaagcg ggagcacgtt tttctcaagg tatttcccaa gaggggaaaa    20940
atcatacaga taatttcgtt tgagaataag tgttttgaga agggcaaacc actcaggctg    21000
ctgtttgtaa acctgtttcg gggaaagaga aagccacatt tgcttcatga gatcggtacc    21060 tttcgggggta agcgccgcgc gggaagcaca ccacacgccg ttgatacttc ccaccgaagt    21120
tccggctaca gcaagaattt cgttgtcttt aagcgctcct tccctcacca gacaggaaat    21180
gacgcccgcc tgaaaagcac ctttggctcc tccccccgac aggatcagca gttttttcat    21240 tttttaattaa ataatgctca ttttcccgat ggaagcatgg aaatccactt caatttggca    21300
aatccgtctt ccgttttccc gttgatcata tatgcgtagg ctccaaagac gtgagctatc    21360
ttgcaatact cctcttcgtt gtcaataaag attgtatagt ggttgggtgg aatgattcca    21420
tagatgagtt cgtttacttt cccgattttt ttgcccccga caatgcggtt gggaagtgga    21480
agattatgtt ttttcaaata cgactcgatg ttttccccggt ggtttgcgct caggatgtaa    21540
aggcggtgat agttcggatt tcttttttacc agatcgtaaa gataggtgta caggttatga    21600
aatttcgtaa tcgttccgtc gaagtctata cacaccgcca ccttgattgg tttgacaaga    21660
atccgggaga gcaatatatg agcggatttg tgcatagtca tagacacctg atccggtgaa    21720
agatcgataa tgcggggaaa tttgtaaatg cggcggagac ggttggtaag gtagcggatg    21780
tatctatcca ttcccatgta cttctcgata atatcaaggt attccggatt tttccttaca    21840
aacacctctt tcatcaggtg tttaatatga atggtttccc gtcgggtgag aagaagtttt    21900
gttaaacctc tcacccgcaa ctcttcgaga atctccggag ataaatcttc gaactggaga    21960
taaagcgttt cgtcaatggt ctgcatattc atagtttact caggtatttt tttgaacatt    22020
gtattaatgg tgtcgatttt cttgatgtaa tcaacgaatt tgacaccaag ttttcctgta    22080
acatttccga taagaatatt ggaagcgttc aatgccagtg cgggagtcag atttgaaagt    22140
cttgcaattt caaacagcgt cgggagaata tggtttttat tttcgatttc ttccatcaaa    22200
atggcgtcta cggcgttgta ttccaccaac tttttatccg ggtagacagg aatctcatga    22260
tagaatctta cgtcgaaatc caccttacct tctcctattt cctctcgcgc aatatagtcg    22320
agccggtagg actccaactc tttgtatgcc acaaaggagc gataaagccg catgtaatca    22380
aaaaacacaa attctacagg ggtacgggga ttgaaataga atggtaggtt tcgatcggaa    22440
attttccgca ccagcttcca gtccggaagc aacttatcac taatgacatt cacctcatgg    22500
atatgactac gaatgagcag gtagggataa tcgaactgat aaccgttcca tgcgagcatg    22560
```

```
aaagtaaatt ttggtttcag cacattccag aaatactcga gcaatctttt ttccgaaagg   22620
aatgttctgt aatgaatttc aaatgtgtta tccctacgc tggtggtaaa tttgttaaag   22680
ttatcgatat gagcctccgg gttggtgata aggagaagca ctaccaccac cggttttcca   22740
tacggtttga tggaaatgga ataaactggg tctctccacg ggtcgggaaa gcttttttc    22800 ggggaaatcg tctcaatatc gataaagacg cactgagaca aagcttccgg cgtgatgtgg   22860
cttttttgtt ctctgatgta ataggatata gcctcagcct caatcttccc tcgattctgc   22920
tgagcgatgc gcttcaaatg tggggtacg ggtgattgaa ataagtgttt tttcccctcg    22980
attagctcca ctccgtaaat tttcatcgat cggggtata cgcttgcgct tagcgtgatc   23040
ttcataattc tccttcaggt cttcttcgag gaaatcgttt aacgattgaa gcaactgata   23100
ataagcttcg cgggtttcga gcatgtcgaa tacttgcctg tgaaaaaaca gaaatctct    23160 tatcttgcgc gtggctccga tcagaagacg gtgtttccgc tggaggatgt tatacctat    23220 gatataagta atcagcaccc cacttacggt tgccgcaata gcaaccccca accagaaata   23280
tacttcctgc atggtttctt tttttcttca aaaaaacctt tccgtgaaaa aatagtttca   23340
actggtaact gcaaacaaac ataaggagag agtcatgctc gactttatc gctgctttgt    23400 caaaatcttt cagaatagct acttcgccaa cccaacaaaa taccggtttg gcgaaaaggt   23460
cagagaagca gtgttcaact ggggagcacg cgtggcacac cacgacatca attcgcgaga   23520
aaccgaaatc gttgcagatc cggagatgga tgattatttc agaagatcat ttttctccga   23580 aaaccctat atgcttgtta aaattaccca tcccgatgaa tcgatgataa atacggtaat   23640
atggcaaagc aagcgatatg aaaactttt ccgcgtctat caactcattc gcacaattgc    23700
acagatgaga gaagaagaag tcgataacta catgaatcag atcatgccgt ttattgcgtt   23760
gaatctcaat acgatcaatc gctatatgaa caaaacaaat cttctctttc aaaccccta    23820 tgatgagtta tacggttca ctctgctttt caagtcggta attcgcattg ccgaagaaga    23880
aaacgaactg gagtatcttg cgaataaaga tgtcattgat agttataata agaagattga   23940 ggaattttc aataccgatg aaaatatcgc tacatttgga tatgttctaa aagatatgct    24000
gtctcactgc attattgcca tcggtatgat cctgctggaa gcgaaggata aaacacacat   24060
gaagttttat gaggaacttg gtgagtttat ggcggaaata ggtaaggtat acttaaaagt   24120
gatagaggaa ggtgagaaag atatgaatgc gctgacgcat ttatacctct ggtgtatgat   24180
tgccggttgt atcattaaca tgttgaacgt caggattccg gatgaattgc ggttggctgc   24240
tatcatggtt gaagaaacgc ttgcctcgca ccaactgcaa ccctttattt cgttaaactg   24300 aagagggta tgatacagaa aacaaccccg tataaaaact acaaaaagta catggatcag    24360
cggggagaag tgctgagacc gcaccccgc aagaaggtat atatcccatt tcttattgcg    24420
gaatgtggaa cttatctatg gaacgacata agaaacatga tgtttgcgct tccggggtgg   24480
aaagatgtgg tgaaaaaata cggtgtgggg gaaaaatcca cccggagcc tttctatgat    24540 ttcctttcgc tttttatcaa gaatactacg ctttacagtg attatagaac caaacaaacg   24600 cttttttcaat cgcgaataga gcgcataaaa atggaagagg aagtctggaa tctttccaat   24660
gcactgatca atctgttctt ttatctgaaa gagcattatc cctattattt ctcaaaagag   24720
tttgtctttt actttgacat taatttctat ttcaggaagc tcacatttta tgatattctt   24780 gccgggaag atttgcggaa taaaatcaac gacacatttc agaaaatgct ctctaaaggt    24840
tacacggtac accttcaaa aatgaaacct cagagtagag aagattatct atgtttgcgt    24900
```

```
tatgccgaat atatggaagc tattatggct cgagatgagt tcaagcagga aatggatatg      24960
aaagggagtg ggaatctttt ttatcttatt gatggtttta aatgggggtt gataaataga      25020
aaagatgaag tagaatttgt tgtactggta aggtaaaaac tatataaata aaagggggtta     25080 gtttatggcg agctggactt acgataccac ttcgcgtatt ctgtcaatta ccgttagtgt      25140
ggtggatctc gacaataacg atgtactggt ttacaccggt agcaattatc ctacatggtt      25200
gagtccgccg accacttcgt acgtttccgg ttcgttgtct ccaaagcagt ttgatgtgta      25260
tatcagcggt agcacgctca acgttcagac agggtcttat caggttgatt tgcttgccat      25320
tgaacagggt gtgtcgttcc cgctcacctc ttcggcaagc ttcacgatta cggttacggc      25380
ggtttaacaa attttaggca agaagtctcc atcctctaca gggtggagat gaattgccta      25440
ttgacaaaat tcagtggtgt attacaataa agcaagatg tttagagcat acaaatacag       25500
gatatatcct aacaaaaaac aaaagaacc cttagagaaa acttttggtt gtgtggggtt        25560
ctactggaac agggcattag aaatcaaact caaagcttta ggaaataaag agaaaatacc      25620
acaggtcttg cccgccttaa gggtggtagg gtcggaacga cccgaactta tgcctgtgga      25680
ggagcgggta gctccgatga agcaggaagc tccatcttct acaagatgga gtagttcact      25740
tcacagaaac tttatttctg ttttatcgtt ttttccgtaa aaaaaagaa attatggttg        25800 taaaactacc gctgcatgat ttttaccctg aaggttcacc tttcaaaacc gaaacttta      25860 cggtaaaaga ccccaccatt gaagacgaag accgccttt caacccggat cgcatcaagg       25920
ggggatatgc tctggatgat tttgtgagag gactccttcc cgaagaggct cagcgccagt      25980
acggaaacat gttcctcatt gacaggaatt tcattctgta tgccgtcagg gtggcaatgt      26040
tcggagacac cattgaattt cgggaaaaca tcgaatgttc tcattgcggc gcttcgcttc      26100
gggaggctac catagacagc gaggttttta ttcccgaaaa tcgtaagttt gagttaaaag      26160 aaggggggtta ttttatccgt tttaagttgc ttaccgtttc agatcagaat gttatgagaa      26220
aagatccact catgaaaagc aactttctga cgcgcacgct ttattacgta atcgatacga      26280
ttgaaaaaga agagcgac attaccgaca aatatgcgct tatccgttct attcctatt         26340 cacttggcac caagatcaga gagtttctga atacacaata tcctcgatt gatattttca       26400 tcaaatgcgg ttcgtgcgaa agcaccatcc cctttgagat gaacgaatcc ttttttttgga     26460 ataagttatg attcagaaga agagcttgaa aaaatcgtgg tagaacggta tgaagcccga     26520
aggaaattgc ttctctttct gaaagaactg gataccattt ccagtttaaa aacgaaaatt      26580
tctatatcag aactccgggt aattgccat atgtatacccc agcaactgga agagcaggaa      26640
agagagttca agcgttttcg ggaccgcac tgaagtcaag cgtggcgtag tcaaattgaa       26700
gggtaagctg cacgttcaca agacccgaag catcggagaa gtcgagcgag tcgccgttga     26760
tgtcggcaac ccaggctccg tggaaagtcc attgttcaat tacggcaccc tgaggatcaa      26820
gaagcagaag ctggatattt ttcttgtaaa catcctgata gccgtcgcgc ccggtggtag      26880
gatcgtggtg tgcaagtacc cactggtaaa ccgccatcat ccccgattcc tcgattggat     26940
cataaagcgt caggttgatt gggttccagc taattttttcc cttatatttg aagtaggtgt    27000
taatgtggtg cacttcgccg acggcaaagc tgaattagg acgcgccgaa gcgtagacca       27060
tgtaggcggg aatcccgtcg atctgcatga ggaaaaggcg tttctgcttg ggttcaaaac     27120
gccggaaaag catgttttca acaacgcgtg ccatatcgtt cctttttctt taaatatgta     27180
taaatcgttt ttcaaaaaaa tgacagggaa aaatattaa agttgacaat aacaacaaa       27240 accggaaaaa atatgtatag ggtaaacgta aaagaagtag accttcgat taccccctgaa     27300
```

```
gtcgggacac cggtccaaac ggcgcttgta ggtgcgttcg atctaccgat tcccagcgaa   27360
cttccggtat cggtaacccc cgatgaattc cgccgcgtcg atcaaccga actcagtctc   27420 attgcagatt cgctggtggg tggtcaggag gttacggtga tcagaccgcg aggagaaacg   27480
caatcgctga atgcggcatt tgttgtggtg ggtggttata atgtaaccct tggtgccttc   27540
aacgttttct atctgatgtt tctggggtat gatcctcaga aaggatatac tgatgtgtct   27600
tatgtagatg tgcaattggc tggtacccca acggatacca ttctgttcag ctactcgctg   27660
gacggttctt cgacaacgca ttcacttacc ataaatctaa acgcccccag tgttacgcta   27720
ccttctaata tcgtaccgct cttttttctac tatgaacctt atacgggttc gattacgctc   27780
cagagttccg ttaactatag tggattaaca ctgaattata cggtcagcaa agcgaccact   27840
ccttgggtgt atttttgctga atatggcacg ccaacatctt ctcttacgct ttataaagga   27900
ttttatctgg aaggaattga cctgaacagc tttaacaaac aatttgttgt atctatcgaa   27960
aatattacgg taaatagaga aaaaggtcag gtgctttatc cttcgtttga tgtggtggta   28020
cacttccggg atattagggg ggtcagtgcc aataccgaat atattcgctt ccgtcaggtc   28080
aatctcaacc ctgaatctcc gaattatatc gagcgcgtaa ttggcaacat gacctttgag   28140
tttgacggtg agcgcattgt tacaggcggt gaatacccca atcaggtacc cttcctccgc   28200
gtggtggtct ctcaggatat taagcaaaac gtcgccgggg ttgaaaagtg ggttccggtt   28260
ggatttgaag gtatttattc tgtaggcgac ttcactgtta ttgttaacga attgaccaat   28320
gtgtcaatcc cggttacgga ttcggctatt attccgccca tgcggtttac ccgcattgaa   28380
cagattacgc tgtcgggcgg tgcttcgttc agcgtgatca gcaatcaacc gtatggtttc   28440
aatattcagg attctcgtca tagctactgg ctctcacctt tcaaagatga tgaactgata   28500
atcggaaccg aactggtact tccggctctg gatgtttcaa cggaattcgg agtttcaagt   28560
tgggaagaag cacttcctga attcagcttc ctgatgccgt tccagggcgg ttcagacgga   28620
tacattcgcg ttgatgaaaa tgagccggat acaatcgggc gcgtgaagat cactccggca   28680
ttgcttgcca actatgaaag gttgcttccg cttctgacgg aagatcaatt cgatctggtg   28740
ctcacgccct atctgacgtt tgctgatcat gccggaacgg tgaatgcttt catcaatcgc   28800
gccgaaaaca ggttcctata tctgtttgac attgccggag atgatgatac cgaaaatctg   28860
gctatttcgc ttgctggata tatcaactcc agcttcgcaa ctacgttctt tccgtgggtg   28920
cgtcgtctga ccaataaggg aatgcgtacg gttccggctt ctcttgcagc ctaccggagc   28980
attcgcacca ccgatccgga gacgggtctg gctccggtgg gagcgcggcg cggcgtggta   29040
acgggcgagc cggtgcgtca ggtggattgg gaagacctgt acaacaaccg aatcaacccg   29100
atcgttcgcg tcggaaacga tgtgcttctc ttcggtcaga agacgatgct caatgtcaat   29160
tcggcgctca atcgaatcaa cgtgcgtcga ctcctgattg ttatgcgcaa tcggatttct   29220
cagattcttt ccagctacct gtttgagaac aacaccagtg aaaaccggct tcgtgccgaa   29280
gcgctggtgc gccagtattt ggaatcactc cgtctccggg gcgctgtaac cgactatgag   29340
gtggcgatcg attcggttac cacaccgacg gatatcgaca acaacacgct ccgcgcacgg   29400
gttacggtgc agcccgcccg ctcgatcgaa tacatcgata ttacctttgt tatcacgccg   29460
acaggcgtag aaatcacctg agaaataaac ctttcaaaat ataaacccgc ctatcaaaag   29520
gggcgggttt ttttatttaa aataaaatga agtttaacaa ctgggttgag ataccgacg   29580 acgtactccg acttgagtat taccttgagt acgaaattcg ccggtggaga tatcagtatt   29640
```

```
gtgatccgtt ccccactttt gaagatttca aagaggcggt caaaaaagcc cctcgaatta    29700
tcgtaacgcc ggaacttgat aaaattataa gaaatcgttc tcgaacccgc acgtttgacg    29760
aactgcttgc attgattaaa acttaccggg gatatccgaa atttcgcaat gaaaagacgc    29820
ttcaggctat atatgacggg tttaaaaaca ataaacccat gaaaatgccg atcgtgttgg    29880
agcttcccga cggaacatta cgggttatgt ctggaaatac ccgtatggat gtggcattcc    29940
agctcgggat aaaccccaaa gttattctgg tgaaggttcc tgataggtgc cattaatcca    30000
cactttccat atcaccatac tgatctacaa tgtaaatctt gttgcagaat tcttttaaatt   30060 tattcagcgg aaccactttg gggttggtga tagcccattc gtttacgata aatgcgtgga    30120
gacgcgatcc catttctttc aaatccctct ggatttgttc aacttcatca tcccattccc    30180
catcacttat cttatggatt cctccacttg gtacgggttt gccaagatag tgaaaaatga    30240
aagggtggga ggagtcgttt ttaagccgct gcaggatttt ctgacctgct ttcgaggaaa    30300
cgctgaacat tttcttttaa ataagattca taatcttcaa ttagcggaaa gtgttcaagc    30360
tgtttgagca gggtgttaac ttcataggca aaacgaaagc gggagttctg gtagaagtct    30420
ccgattgtta ccggaattct gaaatcagga atgttttttga tttcattgtc ttcaatattg    30480
aagacgaaat agcagtgaat gagcgggttt tgaagctctt gcttgataac ataacgatcg    30540
aacattttga tatatttcca gatcacttcc cggttgttca aatagatttc ttttgcccga    30600
ttcgggagaa actttgttat gaagaaatcg tcaagcagct cttcgatctc acttagtgca    30660
ctggtctgct tgttaataaa gcttttaatt actccgttga atccccaag cacacattcg    30720 gagctatcgt gcatgagcac acaatagccg aaaagcgcat cgctacacac ttcgcgagcc    30780
acgtcgtaaa caatcagact atgttcgagc acggaataaa aatatttttcc tccgtttccc    30840 tgatagcggc aaatgttgga gagccttgca gcaacatctt caatggtaat acggtgaagg    30900
ctcgggtgca attcgagttt catggtgtta tgactgtttg gttcacacga cacaatcctt    30960
aaagaggata aggttaaaag aggttccctt ccttcaatta aaattcaaaa atgtcaatat    31020
caatgtcaag atcagtgtcg tcttcggttt tacgttttcg aagaacataa tcgacgtaat    31080
ctatatggac cacaaagtag gaggtatcgt aaatctgaac caaaatcgca ttgacaaacc    31140
gttcaacata cttttttggag gaaaagaaag catttatcaa aatatctaac atcatcttat    31200
aatacctatc gtctgtgttc attacatttt taacaagtac atctttaatt tcatctaata    31260
tagatttgtt ttgaggtata gtttttattg cttgatctgt gatagctttc aataattcat    31320
cgtcattaag tattgttatt acagttttcc ataaatttgt aatcatattg ctgttatttg    31380
aagagaaaaa gttgcgtggg tcacttaaat gcaaaactac acttggtata aataaacggt    31440
aagtattact tacattatct tttaatccat tatcttttaa tcccagaaga gatttatagg    31500
tatcgataat tatagaaatt ttgtcaacat ccattataat atctttgtat ttaagtatat    31560
tttctctggt ggcgtcatta aaatctcttg tcggggtacc aaacagcgtt ttaataatct    31620
catctttcag tttaggtata atctcattta aaatttcctc tcttttttgat tcgtattgtt    31680 ttactttgtt ttctataact aaagacgcga gaaatgtaga aaaaaggtca aatactgttt    31740
ttttggtctt tcattatta ggtctcacca gatcttgata tttataatct ataaaaaatt    31800
tcaaattgtt ttctatttt tttctgttta tgttaataaa tttatctctg agcgttttat    31860
atacgacttc gttttgaaga tggaaatctc ccacaagatc tatggctgac gaactttctg    31920
gtggtatgaa ttgaagtttg acgttcttca caggggaga atcctcttca tagttggctt    31980
ctgcaattct aaacgtttcg gagctaatta tatctgaaat aacttccagt tgggactctc    32040
```

```
tgataaagaa ggaaataaaa tcttttattt tatctttcaa ttgattccag agatcgtaac    32100
cgggtacgta ttcctgaaaa tctgtattca accatatatt aagtactttt cccacacttt    32160
ctattccctc ctttatttcc ttactattaa cagataaacc aatgactttg ttaataacat    32220
tttgtgcaat agttttaact atacccctcaa tgactttttc atccaaactc tgagagggtt    32280
gaagaatata gatgttagat acaaggttct ggagtaatag tagggcttcg ggggaaacat    32340
ttttcatgaa tttatctaaa gtggagtaaa gctcttcgag ttctttcttt gctttatcac    32400
tgagaccgat tatttccgct attttaaagt taatctcttt aataatgggc aaaggtagcg    32460
aaagtgtttc gagattttga ttgaactggt ttttatactc tctgatatcg gttgatttgt    32520
aagtaatgac atgggcaatg acgccgctgg tttcaattgt tccggtaaat gtggatactt    32580
ttattttatg gtaaaagtca tttctcgggt gtataaagag aataaaaaca taatcatgtt    32640
tataattatc ccaatagcta tcgttttgag caatacagac ggtggtactt ttgttggtgt    32700
tggtttcggt taacatttct ttgattcctt gataggatat ttcaggtaaa agtcgaacaa    32760
gtacggcatc gctatcttcc atttccggtt tattatgata gacaagttct atgtccccgt    32820
tcttgatata ttttctgacg gcttccatgg tgttgttcca gcgatccagg tagcgaaccg    32880
tataagaggg gaggtatgta tcgatgatct gctcgagatc gataaagctt ttaataaact    32940
tgaacttcat agaatgaagt tcgtcttttc ttccctcctg actcaatttt ttattgataa    33000 caaaagagc cgccagttta tctacattgc tgagcatgtt atgataataa aaacgattct    33060
ccaccggaat atgactttca tccgatcgat ttgtatacat tgctacaata ccctgtagaa    33120
taaaaacctg agcctgctcc ggaagaggtg tgttgtaggt ggttttttgcc gattgcataa    33180 ttcgatcgac aagttctttt ttgaccttat cttttacaaa actgaaaaac atactttaaa    33240
gctcttgctc tgtagccgtt tccggatcaa tttctatatt gagtgtgggg tcttcgttta    33300 tttttttgtgc cagcttacgt gcaaaattaa tatcgaattg catatttgta gacttttatt    33360
ttaaataact tttcgttttc gggtataaaa aggtctggtt ttgctggtgg attcctccac    33420
ctgaatgttc agcgagaagt tcggatcacg cggaaattcc tgatagtttt ccatatgcat    33480
taaaattttc aggtgatagt ttatttccgc cacaaatacc agttcatcag acgacgggtt    33540
gatcatacga tcggaaattc cttctacgac aatatcccat accgccgcat tgtctttggt    33600
aaggataaga tcgggtctta cgtttgagag aatctgagtg atctcgcttt cttttgtaag    33660
ataataaaaa gcacgatagt tgactttata gggaaccggc accctgtact gaatggtgga    33720
ttggtgttga ttttccgtaa aggtaagaaa agcaggaaaa ttctgtataa cttcgattcc    33780
ttctcgcatg acaacaacga agggatactc cactttgaac atatccgtta ccatcgattt    33840
cctttgcgcc tgagatttgt cgaaaataat gcgcggtttg gtgccaagag ccttttgata    33900
gatttctttt gcaaaaacta cggcaaagta atcggctgta ataatttcgt tcattcttct    33960
tcagggaatg gaagttcttc ttcaccacca cccgtttctt cttcgaattc ttcgaaggct    34020
ccgccaagat taagttcgcc gcccagttct tctccgcctt ccgttccgaa atcgaattcc    34080
gttcttcctc ttggcgattc gatcggggag ccgcgctcgc caaggaagtc ggcggggtt    34140 gtttcctcac cgaatccgcc cgtgtcgaaa agaccgccgc caccggctgc ttccgccact    34200
tcctcctggg gcttgagatc gtagggaatc tgaagaatgt tactataaat ccagtcttca    34260
cgaacccagc ctttgaggcg ttcggcaata ccgattcgct gctcaatcac ggcaaagcgc    34320
tcaccttcca caatcgaatt cgagcggttc attaccaggc ggaaatcctg atcggcaaac    34380
```

```
tctttgttca tgcgcaccat gcgttcgagt tcttccacaa agaaccctg  aatgcgtttg  34440 atcgtgttgt tgaatttgat atcctgagta gccagtgtgt ttttagcatt cacgtctcct  34500
tcataaccaa tgaacgcctt tggtaccttg agtgcggaga tgagtcggtt gagcatgtat  34560
tccacatctt cagcaagatc tactttggaa ccctgaagaa tatcgatttc caccgcacga  34620
cgatctccgc gccggggaat gaagtaatct tgagaatgc  tttcgataga aaagtagtta  34680
tcgattccga gaaattgatt ctgattattt cttacccaat agtctcgctt atactgcatg  34740
gcaatattgg tcagatattc gttgatcttg tcgggcggca cgtttccgac atctacgtaa  34800
aacacccgtc tatcgacact acgaaccaca cggtaaagca tgagcgcatc ttccatgagt  34860
cgaagctggt tccatatcgc tcgagcactt tcaaggtagc ttctaccata ggggaagaag  34920
ttggtgtcga ttttgtgaga aaagtgaatg acatcttcct caggaatatc ttcgttaaag  34980
tatccgctta caacgttacg gtaaacgtcg gtaataacat ataccaggt  atccgtttcg  35040 gggttatatc gctttgagaa aatgtaagga gagaccacct gaaattttc  gatcgtgcca  35100 tccgaacctt tttcaagaat atgaagaaac atatctccgt atttgatcat gttgcgaatg  35160
ataggatagg cgttcttttc aatatttata acataatcca gataggagag tattgctttt  35220
gcaagctcaa tgtctttgt  taccacatcc acaatattac cgttttcgtt gggaatcgtg  35280
cattcatctg caatgatatc cagcaccgtg aaataagcg  gatcggtata atccatgcga  35340
tcgtacatat cgtagaggaa aaaccggttg aattctattc ctccgtagaa cctgctcgca  35400 tacccgctg  tcgcaaacgg gtggtacatg ttaatcggaa tcatggaaga gccacccgca  35460
ccgtgcggcg ctcccatacc atacatcgga gaaggaaat  tggtgaagtt gacagcttcg  35520
ttcagttttt tatattttc  cagagacggc atattctcca cttttttgtt aaataacatt  35580
aacctaataa tgtaccaaat aacgaaatgg tttcgtttat ttaaaagaaa atgacctatc  35640
gggaagccag agcacttttc aacaagatca aaacactccc tgattataga aaccgcgttg  35700
tcattcggat gtctgaaatc agagaaagac ccaccttcaa ccctcgagga caatataata  35760 ccacacccc  cggcacttat gcctatccac ttggcttcgt actggacatc ggggtggg   35820 gcgaggattt tgtcgatttt attgcgggta ttatgctttt gccctacgct tcacatgccg  35880
aatgggtaca tatctttac  ataaaagaca tgggttgttt tctgaatctt ggggataaag  35940
aggatacaga ggaattcctg agaaagtatg cagagaaaaa tccttttata aatactttaa  36000
tagagcacat tcgcatttat cagccgataa atgataatac gctctttccc attctaaacc  36060
gctatcttgt cggaatgcct tatgaaaaca tatcaagcga agagtttcac cagagtttca  36120
acagggttct ggaaaagctg aaagaaggat acatagacat tttcaaaggt gtttaccagc  36180
atatcacccc agatgacgca cctgctgttg ctttcgtgaa cgaattcaga gatttttatt  36240
ccaatctggg ggattatcac actggaaaaa atatactgga agtggcaata gcccgaattg  36300
tgttcgccgt tttcagacgt catgaactta tagaaatgat cgaagcaatg atcggtaatg  36360
caccgggaga aattacctcc tcacgcttta tcaactatct tccggtttct gattccagaa  36420
gtctgagtgc atttacccga tggtttgcca ttacacatcg cctgttttac tatgctttca  36480 ataaagggt  aatcagagag caatatcttg aagaatcggc tacgctgttt gtggatatga  36540
ttttcaccat tgccttttca aggaaaaaa  taagagctgc tatggataca atgttcgaaa  36600
tgttaataga tcaaatcaaa gataaaggta tacccaaatc ctatcgggtt tacagcgaac  36660
ttggttattg cggaatatac gatccgggaa ccggcggtgt gcatgaagcc gaacctgctc  36720
aggtggtctg gtgggatccc tccgtggtgg aatactacgg ggcgattccc aacataggga  36780
```

```
tgcgagaacg taaaattcag aacctgaagg attatataac cgcccttgac gtggtcagat    36840 ttttttgtcaa ggtgtttata tacaataaac atttacttac acaagaaccc cgtttgttta    36900
atcaatcggc tgaggatatt gcttggcatt ttaaaagaat atttttataag aaagaattca    36960 tttaccttt tgaaaaaggt ttgcggatga ttagtagatt tatcaaaaca ggaaatgtaa    37020
atcagttgat gtctcttatt catgatgtac tcatgttgca ccttagaaca gatctcctcg    37080
cgagggtatc tgcagtttat agatcatact ctcttgaaga ttattataac gaagaactca    37140
aacatatgaa gagggtggta ggtgatattg ccgataacat ggttgcactt cttacaaatt    37200
acgccgtgga tattctgacc ggtaaagagc aggttaagga tatagacagc gcatttttccc    37260 attatctcga tcatctcaga gaaaaacttc aagaattgtt agataagtct gctttagagt    37320
tgcgcggaaa agcaggtaca aaaacactat tgcaaagatc tttagcagta gagtcgggga    37380
tagagtctat tctttcagga attatcttca tgagaaagtt tctggaagct tatgattcgg    37440
atagagagaa gattgaggaa gcgttcaggg tggtaaaaga aagactaagg gattaaatac    37500
tggtaattgg gattgtgtgg aatgggtatt tttgaaaaga aggtgaatct gaaagagggg    37560
tggatccacc ttcaacatt tccgtagaaa gaggcaaaaa ggggagaatg ctatgaagat    37620
caaaaaggta attatagcgc tgctgttttct actcacagcc ttccagcttg ggggattat    37680 ggcattgtat ctttttccgc gataagcgcc tgtagctcaa ccggaaagag caccagcctt    37740
ctaagctggt ggttgtgggt tcgagtccca ccgggcgctc agtgtaatc agaaacaaaa    37800 aaagggaggg agtcatgaca gtcatatggg caatctttttt tatagtcatg gtgttgatgg    37860
aaattcgaac ctttcgggta agaggtatc tggaagatca ctccacccga caaggttctt    37920
atgcaaccga atggtattac cgggtggtga atgaaaagga ggaacgtaaa aaaccgggtt    37980
cgcaatggga tttgtaagaa aaaaagagcg ccttattatc aagcgtgatt tcgacgcgct    38040
taaatttgaa gacgcgttcg atcttgagat cgtgtttcac gtcaaccccg aagttgaaat    38100
tattgatcgg ggagaagacg tggttgtcgt atatgccccg cttggcattt tgggaagcgg    38160
ggaaacagtt gaagaggcaa tgaatagttt gcttcttcag gctgtaaagg aatataaaga    38220
gagcacttat gaaggagagc gagagatact tcgttccttt ataaagttgt acacgtcgtt    38280
tctcccgccc gactggaaaa gtcgggtttg agtaataggg cattcgtctg ctctcatgag    38340
taaccgataa ccaaacaaac ggaggtagcc atgaaagagg tcagcgtcac ccatgtcgtc    38400
gtttgcccct tctgtggcaa gacgggcgaa gtcaccatta cggcggatgg gagtggtccc    38460
cgcctcgtgg aaatggagcg catttgcccc cacgtagata ctgaatacga cgaaagaaag    38520
cgggggattt acgtacattt cagtgacggc gaaaggggg actacgtctt cctatacgcc    38580 cccccttgcgc tgtacgtccg ggagggcgat ccccatctga tcgcccgtgc gctccgccgg    38640
cggggcttta aggtacgggt cgacgggcgc cacatcatct tcaagacacc cgtctacccg    38700
tatccggtgg acttggcgct taggcagtat atgcttaacg ccgggcgcac ggtctcatac    38760
aaacacgtgc atctgtgaag attatgtgag ggggttgcgc ggcgcttggc attttcgtat    38820
attagaactg tcaccaacca aacaaaccaa ggaggtagcc acgaaagcga ttgacgttct    38880
caagacattc ccagccccgg acagcttcga gggcgtctat tactgtccgg agcatccaga    38940
ggttgaaatc aaagaaaccg tccgttggac ggaggttcca aaccccaacc ccgacgcccg    39000
caacccggtc gcagtacacc gggttgtgga ccgctggtgc ccggtctgcg ggagaccggc    39060
tgttctggga gctcgatccg catgacgggt gtttcggcga tattcgcaat cttcgcaacg    39120
```

```
ccgaagcaaa gcttgcccgc cacattttaa agtaatttcc gtttatattt acttatattt   39180
acataggggt ttagaacaaa ccggaagata ttatgaagtg gtttaaacga cttacgacgc   39240
tggagatttc ccttcttatt cctctcttta tttccttgag cgtttacttc tccactcagg   39300
gagtcgccaa atttgtggcg cttcctgtgt gggtggtggc actggtaata gcggctattg   39360
acgtggcaaa gttcgtaagt gtgggtctcc ttgttaccac aagggatgg ctgctcaaaa    39420 caattctgat tccggtcatc ctgtgcgccg tctttgccac ttctttcagt ttttatgcgg   39480
cacttgttta ttcacacgcg gagtcggtgt cttcagagaa agttgaaaac atcacagaag   39540
ctaccataac tcgtgaaacc gttcagcgtc agatcgcgcg ttatgagcag cttcttgagg   39600
aggttgaccg ttctattgaa aatatgaaca acacaaccac agagagcatc tggcaagaac   39660
gtctccgcaa gcgagagttg gagtcgctgg tgaatcgaaa ggaggagtac cttgccgcta   39720
ttgactctct tgaagccgtt cttgtaagca gcacggtgga atcgaatcag cgtcaaaatc   39780 tattttcct caactatatt actcccaact tctatttcgt gcttcttacg atcattttcg    39840
atccgcttgc cgttcttctt tacgcgctgt ttgtgcgcat gctgaagcaa aatgcgcgtg   39900
aggaagatga aaagaagtg aaagaggaaa aaacgggagt ggaggttgtg aaacctaatg    39960
aacccgaaga gcaggatttc gtttccaagc aagaggaagc ggagcagctg ctgatggata   40020 aagttttca aaccaaacgc tttgcatttg atccaacccg aatgcaaccc cagaaggtgg    40080
ttatacggga aaaaggagg aggtgatatg tacattgtaa aaaagtcag atattgagt      40140 gagacggcaa cggtaatcgt cgaatattca gattacaggg caaatgtatg ggttgggaag   40200
ggaatctcct gtagagcctt tctcaaaagc aaagaggtta gaacagggt aatcccttac     40260 ctgaccattt acaaaagata ccccagaaat ggaaagctac tggaagattt cttaaaatcg   40320
atggaacaac aatatgtaca acatacgcgt caacacatat agtgtagggc tgcattcgca   40380
ccaagttccg attctcaaag cagccaacga tccttccatt gttgatcaca acatgtatct   40440
gtacattacc gcccgccacc ccttttgcg gctcaagata gatttcacgt ttaacggcaa    40500
caaaagggtg gcgtcatcgg caattattc catgcacaac aggggaaag atctgattaa    40560 agaatataag ctgttcgatc ttgatatata caaaccgaca actgcttcgt ataaaccctc   40620
agataagacc aagactgtaa agttgattta taacttttaa atgataatag acgttgggtg   40680
attatgtatt gtcttcgata taaaatagca gatatacgtt gtgccgccct taacgtacat   40740
gcgtcgaaag tggcacccc ctcctatgta gacatagtga ttaagggggt ttttaagata    40800
aaaaaagggg cgctcagtat cgcggttcat cctgatacac ctgtgggaga cataaggttt   40860
gattgtctca tgaaggttta tggaagcgga gatgtgtttg aaatacactg ttttaaaatc   40920
atttttcatt tgaatgatat taaaaagagg tgttatcgga atcttttaaa gttggttata   40980
agttagtgta aatatgtggg ttctaaaacg gcaagagcag gaaatagggga taaagagtca   41040 ggatacgccg attctggctc ctattaatgc tgaggtggaa atacacatag aaaagtatat   41100
aggcggattt ccgaagacaa aaggcttgta tgcagaagtg atctatgcgt caaaatataa   41160
caaaccggtt gttttgcgc aaaccttaaa tgcgaactac gaaatgtact tatgttctat    41220
tggtatttat aaaaacgtcg gaagacagaa taacattata aacatcttaa aactttatgt   41280
aaacctgtaa caccatgtac gttttaaaaa ttaaaaaata cagctttcat accgatttt    41340 acaaaattcc ggcaaatggt atggtacggg atcctgagaa tgggtatatt gatctttgtc   41400
tcaaaacgga actcccgtta tgtgctttct ttgtaaacta tgaggaagaa gatgaaccgc   41460 gcgttttgt tataaaagag gctggaaaag atcctcagga aactatcgta gaatttattg    41520
```

-continued

```
taagtaaaaa ctttcccatt aataggaatt tcaacataat caaactgata tttgcgccat   41580
gatggttgtt gccggtagaa attacaagct ggaatccagc gaaatgctga ttcccaacgt   41640
ggtggttaca tccaaaaacc gaatctataa cgtttcgata tgggttatag acatcggata   41700
tttctatgcg ggaaatgaac gggggtatct tggattaaga tgtgggggttg aaaaaacgtt  41760 tactggcttt aaaattaatg tctataaaac cacaaatcgc gggaagtgat atgtatatga   41820
taagattgaa atgccacgat tatcccaata cggtcaacag caaaaaaatg gttaattaca   41880
aaataactct gaaatcagaa cacccatcaa acacacttac cattctgata aactgggttt   41940
caaccaatat cgaaagatat ggcaaccata ttatgtttca gcgtcccggt tattacctga   42000
gcgctacgtt tttgtttaaa aaacatcttt atttcaaagg cggttaccat ctacaaagct   42060
ttcgactgta aaaaatgtaa accgatatgt atctcataag acatagtctc aaaaatagggtt  42120 tgcctatcc agaggatcct tactacaaac caccggtttc caccggcggg aaatgggtta   42180
cgcatctggg aaagctttgt aaaatagaat ttcacgcact ggttttgcag aaggaaatgt   42240
gggaagagat aagaagtagg aacaaatcac tattcaacga tcggattcgc aaagtacttt   42300
tgtacgatac tgaagaaaac ctatttgcca tatataagat aatctgatgt ttctgcttaa   42360
gacaacaccg cgcaatcaca atccgcgtca ggtatggttg aaactacctg accagagacg   42420 ggtgttttttt gaggtttcct acagattcgt agaaatttca catgcgactg gaaaccgtgt   42480
taacagaatt ctattacaac tcctgtcgga atatcatttt acatttgtaa aaaggcgga    42540 ctatgctgct ggtcaaaaac agccacatcg atcccaatga tggtgaaatg cggctaaaat   42600
acagccgcgt tatggatgtt aaaatttatc ttggggcgtt tgggaaatac ccaaacccccc  42660 gaagggtgtc ttatagtctg gcacccttttg atgaactgtt tgagtttgca agctggatgt   42720
cacttttgat gatagaaaag cacataaacc ggaaaaagta atatgtacgt gtttaaagta   42780
agttatttta tgaacggcga gccgataggc atacgtaccc tttcaaggtg ggtgcaggtt   42840
gaaattgcct actggggtaa agaaggtaca cgttataaaa gagttaccgg tgggagattt   42900
gaggaaaatg attactggta cgaaatagag ataaaaaaat agaatgtgtc attatgtatc   42960
ttatgagaat gaataaaagt gtaccaataa cacccatttc cgggagggggg agtacactga   43020 gcgggcatag cgagattaga ataggagccg cgtgttttcg cgccatgcac tggacttata   43080
taataagtgt acacataccg aacaatcagt ttagtgtttg tttaatggaa aaaagagaat   43140
taataaacgt attttagac aagcatataa aatgtacgta ttaagtacag gtgttgatga   43200
tccactattt atgaccggaa cttctacacc gggtgtgatc actcccaaag agggttttta   43260
tacaacccag aagtttattc gtgtgtggtt ttttgtacgc tactacagtg ttcccccaaa   43320
atcccacaac gttgtacatt ttaccagcgc caaccattat aaactataa aaaaattcta    43380 ttatgtatac tattaaatta acaaaggggg ttaaaaacaa cgaatgtttt gtggttgtcg   43440
gaaacgaaat tctctccaat gacccccattg taaactataa tatatttagc aaacaggatg  43500
atctgttcgc atttacaatt caatactggc atagcttaag aacactggga ccagaaggca   43560
caccacttga tctggaactg acgtctaatg cgataaatct tggaaggatt tataacgaag   43620
aagatgaacc cttcccggat ttcattttttg aaaaactgat atataaagac tttcaagaaa   43680
gctctaaatt tgggtggtga tgtatataac aatcagaaaa caaatcgaat cggtagtata   43740
cgtagaacct gaattgctat atcatatgtt cgtagaaatg ctgggatacg atgtggtagt   43800
ttatacgcta tatgccgccc aatgtaccaa atatcccgat aataaaacgg gggtggttaa   43860
```

-continued

```
gatgtttagt aaaaagaagg tgttttatgt gctgaaggtg ataaaagtga gcaggaaacc   43920
ttctttctgg aaacgtcttt tagaatgggt aaaagctatt atcaggggt gatatgtatt   43980
acctcaagtt gccggtagca aagcactcac cctttgattg tatctgggtg ttgtttatga   44040
tacattactt tcctgtaagt gtttctttaa acaccccgaa cgctgtatat tttaacatca   44100
aaaattttaa acttattaag agaatttatc aaaggttata atgtggaaca atcaactttg   44160
gggtgatcac aatgattgta cttaaaacac cgatactcag agttacttcg tggttagata   44220
ttagaaccgt tttgtacgtt gaggggattg gatttgttac cagaatcccc tggatgtggg   44280
atattatctt tgaaattgtt tacgtttata ataaaattga gcgtaatgct tgttattata   44340
ccaattacat caatttcact ttgaatcttg attcagtagg cggtaaagcg tttgctgtgt   44400
tgaaaggggt cgcaccagaa caggtttttt ccattattat ggtggttaga agatagaaag   44460
gtgtcatgtt cgtattgaaa atgcgtgttg tcgaaaagat tagagatcat tatgtacctt   44520
ccgactatag atctttata cgtcttggta actatacttg gttctatctt ttttatcatg   44580
acacccatga cataccgttg acaccggcgc ataatacctt cccacaaacg tttgccgcca   44640
tgcagacgct cacggtcaaa tgcaagctgg tcctctctaa ggagcagcga gaagcacttg   44700
acaccaccat gcgagcgttt gccgccgcgt gcaacgatgc aatcgccgtc ggtcgaagac   44760
tgaataccgc gtcgaacatt cgcatccacc gcgtctgcta cagcgacctc agagcaaggc   44820
atggtcttac agccaaccTt gccgtccgtg ccattgcccg agcagcaggc attctcaaag   44880
tcaagaagcg ccagtgcagt acagtacgcc cgacaagcat cgactacgac gcccgcatct   44940
tctccttccg agaagccaac aagcgccgtg gtctggaaga cgcggcaagg agactactac   45000
atcggtatcc acattaacgt agagacgccc ccacctgaag atgagcacgg gtggattggc   45060
gtcgaccttg gaatcgcgag cattgccacg ctgagcgacg gcacggtgtt cagcggcgac   45120
cagatagagc gggtccgtgc tcggtatgaa agaacccgcc gctccctcca gcgaaaaggc   45180
acgaggggcg caaagcgcgt cctgaaacgg ctctcgggaa gggagcggcg cttccagcag   45240
gcgatcaacc acaccatcag tcgccgtatc gtagaccggg ctatcgccga gggtaagggt   45300
gtccggctcg aagacctcag cggcattcgc aaaagtgtgc gcgttcgaaa atcgcagcgc   45360
agaagaatcc accgctgggc gttctatgat ttgcgcatta aaatcgcgta caagtgcgcc   45420
cttgccgggg tgcccttcga gctgattgat ccccgatata cgtctcagcg ctgtccggtc   45480
tgcgggcata ccgagagggc aaaccgcaag agccagagca agtttgtctg ccgctcgtgc   45540
ggattggaag cgaacgccga tgtggttggc gcaattaaca ttgcactcgg gggcgttgtc   45600
aaccgtcccg aagtagcgcc cgatgatgtc gaagcggtgt tgcatggtca gcgccgaact   45660
gagacggagg gcagctacaa gcccacgact gaagtcgtgg gtagttgatg aatatccata   45720
gccatttatt taatcaaaaa tgcttctcga aagccgaaaa ggagaattcc tacaacagga   45780
aattcttcgg ttgtataaaa cctatgggga tcgtcttctg gtaagatttt ccagcgccga   45840
acgcgaaacc ttcaatcccg acgccgacta tttcacaacg cctatcggta cttacgccta   45900
tcctgtcggt gctatcttcc acatttcgga agacgatgtg gtgatcgatc ccgacatgta   45960
cggggtttcc gaaagaaaat atatttattt ttttgtggca agtaaagatg cttcttggct   46020
taacatatcc tctcaacatc cggcgtttga aattcccctt gttttgtaca accagttcag   46080
aaattatgcc gatctctatg acgtttcact ggatgatgtt ttccggaatc gaaacagtat   46140
ggaaagctat cttacctact ggtgctttgc cattgcatcc cgtgtttttct ccgatcttac   46200
agagacactc aagcagaact tgatggaatt gcttcgaaaa gatcttcccc gtatgcgggg   46260
```

```
atattatcag gagctttcaa atatttgcag ggaatttgac gtcgatgttt caagattcta     46320
tcatgcacgt aacaatcccg aagaatggct caatttgctg attgcagaac ttcttgaccg     46380
gctcaacagc ggcttcagac acatgaaatc agccggggat gtaaagcata agtatttcat     46440
gtatcctctg atcgttttta taacattgct tcacaacagg tatgcacctt atccgaattc     46500
cattgaagcg gcttataata taggagccaa aaaagaccct gttgttctga cgggtttcct     46560
tcgaaaggtg ggatatgatg gaatctggga tcatggcacc ggagccattc actccaatga     46620
acccgctcag gtggtctggt ggaaacccac tgctgcaagg ctggtgaaca aaatggataa     46680
ccctctttat gtttcgcctt cctccatagg attcggttat cttgcgtttg ccgatgaagg     46740
ggttgcaccc tccaatgaaa aacagaaaaa atatttatgg aatctgattt taagtggtaa     46800
aatggatgag tttattgaaa tcatggatat gatcatgtac cgtaagtatc ttgcagcgct     46860
tttcaacgcg ttttttgaatg aaagacgggt ggctctcaaa cacgctatcg gattcaaggc     46920
attcaaggaa tatctcaagc aaaatgcaga ggaaatcaga aacttttttca gagtgagcag     46980 caatgcgccg gtgcagcttg tatgggaccg gttcagaaaa gcattcagaa tttctgaatt     47040
acttcgaaac tacgaagaat tgattgaccg gcacccttat gaggtggatg attttgccca     47100
caagcttctt ggtaatttta actttttgaa agaactgatt aagcccacca gactataaaa     47160
cgcaaaataa ttaaaaaaat gaaagttaat taaaataaaa ggaggtcaaa atgaagaggt     47220
tgacaaaaga acagtttatt aacaattttc acgagcccaa ctcgctgcat ttgttcccat     47280
ctatagagga tttcattaac cctcgacaag gagatattac tcaatcctac tgttatgtat     47340
tacctgttca ggatttaaaa atcgacaaca aaatgggcat accggtaaat tttgatttat     47400
cacaggcttt aaataagatg ataggttcta aaggtgagtt gaacaaaaat ttgatcaaac     47460
aaaaaaactc ggcacttaag gaattaaaaa atatattaca gaagtttcac aaaattttac     47520
aatcattaaa atctaatttt aatgaaggga tagcactggt ttttcattcc tttttttttta     47580 tgaaaaagtg cactcctttg atcatgctcg cgcatcgtat gattatgtaa aaagcaaccc     47640
caaaagtgtt ttagagccac tcaatgaagc attaaaatac gatgaagaaa tcgtcgagga     47700
agctattaga gaaacagtat cagattatct ggaaagtgga gactggtatg atatgattga     47760
aaatgcagtc gaaaagtatt tgaggggtta attaaaagaa aaccatgctt gatcagcttc     47820
tttctctttc cgggctttac tttgatcaac agcttttttgc gggttcaccg ggagagttgt     47880
ttttgcggtt ggtggcggaa gcactcgatg aagcggagtt caatgtaagg agtctgcaga     47940
accgaagcta tccgctgact gtagagaata ctgatgatct gctgagactg gcacacctga     48000
acggtgtaag tattaccccc tacgttcagg gaattgtcaa agcagaactt cttgttactt     48060
tccccatttc ggttaccaca tctgttcctg acttgacaac acatgcaccg gaaattctct     48120
acatggatat tcttgccgat acggattatt tctatctgga ttataccgat ttccgccaga     48180
ccgatacccg tatcattacc accagcacca atcttatcta ctcaagagac gtagtctttc     48240
gtcatggtag ggttgagcgg agaagctatc cggtaagtca gacgatcccc ttcatgatgt     48300
tagaacttga ggaagatgtg gtggatgtta agaacgtttt cgtggaatac cctgatggaa     48360
ggctggtcaa gttttaccgc tcacgtaatc ttcatgaaaa tctggtggtt gaaaatgcgg     48420
taatttacaa cacccgccac atttacgacg tggtgttttc tcggggaga gtgcatttgc     48480 ttttcggtag aaagatttct ctggaagacc cgatttcaca taccggctat acttttcccg     48540
ccggaagcac catatatgtc gacacggttg caatcgatcc gactaccctg aacagcttca     48600
```

```
ttccggaact tgaagcagat atcaaaaccg ttaagatcaa caaccgtatt ggggcaaccc   48660
ctcagattca ggtgctcacc gaaggtggat acacttcccg tcttaaagac atcgaatatc   48720
tcaaacggga actgcttgtc gctcttcaga aagacgaact ggaaagagaa atcgcaaaat   48780
atttcgataa atacagattc gttcgagaag atgatattgt ctatgtggaa ggagccatat   48840
accgcaacgg tagattcacc ttccacgaag ccgatcgatt ctatatgcag aaagtggttt   48900
ccacctacaa ccgcaacatg atcgtcagga aaattccgat cacccccctc aagatcatca   48960
ttcgcgcttc caacattctg aaccccggag aactgatcac tttcgtaaaa gattatatca   49020
gaaaacttcc gatcggtgga acgtggatca caaatgaact tgtggggtta ataaaagaaa   49080
aattcaatgt cgtatgtgtg ctggaaattt attttggaga aacttatgcc gaaaggtttt   49140
cggaagatat tatcatctac gacggcgtac tcgacgttga agtgtagaa gtcaaacccg    49200 tactggtttg atgggcgct atgcaaaaac caagggaagg aaatttcaga actttgtaaa    49260
atcgctgctt gaatccacct tcaaaaattg gagcttcaag acagcaatca tgggcgaatc   49320
aggttcagat gtcaagatat ttccggagca gatttttttcg gttgaagtaa acaccacaa    49380 aaacggattg atcagaaagg atgatatgcc ttctgaaacc gtactcaagc aagcacgcga   49440
gcttatccgt aaggaaaaca gtcatttctg tttgatcgtt ttgaaggaga attacaaaac   49500
cccacaatat tttgtgcttt atcgaaacgg aaagctgaga aagctggaag atatatcgga   49560
gcttaaggaa attgtaaaaa gatataaatg atagttactt tgagagaaag accgtattgg   49620
agatatattt acctgttgaa aattccatag cggcgcttaa gcaaaaactg gcaaggttag   49680
ccgctgcaaa cgaaaccgca ggtggaacgc ctggaccccc cattttgctg aactcctgag   49740
caaacttgcg catcatcttc gtcatgaaag aattgaaaga ttttccaaga agcgcatttt   49800
cggtagcgct actggtattg cctatataaa ccctgtctcc atgtagatac atccgttcgg   49860
tggaaatcct cacctttctc tccgcaccca ttagcaattc ttcctgcatg gcaaggtgca   49920
atttttttgc agccacaagg attcgctcac gttgcagcag gtgcagtgaa tccgatctta   49980
ttttaacaac gtaaccgcca ctttcttcat ccaccgactc attcttgaaa gatattttat   50040
atgatttcag atttacctga tcgccgtcta ttttaccata gattccatac ggggatttat   50100
cttcgtcgac agaagtggtt aaatcgtcag agacttcatc actgtacttt ccaagaaaca   50160
gatttccctc ttcgtcaaac catagcgcct gcattccctt tccgttgaga aaatattcac   50220
ccggaaacga tcttatccgt gcccgtttca attgattaat cgtaacacca ctttcattgt   50280
cgttggtggt ttgaaggtag tttgacatgt tgacggggaa ggggaaatac cagagccttc   50340
cattgatttc cacataagca aggagatcac ccacctcagg ataaaatcct atgtgcacga   50400
aaaatggata ggctacacca atcacttctt cagaaatgtc tttgattctg accgccatgt   50460
atctttcggg agtatcgaca tcatctactt ccagtaccaa tccgaatttt accggagatg   50520
aaaagaaaga tattttgctg cttttgttag aaaagaattc ctgagtgttg aaccccattt   50580
tttattttat ttttgttagt taaacatata aactatatag ttttcttttta aataaaacac   50640 caaatgattt ttaacacttc atactattga agatttttca gaatacgatc cacgaccgtg   50700
ttccattttc ggttatcctt atattcacca acaatctctc ctgctatctc gaataccgct   50760
tctccaaaat accacaaatg ttttttccagt tctacgtgca catgatattc gttcctttca   50820
atatagtctt caattaatcg tttgataaaa tgatgtaaaa cgtattcacc ttcgaatctt   50880
tctttaacat aaaacaccac aatttctgct cccagagata ccgcatctgt acctctttga   50940
ctgataggtt catcataacg cattccaacc acaatactca taagaacttc tgagggtaat   51000
```

```
ggatgacctt catgagagtg gaaaagatag tggttagtta ttttagtcag cagcttttt    51060
accgtctctc tatccagaaa gtgtgtgtag ttattgattc tatcttcaat atagtcaacg   51120
aattccaatt gcagtttggt gaatataaat tcttcttggg cgtatagttt atcatataca   51180
aaatctacaa gatcatcatt ttgttcattg tactgatcaa taatggaagt aacaattttt   51240
tctatcttat tctctataaa tttatctacg ttcaatgcgt gtttaaacc ttcctttata    51300
atctctaaaa tttcggggtc tgataaataa tcttcccaca aatcatcttt aagcatatct   51360
ttataaacaa tgaaggcaat cgcatctttt accggttcgg gaatgtgtgg aataaggtct   51420
tcaggttcat ttatgcgtat tgctctttcg atcaacaaac gaatataaaa atctatagat   51480
tcggggtttt gaatattaaa gtcaagtatc ctatcaaggt ctgttctgtc atcaatgcca   51540
tattttagca acagtctctg cttataagat ggaatagacg gcacctgttc cacaataaat   51600
tcataaagag gagaaccctc tttaagattg attacaaaaa ggtctctcaa ataattagca   51660
gccgtcatct ttactcgagc attgacaaac gccatttta taacgtgggg ttcattatag    51720
ttttgaacaa cattaaaaag tgaatgaaaa tgttcagttg attcggctac tattagtttc   51780
ccatttctgg ttcccactat cataaaagaa taaaacaggg atgtgaaata ttccttgccg   51840
gttatgctgt atggaaaatt agactttcgt agtccacaaa aaacaagggc tacgcccctg   51900
tcaacaattg atttcaactt gtttaatatt tgcgaacctt tggtttttat ctcattttgt   51960
ttatgaataa tgaagtttct aagttgcaaa aattgatctt gggtgaccct tgatgaatgc   52020
ttatagatat aattgaatgt ttctaataag tggtgattca agggaatgcc ttcttgggga   52080
tgaaaactaa gttttctac gggtaaaaca taacaccttta aaaacagcga atccccacta   52140
tcgtttggta aaacatacat gaaccagtta attgaagaaa aaaagcttaa cgcctctttg   52200
ctgtggaagt tatccgcaaa ttgttctctt gtcagtatca gcataaacc taagcaaagt    52260
ttattataca aggtaaattt ggattaaata ataaccagac ttctcagatg taattattcg   52320
tcttttccaa ccacatcaga ataaaacgtt tctatttcgt taagatcttt gttgatcaga   52380
gtttcaattt gtttttttca gccccatgac acaccctcca ttttttggca tactaaacaa   52440
ggcaaaaccc agacagttcc atagccgccg acttatttaa agaaaaataa atgaaaaatg   52500
cttcaagtac tgaaagacac ctattaaac agcgcttccc cgcataacaa ctatggagcc   52560
gacgaaattc tccggctcaa tgccacttcc agcattgcat tgcagtttga aaacccgatt   52620
ggaacgggtt atgagattcg cctgtttgtt gccgacgcgt ggattcccca tgtagaatat   52680
ctgggtgggg gaagctatca ccggctgctc ctcaccgttt cgctctacag cttttctatg   52740
gatgaaggat atggaaccga agtagaaccg cttataagcc agagtttcaa ctatgcgtcg   52800
ctgtcaacgc ttcctttacc actggaagtt cgcacggtaa gcgcatttat tcatctggca   52860
ccgctcaagc ggcgtatggt aagcattcca cttacaaact ttttcaacgc cggaaacttt   52920
gttcttatcg aatcggctga ggaaatggcg gtcaacttt tcagcagaca gacgcgcacg    52980
gctttcattc cctatactat tccgacagta tccttgcagc cccggcgct tcagacttc     53040
gtatacgata cccgcataga cgactacgga gtatatctgc aggcttggga gcggaagatt   53100
cccattgcgg taaggggtta tctcatgcag acgctgtcat acatagacct ctcaaccgta   53160
tggtttgaag tatacgtgtt cgacatgatc accggtgagg aacactatta tacatcgctg   53220
cttcccactc ccgttgggaa taactggtac tatattgaca tgagccgtgt caatatgaaa   53280
agaacccagt atgtgagact caaaccggtt ggaagcacca acgacatttt cctttccttc   53340
```

```
cacaaccgct atctgagact atgaacaccc aacagattat aaaacaggag cttgaaaaat   53400
gtaaaaacga tccgatttat ttcattcgta aatatgtgaa aatccagcac ccgatcaagc   53460
gcgtcatacc gttcgatcta tacccgattc aggagaaact cattaacttt tatcatacac   53520
accgatatgt aatcacggaa aaaccccgcc agatgggtgt aacgtggtgt gcagtggcgt   53580
atgcacttca tcagatgatc ttcaactcca actacaaggt actgattgca gccaacaagg   53640
aagccacggc aaaaaacgtg ctggaacgta tcaagtttgc ttatgagcag cttcccagat   53700
ttcttcagat taaaaaacgt acatggaata aaacctatat cgaattttcc aactattctt   53760
ccgcaagagc cgtctcttcc aaaagtgatt ctggacgttc ggaaagtatt acgcttctga   53820
ttgtggaaga agccgcgttc atttccaaca tggaggaact ctgggcttcg gtgcagcaga   53880
cgcttgccac cggtggtaaa tgtatcgtca actccaccta caacgggggtt ggaaactggt   53940 acgaacgcac aatccgagcc gccaaggaag gaaaagcga attcaagtat tttggtatca   54000
aatggagtga tcatcctgag cgagatgaaa atggtttga ggagcaaaaa agattgcttc   54060
ccccacgtgt gtttgctcag gagattctct gcattcctca gggttcggga gaaaacgtca   54120
ttccgttcca tttgatcaga gaagaagaat ttatcgatcc gtttgtggta aaatacggtg   54180
gagattactg ggagtggtac cgcaaacccg gttattactt tatcagcgta gaccctgctt   54240
cgggtagagg ggaagatcga tccgccgtag gtgtgcaggt gctgtgggta gaccctcaga   54300
cgctcaccat tgaacaggtg gcggaattcg cctccgataa aacctcgctt cccgtcatgc   54360
gtcaggtgat caagcagatt tatgacgaat tcaaaccaca actcattttc atcgagacaa   54420
acggtatcgg catgggctc tatcagttca tggaagctta cacgcccagt attgtaggat   54480
actataccac acagcggaaa aaggtgcacg gatcggacct tctggcaaaa ctctacgaag   54540
acggtagatt gattctgaga tcgaaaagac tcttggagca gcttcagcgc acaacatggg   54600
ttaaaaacaa agtggaaaca gcaggaagaa atgacctta catggcgctt atcaacggtc   54660
tcatggctat cgctactcac gaaatcatgg aagccaaccc tgaatgggaa aagattaacg   54720
taaccttcaa cagttatctt gggaataagg taaccccccag cacgctcgac atcaaccaag   54780
agtttggagg agaatttacc tatatcgcca caccgaaggt aaatcctgat ctgaacaaaa   54840
atctattaat tcaaaaaaaa tccgaagatt tcatctggta tatctgaaaa cggctttcca   54900
cacaatccca attaccagta tttaatatcc ctctctgata tactccccccg ttatttaaaa   54960 gaaaatgcca ctgagtagag acatcataaa tcgaatcaaa gagaaacagg atactctcag   55020
agagaatatt acctacagcg caaagcttct caagaagatt acagaaacca accttcagaa   55080
attcttttca gagacgctta catgggggat aagggaagcc aaaaaccttg tactggcaca   55140
acttcctcct gaatacagaa ctcaaaatct aaacaacccc acacttactc ttcactggtt   55200
taccttcaat ttcaatccct ttgtttacaa acgcgaagtt aaaagcaaac tttatgattc   55260
tccgactccc aaggtttatc ctcttaaaag ccatgattat gggtatagaa cggagctttt   55320
gagtgggtct ccggttcctg ctcccaacct tcgctatatt gtcagataca atcctgaaac   55380
cgatcgtctt gaagctcgca cggtggatat taccaccgaa gaaggaatca gatatgtgtg   55440
gggtgcgtcg ggtaatattc ctcaggatac gctcgagttt acatcgctac gtggtcttgg   55500
taaagacgat atgatcgatc tggctcagag cggcgttccc tatgagaact cgctggtgca   55560
gcttttccga aacagagctt ccattgggtt tcagtatgat gaagaccttc gcaaacccat   55620
tcaggtggat cgtatcaata tggaaggatt tactcagaac gaatcggaga ttatcaatga   55680
ttatgttacg ttctatttca agagcgtagt gagcggctgg atatgtcagt tcagagcttt   55740
```

```
tatcaacagt tttggtgaat ccaccaacgc ttcatacaac actcaggatt atatcttcaa    55800
catcatcaaa atgtattcgt atatcaatgt agagaccacc tataacattt cgttcaccct    55860
gtttcctatg agtaagcagg agctttcaaa aatatgggt aagctctcat ttctcaaagc     55920
acacctgttt ccggcaaagc gggtaacacc cggcggcaac tttgtacctc cggtacttga    55980
agtaacgctt ggcaacgtct ggagaaaaag gaaggtgctt cttacttctc tcaatatctc    56040
attcggggaa gataccgtat gggaactgga tccaggtatg caacttcccc agtggatcaa    56100
agtggatctg aatttgattt tgctgtacga acagaatatt accacggaag actggcttca    56160
aaaccgcgtt aaaatgttcg attatacgac aaacaagccg ccttctacgc ttgccgcctc    56220
cgactccatg atcgatcccg caacaggcgt ggcacttgac atttcgacgt tcaaataccc    56280
ggaacccgaa agttttaacc tgaaacttgc aaaactcgat atacttaaaa accttggata    56340
aattatgaaa gtatattctt tttcgggaac gcgacgcgct cagaacatag ccgtacagga    56400
atatggagat tactcctact ggcaagatat gctgcttgca acggtatttt actccggatc    56460
gatcattccc ccgtatgttc cgtcgctttc catttacacc ccggaggaac tcgagaaccg    56520
tctggtagat aaataccata ttcccgatct gaaatatttt taacctatgc tgataagaag    56580
cctgcaccct tccgttgtaa agtatatcag acaatttgct tcgacatcga cggttcagaa    56640
gatttccgca aggcttgtgt tcatggtgcg cgtgagagac gccgcacctt tcagagcgta    56700
caacattgtc ttaaacaaca taaatttcta taccattgaa aacgaaatca ctcctgatct    56760
ccagtcgtac tacgattatc ttccggctcc agctattctt tcggtggacg tcgatccggc    56820
tcctgacggg atatacggta tgatggcgcg tgccaccgtc aatgtgcgtt gcttttctct    56880
caaacaactt cgggaactgg agtggagcct gtttccggga attacggcgc tcattgaagt    56940
agtgcgcaca aacaatgaaa ttcccgtgga tttattttct gatcgctatg tgcgaaatcc    57000
ttcgcttctg aaagacattc ttttagccc gcaatcggta atcaaactcc atgagagaga    57060
tgaaggcaat aggatatttt tccccggaat acttaaaaga acaaatgttt cgtataacaa    57120
caatacccttt gacattacct ttgagtttag taattttagt atagcttccg tattttttc    57180
tcgaaactac gatattaagg atgtagagac ggctcgaaaa acgctggctg gtttctacaa    57240
tgagcgctgg agtacgcttt ccagccagaa gaaagtcaga tcgggtcagg atctgaacct    57300
tgacagaacc tatcagatgt tcggtggggg gaataaagca tttcccgccg aaaagggtat    57360
tgaagtgggc gtgggtactc atttcgatac aggcgacaaa actttcgccc cttcgcttcc    57420
ttccaacacc ttcgagtcgc tggaatatat tcgttttgaa gatttcctga aggaaattct    57480
gattccctat attcgggaca cctacccgga agatgttcct ccggaaatgg caattctacc    57540
gatcgacata gacaactcct atatgttcat tcataaacac ttgagaacca acaacgtaga    57600
tatcattttc ccaaccgaat acatggtgtt cgattctacg aatatgacgc cggattacat    57660
tatgggattt tcagattatg aggatcatgc agagtggttc gagaagaatt tcgggaaacc    57720
ttacacccgt caccgattg gatcagttgg taaagtgggg aaagtgatgt tggctcgaaa    57780
gtatctttcc gaactgatcg gagaattcga acgcggcgac gacaagccgt tcagtttcat    57840
tattgataga atcattcagg atataaataa atccacctat ggcttttctc agcttttcct    57900
gatgaaggtg ggagagcaat acgtcattta tgataataga cttctggatg tagagacgcc    57960
tgttcagcag gtggaaaaca aatcccgtct tgaaccggaa gaaatcaaga tatgggaact    58020
tcacgacatc agctatacgc tggatattcc tgaatatctt gcgatggcgg taatgatgaa    58080
```

```
gcgtctttca gactcgctga ataccaacgt caacgatcca gtggatttcc ttattcccgg    58140
ttccgttgag gatgtggtgc tgaagacgct taccggagag cgtgtgaaag gaaccgcgct    58200
ggaagatacc acggaaagtt cggatgtggt tgttaccaag gtgaacctga gcgctgaagt    58260
aatccgtgca ctcatgaaca atcccaattt cagagcgctc atgaatgtaa tcaaagaaaa    58320
tgaatcgggg ggcaactacg aagccattga aatagaacat attatagcaa aacacggaag    58380
ttatgataac gcttttgcgc tggcgcggct ggcgaacacc cgctttgcgc ggggtaaagt    58440
gtggtatcgg gtaagaggcg atcagaaaga ggaaattacc ggagagcttg taagaaaggt    58500
cgaacaggct tccagcttca gcgatctggt tacgcacccg ttcgtcgatg tgccgaaatc    58560
tcaggtgtcg cttccggttt ctcccggaag atataccacc gcctgtggcg cttaccagtt    58620
tacgaaaaca acatggcggt ggatcgagag agagtacgcc gatctgtggc gggagcttag    58680
taagaaagcg gatgtggcgg tggattccgc cggaaatgaa atggtggtta ccggtcttcc    58740
acccgctacg gtatatgaat atcaggcggt tgtcgacact accgttcagt ctcgaattgt    58800
ggttcctccc acccccgtca atcaggatta catggtggca atttatctca cgatcattct    58860
caacaacgca aaccttaccg aagaagagtg gaatctgttt ttgaacgaag gattcgggtt    58920
taagcgtgag gaaatagtta aagaaaaact taccacccat tttgcttccc tcagaaaagt    58980
caatctcaat gcttcaatca gaagagacgc gtttgagcgc aaaggaaatg tcagtacatt    59040
tttgagtata aaacataagg atctgagcga aacaaaaagt gttaaatcta ttacatttga    59100
tgtaacgaag gttgacgata gatatgtagc ctacattccc atgcacctgt caacctatta    59160
caaagtgctt ctttatatgg gcacgctccc ggaaagacag cggggggaagg gtgctcagta    59220
tctgaccggt attacactca acataacggt tccgggtaat tcgctctgga ggattttttga    59280
cacgttcaaa atagaaggta ttcccgaaat ctattatgaa aacggctatt tcattgtaac    59340
gaaaatctcc cacaacatat caggcggaac atggaccacc ggggttacgg caaaatactt    59400
ttacacgggc aaaacgtaaa aaaaaactat gagcaagtac tttctaaaac caacttctta    59460
cgcttccgac gtttatcttg caccacacgt tcccgaactg gaatacgttc caaaggaact    59520
gataaaaggg tttgacatgc tcctcaactg gatcagtgca ctggaaacaa atcatctgtt    59580
ttacagcgca atcaactatc tggctaaaga ttaccatgta aagaaacacc gcgaatatgt    59640
gatccatttc atttatccta aattcaatct ttcggaaaag gattatccag aaaaagatga    59700
agattcccctt attatgcttc ccgatcaccc ttttgctcgg caccgcaaag aggaaatctt    59760
aaaaccattt aagggtagat atcttgcgtt taccgcttcc ggaagatatc agtttattcg    59820
atccacatgg aaacatcttg taatgaatta tcacactcag aaaattaccg ccttttcttc    59880
gctaaatcag gattatcttg cgctgtgtct tgtaagggaa gccttaatgc gcgttaaggc    59940
aacggggaat aaacggtata tgaacctctg ggagtatttt atagactacg gatatattca    60000
tttcgatgaa ttcatgcacc ataaacaggt agtatatgcc ctttcaatgg tatgggaagc    60060
tttccagaaa tttcctgagg ggcttcagag tgatgaattt attaaagaat atgaaaagct    60120
ctatcgctga cgagtttctg ttacataccc cgtcgatttg atctgcataa tcgcttctct    60180
tctggtagag tcgtacagga tagaagtctc atgatccatg taacccaact ctccggcttt    60240
ttcatgaagg ataccgctca gcgtctgcgc caggttcgag ttgggaagaa tacccggcgt    60300
gatttcgata agatattttc ctccctgttt cgatccgttg agtttgccgc cccaagacc    60360
aaattcccgc aaaacagatt tcaaccttcc gacgttaatt tctttgcttt gagccgtaac    60420
gtatatcgag atcgtattcc gctctttttc ctgctggtat ttgtggttga acaccacttc    60480
```

-continued

```
gatcttttca ggggtttcaa aagcagtttg cagtctggag acaaaacgct caagtaccgg    60540
aatgcggagc gcggctttta caagttgacg cgttcccttc ttctggataa ttttgtgaga    60600
gcgctgaatg atgaatgaaa gatgctgaag cacttccaca gtgaattcgg caatgctttc    60660
gtctacttcg gcaagctgat cgtcgggtaa attgtcggct tcttccagcg attgataaag    60720
tgcgttaatg tattgcctta cttcatcagg gatatagaaa tgcatgaccg gctcaactct    60780
gaaaggtagc gtgccgtaaa aaagtacggc atgaccgttt tctctgttaa tttcgatcat    60840
ggtggtaccg atattctgta aataattacc ttcaatcggc acccttcttt tggacgcccg    60900
ctccagagga atctccatct cctcctgttc gatttcttcc tcttcttcct cctcttcttc    60960
ctgagctaaa acaagcatgt catcttcttc ttcctcgaca taagcaggct caccggtggt    61020
cttgaagaat tggagcgtaa tgattgccac ctcttgcggc tgaggaagtc tgatcacacc    61080
accttctccc cacccggcg gcggctcaaa acccatgcga atcagcgctt gcatttcctc    61140
cggggttgga gccggaagtt ccataccccc ttcggtaatc tgacagataa ttgaaagctc    61200
cgggggattg atgcgcctta cgtaaacgat gcgatcgtaa gggctgtacg caccgacgta    61260
ttcgtgctcc tgcaaagtgg aaaaatagga agaaatgtc tgtattccct ttagcggatt    61320
cattttcttt taaatatatg cttcttcagg aacaagcgaa atggtgggag gagacgtgat    61380
tcgggaaaaa tctttaaatt cataatcatt cccacgatac agtagatatg gagagattcc    61440
ccctacaggc aaaggtggtg tgggttttct tgggggagta ccaccgccgc cgggttcatc    61500
ttcatcgtca tccatatctt tgtttctttt tccaccaaac agattttggc ggtattttgc    61560
ctcgaaaata atttcaataa tgtagtaaag aacaacgcac atgacgatac aggcgagcag    61620
aaaaacgctg acgacaaata tgtactggat caggtactcc atgttacaaa ccgttcaaaa    61680
caacttttac atacgggttt ataatggctt acctccggca caattaaata agggtcttcc    61740
agagggttca ggtaacccat tcccctcaaa tccacacttc cattcacaaa tcgtatgttg    61800
tattgcgttg gattaccgca ctcacaacga ctggaaatgt ttatttttaat gggattgtat    61860
ttttcttcga tctgtttcca taccggaaat tctcttccaa gatagtcggt tctgagaccg    61920
ctgagcacca cttctatttt ccacgaaaaa ataaattcga tctcttcagg tgttgcaaac    61980
tggaattcat caacggctat gagcaacac ctaccggttt taagctggag atattcggct    62040
tcataaaatg tgggttttg aatgaagtcg gtaagattgt aaacgcaaga atgggtaaat    62100
ccgcttcgag atttcaaggt aggggaatag ccgtaaatgc ttccgggttt aaagacaaga    62160
taatcgtcaa agtttctaa aagttttata agaaaatgag ttttacccga tgccatcgcc    62220
ccgttgatga cggtaacgga gcgggttgag cgttccttca gaaatttat aacagcctta    62280
tccagttcga tattgtgcag ggtggtatct ccggaaagcg tctcagggaa atcgtacttc    62340
atagttgatt tatttttaag ccgaagtctc tgaccacaag gggtttgtca tcggttctac    62400
cccagttgtc gatcagggta aaatcctcac ccagcagatt gaattgccga atcagcctta    62460
cggtttcccg gattacagga ttttaagaa cggtgaagta aaaagtgtgc ctatcttcta    62520
cgcttacgtt gtcaagcgtg agtctattaa tggcatttcc aaatatatcg gcaaaacgcc    62580
tatcataagc agaaaccacc tcgaaaccct cgaacgttgc gtcttcccgt aagtagcgtt    62640
tccggataaa cccttcaatc agaacactat aaacatcaaa gtcaatatca gcgacacttt    62700
caaaataggc ttcattgaca ggtgcgacaa attcggtgat tagaaccca ccttctttga    62760
aaacctgagc gtagtcgacg gcgatttcac ttcctgacct acgcaccacc tcatattcgg    62820
```

```
taatgttctg tttgattcca ttgtcattat gagcaatttt caaaaccagt tcggtgtcgg    62880
gtattctgaa tacttctctc cctcttcccc ttttgacggg ttcaaggtat ttcttttgag    62940
ccagaaggta agccgcgcga agcgggtttt cacttcgctg aaagtaagtc agaatatccc    63000
ggagcgtgtc tgtttctttt aaggttatca taggctaatc cagtgttata tcatacatga    63060
tttgtgcggc aaccacttct ttaaaatatt caacgaaatc tctgtcgtct ctaacgtcct    63120
ttaaatactt ttctatttcc ggttttacat attcaaaaaa ctcatccata taacttgtt    63180 tgataaataa tgtaaaatga tccccctctt catccatatt gagtttgtta atgataacac    63240
cataagcaat tcgtataaag gtttgtacat ctattacgtg gcgaaggtct ttctgaataa    63300
ggatattttc tatcttatgc tttattggaa aatatccgga aagaaaccga atcgcttcct    63360
caagattttt gctgacaaaa gctataatat cgctctgcag ttttcgcaaa atataatgat    63420
aatgtgcatc ttcgatttta taataagccg catctctgag ataatcgtat atctgatccg    63480
cgatattaag atgatctatt gcttccttta tggcttttgc tttgaaattt ctgtcaaaga    63540
aaattgggtg ttgccttctt tcctcttctt caaatttacg tacaacatat tgtgcgatcg    63600
gatttaaatg atcttgcccg taatgataag ccgcgaatct tatgacattt gaccagaaat    63660
attcgatttg gggaggaaaa agcacattta ttagactggt tccaccgtat tcttcataaa    63720
gaaaagagcg aacacaccag cggataatgt cttcgttatt tttataatcc gacagaatca    63780
aataaacctg attggtggga tcgaagccgc caagtacatc tcgagtcaat tttgagattg    63840
tctctttcag ttcaaaagaa ggggtggttt cttttagcag gaatatcatt ccgtccccgc    63900
ggggtatttt accttcgtgg atgtaaaaat agtagtacat ttcacgggtt acaatgatat    63960
tccagagagg agtagccacc cattgataaa cttcgtcatc ataccgcgcc cctataagta    64020
tagaacccat aaacagaaaa tctatatctc gatactttc attgagcgtg cttacctcaa    64080
taatcacaaa aaaatggtct gtcatggact tcaattttct ttccaataac accaatgttt    64140 ttcctgttttt tatcaacgct ttccgtgttt cttcaagtag ttcacccgcc cattggtgct    64200 gtcttaatt ttcttcaatg aaattttgt aaatctgttg gtacataaca tttgacaggc    64260
ttgttctggt aagatcctct gaagtcaata tgaaatagtt ggtgttgtaa taatatgggg    64320
tgtttggggg caaattggtt ttaataaact gttgacttaa cccgttgaac aacggtttat    64380
taagaacaaa ggtatcggtg tttatcgttt ccattggttt ttatttaaat aaaaagaacg    64440
tatgagagaa cctttttctgt ttcgagatcc gacaatcgaa agctttggaa gcttttttatt    64500 ggaataccttt gacattcagg aagttcgtgt taaaaccgaa ttttttcggcg gtaaactgca    64560 aaaactcaaa gatggttatc atttttccgga tgtaaaactt aaacccggta aagatgtcga    64620
aaagttccga actctgtgca acgcattcgg gtttgatgtg gaaatatccg aaaacgggat    64680
aacgttcaca aaaagacagg aatattgttt tatcgaggag gctctgaaaa aggcgacaga    64740
gaaatatcag attttcgttc ttgcaccaat agaagttgat cttgttttta catgttgcaa    64800
ccagatattt gtcgaatatg aaatatgagc actgttaaaa tacctttagc cgttaacata    64860
tacgacccca agggcgacga atgggaattt atctacagca actatgcggt agaagttgta    64920
ggaagtgaat atctggttcc ggttgtaaca ctgaaaaccg gatcggttaa ctatttcaga    64980
ttcaatgtgc ttctaaccta ctctcagacc gggtctttcc ccctttatct gaattttctg    65040
aacaaaaaca ccaatcagat caatgtagtt taccgaaata tcagttacag ttatatcagt    65100
tccagcaatg tgaactggta tcccacaagt atatccggtc ttcttggttg gtggcaagca    65160
tatcatccgt cacgtgttaa agattacatc atagaccgca ctgaaaacca gagccatctg    65220
```

```
gtaaaaattg aaaggtatac ctataatgat cagtggctta accctacaac aacattcgtt   65280
tctcatgaga gtaataggat aaaaatgatg cttccaatga atgatttgat tgataatcac   65340
gggaataact gggtgtcaga accccgaaat tcttatgtag gatatgtttc acaatctcag   65400
aaattcctgt cgaaggaata cacttttttc tatgttttt cggtagttga aaaaacccc   65460 tatgtaacag taagtgggga gccgctgata ccgggtgctg catatcccgc cctttcaaca   65520
agctattact ctattattcc caagggtggc gaatatctgg ctggtttaca tatatttcgt   65580
tctaaaactt atagttctgt aaacgataaa atgaatacgg cttctcttat gattcttttt   65640
accacctatc ccgttataag tagttctacg tttgctccgg aatataaggg ggataatgaa   65700
aacgcttttt ccaatacaca atatcgcata caccccgcta tagcggctat cggagagaaa   65760
gatttaaagt ctcattatgt tccgggaata agaatagtct atcatacaga atctacaatg   65820
aacccgggag ttcagcttta tgagctttat cttggttata agaataccac ttcactttat   65880
gaactggaag taacttcttc agatatagca cgttttgatg tacctaccat tgtagggtac   65940
cgcattaaac aaagtggtag cgttatttct tattctgtta ctttgaacaa tgaaccgccg   66000
gtatggtatg taattacggc aagcattcct tccatcgatc tttctgatcc gattttacc   66060 gatcatagaa acgaagccgg cattattata gggtcgctgt acgggtatct atatgattat   66120
cagcttggag atgtcggaaa tctttcggct atttatcggt ggggatccaa gggtatttac   66180
ttttatgaag cactgttata tacccgctcg cttgacgatg cagaatacca gcaagtgaac   66240
gaacaccttg ttaagaaata ccgattcggg ctgtaatggg aagaataaat acgacatatt   66300
ttatttatct gtatttcccg cgtatagata taagcggtct tgataatata catattgaaa   66360
tagaaatatt gggtggcttt agttttacac ccgtttctta tacctacaat acatctggct   66420
cttttattac aacagaaacc cccgttgtca gggtgatgga aaatcgcaca ccggatatat   66480
accttcatgt tgtgagttta agtgctttat atagtaattt cgaccctct cttcattctt   66540 ggcatatctg gcttgatttc acaaggctta cggcttctaa aaccgacggt caacctgttt   66600
atacatcgga tatacaatcc attcagagtg atatatctat ggaaaactcc ggaggctata   66660
cgtattatga aaatattatg aatgggcttc ctatggtgcg aaccaacaat acaggattga   66720
caaaaaccgg tggcattctg acggatgatc cgatcatggt agtcgcagcg gtttatatca   66780
gccaatccgc tacatattgt cgtcttataa gctggggata tagtattaat gaagcatggg   66840
atgtatatgc tgagttttct ggcgcgttgg taagatttat atttgtcacc gatacggcga   66900
cggctgggag cggtcctact ataaccagtg actggttcag ttatcctcag gggtttgtac   66960
ttgccgcatg gcaagaggat gacgaaacca tgcatttccg gattatggat gaaagcggaa   67020
atgagtacga ttatcctgta attaccggac gcggggggcgg attttcaaac ttcagattgt   67080
tcgatattta ttatccaagt tacaactggg gatttaataa ttatgtggga gaaatcattg   67140
ttcacaatga tatatatatg gttgaagacg tctttcatta tatggctttc aaatgggtgc   67200
cgggattaac cggaagggtg cggataaatc gcttgtggga aaatctttat aaacctgaat   67260
tatatacatc gctcaatagt gttgtactta ttacaggctc aacatctttt accggttcta   67320
ttattaataa cgatccaatt attctaactt caataaataa catagataca ctacaatgga   67380
acccgcaatt taccggatct attgtcaata acaacccaat catcctaacc ccgtaaaaca   67440
acatagatac actacaatgg aacccgcaat ttaccggatc tattgtcaat aacaaccctg   67500
ttttgttaac aacgataagt aacgtattac ttttgatgtt taattaataa aaaaccacg   67560
```

```
aaagctatgc cttattattt cgagtttaaa gttagagaac tggatcttga accggtaagt    67620
gtaacgctct ctccggctcc aagttgggtt tcggtttata aatacaacac ccagccttt     67680
gaccaatttt acggaactta tgacattaca gtgtttctgg tagcaaaccc accccggga     67740
acaccggatg gtacctattc gatagggctt actttgagcg acgcgctggg cggaataacc    67800
acacattcag tcaatttcat aatcaacact tctggaacca ttacatttga tcctgtttcg    67860
gtgccgggc tctgggttg gtggcaaccc ggaaactggc ttactcagag cagtgatact      67920
ttcaatgatg tggctatatg gtatgacgct tctccggggg cacatcatct tacacttgat    67980
aggagaatta ctattttacc atggaatagt acagatgctg gaagtgctta tgtcggatct    68040
tacataaaaa cactttcgga taattcactt ctgttttcat ggagccatgt caatcaccaa    68100
tttgccaata tgaattattc gtcggggct gataactaca aacccgaaaa tgttttgatt     68160
acaaaagata cttctttta ctccaatcag tactctattt tctttgttta tagaaatcat     68220
ctcgactggt tttctcatcg tataaccgga atgagattaa ctataaatca ctatgaatac    68280
tgggcaacca atatatggga ctttgatgtt gaacgggta ataatcatct tgcaatgccg     68340
gtctattccc cggtggtgat taacagacg gcgccttata caaccgtctc ttatggatca     68400
tactggaatg acgattataa tcacgggttt gtcggcggct ggtttattgc gttctgtctt    68460
cctccctatg ccgctaatcc gtcagccaga gacgcttatt actatgatga cggggggcgga 68520
cttaccacca tgagcgtatt caactatgcc cccggctatt accagaataa tgttccgcat    68580
caaccttata ttaccatatt caaagttaat aaatatgctt ctcaaacaga tgggtctctc    68640
ggtattcacc ctattaaatt gttttattac accaatgaag aatatgcgtc tatgtcgcta    68700
attgaaagaa acaacaggtt cagcagattt gtctttacta aagatcagtg gaatgctgtt    68760
ggatatattg ttgaggaaaa tcccttatt tccaacagcg ttgttatcgg ttattcctac     68820
acttacagca tttatttcaa cgaaacaact tccgttacaa aatctctgga agtaacatttt   68880
tatgacataa atggcaattt cagaccccg acaacttatg cttatattga cggttcagac    68940
aaccagcagg catatataga cgtatatggt gggtttggca taggaacacg ttttgcgaca   69000
gctcagagtc aatattatgc caacaccggt actataggat ggagaactta taactttaca   69060
cccggggtgt tttctctctc tttcaaggaa tgtctgtttt atacccgcgc attatggaac   69120
gaagcgcccc agatcatgga ttatcttatg aaaaacacg gtatcccgtt tgtaagctga    69180
tatgctggaa tttacctaca gtggtacgtt ttcatacccg gatagtcaaa cactttccag   69240
tttttactgg attattaacg ccccgtctgg aagtgttgtt acttattccg aaattttaaa   69300
ccccccgctt aaagaaatcc ctattgaagt aaccatttcc ctcgatacca caagtatacc   69360
gtcaggaaat gtaacatgga gtgttaactt ttttgcatat acaaccacct ctattacagg   69420
agaagtttat ctttatattt ccaatatctc aggattggaa ccatatagca tatctatctt   69480
tctgacttca agtatgaga aagaagggct ctggagaaat ctcgggttgg gtgaatcttt    69540
ttactgctat tcgctttcca ccactccgaa tgtacgattt atcaaacaca ccatttctct   69600
tcagagtatc agtttgatac cagccggtgg tagtatcaaa tgggaaaaac ccccggaaaa   69660
aacttattat tcttttttcga ttttcgccaa agggttttc cttagaacag ttgattttga    69720
ggggttgact acaagtcagc ttagctggta taatgatatt ccatttgctg tttcaggagc    69780
ctatctgtat accggatcag gatttccgct cattactttt atcaaccaga gtatgcttta   69840
tctggtaact tcatcggggg acttcagtaa cttttgtttt agagatctga caactaacac    69900
cgatgtgttt tctttcagtg tggaatatcc aacgctttct cttgcaagaa tatatatcac    69960
```

```
ctacgatggg aatgattttg tcataacatt cagcagtact gttagtgatt attactatac   70020
ctataatttg cccggactca gttttttctga tcatctactt attgggaatt atcaatcttt   70080
ttcgggtcat tccgcatgga actcttttat tgtacttgac tataatgcga caggaagtgc   70140
gtaccagaca ataagcaacc tgatatgagc cattttgatg aactacacga acattacagc   70200
accaccacgc tcagcgttaa cggggtagtg gtaagtcata gttacagagc atttccttcg   70260
cttagctacg ttgaaattac gctgtacaac gtacctgcac ctactggatc aaattatttc   70320
tttgtttatg atcacgttta caatcaaaac atatttcttt atgcgctgaa acctcaggat   70380
atagggaaag aaattctgga aacggttagt ttcaggatta ttgttgattg atcatcaata   70440
gataataaat tctggttttg taagcgtaat attgatctca aaccaccgt cttcgataaa   70500 cagtgcccct gctcctgaaa gtgtgtaatt tcctgtaatt atattgattc ttctgttgaa   70560
atgggatgta gtcaattccc atatactacc acccgaaaca aacgtctcaa attcttcttc   70620
ctctataaca ggttgatgtt ctatctcaac cagactcata gaagcaatta tggtgcgcct   70680
gtagttgaat tcagatatat gattcatttc tattgtgctg taggaaacga gtcggaattg   70740
ttgatgttcg ggaatggtga taaccgaaag agatatcccg tctactttgt gagaaaagaa   70800
aattctgttt tgagcgaagt ttgagtaaat agagtcgtgg gttttggtat atgtcccaag   70860
cccgatatat ctcaaataat atcttaccgg atattccaga ctaccgctga agttgtagat   70920
tttatcaaga atgcgttcct gaagtgcagc atatcgtatt tcacttgctg taaatacata   70980
aggtatggtg gtgcggatat acgggaatgt aatataatcc agttcagagc cggtaagtgc   71040
tatgatacct ttgaaaatct catttggaaa cgtgatataa cttatagata attgtgtata   71100
ggtataaaga taggtaagtc tcctgttttc aaacgtttct acaaaggaaa tggtatccat   71160
tgaatggctt gcgaagaaaa agagataatt ttcaatcaga tgctgtaaag tagcattaac   71220
aagagatttt gttaaacgat taaaatagag ggttctgttg aaatgaaaag atacataatc   71280
taacccgtaa ttattggttc gaagtgcaat aagatcagtg ttttgctcaa caggagcatt   71340
tacaaaccct gaaagcgttc taaaaagggt atatattttc cccgtctgaa aagcctctaa   71400
gttcaatccg atcggatcgg taagatatcc cctgaaatat ttttcattgc gcaattgtgt   71460
attgaagctt acgtaatagc tgaaggagta aagggtagtt ggatcaactg tatcgtgaac   71520
aggaggaaca atcaaatcat aagtcatggg gagaaagtct atttttttcaa tgctgattgg   71580 atcataaaac tcattttttcc acccaatgcg gttgaacaca aagaacggag gaactccttc   71640
ggtggaataa gtgccagcgg gtatggaacc agacaaaacg aattctgaat aagtgggtct   71700
gtaggtgtaa agccgataga tgatagattg ggaatactga gatgtagtag actgatgata   71760
taccgaaacg gtgaacgaat gggttccgga tacgaaccca ctcattgtga tataaagaac   71820
caattctttg tattcaggat ttccctgata gaaattatca attatgctgt gcgaaaaaac   71880
aaaaggtgga agggatgata ccacttccac ctgattgaga aatacccttc ttacagggta   71940
agaaactgaa taagtcatgg tttcatatca tcacttaagg attacaaagt ggtcagcatg   72000
aacgtctgca cggttcataa gcgtgaagct acgcgcggca agatactgtt caagcaggat   72060
aatatcgcgc tccgtcggtg atttgataat aaccagttcg taaatgctac cgacaagcgg   72120
gcgcacgccg tcggtaccaa ttgtgagaat attgattccg tctggaccca ccgccacatt   72180
gttcatcaag gggataccgg aaatccggag cgaactgttc ccgctgaaca cacccactac   72240
cacctgatcg cgggtagcga gtgaaagcgt atattccgtg ctggagcctc cgattcccca   72300
```

```
gttgtgggc  atttcacaga  aaatatgggg  gttgacagaa  agtgtaccac  cggagaacaa  72360
cccaccgttg  gcgaaagaac  ccacaatacc  gatagcgaac  ggctgctcga  tttccagacc  72420
ggtaccttcg  agacccatcg  accgaagcca  ttcgtttcca  cggaacacca  ccgccgacaa  72480
tccgttgtat  gcatcccgca  cgaaaatggg  ctggttatcc  gggttggatt  gtgtgaggga  72540
gtaagataga  taagccgatg  ttgaaacata  tgctggcacc  cacgcatcaa  ccttatcgcc  72600
cgtgttgtag  gaagccgtga  gggtgttcgc  atcaaagcga  agcaccactt  tgggcaccca  72660
gctttcaatg  gtttccgccg  gatcgacaaa  ataggggatg  ttatatttct  tagccagata  72720
gttttcaacg  ttctgacgtt  cagcgttggt  aagtttacgg  tcaaacacgc  atagctcagc  72780
aatatagcct  ctcaggttcc  accctatgaa  catattcgat  tcaacacggt  taccggtctt  72840
accttccata  taccgcacac  cgttgatgta  aatgcggtca  agcggatatt  tggggtggga  72900
agtagcaaag  cgaacatcgt  tggttgttgg  cgaaccagag  agaccactaa  tgtggtacag  72960
attgacatat  gaacctgttt  cattttcaag  tatcaccgta  atgatattcc  agtcattcag  73020
gggtacaaaa  gcgtctgcgg  gttgtggaac  agtattgtac  ccaccgtaag  agtccggtag  73080
tgcgttggag  actcgagggt  tgcgatatga  agagttcaaa  taaatccagt  gttcaacctg  73140
attttctttt  acttcaaggc  ggggcacaat  tactgaataa  ctgtgaacat  tattttcatc  73200
aaccattctg  aaataaggta  catccgtatc  gtctgtgttg  tgagtatccg  actttggttg  73260
aggatcccac  atggagaaca  tccacagaaa  cctacccgga  atgtttccgt  aatttactga  73320
attgttagga  atgggattag  aagaattggt  tgtaatattg  ctgtaattcg  gatgataaac  73380
ccacaccgat  ccactctgca  caaacacccc  agatgtcgta  tccgggagtc  tatccagttt  73440
ggcaaccatg  ataatggtgc  gttcagtatt  ctgagaataa  tctccggtgc  ccggatagtt  73500
aatacgcata  accgaaccgg  aaccgaaata  ccaagccgga  taaccgttga  caatattttc  73560
gacgaaaata  ggtttgcgga  aatcgttaac  ctgagtagct  ttaaatccgg  aatatgcggg  73620
aacaaggttg  ggaatttcgt  caacgtaatc  gccggtttca  agctgaggag  tggagccgtc  73680
ggcgctcatc  cagattttgc  agttggggac  gtccgacggc  gaagaatacg  cattgatcgt  73740
ctgaacataa  atgggataag  tgcgaactgt  ttccggggta  acgccatcgg  tagagcgtac  73800
cgtaatgctg  taggtgcccg  gcgctacacc  cgacagatca  ccgtatacac  tcagaatccc  73860
ttcggtgcgc  ccgtcgggaa  gaatggactg  ggtaaaatca  tatccggtaa  cccagctcgg  73920
ggcggcggaa  accgtagcag  taatcgtatt  accgtcgtta  tcgtagatat  aaatggaaaa  73980
cgttacggtg  ttagaactct  ggtaagtcgg  cattgtttat  cccggttttg  ttttaaatat  74040
tcttatttca  ctcaaaataa  aaagtcaaat  agagataagg  cacagaaata  ctgctatagt  74100
cattgatgga  gtctatatag  tcttttccaa  tatacatgtg  tgtgataaca  tctccgctat  74160
tatagtcata  catcaagatg  tattcggcta  catcgggagg  aatgttgttc  ataaagaacc  74220
ctgaaaatgt  tatggagtaa  atatttccgt  caaactgttc  gtcaatcata  ctgacagttt  74280
gcgtcagatc  cccccccact  acccgttaca  acatacaaac  tgaaagatga  gtgtgtaacg  74340
ttaaattccg  gataataaga  attaaccggc  accactgaaa  gagttttttcc  atagaaaata  74400 tttcttaccg  cttcttttaaa  agcattcatt  atggtttctt  ttcggtaaaa  aggttcggtg  74460
ttgtaagata  gattgataaa  tccatagatt  ttatctctgt  atagagagta  actgtaacct  74520
actctatagt  taattaagtt  gtattcctga  tttagtgtat  ggttaacagg  ctgactgtat  74580
acccatttgt  aagcaagcca  gcggtgtttt  tcatacatgc  tggatataag  cggctttcga  74640
gagatcacag  gcgatgtgtt  tctttgagta  gcatttatcc  agtaattgat  aggcgattcc  74700
```

```
accttctgc tcatgatgtt tgttctattt ccggcaatga tcgctcttct taatgtgtgt   74760
ttattaatcg ttttgaacaa ttgtcgatag atagtgcggg tcttgttttt gacagtgttt   74820
ccggttctat gatatgctat aagtatctgt cggagttggt tgagatcaag gagaaaattt   74880
tgagttttct ttacagaagt gagcaggacg ttaccctgaa aacttggaaa gaagtctctg   74940
gtggtacgga taacttcccg gattttaaa agtctccggt caaaatgggg gatatcatag   75000
cttgcataaa tgttagtgcc cctgaagaac aatccgatta ttctatcaat ggttgtttta   75060
tagtttaatt ttattgtgcg tatggttaat tttatcaaac gttgcatctg atttgctata   75120
aggttaaggt acttttaaa actcagaagt ctgatggtta catatggctc taaggtggaa   75180
taaatgattt ttccaacaaa tctgacctgt ttaataatct gttggtaaaa acgtagcaca   75240
tagttaaccg gtgtgtatcc ggtcaaagtt ttaaagaaag ttttattcac cagagtcgat   75300
ttaatgagtg atctggtctt gatgatagtt ttaataaaaa agtttttgat tgaattcaac   75360
agactgttaa aggaggtaga tatatttaaa actttaaaaa attcttcagt gctccataca   75420
aaagcggaaa gcaatttatt gaaagttttt aaattgggaa atctcagttt taaagtgggg   75480
gtgtagttga caggtgtgtt ttttgttttc aagatatact tgaactcatt agaactaaga   75540
ggttggttga cagcattata tccattgaaa agcgtaagtg cgtaggggtt gtcgtagttg   75600
ttgtcaagga aaagtcgaag tgctgtcggg tcatcatttt ctatcaacag cggatcatca   75660
atcgggtcta tataaggatc atagggaacg gaaaatatat ccctgaaatc gtttgtcgaa   75720
gtataaatat aagataatgt atagttaaag attaccgact ttgtttcata tttgtcagtt   75780
gaataaaacc tgaaccgtat acttccagta taccagtcag gcggaaagga agatgccgtt   75840
aaaagattga gataggttat agtagacccg gagtgcgata caccaaacca gaacttattg   75900 ggtgggatt gttgaacgat aagtgggctg aatactcctc ttcctttgtg gtctacttta   75960
aatctcattt tgttcgtagg ttatgtcata ttcgtccagt atcaaagcgt tgtcaacaaa   76020
tagagaattt tcatatccgt gcatgaatgg aatgggttct ccatcgagtg atatgtcttg   76080
aataccaatg aatatgggaa aatacagact gatcgatata tccattactt ctataatcgg   76140
ataatgatat tcgatagtta tattgaatac tgttatttca gggtaattca aacttatggt   76200
gaagataaac ccatattcca taagagggtg atatagatta attgaaatgg tgttgaagtt   76260
aatgtcaaaa tcgagggtgg attcatattg tgtgctgaac gttttgccgt ttatgtcgct   76320
gagatcaggt gaataaagat aaatattaaa atcgagggg gtatctataa tcaaagcttc   76380
catatctata taatagaggt ctatatcggc aatctttttt ccttgataat acacatcata   76440
ttccagatct tttgaaaaac tggtactgaa aaaataccgg taagtgtcaa acagatcaag   76500
aattattgaa actgtgtgtt cgttttggaa gaccagacta taactgacat ctgaaactaa   76560
cgtcagacta ctggtactta caggatatct gaaatcaatg tctctataac gtaaatacct   76620
gtcggctgat tcggtatata cttttattat gtaatctgta ttaatactca taatttatcg   76680
atataagttc gtttccctt ttaaccagaa tagtactgat gggtacattt ccgttcatga   76740
attcaccaag catatcgata taaaatctca cttcttccct cacttccagc ataagtgtgg   76800
ggggtatttc aagatagaca ataccatctt gataggaacc ttttacatat tcacggtttt   76860
tataccaatt gatatatcgg ctcatagaat gttgaatttt ccaatcgtct ttttaaagg   76920 aaaacattcc ttcatatttg ttgaagggat cgtaaacgaa accgacgtag tctttcatgt   76980
ttttctttaa ataaacaggc ggttgtgttt ttattcagaa aaaacttatt taagaaaaa   77040
```

```
agatgtatac cgaactgttc aagaaaagca acccgcacaa ctcatattac tatcattacg   77100
tgcattttga cagtaattca aacacacatt caatcgatgt tcccggcgga aatgcgctca   77160
aaaacattct tattgtgggt aacgcttcta ccccttattt tgtctctttt aaaatctata   77220
catcgcatag cgggtttgtg ccggttccag tatcctacga ttacgaagcg cttggaaaca   77280
atgcgctgat tacccctaat atctcttcat ttgcagtttt ttcctctatt caaacctcat   77340
cgcttcgcat tagcattacc aatatcaccc cgtttagcgg aagtgtttac atactgttta   77400
aagtcgagta acgtatgttt tacgaacctt ctgtaagctt ttttgcagta tatcctcagt   77460
acagcaccag cgcggctttt ctcacagaat tcaataaatc atcggcgtgg gtgctccaca   77520
aactgggcta cccggtggta tcggtggaat tgacgaaaga tcagcttatg tttctctttc   77580
acgaagcatg gcaagaatac tctcagtata tttcagaatt tctgattcag gaaaactatg   77640
ataacgtttt aataaaaaac attttccaga cggaagggga aatctttgag aagtttccca   77700
aacctaacag ttcgcttatc atcgagcttt ctgatcgcta tggaatgtac gacatgaaca   77760
ccgaatatgt aatcattcca cttaccgctt ctcaatcggt ttatgacttg aagaattaca   77820
ttaccgcatc cggaaaaatt cacgttcagc aggtgcttgt caatagaccg cgcgttggtc   77880
ttggttctac gctgtacggt aatgcttttg tcttcaacaa ctattctccc ttcaccgtag   77940
gatacggcgc gggctggaat atcggtcagg tgctcacgcc gctttcctat cttgccacca   78000
ccatgcaggc taccgatctt gcctacaata tgtatcgcaa gctccacttc tttgaaattg   78060
tctctggaag tatgattcgc atttctcctg ttcccgattc caacgactcc cggcttacaa   78120
tcagatacaa actggaacgg gaagaaggtg atcttattga aatgtacaat tcaatatttt   78180
atacgaaaac aggtctcctc gatctggaaa aactaaatga aaactcccct attgtgcttc   78240
ggcatatctt cctcatgaag gtgatcgata cgcttatttt catccgcaag aagtacgaca   78300
actacgcact tcccaatgcg gaacttacgc tgaacgtcga caacctgaag gaactcaggg   78360
aatccaccaa ggaaaagatc gacaaataca agagtggct tgacaacatg aaacttcacg   78420
caaggcttca gcggaaagga gaagaagcag aagcgctgga gcgggaactc cagcgctatc   78480
ctatggggtt cctatttatg taatctctca cctgcaatca ctcagcgtgc aggcgcccat   78540
ggggtgatct cctctaccgg gctttttgaa cggcggtgga atcttatgtc ccggtttgtg   78600
gtgtgcagta acttcctcaa cctttccata ggttgtgagc atgggggtaa tccacctttt   78660
catggcttct ccgatttttt attgttggtt cttatagata aataaccctg tggcacgcat   78720
cgtaagtgaa aaaccacccc aacagccacc accggttcac ataacggaaa aattctttgc   78780 ctttttaaa ctcttcatg attgttcttc ttttggaaga ttcagcttaa tggtgatata   78840
atccgagtcg gggaattctt ttcttaaatc ctccagcgac tcatacacaa aaatcatccc   78900
gacggcaccg gtgttagcta tcttagaaag tggatagacg actttctgaa cgccgttatt   78960
gatgacaacc tgcaggtcat ccagaaagtt aagctgcatc gcgacgtaat acacgcgctc   79020
ttcgttattg ttgtcgttca tggcacacag ggttttaagg ttacgcatgg tagtctattt   79080
ttacaatgta ggttttgtcg ttatattcta tcatgtgata atgcgcctga taaatatggg   79140
ttccttccag aaatagggc tcgttacctt caaggtagac gaacaccata tcttcgtctc   79200
cacccccctg agaaaggcgg ataaagggag tgtgctgact ctggtgagta ataccgataa   79260
caacatcggg gttttctcg ataaaatcga gaatttcccg ctcctgttca gtgggttcaa   79320
aatgcttcca ttgatacacc cggtaggggc gattcgaagc gatgtaatag ggaagagaag   79380
ctacatgtcg gttataaata tccagaacaa tctcttcaat atcagtattt tctttatttt   79440
```

```
taatttcttc ctcgagtagc atgttaagat caagtatcat gtgagccagc gtgctgactt      79500
ctgcttcatg catttaata cctttctttt caaggatacg aacaatgcct tcagtgtcga      79560
atttgagaat catggcgcta atgggtttag ttttcactct ctacaagaaa acgaataaga      79620
tcctcaacgg ttttttatctt tgtagtattt tcaacatacc cgagactttt cagcagatca    79680
attgttttct ctgaaatgat ctgacagtat tgtctctat ctatgtattt tttaacgatt      79740
tcaagaccct cctcatcatc ctcacgtatg ctaagtgcgt ggatattgcg gagcctgttg     79800
atatgcgttt tctttcccgc tttcagaata tcccacacgc cgctcccatg ttcggggtta    79860
acttcttcca gagaaagcgg gagattggtt ctggaaggat ccagcatggt gcagtagaac    79920
cagtagatct tgtctcccat ttgcgggggt ttgcatccta taatggaagc gaaaagcgct    79980
cccttataat gaatgggaag tgtatggtca tacattttta tgaatatctc agagattggg    80040
acattctcct ttttcatctt cataacttcc tctacatact ccacatatct ttcggcgctg    80100
tcagacgaag atattttcat tttgtgatag agatcttcaa tagaccagaa attcttttga    80160
gacacaaagt tattgtagaa cgctatggtg gcggaaatga catcgatgtc gggttggctg    80220
atatacttca ggtaacccct gaaatacttc ttgacaattt caggcaccga agagttgatc    80280
acttcgattc ccttcatctc ttctttaccg tctacagtaa ccgcaaagta gcggttgatt    80340
tctttgataa gaatggattt gaacacgaac tcctgcttta actccagctt gaaatcttct    80400
cttgcattaa agttatttc catatagtca ttgataaaag agttgagatg ttcttgaagc     80460
tcaccggctt ccgccaccgg atcatccgta aaagctttga cgaaaatgga gtcggtatgc    80520
gaataaatga agcgatcgcg aatctgagaa atcacggagc gaatagacat gcgcccggcg    80580
gcggttacac tttccgcaat gggaaggcac cccatgtaca ccgaacggtt tccgaagata    80640
ccgtacatgg agttcatcat aattttaagt gcccattgac ggaaatggtg ttccatgttg    80700
ccagtttctt tgaaaagctt acgttcttcc ttacgtcggg tgaaaatctc ccgaatgata    80760
gaaggaagca cgccaaccgg ctctttcctg taaaaccagc agatacccga cgggttgggc    80820
accataatga tatttcgact ttttaaaaat tgccggagtt cctcaaagct gttgatgaca    80880 aagagggtt cactccggta agaagggttc atccctgaat cgaagatgta gagggaaac     80940 ccgaattccg gttcttcctg atctaccgga atcactttgt tctccacccg catacacccg    81000
taaaactccg ttacgaacgt agcgggatcg atattgaatt tgctgattac agagggtac    81060 agcgatgtaa aatcaagatc gaatacgttg aagtaaatat cggggttggt aagttcaatg    81120
taagcaccgc gataacgata cttgttgatg ttcatagcag aatacgtttg ttttacattg    81180
cgggatcaaa atgggtatct ttcacctcga taagtaggt gtcttttaaa tcacatttgt     81240
ataatacgcc atcgagtgga gaaagatcaa taattctcaa aacttcatcc gtatagaatt    81300
ttcgctcgat aagattatgc gtttccagac gtttgcagta ctcgaagata gcgtctccaa    81360
caacatagct ttccaggtgc cagcaggcaa gcccatcata atgataaagc ccccaccaac    81420
catttgctct ttccctgacc actgcaggga taaccccag atcttcaaga aatgcttcaa     81480 gtttatttc atccatataa agcaaatcgc gtcgcattat gttttttccc cgctcctcaa    81540
gaaacgcatc aacatacatc cacccggttt catcccggat aagcttgcga agtgaagggt    81600
atgcctcaac cgatgtaaac ccggtcttca aatcggtaat aatatcccgc gaaaaccgca    81660
taacgaaata ataaggggtt tcgtagtcga taagttttc aataatttta atgatttcgt     81720
acttcatggc taaaacgcta cttcatggct aatacgctac ggttagttta agtgtcgggt    81780
```

```
aaacctttcc attaactaat gccacgccca ccccccgta aatggatccg aaaaatctct    81840
tctggaaaga aaagtcgtaa taattgagcc ctacggaagc gctgataagg ttgtgcgttt    81900
ttctaacctt cagcgcaaaa tcttcctgca tgaaacgtcc ggtttccggg ttgaaaaacg    81960
ttacgcggag cgtgttgccc ttccacgtgg catatctttc cggaagaagc ccgtagagtt    82020
tcatgtccac cggcttcgga cactccaccg tgtcaatctt ccccacgggc gtctcccggt    82080
aaatgatctg tttgaccggc tgggcaaact tcccttcaac cttcaattct gaaggaaaaa    82140
ctctgtccga aagttccact ctgacttccg gtctgtaaac ggtgcggttg acgtaaagat    82200
gtatgttaac cgcgatcagg atcaaaagga gtgcttcttt ccagtacttc ataagtcttc    82260
ctcttcttgg aatttgtctt cttcgtctct gatcatagcg tatagaatga tcagatagtt    82320
aattgcgtca atgattctac cttcgacagc atcccgctgg ttttaaccc ctctgatcca    82380
gcgtgccacc cctcttaaat gtttatccag aaatacatac agcacttctt cccttgaaat    82440
acccaatcgc tttgcagttt cttcaaaatt ctgaaataca ttgtcggttt cggcatactc    82500
ctgttgggct tggagtcgga cacgatttac ttctccaata agctctttta caatgcgttc    82560
gaattttgtg gtattcatgg atttcctcca ttaagtttct ggtatttatc ttatttaaag    82620
aaaagatga atactccccg caaaatattt cttaatccac ccacctcaag atccctacag    82680
gatattgaat acctttacct caccaacaaa cacatcatta ccggcgcgat aaataaagcc    82740
ggtatgagca ttgatgaagc ttgtgaatgt gttgtggggg ggatcgtgct cgaatataaa    82800
gaaacacacg gcatcaatat ttttgataat ctgactatgg cggtggagta tttcattaac    82860
aggtacaaag aggatttaaa aaccgggcgc atttaactca tcatcttttc gttgataaat    82920
tgaatgagtt cctgtacgga aggataaaac tgttcctcga aaatctggtg gtttgtcttt    82980
atcaattctt caagtttatc cacatccgcc ccgatctttt caaaaaggt acgggcttcg    83040
gaaaacagtt cccctctggt ttcacattcg gtataaacca aagaggaac cataacccgg    83100
tagaaaaatt cttccggtgc ttccctatca acatactctt caataagttt ctctgtaata    83160
ggaaccccgc acgcctcaaa cacgtcatcc tgcacggcga agtgaatgac gccgttatac    83220
aaaaggtgcc gcaaccgcac cttccacatc agggaagggt cggttacgaa ctcatacacc    83280
atttggagag cattctcgag aggaacctcc tttaacggaa gctcctcaat ttcttcttcg    83340
atcgggtaga agacgttctc ttctttggag aacttacgct ccggggtaat tataatccag    83400
agcgcttctt tgacctgagc agcgttcaag ttgcccatgt tgtacctcct tgttttttgtt    83460
agttacagat taaacaattt gctggttttc tcgaactcct cgaaccactg tttccggagt    83520
tcatccgaac ccctgtattt caggggcttg ctatcttctt taactttcga ttccggttca    83580
ggttgctcct gggtttcgag tttcagggga atttcaactt tccctttgag ttctttgagc    83640
ttgttctcaa tacccggcgg aacaatccga ttttgaaga ccagttccac cgctttgtta    83700
atcacttcat cagcggcttt acgggtgcgc tgataaatgg catcctgctg agcctctttg    83760
agtaaataca agcgcggcg tttagataa tcctcgctgg cgcatctctg catggtgaac    83820
tccagcgaac gtcggttgtg gatttcgctg ttagccataa ggctctccca ccacatatac    83880
tctttttcag aattgaggat ataagccccc ttgaatctga cataggtatc ctcatcaagc    83940
ttgaaccagt atgcatcata gaaactgtac ccccgcaagg aatcgtcaat aacgtacccc    84000
gcaaggggtt cgacaaaaac aagctccaga tcggctactg atagtacatc gatcatatag    84060
tcgcatcctt tgttcatagc gtcttttgaat ttttctctaa tcatggcttt ttcctccttt    84120
ggtttatcgt taaacccacc aacgtcaaaa agagggagtt tgttttttcgg atggagacag    84180
```

```
aattcggagt ttttgggcat accccgcttc cagtgttcca cccagctatg acatacttcc   84240
tcaaacatat cggggtatgt ctctctgaac ttgggaatta cgtatcgata gaattcgata   84300
tcgtatttga atagcgcatt tcttataacc gtaggatctt tttccattgt gctctgtacg   84360
cggagatttc tatgaaaatc aagactctgg tacaggaaga aaaacgttgc gttcacaaca   84420
aaaagatatg ctgtaaactc gatccaacta aatgctctat attcggttgc aacagggtaa   84480
aatttgtaaa gccagtagcc cacgaaacca aacgccacaa ccttcaaagg ttcgtgtacc   84540
ttgttcacaa cacgcgggct gtaaagctta aacccgaaa gcacgttgta cgtgccggta    84600
acgaaccacc tcccaatcca acacaaaccg atagaacccg atacaagaat ggtgatcatt   84660
gtctggctca tgtgggcgac ggcttcgtgg tgcccgagca taaacgggaa accaataaac   84720
cgcccgaata ttagcaagac cgggaatgac agaaggtccc cggttataat gcagacggcg   84780
gcaatgaatg caatccacgc aataccggcg gcaaacgtaa acgacagata aagggcgtcg   84840
ttaaacgctt ccgcctcctt gcgccacagc ttcaaattat ctccataata aaaccccaga   84900
accggaaccg ctacaagata gcgatccagc ccctccacca cttccttctt gctcaactca   84960
agttcgccct taccccactt gaggagctta tctcgataaa gcttgaaagc tgtaagggcg   85020
tactttcttg ttactccggc gtacatggct ttccgggttt gagttatcaa tctgcttata   85080
acatacgccg gaaatccaga aaagtcaagg ggattacgtt aattttttac gaagaagaag   85140
acgtgctacg tcgtcaaagt aaatggcggt tttagtggcg ttgagacgct tgactttgag   85200
cggtttataa agtctgttct tgataaaaaa cgaagctctg ataattttcc agacgtttac   85260
gtaaaaacta ctattctttt cgtaaaaaat gcagagggcg ataaaatcgt cagattgggg   85320
gttatagaca agccggtcat ttttctgaaa cacccaagac ctctctattc tggtgtatct   85380
atatctgggt acatcctcac aggttttaac atgtatatat ctaccctcgc atatcagatc   85440
agccgcatag gatttgtctg aagtgatagt cagatcgggt ggggtgcatt cataaccaag   85500
gttggtgaga tattcataaa cggcgaattc tcctatttta ccaacaaaat aattccattt   85560
tattctttcg gggttgtgct ggtggcgctt tttgtattgc tcaagcacaa tcccgtcgtt   85620
tatctgattc ttagcatatt ccatgcagat gggcacatac tgatctactt ttatcatctt   85680
acccacccctt acccaagagc gatacttgtg gacggattga taaggtacat caccgccgtt   85740
tcacggtaaa acgttgattt tgtgtaatgg atcccaagcg aagagacaaa gggagttccc   85800
ggataagcca tttgtgtgtt gtatctattg acaccgcttt tcggaaatgt atctgctaca   85860
atggaaaaga ccgcaccctc gcgctctgtt gctatacggt cgactgtaac ggtatccgga   85920
attggaattt caccatcgaa agatttgaac atactgaaag aaaattgctc aaaatgaggg   85980
attgactgag tcatctgaaa tgcgtagaaa ggtttacctt caattaccac tcccgcgaag   86040
aaattctctc cggcaaaaag ctgacgaagc aacaagatag cgtcgcgggt tttgtttacc   86100
acctcaagca tatcctgatt gcgggtttca ataacgtgta cattatcccc ctccgccaga   86160
tttctaacgc ggttggaaag atttcgctgc aaaaacacca cggcggaata aggagtatct   86220
tcgagttttt gaacagggtt ttcggtaatg atatgatccg gttgataaat cgagccttcg   86280
aaagcgttat ccgtaatgac tccgatatgt ctcagattgg attccatgta ggaaagcgtt   86340
gaaacataat aactgtaact gatcgtcgat gtggtaacct ctggaaacat gctgtaggtg   86400
tggttgtcaa tgagccacat tgagatagta ctgtcagatg tacctttcag gtagaaataa   86460
accgaagtgg aaataacagt aggcattacc atcatcatgt agctcatgct gtaaagctga   86520
```

-continued

```
tctattccgg ggaaaagcag cgtaatcact ttcccctgaa gcaccacatt gaacggaagc    86580
agcgaaagac cattttccaa atctctcatg tagcagacgc cgtggaaatt cagactatct    86640
acaacaaaac cggaattatc aataacattt acagaaactg aagttataag ctcgccgcga    86700
gatgtataga ccggatagtt aaaagccccg gttacataat aggggttggc gttgctgacg    86760
gtaatggaga aggtaataga atcgagaaag ctattggcgg taacttcata atattctcta    86820
atatccttat gttcattata gggaatgaac ccgtaaaacg taaaataatt attcaacaca    86880
atatcttccg gaggaatgtt ttgacttacc ggtataatgt gttccgtgat gtaatactga    86940
tcccccagaa acgcgtcatg aatgatcaca tcaaactgat aatctttatt tcgtaaatcc    87000
agcgattcag ccagcgtgtt taaccattta actttcattt tgcgattgaa ggcgtgatag    87060
gtaatacgat tgatctgatc gtgcagcgcg tcgaacgcat cgagaagttt ccggtaagc    87120 tgctcaagcg tttgagacgg gttctgagtt gtcggttcat tcaaatatat tgtttccaca    87180
aactgaagat cattgcggaa gtagaaaaca tccatgatat tcccgatcat atccatatag    87240
gtgagatatg aaggatcgaa cacttcttca ggaagtcttg aagaaaggcg atacgggttg    87300
gatacgtcgt attcagtcgc agcataaagg tgcatatcaa gaagcacctg atacggattg    87360
acgcccggat aaattgaaga aaacgaagga atacttctt cccagaaatg tatggggagc    87420
agataaaagg tacccggaag cgatgtcgag ttgtagtagt aatccagata tcccagcgcg    87480
taactctgac gaatggagtc gtctctaaag taatggttga tgtgcgttac gtcttccgaa    87540
gcaaaccatt taatgaatgg aaggaagcta tcgtagagtt tatttttat ttccttatat    87600 ttttcagcct tctccggata aaacctgaaa agcgtggtga taatctcatc atatttcctg    87660
agcagcgtga ttccttttgaa cgccgcctga atgagcgctt ctgctgaccc gaatttgaca    87720
aatccggaga gcagatggaa attggatttc tgctccatac ttccgaagct aaaagacggg    87780
atataggtgt tgattcgatt gtattcaatg tattccagta gatcgacggg actcctatct    87840
tcaaattcga gatgaaacac gttgttggca aacgcatctt ccctacccccc aatggcgctg    87900 aaggtaaccg tgtctgtttc cgtgagattt accggaatgg attcctgcaa atccacctga    87960
cgcacaagat acacttcttt tgtcgagtga aggagtgatg aagttccata tacataaaac    88020
gtttcctgat aataaaccgg ggtacccagt ttatgaatat tcccgtttac tttaaccaga    88080
atactgtagc tattctggat tcgagcggtt acttcagcgt aatagttgaa caggtcttca    88140
aaagtgatac tggtgctgat gtagttttca aaagcttcgt taatctggtt ttcaagttgt    88200
tctatggctt cgacggcaaa tgaaatggtg aggaatatct gattgagacc ggtttgcgca    88260
gaaaggtatt ctttcgaaag tggttcggct tcttcaagaa cttgctgata agcggaaatt    88320
tcattttgat aaaaattatt gaaaaactcc tgtacatcgt tgaaactgac ggtagaggtg    88380
agttccagcc gggaggttgt aaaactaaac gcctgctctt ctacgtagct gtaagttcct    88440 aatttttga aataagcgta gacgggatag gagtctacag agaaggtata aacaaacgga    88500
agcgaaatgg tgggttttc aattccttca aaaacttcag ccggaacaga gtcaaccacc    88560
agatagacgt ttccacttct tacatacttg gaggttactt tgccaataaa atcaacgaaa    88620
taaatgattt ccccggctga agaaccgctg aagtgttcaa tgtaaatgta aggatttgtg    88680
taggaaagag aatatggagt aaacccggct acaatttgag aacccgaaat aattataaaa    88740
tcttgcattc ctcttttctt gttaaataat aacgcaataa gtcaagtgca tctttgggat    88800
agaaaggctg atagtctttc atggaatgtg gatattcgcc ccagtctttg taaccggcgg    88860
gaggaaacag aaaaccaact ttacatacgc cgctatagag ttccaacact ttagaaattt    88920
```

```
cttcaacgct tacatccgaa tcaaaacaga acaccagttc tttaaccttt aatttttgca    88980
caacgtagga atccggaata cgattctttc cacagagtac gcacattccc acacccaacc    89040
catccgttgc atgggaagc atatcgaaca ttccctcgaa cagataaatc tttccttttc     89100
gagccgcttc gtagaaatag accgggagct tacccaccat ataggaaaga taccgaacct    89160
tatcgaaagg ttgatagaat tgaacgtttc ctatggaatc accgaaggca acccgctttt    89220
catctaccac cttgaaaaat ccttttgacg acatatagct gagaagttcc ggttttaccc    89280
ggcgctcttc aatgatgtgt ttgataaccg gatattcgat attttcctct gaaagaggag    89340
ccgccttttt aaaagcgag cggtagtaaa agttttcttt gacgtttgtc tgttcaacat      89400
ccgtaaaatc gatatcaccc gaattcttat aatatgaaat gagttcgaca ggtttaaatc     89460
cgaaaatgcg ctcgaagtct ctataaacgg tgcctgaaaa cccacaacgg aaacagatga    89520 aaagagggc gtctatggaa aagtaaagcg tgagtcggcg ttgttttta tgcgggcgc         89580 acttagggca caaacaggct acttctttac cgcccccggc aactttagct tcgctgaagt     89640
atttggtgag gatttctaca atcatggttt tttctacaaa aactctaagg aatcacaatg    89700
gttcccggtg tagtaatcac aggatgattt aaagtaatgt tcacatcggt taccgttata    89760
tccggcggaa tcgttgaaat gtcaatcggg atatcgcagt atttgctctg agaaatctct    89820
acggcttcga cggttacgga aaaattgaaa tcatcgtcgg tatcgaatgc agccatgaaa    89880
aactgttcat cggtacgtac gttgacaatt cataccatc ttctggattc cccaagcacc      89940
agatctcccg gttgtggaaa atagtcgaat tctttcagca cattcctaag aagatgaagt    90000
cggagtttcc gcaccgatcg cattccaacc tcctctgaag ccggttcccc aacctcatat    90060
tccacacgac aggggatccg gtacatttta tattctctaa tatctttctt aggagactct     90120
ccatacagat agtgcaatac gtcgttttcg tcatcttcca ccgcgttttc aataatacga    90180 acaaaagga gttggcgtt gagaatatcc tcaagcgctt caagggcaaa atgctgaaga      90240
agattgagtt cccgtcttcc ccagaaaaga ggattacgct ttttatcat ttttatttaa      90300 ataccccctt tcaattctc tccgttagaa gcttcttttc cgacttttgc attttctctt       90360
cgtcgccgtc aaggcgggca aaaaaccaac ttttatcatg ataatccata agtcgaagag    90420
cgaacctttt gcgaaactct ccggggtttt cttccggaga aacctgttcg gaatctcttt    90480
tataaatcgt atcaaaagat gactcaagct gatttcgcat atcggtataa atttctttga    90540
gtttcatcac ggtttcctgt tcatccgggg taagtacaaa atcatcaagt ttgttttcaa    90600
gaaaaagatc ggcgagcttc tcaggagtga ttgtagtttt aatccggtgg agctccagat    90660
ataccgggtg cttgatcttt gtgcggtaat aaacacgcgg ggcaatttcc tgtacggcta    90720
caaatccttc atataccacc tcataaccgt ctctcaggct tttgaaaagc ggtgtaactt    90780
cctcaaatag ttcctgaagg cgattggcac gaaaaagagt atagttttgc tcttgagaca    90840
gaacagccgg tagcttaaga tttattttc cgccactttc gttgaaaatg cgtacggctt       90900
cttcggaggg accccacctcg aaatatccct tctccggatc caccgaacgc acaccgatca    90960
gaatgatatt tggctcctca taaggaacca ccactcgcgc gtccggatga accatttcaa      91020
atatgtaaca gtatgaggag ttcaaatgat agagaaggta aggcggatat ttcttttcaa    91080
aggtttccca gaacaattct cgatatgttt tatccatatg agtggtaacc attccgtttt    91140
tgacaatgga tccatttgcg tcaatactcc caagagtgtg aatttccac ccttcatcat      91200 aatataaaac cacacaagta ccatccagct tttcaaccag tttcatggga agtttgaaca    91260
```

-continued

```
tgaaaccggc tttgcgcttt tcattcaggg gagacgcgta acgaagcgtc tgataatagt   91320
ttacgatttc cggctggagt tcttcccccc agttgaaaaa tttgtcaaag ggataagaca   91380
gaactttcca accactatcc gttttgcgga aatcgcccc cgcacaggca aggtgatata    91440
tcttatcaaa cttacaacca aggtgatatt tgaacatgta tagatcaccc cggttttgc    91500
acataatccc ctccttgcga agggattcga cggctacttc cggagactca aaagagttca   91560
ggtgttcgat aaggtactca accgggtatt ttacgttcat cgattccata gcgtactata   91620
agtcttgttt tgagttttcg gaagcgtcgg ttgatcaggg agttcgtcta caacttcata   91680
gtttccggat aggaaaccgt agcaatcaca cacctcctcc gtaaatctgt ttacgggaat   91740
tggttacaag ttttcagct acgcgcaaca ttttgttact ccacttttca accggggttt    91800
ccacaaggaa atgaccaata cgggtatcaa accggttgaa gcccacattg ttgcgctgag   91860
ccgcgcggtc tttatccagc gccgccacga tcgccagctt ctgctgaagc tccagcgcat   91920
aaccccgctc ttcctccgaa atggttttac tttcttcttc ctcctcccgc tgctgcttct   91980
gctcagacgt agtaatcaca tcgagcagag atacaggctt ctcaagttga gtcttcatac   92040
gctcatgatt gagtgccttt tcgataattt caatcttgcg cgtcaggtaa tcggcaaagt   92100
tttcatccag cgtatgacgc gcaacaatgt agtgaatatc cacacattcg gcttcctgac   92160
caatgcggtg gagacgatct tccgcctgca ggatattgcc gggtacccag tccaattcca   92220
caaacacggc ggtcttagca cgcgtcagcg taatgccgac accagccgcc agaatgctgc   92280
agagcaccac gtccaccta ccactctgaa aatcctccac cgccttttga cgctgcacca    92340
cattttcctc gccggtaatg cgggcgtagg taataccttt agcttcaagc accttctgaa   92400
tgatctcgaa cacatcatga tggtgtgcaa acacaaccaa cccgtccact tcttcctctt   92460
tcacaagaga aacaatatag tcagcagcga acggggcttt gtgaatggca taaaagcgcc   92520
gcatttctgc aacgcgctca aacataacct tcattttttc atcaaactcc gccattgcct   92580
cagccagatc agcgctttca accccaaccc gctcaaactc gcggagaacg gaaatataat   92640
ttttgagatt ctggagatct tcagccagct tgaaaatttc ttcttcagca aacatcttat   92700
taagttttac aggaacgatt ttacggcttt tcggcggaag ctccttgagc acatcttttt   92760
tcaagcgacg aatcatgata gtggagcgaa gctttccctg aagttcttca aggttacttg   92820
caccacgaaa atcccaacca tacccattat agtaagcgtt gcaataccgc ttggcgtagc   92880
cccagaaatt accaaacacc ttcggagccg ccatctcaag aatgggataa agctcaatcg   92940
gtctattgac gataggagta ccggtaagaa agagcacctt cccgcccgtg tctatggaag   93000
atttgacaat agattttaca aacccggagc gcttcgtctt cgggttttg atataatggc     93060
attcgtctac gatcacaaga tcgtaagcat aatcctcttc cgaaatgcgg tggagaatgt   93120
cataattgat aatgtaaatg gtgttttca gagaaaaatc gacttcattg ccgttaacca    93180
caataattc ttttcgtga accacccagc gcttcaattc ccgctcccag ttgtacttca     93240
gagaagcggg acacactacc agcacgcgat cggggttcat tacattgata accccggcgc   93300
tctgaattgt ttttccggta cccatttcgt ctgcaatgag agcacccgga tattctttaa   93360
aaacttcggt aacaaaatgc accccgcct tctgaaatgg gaaataatca tatccggtag    93420
gtgcaggtac ggcaaaatcg ctgctggtga cgctgctgag ctcgagcttg tgatttttt    93480
cttccaggag aaggttgtac tgctgagcag ccttttcgtc gaaataacct tcagttttac   93540
tcgcataatc gagaattgtc gtataccata ccctcttatc cggatcccac ttccacccgg   93600
cattttggg gatcagacgt tcttcgtagg ttccttcca ctcgaaccgg ttgttgtaag     93660
```

```
taacgtagcc catgaccgcc ctgtctttgg ctgtcaatct gctgataata tacgacactg   93720
aacaagaaaa gtcaacccct tgacagaaat ttcaattaga agggaaacga aagttgaaca   93780
aacaggtgat tgaaatgctt ccgatagcgc gtcggaagat caaaggtgtc gtggataaac   93840
ttttcaaatt catcttttc accctctaaa acatcatcaa gccatagtct tcgacgttca   93900
aggctcccaa taatcgcctc aatcggatat gcttctataa aagcattacc gggataatca   93960
tctacaacac tcctcacaac ttcttcaatg tttgttgtat ctatcaatcc cctttccgta   94020
taatacacta tatgtggttc ttcgtttgat ccgtaatctg attctaagta tactataact   94080
tcatattcta ctatatcttt aacatactcg ataatacttt ctattccact ttcaaccatt   94140
tcctctactt tctcccccca ctcttcatca aaatgatcta aaatatcatc cgagttgatt   94200
attttttcta taagatcata gtttacattt tcaggtttaa ttgtgctgta aaaatattca   94260
aaacagccgg ttgtcgacat atttttataa agagaagcaa ctacatcggg atatgcttcg   94320
tgttccgccc atttaccaat atgttgtttg aaaagaaaat aggcgatacg ataagaacct   94380
ctgttggctc tcctttttc tatatcttct ggcaactcta tattaagata ttcatgaagg   94440
tctttaatac cctccgcttc ccccatatga tcaattgcga tatctacaaa ttgtcttatg   94500
agatcgacaa ccaccgaaag attgatatat tcctcgaatt tattcttctg ataaagcaca   94560
aatacctgca gggtttcagc gggaatataa acagtatcat aattataagc gaggacgctc   94620
cttacactgt ctaaagccat attaatataa tattcgattg catcttctga aggtgcaaga   94680
ttttctacca gatggggata ttttcagca atcacatcca gcatccgcgc cgcataagta   94740
gcatagggtt cttcgtcaat cggtaccatt gtattatcag gaaggtgaaa ttcctttccc   94800
ttaccaaatg tagcgattgc gtaaacaagt ccgtcatacg gattgctact atcggcttcg   94860
aaatctattc ccggtttgat cgccgaagga tgaaataccc ccacgaacaa gggataataa   94920
tagttgaaat gttgatcgcc aagtcccaca cacacatgaa tatgattacc aatcatcccg   94980
agaatacgtc tgttttccac cacattttgg gggtgatata tgatcataga attgtcttcg   95040
tagataatca aatccgcata ttctgtgtgc ataagctgac gaaacttctc ccacaatgcc   95100
agataagaag cccccaccte ttccactttt ccggcgcgtt gatatgcccc aacgactttt   95160
ccgggatcga gaagctgaag gttatccgta agatcaaatt ccctcaaaac ggagggttgg   95220
tgtcgcaccg aaaaatacca gcgaaatggc tcgatgtaaa gagggagatc gatcggatcg   95280
attttgtcgc tcatcaccat acgataaaaa tattcaacca gcgcatttgt cgagataagg   95340
ttatattcgg gattgttgcg aagcggctca aaaatagact gagcaacttt gtgaagaata   95400
tttccaaaaa ataaaatacg ctcccccgga tcacggggaa cttctccaag atttaattgc   95460
tgagccagaa acctgagttt gttttcggga agttttgcaa gtagttcttt accectacgg   95520 gaccccggag caggaaaagt aaacgccatt ttttatttt aaataactac gccccaaaat   95580
ccacataaag atagcaaatt ttccagctat cctccatcga gatagtatat ttttatccc   95640 cctctttttt aatctgataa tcttccttac cgacataatg taaaaattgc cttataagtt   95700
gccacaacct atcatattcc tccgtttcat cagtgcaagc cagcttgtac tgataatcaa   95760
cgaaggacat atcgtttatt tcatcataaa aattgtcatt gccccccaca atgataactt   95820
ctggatcaaa tacaacccat tcgataaaat caagcataaa ctggcttaat tccggatttt   95880
taagaatata acgccagttc cagcgcgatt catgatcaca tcgatcaagc ctttctatca   95940
ccttataatc ttcattatat ctggcaagta gaaaacgtct catttcggca acgttcatat   96000
```

```
cgtagctcag attatctgaa atatcgttca acatctcccg aagtgcgtct ataaagagac    96060
gcttgatagg ctcgcgttca acatcaatt ctacaaactt cacaaccaca caatccagtt    96120
ctctatgatt tttcagataa gcgtcaatgt atatatccga cgccgcgttg gcaatcagat    96180
agcacatctt agccagcggc gttttgcaga caaaaaattc ccacccgaaa tcgcaagggt    96240
aaaaatcctc cttcaccctta tcaggataac ggctgataag gatggagtgg gaagacgatg    96300
aatttgtgga aagaccgaaa cgaatgaatg ctttcatgac ttcctccttt gtttgtcaat    96360
ggttacatag acaacgtaaa aaacaacggt aagaataaaa agaagtaaaa actttatgtt    96420
caaccagaag ggattctctc ctcttagcac cagcgctgca gggtttctca agtataatga    96480
aagataaacc aaatacagcg caagcgccag cgaaatagag cctatcagta ttttgaacac    96540
tttcatagtt ttttccagat gttgagaaaa gttaccggat cgaacagttt ttccctcgac    96600
accctgaaac ccttttcttt caaataggat cccggagcaa caagtgcttc cggctcactc    96660
atgtcgatgt agcaggaaaa aagtccttcc tgatcggtag tgctatgtgg aaattctctt    96720
ttgaacaccg ggtaagtttt aacaaaaagg gaatccaccg aaatggtgag ttctttcata    96780
aaatacttca ccgcttccag tgtcttgttt tctggaattg gtatgttatt ataagtttct    96840
cccctcccca ctttcttaaa accaagtagc agaagatggc tcccctctac ctgagaaagc    96900
atttgcatca tttcaatggt ttcttcaaag gaacgctcc cccatacgtg ctgagccacc    96960
agttgcacat tgggggggctt ctgattcaga agatcgatat acgactccac cgatttcaaa    97020
ccatgcacgc tgaaacctat cccaaaaagc cgattcggaa ataatgccg gtagaacttc    97080 ataagctttc gggcaaacga agcattgaag gtggttacgt taacataacc ccggctgaac    97140
gttttgacaa tgcgatataa ctcttccaga aatctcccct tccagaaaaa gcaggggtct    97200 ccaccccta tgctgagttc gtaggtaccc atttcgttta acattcgtgc gaaccggatc    97260
atgtcacccg gatcacactc tgatcccctcc ggggtggagt tttcataaca gaaagcacac    97320
ccaaaattac acacgttgga gggtttgaca tcaacgatat gcggcacctg agtcttaaac    97380
atgattacct ctgagttttg ttttcggtgc gtatgttttc cacaaaaact acataggctg    97440
aaaatacacc aagaataaaa atctgagcaa accccacaac ccccgttttt ggatttactt    97500
ccgcttttac ttcaaaaacg atacatatga ttcaaaggtc tttgattttc ggaatttctt    97560
cacaaactgc tcaagggctt cgtaaacgtc ggggcgaacc aagttcttct ccttcgtgaa    97620
caccacccgc cttgactccc agtcaacccc gaagttaaaa aagttattaa ggctgacaca    97680
aagcgaagtg agggggaaact catatatttt tacaatttcc ccatttctgt ctataagcac    97740
cgaataatat cctctaaaag cgtcgcacag gttgcgcaca gtctccagaa aatccgaaac    97800
cggcgcaaag tcttcaagca catagcaggt tagttgaacg gctttttctt cattcaggtg    97860
cgttacggaa tacattaccg gcttgactac catacttcct ccgttttttt gaccggaaaa    97920
ccgaatcaaa acaccagagt tccattccac acaatactaa ttaccagtat ttaattccct    97980
gttatttcac atacccctctg gatcattctg ttttctttct tatatattcc attgtcagtt    98040
gaaaccaaac agatgagcca tgccgaactt cattacaaac atcaggaatt cccgttttaa    98100
ggaagttctg accgaaatgt accattgcca tcacgaaagc gagtaccacc ttgagggaaa    98160
tgttttaaat cacacgctta tggtattgca ggtggtagta aagataaccg ctgatcaccg    98220
ggagcaaact aatctatcct taaccgccct tcttcatgat agtgggaaac cctatacccg    98280
tgttgtcgaa aggggaagag taatgttccc cggtcatgaa ggggtgtcta cgtatatcgc    98340
tcctcttctg ctgtgtgaag tattgaggga ttccctcatc acaccaaaag acgccattca    98400
```

```
aatcctttac ggcgtcaatt accatatgtt gcactggaaa aatccaaacc ttttatgcg    98460
gcttttcacc gaaatggtta attatacctg tttatataac ttcttgaaaa aattcaatca    98520
gtgtgatcta aagggtaggg tttctacaaa accccaaaag caggaattcc ccgtaatcca    98580
ttattttgag aatacccga tcggtactgt tgagcgccat gtttatttta tgatcggggt    98640
tccggggagt ggaaagagca cgtttcttca gaaagttgga gaggggcga ttgtatcccg    98700
tgatgaaatc atgatggaat acgccgctga aatagggatc acaggagact acaatactgt    98760
tttccgggag attcacaaca accctatgca taaaaccaag gtcaacaacc gctacatgaa    98820
cgctttccgt aaggcggttg aagagaatga aaaggtattt gtagacgcaa ccaacatgag    98880
ttataagagc cggagacgtt tttacaatgc gcttcggcgg gatattgcgg aaaccgtggg    98940
ttaccattat atcgtaatgc ttcccgatta ttttacgtgc attgaacgcg ccgaaaatcg    99000
ggaaggaaag tcgatttcaa gggaagtggt aaccgatatt gcgcggagtc tgcttcttcc    99060
gtgcagggaa catcccaaca gcattgatac gacaatttat atgtctgatg gcatgatga    99120
acatgtgttg agagtagctt ggtagttttt aagattcgac gatgctcccc ctgctcaagc    99180
gggggatttt tttatttaat caaaaagtgg aacctttaga gaaactactt gccgttctca    99240
aaaagcttga agcgtttgag gaatatcttt caaagataga tcttggaacg ctggatcagg    99300
tgattacccg gcttagaaag ctccgggaat ccaacgaaaa actgtacaaa gactatcttg    99360
aagaacttga aaagcttttc agcaccaatc aggaaacgct cgaaaagctg gtagacgccc    99420
tttcggagtt tacggaagag gaaaaggaaa aacttgaaaa tttccttgag acgcaccaga    99480
aagacgccgc acgacttctt ggatatattg acgtttttga agcgtcgtgg aaacacatga    99540
gcgccgaaca acgggcggca tttgaatcct ttatcgacag actcagagaa cttcgtagaa    99600
acctcaatct cgatcgattc aagacggaaa cagcattcga tgttttcgac aaagcacgaa    99660
gagaccttgg ggtgccttat gaatatatca atcggtttgc attagacttt atcagatttc    99720
gccagcgatc agaaattttc ttcaaacaga tcatggcatt tttcacctat gaaagggtga    99780
caaggtatac cgcttatgga atggcaatta atctggtaca gggggcgctt gaacgctaca    99840
ttgaaactac tgatgaagtg atcagagtta ccggtattta caaccggctg cttagggatc    99900
aggcgcttca gttttaccgc gcaaatattg atctgagacg cttcggtgtt cagctccggg    99960
atactacccg ctttattgcc gaattttatg catttacgcg cacgcgcgat ccgttcgcgt   100020
tgatagctca gacagcagcg ggtgctggag acaacatcga cggattcatg cgtcagatga   100080
ttctcttgaa tcagcgcctg aatattgaca gccgcacgct aacacgtaac atgctacttg   100140
cagctaccac gctggaagat aatatcatgc aacatattca gcttatcact gcttttgcaa   100200
atgaagcaaa tttgagcgct accgaactgg tcagcgatct tgttgaaagt tattcagaat   100260
ttgtcgtgct gcttggaagc ggggcgcgtc agatacgcgca aactcagatt gcactggcgc   100320
ggtggaatat gtcgctcaga gacggcatga atattctgaa aggtctctat caatctcagg   100380
aatcggtgat cgactcgctc attcagattc agattctctc gcgccagccg gttgatttcg   100440
aacgcttctt tggagccatg ctcaccggcg acattgaagg aatcgtcgat cagcttgcgg   100500
aaatggcaat gcagatgcgg ggcatgatgg atgaactccc catttatcgt atgcagtttg   100560
agcgggcact tgaagggttg ggcttaacct ccgagcagat cgcaacgatt cttggaaagt   100620
ccagagagca gcttacaggg ttcggcacta tcgtggaaga tttccgccgg aagctttcac   100680
ctgaaatgct tatccagact tttgatgaac ttctgagacc caacgaatgg gaagaattga   100740
```

```
agaatgcggt ggatgcattc ttcgagacgt ttatgcttta cggcgctgaa ctcattcgca   100800
acatgattcc ggtgcttaga attctgacac agggaatgca attgatgttc aagtggtctc   100860
aggctatgac cgatcttatc gataaggttg gtagccttgg tggattgttg aaagacaacg   100920
ttcttggaga tttcttcaaa agcatttccg cgtttcttgg acccggtgcc gcgctttacg   100980
ctattgcgaa tatcgaaaag cttggaactg cactcaagat gttatttgat ttaatcattt   101040
ccattcctcg ccgcattggg ggaggggttg taaaccgtat tggttccttt ttcagtcgtc   101100
ttggagatgt gttcaagaag ttcttcggta gccgggaaat gaaacaggtt gcggaggatg   101160
caacttcaag aagaggaatt ctccgtcgaa tcaccggtgg agtcaaagat tttaccaaaa   101220
acctctttca aagcttttcg cttggatcga tcgttcgttt tacagcagcg gtgggggtgc   101280
tggttggtgg tatttatctt ttcggaaaag ctgtgaaatc acttcaggga atcgactggg   101340
gtgagacttc gaaaggattg cttgccttct ttggagcgct taccactacg gtagggttga   101400
tcagtcttgg tggtcttctt tcacttcccg cacttcttac cggtcttgca gcttccatag   101460
gcgctattgc cgtggtggcg ggcggtctct atctcaccgg tgaagctatg ggagtgtttg   101520
ccagcaacct tcagagactt gcttccacgc tggaaaccta ccccaatctg acttccggta   101580
tattccgtct ggctggagca cttggtacgc ttggtgccgt cggtacgatt gctgctccgg   101640
gcatgctggt tggagctatt accgaagccg taagtgcggc gatcaaaccc gatgtggctg   101700
taaaagccat tatcgatcca gatgtaatta ccgccggaga aaaactgatc gcaaacaaac   101760
ttgaccggat tattgcgctg cttacggaaa tgcaaaatag aacggagcca agagtggtta   101820
cgctgaataa gccggaaaag ccggttgaaa aaccaatctt cagcacattt aacttttaat   101880
cttcatcctt ttcttctccc tttttccaga ccggatgata ccagtcgttt tctttcatca   101940
ggttgatgta aaatacatat ttataatttt caaattttttc attcatgcga agcttataga   102000
gataatcatc tttgaacttt tggataggta ttcttcctcc aacataaagc agaccacctt   102060
ttcccaccac aaagaacata tcttcgggga aacgtttgat ctgaagcact tcgatcacat   102120
cgtcaatggt aaaaaacttg tatgcggttt ctttggatgc gttgtaaatg taataatgat   102180
gcgcaacgtt ggattttctg ttatccgtaa tcatagaagt ttctgcttaa gtagctaaat   102240
atcactatta ataaccgga tttgatattt aagaaaaag atgaaattaa ccgatctcag   102300
aaataaagtt acaaacgcat ataaccagat ttccaagcag aaccgcgagt taatcgccgc   102360
caaacttcgt aaagactcca gtgccaccat ttacttcggg gctgctgtcg aaaaacttga   102420
cgacgctacg atcaaagaac gtatgatcga cgtttttgcc acgatcattg ctcaggcgta   102480
tgatcgcgcg atttccttgc gcaaaggaaa accgacacat ctaccctccc ctcagtcaat   102540
ggtacttacg ctggcaagat tttacgtgga aaatgaagac attacgctca gcaaacttaa   102600
cgaaatttcc attgcgctgg gctggtatat cgcgctggta aacgaaccga atttgcttca   102660
aaaatacaac ctccccaaac agatcacgga acttgagccg gagcagcttc tgcacactta   102720
caaccagatc gcaagatatt ccgacaccta tcaggtggaa ctggtaaatc gctataaaga   102780
aattatcgat ttcctgacgc aaaacggtga agagttctgg gaaaagaat acggggttat   102840
tttcaaacct tcctcttacg aaatcaacgc caaagtgctt cagcttgcct ccgatcgtct   102900
ttttatctgc accgcactta accctatttt ccacgcacac tattatcctt actatgtgct   102960
tgtagtcaac ccggcttaca agggagacgg caatgttcac tatatcaaag acggcgtcaa   103020
gggatattca ggtatggagt tttatcttgc caccttctcc gacaaacacc cctaccagaa   103080
gggattattt gctcagtttc gtagccagta taatatcgcc accctctca gctttatcga   103140
```

-continued

```
aagcagactg tatctggggg attttatgga gttttgtgg aaacgtaaag atcttcagcc 103200
gcatatctct aaactcataa acctttacaa acaacacccg gcttatcttt tcgatgagaa 103260
cgcaatgaaa aggtttgtgg aaaatgagct tttcgatttc aaaaatatca acgactcacc 103320
cggcgcacgc gaagccgtag cttattttta ttccaagatc gacaaccgtt cttttatcga 103380
ggggctgact ccgctgatcg gagccgccgt tgaaacggtt atggaatcgg gagaagaccc 103440
caattacaaa aatgtacttc cggtgctggt agagcttatg gtcaaaaaca actacgctat 103500
gaaaaagatt gaagaagctg taatcgaagc ggtgcataga aaagcggaaa acattctcaa 103560
attcaccccg gaagaccata tcagatatat ggcaattcat ttcgctcata aaaatattcc 103620
ttcaaattct gaagaagaag gaagagattt tgccgaacag atttattata acataatcag 103680
acctcagatt acaggcacct caccgtatgc tattatgttt aaacgtttta tatattcaat 103740
cattcttgcc gaaatgaaag gtattctcaa aaacaagata aatcaggtgg ttaaagaaat 103800
ggaagaagaa ttcgggtttg gagacatttc ccttgccgat ttcgactggg ggggcggtga 103860
agaagacgaa gattcgttcg aaatggaact ttaactggaa gtgtacaccg tttctccgac 103920
gatatagaga cgctgtccac gagatgttct tgaaacctga aaggtggcat tgtaaatgtc 103980
gtgatcttca accacttctt caagcttttt cttaatatct cgataaagaa atgacttttc 104040
atccacgtag aagaagtaca tccacgtctg atactcttct ccccccattt tttccgaaga 104100
gtgatcttcc tgatacaggt gaaatccgta atcctttaaa ataggtatat gttttttgat 104160
ggcgtcggat gaagcctcgc ttccgtcata aaataccttg agaatcatat tctccattcc 104220
ggtggaagga atgacaactt tcccttcttc cgtatacgca ccctgaatgg caataagcag 104280
cagccccgga gatatttcat caaagaactg gtaggtatcc tcgacggcgc gaatatcggt 104340
aatcaatgta atcttggttt tacctttttt gacaaggttg cgaagggcaa aaatggaaag 104400
gaaaacaacc gcttcgagaa cctgatccgg agacaaatct tccgatcttc ttatgcttaa 104460
gaaatactcc cggtggtagt ctctcagacg aaatctcaga tcttcctctt tcctcaaaac 104520
cctcgcaatg cgacggtctg tttcaacaat gaagtcggta tgcgttattt ttttctccca 104580
ttctccgtcg aaaaattcta catcgtaaac aataaaacct atcgtgttgt agtggtagtt 104640
gatttctact tcgattcccc atgaactatc aggcgcacga aacagaaagt ttcgcggggc 104700
aagcttccac ttctccagaa ccgcgctttg aaaattgacg aagtttgtaa tgattttcct 104760
gagtgcattc ctcagttcac tcataaatag cgataaagag ttttctcaac cgtttccaat 104820
atctgaagcg actgtttggt tccaaatcga gattcctgaa gcactcttgc actttgaaaa 104880
gaaggaacgc ctacaacatc tatcgctgtg ataaagaagt cgtcaacaat ttctacccgt 104940
ttttgctggc ggtaacctac tttggtttta ccgctcccac gaagggaaaa cccgaaattg 105000
ataccgtttt caagaagcga tttgaccaga tttccgtaag gagttgggag aatgcggaat 105060
tttccgtaca ctttatttcc ttccatccat acgtctaccc actgcacggc aaggcgctca 105120
agcgacacga acccgattcg aaaatcgttc tggtagggt gatccagctc gccgtacatc 105180 tgacccttt caatctcctg cttcatacgc tccactgctt tttttacggc ttccggcgtg 105240
tagagtgtac cattgtcgga aatgacgtcg gcttccataa tcagagccgt ataagtttta 105300
tcgttaactt ccatagcggt tattcttcag ttttattgtt ttcttcttcc tttttgtctt 105360
cggcgtacag gaaaacggct tccaccgaag gaagcatttc gcgaagccgc gcaagcacat 105420
cggtaagcgc aaccagcttg gaaacacttc cgcgagaagc ttcgatcgtg ttgataagct 105480
```

-continued

```
cgcgaatgta attgcgatag ttttcatcca gcgtaatctt gtcaatgatc tcttcgatca    105540
tttcacacaa ttcctcgctc acgcgggcaa tatccttttc cagttcttcc gtgatttttt    105600
cggcttcttt caccctcttt tcttcgggga tttcataact attctgatcg ttttcctcct    105660
ccattaacac cttttcctct tcatctttct tgtcctgctt gacatcttta cggattttttt   105720 ccacatcacg gctggagtaa cctaccggcg cgtcataccc cgcaatgtcg ccggtggtgg    105780
tcatctcctc gatctgtttc aacgccgatt cataaaggtg cgagaggatt gccgccactt    105840
tagcaggttt ccttgcgctc aggaaaagct cagccacacc agccgcgcga taaatgcggg    105900
gatcgatacg ggtttcgtaa acttttgaaa gctgttttc tccaatgatc ttttccagcg     105960
cttcatggaa accgttgtac tggcgctttt tgcggtattc gtggacgaaa tagggaaccc    106020
tttcatattc ctgatctatg caggcttcga caattttggt aatgtaataa acatcgtcag    106080
attccacgaa attcatcaat tcacttgcgg aagccgactc cagcaatttc ttgtcttccg    106140
aagaagcctt catgaactgg aatagaagga ttatatcctt ctgcttcata caacctttt    106200 ttttcttaaa taaataaat cgaaggagaa ttaaacaact acggtattat aaccccatcc     106260
accgatatag ttgtaattgt ggctggtttt atatacgggt aacagtcatg aaatactctg    106320
tttctgatgt ggcgaatttg ttcttgtgtc atatcacccg gtattagagt ggaattcaga    106380
taggctgcat ctttagttat tgctatgtga tacaaaaggg gcgccatttc actgtaagtg    106440
tgtgtatctc taaatataag tctattattc aaataaaatg aaacagtaag atcattacta    106500
agagggtcca tttcataatg aaattcatgg aacacaaaat aagaccggtt tggattataa    106560
aatccccatt cagatactgt tatactatga gttactttct ttgttaaaaa tggggtaact    106620
atagtcgaat aagttactcg aatacccaga ttcccggaag ataatgtaga ataatatatt    106680
gaaataatat tttcaccact taaaattcta cctatgtaac taacatctac attgaacacc    106740
gaagagtcat ctgcataacc gtcaagaaat attgtctgaa ataaatggaa tttttctttt    106800
ttaccattta taaaaagttc gatattgttt acagttcccc aataatccaa atcgtaaaaa    106860
agactaaaag aataattggg gaaatgactc tgatacgccg cttgactacc accagcatag    106920
ctatctgcaa tataaaattg attccatcta cttatagctc cataattgat atttgccctg    106980
gcaataaaag cattatgacc aaaatcatag aaaaagaag aattaaaaaa ctttgttcta    107040
actgattggg taccatttat tccatctgta tattcggtta ctatataata gcccgaaccc    107100
gtttcaatag tggggtgatc tgttttgatt aaataatata catctctgac gctcatactc    107160
cctttatatc ccccagctac cagatattga ttggaaactg aaaccgtcaa ccagtcgggt    107220
aaaaagggtg taacatcaac accatttata gccgaaacat aagtgttcaa gacactgatg    107280
ttatcttgat ccgggtcaaa taacgaaaat gaaatggtaa catagccgtt tgcatccggg    107340
gtatataaaa tctggtatgc cataacttaa atgtttttta ttaaatatta caagctgtaa    107400
atgaagactg cagccgcaac cgaagaagta acctgtcaa gtctgaacaa ttcgtaaata    107460
aatttaatat tatcacttcc ggcaactccg ctgtatgaaa cacccctg tctgcgtgtg     107520 atgatattgt cggtaagcat ataaacatac atgctgttgg taacataagg agggaaacca    107580
tctggattga tccaattgac aacatagcta tgggtttctc ccggagcaat tgatgaagag    107640
ggataagtgt acaccgtaga gttagtaaca aactcaaaat aagatgtact gttatacgta    107700
tcgggtgtgg aaccgctcaa tgtataaaat agagaaaaag tgttgttaat atgagacata    107760
attgaaaggg taaacgaaaa tgtatacggt tgtgtcgaaa gagtccccat taaagacgga    107820
taatcaacag atcgactgct cagtatgttg aatgacttac cttcatataa cagcatattg    107880
```

```
tacttatact tatgataata atattttcga atcatagaga ctgtaggagc cgggagagaa 107940
gtactaaaaa cagcgatttc gtaaaattta aaagcagggt ctccagcatg atctctgata 108000
agcaatctgt taatatctcg ccttgtgtct gtattatact tttcaccaac aaaaactccg 108060
ttgatataaa atgatgttgt agaattgtta tgagacactt caaaagaag aggataagat 108120 aatacatctg agtaagaaaa ctccagacca tagccactac acgtatatgc ggtgctccca 108180
acagaagaac cgctatcaag actgaaaagc actacattta gtttattgtt gttgtttaca 108240
aaccctgttc ctataaagcg gttgttgtct gtactggtat ttaacatcat cacatccata 108300
aactgggaaa tgctatgtag cattgcagga gcaaaaacca taaaaacatg gaatggtgaa 108360
tctgggttat tgtctaacag attaacacta aatgtgttgt tataattata actatttata 108420
tggctggcaa gataagaata gcctttgtcc cagtaataat gccaaccttg ccctgttgaa 108480
tataaagata catggcgatt acccgttaaa gacggtaaaa cagaaatggt tggggtatat 108540
ccactttgtg ttatagttat atactcgaca ctccaaattt cacttaaact actcaaagaa 108600
acaatttcaa aattggaagt aaaaagagac agattataaa actttacgtt attatcaaaa 108660
tacacataaa cacccatatc atacacactt tcaagggaaa aagacgggtg tgtatggtca 108720
aaagatattg taacatcaat gacacttctg gtgccgatgt aatataaaga actggtaaca 108780
accgtaaacc agggcggtgt aacagaaaaa gatatattat tttctttcaa tatggaagca 108840
cttactgaaa agggtattcc ataatcatct ttcactgaaa aggtgataat gatggagtta 108900
ctgcttatta tgtaatctct gttcatctca ttctttaaaa tttaaaacctt aaataatcaa 108960 gatcaacttc gggggttgtg gttggataac ttttattggc tgctttaagc tcccatttaa 109020
acccggcatt agaaaatggt ggaacttgag aatatgtatc aaacggataa tttgccgcct 109080
tgagttccca tttaaacccg gcattagaaa atggtggaac ttgagaatat gtatcaaacg 109140
gataatttgc cgccttgagt tcccatttaa acccggcatt agaaaatggt ggaacttgag 109200
aatatgtatc atatggtatt tcagatgata caagttgggt gttaagagca gcggaagggg 109260
ttaaccctaa actctggaag gaattttttca tagaagaatt gctattagtc agataaacgt 109320
tactaacagg cacataattt accaccggag caatctgtct gacaaatttt gataccgctc 109380
caataaacga cacgcttaca ctcgatttgg gagatttgaa aagtccccat gcacttccgg 109440
ttaccgctga aaagaaaagg agattgaccg gctcattcca gacgttttcc caatcgactt 109500
ccagcgcacc catttgagga gatgagtaga aagtcagatt gttacccgta cttttgaaa 109560 caacgtttgc tccggatgac gtcagataga aatactgagt agatgtagag acatatactg 109620
agaagtaaga aagataactt accgtcagaa atcctgaatt aattggggttg aagaaatagg 109680 gtgatgtggt tgtataactg gcatatttca aataaggtgt attatccgtg taatacagaa 109740
cacttgtcga ataattcaaa tccatgaaaa tgcttgccgt tccgaaaaag tcggagaagg 109800
tgactaaata gggtgatttc cgaaccatgt atgttccatt atcagccgaa acgataaaaa 109860 cagatttgt tatatcgtaa agtaatgcgt tgaatgtggt gctaccctga ttggaaaatg 109920
ttatataatc ttcaatatat ccgccgccaa ggaaaagacg tttgattgag acggtttcgg 109980
tgctggatgt cgtgtaataa tccaaccaga acacatcata tccccatgca gctaccccac 110040
cgtattgaat gctggtggtg gtaacctgtt tataacttcc actggaatcc aggagtccca 110100
cttctccgga agatccatcg tgcagattga gaaagagtgc gggagattga tcgtaaagaa 110160
atccaagcga tacgattata tccgaagggg tagtaatatc cgggaagtaa agagagatat 110220
```

```
tcgggtctgt agttgtaatg ttcgggaaat acagttctat attaacgtcg gatgtagtaa  110280
tcggaggcgg ttcacttggg gatggggggcg gaggaggaac atacgaataa gagggggatca  110340
gaatcttctg cacgaaaaca taagcttcat ccagcttgat cggttgagaa aacttcgata  110400
caaacaccac gtcccccattc tgattcattc catagattcc gctgacataa ggagaaaccc  110460
ccggaacagc cgtgggattg gtggtaaagt ttttggctac aaattcggca acgagaagct  110520
tcagaggctg caattcataa agcgtaaggg taaagaaaag cggggaaata gccggtactt  110580
tctttcccac aaccacaaac gattcatttc gaacaaggat aaaatccggg tgatcataat  110640
aactgtcatt cacaagcgag ataggatttc ctccatacgt aatggaatgt atgtgatagt  110700
actgtcgctt gattctcaca atttcaaaag tgagcgcatc aaaatcgata ttcagcttac  110760
gaaaaagatc gataaaaagc gcacgaatct gagctttgag ttgatcatcc ggggcaattt  110820
ccagttttat attatcattt tcgtagctac cgggagaagg gaaaccaaca acttcggtga  110880
atactttat atcggtttta taaaaatcct tcgctctcat tttatacttg atgttcttct  110940
ctattaaata agaaaagttt attcagggggc tacctttgat aatattccct gtacacccag  111000
ccggtaaacc caaggtccag aagtttggga atatcccctt ctcttcccca ctgctttttc  111060
tgaaatacat ccccccacgtt cagatcaaaa ctcataaccg gatcctgtaa atcttcaatg  111120
taacggctgg cgaaaccgtt atctctgatc ctcaaaattt cttcatcggt tatctgatca  111180
tgaggaagat cataaagctc tatcagctta cgacaggatt gaatatagcg gttatcttca  111240
taaaaattag gcggatgtgg gttaatccag ccggataaaa tatcggaata aaccttaccg  111300
gcaatcagtt cgtgagcttt gttttttcata tcgggttcga gaatatccag aagtatataa  111360
agctcttgat aggtttttaac cggctcataa tacctgagta tggaagcgat cgccattctg  111420
gttttttgtgt tctcataaaa agcatggagt tccggtagaa tatactccgc cgaagaatgt  111480
cttattatat ccacttccgc catattctga gccatacccct tttgattgta tgcaattttt  111540
ataacataag gagttccaac tatgcgataa accttacgag aagaaccacc tcctatatac  111600
tccacagaag gcaattcatc catcaaagct ttaagtgctc tgaaggaaag atgattgttc  111660
agcaactctt caaaatactc aaataaatcc tgatctaacg atatgttgta accgtaaaca  111720
atttttctctt tcattacttc ttcttattgt ttttctccgt tcgcttaaga taagcgcgag  111780
ccgatttgaa aacccgtttta ttactggtat ttgctgcaaa attgatcatt ttcatagccc  111840
gatctctacc cactttttctg ataagggcac gcgccagcga ttcacccgac ttgtacacat  111900
catcaatatc tttgtctttg gggattccaa gcacttcatg catttttcccg cgcttgactt  111960
taccgctttt gaatgcttat tgaatccact tttcttcctt tttagcctca gccagtttac  112020
gtttcttgag ttccttgata tacttcagag cgcggtcata aatattgtgt tcaggggttga  112080
cgttggcggc aaaaaccaac atccccacgg cttctttgta cgaaactttc ttcaggagat  112140
cacgcaccaa tttgcggtga tctttgtaat gatcgacaat atcttcatct tcggggattc  112200
caagcacttc cttcatgtgc ccggcttcac gcttgacctt gctcacccag tcttttttccc  112260
gcgcttctgc aacggtttcc ccaccttcat ccagaagtgc aatagcttcc gtatagaaga  112320
aagaatcccc ctccgtttct tccagaacgc gcaacgcttc tttcagaagc tccttgtgtt  112380
caatatgcat acgctttgcc atttttcaaca aatctttgac aaaagaccgg gcatcataac  112440
cgtaatactt ggcgacagaa acgacggaag gaactccaag atacttacgc aacttcattg  112500
ctatgcgttc agccgttgcc tctggattac ccatctttttg aatgagttct tcgcgggtga  112560
cattttcggt cagcagtttc tggcgaaatt cgttaagctt ggttctggtc tcctgcaaaa  112620
```

```
gccgcgcaac acggagaatt tcctttcggt tcatatctta ttctcctttt cttttaatta 112680
aagaaaaata aagactctat gaaaacagaa gacagaaaaa aacttgctca ggaaatcctc 112740
gacaaaatcg taaacaaagc catgcagctt gaaacgttga ttgacgatga atacaactat 112800
ctcaacagaa ccagtgtgct ggttgaagag gagagcaatc tgatgtcggc aaaggctcga 112860
atgcttgagc tacatattaa gattctcgac acgctgcaga aagtgtataa agatctgaaa 112920
gaagggattc aggaagaaga cgaaacggaa aagattctca tggagattat caatcagagc 112980
aaggctaacc tgtgaaaaca ggtagttcat tcaattttt agctatattg attccctgag 113040
ctatcacctg atccatgttg taatagttat aagtagccag tctacccacc agtataatcc 113100
catggcactc cagttcgttc ttcatagaag ccgccttttc tctgtaggtt ttcttgttaa 113160
tcggataggc tttgaacgaa ttttcctgag gatgttgaga gggatactct atggtataaa 113220
ccctgtcaag attcagcctg gagtgatcga taacgcgggt aaagggttct ctatcagagg 113280
aaagatgaaa tccgatggat tcgagcgtac tccactcttt cagtttgcga agcacatagg 113340
gatcggaaga tataccttca gttttttctc tggtttcaat tctgagatga atgtaaggga 113400
gatgttcttc tttacctgtt actctctggt aaagcctatc aaggtccccg gtataaataa 113460
aagggttatt ttttatgtcg tttagatgat caagcgcgtc ttcggaataa actatattga 113520
ctaccggcac ataatttctg atataatcaa tcatccgtat aatcattttc cagtaaccat 113580
caaccgggag cgccaccatt ttatcgtcaa aataagagtg atatcttttc cagtcggtaa 113640
agaagggaac gcgggaagct accgttttta ccatctcttc atcccagtaa tctccccaca 113700
ccttttttga gtaaggggca taccagtttt catagacgaa agatttaagc ggttccggga 113760
gattgcctac cggaattttt ctgttaagaa gttcttcttc cagctcaatt tctccaagat 113820
acagccgcac ccagaaaaga gatgaaggaa taaatgaaca tatatcattt tcggtaacag 113880
cataggcatt gtaactgata gagtaaaagg aagagaatcg cgacacaaat ttgatcactt 113940
cgggggaatt ggtatgaaag atatgaaccc cgtatcggtg atatttttc ccccggtcaa 114000
aatcccagac gttcccaccg gggtggttgc gcttttcaaa aaaagtaatc tcttcaaatc 114060
tgaagccacg atcaaggaga gaaataacgg tgctgagtgc cgcaagacct gttcccccta 114120
caaacaaccg tttcataatt ttctgacctc cgggtctctt agcacttgag gaaacatacc 114180
ctgtacctgc tttccgacaa aataatccat gttgacgcgc cgaacggaga atatccgaga 114240
aggtctgtac atatgtgcgt gagataaata cggaagcgtg gcatatctcc acttgaacgc 114300
atgtgccaca tggattaaaa aagtttccgt gtgggttgga agataatcgt aatactttct 114360
cagagattcg agataatacc tgttaataac gtgcccccg tcaagatgca tgaaaacgcc 114420
gcgcttgtgc agtttgtttg aagtgaaata attgtagaca taatcggcat attcattaaa 114480
aagctttaca tcgaaataat cgagaaaatg ttcttctctg ataacaatct ctctccagtc 114540
tttttttgcg aaagtctcca cataacatgc ggcggcgtaa atgtaatatc cctcagggt 114600
ttttaacctt tcatcggcaa gatgatcggg aagctcaatt cgctcatacg gatctttgaa 114660
aggtgtttcg ttttgatagg gaacaacccc gtaaggttct accatgttgg agcaaatcat 114720
aaaatattta tcgaaacacc cctcctcgaa tgctttatcc aaccctttca gatatgccgg 114780
gggaatataa acatcgtcgt gcacaaacac cccggcttct acaccaagaa gaccaagtgc 114840
gtcaataaat gcagcaaact gagagtactg aatttcatct acaagaaaaa cattaagttt 114900
gtgatgttcc agttgatttt taagccacga tctccaaact tctttatctt ttaccggttg 114960
```

```
aaggttgaaa tgctggagca atttataatc cgggtgaaag cgcatttccg gataaacaaa   115020
aatataaaaa taatcccgaa ggtgtgaaat gtgtgggtaa atattttttaa gccacacttc   115080 gggaatttcc ccgagcgtta tcattacaaa ggcgatttcc ccgcgataaa aagaagggtt   115140
cggggaagaa gaaatcttct caaccttcat tgttttccgc aattttaatt acaacccggt   115200
tttcttcaaa gttaagctcg aattccttt ccgacgcatt gattccaagt tcttccagtt     115260 cctttttgaag ttcccccatg atcttcatgc gctcccgctt ggctttaagc gcatgctcga   115320
atacgttcac atcgccttca tcgacgattt ccaccagcat atcaaagaca agcaccgcca   115380
tttcaatgta ggcgttgcgg agttgcattt cacgaagtgc aagggatttg agctggtcaa   115440
ccttctcttt gtcttctacg acaatggtat tttcagagcg tgtaacggta ggttcaccca   115500
ctttaatgaa atctttcct ttcatggctt ttttttgatga aaaacgatc gggttcaaga     115560 aaggtttcag aaggtgttaa gcggatattc ttcagacgcc tgagcttccg aagccgcatc   115620
gtaatcgcca accgtaatat aaatatcctc aattccaaaa aattgggcg gatagcgaaa     115680 ttcataaagc gtaagttcag acggcgttac aacaatatca aatatccaca caccaccttc   115740
atcatttcca agaataatcg cttttgcagtt gatcttatcc gattcggtaa agaaaggttt   115800
gcttctgaga acaaatcttc tccctaccgc aacaaaaagg ttggtgccgc tttccgggta   115860
aaaatcgacg tcgttgtctt cagaatcaac gatggtaaac acattgggtt gaatataaag   115920
cgtataagat ttgttgactc cataagcggt ttgtggttcg atgataaagt tctgaggata   115980
ctgtgtttca tagaggatat ttacgtttac gatcatcggc atgaaatccc ttcgatcccc   116040
ttcatccgtt tcatacagcg taaccagatg aaatttgctg tcaaaaatat tccccacttc   116100
gcgaggttga cgaatgatag aaacagttgg ggagtataca ttataaacca cttcgtcatc   116160
tgaaagggcg aattttccca tcgtacgaag ataatcggca atggagattt tctggcgaat   116220
gagctttgca atcaaacgct gaccgtattc tgtaagagac gccgtaacaa gcatatcaga   116280
attccacctt cagtttaatc acgtattcat cttcgttggt cttacgaagc ggagaggaaa   116340
gtcttccaag cgccacaagc tgattgttct gatcatagat tccaacggtg gtaatataag   116400
taccctgatc aggatacaaa atgcgtccgg aagtgggatc gtagaatgtg ggattgagcg   116460
agtaattgaa ttcgccagcc tttacgcgac agaaaataac catagagtga atgttatcca   116520
ccattgaaag cgtcatgtca agaataaggt tggcgatgtt ttcatgaagt ttcgcaacgc   116580
caccgaccgg aggattgctg tcaatcggga atccggttgg atccagcatg taaagcgaag   116640
tgctgtatcc ccccgatcca accccaagcg aatgagagac aaaatcgccg catgcatcca   116700
gatcgatcag aagcagcgcc gactgaggga atacgattcc aaacaccttc tgagttatgg   116760
agtgggttac aggaaccgcc tttccactct gaagtgaacc cgacaccaga tagtagaacg   116820
gctgcacctg ggtgcggatc ggagtagcga ggttggttc gccgctgttg tcaaccagag    116880
acagggttgc gcggtttgat ccgtcggtga agacaggtt aatctggaaa ttaccaacat     116940
caattgtatc ggcaaaatta tggaaggaga ctaccatgaa gttcttaagt tcactgaatc   117000
cggcaccggg atttgcggga tcacgggaa cagtaataac atcagaagcc agattggttt    117060
tgaattgatt gataaaagcc agataatgct ttcgagtaat ttcattagtt ccaccgccat   117120
agttcccttt ggaagcaaac gccacggaaa actccggatc ggtggtaagc gatcctttga   117180
agatattcac atagtaatcg ttgtaatgat cgggttgcga agaataagtt acaaaatcgt   117240
ttcgtgcaat aactccgctt ttatcccaga accccgaaac ggctacattt ctcgtgctgt   117300
acaccacgtc gtcaatttgc ttgaagacaa acccctgagg ctgcggagcc gtctcagctt   117360
```

```
ccgtagcgat gttgttgaca acgtttcgta tagtttcgag ctcttccgta gtgatagaca 117420
gattcgattg cagatagttc agaaatccct gcaaaatctg tcgcttggaa taatcggtaa 117480
ccgttccaag tagcgtggta atgtaggaaa taagttgctc tctcataatc ttatgtaatc 117540
agttttactt tcagttcagc ttgtgcacca ctttcgttgc ccctgataag cacaatggtt 117600
tcggtgttgg gcgtagccgt ttgcgccggt tcgatcacaa acttgcgccc ggaaatcgct 117660
ttatagtcgg ggttgcttgt cgggaagggg aacggcgcct gtgtcgacgg ttcagcaaca 117720
gaaatgttta gctgtttgct atcataaagc aatgaataac caagaatctt atcaagtgca 117780
accacaaact ttgtacttgg gatgaagaga tatcggcgaa ggttatctgt agaagtaacc 117840
ctgagcacga tttcactctg atccagaagc aaaatgggaa tttcgttgac aatgatattc 117900
ggatcgccta ccacactgaa aagatgatag cgcggcactt caaacggctt gggttctacc 117960
agcgaatagc tcagaatttg cggagggtta cccgcgcttg cagaaaacac atattcataa 118020
tcgattccgt cgtcagaaag tgcaaagtag gcaatatcga aactaccgga cgcaaacaac 118080
cttctaccgt atgccgtgag cgtggctacg aatataccg tgttttctga tttggtgggg 118140
ataaacattt ttttctttaa ataaagtttt cagttaccca ctacaagttt taaaagctca 118200
accagtatcg aagggtctac aatagccagc gcaatgaagg gaaaaagtgg caaaatcaac 118260
ccgacaataa atccggtgag tagcaatttg atgaacagtt gttgttgatc ttttctgttc 118320
tgcaatgcat tgtcataagc gccctgcaat agatcacgat attttcacc cacctccgtt 118380
ttatctttaa gagactcgat ttgaacgctc agtcgattca atatatcttc tatatcatca 118440
agttttctc taatgttgtt tctatcctgt acaacggttc tgagcacatc tttaatatct 118500
ttaatcattt caatgatgtt cgatagaatg aaacgtatct gataatctct gtcaaactgt 118560
tcttcgttca tccctgtttt taaattaaat aaaaaggggg agacgacacg tagtacatct 118620
cccccataaa attatttttt atgcgaatta aggcgtgcgc ttttccagaa gatacatcgt 118680
aagaacatcg ccatttacag caagcagttt ggtaccttcc cggttgggga aaggattgat 118740
ccggttgaaa tcaatgcggc gcatttcctg acgactatcc ttttcaaaat ggtttctcag 118800
gaaattcaga gcatttagcg tataatacat gtcattttct ttccagtagt gcgcaatgat 118860
cttgcgtttg tggttcagca cgaaatcctt ttcgcggtgg aattccggaa cggaataaat 118920
gacattatcc accagcgagc agtaatcggc aagatcctga agatgagcat attcagttga 118980
aagaatatca ggaacctcgc tgggaatgta cgtgtcataa tccccgtaaa caattccccg 119040
gatattagcc gcattgtaag tcgaagactc gacaaaatgc gttttcaacc gcttgtctga 119100
gtaatccttg gaaaacagaa atatccggct tggattttca ggatcgtcga acattaaaag 119160
cttttcagcc ttaacaaacc actcatattc cgacttgaat accggcttga aatagaacac 119220
ggtgcggaat tgagtggaac gtcgagagcg tcttggtttt gccaacgtac ccatagtctt 119280
tctcctattt ttttttgtt tggttttaaa tacattctgt gtaacaataa aaattcataa 119340
aggtttcaaa gatttttaca atttcttatt taaagaaaaa tgcccgcaaa atcaagaaaa 119400
caacagagat atatattcta tctcagaaac aaatatggat caccggaaaa aaccccccaag 119460
aaatacaaat ggatatggca caaagattgg gagaaactgg aggaagccaa acgtaaaaag 119520
aaaaagaaga aaagacgtaa aaataaacgc tcttacctga agccggattc ctattataag 119580
aaaccatacg gttattacgg aatctggtat taccattatg atgacggtgt ggatgatggg 119640
ggagatgcgg gtgatggtgg aagtggtgct ggtgtgggtg aagctaaagg tgcaaaacct 119700
```

```
gctaagaaat ctaaaaaaga agtgctccgc gatcttgagg tcaaactgca cgacttcaac  119760
aaggagttga aaaaactcct cgagaatctc ggattctaaa aaaagaaagc cggggaatca  119820
accccggcat ttttttgtttc accaaggtaa atcgttatta ccgtctgac acgactcaat  119880 caattcctct tcttccggtt cttcttcttc ataactgtaa aaccatatat gaaagtaata  119940
tccccgccct tcttcccact ctcgcatttg ctgctcttcg aagacgtctt gcaaaaaacg  120000 cttttgtcaaa ctcatggctc cctcctattt ttggttgaca atcgattct actggtaata  120060 tacgcattga tcagagaaaa gtcaaatgaa gaatctgtta aacagagata tatccgcact  120120
cagcggaagt gtagatgtca acctcagata caatcttata aagttttttc attagcacca  120180
caaagtcttc ttccggaagc tctaatagca attcctcatt atatttgaga aggggaagca  120240
tagctttact tccgctaccc accgaataat agggatcacg aatgaacatt gtcgtgaaat  120300
tgtcggatac cacaaacacc ccgtgctgac tgattcccat aattttcccg ttcatatccc  120360
cattatcatt cagaagattc aacccccttca gatgatctct ccacttgtac gtaaacgtct  120420
ctacaatcgt gtttttgctg taggattctc tgttaaagat aagcggcgag gaaaattttg  120480
caaaggcgtt ctgatagatt acccttccga caaaaccaag cggaattcga tccaccagtt  120540
cggacggcgt ctgaatatcc agaaaagcgg ctttgggtc atccctgacc accagcatgc  120600
cgtccattgt ggtggtatag tcaaaaaaaa cataccgctt atcggctctg tcaatggcta  120660
ctaccgtgct catgattatt taagggtttg cgttaaggtg tctttcaaat gatacacaat  120720
gtctctaatc tcagcaggta taagttctct gatggtaaaa aattcgtcag gaaatattat  120780
ctgtctcaga ttaatatatc ctattcggtt gtgatagcga actccgttcc ccaccgctac  120840
cacaatatgc tcgaaaggtg agcggtgtcc gttttttgtaa agtcttcttg caagttttaa  120900 attttttatct aagtcggatt catcagaagc ataggaaacg cgggctatac gcgccaccga  120960
tgtaaccagt agtttggaat tcaattcctc cggtgaaata actccctgaa gaggatcgac  121020
aatatctccg ggattggctt cgaaagccgg ggagttgtcg tagatatagc gaatcaggag  121080 cgctatttt cggaattcgg gttgtgcgtc ggaagcgcaa cgaagtctga aaagttgtc  121140 aagcgaatac ggatcggcaa tggaagcgat gacatctgta tatgcatagg gtgaaagtat  121200
tcgattagcg tgttgcttgt gtacattgag tttctcgagc acaaaatgca accccgctga  121260
tgtatataac ccggtatacc aacaccacct tgccagcaca tctttccacc ctcctatttt  121320
tttatcggaa aacattgccc ctgagttttc cacaaaatca tctggaacaa agggggttttc  121380 aagtacacgc ttccggtatt ttttcaagga aatggctctt gtagaagcgg cattcctcga  121440
aaaggcgcga tgtgtattaa attcagccag tatgactgtg ggaatttgaa agcgaaagca  121500
gaagaagata tcgttattcg tcttcgtttt gatcagatac cacaccattg ctttctgagt  121560 ttttttccatt taaaaccgat ccatttaaac aaagtttcat ttctctgatt tcatctttca  121620
gggtttcaga aaggtgtaat atttcatccc actcgcgagt attgcgctca aaaatctcaa  121680
ctccactgga aacatcactc atcattttt tcctccttgt gtttaatgtt gtggtaaatc  121740
tataatttgc gggtgttgcc agaagcgcat ttcatagata ccccactttc ttttaaataa  121800
aagaaaaata actttttttta aaaaattatt taccccggtc gtcaagtctt ccaatatccg  121860 gctcttata gggatgaatg cgatatttct tctggaaaaa ctccttccac tccggcgatt  121920
tttcaaatac gacatccaga ttgtcgataa gtgcctttgc caccatgtgt ttgcagattc  121980 tccccggta gtaatgatcc gggcacgtac atttgaatgt gcgggtgtca aaattgacgc  122040
gcgttacgta ttttttgtag gagccgcttt cgagagtatc acgggcgcgt tcaagcagcg  122100
```

```
ttctcccctg tttgtctttc tgagtctgac accatttgag aaaagagagg agttgtttat  122160
atcgcttatc gaacgtttca agccgcttgc gctcgcgttc ttcaatagag cgcttgagtt  122220
cttcagcctt ttgctgtctc tcttttatac ttggcggcgg catacgctca gatgtttaaa  122280
attctccgaa gcagactttc gatctgatct tcggtaaaat ctcttttgga tatataaagc  122340
acaagattgc gctccgtgtt gttttcggt ggggtgtttc ctttgagaag gtttctgaaa   122400
tattcgatga actctttttt aagctctttt tccgactttc cggttttatt ctgcacaagt  122460
gttttttcgg tggaagtagc ctcttcttcg ttgacggcga cattatatat agagagcatg  122520
agaaacatct ctaccgccgg atcggtagca tgacgtgcag ccatatcggc acttcggcgc  122580
tgaatggctt catatagcag tgattcctcg cgggtcattc ttttctgtta aataaatgtg  122640
aatccgtagg aaagggaaaa catcagggga aagcacacat ataagaacca gaacccagaa  122700
caaaaaatag gaggaaggtt atgggtaaga tcgatgtttc gaacatcaaa accgccgttg  122760
ccatctccca gaaagccaat gttcctcttt atctgtgggg tggtgtggga atctccaaaa  122820
cccaacaaat ctatcagtat gccaccagca ccaatcaaaa atgtgctgtc gttacgggt   122880
tggcaataga tccaaccgac gtagtgggtc attacattgc cgacttcaat aaacgtatca  122940
cctaccagac caaaccctat ctttatgaac tcttcggtga ggaagagcgg ggaatcatct  123000
tccttgacga attcaacaac tcagaaagtg atgtgatggg ggtgtttcta aagcttctcg  123060
acgaaaagag gcttggaagc tacaaactcc ctgatggaat tcacatcatt gcagccggta  123120
atccccccga actggctcca aatgcttcct cgcttccgct tgccgtcgct actcgatttg  123180
cccatcttta tgtggaagcg gatttcatct cccttaagag atggttgaaa ggagcggaag  123240
atgaagagga ttatgtaaag attttcaatc ttgaagtcgg ggaagatgtt gttcagcagg  123300
tgttcgatat tttcgttgac tactgcattg aaaacggtct tttcccggct tcagaagatt  123360
ctcgtagttg cgagtgggag gggagcctga attaccgcac attgcactat gcagcaaaaa  123420
tcggggctgt atacaaagtt gcttacaaaa atgtatcaaa tcaatcgaca ctgtataatg  123480
taactgtaga aatgatccac ggtctggttg gaaccatcgc ttccaacctg atggaacatc  123540
ttgaaaacaa gtggcttcca tcggcaaaag agattctcga aaactatgat attgtgctca  123600
agcatcgaga cgcctatgcc gcccttgcct acaaccttat gagcggcatt caggaagaag  123660
actatccgag gttggtggat ttcatgcaat ggttagaaaa gaaaaacgaa cttgtaatgc  123720
ttgcggcgat agtggaatct ttccagtcgt tcattccgaa gaaaaggttt ctgacaagcc  123780
ggttcgaata ctacaaccag attttcaaaa tcattaatcg atcgctggac gtctataaga  123840
aagtcaaacc cacaaacaac aagtgattga ttatggaacc gattgtcgaa aaaaagctct  123900
atgaactgat taactgcatt gtaaaaaatc atacccact cgccatgatt ctttcccgaa   123960
tcaaagtgcg ggtaggggt agggataaat acacactggg actctgcaaa gaacgggaaa   124020
tcattctcag ccggtgtctc tttgatgatg aaatcgttta tcccaaactt gtatttatca  124080
aagaccccga caccggcgag atcgtagact atgatattga agactatgtt gccaaaatcg  124140
atgatgaagg gcggtatcat accctgctgg aagaaatcat tcatgccggt ctcatgcacc  124200
ccatgcgtgt agaccggttt cagaaaacat atcaggagct ttttgaaaag aacaagcggc  124260
tggtgaattt tctgtacctt tgtcttgagg ttgagcgtca tgcaatacat accgctgtag  124320
ccaacatcga tctacttaag cccgtgttca agacaacac gcgggatgaa aagattgtgg   124380
aattcattaa agttattcaa catgatcatc ccgatcaaaa gctgtttggg tttacttttg  124440
```

```
aaagactgtt tttgaagtat ctcaacgatt ttgagggagg taaaattgca gcccccgcaa   124500
tttacgatct gatggaatac gacgggaata ccgttcccga caagttcata gaagcaatcg   124560
aaaaatctct tcataaaggg aaaaagtatg gaaatcagac actggatgaa atctttgaaa   124620
tccggcgtgt ggatcaaaag gggttgcaat tgacgcaact cctgaagcag atttgcttcc   124680
gcagggcacg taaaaaaccc tcgctgcacg tgctcgacaa aaagcggaag cactacgaac   124740
cgctcaggtt tgggaaaatc aaagaaaaaa cttcaaatat cgccattatt ctggatgtgt   124800
cgggaagtat gcttcgtgat ttcaaaaagc atcgcctgat tgacatcgcg acaagtatga   124860
tcgtggaaac tttcaaaaac gcacccaata tcgatgtata catcggagat accgaaatca   124920
aggataaagc gaagatccgc accctgtttt cccgtttcaa aggggcggt ggaaccgata   124980 tgtctaacat ctataaacaa ctgaaagatc gataccagaa aatactggtt gttaccgacg   125040
gggagacacc cttccccgaa ccaaaagact accgccctca ggatacttt atcatcatta   125100 atgatgaaat gcccgaaatt cccaattaca tcaaaaccct gaaggtgaaa ctatgaacga   125160 aaagcgttc cagttccgca atcttctaaa ggaagtgatc ggcatgcgaa tcctcgagcg   125220
attcaaccac atagaacctg aaggaaaaag gaaatgggta attttatccg cctacattct   125280
aatagtggaa gaagaaaatg cacccccagat ctgcaaggaa cttgttcgaa acaatacaga   125340
gatagatcct ctggaatttg tcagatcttt caaagaagaa cttataaaca tgatcgaaaa   125400
tcaaaattat cgaaatgaat tgagaaata cgttgcaaac tacgcgatag aaaacgaaat   125460
caattacaga aacatgatag caaacttttt ctgatataaa aaggaaaacc cccggttcat   125520
caccgggggc ttcctcagcg tctattccct atcgggtaag ttccgccatt acggctgcag   125580
gagcttcaca tacagcagac catagaactc tggacgcacc acctccagag cgtagcgggt   125640
catcagacca cgccggtaag agaagttaac gggatcgacg atcgtcggcg tgaacagcag   125700
cggcacatac ggagcgtaaa ccgcacccgt ttgccacggc gtgttcagat cttgattacc   125760
catgatgatc accggctggt tctgatagat gttcttgtac aggcggtagc gtccctgcac   125820
catacctaca tagaagatac cggtaccacc atcgcggttg tcgttacccg gcgtaaagcc   125880
cggcatcgac tccagcagcg cagccacctg tgggctggta acaaggaagt tggcacccgc   125940
aaccgccgtc ttctgctgaa tgcggttgct gaccttgttc agttcgatca tcagggtagc   126000
caaccattcc tgcttcgagc cgtagaagtt gccggcaaca aagttacccg acgtttcatc   126060
gtagtattca ccgaccactt ccgaccagaa gccatagttg tcagtgcgcc gggcatgcgc   126120
catgatcgtc gacaggattt ccagatcgat ctcacgggca atatactgag acatgagcgt   126180
aacgatttcg ttttcaagat cgacgcccctt atgataggcg gcgagatcct gcatcgcttc   126240
cggcgtccag gcggcacgca gcttacgggt cttggtagcc accggacggc tccgaagctc   126300
aaggttgatc tccggaatat ccagcgactg gaatccggga tccggatagt caggatccgt   126360
cgactggtct tcgaagtcgt ttcgagcatc gatgtagtag accagatcaa ggtcttgagt   126420
cgacggagta ccaccggcaa cggtcgcaaa gtcagagccg gttacgaaga caaccgcgc   126480 gtacagcgcc gaaccgacgg caccgacgat ccggttgtag cgcggaagcg ggtaagcgac   126540
cgtgttttca ggatcaccgg aagcgtcgtc atattgccag aagcgcaccg tattcacatc   126600
ggcgacaccg ggaagcgacg caaccggcac atccacatag tacaccgcac cgctcgagac   126660
cagtgaagca atgccggtgt caaaaccgac atcccgcatc gtcgcctgct gggcggtagc   126720
cagatccacg tgatcgtgg tctcatactc ccgacgcgac aggcgagcgt tttcatcata   126780
cagaccgccc gtagccgtgt cggtggtcag accggtacca ccgtagaccg agccgtttcc   126840
```

```
gggaagctca ggcgacttga aatccagata gaagaccaga cctgttggga gcgacagcgg   126900
ctgcaccgac accagatccg tcgcacgcag gttggcgaac acacggcgca caatcggaag   126960
tgccagattc cagccgtcaa cctccgtggt ctgggtggtc tccatcaggt gcttcttagc   127020
ctcgcggtac tggttctcca gcagggtagc gagcgtatgc cgctcccagt cgttacggca   127080
accctccaga agcggttgcc acttctcgat aagttgttcg ttaattttcg gttggctcat   127140
tttactctta tttttttttt gttttaaatc tctaaaaaca ttcggtattt aaccgaatta   127200
gagtccggca agacgcttaa tgcgctccag atccaacagc ggatcctcaa ccgaacccga   127260
cgtgcgggat tcggcgacag gtttcaccac acgggtttcc tgcagcttgc gcttgatccg   127320
ctcacgaatg cgctggcggg taacttcgtc aatgacgggc ttcttcaccc ggctttcccg   127380
catacggcgc ggcgtcggac acgaagcagc ttccgccatt tcctccgtct cctcaccagc   127440
caccttgcga agcagttcga tagcctcctc tacgcgctca agaagcgtgt gcaaaagatc   127500
catttcttca cgcacatgct cctcgctttc gacggcaccc ttgatgtcaa catcaatatc   127560
gagttcttcg tcgtccgaaa gatcggcatc ctttaactcg atttcggctt ccagctcgcc   127620
gtcttcgtcg acgtcttcaa catcgatttt gatgtcttcg tcatccagat ccagttccag   127680
atcctcctca tcgagatcca gttccagatc ttcgtcttcg tgttcggctt cggtaatccg   127740
acgcttcatt ttgtgtttag cttctcgcat ttcttcctgt tgtttagttt cccaggcttt   127800
ttgcaacgtt tgcgcgactt cttcggcaaa cgaagcaagc gtgtcatcgt cagtttcatc   127860
aaccttcgct tccgtcaggg gattaccttc aggctcttcc acctgctcaa gctcttcttc   127920
gagttccttc aaagcctccc gaatttcttc ggtgatcgag tgaatggaag cttcctgaag   127980
atgcctcttc tgcttttcct gacgaagcga ctcaaggtaa cccacaaagt ctttaaattc   128040
ctgcataact caaatttaaa tatatttaat cgccattcat tttaaaaaat ggcacctgct   128100
acgtgggaat attaaacccc acatcaaatt taaatatata ttttccgca cgaaataaaa   128160 aaaagggaga gaaactgatc tctcccccag gggtaacatg tattttataa cttgtgaact   128220
accaccacct atagatgtgg atggcttcgt ggtcaaggta gctcttgcta ccagattccc   128280
cacgctcaaa gggctgttcc atccccgaat ttgccaatta ttggctaatt aaatcacttt   128340
cttcttcaca agcgcctcgc gcaatctatg gcgtgctctg ttgattcgag atttgacggt   128400
tccgatagga atgttgtttt tctcagccag cgcctgcatg gcacatttt ccttcaactc   128460 catgtactgt ttcattatat tgtaaaacgg gttatcgcct ttttcaagtt cttcctgaat   128520
cacctccacc gcacgtttca attcatactg ctcatcaagc agcggctctc cggattcaat   128580
ttctacaggg gtatcccgat ctccaaatgt aatttcttcc atgtaaatcc tgggaccacg   128640
tcgagaattg tatcgataac gggtaattac aacggatttg aatacagtgt aaatatacgt   128700
agcgaaagaa gctccttcaa ccacgctata ggaatcaaat ctaagaagcc ttagaaacgt   128760
atcctgcacc atatcctcga tttcatgctc cgactttgta tatttctttc cgaaattttt   128820
gagccgctca gcatacctac tgtaaagcac ttcataacgg atttcgagcg gaacgttctg   128880
aaggaaaagt tcttcgtcgg tcatctgata gtatttacgc ttatccataa cttctcctct   128940
gttttaaagg ttgaaaatga tttcgtagcc gtcaatgcgg tcatcagtta tgagcttgtc   129000
ataaagatcg tcaatctttt ctatgttgtc ataaatcatg agcatttcat caatatcatg   129060
cacaacaaca gaaatgtaat aaccgttttc ttcatcaaaa cagagttcgg cgtagctttt   129120
atgaagatcc cccacacatt ttttgatatt ctctacaaat acttctacag gataatatct   129180
```

```
aaccagacaa aaatcgagat gcggaagcac actgttcatt atctgctcca gcacctcttc   129240
attagaaatc agcagttcat aatcgtcaat ggtatttaca ttgtagacaa gatggttgtt   129300
ggatgtaata gtaggaatga cttcgtgagt tgggttgaaa tatgtgttta ccagatcttg   129360
aacggaatcg agcgcgtcgc gataatcaat tttagtctcc atagccatat cctaaaaggt   129420
tggttgatat ataccggtta tggaaaataa aaaggggag agagggtgtt cctttccca    129480 caccctctct ccgcgtttat agggaaagtc gtcatcgaag tagccctcaa tctcctccat   129540
cgaatgagat tcttttttcgg gagagattca ccttttttctt ggggggatta caaaattcct   129600
cttccgcggg atcaaagccc ctaatggaga atctcttcct ggcggagcg ggttcatgct    129660 tccccaatca ttgttatttc cccagacaaa cacatggacg tctcttccac caacaaaacg   129720
aacttctccc gaatcggcgg agatgttcgg gagttcaccg cgaacccgga tcagggatcc   129780
caccccggct ttccgcacaa gatcggaagg tcccgttgta aaagtaaatg ttgaaccact   129840
cggtgctttc ttgctgaccg tcccaccgac ggaccgccag ccgtacggtg gtataactgt   129900
ttccgcta                                                            129908
```

<210> SEQ ID NO 2
<211> LENGTH: 892
<212> TYPE: PRT
<213> ORGANISM: Vaccinia virus (strain Copenhagen)

<400> SEQUENCE: 2

```
Gln Asn Ala Thr Met Asp Glu Phe Leu Asn Ile Ser Trp Phe Tyr Ile
 1               5                  10                  15

Ser Asn Gly Ile Ser Pro Asp Gly Cys Tyr Ser Leu Asp Glu Gln Tyr
                20                  25                  30

Leu Thr Lys Ile Asn Asn Gly Cys Tyr His Cys Asp Asp Pro Arg Asn
             35                  40                  45

Cys Phe Ala Lys Lys Ile Pro Arg Phe Asp Ile Pro Arg Ser Tyr Leu
         50                  55                  60

Phe Leu Asp Ile Glu Cys His Phe Asp Lys Lys Phe Pro Ser Val Phe
 65                  70                  75                  80

Ile Asn Pro Ile Ser His Thr Ser Tyr Cys Tyr Ile Asp Leu Ser Gly
                 85                  90                  95

Lys Arg Leu Leu Phe Thr Leu Ile Asn Glu Glu Met Leu Thr Glu Gln
            100                 105                 110

Glu Ile Gln Glu Ala Val Asp Arg Gly Cys Leu Arg Ile Gln Ser Leu
        115                 120                 125

Met Glu Met Asp Tyr Glu Arg Glu Leu Val Leu Cys Ser Glu Ile Val
    130                 135                 140

Leu Leu Arg Ile Ala Lys Gln Leu Leu Glu Leu Thr Phe Asp Tyr Val
145                 150                 155                 160

Val Thr Phe Asn Gly His Asn Phe Asp Leu Arg Tyr Ile Thr Asn Arg
                165                 170                 175

Leu Glu Leu Leu Thr Gly Glu Lys Ile Ile Phe Arg Ser Pro Asp Lys
            180                 185                 190

Lys Glu Ala Val His Leu Cys Ile Tyr Glu Arg Asn Gln Ser Ser His
        195                 200                 205

Lys Gly Val Gly Gly Met Ala Asn Thr Thr Phe His Val Asn Asn Asn
    210                 215                 220

Asn Gly Thr Ile Phe Phe Asp Leu Tyr Ser Phe Ile Gln Lys Ser Glu
225                 230                 235                 240
```

-continued

```
Lys Leu Asp Ser Tyr Lys Leu Asp Ser Ile Ser Lys Asn Ala Phe Ser
                245                 250                 255
Cys Met Gly Lys Val Leu Asn Arg Gly Val Arg Glu Met Thr Phe Ile
                260                 265                 270
Gly Asp Asp Thr Thr Asp Ala Lys Gly Lys Ala Ala Phe Ala Lys
                275                 280                 285
Val Leu Thr Thr Gly Asn Tyr Val Thr Val Asp Glu Asp Ile Ile Cys
                290                 295                 300
Lys Val Ile Arg Lys Asp Ile Trp Glu Asn Gly Phe Lys Val Val Leu
305                 310                 315                 320
Leu Cys Pro Thr Leu Pro Asn Asp Thr Tyr Lys Leu Ser Phe Gly Lys
                325                 330                 335
Asp Asp Val Asp Leu Ala Gln Met Tyr Lys Asp Tyr Asn Leu Asn Ile
                340                 345                 350
Ala Leu Asp Met Ala Arg Tyr Cys Ile His Asp Ala Cys Leu Cys Gln
                355                 360                 365
Tyr Leu Trp Glu Tyr Tyr Gly Val Glu Thr Lys Thr Asp Ala Gly Ala
                370                 375                 380
Ser Thr Tyr Val Leu Pro Gln Ser Met Val Phe Glu Tyr Arg Ala Ser
385                 390                 395                 400
Thr Val Ile Lys Gly Pro Leu Lys Leu Leu Glu Thr Lys Thr
                405                 410                 415
Ile Leu Val Arg Ser Glu Thr Lys Gln Lys Phe Pro Tyr Glu Gly Gly
                420                 425                 430
Lys Val Phe Ala Pro Lys Gln Lys Met Phe Ser Asn Asn Val Leu Ile
                435                 440                 445
Phe Asp Tyr Asn Ser Leu Tyr Pro Asn Val Cys Ile Phe Gly Asn Leu
                450                 455                 460
Ser Pro Glu Thr Leu Val Gly Val Val Ser Thr Asn Arg Leu Glu
465                 470                 475                 480
Glu Glu Ile Asn Asn Gln Leu Leu Gln Lys Tyr Pro Pro Arg
                485                 490                 495
Tyr Ile Thr Val His Cys Glu Pro Arg Leu Pro Asn Leu Ile Ser Glu
                500                 505                 510
Ile Ala Ile Phe Asp Arg Ser Ile Glu Gly Thr Ile Pro Arg Leu Leu
                515                 520                 525
Arg Thr Phe Leu Ala Glu Arg Ala Arg Tyr Lys Lys Met Leu Lys Gln
                530                 535                 540
Ala Thr Ser Ser Thr Glu Lys Ala Ile Tyr Asp Ser Met Gln Tyr Thr
545                 550                 555                 560
Tyr Lys Ile Val Ala Asn Ser Val Tyr Gly Leu Met Gly Phe Arg Asn
                565                 570                 575
Ser Ala Leu Tyr Ser Tyr Ala Ser Ala Lys Ser Cys Thr Ser Ile Gly
                580                 585                 590
Arg Arg Met Ile Leu Tyr Leu Glu Ser Val Leu Asn Gly Ala Glu Leu
                595                 600                 605
Ser Asn Gly Met Leu Arg Phe Ala Asn Pro Leu Ser Asn Pro Phe Tyr
                610                 615                 620
Met Asp Asp Arg Asp Ile Asn Pro Ile Val Lys Thr Ser Leu Pro Ile
625                 630                 635                 640
Asp Tyr Arg Phe Arg Phe Arg Ser Val Tyr Gly Asp Thr Asp Ser Val
                645                 650                 655
Phe Thr Glu Ile Asp Ser Gln Asp Val Asp Lys Ser Ile Glu Ile Ala
```

```
                    660                 665                 670
Lys Glu Leu Glu Arg Leu Ile Asn Asn Arg Val Leu Phe Asn Asn Phe
            675                 680                 685
Lys Ile Glu Phe Glu Ala Val Tyr Lys Asn Leu Ile Met Gln Ser Lys
        690                 695                 700
Lys Lys Tyr Thr Thr Met Lys Tyr Ser Ala Ser Ser Asn Ser Lys Ser
705                 710                 715                 720
Val Pro Glu Arg Ile Asn Lys Gly Thr Ser Glu Thr Arg Arg Asp Val
                725                 730                 735
Ser Lys Phe His Lys Asn Met Ile Lys Thr Tyr Lys Thr Arg Leu Ser
            740                 745                 750
Glu Met Leu Ser Glu Gly Arg Met Asn Ser Asn Gln Val Cys Ile Asp
        755                 760                 765
Ile Leu Arg Ser Leu Glu Thr Asp Leu Arg Ser Glu Phe Asp Ser Arg
    770                 775                 780
Ser Ser Pro Leu Glu Leu Phe Met Leu Ser Arg Met His His Ser Asn
785                 790                 795                 800
Tyr Lys Ser Ala Asp Asn Pro Asn Met Tyr Leu Val Thr Glu Tyr Asn
                805                 810                 815
Lys Asn Asn Pro Glu Thr Ile Glu Leu Gly Glu Arg Tyr Tyr Phe Ala
            820                 825                 830
Tyr Ile Cys Pro Ala Asn Val Pro Trp Thr Lys Lys Leu Val Asn Ile
        835                 840                 845
Lys Thr Tyr Glu Thr Ile Ile Asp Arg Ser Phe Lys Leu Gly Ser Asp
    850                 855                 860
Gln Arg Ile Phe Tyr Glu Val Tyr Phe Lys Arg Leu Thr Ser Glu Ile
865                 870                 875                 880
Val Asn Leu Leu Asp Asn Lys Val Leu Cys Ile Ser
                885                 890

<210> SEQ ID NO 3
<211> LENGTH: 892
<212> TYPE: PRT
<213> ORGANISM: Vaccinia virus (strain WR)

<400> SEQUENCE: 3

Gln Asn Ala Thr Met Asp Glu Phe Leu Asn Ile Ser Trp Phe Tyr Ile
1               5                   10                  15
Ser Asn Gly Ile Ser Pro Asp Gly Cys Tyr Ser Leu Asp Glu Gln Tyr
            20                  25                  30
Leu Thr Lys Ile Asn Asn Gly Cys Tyr His Cys Asp Asp Pro Arg Asn
        35                  40                  45
Cys Phe Ala Lys Lys Ile Pro Arg Phe Asp Ile Pro Arg Ser Tyr Leu
    50                  55                  60
Phe Leu Asp Ile Glu Cys His Phe Asp Lys Lys Phe Pro Ser Val Phe
65                  70                  75                  80
Ile Asn Pro Ile Ser His Thr Ser Tyr Cys Tyr Ile Asp Leu Ser Gly
                85                  90                  95
Lys Arg Leu Leu Phe Thr Leu Ile Asn Glu Glu Met Leu Thr Glu Gln
            100                 105                 110
Glu Ile Gln Glu Ala Val Asp Arg Gly Cys Leu Arg Ile Gln Ser Leu
        115                 120                 125
Met Glu Met Asp Tyr Glu Arg Glu Leu Val Leu Cys Ser Glu Ile Val
    130                 135                 140
```

-continued

Leu Leu Arg Ile Ala Lys Gln Leu Leu Glu Leu Thr Phe Asp Tyr Val
145                 150                 155                 160

Val Thr Phe Asn Gly His Asn Phe Asp Leu Arg Tyr Ile Thr Asn Arg
                165                 170                 175

Leu Glu Leu Thr Gly Glu Lys Ile Ile Phe Arg Ser Pro Asp Lys
            180                 185                 190

Lys Glu Ala Val Tyr Leu Cys Ile Tyr Glu Arg Asn Gln Ser Ser His
        195                 200                 205

Lys Gly Val Gly Gly Met Ala Asn Thr Thr Phe His Val Asn Asn Asn
    210                 215                 220

Asn Gly Thr Ile Phe Phe Asp Leu Tyr Ser Phe Ile Gln Lys Ser Glu
225                 230                 235                 240

Lys Leu Asp Ser Tyr Lys Leu Asp Ser Ile Ser Lys Asn Ala Phe Ser
                245                 250                 255

Cys Met Gly Lys Val Leu Asn Arg Gly Val Arg Glu Met Thr Phe Ile
                260                 265                 270

Gly Asp Asp Thr Thr Asp Ala Lys Gly Lys Ala Ala Phe Ala Lys
            275                 280                 285

Val Leu Thr Thr Gly Asn Tyr Val Thr Val Asp Glu Asp Ile Ile Cys
    290                 295                 300

Lys Val Ile Arg Lys Asp Ile Trp Glu Asn Gly Phe Lys Val Val Leu
305                 310                 315                 320

Leu Cys Pro Thr Leu Pro Asn Asp Thr Tyr Lys Leu Ser Phe Gly Lys
                325                 330                 335

Asp Asp Val Asp Leu Ala Gln Met Tyr Lys Asp Tyr Asn Leu Asn Ile
            340                 345                 350

Ala Leu Asp Met Ala Arg Tyr Cys Ile His Asp Ala Cys Leu Cys Gln
        355                 360                 365

Tyr Leu Trp Glu Tyr Tyr Gly Val Glu Thr Lys Thr Asp Ala Gly Ala
    370                 375                 380

Ser Thr Tyr Val Leu Pro Gln Ser Met Val Phe Glu Tyr Arg Ala Ser
385                 390                 395                 400

Thr Val Ile Lys Gly Pro Leu Leu Lys Leu Leu Leu Glu Thr Lys Thr
                405                 410                 415

Ile Leu Val Arg Ser Glu Thr Lys Gln Lys Phe Pro Tyr Glu Gly Gly
            420                 425                 430

Lys Val Phe Ala Pro Lys Gln Lys Met Phe Ser Asn Asn Val Leu Ile
        435                 440                 445

Phe Asp Tyr Asn Ser Leu Tyr Pro Asn Val Cys Ile Phe Gly Asn Leu
    450                 455                 460

Ser Pro Glu Thr Leu Val Gly Val Val Ser Thr Asn Arg Leu Glu
465                 470                 475                 480

Glu Glu Ile Asn Asn Gln Leu Leu Gln Lys Tyr Pro Pro Arg
                485                 490                 495

Tyr Ile Thr Val His Cys Glu Pro Arg Leu Pro Asn Leu Ile Ser Glu
            500                 505                 510

Ile Ala Ile Phe Asp Arg Ser Ile Glu Gly Thr Ile Pro Arg Leu Leu
        515                 520                 525

Arg Thr Phe Leu Ala Glu Arg Ala Arg Tyr Lys Lys Met Leu Lys Gln
    530                 535                 540

Ala Thr Ser Ser Thr Glu Lys Ala Ile Tyr Asp Ser Met Gln Tyr Thr
545                 550                 555                 560

Tyr Lys Ile Val Ala Asn Ser Val Tyr Gly Leu Met Gly Phe Arg Asn

```
                565                 570                 575
Ser Ala Leu Tyr Ser Tyr Ala Ser Ala Lys Ser Cys Thr Ser Ile Gly
            580                 585                 590

Arg Arg Met Ile Leu Tyr Leu Glu Ser Val Leu Asn Gly Ala Glu Leu
            595                 600                 605

Ser Asn Gly Met Leu Arg Phe Ala Asn Pro Leu Ser Asn Pro Phe Tyr
            610                 615                 620

Met Asp Asp Arg Asp Ile Asn Pro Ile Val Lys Thr Ser Leu Pro Ile
625                 630                 635                 640

Asp Tyr Arg Phe Arg Phe Arg Ser Val Tyr Gly Asp Thr Asp Ser Val
            645                 650                 655

Phe Thr Glu Ile Asp Ser Gln Asp Val Asp Lys Ser Ile Glu Ile Ala
            660                 665                 670

Lys Glu Leu Glu Arg Leu Ile Asn Asn Arg Val Leu Phe Asn Asn Phe
            675                 680                 685

Lys Ile Glu Phe Glu Ala Val Tyr Lys Asn Leu Ile Met Gln Ser Lys
            690                 695                 700

Lys Lys Tyr Thr Thr Met Lys Tyr Ser Ala Ser Ser Asn Ser Lys Ser
705                 710                 715                 720

Val Pro Glu Arg Ile Asn Lys Gly Thr Ser Glu Thr Arg Arg Asp Val
            725                 730                 735

Ser Lys Phe His Lys Asn Met Ile Lys Thr Tyr Lys Thr Arg Leu Ser
            740                 745                 750

Glu Met Leu Ser Glu Gly Arg Met Asn Ser Asn Gln Val Cys Ile Asp
            755                 760                 765

Ile Leu Arg Ser Leu Glu Thr Asp Leu Arg Ser Glu Phe Asp Ser Arg
770                 775                 780

Ser Ser Pro Leu Glu Leu Phe Met Leu Ser Arg Met His His Ser Asn
785                 790                 795                 800

Tyr Lys Ser Ala Asp Asn Pro Asn Met Tyr Leu Val Thr Glu Tyr Asn
            805                 810                 815

Lys Asn Asn Pro Glu Thr Ile Glu Leu Gly Glu Arg Tyr Tyr Phe Ala
            820                 825                 830

Tyr Ile Cys Pro Ala Asn Val Pro Trp Thr Lys Lys Leu Val Asn Ile
            835                 840                 845

Lys Thr Tyr Glu Thr Ile Ile Asp Arg Ser Phe Lys Leu Gly Ser Asp
            850                 855                 860

Gln Arg Ile Phe Tyr Glu Val Tyr Phe Lys Arg Leu Thr Ser Glu Ile
865                 870                 875                 880

Val Asn Leu Leu Asp Asn Lys Val Leu Cys Ile Ser
            885                 890

<210> SEQ ID NO 4
<211> LENGTH: 891
<212> TYPE: PRT
<213> ORGANISM: Variola virus

<400> SEQUENCE: 4

Gln Asn Ala Thr Met Asp Glu Phe Leu Asn Ile Ser Trp Phe Tyr Ile
1               5                   10                  15

Ser Asn Gly Ile Ser Pro Asp Gly Cys Tyr Ser Leu Asp Asp Gln Tyr
            20                  25                  30

Leu Thr Lys Ile Asn Asn Gly Cys Tyr His Cys Gly Asp Pro Arg Asn
        35                  40                  45
```

-continued

```
Cys Phe Ala Lys Glu Ile Pro Arg Phe Asp Ile Pro Arg Ser Tyr Leu
     50              55              60
Phe Leu Asp Ile Glu Cys His Phe Asp Lys Lys Phe Pro Ser Val Phe
65              70              75              80
Ile Asn Pro Ile Ser His Thr Ser Tyr Cys Tyr Ile Asp Leu Ser Gly
             85              90              95
Lys Arg Leu Leu Phe Thr Leu Ile Asn Glu Glu Met Leu Thr Glu Gln
            100             105             110
Glu Ile Gln Glu Ala Val Asp Arg Gly Cys Leu Arg Ile Gln Ser Leu
            115             120             125
Met Glu Met Asp Tyr Glu Arg Glu Leu Val Leu Cys Ser Glu Ile Val
    130             135             140
Leu Leu Gln Ile Ala Lys Gln Leu Leu Glu Leu Thr Phe Asp Tyr Ile
145             150             155             160
Val Thr Phe Asn Gly His Asn Phe Asp Leu Arg Tyr Ile Thr Asn Arg
                165             170             175
Leu Glu Leu Leu Thr Gly Glu Lys Ile Ile Phe Arg Ser Pro Asp Lys
            180             185             190
Lys Glu Ala Val His Leu Cys Ile Tyr Glu Arg Asn Gln Ser Ser His
            195             200             205
Lys Gly Val Gly Gly Met Ala Asn Thr Thr Phe His Val Asn Asn Asn
210             215             220
Asn Gly Thr Ile Phe Phe Asp Leu Tyr Ser Phe Ile Gln Lys Ser Glu
225             230             235             240
Lys Leu Asp Ser Tyr Lys Leu Asp Ser Ile Ser Lys Asn Ala Phe Ser
                245             250             255
Cys Met Gly Lys Val Leu Asn Arg Gly Val Arg Glu Met Thr Phe Ile
            260             265             270
Gly Asp Asp Thr Thr Asp Ala Lys Gly Lys Ala Ala Val Phe Ala Lys
            275             280             285
Val Leu Thr Thr Gly Asn Tyr Val Thr Val Asp Asp Ile Ile Cys Lys
    290             295             300
Val Ile His Lys Asp Ile Trp Glu Asn Gly Phe Lys Val Val Leu Ser
305             310             315             320
Cys Pro Thr Leu Thr Asn Asp Thr Tyr Lys Leu Ser Phe Gly Lys Asp
                325             330             335
Asp Val Asp Leu Ala Gln Met Tyr Lys Asp Tyr Asn Leu Asn Ile Ala
            340             345             350
Leu Asp Met Ala Arg Tyr Cys Ile His Asp Ala Cys Leu Cys Gln Tyr
            355             360             365
Leu Trp Glu Tyr Tyr Gly Val Glu Thr Lys Thr Asp Ala Gly Ala Ser
    370             375             380
Thr Tyr Val Leu Pro Gln Ser Met Val Phe Gly Tyr Lys Ala Ser Thr
385             390             395             400
Val Ile Lys Gly Pro Leu Leu Lys Leu Leu Glu Thr Lys Thr Ile
                405             410             415
Leu Val Arg Ser Glu Thr Lys Gln Lys Phe Pro Tyr Glu Gly Gly Lys
            420             425             430
Val Phe Ala Pro Lys Gln Lys Met Phe Ser Asn Asn Val Leu Ile Phe
            435             440             445
Asp Tyr Asn Ser Leu Tyr Pro Asn Val Cys Ile Phe Gly Asn Leu Ser
    450             455             460
Pro Glu Thr Leu Val Gly Val Val Val Ser Ser Asn Arg Leu Glu Glu
```

-continued

```
           465                 470                 475                 480
Glu Ile Asn Asn Gln Leu Leu Leu Gln Lys Tyr Pro Pro Arg Tyr
                485                 490                 495
Ile Thr Val His Cys Glu Pro Arg Leu Pro Asn Leu Ile Ser Glu Ile
                500                 505                 510
Ala Ile Phe Asp Arg Ser Ile Glu Gly Thr Ile Pro Arg Leu Leu Arg
                515                 520                 525
Thr Phe Leu Ala Glu Arg Ala Arg Tyr Lys Lys Met Leu Lys Gln Ala
                530                 535                 540
Thr Ser Ser Thr Glu Lys Ala Ile Tyr Asp Ser Met Gln Tyr Thr Tyr
545                 550                 555                 560
Lys Ile Ile Ala Asn Ser Val Tyr Gly Leu Met Gly Phe Arg Asn Ser
                565                 570                 575
Ala Leu Tyr Ser Tyr Ala Ser Ala Lys Ser Cys Thr Ser Ile Gly Arg
                580                 585                 590
Arg Met Ile Leu Tyr Leu Glu Ser Val Leu Asn Gly Ala Glu Leu Ser
                595                 600                 605
Asn Gly Met Leu Arg Phe Ala Asn Pro Leu Ser Asn Pro Phe Tyr Met
                610                 615                 620
Asp Asp Arg Asp Ile Asn Pro Ile Val Lys Thr Ser Leu Pro Ile Asp
625                 630                 635                 640
Tyr Arg Phe Arg Phe Arg Ser Val Tyr Gly Asp Thr Asp Ser Val Phe
                645                 650                 655
Thr Glu Ile Asp Ser Gln Asp Val Asp Lys Ser Ile Glu Ile Ala Lys
                660                 665                 670
Glu Leu Glu Arg Leu Ile Asn Ser Arg Val Leu Phe Asn Asn Phe Lys
                675                 680                 685
Ile Glu Phe Glu Ala Val Tyr Lys Asn Leu Ile Met Gln Ser Lys Lys
                690                 695                 700
Lys Tyr Thr Thr Met Lys Tyr Ser Ala Ser Ser Asn Ser Lys Ser Val
705                 710                 715                 720
Pro Glu Arg Ile Asn Lys Gly Thr Ser Glu Thr Arg Arg Asp Val Ser
                725                 730                 735
Lys Phe His Lys Asn Met Ile Lys Ile Tyr Lys Thr Arg Leu Ser Glu
                740                 745                 750
Met Leu Ser Glu Gly Arg Met Asn Ser Asn Gln Val Cys Ile Asp Ile
                755                 760                 765
Leu Arg Ser Leu Glu Thr Asp Leu Arg Ser Glu Phe Asp Ser Arg Ser
                770                 775                 780
Ser Pro Leu Glu Leu Phe Met Leu Ser Arg Met His His Leu Asn Tyr
785                 790                 795                 800
Lys Ser Ala Asp Asn Pro Asn Met Tyr Leu Val Thr Glu Tyr Asn Lys
                805                 810                 815
Asn Asn Pro Glu Thr Ile Glu Leu Gly Glu Arg Tyr Tyr Phe Ala Tyr
                820                 825                 830
Ile Cys Pro Ala Asn Val Pro Trp Thr Lys Lys Leu Val Asn Ile Lys
                835                 840                 845
Thr Tyr Glu Thr Ile Ile Asp Arg Ser Phe Lys Leu Gly Ser Asp Gln
                850                 855                 860
Arg Ile Phe Tyr Glu Val Tyr Phe Lys Arg Leu Thr Ser Glu Ile Val
865                 870                 875                 880
Asn Leu Leu Asp Asn Lys Val Leu Cys Ile Ser
                885                 890
```

-continued

<210> SEQ ID NO 5
<211> LENGTH: 874
<212> TYPE: PRT
<213> ORGANISM: Fowlpox virus

<400> SEQUENCE: 5

```
Glu Lys Gln Tyr Leu Gln Glu Tyr Leu Asp Ile Thr Trp Phe Tyr Leu
 1               5                  10                  15

Leu Asn Asn Ile Thr Pro Asp Gly Cys Tyr Lys Ile Asp Ile Glu His
            20                  25                  30

Leu Thr Pro Ile Lys Lys Asp Cys Tyr His Cys Asp Asp Val Ser Lys
        35                  40                  45

Val Phe Ile Gln Glu Ile Pro Ile Phe Glu Val Lys Phe Thr Tyr Leu
    50                  55                  60

Leu Phe Asp Ile Glu Cys Gln Phe Asp Lys Lys Phe Pro Ser Val Phe
65                  70                  75                  80

Val Asn Pro Ile Ser His Ile Ser Cys Trp Ile Ile Asp Lys Val Thr
                85                  90                  95

Glu Tyr Lys Phe Thr Leu Ile Asn Thr Asp Ile Leu Pro Asp Lys Glu
            100                 105                 110

Pro Ser Ile Leu His His Lys Asp Phe Ser Pro Lys Asp Arg Ile Thr
        115                 120                 125

Tyr Cys Thr Glu Ile Val Met Leu Leu Ile Met Lys Lys Ile Leu Glu
    130                 135                 140

His Arg Phe Asp Phe Val Ile Thr Phe Asn Gly Asn Asn Phe Asp Ile
145                 150                 155                 160

Arg Tyr Ile Ser Gly Arg Leu Glu Ile Leu Glu Lys Ser Phe Ile Tyr
                165                 170                 175

Phe Ser Leu Pro Asp Ala Thr Glu Thr Val Lys Leu Lys Ile Phe Glu
            180                 185                 190

Arg Phe Val Thr Gly Gly Thr Phe Thr Asn Lys Thr Tyr His Ile Asn
        195                 200                 205

Asn Asn Asn Gly Val Met Phe Phe Asp Leu Tyr Ala Phe Ile Gln Lys
    210                 215                 220

Thr Glu Arg Leu Asp Ser Tyr Lys Leu Asp Ser Ile Ser Lys Asn Ile
225                 230                 235                 240

Phe Asn Cys Asn Val Ala Ile Lys Glu Ile Asp Asp Thr Ile Leu Thr
                245                 250                 255

Leu Glu Ala Thr Val Lys Asp Asn Ser Lys Asp Lys Leu Ser Ile Phe
            260                 265                 270

Ser Arg Val Leu Glu Thr Gly Asn Tyr Ile Thr Ile Gly Asp Asn Asn
        275                 280                 285

Val Ser Lys Ile Val Tyr Lys Asp Ile Asn Gln Asp Ser Phe Ile Ile
    290                 295                 300

Lys Val Ile Ser Asn Arg Asp Tyr Glu Ile Gly Ser Val His Asn Ile
305                 310                 315                 320

Ser Phe Gly Lys Asp Asp Val Asp Leu Lys Asp Met Tyr Lys Asn Tyr
                325                 330                 335

Asn Leu Glu Ile Ala Leu Asp Met Glu Arg Tyr Cys Ile His Asp Ala
            340                 345                 350

Cys Leu Cys Lys Tyr Ile Trp Asp Tyr Tyr Arg Val Pro Ser Lys Ile
        355                 360                 365

Asn Ala Ala Ser Ser Thr Tyr Leu Leu Pro Gln Ser Leu Ala Leu Glu
```

```
                   370                 375                 380
Tyr Arg Ala Ser Thr Leu Ile Lys Gly Pro Leu Leu Lys Leu Leu Leu
385                 390                 395                 400

Glu Glu Arg Val Ile Tyr Thr Arg Lys Ile Thr Lys Val Arg Tyr Pro
                405                 410                 415

Tyr Ile Gly Gly Lys Val Phe Leu Pro Ser Gln Lys Thr Phe Glu Asn
                420                 425                 430

Asn Val Met Ile Phe Asp Tyr Asn Ser Leu Tyr Pro Asn Val Cys Ile
                435                 440                 445

Tyr Gly Asn Leu Ser Pro Glu Lys Leu Val Cys Ile Leu Leu Asn Ser
450                 455                 460

Asn Lys Leu Glu Ser Glu Ile Asn Met Arg Thr Ile Lys Ser Lys Tyr
465                 470                 475                 480

Pro Tyr Pro Glu Tyr Val Cys Val Ser Cys Glu Ser Arg Leu Ser Asp
                485                 490                 495

Tyr Tyr Ser Glu Ile Ile Val Tyr Asp Arg Arg Glu Lys Gly Ile Ile
                500                 505                 510

Pro Lys Leu Leu Glu Met Phe Ile Gly Lys Arg Lys Glu Tyr Lys Asn
                515                 520                 525

Leu Leu Lys Thr Ala Ser Thr Thr Ile Glu Ser Thr Leu Tyr Asp Ser
530                 535                 540

Leu Gln Tyr Ile Tyr Lys Ile Ile Ala Asn Ser Val Tyr Gly Leu Met
545                 550                 555                 560

Gly Phe Ser Asn Ser Thr Leu Tyr Ser Tyr Ser Ser Ala Lys Thr Cys
                565                 570                 575

Thr Thr Ile Gly Arg Asn Met Ile Thr Tyr Leu Asp Ser Ile Met Asn
                580                 585                 590

Gly Ala Val Trp Glu Asn Asp Lys Leu Ile Leu Ala Asp Phe Pro Arg
                595                 600                 605

Asn Ile Phe Ser Gly Glu Thr Met Phe Asn Lys Glu Leu Glu Val Pro
                610                 615                 620

Asn Met Asn Glu Ser Phe Lys Phe Arg Ser Val Tyr Gly Asp Thr Asp
625                 630                 635                 640

Ser Ile Phe Ser Glu Ile Ser Thr Lys Asp Ile Glu Lys Thr Ala Lys
                645                 650                 655

Ile Ala Lys His Leu Glu His Ile Ile Asn Thr Lys Ile Leu His Ala
                660                 665                 670

Asn Phe Lys Ile Glu Phe Glu Ala Ile Tyr Thr Gln Leu Ile Leu Gln
                675                 680                 685

Ser Lys Lys Lys Tyr Thr Thr Ile Lys Tyr Leu Ala Asn Tyr Lys Pro
                690                 695                 700

Gly Asp Lys Pro Ile Arg Val Asn Lys Gly Thr Ser Glu Thr Arg Arg
705                 710                 715                 720

Asp Val Ala Leu Phe His Lys His Met Ile Gln Arg Tyr Lys Asp Met
                725                 730                 735

Leu Met Lys Leu Leu Met Gln Ser Lys Gly Gln Gln Glu Ile Thr Arg
                740                 745                 750

Leu Ile Leu Gln Ser Leu Glu Thr Asp Met Ile Ser Glu Phe Thr His
                755                 760                 765

Asn Arg Glu Phe Glu Lys Tyr Leu Leu Ser Arg Lys His His Asn Asn
                770                 775                 780

Tyr Lys Ser Ala Thr His Ser Asn Phe Glu Leu Val Lys Arg Tyr Asn
785                 790                 795                 800
```

```
Leu Glu Asn Thr Glu Lys Ile Glu Ile Gly Glu Arg Tyr Tyr Ile
                805                 810                 815
Tyr Ile Cys Asp Ile Ser Leu Pro Trp Gln Lys Lys Leu Cys Asn Ile
                820                 825                 830
Leu Ser Tyr Glu Val Ile Ala Asp Ser Lys Phe Tyr Leu Pro Lys Asp
                835                 840                 845
Lys Arg Ile Phe Tyr Glu Ile Tyr Phe Lys Arg Ile Ala Ser Glu Val
                850                 855                 860
Val Asn Leu Leu Thr Asp Lys Thr Gln Cys
865                 870

<210> SEQ ID NO 6
<211> LENGTH: 738
<212> TYPE: PRT
<213> ORGANISM: Bos taurus (Bovine)

<400> SEQUENCE: 6

Pro Ser Phe Ala Pro Tyr Glu Ala Asn Val Asp Phe Glu Ile Arg Phe
1               5                   10                  15
Met Val Asp Thr Asp Ile Val Gly Cys Asn Trp Leu Glu Leu Pro Ala
                20                  25                  30
Gly Lys Tyr Ile Leu Arg Pro Glu Gly Lys Ala Thr Leu Cys Gln Leu
                35                  40                  45
Glu Ala Asp Val Leu Trp Ser Asp Val Ile Ser His Pro Pro Glu Gly
        50                  55                  60
Glu Trp Gln Arg Ile Ala Pro Leu Arg Val Leu Ser Phe Asp Ile Glu
65                  70                  75                  80
Cys Ala Gly Arg Lys Gly Ile Phe Pro Glu Pro Glu Arg Asp Pro Val
                85                  90                  95
Ile Gln Ile Cys Ser Leu Gly Leu Arg Trp Gly Glu Pro Glu Pro Phe
                100                 105                 110
Leu Arg Leu Ala Leu Thr Leu Arg Pro Cys Ala Pro Ile Leu Gly Ala
                115                 120                 125
Lys Val Gln Ser Tyr Glu Arg Glu Glu Asp Leu Leu Gln Ala Trp Ser
        130                 135                 140
Thr Phe Ile Arg Ile Met Asp Pro Asp Val Ile Thr Gly Tyr Asn Ile
145                 150                 155                 160
Gln Asn Phe Asp Leu Pro Tyr Leu Ile Ser Arg Ala Gln Thr Leu Lys
                165                 170                 175
Val Pro Gly Phe Pro Leu Leu Gly Arg Val Ile Gly Leu Arg Ser Asn
                180                 185                 190
Ile Arg Glu Ser Ser Phe Gln Ser Arg Gln Thr Gly Arg Arg Asp Ser
                195                 200                 205
Lys Val Val Ser Met Val Gly Arg Val Gln Met Asp Met Leu Gln Val
        210                 215                 220
Leu Leu Arg Glu Tyr Lys Leu Arg Ser Tyr Thr Leu Asn Ala Val Ser
225                 230                 235                 240
Phe His Phe Leu Gly Glu Gln Lys Glu Asp Val Gln His Ser Ile Ile
                245                 250                 255
Thr Asp Leu Gln Asn Gly Asn Asp Gln Thr Arg Arg Arg Leu Ala Val
                260                 265                 270
Tyr Cys Leu Lys Asp Ala Phe Leu Pro Leu Arg Leu Leu Glu Arg Leu
                275                 280                 285
Met Val Leu Val Asn Ala Met Glu Met Ala Arg Val Thr Gly Val Pro
```

-continued

```
            290                 295                 300
Leu Gly Tyr Leu Leu Ser Arg Gly Gln Gln Val Lys Val Ser Gln
305                 310                 315                 320

Leu Leu Arg Gln Ala Met Arg Gln Gly Leu Leu Met Pro Val Lys
                325                 330                 335

Thr Glu Gly Gly Glu Asp Tyr Thr Gly Ala Thr Val Ile Glu Pro Leu
                340                 345                 350

Lys Gly Tyr Tyr Asp Val Pro Ile Ala Thr Leu Asp Phe Ser Ser Leu
                355                 360                 365

Tyr Pro Ser Ile Met Met Ala His Asn Leu Cys Tyr Thr Thr Leu Leu
370                 375                 380

Arg Pro Gly Ala Ala Gln Lys Leu Gly Leu Thr Glu Asp Gln Phe Ile
385                 390                 395                 400

Lys Thr Pro Thr Gly Asp Glu Phe Val Lys Ala Ser Val Arg Lys Gly
                405                 410                 415

Leu Leu Pro Gln Ile Leu Glu Asn Leu Leu Ser Ala Arg Lys Arg Ala
                420                 425                 430

Lys Ala Glu Leu Ala Lys Glu Thr Asp Pro Leu Arg Arg Gln Val Leu
                435                 440                 445

Asp Gly Arg Gln Leu Ala Leu Lys Val Ser Ala Asn Ser Val Tyr Gly
450                 455                 460

Phe Thr Gly Ala Gln Val Gly Arg Leu Pro Cys Leu Glu Ile Ser Gln
465                 470                 475                 480

Ser Val Thr Gly Phe Gly Arg Gln Met Ile Glu Lys Thr Lys Gln Leu
                485                 490                 495

Val Glu Thr Lys Tyr Thr Val Glu Asn Gly Tyr Ser Thr Ser Ala Lys
                500                 505                 510

Val Val Tyr Gly Asp Thr Asp Ser Val Met Cys Arg Phe Gly Val Ser
                515                 520                 525

Ser Val Ala Glu Ala Met Ala Leu Gly Arg Glu Ala Ala Asp Trp Val
                530                 535                 540

Ser Gly His Phe Pro Ser Pro Ile Arg Leu Glu Phe Glu Lys Val Tyr
545                 550                 555                 560

Phe Pro Tyr Leu Leu Ile Ser Lys Lys Arg Tyr Ala Gly Leu Leu Phe
                565                 570                 575

Ser Ser Arg Pro Asp Ala His Asp Arg Met Asp Cys Lys Gly Leu Glu
                580                 585                 590

Ala Val Arg Arg Asp Asn Cys Pro Leu Val Ala Asn Leu Val Thr Ala
                595                 600                 605

Ser Leu Arg Arg Leu Leu Ile Asp Arg Asp Pro Ser Gly Ala Val Ala
                610                 615                 620

His Ala Gln Asp Val Ile Ser Asp Leu Leu Cys Asn Arg Ile Asp Ile
625                 630                 635                 640

Ser Gln Leu Val Ile Thr Lys Glu Leu Thr Arg Ala Ala Ala Asp Tyr
                645                 650                 655

Ala Gly Lys Gln Ala His Val Glu Leu Ala Glu Arg Met Arg Lys Arg
                660                 665                 670

Asp Pro Gly Ser Ala Pro Ser Leu Gly Asp Arg Val Pro Tyr Val Ile
                675                 680                 685

Ile Ser Ala Ala Lys Gly Val Ala Ala Tyr Met Lys Ser Glu Asp Pro
                690                 695                 700

Leu Phe Val Leu Glu His Ser Leu Pro Ile Asp Thr Gln Tyr Tyr Leu
705                 710                 715                 720
```

Glu Gln Gln Leu Ala Lys Pro Leu Leu Arg Ile Phe Glu Pro Ile Leu
            725                 730                 735

Gly Glu

<210> SEQ ID NO 7
<211> LENGTH: 738
<212> TYPE: PRT
<213> ORGANISM: Homo sapiens

<400> SEQUENCE: 7

Pro Ser Phe Ala Pro Tyr Glu Ala Asn Val Asp Phe Glu Ile Arg Phe
1               5                   10                  15

Met Val Asp Thr Asp Ile Val Gly Cys Asn Trp Leu Glu Leu Pro Ala
            20                  25                  30

Gly Lys Tyr Ala Leu Arg Leu Lys Glu Lys Ala Thr Gln Cys Gln Leu
        35                  40                  45

Glu Ala Asp Val Leu Trp Ser Asp Val Val Ser His Pro Pro Glu Gly
    50                  55                  60

Pro Trp Gln Arg Ile Ala Pro Leu Arg Val Leu Ser Phe Asp Ile Glu
65                  70                  75                  80

Cys Ala Gly Arg Lys Gly Ile Phe Pro Glu Pro Glu Arg Asp Pro Val
                85                  90                  95

Ile Gln Ile Cys Ser Leu Gly Leu Arg Trp Gly Pro Glu Pro Phe
            100                 105                 110

Leu Arg Leu Ala Leu Thr Leu Arg Pro Cys Ala Pro Ile Leu Gly Ala
        115                 120                 125

Lys Val Gln Ser Tyr Glu Lys Glu Asp Leu Leu Gln Ala Trp Ser
    130                 135                 140

Thr Phe Ile Arg Ile Met Asp Pro Asp Val Ile Thr Gly Tyr Asn Ile
145                 150                 155                 160

Gln Asn Phe Asp Leu Pro Tyr Leu Ile Ser Arg Ala Gln Thr Leu Lys
                165                 170                 175

Val Gln Thr Phe Pro Phe Leu Gly Arg Val Ala Gly Leu Cys Ser Asn
            180                 185                 190

Ile Arg Asp Ser Ser Phe Gln Ser Lys Gln Thr Gly Arg Arg Asp Thr
        195                 200                 205

Lys Val Val Ser Met Val Gly Arg Val Gln Met Asp Met Leu Gln Val
    210                 215                 220

Leu Leu Arg Glu Tyr Lys Leu Arg Ser His Thr Leu Asn Ala Val Ser
225                 230                 235                 240

Phe His Phe Leu Gly Glu Gln Lys Glu Asp Val Gln His Ser Ile Ile
                245                 250                 255

Thr Asp Leu Gln Asn Gly Asn Asp Gln Thr Arg Arg Arg Leu Ala Val
            260                 265                 270

Tyr Cys Leu Lys Asp Ala Tyr Leu Pro Leu Arg Leu Leu Glu Arg Leu
        275                 280                 285

Met Val Leu Val Asn Ala Val Glu Met Ala Arg Val Thr Gly Val Pro
    290                 295                 300

Leu Ser Tyr Leu Leu Ser Arg Gly Gln Gln Val Lys Val Val Ser Gln
305                 310                 315                 320

Leu Leu Arg Gln Ala Met His Glu Gly Leu Leu Met Pro Val Val Lys
                325                 330                 335

Ser Glu Gly Gly Glu Asp Tyr Thr Gly Ala Thr Val Ile Glu Pro Leu
            340                 345                 350

```
Lys Gly Tyr Tyr Asp Val Pro Ile Ala Thr Leu Asp Phe Ser Ser Leu
        355                 360                 365

Tyr Pro Ser Ile Met Met Ala His Asn Leu Cys Tyr Thr Thr Leu Leu
370                 375                 380

Arg Pro Gly Thr Ala Gln Lys Leu Gly Leu Thr Glu Asp Gln Phe Ile
385                 390                 395                 400

Arg Thr Pro Thr Gly Asp Glu Phe Val Lys Thr Ser Val Arg Lys Gly
                405                 410                 415

Leu Leu Pro Gln Ile Leu Glu Asn Leu Leu Ser Ala Arg Lys Arg Ala
                420                 425                 430

Lys Ala Glu Leu Ala Lys Glu Thr Asp Pro Leu Arg Arg Gln Val Leu
                435                 440                 445

Asp Gly Arg Gln Leu Ala Leu Lys Val Ser Ala Asn Ser Val Tyr Gly
                450                 455                 460

Phe Thr Gly Ala Gln Val Gly Lys Leu Pro Cys Leu Glu Ile Ser Gln
465                 470                 475                 480

Ser Val Thr Gly Phe Gly Arg Gln Met Ile Glu Lys Thr Lys Gln Leu
                485                 490                 495

Val Glu Ser Lys Tyr Thr Val Glu Asn Gly Tyr Ser Thr Ser Ala Lys
                500                 505                 510

Val Val Tyr Gly Asp Thr Asp Ser Val Met Cys Arg Phe Gly Val Ser
                515                 520                 525

Ser Val Ala Glu Ala Met Ala Leu Gly Arg Glu Ala Ala Asp Trp Val
                530                 535                 540

Ser Gly His Phe Pro Ser Pro Ile Arg Leu Glu Phe Glu Lys Val Tyr
545                 550                 555                 560

Phe Pro Tyr Leu Leu Ile Ser Lys Lys Arg Tyr Ala Gly Leu Leu Phe
                565                 570                 575

Ser Ser Arg Pro Asp Ala His Asp Arg Met Asp Cys Lys Gly Leu Glu
                580                 585                 590

Ala Val Arg Arg Asp Asn Cys Pro Leu Val Ala Asn Leu Val Thr Ala
                595                 600                 605

Ser Leu Arg Arg Leu Leu Ile Asp Arg Asp Pro Glu Gly Ala Val Ala
610                 615                 620

His Ala Gln Asp Val Ile Ser Asp Leu Leu Cys Asn Arg Ile Asp Ile
625                 630                 635                 640

Ser Gln Leu Val Ile Thr Lys Glu Leu Thr Arg Ala Ala Ser Asp Tyr
                645                 650                 655

Ala Gly Lys Gln Ala His Val Glu Leu Ala Glu Arg Met Arg Lys Arg
                660                 665                 670

Asp Pro Gly Ser Ala Pro Ser Leu Gly Asp Arg Val Pro Tyr Val Ile
                675                 680                 685

Ile Ser Ala Ala Lys Gly Val Ala Ala Tyr Met Lys Ser Glu Asp Pro
690                 695                 700

Leu Phe Val Leu Glu His Ser Leu Pro Ile Asp Thr Gln Tyr Tyr Leu
705                 710                 715                 720

Glu Gln Gln Leu Ala Lys Pro Leu Leu Arg Ile Phe Glu Pro Ile Leu
                725                 730                 735

Gly Glu

<210> SEQ ID NO 8
<211> LENGTH: 734
<212> TYPE: PRT
```

<213> ORGANISM: Candida albicans (Yeast)

<400> SEQUENCE: 8

```
Ile Asp Pro Cys Ile Thr Tyr Asp Asn Ile Asn Tyr Leu Leu Arg Leu
1               5                   10                  15

Met Ile Asp Cys Lys Ile Thr Gly Met Ser Trp Ile Thr Leu Pro Arg
            20                  25                  30

Asp Lys Tyr Lys Ile Val Asn Asn Lys Ile Ser Thr Cys Gln Ile Glu
        35                  40                  45

Cys Ser Ile Asp Tyr Arg Asp Leu Ile Ser His Pro Pro Glu Gly Glu
    50                  55                  60

Trp Leu Lys Met Ala Pro Leu Arg Ile Leu Ser Phe Asp Ile Glu Cys
65                  70                  75                  80

Ala Gly Arg Lys Gly Val Phe Pro Glu Ala Glu His Asp Pro Val Ile
                85                  90                  95

Gln Ile Ala Asn Val Val Gln Lys Ser Gly Glu Ser Lys Pro Phe Val
            100                 105                 110

Arg Asn Val Phe Thr Val Asn Thr Cys Ser Ser Ile Ile Gly Ser Gln
        115                 120                 125

Ile Phe Glu His Gln Arg Glu Glu Asp Met Leu Met His Trp Lys Glu
    130                 135                 140

Phe Ile Thr Lys Val Asp Pro Asp Val Ile Ile Gly Tyr Asn Thr Ala
145                 150                 155                 160

Asn Phe Asp Ile Pro Tyr Val Leu Asn Arg Ala Lys Ala Leu Gly Leu
                165                 170                 175

Asn Asp Phe Pro Phe Phe Gly Arg Leu Lys Arg Val Lys Gln Glu Ile
            180                 185                 190

Lys Asp Ala Val Phe Ser Ser Arg Ala Tyr Gly Thr Arg Glu Asn Lys
        195                 200                 205

Val Val Asn Ile Asp Gly Arg Met Gln Leu Asp Leu Leu Gln Phe Ile
    210                 215                 220

Gln Arg Glu Tyr Lys Leu Arg Ser Tyr Thr Leu Asn Ser Val Ser Ala
225                 230                 235                 240

His Phe Leu Gly Glu Gln Lys Glu Asp Val Gln His Ser Ile Ile Thr
                245                 250                 255

Asp Leu Gln Asn Gly Thr Lys Glu Thr Arg Arg Leu Ala Val Tyr
            260                 265                 270

Cys Leu Lys Asp Ala Phe Leu Pro Leu Arg Leu Leu Asp Lys Leu Met
        275                 280                 285

Cys Leu Val Asn Tyr Thr Glu Met Ala Arg Val Thr Gly Val Pro Phe
    290                 295                 300

Ser Tyr Leu Leu Ser Arg Gly Gln Gln Ile Lys Val Ile Ser Gln Leu
305                 310                 315                 320

Phe Arg Lys Cys Leu Gln Glu Asp Ile Val Ile Pro Asn Leu Lys Ser
                325                 330                 335

Glu Gly Ser Asn Glu Glu Tyr Glu Gly Ala Thr Val Ile Glu Pro Glu
            340                 345                 350

Arg Gly Tyr Tyr Asp Val Pro Ile Ala Thr Leu Asp Phe Ser Ser Leu
        355                 360                 365

Tyr Pro Ser Ile Met Met Ala His Asn Leu Cys Tyr Thr Thr Leu Leu
    370                 375                 380

Asn Lys Asn Ser Ile Lys Ala Phe Gly Leu Thr Glu Asp Asp Tyr Thr
385                 390                 395                 400
```

-continued

```
Lys Thr Pro Asn Gly Asp Tyr Phe Val His Ser Asn Leu Arg Lys Gly
                405                 410                 415

Ile Leu Pro Thr Ile Leu Asp Glu Leu Leu Thr Ala Arg Lys Lys Ala
            420                 425                 430

Lys Ala Asp Leu Lys Lys Glu Thr Asp Pro Phe Lys Lys Asp Val Leu
        435                 440                 445

Asn Gly Arg Gln Leu Ala Leu Lys Ile Ser Ala Asn Ser Val Tyr Gly
    450                 455                 460

Phe Thr Gly Ala Thr Val Gly Lys Leu Pro Cys Leu Ala Ile Ser Ser
465                 470                 475                 480

Ser Val Thr Ala Phe Gly Arg Glu Met Ile Glu Lys Thr Lys Asn Glu
                485                 490                 495

Val Gln Glu Tyr Tyr Ser Lys Lys Asn Gly His Pro Tyr Asp Ala Lys
            500                 505                 510

Val Ile Tyr Gly Asp Thr Asp Ser Val Met Val Lys Phe Gly Tyr Gln
        515                 520                 525

Asp Leu Glu Thr Cys Met Lys Leu Gly Glu Glu Ala Ala Asn Tyr Val
    530                 535                 540

Ser Thr Lys Phe Lys Asn Pro Ile Lys Leu Glu Phe Glu Lys Val Tyr
545                 550                 555                 560

Phe Pro Tyr Leu Leu Ile Asn Lys Lys Arg Tyr Ala Gly Leu Tyr Trp
                565                 570                 575

Thr Arg Pro Glu Lys Phe Asp Lys Met Asp Thr Lys Gly Ile Glu Thr
            580                 585                 590

Val Arg Arg Asp Asn Cys Gln Leu Val Gln Asn Val Ile Thr Lys Val
        595                 600                 605

Leu Glu Phe Ile Leu Glu Glu Arg Asp Val Pro Lys Ala Gln Arg Phe
    610                 615                 620

Val Lys Gln Thr Ile Ala Asp Leu Leu Gln Asn Arg Ile Asp Leu Ser
625                 630                 635                 640

Gln Leu Val Ile Thr Lys Ala Tyr Ser Lys His Asp Tyr Ser Ala Lys
                645                 650                 655

Gln Ala His Val Glu Leu Ala Glu Arg Met Arg Lys Arg Asp Pro Gly
            660                 665                 670

Ser Ala Pro Thr Leu Gly Asp Arg Val Ala Tyr Val Ile Ile Lys Thr
        675                 680                 685

Gly Gly Asp Lys Asn Tyr Glu Lys Ser Glu Asp Pro Leu Tyr Val Leu
    690                 695                 700

Glu Asn Ser Leu Pro Ile Asp Val Lys Tyr Tyr Leu Asp Gln Gln Leu
705                 710                 715                 720

Thr Lys Pro Leu Glu Arg Ile Phe Ile Pro Ile Leu Gly Glu
                725                 730
```

<210> SEQ ID NO 9
<211> LENGTH: 734
<212> TYPE: PRT
<213> ORGANISM: Saccharomyces cerevisiae

<400> SEQUENCE: 9

```
Ser Asn Gly Thr Thr Tyr Asp Asn Ile Ala Tyr Thr Leu Arg Leu
 1               5                  10                  15

Met Val Asp Cys Gly Ile Val Gly Met Ser Trp Ile Thr Leu Pro Lys
                20                  25                  30

Gly Lys Tyr Ser Met Ile Glu Pro Asn Asn Arg Val Ser Ser Cys Gln
            35                  40                  45
```

-continued

```
Leu Glu Val Ser Ile Asn Tyr Arg Asn Leu Ile Ala His Pro Ala Glu
     50                  55                  60

Gly Asp Trp Ser His Thr Ala Pro Leu Arg Ile Met Ser Phe Asp Ile
 65                  70                  75                  80

Glu Cys Ala Gly Arg Ile Gly Val Phe Pro Glu Pro Glu Tyr Asp Pro
                 85                  90                  95

Val Ile Gln Ile Ala Asn Val Val Ser Ile Ala Gly Ala Lys Lys Pro
            100                 105                 110

Phe Ile Arg Asn Val Phe Thr Leu Asn Thr Cys Ser Pro Ile Thr Gly
        115                 120                 125

Ser Met Ile Phe Ser His Ala Thr Glu Glu Met Leu Ser Asn Trp
    130                 135                 140

Arg Asn Phe Ile Ile Lys Val Asp Pro Asp Val Ile Ile Gly Tyr Asn
145                 150                 155                 160

Thr Thr Asn Phe Asp Ile Pro Tyr Leu Leu Asn Arg Ala Lys Ala Leu
                165                 170                 175

Lys Val Asn Asp Phe Pro Tyr Phe Gly Arg Leu Lys Thr Val Lys Gln
            180                 185                 190

Glu Ile Lys Glu Ser Val Phe Ser Ser Lys Ala Tyr Gly Thr Arg Glu
        195                 200                 205

Thr Lys Asn Val Asn Ile Asp Gly Arg Leu Gln Leu Asp Leu Leu Gln
    210                 215                 220

Phe Ile Gln Arg Glu Tyr Lys Leu Arg Ser Tyr Thr Leu Asn Ala Val
225                 230                 235                 240

Ser Ala His Phe Leu Gly Glu Gln Lys Glu Asp Val His Tyr Ser Ile
                245                 250                 255

Ile Ser Asp Leu Gln Asn Gly Asp Ser Glu Thr Arg Arg Leu Ala
            260                 265                 270

Val Tyr Cys Leu Lys Asp Ala Tyr Leu Pro Leu Arg Leu Met Glu Lys
    275                 280                 285

Leu Met Ala Leu Val Asn Tyr Thr Glu Met Ala Arg Val Thr Gly Val
    290                 295                 300

Pro Phe Ser Tyr Leu Leu Ala Arg Gly Gln Gln Ile Lys Val Val Ser
305                 310                 315                 320

Gln Leu Phe Arg Lys Cys Leu Glu Ile Asp Thr Val Ile Pro Asn Met
                325                 330                 335

Gln Ser Gln Ala Ser Asp Asp Gln Tyr Glu Gly Ala Thr Val Ile Glu
            340                 345                 350

Pro Ile Arg Gly Tyr Tyr Asp Val Pro Ile Ala Thr Leu Asp Phe Asn
        355                 360                 365

Ser Leu Tyr Pro Ser Ile Met Met Ala His Asn Leu Cys Tyr Thr Thr
    370                 375                 380

Leu Cys Asn Lys Ala Thr Val Glu Arg Leu Asn Leu Lys Ile Asp Glu
385                 390                 395                 400

Asp Tyr Val Ile Thr Pro Asn Gly Asp Tyr Phe Val Thr Thr Lys Arg
                405                 410                 415

Arg Arg Gly Ile Leu Pro Ile Ile Leu Asp Glu Leu Ile Ser Ala Arg
            420                 425                 430

Lys Arg Ala Lys Lys Asp Leu Arg Asp Glu Lys Asp Pro Phe Lys Arg
        435                 440                 445

Asp Val Leu Asn Gly Arg Gln Leu Ala Leu Lys Ile Ser Ala Asn Ser
450                 455                 460
```

-continued

```
Val Tyr Gly Phe Thr Gly Ala Thr Val Gly Lys Leu Pro Cys Leu Ala
465                 470                 475                 480

Ile Ser Ser Ser Val Thr Ala Tyr Gly Arg Thr Met Ile Leu Lys Thr
                485                 490                 495

Lys Thr Ala Val Gln Glu Lys Tyr Cys Ile Lys Asn Gly Tyr Lys His
            500                 505                 510

Asp Ala Val Val Tyr Gly Asp Thr Asp Ser Val Met Val Lys Phe
            515                 520                 525

Gly Thr Thr Asp Leu Lys Glu Ala Met Asp Leu Gly Thr Glu Ala Ala
530                 535                 540

Lys Tyr Val Ser Thr Leu Phe Lys His Pro Ile Asn Leu Glu Phe Glu
545                 550                 555                 560

Lys Ala Tyr Phe Pro Tyr Leu Leu Ile Asn Lys Lys Arg Tyr Ala Gly
                565                 570                 575

Leu Phe Trp Thr Asn Pro Asp Lys Phe Asp Lys Leu Asp Gln Lys Gly
                580                 585                 590

Leu Ala Ser Val Arg Arg Asp Ser Cys Ser Leu Val Ser Ile Val Met
                595                 600                 605

Asn Lys Val Leu Lys Lys Ile Leu Ile Glu Arg Asn Val Asp Gly Ala
            610                 615                 620

Leu Ala Phe Val Arg Glu Thr Ile Asn Asp Ile Leu His Asn Arg Val
625                 630                 635                 640

Asp Ile Ser Lys Leu Ile Ile Ser Lys Thr Leu Ala Pro Asn Tyr Thr
                645                 650                 655

Asn Pro Gln Pro His Ala Val Leu Ala Glu Arg Met Lys Arg Arg Glu
            660                 665                 670

Gly Val Gly Pro Asn Val Gly Asp Arg Val Asp Tyr Val Ile Ile Gly
                675                 680                 685

Gly Asn Asp Lys Leu Tyr Asn Arg Ala Glu Asp Pro Leu Phe Val Leu
690                 695                 700

Glu Asn Asn Ile Gln Val Asp Ser Arg Tyr Tyr Leu Thr Asn Gln Leu
705                 710                 715                 720

Gln Asn Pro Ile Ile Ser Ile Val Ala Pro Ile Ile Gly Asp
                725                 730
```

SEQ ID NO 10
<211> LENGTH: 735
<212> TYPE: PRT
<213> ORGANISM: Schizosaccharomyces pombe

<400> SEQUENCE: 10

```
Val Gly Val Thr Thr Phe Glu Ser Asn Thr Gln Tyr Leu Leu Arg Phe
1               5                   10                  15

Met Ile Asp Cys Asp Val Val Gly Met Asn Trp Ile His Leu Pro Ala
                20                  25                  30

Ser Lys Tyr Gln Phe Arg Tyr Gln Asn Arg Val Ser Asn Cys Gln Ile
            35                  40                  45

Glu Ala Trp Ile Asn Tyr Lys Asp Leu Ile Ser Leu Pro Ala Glu Gly
        50                  55                  60

Gln Trp Ser Lys Met Ala Pro Leu Arg Ile Met Ser Phe Asp Ile Glu
65                  70                  75                  80

Cys Ala Gly Arg Lys Gly Val Phe Pro Asp Pro Ser Ile Asp Pro Val
                85                  90                  95

Ile Gln Ile Ala Ser Ile Val Thr Gln Tyr Gly Asp Ser Thr Pro Phe
            100                 105                 110
```

-continued

Val Arg Asn Val Phe Cys Val Asp Thr Cys Ser Gln Ile Val Gly Thr
    115                 120                 125

Gln Val Tyr Glu Phe Gln Asn Gln Ala Glu Met Leu Ser Ser Trp Ser
    130                 135                 140

Lys Phe Val Arg Asp Val Asp Pro Asp Val Leu Ile Gly Tyr Asn Ile
145                 150                 155                 160

Cys Asn Phe Asp Ile Pro Tyr Leu Leu Asp Arg Ala Lys Ser Leu Arg
                165                 170                 175

Ile His Asn Phe Pro Leu Leu Gly Arg Ile His Asn Phe Phe Ser Val
                180                 185                 190

Ala Lys Glu Thr Ser Phe Ser Ser Lys Ala Tyr Gly Thr Arg Glu Ser
            195                 200                 205

Lys Thr Thr Ser Ile Pro Gly Arg Leu Gln Leu Asp Met Leu Gln Val
    210                 215                 220

Met Gln Arg Asp Phe Lys Leu Arg Ser Tyr Ser Leu Asn Ala Val Cys
225                 230                 235                 240

Ser Gln Phe Leu Gly Glu Gln Lys Glu Asp Val His Tyr Ser Ile Ile
                245                 250                 255

Thr Asp Leu Gln Asn Gly Thr Ala Asp Ser Arg Arg Arg Leu Ala Ile
                260                 265                 270

Tyr Cys Leu Lys Asp Ala Tyr Leu Pro Gln Arg Leu Met Asp Lys Leu
            275                 280                 285

Met Cys Phe Val Asn Tyr Thr Glu Met Ala Arg Val Thr Gly Val Pro
    290                 295                 300

Phe Asn Phe Leu Leu Ala Arg Gly Gln Gln Ile Lys Val Ile Ser Gln
305                 310                 315                 320

Leu Phe Cys Lys Ala Leu Gln His Asp Leu Val Pro Asn Ile Arg
                325                 330                 335

Val Asn Gly Thr Asp Glu Gln Tyr Glu Gly Ala Thr Val Ile Glu Pro
                340                 345                 350

Ile Lys Gly Tyr Tyr Asp Thr Pro Ile Ala Thr Leu Asp Phe Ser Ser
            355                 360                 365

Leu Tyr Pro Ser Ile Met Gln Ala His Asn Leu Cys Tyr Thr Thr Leu
    370                 375                 380

Leu Asp Ser Asn Thr Ala Glu Leu Leu Lys Leu Lys Gln Asp Val Asp
385                 390                 395                 400

Tyr Ser Val Thr Pro Asn Gly Asp Tyr Phe Val Lys Pro His Val Arg
                405                 410                 415

Lys Gly Leu Leu Pro Ile Ile Leu Ala Asp Leu Leu Asn Ala Arg Lys
            420                 425                 430

Lys Ala Lys Ala Asp Leu Lys Lys Glu Thr Asp Pro Phe Lys Lys Ala
    435                 440                 445

Val Leu Asp Gly Arg Gln Leu Ala Leu Lys Val Ser Ala Asn Ser Val
    450                 455                 460

Tyr Gly Phe Thr Gly Ala Thr Asn Gly Arg Leu Pro Cys Leu Ala Ile
465                 470                 475                 480

Ser Ser Ser Val Thr Ser Tyr Gly Arg Gln Met Ile Glu Lys Thr Lys
                485                 490                 495

Asp Val Val Glu Lys Arg Tyr Arg Ile Glu Asn Gly Tyr Ser His Asp
            500                 505                 510

Ala Val Val Ile Tyr Gly Asp Thr Asp Ser Val Met Val Lys Phe Gly
    515                 520                 525

-continued

```
Val Lys Thr Leu Pro Glu Ala Met Lys Leu Gly Glu Ala Ala Asn
    530                 535                 540

Tyr Val Ser Asp Gln Phe Pro Asn Pro Ile Asn Trp Ser Phe Ser Thr
545                 550                 555                 560

Phe Pro Tyr Leu Leu Ile Ser Lys Lys Arg Tyr Ala Gly Leu Phe Trp
                565                 570                 575

Thr Arg Thr Asp Thr Tyr Asp Lys Met Asp Ser Lys Gly Ile Glu Thr
            580                 585                 590

Val Arg Arg Asp Asn Cys Pro Leu Val Ser Tyr Val Ile Asp Thr Ala
        595                 600                 605

Leu Arg Lys Met Leu Ile Asp Gln Asp Val Glu Gly Ala Gln Leu Phe
    610                 615                 620

Thr Lys Lys Val Ile Ser Asp Leu Leu Gln Asn Lys Ile Asp Met Ser
625                 630                 635                 640

Gln His Val Ile Thr Lys Ala Leu Ser Lys Thr Asp Tyr Ala Ala Lys
                645                 650                 655

Met Ala His Val Glu Leu Ala Glu Arg Met Arg Lys Arg Asp Ala Gly
            660                 665                 670

Ser Ala Pro Ala Ile Gly Asp Arg Val Ala Tyr Val Ile Ile Lys Gly
        675                 680                 685

Ala Gln Gly Asp Gln Phe Tyr Met Arg Ser Glu Asp Pro Ile Tyr Val
    690                 695                 700

Leu Glu Asn Asn Ile Pro Ile Asp Ala Lys Tyr Tyr Leu Glu Asn Gln
705                 710                 715                 720

Leu Ser Lys Pro Leu Leu Arg Ile Phe Glu Pro Ile Leu Gly Glu
                725                 730                 735

<210> SEQ ID NO 11
<211> LENGTH: 741
<212> TYPE: PRT
<213> ORGANISM: Plasmodium falciparum

<400> SEQUENCE: 11

Ile Gly Gly Ile Val Tyr Glu Ala Asn Leu Pro Phe Ile Leu Arg Tyr
1               5                   10                  15

Ile Ile Asp His Lys Ile Thr Gly Ser Ser Trp Ile Asn Cys Lys Lys
                20                  25                  30

Gly His Tyr Tyr Ile Arg Asn Lys Asn Lys Lys Ile Ser Asn Cys Thr
            35                  40                  45

Phe Glu Ile Asp Ile Ser Tyr Glu His Val Glu Pro Ile Thr Leu Glu
        50                  55                  60

Asn Glu Tyr Gln Gln Ile Pro Lys Leu Arg Ile Leu Ser Phe Asp Ile
65                  70                  75                  80

Glu Cys Ile Lys Leu Asp Gly Lys Gly Phe Pro Glu Ala Lys Asn Asp
                85                  90                  95

Pro Ile Ile Gln Ile Ser Ser Ile Leu Tyr Phe Gln Gly Glu Pro Ile
            100                 105                 110

Asp Asn Cys Thr Lys Phe Ile Phe Thr Leu Leu Glu Cys Ala Ser Ile
        115                 120                 125

Pro Gly Ser Asn Val Ile Trp Phe Asn Asp Glu Lys Thr Leu Leu Glu
    130                 135                 140

Ala Trp Asn Glu Phe Ile Ile Arg Ile Asp Pro Asp Phe Leu Thr Gly
145                 150                 155                 160

Tyr Asn Ile Ile Asn Phe Asp Leu Pro Tyr Ile Leu Asn Arg Gly Thr
                165                 170                 175
```

```
Ala Leu Asn Leu Lys Lys Leu Lys Phe Leu Gly Arg Ile Lys Asn Val
            180                 185                 190

Ala Ser Thr Val Lys Asp Ser Ser Phe Ser Lys Gln Phe Gly Thr
        195                 200                 205

His Glu Thr Lys Glu Ile Asn Ile Phe Gly Arg Ile Gln Phe Asp Val
        210                 215                 220

Tyr Asp Leu Ile Lys Arg Asp Tyr Lys Leu Lys Ser Tyr Thr Leu Asn
225                 230                 235                 240

Tyr Val Ser Phe Glu Phe Leu Lys Glu Gln Lys Glu Asp Val His Tyr
                245                 250                 255

Ser Ile Met Asn Asp Leu Gln Asn Glu Ser Pro Glu Ser Arg Lys Arg
            260                 265                 270

Ile Ala Thr Tyr Cys Ile Lys Asp Gly Val Leu Pro Leu Arg Leu Ile
            275                 280                 285

Asp Lys Leu Leu Phe Ile Tyr Asn Tyr Val Glu Met Ala Arg Val Thr
        290                 295                 300

Gly Thr Pro Phe Val Tyr Leu Leu Thr Arg Gly Gln Gln Ile Lys Val
305                 310                 315                 320

Thr Ser Gln Leu Tyr Arg Lys Cys Lys Glu Leu Asn Tyr Val Ile Pro
                325                 330                 335

Ser Thr Tyr Met Lys Val Asn Thr Asn Glu Lys Tyr Glu Gly Ala Thr
            340                 345                 350

Val Leu Glu Pro Ile Lys Gly Tyr Tyr Ile Glu Pro Ile Ser Thr Leu
        355                 360                 365

Asp Phe Ala Ser Leu Tyr Pro Ser Ile Met Ile Ala His Asn Leu Cys
    370                 375                 380

Tyr Ser Thr Leu Ile Lys Ser Asn His Glu Val Ser Asp Leu Gln Asn
385                 390                 395                 400

Asp Asp Ile Thr Thr Ile Gln Gly Lys Asn Asn Leu Lys Phe Val Lys
                405                 410                 415

Lys Asn Val Lys Lys Gly Ile Leu Pro Leu Ile Val Glu Glu Leu Ile
            420                 425                 430

Glu Ala Arg Lys Lys Val Lys Leu Leu Ile Lys Asn Glu Lys Asn Asn
        435                 440                 445

Ile Thr Lys Met Val Leu Asn Gly Arg Gln Leu Ala Leu Lys Ile Ser
        450                 455                 460

Ala Asn Ser Val Tyr Gly Tyr Thr Gly Ala Ser Ser Gly Gly Gln Leu
465                 470                 475                 480

Pro Cys Leu Glu Val Ala Val Ser Ile Thr Thr Leu Gly Arg Ser Met
                485                 490                 495

Ile Glu Lys Thr Lys Glu Arg Val Glu Ser Phe Tyr Cys Lys Ser Asn
            500                 505                 510

Gly Tyr Glu His Asn Ser Thr Val Ile Tyr Gly Asp Thr Asp Ser Val
        515                 520                 525

Met Val Lys Phe Gly Thr Asn Asn Ile Glu Glu Ala Met Thr Leu Gly
530                 535                 540

Lys Asp Ala Ala Glu Arg Ile Ser Lys Glu Phe Leu Ser Pro Ile Lys
545                 550                 555                 560

Leu Glu Phe Glu Lys Val Tyr Cys Pro Tyr Leu Leu Leu Asn Lys Lys
                565                 570                 575

Arg Tyr Ala Gly Leu Leu Tyr Thr Asn Pro Asn Lys His Asp Lys Met
            580                 585                 590
```

-continued

```
Asp Cys Lys Gly Ile Glu Thr Val Arg Arg Asp Phe Cys Ile Leu Ile
            595                 600                 605

Gln Gln Met Met Glu Thr Val Leu Asn Lys Leu Leu Ile Glu Lys Asn
        610                 615                 620

Leu Asn Ser Ala Ile Glu Tyr Thr Lys Ser Lys Ile Lys Glu Leu Leu
625                 630                 635                 640

Thr Asn Asn Ile Asp Met Ser Leu Leu Val Val Thr Lys Ser Leu Gly
                645                 650                 655

Lys Thr Asp Tyr Glu Thr Arg Leu Pro His Val Glu Leu Ala Lys Lys
            660                 665                 670

Leu Lys Gln Arg Asp Ser Ala Thr Ala Pro Asn Val Gly Asp Arg Val
        675                 680                 685

Ser Tyr Ile Ile Val Lys Gly Val Lys Gly Gln Ala Gln Tyr Glu Arg
        690                 695                 700

Ala Glu Asp Pro Leu Tyr Val Leu Asp Asn Asn Leu Ala Ile Asp Tyr
705                 710                 715                 720

Asn His Tyr Leu Asp Ala Ile Lys Ser Pro Leu Ser Arg Ile Phe Glu
                725                 730                 735

Val Ile Met Gln Asn
            740

<210> SEQ ID NO 12
<211> LENGTH: 744
<212> TYPE: PRT
<213> ORGANISM: Chlorella virus NY-2A

<400> SEQUENCE: 12

Glu Tyr Gln Ile Tyr Glu Ser Ser Val Asp Pro Ile Ile Arg Ile Phe
1               5                   10                  15

His Leu Arg Asn Ile Asn Pro Ala Asp Trp Met His Val Ser Lys Ala
            20                  25                  30

Phe Pro Val Glu Thr Arg Ile Ser Asn Ser Asp Ile Glu Val Glu Thr
        35                  40                  45

Ser Phe Gln His Leu Gly Pro Ser Asp Leu Lys Glu Val Pro Pro Leu
    50                  55                  60

Ile Ile Ala Ser Trp Asp Ile Glu Thr Tyr Ser Lys Asp Arg Lys Phe
65                  70                  75                  80

Pro Leu Ala Glu Asn Pro Ala Asp Tyr Cys Ile Gln Ile Ala Thr Thr
                85                  90                  95

Phe Gln Lys Tyr Gly Glu Pro Glu Pro Tyr Arg Arg Val Val Val Cys
            100                 105                 110

Tyr Lys Gln Thr Ala Ser Val Glu Gly Val Glu Ile Ile Ser Cys Ala
        115                 120                 125

Glu Glu Ala Asp Val Met Asn Thr Trp Met Thr Ile Leu Gln Asp Glu
    130                 135                 140

Ile Thr Asp Val Ser Ile Gly Tyr Asn Leu Trp Gln Tyr Asp Leu Arg
145                 150                 155                 160

Tyr Ile His Gly Arg Ser Met Met Cys Val Asp Asp Ile Thr Gly Glu
                165                 170                 175

Asp Asn Val Arg Leu Lys Asn Leu Gly Arg Leu Leu Val Gly Gly Gly
            180                 185                 190

Glu Val Ile Glu Arg Asp Leu Ser Ser Asn Ala Phe Gly Gln Asn Lys
        195                 200                 205

Phe Phe Leu Leu Asp Met Pro Gly Val Met Gln Ile Asp Leu Leu Gln
    210                 215                 220
```

```
                                    -continued

Trp Phe Arg Lys Asn Arg Asn Leu Glu Ser Tyr Ser Leu Asn Asn Val
225                 230                 235                 240

Ser Lys Leu Tyr Leu Gly Asp Gln Lys Asn Asp Leu Pro Ala Met Gln
            245                 250                 255

Ile Phe Glu Lys Phe Glu Gly Gly Ala Asp Asp Arg Ala Ile Ile Ala
                260                 265                 270

Ala Tyr Ala Arg Lys Asp Thr Asp Leu Pro Leu Lys Leu Leu Lys Lys
        275                 280                 285

Met Ala Ile Leu Glu Asp Ile Thr Glu Met Ala Asn Ala Val Lys Val
290                 295                 300

Pro Val Asp Tyr Ile Asn Phe Arg Gly Gln Gln Val Arg Ala Phe Ser
305                 310                 315                 320

Cys Leu Val Gly Lys Ala Arg Gln Met Asn Tyr Ala Ile Pro Asp Asp
                325                 330                 335

Lys Met Trp Thr Val Asp Gly Lys Tyr Glu Gly Ala Thr Val Leu Asp
                340                 345                 350

Ala Lys Lys Gly Ala Tyr Phe Thr Ser Ile Ala Ala Leu Asp Phe Ala
        355                 360                 365

Ser Leu Tyr Pro Ser Ile Ile Arg Ala His Asn Met Ser Pro Glu Thr
370                 375                 380

Leu Val Met Asp Lys Arg Phe Glu Asn Leu Pro Gly Ile Glu Tyr Tyr
385                 390                 395                 400

Glu Ile Glu Thr Gly Leu Gly Thr Phe Lys Tyr Pro Gln Lys Asn Asp
                405                 410                 415

Glu Thr Gly Glu Gly Gln Gly Val Val Pro Ala Leu Leu Asp Asp Leu
                420                 425                 430

Ala Lys Phe Arg Lys Gln Ala Lys Lys His Met Ala Glu Ala Lys Lys
        435                 440                 445

Asn Asp Asp Glu Phe Arg Glu Ala Leu Tyr Asp Ala Gln Gln Arg Ser
450                 455                 460

Tyr Lys Ile Val Met Asn Ser Val Tyr Gly Phe Leu Gly Ala Ser Arg
465                 470                 475                 480

Gly Phe Ile Pro Cys Val Pro Ile Ala Ala Ser Val Thr Ala Thr Gly
                485                 490                 495

Arg Lys Met Ile Glu His Thr Ala Lys Arg Val Thr Glu Leu Leu Pro
                500                 505                 510

Gly Ser Glu Val Ile Tyr Gly Asp Thr Asp Ser Val Met Ile Arg Met
        515                 520                 525

Lys Leu Pro Asp Asp Lys Ile His Asp Met Asp Glu Gln Phe Lys Met
530                 535                 540

Ala Lys Trp Leu Ala Gly Glu Ile Thr Lys Asp Phe Lys Ala Pro Asn
545                 550                 555                 560

Asp Leu Glu Phe Glu Lys Ile Tyr Tyr Pro Tyr Ile Leu Tyr Ser Lys
                565                 570                 575

Lys Arg Tyr Ala Ala Ile Lys Phe Glu Asp Pro Asp Glu Lys Gly Lys
        580                 585                 590

Val Asp Val Lys Gly Leu Ala Leu Val Arg Arg Asp Phe Ser Pro Ile
        595                 600                 605

Thr Arg Glu Ile Leu Lys Glu Ser Leu Asp Thr Ile Leu Phe Lys Lys
        610                 615                 620

Asp Thr Pro Thr Ala Val Thr Glu Thr Val Glu Cys Ile Arg Lys Val
625                 630                 635                 640
```

```
Leu Asp Asn Glu Tyr Pro Met Glu Lys Phe Thr Met Ser Lys Thr Leu
                645                 650                 655

Lys Thr Gly Tyr Lys Asn Glu Cys Gln Pro His Leu His Val Ser Asn
            660                 665                 670

Lys Ile Phe Glu Arg Thr Gly Phe Pro Val Pro Ser Gly Ala Arg Val
        675                 680                 685

Pro Phe Val Tyr Ile Glu Asp Lys Lys Asn Leu Asp Thr Lys Gln Ser
    690                 695                 700

Phe Arg Ala Glu Asp Pro Thr Phe Ala Gln Glu Asn Asp Leu Ile Val
705                 710                 715                 720

Asp Arg Leu Phe Tyr Ile Glu His Gln Leu Met Lys Pro Ile Cys Ser
                725                 730                 735

Leu Phe Glu Pro Leu Leu Asp Asp
            740

<210> SEQ ID NO 13
<211> LENGTH: 743
<212> TYPE: PRT
<213> ORGANISM: Paramecium bursaria chlorella virus 1

<400> SEQUENCE: 13

Tyr Gln Ile Tyr Glu Ser Ser Val Asp Pro Ile Ile Arg Val Phe His
1               5                   10                  15

Leu Arg Asn Ile Asn Pro Ala Asp Trp Ile Arg Val Ser Lys Ala Tyr
            20                  25                  30

Pro Ala Gln Thr Arg Ile Ser Asn Ser Asp Ile Glu Val Glu Thr Ser
        35                  40                  45

Phe Gln His Leu Gly Pro Val Glu Asp Lys Thr Val Pro Pro Leu Val
    50                  55                  60

Ile Ala Ser Trp Asp Ile Glu Thr Tyr Ser Lys Asp Arg Lys Phe Pro
65                  70                  75                  80

Leu Ala Glu Asn Pro Thr Asp Tyr Cys Ile Gln Ile Ala Thr Thr Phe
                85                  90                  95

Gln Lys Tyr Gly Glu Pro Glu Pro Tyr Arg Arg Val Val Cys Tyr
            100                 105                 110

Lys Gln Thr Ala Pro Val Glu Gly Val Glu Ile Ile Ser Cys Leu Glu
        115                 120                 125

Glu Ser Asp Val Met Asn Thr Trp Met Lys Ile Leu Gln Asp Glu Lys
    130                 135                 140

Thr Asp Val Ser Ile Gly Tyr Asn Thr Trp Gln Tyr Asp Leu Arg Tyr
145                 150                 155                 160

Val His Gly Arg Thr Gln Met Cys Val Asp Asp Met Thr Gly Glu Asp
                165                 170                 175

Lys Val Lys Leu Ser Asn Leu Gly Arg Leu Leu Ser Gly Gly Gly Glu
            180                 185                 190

Val Val Glu Arg Asp Leu Ser Ser Asn Ala Phe Gly Gln Asn Lys Phe
        195                 200                 205

Phe Leu Leu Asp Met Pro Gly Val Met Gln Ile Asp Leu Leu Gln Trp
    210                 215                 220

Phe Arg Lys Asn Arg Asn Leu Glu Ser Tyr Ser Leu Asn Asn Val Ser
225                 230                 235                 240

Lys Leu Tyr Leu Gly Asp Gln Lys Asn Asp Leu Pro Ala Met Gln Ile
                245                 250                 255

Phe Glu Lys Phe Glu Gly Asn Ala Glu Asp Arg Ala Ile Ile Ala Ala
            260                 265                 270
```

-continued

```
Tyr Ala Ala Lys Asp Thr Asp Leu Pro Leu Lys Leu Leu Lys Lys Met
            275                 280                 285
Ala Ile Leu Glu Asp Leu Thr Glu Met Ala Asn Ala Val Lys Val Pro
290                 295                 300
Val Asp Tyr Ile Asn Phe Arg Gly Gln Gln Ile Arg Ala Phe Ser Cys
305                 310                 315                 320
Leu Val Gly Lys Ala Arg Gln Met Asn Tyr Ala Ile Pro Asp Asp Lys
            325                 330                 335
Ala Trp Ala Thr Glu Gly Lys Tyr Glu Gly Ala Thr Val Leu Asp Ala
            340                 345                 350
Lys Lys Gly Ala Tyr Phe Thr Pro Ile Ala Ala Leu Asp Phe Ala Ser
            355                 360                 365
Leu Tyr Pro Ser Ile Ile Arg Ala His Asn Met Ser Pro Glu Thr Leu
            370                 375                 380
Val Met Glu Lys Arg Phe Glu Asn Val Pro Gly Val Glu Tyr Tyr Glu
385                 390                 395                 400
Ile Glu Thr Gly Leu Gly Lys Phe Lys Tyr Ala Gln Lys Asn Asp Glu
            405                 410                 415
Thr Gly Glu Gly Gln Gly Val Val Pro Ala Leu Leu Asp Asp Leu Ala
            420                 425                 430
Lys Phe Arg Lys Leu Ala Lys Lys His Met Ala Glu Ala Lys Arg Asn
            435                 440                 445
Gly Asp Asp Phe Lys Glu Ala Leu Tyr Asp Ala Gln Gln Arg Ser Phe
450                 455                 460
Lys Val Val Met Asn Ser Val Tyr Gly Phe Leu Gly Ala Ser Lys Gly
465                 470                 475                 480
Phe Ile Pro Cys Val Pro Ile Ala Ala Ser Val Thr Ala Thr Gly Arg
            485                 490                 495
Lys Met Ile Glu His Thr Ala Lys Arg Ala Val Glu Leu Leu Pro Gly
            500                 505                 510
Ser Glu Val Ile Tyr Gly Asp Thr Asp Ser Val Met Val Lys Met Lys
            515                 520                 525
Leu Pro Asp Asp Lys Val His Asp Met Asp Glu Gln Phe Lys Met Ala
530                 535                 540
Lys Trp Leu Ala Gly Glu Ile Thr Lys Asp Phe Arg Ala Pro Asn Asp
545                 550                 555                 560
Leu Glu Phe Glu Lys Ile Tyr Tyr Pro Tyr Ile Leu Tyr Ser Lys Lys
            565                 570                 575
Arg Tyr Ala Ala Val Lys Phe Glu Glu Pro Asp Glu Lys Gly Lys Val
            580                 585                 590
Asp Val Lys Gly Leu Ala Leu Val Arg Arg Asp Phe Ser Pro Ile Thr
            595                 600                 605
Arg Asp Ile Leu Lys Glu Ser Leu Asp Thr Ile Leu Tyr Lys Lys Asp
            610                 615                 620
Thr Pro Thr Ala Val Ser Glu Thr Leu Glu Arg Ile Arg Lys Val Leu
625                 630                 635                 640
Asp Asn Glu Tyr Pro Met Glu Lys Phe Met Met Ser Lys Leu Leu Lys
            645                 650                 655
Thr Gly Tyr Lys Asn Glu Cys Gln Pro His Leu His Val Ala Asn Lys
            660                 665                 670
Ile Tyr Glu Arg Thr Gly Phe Pro Val Pro Ser Gly Ala Arg Val Pro
            675                 680                 685
```

-continued

```
Phe Val Tyr Ile Glu Asp Lys Lys Asn Pro Asp Ile Lys Gln Ser Phe
    690                 695                 700
Lys Ala Glu Asp Pro Thr Phe Ala Gln Asp Asn Gly Leu Ile Val Asp
705                 710                 715                 720
Arg Leu Phe Tyr Ile Glu His Gln Leu Leu Lys Pro Ile Cys Ser Leu
                725                 730                 735
Phe Glu Pro Leu Leu Asp Asp
            740
```

<210> SEQ ID NO 14
<211> LENGTH: 773
<212> TYPE: PRT
<213> ORGANISM: Epstein-barr virus (strain B95-8)

<400> SEQUENCE: 14

```
Gly Cys Arg Ile Phe Glu Ala Asn Val Asp Ala Thr Arg Arg Phe Val
1               5                   10                  15
Leu Asp Asn Asp Phe Val Thr Phe Gly Trp Tyr Ser Cys Arg Arg Ala
                20                  25                  30
Ile Pro Arg Leu Gln His Arg Asp Ser Tyr Ala Glu Leu Glu Tyr Asp
                35                  40                  45
Cys Glu Val Gly Asp Leu Ser Val Arg Arg Glu Asp Ser Ser Trp Pro
    50                  55                  60
Ser Tyr Gln Ala Leu Ala Phe Asp Ile Glu Cys Leu Gly Glu Glu Gly
65                  70                  75                  80
Phe Pro Thr Ala Thr Asn Glu Ala Asp Leu Ile Leu Gln Ile Ser Cys
                85                  90                  95
Val Leu Trp Ser Thr Gly Glu Glu Ala Gly Arg Tyr Arg Arg Ile Leu
                100                 105                 110
Leu Thr Leu Gly Thr Cys Glu Asp Ile Glu Gly Val Glu Val Tyr Glu
            115                 120                 125
Phe Pro Ser Glu Leu Asp Met Leu Tyr Ala Phe Phe Gln Leu Ile Arg
    130                 135                 140
Asp Leu Ser Val Glu Ile Val Thr Gly Tyr Asn Val Ala Asn Phe Asp
145                 150                 155                 160
Trp Pro Tyr Ile Leu Asp Arg Ala Arg His Ile Tyr Ser Ile Asn Pro
                165                 170                 175
Ala Ser Leu Gly Lys Ile Arg Ala Gly Gly Val Cys Glu Val Arg Arg
                180                 185                 190
Pro His Asp Ala Gly Lys Gly Phe Leu Arg Ala Asn Thr Lys Val Arg
            195                 200                 205
Ile Thr Gly Leu Ile Pro Ile Asp Met Tyr Ala Val Cys Arg Asp Lys
    210                 215                 220
Leu Ser Leu Ser Asp Tyr Lys Leu Asp Thr Val Ala Arg His Leu Leu
225                 230                 235                 240
Gly Ala Lys Lys Glu Asp Val His Tyr Lys Glu Ile Pro Arg Leu Phe
                245                 250                 255
Ala Ala Gly Pro Glu Gly Arg Arg Leu Gly Met Tyr Cys Val Gln
            260                 265                 270
Asp Ser Ala Leu Val Met Asp Leu Leu Asn His Phe Val Ile His Val
    275                 280                 285
Glu Val Ala Glu Ile Ala Lys Ile Ala His Ile Pro Cys Arg Arg Val
    290                 295                 300
Leu Asp Asp Gly Gln Gln Ile Arg Val Phe Ser Cys Leu Leu Ala Ala
305                 310                 315                 320
```

```
Ala Gln Lys Glu Asn Phe Ile Leu Pro Met Pro Ser Ala Ser Asp Arg
                325                 330                 335

Asp Gly Tyr Gln Gly Ala Thr Val Ile Gln Pro Leu Ser Gly Phe Tyr
            340                 345                 350

Asn Ser Pro Val Leu Val Val Asp Phe Ala Ser Leu Tyr Pro Ser Ile
        355                 360                 365

Ile Gln Ala His Asn Leu Cys Tyr Ser Thr Met Ile Thr Pro Gly Glu
    370                 375                 380

Glu His Arg Leu Ala Gly Leu Arg Pro Gly Glu Asp Tyr Glu Ser Phe
385                 390                 395                 400

Arg Leu Thr Gly Gly Val Tyr His Phe Val Lys Lys His Val His Glu
                405                 410                 415

Ser Phe Leu Ala Ser Leu Leu Thr Ser Trp Leu Ala Lys Arg Lys Ala
            420                 425                 430

Ile Lys Lys Leu Leu Ala Ala Cys Glu Asp Pro Arg Gln Arg Thr Ile
        435                 440                 445

Leu Asp Lys Gln Gln Leu Ala Ile Lys Cys Thr Cys Asn Ala Val Tyr
    450                 455                 460

Gly Phe Thr Gly Val Ala Asn Gly Leu Phe Pro Cys Leu Ser Ile Ala
465                 470                 475                 480

Glu Thr Val Thr Leu Gln Gly Arg Thr Met Leu Glu Arg Ala Lys Ala
                485                 490                 495

Phe Val Glu Ala Leu Ser Pro Ala Asn Leu Gln Ala Leu Ala Pro Ser
            500                 505                 510

Pro Asp Ala Trp Ala Pro Leu Asn Pro Glu Gly Gln Leu Arg Val Ile
        515                 520                 525

Tyr Gly Asp Thr Asp Ser Leu Phe Ile Glu Cys Arg Gly Phe Ser Glu
    530                 535                 540

Ser Glu Thr Leu Arg Phe Ala Asp Ala Leu Ala Ala His Thr Thr Arg
545                 550                 555                 560

Ser Leu Phe Val Ala Pro Ile Ser Leu Glu Ala Glu Lys Thr Phe Ser
                565                 570                 575

Cys Leu Met Leu Ile Thr Lys Lys Arg Tyr Val Gly Val Leu Thr Asp
            580                 585                 590

Gly Lys Thr Leu Met Lys Gly Val Glu Leu Val Arg Lys Thr Ala Cys
        595                 600                 605

Lys Phe Val Gln Thr Arg Cys Arg Arg Val Leu Asp Leu Val Leu Ala
    610                 615                 620

Asp Ala Arg Val Lys Glu Ala Ala Ser Leu Leu Ser His Arg Pro Phe
625                 630                 635                 640

Gln Glu Ser Phe Thr Gln Gly Leu Pro Val Gly Phe Leu Pro Val Ile
                645                 650                 655

Asp Ile Leu Asn Gln Ala Tyr Thr Asp Leu Arg Glu Gly Arg Val Pro
            660                 665                 670

Met Gly Glu Leu Cys Phe Ser Thr Glu Leu Ser Arg Lys Leu Ser Ala
        675                 680                 685

Tyr Lys Ser Thr Gln Met Pro His Leu Ala Val Tyr Gln Lys Phe Val
    690                 695                 700

Glu Arg Asn Glu Glu Leu Pro Gln Ile His Asp Arg Ile Gln Tyr Val
705                 710                 715                 720

Phe Val Glu Pro Lys Gly Gly Val Lys Gly Ala Arg Lys Thr Glu Met
                725                 730                 735
```

```
Ala Glu Asp Pro Ala Tyr Ala Glu Arg His Gly Val Pro Val Ala Val
            740                 745                 750

Asp His Tyr Phe Asp Lys Leu Leu Gln Gly Ala Ala Asn Ile Leu Gln
            755                 760                 765

Cys Leu Phe Asp Asn
    770

<210> SEQ ID NO 15
<211> LENGTH: 764
<212> TYPE: PRT
<213> ORGANISM: Herpesvirus saimiri (strain 11)

<400> SEQUENCE: 15

Gly Cys Glu Val Phe Glu Thr Asn Val Asp Ala Ile Arg Arg Phe Val
  1               5                  10                  15

Ile Asp Asn Asp Phe Ser Thr Phe Gly Trp Tyr Thr Cys Lys Ser Ala
             20                  25                  30

Cys Pro Arg Ile Thr Asn Arg Asp Ser His Thr Asp Ile Glu Phe Asp
         35                  40                  45

Cys Gly Tyr Tyr Asp Leu Glu Phe His Ala Asp Arg Thr Glu Trp Pro
     50                  55                  60

Pro Tyr Asn Ile Met Ser Phe Asp Ile Glu Cys Ile Gly Glu Lys Gly
 65                  70                  75                  80

Phe Pro Cys Ala Lys Asn Glu Gly Asp Leu Ile Ile Gln Ile Ser Cys
                 85                  90                  95

Val Phe Trp His Ala Gly Ala Leu Asp Thr Thr Arg Asn Met Leu Leu
            100                 105                 110

Ser Leu Gly Thr Cys Ser Ala Val Glu Asn Thr Glu Val Tyr Glu Phe
        115                 120                 125

Pro Ser Glu Ile Asp Met Leu His Gly Phe Phe Ser Leu Ile Arg Asp
    130                 135                 140

Phe Asn Val Glu Ile Ile Thr Gly Tyr Asn Ile Ser Asn Phe Asp Leu
145                 150                 155                 160

Pro Tyr Leu Ile Asp Arg Ala Thr Gln Ile Tyr Asn Ile Lys Leu Ser
                165                 170                 175

Asp Tyr Ser Arg Val Lys Thr Gly Ser Ile Phe Gln Val His Thr Pro
            180                 185                 190

Lys Asp Thr Gly Asn Gly Phe Met Arg Ser Val Ser Lys Ile Lys Ile
        195                 200                 205

Ser Gly Ile Ile Ala Ile Asp Met Tyr Ile Val Cys Lys Asp Lys Leu
    210                 215                 220

Ser Leu Ser Asn Tyr Lys Leu Asp Thr Val Ala Asn His Cys Ile Gly
225                 230                 235                 240

Ala Lys Lys Glu Asp Val Ser Tyr Lys Asp Ile Met Pro Leu Phe Met
                245                 250                 255

Ser Gly Pro Glu Gly Arg Ala Lys Ile Gly Leu Tyr Cys Val Ile Asp
            260                 265                 270

Ser Val Leu Val Met Lys Leu Leu Lys Phe Phe Met Ile His Val Glu
        275                 280                 285

Ile Ser Glu Ile Ala Lys Leu Ala Lys Ile Pro Thr Arg Arg Val Leu
    290                 295                 300

Thr Asp Gly Gln Gln Ile Arg Val Phe Ser Cys Leu Leu Ala Ala Ala
305                 310                 315                 320

Arg Ala Glu Asn Tyr Ile Leu Pro Val Ser Asn Asp Val Asn Ala Asp
                325                 330                 335
```

-continued

```
Gly Phe Gln Gly Ala Thr Val Ile Asn Pro Ile Pro Gly Phe Tyr Asn
            340                 345                 350
Asn Ala Val Leu Val Val Asp Phe Ala Ser Leu Tyr Pro Ser Ile Ile
            355                 360                 365
Gln Ala His Asn Leu Cys Tyr Ser Thr Leu Ile Pro His His Ala Leu
            370                 375                 380
His Asn Tyr Pro His Leu Lys Ser Ser Asp Tyr Glu Thr Phe Met Leu
385                 390                 395                 400
Ser Ser Gly Pro Ile His Phe Val Lys Lys His Ile Gln Ala Ser Leu
                405                 410                 415
Leu Ser Arg Leu Leu Thr Val Trp Leu Ser Arg Lys Ala Ile Arg
            420                 425                 430
Gln Lys Leu Ala Glu Cys Glu Asp Leu Asp Thr Lys Thr Ile Leu Asp
            435                 440                 445
Lys Gln Gln Leu Ala Ile Lys Val Thr Cys Asn Ala Val Tyr Gly Phe
450                 455                 460
Thr Gly Val Ala Ser Gly Leu Leu Pro Cys Ile Ser Ile Ala Glu Thr
465                 470                 475                 480
Val Thr Leu Gln Gly Arg Thr Met Leu Glu Lys Ser Lys Ile Phe Ile
                485                 490                 495
Glu Ala Met Thr Pro Asp Thr Leu Gln Glu Ile Val Pro His Ile Val
                500                 505                 510
Lys His Glu Pro Asp Ala Lys Phe Arg Val Ile Tyr Gly Asp Thr Asp
                515                 520                 525
Ser Leu Phe Val Glu Cys Val Gly Tyr Ser Val Asp Thr Val Val Lys
            530                 535                 540
Phe Gly Asp Phe Leu Ala Ala Phe Thr Ser Glu Lys Leu Phe Asn Ala
545                 550                 555                 560
Pro Ile Lys Leu Glu Ser Glu Lys Thr Phe Gln Cys Leu Leu Leu Leu
                565                 570                 575
Ala Lys Lys Arg Tyr Ile Gly Ile Leu Ser Asn Asp Lys Leu Leu Met
            580                 585                 590
Lys Gly Val Asp Leu Val Arg Lys Thr Ala Cys Lys Phe Val Gln Asn
            595                 600                 605
Thr Ser Ser Lys Ile Leu Asn Leu Ile Leu Lys Asp Pro Glu Val Lys
            610                 615                 620
Ala Ala Ala Gln Leu Leu Ser Thr Lys Asp Pro Asp Tyr Ala Phe Arg
625                 630                 635                 640
Glu Gly Leu Pro Asp Gly Phe Leu Lys Val Ile Asp Ile Leu Asn Glu
                645                 650                 655
Ser His Lys Asn Leu Arg Thr Gly Gln Val Pro Val Glu Glu Leu Thr
            660                 665                 670
Phe Ser Thr Glu Leu Ser Arg Pro Ile Ser Ser Tyr Lys Thr Glu Asn
            675                 680                 685
Leu Pro His Leu Thr Val Tyr Lys Lys Ile Ile Thr Arg His Glu Glu
        690                 695                 700
Pro Pro Gln Val His Asp Arg Ile Pro Tyr Val Phe Val Gly Lys Thr
705                 710                 715                 720
Thr Ser Cys Ile Ser Asn Met Ala Glu Asp Pro Thr Tyr Thr Val Gln
                725                 730                 735
Asn Asn Ile Pro Ile Ala Val Asp Leu Tyr Phe Asp Lys Leu Ile His
            740                 745                 750
```

```
Gly Val Ala Asn Ile Ile Gln Cys Leu Phe Lys Asp
        755                 760
```

<210> SEQ ID NO 16
<211> LENGTH: 892
<212> TYPE: PRT
<213> ORGANISM: Herpes simplex virus (type 1/strain 17)

<400> SEQUENCE: 16

```
Pro Ala Ile Lys Lys Tyr Glu Gly Gly Val Asp Ala Thr Thr Arg Phe
 1               5                  10                  15
Ile Leu Asp Asn Pro Gly Phe Val Thr Phe Gly Trp Tyr Arg Leu Lys
            20                  25                  30
Pro Gly Arg Asn Asn Thr Leu Ala Gln Pro Ala Ala Pro Met Ala Phe
        35                  40                  45
Gly Thr Ser Ser Asp Val Glu Phe Asn Cys Thr Ala Asp Asn Leu Ala
    50                  55                  60
Ile Glu Gly Gly Met Ser Asp Leu Pro Ala Tyr Lys Leu Met Cys Phe
65                  70                  75                  80
Asp Ile Glu Cys Lys Ala Gly Gly Glu Asp Glu Leu Ala Phe Pro Val
                85                  90                  95
Ala Gly His Pro Glu Asp Leu Val Ile Gln Ile Ser Cys Leu Leu Tyr
            100                 105                 110
Asp Leu Ser Thr Thr Ala Leu Glu His Val Leu Leu Phe Ser Leu Gly
        115                 120                 125
Ser Cys Asp Leu Pro Glu Ser His Leu Asn Glu Leu Ala Ala Arg Gly
    130                 135                 140
Leu Pro Thr Pro Val Val Leu Glu Phe Asp Ser Glu Phe Glu Met Leu
145                 150                 155                 160
Leu Ala Phe Met Thr Leu Val Lys Gln Tyr Gly Pro Glu Phe Val Thr
                165                 170                 175
Gly Tyr Asn Ile Ile Asn Phe Asp Trp Pro Phe Leu Leu Ala Lys Leu
            180                 185                 190
Thr Asp Ile Tyr Lys Val Pro Leu Asp Gly Tyr Gly Arg Met Asn Gly
        195                 200                 205
Arg Gly Val Phe Arg Val Trp Asp Ile Gly Gln Ser His Phe Gln Lys
    210                 215                 220
Arg Ser Lys Ile Lys Val Asn Gly Met Val Asn Ile Asp Met Tyr Gly
225                 230                 235                 240
Ile Ile Thr Asp Lys Ile Lys Leu Ser Ser Tyr Lys Leu Asn Ala Val
                245                 250                 255
Ala Glu Ala Val Leu Lys Asp Lys Lys Lys Asp Leu Ser Tyr Arg Asp
            260                 265                 270
Ile Pro Ala Tyr Tyr Ala Ala Gly Pro Ala Gln Arg Gly Val Ile Gly
        275                 280                 285
Glu Tyr Cys Ile Gln Asp Ser Leu Leu Val Gly Gln Leu Phe Phe Lys
    290                 295                 300
Phe Leu Pro His Leu Glu Leu Ser Ala Val Ala Arg Leu Ala Gly Ile
305                 310                 315                 320
Asn Ile Thr Arg Thr Ile Tyr Asp Gly Gln Gln Ile Arg Val Phe Thr
                325                 330                 335
Cys Leu Leu Arg Leu Ala Asp Gln Lys Gly Phe Ile Leu Pro Asp Thr
            340                 345                 350
Gln Gly Arg Phe Arg Gly Ala Gly Gly Glu Ala Pro Lys Arg Pro Ala
        355                 360                 365
```

-continued

```
Ala Ala Arg Glu Asp Glu Glu Arg Pro Glu Glu Gly Glu Asp Glu
    370                 375                 380

Asp Glu Arg Glu Glu Gly Gly Glu Arg Glu Pro Glu Gly Ala Arg
385                 390                 395                 400

Glu Thr Ala Gly Arg His Val Gly Tyr Gln Gly Ala Arg Val Leu Asp
                405                 410                 415

Pro Thr Ser Gly Phe His Val Asn Pro Val Val Phe Asp Phe Ala
            420                 425                 430

Ser Leu Tyr Pro Ser Ile Ile Gln Ala His Asn Leu Cys Phe Ser Thr
            435                 440                 445

Leu Ser Leu Arg Ala Asp Ala Val His Leu Glu Ala Gly Lys Asp
    450                 455                 460

Tyr Leu Glu Ile Glu Val Gly Gly Arg Arg Leu Phe Phe Val Lys Ala
465                 470                 475                 480

His Val Arg Glu Ser Leu Leu Ser Ile Leu Leu Arg Asp Trp Leu Ala
                485                 490                 495

Met Arg Lys Gln Ile Arg Ser Arg Ile Pro Gln Ser Ser Pro Glu Glu
            500                 505                 510

Ala Val Leu Leu Asp Lys Gln Gln Ala Ala Ile Lys Val Val Cys Asn
    515                 520                 525

Ser Val Tyr Gly Phe Thr Gly Val Gln His Gly Leu Leu Pro Cys Leu
    530                 535                 540

His Val Ala Ala Thr Val Thr Thr Ile Gly Arg Glu Met Leu Leu Ala
545                 550                 555                 560

Thr Arg Glu Tyr Val His Ala Arg Trp Ala Ala Phe Glu Gln Leu Leu
                565                 570                 575

Ala Asp Phe Pro Glu Ala Ala Asp Met Arg Ala Pro Gly Pro Tyr Ser
            580                 585                 590

Met Arg Ile Ile Tyr Gly Asp Thr Asp Ser Ile Phe Val Leu Cys Arg
    595                 600                 605

Gly Leu Thr Ala Ala Gly Leu Thr Ala Val Gly Asp Lys Met Ala Ser
    610                 615                 620

His Ile Ser Arg Ala Leu Phe Leu Pro Pro Ile Lys Leu Glu Cys Glu
625                 630                 635                 640

Lys Thr Phe Thr Lys Leu Leu Leu Ile Ala Lys Lys Lys Tyr Ile Gly
                645                 650                 655

Val Ile Tyr Gly Gly Lys Met Leu Ile Lys Gly Val Asp Leu Val Arg
            660                 665                 670

Lys Asn Asn Cys Ala Phe Ile Asn Arg Thr Ser Arg Ala Leu Val Asp
    675                 680                 685

Leu Leu Phe Tyr Asp Asp Thr Val Ser Gly Ala Ala Ala Leu Ala
    690                 695                 700

Glu Arg Pro Ala Glu Glu Trp Leu Ala Arg Pro Leu Pro Glu Gly Leu
705                 710                 715                 720

Gln Ala Phe Gly Ala Val Leu Val Asp Ala His Arg Arg Ile Thr Asp
                725                 730                 735

Pro Glu Arg Asp Ile Gln Asp Phe Val Leu Thr Ala Glu Leu Ser Arg
            740                 745                 750

His Pro Arg Ala Tyr Thr Asn Lys Arg Leu Ala His Leu Thr Val Tyr
    755                 760                 765

Tyr Lys Leu Met Ala Arg Arg Ala Gln Val Pro Ser Ile Lys Asp Arg
    770                 775                 780
```

-continued

```
Ile Pro Tyr Val Ile Val Ala Gln Thr Arg Glu Val Glu Thr Val
785                 790                 795                 800

Ala Arg Leu Ala Ala Leu Arg Glu Leu Asp Ala Ala Pro Gly Asp
            805                 810                 815

Glu Pro Ala Pro Pro Ala Ala Leu Pro Ser Pro Ala Lys Arg Pro Arg
            820                 825                 830

Glu Thr Pro Ser Pro Ala Asp Pro Pro Gly Gly Ala Ser Lys Pro Arg
            835                 840                 845

Lys Leu Leu Val Ser Glu Leu Ala Glu Asp Pro Ala Tyr Ala Ile Ala
    850                 855                 860

His Gly Val Ala Leu Asn Thr Asp Tyr Tyr Phe Ser His Leu Leu Gly
865                 870                 875                 880

Ala Ala Cys Val Thr Phe Lys Ala Leu Phe Gly Asn
            885                 890

<210> SEQ ID NO 17
<211> LENGTH: 896
<212> TYPE: PRT
<213> ORGANISM: Herpes simplex virus (type 2/strain 186)

<400> SEQUENCE: 17

Pro Ala Ile Arg Lys Tyr Glu Gly Gly Val Asp Ala Thr Thr Arg Phe
1               5                   10                  15

Ile Leu Asp Asn Pro Gly Phe Val Thr Phe Gly Trp Tyr Arg Leu Lys
            20                  25                  30

Pro Gly Arg Gly Asn Ala Pro Ala Gln Pro Arg Pro Pro Thr Ala Phe
        35                  40                  45

Gly Thr Ser Ser Asp Val Glu Phe Asn Cys Thr Ala Asp Asn Leu Ala
    50                  55                  60

Val Glu Gly Ala Met Cys Asp Leu Pro Ala Tyr Lys Leu Met Cys Phe
65                  70                  75                  80

Asp Ile Glu Cys Lys Ala Gly Gly Glu Asp Glu Leu Ala Phe Pro Val
                85                  90                  95

Ala Glu Arg Pro Glu Asp Leu Val Ile Gln Ile Ser Cys Leu Leu Tyr
            100                 105                 110

Asp Leu Ser Thr Thr Ala Leu Glu His Ile Leu Leu Phe Ser Leu Gly
        115                 120                 125

Ser Cys Asp Leu Pro Glu Ser His Leu Ser Asp Leu Ala Ser Arg Gly
130                 135                 140

Leu Pro Ala Pro Val Val Leu Gly Phe Asp Ser Glu Phe Glu Met Leu
145                 150                 155                 160

Leu Ala Phe Met Thr Phe Val Lys Gln Tyr Gly Pro Glu Phe Val Thr
                165                 170                 175

Gly Tyr Asn Ile Ile Asn Phe Asp Trp Pro Phe Val Leu Thr Lys Leu
            180                 185                 190

Thr Glu Ile Tyr Lys Val Pro Leu Asp Gly Tyr Gly Arg Met Asn Gly
        195                 200                 205

Arg Gly Val Phe Arg Val Trp Asp Ile Gly Gln Ser His Phe Gln Lys
    210                 215                 220

Arg Ser Lys Ile Lys Val Asn Gly Met Val Asn Ile Asp Met Tyr Gly
225                 230                 235                 240

Ile Ile Thr Asp Lys Val Lys Leu Ser Ser Tyr Lys Leu Asn Ala Val
                245                 250                 255

Ala Glu Ala Val Leu Lys Asp Lys Lys Asp Leu Ser Tyr Arg Asp
            260                 265                 270
```

```
Ile Pro Ala Tyr Tyr Ala Ser Gly Pro Ala Gln Arg Gly Val Ile Gly
        275                 280                 285

Glu Tyr Cys Val Gln Asp Ser Leu Leu Val Gly Gln Leu Phe Phe Lys
    290                 295                 300

Phe Leu Pro His Leu Glu Leu Ser Ala Val Ala Arg Leu Ala Gly Ile
305                 310                 315                 320

Asn Ile Thr Arg Thr Ile Tyr Asp Gly Gln Ile Arg Val Phe Thr
            325                 330                 335

Cys Leu Arg Leu Ala Gly Gln Lys Gly Phe Ile Leu Pro Asp Thr
            340                 345                 350

Gln Gly Arg Phe Arg Gly Leu Asp Lys Glu Ala Pro Lys Arg Pro Ala
        355                 360                 365

Val Pro Arg Gly Glu Gly Arg Pro Gly Asp Gly Asn Gly Asp Glu
    370                 375                 380

Asp Lys Asp Asp Glu Asp Gly Asp Glu Asp Gly Asp Glu Arg Glu
385                 390                 395                 400

Glu Val Ala Arg Glu Thr Gly Arg His Val Gly Tyr Gln Gly Ala
            405                 410                 415

Arg Val Leu Asp Pro Thr Ser Gly Phe His Val Asp Pro Val Val
            420                 425                 430

Phe Asp Phe Ala Ser Leu Tyr Pro Ser Ile Ile Gln Ala His Asn Leu
        435                 440                 445

Cys Phe Ser Thr Leu Ser Leu Arg Pro Glu Ala Val Ala His Leu Glu
    450                 455                 460

Ala Asp Arg Asp Tyr Leu Glu Ile Glu Val Gly Gly Arg Arg Leu Phe
465                 470                 475                 480

Phe Val Lys Ala His Val Arg Glu Ser Leu Leu Ser Ile Leu Leu Arg
            485                 490                 495

Asp Trp Leu Ala Met Arg Lys Gln Ile Arg Ser Arg Ile Pro Gln Ser
        500                 505                 510

Pro Pro Glu Glu Ala Val Leu Leu Asp Lys Gln Gln Ala Ala Ile Lys
    515                 520                 525

Val Val Cys Asn Ser Val Tyr Gly Phe Thr Gly Val Gln His Gly Leu
530                 535                 540

Leu Pro Cys Leu His Val Ala Ala Thr Val Thr Thr Ile Gly Arg Glu
545                 550                 555                 560

Met Leu Leu Ala Thr Arg Ala Tyr Val His Ala Arg Trp Ala Glu Phe
            565                 570                 575

Asp Gln Leu Leu Ala Asp Phe Pro Glu Ala Ala Gly Met Arg Ala Pro
        580                 585                 590

Gly Pro Tyr Ser Met Arg Ile Ile Tyr Gly Asp Thr Asp Ser Ile Phe
    595                 600                 605

Val Leu Cys Arg Gly Leu Thr Gly Glu Ala Leu Val Ala Met Gly Asp
610                 615                 620

Lys Met Ala Ser His Ile Ser Arg Ala Leu Phe Leu Pro Pro Ile Lys
625                 630                 635                 640

Leu Glu Cys Glu Lys Thr Phe Thr Lys Leu Leu Leu Ile Ala Lys Lys
            645                 650                 655

Lys Tyr Ile Gly Val Ile Cys Gly Gly Lys Met Leu Ile Lys Gly Val
        660                 665                 670

Asp Leu Val Arg Lys Asn Asn Cys Ala Phe Ile Asn Arg Thr Ser Arg
    675                 680                 685
```

-continued

```
Ala Leu Val Asp Leu Leu Phe Tyr Asp Asp Thr Val Ser Gly Ala Ala
        690                 695                 700

Ala Ala Leu Ala Glu Arg Pro Ala Glu Glu Trp Leu Ala Arg Pro Leu
705                 710                 715                 720

Pro Glu Gly Leu Gln Ala Phe Gly Ala Val Leu Val Asp Ala His Arg
                725                 730                 735

Arg Ile Thr Asp Pro Glu Arg Asp Ile Gln Asp Phe Val Leu Thr Ala
            740                 745                 750

Glu Leu Ser Arg His Pro Arg Ala Tyr Thr Asn Lys Arg Leu Ala His
        755                 760                 765

Leu Thr Val Tyr Tyr Lys Leu Met Ala Arg Arg Ala Gln Val Pro Ser
    770                 775                 780

Ile Lys Asp Arg Ile Pro Tyr Val Ile Ala Gln Thr Arg Glu Val
785                 790                 795                 800

Glu Glu Thr Val Ala Arg Leu Ala Ala Leu Arg Glu Leu Asp Ala Ala
                805                 810                 815

Ala Pro Gly Asp Glu Pro Ala Pro Ala Ala Leu Pro Ser Pro Ala
            820                 825                 830

Lys Arg Pro Arg Glu Thr Pro Ser His Ala Asp Pro Gly Gly Ala
        835                 840                 845

Ser Lys Pro Arg Lys Leu Leu Val Ser Glu Leu Ala Glu Asp Pro Gly
    850                 855                 860

Tyr Ala Ile Ala Arg Gly Val Pro Leu Asn Thr Asp Tyr Tyr Phe Ser
865                 870                 875                 880

His Leu Gly Ala Ala Cys Val Thr Phe Lys Ala Leu Phe Gly Asn
                885                 890                 895

<210> SEQ ID NO 18
<211> LENGTH: 875
<212> TYPE: PRT
<213> ORGANISM: Equine herpesvirus type 1 (strain Ab4p)

<400> SEQUENCE: 18

Pro Glu Ile Thr Lys Phe Glu Gly Ser Val Asp Val Thr Thr Arg Leu
1               5                   10                  15

Leu Leu Asp Asn Glu Asn Phe Thr Ser Phe Gly Trp Tyr Arg Leu Arg
            20                  25                  30

Pro Gly Thr His Gly Glu Arg Val Gln Leu Arg Pro Val Glu Arg His
        35                  40                  45

Val Thr Ser Ser Asp Val Glu Ile Asn Cys Thr Pro Asp Asn Leu Glu
    50                  55                  60

Pro Ile Pro Asp Glu Ala Ala Trp Pro Asp Tyr Lys Leu Met Cys Phe
65                  70                  75                  80

Asp Ile Glu Cys Lys Ala Gly Thr Gly Asn Glu Met Ala Phe Pro Val
                85                  90                  95

Ala Thr Asn Gln Glu Asp Leu Val Ile Gln Ile Ser Cys Leu Leu Tyr
            100                 105                 110

Ser Leu Ala Thr Gln Asn His Glu His Thr Leu Leu Phe Ser Leu Gly
        115                 120                 125

Ser Cys Asp Ile Ser Glu Glu Tyr Ser Phe Ala Cys Val Gln Arg Gly
    130                 135                 140

Glu Pro Arg Pro Thr Val Leu Glu Phe Asp Ser Glu Tyr Glu Leu Leu
145                 150                 155                 160

Val Ala Phe Leu Thr Phe Leu Lys Gln Tyr Ser Pro Glu Phe Ala Thr
                165                 170                 175
```

-continued

```
Gly Tyr Asn Ile Val Asn Phe Asp Trp Ala Tyr Ile Val Asn Lys Val
            180                 185                 190
Thr Ser Val Tyr Asn Ile Lys Leu Asp Gly Tyr Gly Lys Phe Asn Lys
        195                 200                 205
Gly Gly Leu Phe Lys Val Trp Asp Ile Ala Thr Asn His Phe Gln Lys
            210                 215                 220
Lys Ser Lys Val Lys Ile Asn Gly Leu Ile Ser Leu Asp Met Tyr Ser
225                 230                 235                 240
Val Ala Thr Glu Lys Leu Lys Leu Pro Ser Tyr Lys Leu Asp Ala Val
                245                 250                 255
Val Gly Asp Val Leu Gly Glu His Lys Ile Asp Leu Pro Tyr Lys Glu
            260                 265                 270
Ile Pro Ser Tyr Tyr Ala Gly Pro Asp Arg Arg Gly Val Ile Gly
            275                 280                 285
Glu Tyr Cys Ile Gln Asp Ser Arg Leu Val Gly Lys Leu Phe Phe Lys
    290                 295                 300
Tyr Leu Pro His Leu Glu Leu Ser Ala Val Ala Lys Leu Ala Arg Ile
305                 310                 315                 320
Thr Leu Thr Arg Val Ile Phe Asp Gly Gln Gln Ile Arg Val Tyr Thr
                325                 330                 335
Cys Leu Leu Lys Leu Ala Arg Glu Arg Asn Phe Ile Leu Pro Asp Asn
            340                 345                 350
Arg Arg Arg Phe Asp Ser Gln Ala Asp Ala Ala Ser Glu Thr Ser Glu
            355                 360                 365
Leu Ala Met Asp Ser Gln Ser His Ala Phe Asp Ser Thr Asp Glu Pro
    370                 375                 380
Asp Gly Val Asp Gly Thr Pro Asp Ala Ala Gly Ser Gly Ala Thr Ser
385                 390                 395                 400
Glu Asn Gly Gly Gly Lys Pro Gly Val Gly Arg Ala Val Gly Tyr Gln
                405                 410                 415
Gly Ala Lys Val Leu Asp Pro Val Ser Gly Phe His Val Asp Pro Val
            420                 425                 430
Val Val Phe Asp Phe Ala Ser Leu Tyr Pro Ser Ile Ile Gln Ala His
            435                 440                 445
Asn Leu Cys Phe Thr Thr Leu Ala Leu Asp Glu Val Asp Leu Ala Gly
    450                 455                 460
Leu Gln Pro Ser Val Asp Tyr Ser Thr Phe Glu Val Gly Asp Gln Lys
465                 470                 475                 480
Leu Phe Phe Val His Ala His Ile Arg Glu Ser Leu Leu Gly Ile Leu
                485                 490                 495
Leu Arg Asp Trp Leu Ala Met Arg Lys Ala Val Arg Ala Arg Ile Pro
            500                 505                 510
Thr Ser Thr Pro Glu Glu Ala Val Leu Leu Asp Lys Gln Gln Ser Ala
            515                 520                 525
Ile Lys Val Ile Cys Asn Ser Val Tyr Gly Phe Thr Gly Val Ala Asn
    530                 535                 540
Gly Leu Leu Pro Cys Leu Arg Ile Ala Ala Thr Val Thr Ile Gly
545                 550                 555                 560
Arg Asp Met Leu Leu Lys Thr Arg Asp Tyr Val His Ser Arg Trp Ala
                565                 570                 575
Thr Arg Glu Leu Leu Glu Asp Asn Phe Pro Gly Ala Ile Gly Phe Arg
            580                 585                 590
```

```
Asn His Lys Pro Tyr Ser Val Arg Val Ile Tyr Gly Asp Thr Asp Ser
        595                 600                 605

Val Phe Ile Lys Phe Val Gly Leu Thr Tyr Glu Gly Val Ser Glu Leu
    610                 615                 620

Gly Asp Ala Met Ser Arg Gln Ile Ser Ala Asp Leu Phe Arg Ala Pro
625                 630                 635                 640

Ile Lys Leu Glu Cys Glu Lys Thr Phe Gln Arg Leu Leu Leu Ile Thr
                645                 650                 655

Lys Lys Lys Tyr Ile Gly Val Ile Asn Gly Gly Lys Met Leu Met Lys
                660                 665                 670

Gly Val Asp Leu Val Arg Lys Asn Asn Cys Ser Phe Ile Asn Leu Tyr
                675                 680                 685

Ala Arg His Leu Val Asp Leu Leu Leu Tyr Asp Glu Asp Val Ala Thr
        690                 695                 700

Ala Ala Ala Glu Val Thr Asp Val Pro Pro Ala Glu Trp Val Gly Arg
705                 710                 715                 720

Pro Leu Pro Ser Gly Phe Asp Lys Phe Gly Arg Val Leu Val Glu Ala
                725                 730                 735

Tyr Asn Arg Ile Thr Ala Pro Asn Leu Asp Val Arg Glu Phe Val Met
                740                 745                 750

Thr Ala Glu Leu Ser Arg Ser Pro Glu Ser Tyr Thr Asn Lys Arg Leu
        755                 760                 765

Pro His Leu Thr Val Tyr Phe Lys Leu Ala Met Arg Asn Glu Glu Leu
        770                 775                 780

Pro Ser Val Lys Glu Arg Ile Pro Tyr Val Ile Val Ala Gln Thr Glu
785                 790                 795                 800

Ala Ala Glu Arg Glu Ala Gly Val Val Asn Ser Met Arg Gly Thr Ala
                805                 810                 815

Gln Asn Pro Val Val Thr Lys Thr Ala Arg Pro Gln Pro Lys Arg Lys
                820                 825                 830

Leu Leu Val Ser Asp Leu Ala Glu Asp Pro Thr Tyr Val Ser Glu Asn
                835                 840                 845

Asp Val Pro Leu Asn Thr Asp Tyr Tyr Phe Ser His Leu Leu Gly Thr
850                 855                 860

Ile Ser Val Thr Phe Lys Ala Leu Phe Gly Asn
865                 870                 875

<210> SEQ ID NO 19
<211> LENGTH: 852
<212> TYPE: PRT
<213> ORGANISM: Varicella-zoster virus (strain Dumas)

<400> SEQUENCE: 19

Pro Glu Leu Lys Lys Tyr Glu Gly Arg Val Asp Ala Thr Thr Arg Phe
1               5                   10                  15

Leu Met Asp Asn Pro Gly Phe Val Ser Phe Gly Trp Tyr Gln Leu Lys
                20                  25                  30

Pro Gly Val Asp Gly Glu Arg Val Arg Val Arg Pro Ala Ser Arg Gln
            35                  40                  45

Leu Thr Leu Ser Asp Val Glu Ile Asp Cys Met Ser Asp Asn Leu Gln
    50                  55                  60

Ala Ile Pro Asn Asp Asp Ser Trp Pro Asp Tyr Lys Leu Leu Cys Phe
65              70                  75                  80

Asp Ile Glu Cys Lys Ser Gly Gly Ser Asn Glu Leu Ala Phe Pro Asp
                85                  90                  95
```

-continued

```
Ala Thr His Leu Glu Asp Leu Val Ile Gln Ile Ser Cys Leu Leu Tyr
            100                 105                 110
Ser Ile Pro Arg Gln Ser Leu Glu His Ile Leu Leu Phe Ser Leu Gly
            115                 120                 125
Ser Cys Asp Leu Pro Gln Arg Tyr Val Gln Glu Met Lys Asp Ala Gly
            130                 135                 140
Leu Pro Glu Pro Thr Val Leu Glu Phe Asp Ser Glu Phe Glu Leu Leu
145                 150                 155                 160
Ile Ala Phe Met Thr Leu Val Lys Gln Tyr Ala Pro Glu Phe Ala Thr
                    165                 170                 175
Gly Tyr Asn Ile Val Asn Phe Asp Trp Ala Phe Ile Met Glu Lys Leu
                    180                 185                 190
Asn Ser Ile Tyr Ser Leu Lys Leu Asp Gly Tyr Gly Ser Ile Asn Arg
                195                 200                 205
Gly Gly Leu Phe Lys Ile Trp Asp Val Gly Lys Ser Gly Phe Gln Arg
            210                 215                 220
Arg Ser Lys Val Lys Ile Asn Gly Leu Ile Ser Leu Asp Met Tyr Ala
225                 230                 235                 240
Ile Ala Thr Glu Lys Leu Lys Leu Ser Ser Tyr Lys Leu Asp Ser Val
                    245                 250                 255
Ala Arg Glu Ala Leu Asn Glu Ser Lys Arg Asp Leu Pro Tyr Lys Asp
                260                 265                 270
Ile Pro Gly Tyr Tyr Ala Ser Gly Pro Asn Thr Arg Gly Ile Ile Gly
            275                 280                 285
Glu Tyr Cys Ile Gln Asp Ser Ala Leu Val Gly Lys Leu Phe Phe Lys
            290                 295                 300
Tyr Leu Pro His Leu Glu Leu Ser Ala Val Ala Arg Leu Ala Arg Ile
305                 310                 315                 320
Thr Leu Thr Lys Ala Ile Tyr Asp Gly Gln Gln Val Arg Ile Tyr Thr
                    325                 330                 335
Cys Leu Leu Gly Leu Ala Ser Ser Arg Gly Phe Ile Leu Pro Asp Gly
                340                 345                 350
Gly Tyr Pro Ala Thr Phe Glu Tyr Lys Asp Val Ile Pro Asp Val Gly
            355                 360                 365
Asp Val Glu Glu Glu Met Asp Glu Asp Glu Ser Val Ser Pro Thr Gly
            370                 375                 380
Thr Ser Ser Gly Arg Asn Val Gly Tyr Lys Gly Ala Arg Val Phe Asp
385                 390                 395                 400
Pro Asp Thr Gly Phe Tyr Ile Asp Pro Val Val Leu Asp Phe Ala
                    405                 410                 415
Ser Leu Tyr Pro Ser Ile Ile Gln Ala His Asn Leu Cys Phe Thr Thr
                420                 425                 430
Leu Thr Leu Asn Phe Glu Thr Val Lys Arg Leu Asn Pro Ser Asp Tyr
            435                 440                 445
Ala Thr Phe Thr Val Gly Gly Lys Arg Leu Phe Phe Val Arg Ser Asn
            450                 455                 460
Val Arg Glu Ser Leu Leu Gly Val Leu Leu Lys Asp Trp Leu Ala Met
465                 470                 475                 480
Arg Lys Ala Ile Arg Ala Arg Ile Pro Gly Ser Ser Asp Glu Ala
                    485                 490                 495
Val Leu Leu Asp Lys Gln Gln Ala Ala Ile Lys Val Val Cys Asn Ser
                500                 505                 510
```

-continued

```
Val Tyr Gly Phe Thr Gly Val Ala Gln Gly Phe Leu Pro Cys Leu Tyr
            515                 520                 525
Val Ala Ala Thr Val Thr Thr Ile Gly Arg Gln Met Leu Leu Ser Thr
530                 535                 540
Arg Asp Tyr Ile His Asn Asn Trp Ala Ala Phe Glu Arg Phe Ile Thr
545                 550                 555                 560
Ala Phe Pro Asp Ile Glu Ser Ser Val Leu Ser Gln Lys Ala Tyr Glu
                565                 570                 575
Val Lys Val Ile Tyr Gly Asp Thr Asp Ser Val Phe Ile Arg Phe Lys
            580                 585                 590
Gly Val Ser Val Glu Gly Ile Ala Lys Ile Gly Glu Lys Met Ala His
            595                 600                 605
Ile Ile Ser Thr Ala Leu Phe Cys Pro Pro Ile Lys Leu Glu Cys Glu
610                 615                 620
Lys Thr Phe Ile Lys Leu Leu Leu Ile Thr Lys Lys Tyr Ile Gly
625                 630                 635                 640
Val Ile Tyr Gly Gly Lys Val Leu Met Lys Gly Val Asp Leu Val Arg
                645                 650                 655
Lys Asn Asn Cys Gln Phe Ile Asn Asp Tyr Ala Arg Lys Leu Val Glu
            660                 665                 670
Leu Leu Leu Tyr Asp Asp Thr Val Ser Arg Ala Ala Glu Ala Ser
            675                 680                 685
Cys Val Ser Ile Ala Glu Trp Asn Arg Arg Ala Met Pro Ser Gly Met
690                 695                 700
Ala Gly Phe Gly Arg Ile Ile Ala Asp Ala His Arg Gln Ile Thr Ser
705                 710                 715                 720
Pro Lys Leu Asp Ile Asn Lys Phe Val Met Thr Ala Glu Leu Ser Arg
                725                 730                 735
Pro Pro Ser Ala Tyr Ile Asn Arg Arg Leu Ala His Leu Thr Val Tyr
            740                 745                 750
Tyr Lys Leu Val Met Arg Gln Gly Gln Ile Pro Asn Val Arg Glu Arg
            755                 760                 765
Ile Pro Tyr Val Ile Val Ala Pro Thr Asp Glu Val Glu Ala Asp Ala
770                 775                 780
Lys Ser Val Ala Leu Leu Arg Gly Asp Pro Leu Gln Asn Thr Ala Gly
785                 790                 795                 800
Lys Arg Cys Gly Glu Ala Lys Arg Lys Leu Ile Ile Ser Asp Leu Ala
                805                 810                 815
Glu Asp Pro Ile His Val Thr Ser His Gly Leu Ser Leu Asn Ile Asp
            820                 825                 830
Tyr Tyr Phe Ser His Leu Ile Gly Thr Ala Ser Val Thr Phe Lys Ala
            835                 840                 845
Leu Phe Gly Asn
    850

<210> SEQ ID NO 20
<211> LENGTH: 978
<212> TYPE: PRT
<213> ORGANISM: Human cytomegalovirus (strain AD169)

<400> SEQUENCE: 20

Gly Phe Pro Val Tyr Glu Val Arg Val Asp Pro Leu Thr Arg Leu Val
1               5                   10                  15
Ile Asp Arg Arg Ile Thr Thr Phe Gly Trp Cys Ser Val Asn Arg Tyr
            20                  25                  30
```

-continued

```
Asp Trp Arg Gln Gln Gly Arg Ala Ser Thr Cys Asp Ile Glu Val Asp
     35                  40                  45

Cys Asp Val Ser Asp Leu Val Ala Val Pro Asp Asp Ser Ser Trp Pro
 50                  55                  60

Arg Tyr Arg Cys Leu Ser Phe Asp Ile Glu Cys Met Ser Gly Glu Gly
 65                  70                  75                  80

Gly Phe Pro Cys Ala Glu Lys Ser Asp Asp Ile Val Ile Gln Ile Ser
                 85                  90                  95

Cys Val Cys Tyr Glu Thr Gly Gly Asn Thr Ala Val Asp Gln Gly Ile
             100                 105                 110

Pro Asn Gly Asn Asp Gly Arg Gly Cys Thr Ser Glu Gly Val Ile Phe
         115                 120                 125

Gly His Ser Gly Leu His Leu Phe Thr Ile Gly Thr Cys Gly Gln Val
     130                 135                 140

Gly Pro Asp Val Asp Val Tyr Glu Phe Pro Ser Glu Tyr Glu Leu Leu
145                 150                 155                 160

Leu Gly Phe Met Leu Phe Phe Gln Arg Tyr Ala Pro Ala Phe Val Thr
                 165                 170                 175

Gly Tyr Asn Ile Asn Ser Phe Asp Leu Lys Tyr Ile Leu Thr Arg Leu
             180                 185                 190

Glu Tyr Leu Tyr Lys Val Asp Ser Gln Arg Phe Cys Lys Leu Pro Thr
         195                 200                 205

Ala Gln Gly Gly Arg Phe Phe Leu His Ser Pro Ala Val Gly Phe Lys
     210                 215                 220

Arg Gln Tyr Ala Ala Ala Phe Pro Ser Ala Ser His Asn Asn Pro Ala
225                 230                 235                 240

Ser Thr Ala Ala Thr Lys Val Tyr Ile Ala Gly Ser Val Val Ile Asp
                 245                 250                 255

Met Tyr Pro Val Cys Met Ala Lys Thr Asn Ser Pro Asn Tyr Lys Leu
             260                 265                 270

Asn Thr Met Ala Glu Leu Tyr Leu Arg Gln Arg Lys Asp Asp Leu Ser
         275                 280                 285

Tyr Lys Asp Ile Pro Arg Cys Phe Ala Asn Ala Glu Gly Arg Ala
     290                 295                 300

Gln Val Gly Arg Tyr Cys Leu Gln Asp Ala Val Leu Val Arg Asp Leu
305                 310                 315                 320

Phe Asn Thr Ile Asn Phe His Tyr Glu Ala Gly Ala Ile Ala Arg Leu
                 325                 330                 335

Ala Lys Ile Pro Leu Arg Arg Val Ile Phe Asp Gly Gln Gln Ile Arg
             340                 345                 350

Ile Tyr Thr Ser Leu Leu Asp Glu Cys Ala Cys Arg Asp Phe Ile Leu
         355                 360                 365

Pro Asn His Tyr Ser Lys Gly Thr Thr Val Pro Glu Thr Asn Ser Val
     370                 375                 380

Ala Val Ser Pro Asn Ala Ala Ile Ile Ser Thr Ala Ala Val Pro Gly
385                 390                 395                 400

Asp Ala Gly Ser Val Ala Ala Met Phe Gln Met Ser Pro Pro Leu Gln
                 405                 410                 415

Ser Ala Pro Ser Ser Gln Asp Gly Val Ser Pro Gly Ser Gly Ser Asn
             420                 425                 430

Ser Ser Ser Ser Val Gly Val Phe Ser Val Gly Ser Gly Ser Ser Gly
         435                 440                 445
```

-continued

```
Gly Val Gly Val Ser Asn Asp Asn His Gly Ala Gly Thr Ala Ala
    450                 455                 460
Val Ser Tyr Gln Gly Ala Thr Val Phe Glu Pro Glu Val Gly Tyr Tyr
465                 470                 475                 480
Asn Asp Pro Val Ala Val Phe Asp Phe Ala Ser Leu Tyr Pro Ser Ile
                485                 490                 495
Ile Met Ala His Asn Leu Cys Tyr Ser Thr Leu Val Pro Gly Gly
            500                 505                 510
Glu Tyr Pro Val Asp Pro Ala Asp Val Tyr Ser Val Thr Leu Glu Asn
            515                 520                 525
Gly Val Thr His Arg Phe Val Arg Ala Ser Val Arg Val Ser Val Leu
    530                 535                 540
Ser Glu Leu Leu Asn Lys Trp Val Ser Gln Arg Arg Ala Val Arg Glu
545                 550                 555                 560
Cys Met Arg Glu Cys Gln Asp Pro Val Arg Arg Met Leu Leu Asp Lys
                565                 570                 575
Glu Gln Met Ala Leu Lys Val Thr Cys Asn Ala Phe Tyr Gly Phe Thr
            580                 585                 590
Gly Val Val Asn Gly Met Met Pro Cys Leu Pro Ile Ala Ala Ser Ile
    595                 600                 605
Thr Arg Ile Gly Arg Asp Met Leu Glu Arg Thr Ala Arg Phe Ile Lys
    610                 615                 620
Asp Asn Phe Ser Glu Pro Cys Phe Leu His Asn Phe Asn Gln Glu
625                 630                 635                 640
Asp Tyr Val Val Gly Thr Arg Glu Gly Asp Ser Glu Ser Ser Ala
                645                 650                 655
Leu Pro Glu Gly Leu Glu Thr Ser Ser Gly Gly Ser Asn Glu Arg Arg
            660                 665                 670
Val Glu Ala Arg Val Ile Tyr Gly Asp Thr Asp Ser Val Phe Val Arg
            675                 680                 685
Phe Arg Gly Leu Thr Pro Gln Ala Leu Val Ala Arg Gly Pro Ser Leu
    690                 695                 700
Ala His Tyr Val Thr Ala Cys Leu Phe Val Glu Pro Val Lys Leu Glu
705                 710                 715                 720
Phe Glu Lys Val Phe Val Ser Leu Met Met Ile Cys Lys Lys Arg Tyr
                725                 730                 735
Ile Gly Lys Val Glu Gly Ala Ser Gly Leu Ser Met Lys Gly Val Asp
            740                 745                 750
Leu Val Arg Lys Thr Ala Cys Glu Phe Val Lys Gly Val Thr Arg Asp
    755                 760                 765
Val Leu Ser Leu Leu Phe Glu Asp Arg Glu Val Ser Glu Ala Ala Val
    770                 775                 780
Arg Leu Ser Arg Leu Ser Leu Asp Glu Val Lys Lys Tyr Gly Val Pro
785                 790                 795                 800
Arg Gly Phe Trp Arg Ile Leu Arg Arg Leu Val Gln Ala Arg Asp Asp
                805                 810                 815
Leu Tyr Leu His Arg Val Arg Val Glu Asp Leu Val Leu Ser Ser Val
            820                 825                 830
Leu Ser Lys Asp Ile Ser Leu Tyr Arg Gln Ser Asn Leu Pro His Ile
            835                 840                 845
Ala Val Ile Lys Arg Leu Ala Ala Arg Ser Glu Glu Leu Pro Ser Val
    850                 855                 860
Gly Asp Arg Val Phe Tyr Val Leu Thr Ala Pro Gly Val Arg Thr Ala
```

```
                865                 870                 875                 880
Pro Gln Gly Ser Ser Asp Asn Gly Asp Ser Val Thr Ala Gly Val Val
                    885                 890                 895
Ser Arg Ser Asp Ala Ile Asp Gly Thr Asp Asp Ala Asp Gly Gly
                900                 905                 910
Gly Val Glu Glu Ser Asn Arg Arg Gly Gly Glu Pro Ala Lys Lys Arg
                915                 920                 925
Ala Arg Lys Pro Pro Ser Ala Val Cys Asn Tyr Glu Val Ala Glu Asp
            930                 935                 940
Pro Ser Tyr Val Arg Glu His Gly Val Pro Ile His Ala Asp Lys Tyr
945                 950                 955                 960
Phe Glu Gln Val Leu Lys Ala Val Thr Asn Val Leu Ser Pro Val Phe
                965                 970                 975
Pro Gly

<210> SEQ ID NO 21
<211> LENGTH: 814
<212> TYPE: PRT
<213> ORGANISM: Murine cytomegalovirus (strain Smith)

<400> SEQUENCE: 21

Gly Arg Lys Val Tyr Glu Leu Gly Val Asp Pro Leu Ala Arg Phe Leu
1               5                   10                  15
Ile Asp Arg Lys Ile Pro Ser Phe Gly Trp Cys Leu Ala Arg Arg Tyr
                20                  25                  30
Ser Val Arg Ala Ala Gly Tyr Val Ser Arg Ala Gln Leu Glu Ile Asp
            35                  40                  45
Cys Asp Val Ala Asp Ile Leu Pro Ile Glu Glu Gln Ser Asn Trp Pro
        50                  55                  60
Phe Tyr Arg Cys Leu Ser Phe Asp Ile Glu Cys Met Ser Gly Thr Gly
65                  70                  75                  80
Ala Phe Pro Ala Ala Glu Asn Val Asp Asp Ile Ile Gln Ile Ser
                85                  90                  95
Cys Val Cys Phe Gly Val Gly Glu Met Val His His Ala Tyr Asp Val
                100                 105                 110
His Ala Asp Leu Ser Thr Pro Ala Val Pro Glu Asn His Leu Phe Thr
            115                 120                 125
Ile Gly Pro Cys Ala Pro Ile Pro Asp Val Lys Ile Tyr Thr Phe Pro
        130                 135                 140
Ser Glu Tyr Glu Met Leu Arg Gly Phe Phe Ile Phe Leu Ser Trp Tyr
145                 150                 155                 160
Ser Pro Glu Phe Ile Thr Gly Tyr Asn Ile Asn Gly Phe Asp Ile Lys
                165                 170                 175
Tyr Ile Leu Thr Arg Ala Glu Lys Leu Tyr Lys Met Asp Val Gly Gln
            180                 185                 190
Phe Thr Lys Leu Arg Arg Gly Gly Arg Met Phe Val Phe Ser Pro Glu
        195                 200                 205
Lys Gly Lys Ala Gly Phe Gly Thr Ser Asn Thr Val Lys Val Phe Trp
    210                 215                 220
Ser Gly Thr Val Val Leu Asp Met Tyr Pro Val Cys Thr Ala Lys Ala
225                 230                 235                 240
Ser Ser Pro Asn Tyr Lys Leu Asp Thr Met Ala Glu Ile Tyr Leu Lys
                245                 250                 255
Lys Lys Lys Asp Asp Leu Ser Tyr Lys Glu Ile Pro Val Gln Phe Ser
```

-continued

```
                260                 265                 270
Ala Gly Asp Glu Gly Arg Ala Pro Gly Gly Lys Tyr Cys Leu Gln Asp
            275                 280                 285
Ala Val Leu Val Arg Glu Leu Phe Glu Met Leu Ala Phe His Phe Glu
            290                 295                 300
Ala Ala Ala Ile Ala Arg Leu Ala Arg Ile Pro Leu Arg Lys Val Ile
305                 310                 315                 320
Phe Asp Gly Gln Gln Ile Arg Ile Tyr Thr Cys Leu Leu Glu Glu Cys
                325                 330                 335
Ser Gly Arg Asp Met Ile Leu Pro Asn Met Pro Ser Leu Gly His Gly
            340                 345                 350
Ala Ala Ala Ile Glu Glu Ala Ala Gly Gly Glu Gly Asp Glu
            355                 360                 365
Thr Ser Glu Gly Glu Asn Ser Asn Asn Ser Arg Thr Val Gly Tyr Gln
            370                 375                 380
Gly Ala Thr Val Leu Glu Pro Glu Cys Gly Phe His His Val Pro Val
385                 390                 395                 400
Cys Val Phe Asp Phe Ala Ser Leu Tyr Pro Ser Ile Ile Met Ser Asn
                405                 410                 415
Asn Leu Cys Tyr Ser Thr Leu Leu Val Glu Gly Ser Pro Glu Val Pro
            420                 425                 430
Glu Lys Asp Val Leu Arg Val Glu Ile Gly Asp Gln Cys His Arg Phe
            435                 440                 445
Val Arg Glu Asn Val His Arg Ser Leu Leu Ala Glu Leu Leu Val Arg
            450                 455                 460
Trp Leu Thr Gln Arg Lys Leu Val Arg Glu Ala Met Lys Gln Cys Thr
465                 470                 475                 480
Asn Glu Met Gln Arg Met Ile Met Asp Lys Gln Leu Ala Leu Lys
                485                 490                 495
Val Thr Cys Asn Ala Phe Tyr Gly Phe Thr Gly Val Ala Ala Gly Met
                500                 505                 510
Leu Pro Cys Leu Pro Ile Ala Ala Ser Ile Thr Lys Ile Gly Arg Asp
            515                 520                 525
Met Leu Leu Ala Thr Ala Gly His Ile Glu Asp Arg Cys Asn Arg Pro
            530                 535                 540
Asp Phe Leu Arg Thr Val Leu Gly Leu Pro Pro Glu Ala Ile Asp Pro
545                 550                 555                 560
Glu Ala Leu Arg Val Lys Ile Ile Tyr Gly Asp Thr Asp Ser Val Phe
                565                 570                 575
Ala Ala Phe Tyr Gly Ile Asp Lys Glu Ala Leu Leu Lys Ala Val Gly
                580                 585                 590
Ala Leu Ala Ala Asn Val Thr Asn Ala Leu Phe Lys Glu Pro Val Arg
            595                 600                 605
Leu Glu Phe Glu Lys Met Phe Val Ser Leu Met Met Ile Cys Lys Lys
            610                 615                 620
Arg Tyr Ile Gly Lys Val His Gly Ser Gln Asn Leu Ser Met Lys Gly
625                 630                 635                 640
Val Asp Leu Val Arg Arg Thr Ala Cys Gly Phe Val Lys Ala Val Val
                645                 650                 655
Ser Asp Val Leu His Met Val Phe Asn Asp Glu Thr Val Ser Glu Gly
            660                 665                 670
Thr Met Lys Leu Ser Arg Met Thr Phe Asp Asp Leu Lys Lys Asn Gly
            675                 680                 685
```

Ile Pro Cys Glu Phe Gly Pro Val Ser Arg Leu Cys Arg Ala Arg
    690             695                 700

Asp Asp Leu His Leu Lys Lys Val Pro Val Pro Glu Leu Thr Leu Ser
705                 710                 715                 720

Ser Val Leu Ser Gln Glu Leu Ser Cys Tyr Lys Gln Lys Asn Leu Pro
                725                 730                 735

His Leu Ala Val Ile Arg Arg Leu Ala Ala Arg Lys Glu Glu Leu Pro
            740                 745                 750

Ala Val Gly Asp Arg Val Glu Tyr Val Leu Thr Leu Pro Asp Gly Cys
        755                 760                 765

Lys Lys Asn Val Pro Asn Tyr Glu Ile Ala Glu Asp Pro Arg His Val
770                 775                 780

Val Glu Ala Lys Leu Ser Ile Asn Ala Glu Lys Tyr Tyr Glu Gln Val
785                 790                 795                 800

Val Lys Ala Val Thr Asn Thr Leu Met Pro Val Phe Pro Arg
            805                 810

<210> SEQ ID NO 22
<211> LENGTH: 771
<212> TYPE: PRT
<213> ORGANISM: Herpes simplex virus type 6/strain Uganda-1102

<400> SEQUENCE: 22

Gly Phe Val Val Tyr Glu Ile Asp Val Asp Val Leu Thr Arg Phe Phe
1               5                   10                  15

Val Asp Asn Gly Phe Leu Ser Phe Gly Trp Tyr Asn Val Lys Lys Tyr
            20                  25                  30

Ile Pro Gln Asp Met Gly Lys Gly Ser Asn Leu Glu Val Glu Ile Asn
        35                  40                  45

Cys His Val Ser Asp Leu Val Ser Leu Glu Asp Val Asn Trp Pro Leu
    50                  55                  60

Tyr Gly Cys Trp Ser Phe Asp Ile Glu Cys Leu Gly Gln Asn Gly Asn
65                  70                  75                  80

Phe Pro Asp Ala Glu Asn Leu Gly Asp Ile Val Ile Gln Ile Ser Val
                85                  90                  95

Ile Ser Phe Asp Thr Glu Gly Asp Arg Asp Glu Arg His Leu Phe Thr
            100                 105                 110

Leu Gly Thr Cys Glu Lys Ile Asp Gly Val His Ile Tyr Glu Phe Ala
        115                 120                 125

Ser Glu Phe Glu Leu Leu Leu Gly Phe Phe Ile Phe Leu Arg Ile Glu
    130                 135                 140

Ser Pro Glu Phe Ile Thr Gly Tyr Asn Ile Asn Asn Phe Asp Leu Lys
145                 150                 155                 160

Tyr Leu Cys Ile Arg Met Asp Lys Ile Tyr His Tyr Asp Ile Gly Cys
                165                 170                 175

Phe Ser Lys Leu Lys Asn Gly Lys Ile Gly Ile Ser Val Pro His Glu
            180                 185                 190

Gln Tyr Arg Lys Gly Phe Leu Gln Ala Gln Thr Lys Val Phe Thr Ser
        195                 200                 205

Gly Val Leu Tyr Leu Asp Met Tyr Pro Val Tyr Ser Ser Lys Ile Thr
    210                 215                 220

Ala Gln Asn Tyr Lys Leu Asp Thr Ile Ala Lys Ile Cys Leu Gln Gln
225                 230                 235                 240

Glu Lys Glu Gln Leu Ser Tyr Lys Glu Ile Pro Lys Lys Phe Ile Ser

-continued

```
            245                 250                 255
Gly Pro Ser Gly Arg Ala Val Val Gly Lys Tyr Cys Leu Gln Asp Ser
            260                 265                 270
Val Leu Val Val Arg Leu Phe Lys Gln Ile Asn Tyr His Phe Glu Val
            275                 280                 285
Ala Glu Val Ala Arg Leu Ala His Val Thr Ala Arg Cys Val Val Phe
            290                 295                 300
Glu Gly Gln Gln Lys Lys Ile Phe Pro Cys Ile Leu Thr Glu Ala Lys
305                 310                 315                 320
Arg Arg Asn Met Ile Leu Pro Ser Met Val Ser Ser His Asn Arg Gln
                325                 330                 335
Gly Ile Gly Tyr Lys Gly Ala Thr Val Leu Glu Pro Lys Thr Gly Tyr
                340                 345                 350
Tyr Ala Val Pro Thr Val Phe Asp Phe Gln Ser Leu Tyr Pro Ser
                355                 360                 365
Ile Met Met Ala His Asn Leu Cys Tyr Ser Thr Leu Val Leu Asp Glu
                370                 375                 380
Arg Gln Ile Ala Gly Leu Ser Glu Ser Asp Ile Leu Thr Val Lys Leu
385                 390                 395                 400
Gly Asp Glu Thr His Arg Phe Val Lys Pro Cys Ile Arg Glu Ser Val
                405                 410                 415
Leu Gly Ser Leu Leu Lys Asp Trp Leu Ala Lys Arg Glu Val Lys
                420                 425                 430
Ala Glu Met Gln Asn Cys Ser Asp Pro Met Met Lys Leu Leu Leu Asp
                435                 440                 445
Lys Lys Gln Leu Ala Leu Lys Thr Thr Cys Asn Ser Val Tyr Gly Val
450                 455                 460
Thr Gly Ala Ala His Gly Leu Leu Pro Cys Val Ala Ile Ala Ala Ser
465                 470                 475                 480
Val Thr Cys Leu Gly Arg Glu Met Leu Cys Ser Thr Val Asp Tyr Val
                485                 490                 495
Asn Ser Lys Met Gln Ser Glu Gln Phe Phe Cys Glu Glu Phe Gly Leu
                500                 505                 510
Thr Ser Ser Asp Phe Thr Gly Asp Leu Glu Val Glu Val Ile Tyr Gly
                515                 520                 525
Asp Thr Asp Ser Ile Phe Met Ser Val Arg Asn Met Val Asn Gln Ser
                530                 535                 540
Leu Arg Arg Ile Ala Pro Met Ile Ala Lys His Ile Thr Asp Arg Leu
545                 550                 555                 560
Phe Lys Ser Pro Ile Lys Leu Glu Phe Glu Lys Ile Leu Cys Pro Leu
                565                 570                 575
Ile Leu Ile Cys Lys Lys Arg Tyr Ile Gly Arg Gln Asp Asp Ser Leu
                580                 585                 590
Leu Ile Phe Lys Gly Val Asp Leu Val Arg Lys Thr Ser Cys Asp Phe
                595                 600                 605
Val Lys Gly Val Val Lys Asp Ile Val Asp Leu Leu Phe Phe Asp Glu
            610                 615                 620
Glu Val Gln Thr Ala Ala Val Glu Phe Ser His Met Thr Gln Thr Gln
625                 630                 635                 640
Leu Arg Glu Gln Gly Val Pro Val Gly Ile His Lys Ile Leu Arg Arg
                645                 650                 655
Leu Cys Glu Ala Arg Glu Glu Leu Phe Gln Asn Arg Ala Asp Val Arg
                660                 665                 670
```

```
His Leu Met Leu Ser Ser Val Leu Ser Lys Glu Met Ala Ala Tyr Lys
            675                 680                 685

Gln Pro Asn Leu Ala His Leu Ser Val Ile Arg Arg Leu Ala Gln Arg
        690                 695                 700

Lys Glu Glu Ile Pro Asn Val Gly Asp Arg Ile Met Tyr Val Leu Ile
705                 710                 715                 720

Ala Pro Ser Ile Gly Asn Lys Gln Thr His Asn Tyr Glu Leu Ala Glu
                725                 730                 735

Asp Pro Asn Tyr Val Ile Glu His Lys Ile Pro Ile His Ala Glu Lys
            740                 745                 750

Tyr Phe Asp Gln Ile Ile Lys Ala Val Thr Asn Ala Ile Ser Pro Ile
        755                 760                 765

Phe Pro Lys
    770

<210> SEQ ID NO 23
<211> LENGTH: 757
<212> TYPE: PRT
<213> ORGANISM: Homo sapiens

<400> SEQUENCE: 23

Ser His Val Phe Gly Thr Asn Thr Ser Ser Leu Glu Leu Phe Leu Met
1               5                   10                  15

Asn Arg Lys Ile Lys Gly Pro Cys Trp Leu Glu Val Lys Lys Ser Thr
            20                  25                  30

Ala Leu Asn Gln Pro Val Ser Trp Cys Lys Val Glu Ala Met Ala Leu
        35                  40                  45

Lys Pro Asp Leu Val Asn Val Ile Lys Asp Val Ser Pro Pro Leu
    50                  55                  60

Val Val Met Ala Phe Ser Met Lys Thr Met Gln Asn Ala Lys Asn His
65                  70                  75                  80

Gln Asn Glu Ile Ile Ala Met Ala Leu Val His His Ser Phe Ala
                85                  90                  95

Leu Asp Lys Ala Ala Pro Lys Pro Phe Gln Ser His Phe Cys Val
            100                 105                 110

Val Ser Lys Pro Lys Asp Cys Ile Phe Pro Tyr Ala Phe Lys Glu Val
        115                 120                 125

Ile Glu Lys Lys Asn Val Lys Val Glu Val Ala Ala Thr Glu Arg Thr
    130                 135                 140

Leu Leu Gly Phe Phe Leu Ala Lys Val His Lys Ile Asp Pro Asp Ile
145                 150                 155                 160

Ile Val Gly His Asn Ile Tyr Gly Phe Glu Leu Glu Val Leu Leu Gln
                165                 170                 175

Arg Ile Asn Val Cys Lys Ala Pro His Trp Ser Lys Ile Gly Arg Leu
            180                 185                 190

Lys Arg Ser Asn Met Pro Lys Leu Gly Gly Arg Ser Gly Phe Gly Glu
        195                 200                 205

Arg Asn Ala Thr Cys Gly Arg Met Ile Cys Asp Val Glu Ile Ser Ala
    210                 215                 220

Lys Glu Leu Ile Arg Cys Lys Ser Tyr His Leu Ser Glu Leu Val Gln
225                 230                 235                 240

Gln Ile Leu Lys Thr Glu Arg Val Val Ile Pro Met Glu Asn Ile Gln
                245                 250                 255

Asn Met Tyr Ser Glu Ser Ser Gln Leu Leu Tyr Leu Leu Glu His Thr
```

-continued

```
                  260                 265                 270
Trp Lys Asp Ala Lys Phe Ile Leu Gln Ile Met Cys Glu Leu Asn Val
        275                 280                 285
Leu Pro Leu Ala Leu Gln Ile Thr Asn Ile Ala Gly Asn Ile Met Ser
        290                 295                 300
Arg Thr Leu Met Gly Gly Arg Ser Glu Arg Asn Glu Phe Leu Leu Leu
305                 310                 315                 320
His Ala Phe Tyr Glu Asn Asn Tyr Ile Val Pro Asp Lys Gln Ile Phe
                325                 330                 335
Arg Lys Pro Gln Gln Lys Leu Gly Asp Glu Asp Glu Ile Asp Gly
            340                 345                 350
Asp Thr Asn Lys Tyr Lys Lys Gly Arg Lys Lys Gly Ala Tyr Ala Gly
                355                 360                 365
Gly Leu Val Leu Asp Pro Lys Val Gly Phe Tyr Asp Lys Phe Ile Leu
            370                 375                 380
Leu Leu Asp Phe Asn Ser Leu Tyr Pro Ser Ile Ile Gln Glu Phe Asn
385                 390                 395                 400
Ile Cys Phe Thr Thr Val Gln Arg Val Ala Ser Glu Ala Gln Lys Val
                405                 410                 415
Thr Glu Asp Gly Glu Gln Glu Gln Ile Pro Glu Leu Pro Asp Pro Ser
            420                 425                 430
Leu Glu Met Gly Ile Leu Pro Arg Glu Ile Arg Lys Leu Val Glu Arg
        435                 440                 445
Arg Lys Gln Val Lys Gln Leu Met Lys Gln Asp Leu Asn Pro Asp
        450                 455                 460
Leu Ile Leu Gln Tyr Asp Ile Arg Gln Lys Ala Leu Lys Leu Thr Ala
465                 470                 475                 480
Asn Ser Met Tyr Gly Cys Leu Gly Phe Ser Tyr Ser Arg Phe Tyr Ala
                485                 490                 495
Lys Pro Leu Ala Ala Leu Val Thr Tyr Lys Gly Arg Glu Ile Leu Met
            500                 505                 510
His Thr Lys Glu Met Val Gln Lys Met Asn Leu Glu Val Ile Tyr Gly
        515                 520                 525
Asp Thr Asp Ser Ile Met Ile Asn Thr Asn Ser Thr Asn Leu Glu Glu
        530                 535                 540
Val Phe Lys Leu Gly Asn Lys Val Lys Ser Glu Val Asn Lys Leu Tyr
545                 550                 555                 560
Lys Leu Leu Glu Ile Asp Ile Asp Gly Val Phe Lys Ser Leu Leu Leu
                565                 570                 575
Leu Lys Lys Lys Tyr Ala Ala Leu Val Val Glu Pro Thr Ser Asp
            580                 585                 590
Gly Asn Tyr Val Thr Lys Gln Glu Leu Lys Gly Leu Asp Ile Val Arg
        595                 600                 605
Arg Asp Trp Cys Asp Leu Ala Lys Asp Thr Gly Asn Phe Val Ile Gly
        610                 615                 620
Gln Ile Leu Ser Asp Gln Ser Arg Asp Thr Ile Val Glu Asn Ile Gln
625                 630                 635                 640
Lys Arg Leu Ile Glu Ile Gly Glu Asn Val Leu Asn Gly Ser Val Pro
                645                 650                 655
Val Ser Gln Phe Glu Ile Asn Lys Ala Leu Thr Lys Asp Pro Gln Asp
            660                 665                 670
Tyr Pro Asp Lys Lys Ser Leu Pro His Val His Val Ala Leu Trp Ile
            675                 680                 685
```

-continued

```
Asn Ser Gln Gly Gly Arg Lys Val Lys Ala Gly Asp Thr Val Ser Tyr
        690                 695                 700

Val Ile Cys Gln Asp Gly Ser Asn Leu Thr Ala Ser Gln Arg Ala Tyr
705                 710                 715                 720

Ala Pro Glu Gln Leu Gln Lys Gln Asp Asn Leu Thr Ile Asp Thr Gln
                725                 730                 735

Tyr Tyr Leu Ala Gln Gln Ile His Pro Val Val Ala Arg Ile Cys Glu
                740                 745                 750

Pro Ile Asp Gly Ile
        755

<210> SEQ ID NO 24
<211> LENGTH: 757
<212> TYPE: PRT
<213> ORGANISM: Mus musculus

<400> SEQUENCE: 24

Ser His Val Phe Gly Thr Asn Thr Ser Ser Leu Glu Leu Phe Leu Met
 1               5                  10                  15

Asn Arg Lys Ile Lys Gly Pro Cys Trp Leu Glu Val Lys Asn Pro Gln
            20                  25                  30

Leu Leu Asn Gln Pro Ile Ser Trp Cys Lys Phe Glu Val Met Ala Leu
        35                  40                  45

Lys Pro Asp Leu Val Asn Val Ile Lys Asp Val Ser Pro Pro Leu
 50                  55                  60

Val Val Met Ser Phe Ser Met Lys Thr Met Gln Asn Val Gln Asn His
65                  70                  75                  80

Gln His Glu Ile Ile Ala Met Ala Ala Leu Val His His Ser Phe Ala
                85                  90                  95

Leu Asp Lys Ala Pro Pro Glu Pro Pro Phe Gln Thr His Phe Cys Val
            100                 105                 110

Val Ser Lys Pro Lys Asp Cys Ile Phe Pro Cys Asp Phe Lys Glu Val
        115                 120                 125

Ile Ser Lys Lys Asn Met Lys Val Glu Ile Ala Ala Thr Glu Arg Thr
130                 135                 140

Leu Ile Gly Phe Phe Leu Ala Lys Val His Lys Ile Asp Pro Asp Ile
145                 150                 155                 160

Leu Val Gly His Asn Ile Cys Ser Phe Glu Leu Glu Val Leu Leu Gln
                165                 170                 175

Arg Ile Asn Glu Cys Lys Val Pro Tyr Trp Ser Lys Ile Gly Arg Leu
            180                 185                 190

Arg Arg Ser Asn Met Pro Lys Leu Gly Ser Arg Ser Gly Phe Gly Glu
        195                 200                 205

Arg Asn Ala Thr Cys Gly Arg Met Ile Cys Asp Val Glu Ile Ser Ala
    210                 215                 220

Lys Glu Leu Ile His Cys Lys Ser Tyr His Leu Ser Glu Leu Val Gln
225                 230                 235                 240

Gln Ile Leu Lys Thr Glu Arg Ile Val Ile Pro Thr Glu Asn Ile Arg
                245                 250                 255

Asn Met Tyr Ser Glu Ser Ser Tyr Leu Leu Tyr Leu Leu Glu His Ile
            260                 265                 270

Trp Lys Asp Ala Arg Phe Ile Leu Gln Ile Met Cys Glu Leu Asn Val
        275                 280                 285

Leu Pro Leu Ala Leu Gln Ile Thr Asn Ile Ala Gly Asn Ile Met Ser
```

-continued

```
            290                 295                 300
Arg Thr Leu Met Gly Gly Arg Ser Glu Arg Asn Glu Phe Leu Leu Leu
305                 310                 315                 320

His Ala Phe Tyr Glu Asn Asn Tyr Ile Val Pro Asp Lys Gln Ile Phe
                325                 330                 335

Arg Lys Pro Gln Gln Lys Leu Gly Asp Glu Asp Glu Ile Asp Gly
            340                 345                 350

Asp Thr Asn Lys Tyr Lys Lys Gly Arg Lys Lys Ala Thr Tyr Ala Gly
                355                 360                 365

Gly Leu Val Leu Asp Pro Lys Val Gly Phe Tyr Asp Lys Phe Ile Leu
370                 375                 380

Leu Leu Asp Phe Asn Ser Leu Tyr Pro Ser Ile Ile Gln Glu Phe Asn
385                 390                 395                 400

Ile Cys Phe Thr Thr Val Gln Arg Val Thr Ser Glu Val Gln Lys Ala
                405                 410                 415

Thr Glu Asp Glu Glu Gln Glu Gln Ile Pro Glu Leu Pro Asp Pro Asn
                420                 425                 430

Leu Glu Met Gly Ile Leu Pro Arg Glu Ile Arg Lys Leu Val Glu Arg
                435                 440                 445

Arg Lys Gln Val Lys Gln Leu Met Lys Gln Gln Asp Leu Asn Pro Asp
450                 455                 460

Leu Val Leu Gln Tyr Asp Ile Arg Gln Lys Ala Leu Lys Leu Thr Ala
465                 470                 475                 480

Asn Ser Met Tyr Gly Cys Leu Gly Phe Ser Tyr Ser Arg Phe Tyr Ala
                485                 490                 495

Lys Pro Leu Ala Ala Leu Val Thr Tyr Lys Gly Arg Glu Ile Leu Met
                500                 505                 510

His Thr Lys Asp Met Val Gln Lys Met Asn Leu Glu Val Ile Tyr Gly
                515                 520                 525

Asp Thr Asp Ser Ile Met Ile Asn Thr Asn Ser Thr Asn Leu Glu Glu
                530                 535                 540

Val Phe Lys Leu Gly Asn Lys Val Lys Ser Glu Val Asn Lys Leu Tyr
545                 550                 555                 560

Lys Leu Leu Glu Ile Asp Ile Asp Ala Val Phe Lys Ser Leu Leu Leu
                565                 570                 575

Leu Lys Lys Lys Lys Tyr Ala Ala Leu Val Val Glu Pro Thr Ser Asp
                580                 585                 590

Gly Asn Tyr Ile Thr Lys Gln Glu Leu Lys Gly Leu Asp Ile Val Arg
                595                 600                 605

Arg Asp Trp Cys Asp Leu Ala Lys Asp Thr Gly Asn Phe Val Ile Gly
                610                 615                 620

Gln Ile Leu Ser Asp Gln Ser Arg Asp Thr Ile Val Glu Asn Ile Gln
625                 630                 635                 640

Lys Arg Leu Ile Glu Ile Gly Glu Asn Val Leu Asn Gly Ser Val Pro
                645                 650                 655

Val Ser Gln Phe Glu Ile Asn Lys Ala Leu Thr Lys Asp Pro Gln Asp
                660                 665                 670

Tyr Pro Asp Arg Lys Ser Leu Pro His Val His Val Ala Leu Trp Ile
                675                 680                 685

Asn Ser Gln Gly Gly Arg Lys Val Lys Ala Gly Asp Thr Val Ser Tyr
                690                 695                 700

Val Ile Cys Gln Asp Gly Ser Asn Leu Thr Ala Thr Gln Arg Ala Tyr
705                 710                 715                 720
```

-continued

```
Ala Pro Glu Gln Leu Gln Lys Leu Asp Asn Leu Ala Ile Asp Thr Gln
                725                 730                 735

Tyr Tyr Leu Ala Gln Gln Ile His Pro Val Val Ala Arg Ile Cys Glu
            740                 745                 750

Pro Ile Asp Gly Ile
        755

<210> SEQ ID NO 25
<211> LENGTH: 748
<212> TYPE: PRT
<213> ORGANISM: Drosophila melanogaster

<400> SEQUENCE: 25

Ala His Ile Phe Gly Ala Thr Thr Asn Ala Leu Glu Arg Phe Leu Leu
 1               5                  10                  15

Asp Arg Lys Ile Lys Gly Pro Cys Trp Leu Gln Val Thr Gly Phe Lys
            20                  25                  30

Val Ser Pro Thr Pro Met Ser Trp Cys Asn Thr Glu Val Thr Leu Thr
        35                  40                  45

Glu Pro Lys Asn Val Glu Leu Val Gln Asp Lys Gly Lys Pro Ala Pro
    50                  55                  60

Pro Pro Pro Leu Thr Leu Leu Ser Leu Asn Val Arg Thr Ser Met Asn
65                  70                  75                  80

Pro Lys Thr Ser Arg Asn Glu Ile Cys Met Ile Ser Met Leu Thr His
                85                  90                  95

Asn Arg Phe His Ile Asp Arg Pro Ala Pro Gln Pro Ala Phe Asn Arg
            100                 105                 110

His Met Cys Ala Leu Thr Arg Pro Ala Val Val Ser Trp Pro Leu Asp
        115                 120                 125

Leu Asn Phe Glu Met Ala Lys Tyr Lys Ser Thr Thr Val His Lys His
    130                 135                 140

Asp Ser Glu Arg Ala Leu Leu Ser Trp Phe Leu Ala Gln Tyr Gln Lys
145                 150                 155                 160

Ile Asp Ala Asp Leu Ile Val Thr Phe Asp Ser Met Asp Cys Gln Leu
                165                 170                 175

Asn Val Ile Thr Asp Gln Ile Val Ala Leu Lys Ile Pro Gln Trp Ser
            180                 185                 190

Arg Met Gly Arg Leu Arg Leu Ser Gln Ser Phe Gly Lys Arg Leu Leu
        195                 200                 205

Glu His Phe Val Gly Arg Met Val Cys Asp Val Lys Arg Ser Ala Glu
    210                 215                 220

Glu Cys Ile Arg Ala Arg Ser Tyr Asp Leu Gln Thr Leu Cys Lys Gln
225                 230                 235                 240

Val Leu Lys Leu Lys Glu Ser Glu Arg Met Glu Val Asn Ala Asp Asp
                245                 250                 255

Leu Leu Glu Met Tyr Glu Lys Gly Glu Ser Ile Thr Lys Leu Ile Ser
            260                 265                 270

Leu Thr Met Gln Asp Asn Ser Tyr Leu Leu Arg Leu Met Cys Glu Leu
        275                 280                 285

Asn Ile Met Pro Leu Ala Leu Gln Ile Thr Asn Ile Cys Gly Asn Thr
    290                 295                 300

Met Thr Arg Thr Leu Gln Gly Gly Arg Ser Glu Arg Asn Glu Phe Leu
305                 310                 315                 320

Leu Leu His Ala Ser Thr Glu Lys Asn Tyr Ile Val Pro Asp Lys Lys
```

-continued

```
                325                 330                 335
Pro Val Ser Lys Arg Ser Gly Ala Gly Asp Thr Asp Arg Thr Leu Ser
                340                 345                 350
Gly Ala Asp Ala Thr Met Gln Thr Lys Lys Ala Ala Tyr Ala Gly
                355                 360                 365
Gly Leu Val Leu Glu Pro Met Arg Gly Leu Tyr Glu Lys Tyr Val Leu
                370                 375                 380
Leu Met Asp Leu Asn Ser Leu Tyr Pro Ser Ile Ile Gln Glu Tyr Asn
385                 390                 395                 400
Ile Cys Phe Asn Pro Val Gln Gln Pro Val Asp Ala Asp Glu Leu Pro
                405                 410                 415
Thr Leu Pro Asp Ser Lys Thr Glu Pro Gly Ile Leu Pro Leu Gln Leu
                420                 425                 430
Lys Arg Leu Val Glu Ser Arg Lys Glu Val Lys Lys Leu Met Ala Ala
                435                 440                 445
Pro Asp Leu Ser Pro Glu Leu Gln Met Gln Tyr His Ile Arg Gln Met
                450                 455                 460
Ala Leu Lys Leu Thr Ala Asn Ser Met Tyr Gly Cys Leu Gly Phe Ala
465                 470                 475                 480
His Ser Arg Phe Phe Ala Gln His Leu Ala Ala Leu Val Thr His Lys
                485                 490                 495
Gly Arg Asp Leu Thr Asn Thr Gln Gln Leu Val Gln Lys Met Asn Tyr
                500                 505                 510
Asp Val Val Tyr Gly Asp Thr Asp Ser Leu Met Ile Asn Thr Asn Ile
                515                 520                 525
Thr Asp Tyr Asp Gln Val Tyr Lys Ile Gly His Asn Ile Lys Gln Ser
                530                 535                 540
Val Asn Lys Leu Tyr Lys Gln Leu Glu Leu Asp Ile Asp Gly Val Phe
545                 550                 555                 560
Gly Cys Leu Leu Leu Lys Lys Lys Tyr Ala Ala Ile Lys Leu
                565                 570                 575
Ser Lys Asp Ser Lys Gly Asn Leu Arg Arg Glu Gln Glu His Lys Gly
                580                 585                 590
Leu Asp Ile Val Arg Arg Asp Trp Ser Gln Leu Ala Val Met Val Gly
                595                 600                 605
Lys Ala Val Leu Asp Glu Val Leu Ser Glu Lys Pro Leu Glu Glu Lys
                610                 615                 620
Leu Asp Ala Val His Ala Gln Leu Glu Lys Ile Lys Thr Gln Ile Ala
625                 630                 635                 640
Glu Gly Val Val Pro Leu Pro Leu Phe Val Ile Thr Lys Gln Leu Thr
                645                 650                 655
Arg Thr Pro Gln Asp Tyr Arg Asn Ser Ala Ser Leu Pro His Val Gln
                660                 665                 670
Val Ala Leu Arg Met Asn Arg Glu Arg Asn Arg Tyr Lys Lys Gly
                675                 680                 685
Asp Met Val Asp Leu Cys Asp Cys Leu Asp Gly Thr Thr Asn Ala Ala
                690                 695                 700
Met Gln Arg Ala Tyr His Leu Asp Glu Leu Lys Thr Ser Glu Asp Lys
705                 710                 715                 720
Lys Leu Gln Leu Asp Thr Asn Tyr Tyr Leu Gly His Gln Ile His Pro
                725                 730                 735
Val Val Thr Arg Met Val Glu Val Leu Glu Gly Thr
                740                 745
```

<210> SEQ ID NO 26
<211> LENGTH: 752
<212> TYPE: PRT
<213> ORGANISM: Schizosaccharomyces pombe

<400> SEQUENCE: 26

```
Ser His Val Phe Gly Thr Asn Thr Ala Leu Phe Glu Gln Phe Val Leu
 1               5                  10                  15

Ser Arg Arg Val Met Gly Pro Cys Trp Leu Lys Ile Gln Gln Pro Asn
            20                  25                  30

Phe Asp Ala Val Lys Asn Ala Ser Trp Cys Arg Val Glu Ile Gly Cys
        35                  40                  45

Ser Ser Pro Gln Asn Ile Ser Val Ser Phe Glu Lys Asn Glu Ile Thr
    50                  55                  60

Ser Lys Thr Pro Pro Met Thr Val Met Ser Leu Ala Phe Arg Thr Leu
65                  70                  75                  80

Ile Asn Lys Glu Gln Asn Lys Gln Glu Val Val Met Ile Ser Ala Arg
                85                  90                  95

Ile Phe Glu Asn Val Asp Ile Glu Lys Gly Leu Pro Ala Asn Asp Met
            100                 105                 110

Pro Ser Tyr Ser Phe Ser Leu Ile Arg Pro Leu Lys Gln Ile Phe Pro
        115                 120                 125

Asn Gly Phe Glu Lys Leu Ala Arg Gln His Lys Ser Ser Ile Phe Cys
130                 135                 140

Glu Arg Ser Glu Val Ser Leu Leu Asn Asn Phe Leu Asn Lys Val Arg
145                 150                 155                 160

Thr Tyr Asp Pro Asp Val Tyr Phe Gly His Asp Phe Glu Met Cys Tyr
                165                 170                 175

Ser Val Leu Leu Ser Arg Leu Lys Glu Arg Lys Ile His Asn Trp Ser
            180                 185                 190

Ser Ile Gly Arg Leu Arg Arg Ser Glu Trp Pro Arg Ser Phe Asn Arg
        195                 200                 205

Ser Ser Gln Gln Phe Val Glu Lys Gln Ile Ile Ala Gly Arg Leu Met
    210                 215                 220

Cys Asp Leu Ser Asn Asp Phe Gly Arg Ser Met Ile Lys Ala Gln Ser
225                 230                 235                 240

Trp Ser Leu Ser Glu Ile Val Leu Lys Glu Leu Asp Ile Lys Arg Gln
                245                 250                 255

Asp Ile Asn Gln Glu Lys Ala Leu Gln Ser Trp Thr Asp Thr Ala His
            260                 265                 270

Gly Leu Leu Asp Tyr Leu Val His Cys Glu Ile Asp Thr Phe Phe Ile
        275                 280                 285

Ala Ala Val Ala Phe Lys Ile Gln Met Leu Gln Leu Ser Lys Asn Leu
    290                 295                 300

Thr Asn Ile Ala Gly Asn Ser Trp Ala Arg Thr Leu Thr Gly Thr Arg
305                 310                 315                 320

Ala Glu Arg Asn Glu Tyr Ile Leu Leu His Glu Phe Lys Lys Asn Gly
                325                 330                 335

Tyr Ile Val Pro Asp Lys Gln Gln Ser Ile Arg Arg His Ala Glu Ala
            340                 345                 350

Phe Gly Ala Glu Asp Gly Leu Gln Glu Glu Ser Leu Gly Lys Lys Lys
        355                 360                 365

Asp Lys Tyr Lys Gly Gly Leu Val Phe Glu Pro Gln Lys Gly Leu Tyr
```

```
                370             375             380
Glu Thr Cys Ile Leu Val Met Asp Phe Asn Ser Leu Tyr Pro Ser Ile
385                 390                 395                 400

Ile Gln Glu Tyr Asn Ile Cys Phe Thr Thr Val Asp Arg Ser Pro Ser
                405                 410                 415

Asn Ser Asp Ser Asp Asp Gln Ile Pro Asp Thr Pro Ser Ala Ser Ala
            420                 425                 430

Asn Gln Gly Ile Phe Pro Arg Leu Ile Ala Asn Leu Val Glu Arg Arg
        435                 440                 445

Arg Gln Ile Lys Gly Leu Leu Lys Asp Asn Ser Ala Thr Pro Thr Gln
450                 455                 460

Arg Leu Gln Trp Asp Ile Gln Gln Ala Leu Lys Leu Thr Ala Asn
465                 470                 475                 480

Ser Met Tyr Gly Cys Leu Gly Tyr Thr Lys Ser Arg Phe Tyr Ala Arg
                485                 490                 495

Pro Leu Ala Val Leu Ile Thr Tyr Lys Gly Arg Glu Ala Leu Met Asn
            500                 505                 510

Thr Lys Glu Leu Ala Asp Gln Met Gly Leu Gln Val Ile Tyr Gly Asp
        515                 520                 525

Thr Asp Ser Val Met Leu Asn Thr Asn Val Thr Asp Lys Asn His Ala
530                 535                 540

Leu Arg Ile Gly Asn Glu Phe Lys Glu Lys Val Asn Glu Arg Tyr Ser
545                 550                 555                 560

Lys Leu Glu Ile Asp Ile Asp Asn Val Tyr Gln Arg Met Leu Leu His
                565                 570                 575

Ala Lys Lys Lys Tyr Ala Ala Leu Gln Leu Asp Ser Gln Gly Lys Pro
            580                 585                 590

Asn Leu Asp Val Lys Gly Leu Asp Met Lys Arg Arg Glu Phe Cys Thr
        595                 600                 605

Leu Ala Lys Glu Ala Ser Lys Phe Cys Leu Asp Gln Ile Leu Ser Gly
610                 615                 620

Glu Leu Thr Glu Thr Val Ile Glu Asn Ile His Ser Tyr Leu Met Asp
625                 630                 635                 640

Phe Ser Glu Lys Met Arg Asn Gly Lys Phe Pro Ala Asn Lys Phe Ile
                645                 650                 655

Ile Phe Asn Arg Leu Gly Lys Asn Pro Glu Asp Tyr Pro Asn Gly Lys
            660                 665                 670

Thr Met Pro Phe Val Gln Val Ala Leu Lys Lys Ala Arg Gly Glu
        675                 680                 685

Asn Val Arg Val Gly Asp Val Ile Pro Phe Ile Ala Gly Ser Asp
690                 695                 700

Ala Asp Gly His Pro Ala Asp Arg Ala Tyr Ser Pro Gln Glu Ile Met
705                 710                 715                 720

Asn Thr Asn Ser Thr Leu Val Ile Asp Tyr Asn Tyr Leu Ser His
                725                 730                 735

Gln Ile Leu Pro Pro Ile Glu Arg Val Ile Ala Pro Ile Glu Gly Thr
            740                 745                 750

<210> SEQ ID NO 27
<211> LENGTH: 761
<212> TYPE: PRT
<213> ORGANISM: Saccharomyces cerevisiae

<400> SEQUENCE: 27
```

-continued

| | | | | | | | | | | | | | |
|---|---|---|---|---|---|---|---|---|---|---|---|---|---|
|Tyr|His|Val|Phe|Gly|Gly|Asn|Ser|Asn|Ile|Phe|Glu|Ser|Phe|Val|Ile|
|1| | | |5| | | |10| | | |15| | | |

Gln Asn Arg Ile Met Gly Pro Cys Trp Leu Asp Ile Lys Gly Ala Asp
            20              25              30

Phe Asn Ser Ile Arg Asn Ala Ser His Cys Ala Val Glu Val Ser Val
        35              40              45

Asp Lys Pro Gln Asn Ile Thr Pro Thr Thr Lys Thr Met Pro Asn
 50              55              60

Leu Arg Cys Leu Ser Leu Ser Ile Gln Thr Leu Met Asn Pro Lys Glu
65              70              75              80

Asn Lys Gln Glu Ile Val Ser Ile Thr Leu Ser Ala Tyr Arg Asn Ile
            85              90              95

Ser Leu Asp Ser Pro Ile Pro Glu Asn Ile Lys Pro Asp Asp Leu Cys
        100             105             110

Thr Leu Val Arg Pro Pro Gln Ser Thr Ser Phe Pro Leu Gly Leu Ala
        115             120             125

Ala Leu Ala Lys Gln Lys Leu Pro Gly Arg Val Arg Leu Phe Asn Asn
    130             135             140

Glu Lys Ala Met Leu Ser Cys Phe Cys Ala Met Leu Lys Val Glu Asp
145             150             155             160

Pro Asp Val Ile Ile Gly His Arg Leu Gln Asn Val Tyr Leu Asp Val
            165             170             175

Leu Ala His Arg Met His Asp Leu Asn Ile Pro Thr Phe Ser Ser Ile
            180             185             190

Gly Arg Arg Leu Arg Arg Thr Trp Pro Glu Lys Phe Gly Arg Gly Asn
        195             200             205

Ser Asn Met Asn His Phe Phe Ile Ser Asp Ile Cys Ser Gly Arg Leu
    210             215             220

Ile Cys Asp Ile Ala Asn Glu Met Gly Gln Ser Leu Thr Pro Lys Cys
225             230             235             240

Gln Ser Trp Asp Leu Ser Glu Met Tyr Gln Val Thr Cys Glu Lys Glu
            245             250             255

His Lys Pro Leu Asp Ile Asp Tyr Gln Asn Pro Gln Tyr Gln Asn Asp
            260             265             270

Val Asn Ser Met Thr Met Ala Leu Gln Glu Asn Ile Thr Asn Cys Met
    275             280             285

Ile Ser Ala Glu Val Ser Tyr Arg Ile Gln Leu Leu Thr Leu Thr Lys
290             295             300

Gln Leu Thr Asn Leu Ala Gly Asn Ala Trp Ala Gln Thr Leu Gly Gly
305             310             315             320

Thr Arg Ala Gly Arg Asn Glu Tyr Ile Leu Leu His Glu Phe Ser Arg
            325             330             335

Asn Gly Phe Ile Val Pro Asp Lys Glu Gly Asn Arg Ser Arg Ala Gln
            340             345             350

Lys Gln Arg Gln Asn Glu Glu Asn Ala Asp Ala Pro Val Asn Ser Lys
    355             360             365

Lys Ala Lys Tyr Gln Gly Gly Leu Val Phe Glu Pro Glu Lys Gly Leu
    370             375             380

His Lys Asn Tyr Val Leu Val Met Asp Phe Asn Ser Leu Tyr Pro Ser
385             390             395             400

Ile Ile Gln Glu Phe Asn Ile Cys Phe Thr Thr Val Asp Arg Asn Lys
            405             410             415

Glu Asp Ile Asp Glu Leu Pro Ser Val Pro Pro Ser Glu Val Asp Gln

-continued

```
            420                 425                 430

Gly Val Leu Pro Arg Leu Leu Ala Asn Leu Val Asp Arg Arg Arg Glu
        435                 440                 445

Val Lys Lys Val Met Lys Thr Glu Thr Asp Pro His Lys Arg Val Gln
    450                 455                 460

Cys Asp Ile Arg Gln Gln Ala Leu Lys Leu Thr Ala Asn Ser Met Tyr
465                 470                 475                 480

Gly Cys Leu Gly Tyr Val Asn Ser Arg Phe Tyr Ala Lys Pro Leu Ala
                485                 490                 495

Met Leu Val Thr Asn Lys Gly Arg Glu Ile Leu Met Asn Thr Arg Gln
            500                 505                 510

Leu Ala Glu Ser Met Asn Leu Leu Val Val Tyr Gly Asp Thr Asp Ser
        515                 520                 525

Val Met Ile Asp Thr Gly Cys Asp Asn Tyr Ala Asp Ala Ile Lys Ile
    530                 535                 540

Gly Leu Gly Phe Lys Arg Leu Val Asn Glu Arg Tyr Arg Leu Leu Glu
545                 550                 555                 560

Ile Asp Ile Asp Asn Val Phe Lys Lys Leu Leu Leu His Ala Lys Lys
                565                 570                 575

Lys Tyr Ala Ala Leu Thr Val Asn Leu Asp Lys Asn Gly Asn Gly Thr
            580                 585                 590

Thr Val Leu Glu Val Lys Gly Leu Asp Met Lys Arg Arg Glu Phe Cys
        595                 600                 605

Pro Leu Ser Arg Asp Val Ser Ile His Val Leu Asn Thr Ile Leu Ser
    610                 615                 620

Asp Lys Asp Pro Glu Glu Ala Leu Gln Glu Val Tyr Asp Tyr Leu Glu
625                 630                 635                 640

Asp Ile Arg Ile Lys Val Glu Thr Asn Asn Ile Arg Ile Asp Lys Tyr
                645                 650                 655

Lys Ile Asn Met Lys Leu Ser Lys Asp Pro Lys Ala Tyr Pro Gly Gly
            660                 665                 670

Lys Asn Met Pro Ala Val Gln Val Ala Leu Arg Met Arg Lys Ala Gly
        675                 680                 685

Arg Val Val Lys Ala Gly Ser Val Ile Thr Phe Val Ile Thr Lys Gln
    690                 695                 700

Asp Glu Ile Asp Asn Ala Ala Asp Thr Pro Ala Leu Ser Val Ala Glu
705                 710                 715                 720

Arg Ala His Ala Leu Asn Glu Val Met Ile Lys Ser Asn Asn Leu Ile
                725                 730                 735

Pro Asp Pro Gln Tyr Tyr Leu Glu Lys Gln Ile Phe Ala Pro Val Glu
            740                 745                 750

Arg Leu Leu Glu Arg Ile Asp Ser Phe
        755                 760

<210> SEQ ID NO 28
<211> LENGTH: 761
<212> TYPE: PRT
<213> ORGANISM: Trypanosoma brucei

<400> SEQUENCE: 28

Gln Val Val Val Gly Ala Ser Arg Ser Leu Leu Glu Leu Phe Leu Ile
 1               5                  10                  15

Lys Lys Arg Leu Met Gly Pro Ser Tyr Leu Glu Ile Glu His Leu Val
            20                  25                  30
```

```
Thr Ala Met Asp Arg Val Ser His Cys Lys Thr Glu Phe Leu Val Pro
        35                  40                  45
Ser Pro Lys Asp Ile Lys Val Tyr Asn Ser Ser Lys Pro Pro Pro Pro
        50                  55                  60
Phe Thr Val Ala Ser Ile Gln Leu His Ala Gln Leu Asp Ser Asp Gly
 65                  70                  75                  80
Val Lys Asn Glu Val Ile Ala Ala Ser Ile Ala Leu Tyr Gly Asp Val
                85                  90                  95
Ser Ile Asp Gly Glu Arg Lys Pro Asn Ile Thr Glu Cys Phe Thr Gly
                100                 105                 110
Val Arg Gln Leu Ser Pro Asp Ala Pro Leu Pro Leu Asp Leu Glu Thr
                115                 120                 125
Tyr Cys Leu Ser Lys Arg Met Pro Gly Val His Arg Phe Ile Asn Glu
        130                 135                 140
Arg Ala Leu Leu Thr Trp Phe Ala Glu Thr Leu Ala Ala Leu Asp Pro
145                 150                 155                 160
Asp Ile Ile Val Gly His Asn Ile Ile Gly Tyr Thr Val Glu Thr Leu
                165                 170                 175
Leu Asn Arg Tyr Gln Glu Leu Asn Ile Val Arg Trp Ser Thr Ile Gly
        180                 185                 190
Arg Leu Asp Val Arg Arg Phe Pro Arg Ile Gln Gly Asn Asn Phe Asn
        195                 200                 205
Leu Ala Ile Glu Lys Glu Ala Cys Val Gly Arg Leu Val Val Asp Thr
        210                 215                 220
Tyr Leu Leu Ala Arg Glu Tyr Tyr Lys Ser Thr Asn Tyr Lys Leu Leu
225                 230                 235                 240
Ser Leu Ser Thr Gln Met Glu Ile Lys Gly Ile Thr Asp Asn Arg Gly
                245                 250                 255
His Phe Glu Pro Gly Ser Thr Val Leu Val Lys Asp Ser Met Met Ser
                260                 265                 270
Ser Glu Ala Leu Cys Pro Ile Leu Leu Gln Leu Leu Asn Cys Ala Val
        275                 280                 285
Leu Ser Phe Asn Val Ala Ser Phe Leu Asp Val Ile Pro Leu Thr Lys
        290                 295                 300
Arg Leu Thr Leu Leu Ala Gly Asn Leu Trp Ser Arg Thr Leu Tyr Gly
305                 310                 315                 320
Ala Arg Ser Glu Arg Ile Glu Tyr Leu Leu Leu His Ala Phe His Asn
                325                 330                 335
Leu Lys Phe Val Thr Pro Asp Lys Lys Arg Asp Leu Lys Arg Gly
                340                 345                 350
Arg Glu Asp Asp Asp Glu Gly Lys Arg Lys Thr Lys Tyr Gln Gly
        355                 360                 365
Gly Met Val Leu Glu Pro Lys Ser Gly Leu Tyr Ser Glu Tyr Ile Leu
    370                 375                 380
Leu Leu Asp Phe Asn Ser Leu Tyr Pro Ser Leu Ile Gln Glu Phe Asn
385                 390                 395                 400
Val Cys Tyr Thr Thr Ile Asp Arg Asp Glu Asn Thr Val Ser Ala Glu
                405                 410                 415
Val Pro Pro Pro Glu Ser Leu Ile Cys Leu Ser Cys Arg Ala Ala Gly
                420                 425                 430
Leu Pro Ser Pro Cys Leu His Lys Cys Ile Leu Pro Lys Val Ile Arg
        435                 440                 445
Gly Leu Val Asp Ser Arg Arg Glu Ile Lys Arg Met Met Lys Ser Glu
```

-continued

```
            450                 455                 460
Lys Asp Pro Gly Asn Leu Ala Met Leu Glu Ile Arg Gln Leu Ala Leu
465                 470                 475                 480

Lys Leu Thr Ala Asn Ser Met Tyr Gly Cys Leu Gly Phe Glu Tyr Ser
                485                 490                 495

Arg Phe Tyr Ala Gln Pro Leu Ala Glu Leu Val Thr Arg Gln Gly Arg
            500                 505                 510

Leu Ala Leu Gln Asn Thr Val Glu Leu Ile Pro Gln Ile Ser Pro Ser
                515                 520                 525

Ile Arg Val Ile Tyr Gly Asp Thr Asp Ser Val Met Ile Gln Thr Gly
530                 535                 540

Ile Lys Asp Asp Ile Val Lys Val Arg Asn Leu Gly Phe Glu Ile Lys
545                 550                 555                 560

Gly Lys Val Asn Gln Arg Tyr Gln Ser Leu Glu Leu Asp Ile Asp Gly
                565                 570                 575

Val Phe Arg Ala Met Leu Leu Arg Lys Lys Tyr Ala Ala Leu
                580                 585                 590

Ser Val Val Asp Trp Gln Gly Glu Gly Lys Val Tyr Lys Arg Glu Val
            595                 600                 605

Lys Gly Leu Asp Met Val Arg Arg Asp Trp Cys Pro Leu Ser Gln His
        610                 615                 620

Val Ser Asp Ala Val Leu Lys Arg Ile Leu Asn Ala Glu Gly Gly Glu
625                 630                 635                 640

Asp Ile Leu Asp Phe Val Ile Lys Tyr Met Lys Gly Val Ala Gln Asp
                645                 650                 655

Val Arg Ser Gly Asn Val Tyr Pro Leu Glu Glu Phe Val Ile Ser Lys
            660                 665                 670

Ser Leu Thr Lys Glu Pro Glu Ser Tyr His Gly Thr Gly Tyr Pro His
        675                 680                 685

Ala Val Val Ala Leu Arg Met Lys Gln Arg Lys Glu Gly Val Arg Val
            690                 695                 700

Gly Asp Leu Ile Pro Tyr Val Ile Cys Glu Gly Asp Glu His Ile Asp
705                 710                 715                 720

Asp Lys Ala Tyr His Ile Asp Glu Val Arg Arg Ser Asp Gly Leu Ser
                725                 730                 735

Val Asp Val Glu Trp Tyr Leu Ser Ser Gln Leu Tyr Pro Pro Val Met
            740                 745                 750

Arg Leu Cys Glu His Ile Gln Gly Phe
        755                 760
```

<210> SEQ ID NO 29
<211> LENGTH: 782
<212> TYPE: PRT
<213> ORGANISM: Autographa californica nucleopolynedrovirus

<400> SEQUENCE: 29

```
Asn Ala Ala Cys Leu Asp Lys Phe Leu His Asn Val Asn Arg Val His
1               5                   10                  15

Met Gln Thr Pro Phe Val Glu Gly Ala Tyr Met Arg Phe Lys Lys Thr
                20                  25                  30

Gln Arg Cys Gln Asn Asn Tyr Val Gly Gly Ser Thr Thr Arg Met Phe
            35                  40                  45

Asn Leu Gln His Phe Asn Glu Asp Phe Glu Leu Val Asp Glu Met Thr
        50                  55                  60
```

```
Leu Thr Ser Gly Ile Met Pro Val Leu Ser Cys Tyr Asp Ile Glu Thr
 65                  70                  75                  80

His Ser Asp Gly His Asn Met Ser Lys Ala Ser Val Asp Cys Ile Met
                 85                  90                  95

Ser Ile Gly Phe Val Val Tyr Lys Asn Asp Glu Tyr Ala Lys Phe Cys
            100                 105                 110

Phe Met Tyr His Lys Leu Pro Thr Gln Ile Pro Glu Thr Tyr Asp Asp
        115                 120                 125

Asp Thr Tyr Val Val Met Phe Gln Asn Glu Ile Asp Met Ile Thr Ala
    130                 135                 140

Phe Phe Asp Met Ile Lys Ile Thr Asn Pro Asp Val Ile Leu Asp Phe
145                 150                 155                 160

Asn Gly Asp Val Phe Asp Leu Pro Tyr Ile Leu Gly Arg Leu Asn Lys
                165                 170                 175

Thr Lys Met Leu Leu Lys Arg Tyr Asp Leu Pro Ala Ala Ala Pro Thr
            180                 185                 190

Thr Lys Leu Phe Ile Asn Lys Leu Gly Asn Lys Val Asp Thr Tyr Tyr
        195                 200                 205

Phe Asn Tyr Tyr Ile His Ile Asp Leu Tyr Lys Phe Phe Ser Ser Asp
    210                 215                 220

Ser Asn Gln His Lys Val Glu Asn Phe Gln Leu Asn Thr Ile Ser Ser
225                 230                 235                 240

Tyr Tyr Leu Gly Glu Asn Lys Ile Asp Leu Pro Trp Thr Glu Met Val
                245                 250                 255

Lys Met Tyr Asn Thr Arg Arg Leu Asp Val Ile Ala Lys Tyr Asn Val
            260                 265                 270

Gln Asp Cys Met Leu Pro Ile Lys Leu Phe Val Lys Leu Lys Met Ala
        275                 280                 285

Asp Ser Val Tyr Ser Gln Cys Ile Leu His Arg Leu Cys Thr Asp Asp
    290                 295                 300

Val Ile Cys Asn Ile Ser His Leu Ile Ser Val Ala Cys Phe Tyr Ala
305                 310                 315                 320

Ala Ile Thr Asn Thr Arg Ile Asn Glu Ser Thr Gly Lys Glu Glu Pro
                325                 330                 335

Asp Pro Tyr Phe Phe Asn Lys Asn Asp Leu Ser Ile Ile Ser Gly Gln
            340                 345                 350

Phe Lys Ala Asp Lys Ala Ala Gly Ile Ser Asn Leu Lys Arg Lys
        355                 360                 365

Leu Ile Pro Leu Lys Asn Ile Pro Lys Asp Ala Ile Asn Leu Gly Pro
    370                 375                 380

Ala Asn Gln Thr Val Lys Tyr Lys Gly Gly Lys Val Leu Lys Pro Arg
385                 390                 395                 400

Ala Gly Ile Tyr Lys Asn Ala Phe Ser Leu Asp Phe Asn Ser Leu Tyr
                405                 410                 415

Leu Thr Ile Met Ile Ala Ile Cys Ala Cys Leu Ser Asn Leu Ile Leu
            420                 425                 430

Cys Glu Asp Gly Asn Val Tyr Leu Asn His Asn Ser Arg Ala Ile Val
        435                 440                 445

Val Lys Leu Leu Leu Lys Leu Leu Ser Glu Arg Cys Lys Phe Lys Lys
450                 455                 460

Asn Arg Asp Asn Gln Ser Glu Ser Ala Phe Leu Tyr Asp Leu Tyr Asp
465                 470                 475                 480

Gln Lys Gln Asn Ser Val Lys Arg Thr Ala Asn Ser Ile Tyr Gly Tyr
```

```
                    485                 490                 495
Tyr Gly Ile Phe Tyr Lys Val Leu Ala Asn Tyr Ile Thr Arg Val Gly
                500                 505                 510

Arg Asn Gln Leu Arg Leu Ala Ile Ser Leu Ile Glu Gly Leu Ser Asn
            515                 520                 525

Asp Pro Glu Ile Leu Glu Lys Phe Asn Leu Gly Ser Ile Thr Phe Lys
        530                 535                 540

Val Val Tyr Gly Asp Thr Asp Ser Thr Phe Val Leu Pro Thr Phe Asn
545                 550                 555                 560

Tyr Asn Glu Ile Ser Asn Glu Thr Asp Thr Leu Lys Gln Ile Cys Thr
                565                 570                 575

His Val Glu Thr Arg Val Asn Asn Ser Phe Thr Asp Gly Tyr Lys Met
            580                 585                 590

Ala Phe Glu Asn Leu Met Lys Val Leu Ile Leu Lys Lys Lys Lys
        595                 600                 605

Tyr Cys Tyr Leu Asn Ser Glu Asn Lys Ile Val Tyr Lys Gly Trp Leu
    610                 615                 620

Val Lys Lys Asp Met Pro Val Phe Met Arg Ile Ala Phe Arg Thr Ala
625                 630                 635                 640

Val Glu Gln Ile Leu Arg His Leu Asp Met Asp Lys Cys Leu Gln Ser
                645                 650                 655

Leu Gln Thr Ser Phe Tyr Glu Tyr Tyr Asp Glu Phe Ala Lys Ser Lys
            660                 665                 670

Ser Leu Thr Asp Tyr Ser Phe Ser Met Thr Tyr Asn Asp Asn Pro Gly
        675                 680                 685

Lys Lys Arg Lys Ser Thr Asp Asp Asn Glu Gly Pro Ser Pro Lys Arg
690                 695                 700

Arg Val Ile Thr Val Ala Arg His Cys Arg Glu Ile Leu Val Asn Lys
705                 710                 715                 720

Gly Thr Asp Phe Val Pro Gly Asn Gly Asp Arg Ile Pro Tyr Leu Leu
                725                 730                 735

Ile Asp Ile Glu Gly Lys Val Thr Glu Lys Ala Tyr Pro Leu Arg Leu
            740                 745                 750

Phe Asp Pro Val Lys Met Arg Ile Ser Trp Ile Lys His Met Gly Ile
        755                 760                 765

Leu Cys Thr Phe Met Asn Glu Leu Leu Glu Ile Phe Gly Asp
    770                 775                 780
```

<210> SEQ ID NO 30
<211> LENGTH: 797
<212> TYPE: PRT
<213> ORGANISM: Lymantria dispar multicapsid nuclear polyhedrosis

<400> SEQUENCE: 30

```
Asp Lys Asn Cys Leu Asp Gly Tyr Leu Ala Asp Val Asn Arg Val His
 1               5                  10                  15

Met Gln Thr Ser Leu Leu Glu Gly Gln Tyr Val Arg Phe Lys Asn Ala
            20                  25                  30

His Ala Cys Arg Asp Tyr Arg Leu Ser His Thr Ala Lys Asp Val His
        35                  40                  45

Glu Phe Glu Ser Met Leu Glu Arg Val Gln Val Ser Ala Leu Ser His
    50                  55                  60

Glu Ile Leu Pro Val Val Ala Cys Tyr Asp Ile Glu Thr His Ser Asp
65                  70                  75                  80
```

```
Gly Gln Arg Phe Ser Ala Pro Asp Ala Asp Phe Ile Ile Ser Ile Ala
                 85                  90                  95
Val Val Val Arg Arg Asp Ala Ala Asp Thr Arg Ile Cys Leu Phe Tyr
            100                 105                 110
Ser Pro Asp Asp Pro Val Asp Leu Ser Ser Ser Ser Ser Pro Pro
        115                 120                 125
Ala Ala Pro Asp Thr Ala Ala Val His Phe Arg Ala Glu Arg Asp Met
130                 135                 140
Ile Ala Ala Phe Phe Gln Leu Leu Pro Leu Leu Asn Ala Asp Val Val
145                 150                 155                 160
Leu Asp Phe Asn Gly Asp Lys Phe Asp Leu Pro Phe Leu Thr Gly Arg
                165                 170                 175
Ala Asn Lys Leu Cys Gly Pro Ala Glu Ala Ala Arg Ala Thr Lys Ile
            180                 185                 190
Ala Arg Tyr Asp Leu Ser Pro Val Asn Val Val Thr Gln Gln Ser Tyr
        195                 200                 205
Asp Lys Phe Ser Asn Lys Leu His Ser His Tyr Leu Thr Tyr Tyr Ile
        210                 215                 220
His Ile Asp Leu Tyr Gln Phe Leu Ser Thr Asp Ser Glu His Asn Asp
225                 230                 235                 240
Leu Glu Asn Phe Gln Leu Asn Thr Val Ala Glu His Tyr Leu Lys Lys
                245                 250                 255
Ser Lys Val Asp Leu Pro Ile His Asp Met Leu Gln Met Tyr Gly Glu
            260                 265                 270
Lys Arg Leu Ser Arg Ile Val Glu Tyr Asn Val Gln Asp Cys Val Leu
        275                 280                 285
Pro Val Glu Leu Phe Leu Lys Leu Glu Ile Ala Asp Tyr Met Tyr Thr
        290                 295                 300
Gln Cys Met Leu Leu Tyr Leu Cys Thr Asp Asp Leu Leu Arg Asn Ile
305                 310                 315                 320
Ser His Lys Ile Thr Val Ala Tyr Phe His Leu Ala Leu Thr Asn Thr
                325                 330                 335
Val Ala Arg Arg Pro Asp Pro Thr Pro Asp Pro Tyr Phe Phe Asn Lys
            340                 345                 350
Tyr Asp Leu Ser Val Thr Ser Gly Ala Ser Ala Pro Ser Thr Ser Arg
        355                 360                 365
Pro Ala Asn Ala Ile Asp Leu Ser Gln Leu Lys Arg Thr Pro Val Asp
        370                 375                 380
Ala Ala Arg Ile Pro Pro Ser Ala Val Lys Leu Cys Ser Thr Arg Gln
385                 390                 395                 400
Ser Cys Thr Tyr Lys Gly Gly Lys Val Leu Ser Pro Lys Pro Gly Phe
                405                 410                 415
Asn Arg Trp Val Ala Thr Leu Asp Phe Asn Ala Leu Tyr Pro Thr Ile
            420                 425                 430
Met Met Trp Glu Gly Val Cys Met Ser Ser Asn Val Phe Ile Ala Ser
        435                 440                 445
Asp Gly Asn Val Tyr Leu Asp Lys Asn Val Asn Ala Val Asn Pro Lys
        450                 455                 460
Leu Leu Lys Thr Leu Ser Glu Met Arg Val Arg Tyr Lys Gly Leu Arg
465                 470                 475                 480
Asp Gln Cys Glu Tyr Asn Ser Phe Tyr Lys Leu Tyr Asp Lys Ile
                485                 490                 495
Gln Asn Ala Leu Lys Arg Ile Ala Asn Ser Ile Tyr Gly Tyr Tyr Gly
```

-continued

```
                500                 505                 510
Ile Phe Phe Lys Pro Leu Ala Asn Tyr Ile Thr Lys Met Gly Arg Gly
            515                 520                 525

Lys Leu Lys Glu Val Val Gly Lys Val Glu Ala Met Ser Asp Asp Pro
        530                 535                 540

Arg Ile Leu Arg Glu Phe Gly Leu Ser Lys Ile Asn Phe Ser Val Ile
545                 550                 555                 560

Tyr Gly Asp Thr Asp Ser Cys Phe Ile Arg Val Leu Phe Asp Glu Ala
                565                 570                 575

Glu Trp Arg Arg Thr Ala Ala Arg Pro Arg Ser Ala Pro Ser Cys Arg
            580                 585                 590

Thr Thr Cys Ala Lys Arg Ser Thr Thr Leu Trp Cys Gly Tyr Lys Met
        595                 600                 605

Ser Leu Glu Asn Ile Met Leu Ser Leu Ile Leu Leu Lys Lys Lys Lys
        610                 615                 620

Tyr Cys Tyr Leu Asn Asn Glu Gln Arg Thr Lys Tyr Lys Gly Trp Leu
625                 630                 635                 640

Ile Lys Arg Asp Met Pro Leu Phe Met Arg Lys Ala Phe Arg Ala Thr
                645                 650                 655

Val Asp Ser Phe Ser Ala Ala Thr Arg Arg Val Arg Ala Arg Pro Ala
                660                 665                 670

Arg Arg Glu Met Leu Arg Tyr Tyr Arg Glu Phe Gly Ala Pro Arg Glu
            675                 680                 685

Asn Leu Val Asp Tyr Cys Phe Ser Met Ser Tyr Asn Glu Thr Ser Thr
        690                 695                 700

Thr Ala Lys Arg Arg Lys Glu Glu Asp Pro Ala Arg Lys Pro Val Ile
705                 710                 715                 720

Thr Ile Ala Lys His Cys Arg Glu Leu Leu Ala Asn Pro Gly Val Asp
                725                 730                 735

Phe Leu Pro Gly Asn Gly Asp Arg Ile Gln Tyr Val Leu Val Asp Val
            740                 745                 750

Lys Glu Lys Ile Thr Gln Lys Ala Phe Pro Leu Lys Leu Phe Asp Pro
        755                 760                 765

Asp Ser Pro Thr Leu Gln Ile Ser Trp Leu Lys His Met Asn Ile Leu
770                 775                 780

Cys Thr Phe Met Asn Glu Leu Ile Gln Val Phe Gly Asn
785                 790                 795

<210> SEQ ID NO 31
<211> LENGTH: 745
<212> TYPE: PRT
<213> ORGANISM: Saccharomyces cerevisiae

<400> SEQUENCE: 31

Asn Lys Val Pro Ser Met Gly Asn Lys Lys Thr Glu Ser Gln Ile Ser
 1               5                  10                  15

Met His Thr Pro His Ser Lys Phe Leu Tyr Lys Phe Ala Ser Asp Val
            20                  25                  30

Ser Gly Lys Gln Lys Arg Lys Lys Ser Ser Val His Asp Ser Leu Thr
        35                  40                  45

His Leu Thr Leu Glu Ile His Ala Asn Thr Arg Ser Asp Lys Ile Pro
    50                  55                  60

Asp Pro Ala Ile Asp Glu Val Ser Met Ile Ile Trp Cys Leu Glu Glu
65                  70                  75                  80
```

-continued

```
Glu Thr Phe Pro Leu Asp Leu Asp Ile Ala Tyr Gly Ile Met Ile
                 85                  90                  95

Val His Lys Ala Ser Glu Asp Ser Thr Phe Pro Thr Lys Ile Gln His
                100                 105                 110

Cys Ile Asn Glu Ile Pro Val Met Phe Tyr Glu Ser Glu Phe Glu Met
                115                 120                 125

Phe Glu Ala Leu Thr Asp Leu Val Leu Leu Leu Asp Pro Asp Ile Leu
130                 135                 140

Ser Gly Phe Glu Ile His Asn Phe Ser Trp Gly Tyr Ile Ile Glu Arg
145                 150                 155                 160

Cys Gln Lys Ile His Gln Phe Asp Ile Val Arg Glu Leu Ala Arg Val
                165                 170                 175

Lys Cys Gln Ile Lys Thr Lys Leu Ser Asp Thr Trp Gly Tyr Ala His
                180                 185                 190

Ser Ser Gly Ile Met Ile Thr Gly Arg His Met Ile Asn Ile Trp Arg
        195                 200                 205

Ala Leu Arg Ser Asp Val Asn Leu Thr Gln Tyr Thr Ile Glu Ser Ala
        210                 215                 220

Ala Phe Asn Ile Leu His Lys Arg Leu Pro His Phe Ser Phe Glu Ser
225                 230                 235                 240

Leu Thr Asn Met Trp Asn Ala Lys Lys Ser Thr Thr Glu Leu Lys Thr
                245                 250                 255

Val Leu Asn Tyr Trp Leu Ser Arg Ala Gln Ile Asn Ile Gln Leu Leu
                260                 265                 270

Arg Lys Gln Asp Tyr Ile Ala Arg Asn Ile Glu Gln Ala Arg Leu Ile
                275                 280                 285

Gly Ile Asp Phe His Ser Val Tyr Tyr Arg Gly Ser Gln Phe Lys Val
        290                 295                 300

Glu Ser Phe Leu Ile Arg Ile Cys Lys Ser Glu Ser Phe Ile Leu Leu
305                 310                 315                 320

Ser Pro Gly Lys Lys Asp Val Arg Lys Gln Lys Ala Leu Glu Cys Val
                325                 330                 335

Pro Leu Val Met Glu Pro Glu Ser Ala Phe Tyr Lys Ser Pro Leu Ile
                340                 345                 350

Val Leu Asp Phe Gln Ser Leu Tyr Pro Ser Ile Met Ile Gly Tyr Asn
                355                 360                 365

Tyr Cys Tyr Ser Thr Met Ile Gly Arg Val Arg Glu Ile Asn Leu Thr
        370                 375                 380

Glu Asn Asn Leu Gly Val Ser Lys Phe Ser Leu Pro Arg Asn Ile Leu
385                 390                 395                 400

Ala Leu Leu Lys Asn Asp Val Thr Ile Ala Pro Asn Gly Val Val Tyr
                405                 410                 415

Ala Lys Thr Ser Val Arg Lys Ser Thr Leu Ser Lys Met Leu Thr Asp
                420                 425                 430

Ile Leu Asp Val Arg Val Met Ile Lys Lys Thr Met Asn Glu Ile Gly
                435                 440                 445

Asp Asp Asn Thr Thr Leu Lys Arg Leu Leu Asn Asn Lys Gln Leu Ala
450                 455                 460

Leu Lys Leu Leu Ala Asn Val Thr Tyr Gly Tyr Thr Ser Ala Ser Phe
465                 470                 475                 480

Ser Gly Arg Met Pro Cys Ser Asp Leu Ala Asp Ser Ile Val Gln Thr
                485                 490                 495

Gly Arg Glu Thr Leu Glu Lys Ala Ile Asp Ile Ile Glu Lys Asp Glu
```

-continued

```
                500                 505                 510
Thr Trp Asn Ala Lys Val Val Tyr Gly Asp Thr Asp Ser Leu Phe Val
        515                 520                 525

Tyr Leu Pro Gly Lys Thr Ala Ile Glu Ala Phe Ser Ile Gly His Ala
        530                 535                 540

Met Ala Glu Arg Val Thr Gln Asn Asn Pro Lys Pro Ile Phe Leu Lys
545                 550                 555                 560

Phe Glu Lys Val Tyr His Pro Ser Ile Leu Ile Ser Lys Lys Arg Tyr
                565                 570                 575

Val Gly Phe Ser Tyr Glu Ser Pro Ser Gln Thr Leu Pro Ile Phe Asp
            580                 585                 590

Ala Lys Gly Ile Glu Thr Val Arg Arg Asp Gly Ile Pro Ala Gln Gln
            595                 600                 605

Lys Ile Ile Glu Lys Cys Ile Arg Leu Leu Phe Gln Thr Lys Asp Leu
        610                 615                 620

Ser Lys Ile Lys Lys Tyr Leu Gln Asn Glu Phe Lys Ile Gln Ile
625                 630                 635                 640

Gly Lys Val Ser Ala Gln Asp Phe Cys Phe Ala Lys Glu Val Lys Leu
                645                 650                 655

Gly Ala Tyr Lys Ser Glu Lys Thr Ala Pro Ala Gly Ala Val Val Val
            660                 665                 670

Lys Arg Arg Ile Asn Glu Asp His Arg Ala Glu Pro Gln Tyr Lys Glu
        675                 680                 685

Arg Ile Pro Tyr Leu Val Val Lys Gly Lys Gln Gly Gln Leu Leu Arg
        690                 695                 700

Glu Arg Cys Val Ser Pro Glu Glu Phe Leu Glu Gly Glu Asn Leu Glu
705                 710                 715                 720

Leu Asp Ser Glu Tyr Tyr Ile Asn Lys Ile Leu Ile Pro Pro Leu Asp
                725                 730                 735

Arg Leu Phe Asn Leu Ile Gly Ile Asn
            740                 745
```

<210> SEQ ID NO 32
<211> LENGTH: 727
<212> TYPE: PRT
<213> ORGANISM: Pyrococcus woesei

<400> SEQUENCE: 32

```
Phe Lys Ile Glu His Asp Arg Thr Phe Arg Pro Tyr Ile Tyr Ala Leu
 1               5                  10                  15

Leu Arg Asp Asp Ser Lys Ile Glu Glu Val Lys Lys Ile Thr Gly Glu
            20                  25                  30

Arg His Gly Lys Ile Val Arg Ile Val Asp Val Glu Lys Val Glu Lys
        35                  40                  45

Lys Phe Leu Gly Lys Pro Ile Thr Val Trp Lys Leu Tyr Leu Glu His
    50                  55                  60

Pro Gln Asp Val Pro Thr Ile Arg Glu Lys Val Arg Glu His Pro Ala
65                  70                  75                  80

Val Val Asp Ile Phe Glu Tyr Asp Ile Pro Phe Ala Lys Arg Tyr Leu
                85                  90                  95

Ile Asp Lys Gly Leu Ile Pro Met Glu Gly Glu Glu Leu Lys Ile
            100                 105                 110

Leu Ala Phe Asp Ile Glu Thr Leu Tyr His Glu Gly Glu Glu Phe Gly
        115                 120                 125
```

-continued

```
Lys Gly Pro Ile Ile Met Ile Ser Tyr Ala Asp Glu Asn Ala Lys
    130                 135                 140

Val Ile Thr Trp Lys Asn Ile Asp Leu Pro Tyr Val Glu Val Val Ser
145                 150                 155                 160

Ser Glu Arg Glu Met Ile Lys Arg Phe Leu Arg Ile Ile Arg Glu Lys
                165                 170                 175

Asp Pro Asp Ile Ile Val Thr Tyr Asn Gly Asp Ser Phe Asp Phe Pro
                180                 185                 190

Tyr Leu Ala Lys Arg Ala Glu Lys Leu Gly Ile Lys Leu Thr Ile Gly
            195                 200                 205

Arg Asp Gly Ser Glu Pro Lys Met Gln Arg Ile Gly Asp Met Thr Ala
    210                 215                 220

Val Glu Val Lys Gly Arg Ile His Phe Asp Leu Tyr His Val Ile Thr
225                 230                 235                 240

Arg Thr Ile Asn Leu Pro Thr Tyr Thr Leu Glu Ala Val Tyr Glu Ala
                245                 250                 255

Ile Phe Gly Lys Pro Lys Glu Lys Val Tyr Ala Asp Glu Ile Ala Lys
                260                 265                 270

Ala Trp Glu Ser Gly Glu Asn Leu Glu Arg Val Ala Lys Tyr Ser Met
            275                 280                 285

Glu Asp Ala Lys Ala Thr Tyr Glu Leu Gly Lys Glu Phe Leu Pro Met
    290                 295                 300

Glu Ile Gln Leu Ser Arg Leu Val Gly Gln Pro Leu Trp Asp Val Ser
305                 310                 315                 320

Arg Ser Ser Thr Gly Asn Leu Val Glu Trp Phe Leu Leu Arg Lys Ala
                325                 330                 335

Tyr Glu Arg Asn Glu Val Ala Pro Asn Lys Pro Ser Glu Glu Glu Tyr
                340                 345                 350

Gln Arg Arg Leu Arg Glu Ser Tyr Thr Gly Gly Phe Val Lys Glu Pro
            355                 360                 365

Glu Lys Gly Leu Trp Glu Asn Ile Val Tyr Leu Asp Phe Arg Ala Leu
    370                 375                 380

Tyr Pro Ser Ile Ile Ile Thr His Asn Val Ser Pro Asp Thr Leu Asn
385                 390                 395                 400

Leu Glu Gly Cys Lys Asn Tyr Asp Ile Ala Pro Gln Val Gly His Lys
                405                 410                 415

Phe Cys Lys Asp Ile Pro Gly Phe Ile Pro Ser Leu Leu Gly His Leu
                420                 425                 430

Leu Glu Glu Arg Gln Lys Ile Lys Thr Lys Met Lys Glu Thr Gln Asp
            435                 440                 445

Pro Ile Glu Lys Ile Leu Leu Asp Tyr Arg Gln Lys Ala Ile Lys Leu
    450                 455                 460

Leu Ala Asn Ser Phe Tyr Gly Tyr Tyr Gly Tyr Ala Lys Ala Arg Trp
465                 470                 475                 480

Tyr Cys Lys Glu Cys Ala Glu Ser Val Thr Ala Trp Gly Arg Lys Tyr
                485                 490                 495

Ile Glu Leu Val Trp Lys Glu Leu Glu Lys Phe Gly Phe Lys Val Leu
                500                 505                 510

Leu Tyr Ile Asp Thr Asp Gly Leu Tyr Ala Thr Ile Pro Gly Gly Glu
            515                 520                 525

Ser Glu Glu Ile Lys Lys Lys Ala Leu Glu Phe Val Lys Tyr Ile Asn
    530                 535                 540

Ser Lys Leu Pro Gly Leu Leu Glu Leu Glu Tyr Glu Gly Phe Tyr Lys
```

```
                545                 550                 555                 560

Arg Gly Phe Phe Val Thr Lys Lys Arg Tyr Ala Val Ile Asp Glu Glu
                565                 570                 575

Gly Lys Val Ile Thr Arg Gly Leu Glu Ile Val Arg Arg Asp Trp Ser
                580                 585                 590

Glu Ile Ala Lys Glu Thr Gln Ala Arg Val Leu Glu Thr Ile Leu Lys
                595                 600                 605

His Gly Asp Val Glu Glu Ala Val Arg Ile Val Lys Glu Val Ile Gln
                610                 615                 620

Lys Leu Ala Asn Tyr Glu Ile Pro Pro Glu Lys Leu Ala Ile Tyr Glu
625                 630                 635                 640

Gln Ile Thr Arg Pro Leu His Glu Tyr Lys Ala Ile Gly Pro His Val
                645                 650                 655

Ala Val Ala Lys Lys Leu Ala Ala Lys Gly Val Lys Ile Lys Pro Gly
                660                 665                 670

Met Val Ile Gly Tyr Ile Val Leu Arg Gly Asp Gly Pro Ile Ser Asn
                675                 680                 685

Arg Ala Ile Leu Ala Glu Glu Tyr Asp Pro Lys Lys His Lys Tyr Asp
                690                 695                 700

Ala Glu Tyr Tyr Ile Glu Asn Gln Val Leu Pro Ala Val Leu Arg Ile
705                 710                 715                 720

Leu Glu Gly Phe Gly Tyr Arg
                725

<210> SEQ ID NO 33
<211> LENGTH: 702
<212> TYPE: PRT
<213> ORGANISM: Sulfolobus solfataricus

<400> SEQUENCE: 33

Phe Asn Asn Tyr Met Tyr Asp Ile Gly Leu Ile Pro Gly Met Pro Tyr
1               5                   10                  15

Val Val Lys Asn Gly Lys Leu Glu Ser Val Tyr Leu Ser Leu Asp Glu
                20                  25                  30

Lys Asp Val Glu Glu Ile Lys Lys Ala Phe Ala Asp Ser Asp Glu Met
            35                  40                  45

Thr Arg Gln Met Ala Val Asp Trp Leu Pro Ile Phe Glu Thr Glu Ile
        50                  55                  60

Pro Lys Ile Lys Arg Val Ala Ile Asp Ile Glu Val Tyr Thr Pro Val
65                  70                  75                  80

Lys Gly Arg Ile Pro Asp Ser Gln Lys Ala Glu Phe Pro Ile Ile Ser
                85                  90                  95

Ile Ala Leu Ala Gly Ser Asp Gly Leu Lys Lys Val Leu Val Leu Asn
                100                 105                 110

Arg Asn Asp Val Asn Glu Gly Ser Val Lys Leu Asp Gly Ile Ser Val
            115                 120                 125

Glu Arg Phe Asn Thr Glu Tyr Glu Leu Leu Gly Arg Phe Phe Asp Ile
        130                 135                 140

Leu Leu Glu Tyr Pro Ile Val Leu Thr Phe Asn Gly Asp Asp Phe Asp
145                 150                 155                 160

Leu Pro Tyr Ile Tyr Phe Arg Ala Leu Lys Leu Gly Tyr Phe Pro Glu
                165                 170                 175

Glu Ile Pro Ile Asp Val Ala Gly Lys Asp Glu Ala Lys Tyr Leu Ala
            180                 185                 190
```

-continued

```
Gly Leu His Ile Asp Leu Tyr Lys Phe Phe Asn Lys Ala Val Arg
        195                 200                 205

Asn Tyr Ala Phe Glu Gly Lys Tyr Asn Glu Tyr Asn Leu Asp Ala Val
210                 215                 220

Ala Lys Ala Leu Leu Gly Thr Ser Lys Val Lys Val Asp Thr Leu Ile
225                 230                 235                 240

Ser Phe Leu Asp Val Glu Lys Leu Ile Glu Tyr Asn Phe Arg Asp Ala
                245                 250                 255

Glu Ile Thr Leu Gln Leu Thr Thr Phe Asn Asn Asp Leu Thr Met Lys
                260                 265                 270

Leu Ile Val Leu Phe Ser Arg Ile Ser Arg Leu Gly Ile Glu Glu Leu
                275                 280                 285

Thr Arg Thr Glu Ile Ser Thr Trp Val Lys Asn Leu Tyr Tyr Trp Glu
        290                 295                 300

His Arg Lys Arg Asn Trp Leu Ile Pro Leu Lys Glu Ile Leu Ala
305                 310                 315                 320

Lys Ser Ser Asn Ile Arg Thr Ser Ala Leu Ile Lys Gly Lys Gly Tyr
                325                 330                 335

Lys Gly Ala Val Val Ile Asp Pro Pro Ala Gly Ile Phe Phe Asn Ile
                340                 345                 350

Thr Val Leu Asp Phe Ala Ser Leu Tyr Pro Ser Ile Ile Arg Thr Trp
                355                 360                 365

Asn Leu Ser Tyr Glu Thr Val Asp Ile Gln Gln Cys Lys Lys Pro Tyr
        370                 375                 380

Glu Val Lys Asp Glu Thr Gly Glu Val Leu His Ile Val Cys Met Asp
385                 390                 395                 400

Arg Pro Gly Ile Thr Ala Val Ile Thr Gly Leu Leu Arg Asp Phe Arg
                405                 410                 415

Val Lys Ile Tyr Lys Lys Ala Lys Asn Pro Asn Asn Ser Glu Glu
                420                 425                 430

Gln Lys Leu Leu Tyr Asp Val Val Gln Arg Ala Met Lys Val Phe Ile
        435                 440                 445

Asn Ala Thr Tyr Gly Val Phe Gly Ala Glu Thr Phe Pro Leu Tyr Ala
450                 455                 460

Pro Arg Val Ala Glu Ser Val Thr Ala Leu Gly Arg Tyr Val Ile Thr
465                 470                 475                 480

Ser Thr Val Lys Lys Ala Arg Glu Glu Gly Leu Thr Val Leu Tyr Gly
                485                 490                 495

Asp Thr Asp Ser Leu Phe Leu Leu Asn Pro Pro Lys Asn Ser Leu Glu
                500                 505                 510

Asn Ile Ile Lys Trp Val Lys Thr Thr Phe Asn Leu Asp Leu Glu Val
                515                 520                 525

Asp Lys Thr Tyr Lys Phe Val Ala Phe Ser Gly Leu Lys Lys Asn Tyr
        530                 535                 540

Phe Gly Val Tyr Gln Asp Gly Lys Val Asp Ile Lys Gly Met Leu Val
545                 550                 555                 560

Lys Lys Arg Asn Thr Pro Glu Phe Val Lys Val Phe Asn Glu Val
                565                 570                 575

Lys Glu Leu Met Ile Ser Ile Asn Ser Pro Asn Asp Val Lys Glu Ile
                580                 585                 590

Lys Arg Lys Ile Val Asp Val Lys Gly Ser Tyr Glu Lys Leu Lys
        595                 600                 605

Asn Lys Gly Tyr Asn Leu Asp Glu Leu Ala Phe Lys Val Met Leu Ser
```

-continued

```
            610                 615                 620
Lys Pro Leu Asp Ala Tyr Lys Lys Asn Thr Pro Gln His Val Lys Ala
625                 630                 635                 640

Ala Leu Gln Leu Arg Pro Phe Gly Val Asn Val Leu Pro Arg Asp Ile
                645                 650                 655

Ile Tyr Tyr Val Lys Val Arg Ser Lys Asp Gly Val Lys Pro Val Gln
                660                 665                 670

Leu Ala Lys Val Thr Glu Ile Asp Ala Glu Lys Tyr Leu Glu Ala Leu
                675                 680                 685

Arg Ser Thr Phe Glu Gln Ile Leu Arg Ala Phe Gly Val Ser
            690                 695                 700

<210> SEQ ID NO 34
<211> LENGTH: 719
<212> TYPE: PRT
<213> ORGANISM: Escherichia coli

<400> SEQUENCE: 34

Ala Gln His Ile Leu Gln Gly Glu Gln Gly Phe Arg Leu Thr Pro Leu
1               5                   10                  15

Ala Leu Lys Asp Phe His Arg Gln Pro Val Tyr Gly Leu Tyr Cys Arg
                20                  25                  30

Ala His Arg Gln Leu Met Asn Tyr Glu Lys Arg Leu Arg Glu Gly Gly
            35                  40                  45

Val Thr Val Tyr Glu Ala Asp Val Arg Pro Glu Arg Tyr Leu Met
        50                  55                  60

Glu Arg Phe Ile Thr Ser Pro Val Trp Val Glu Gly Asp Met His Asn
65                  70                  75                  80

Gly Thr Ile Val Asn Ala Arg Leu Lys Pro His Pro Asp Tyr Arg Pro
                85                  90                  95

Pro Leu Lys Trp Val Ser Ile Asp Ile Glu Thr Thr Arg His Gly Glu
                100                 105                 110

Leu Tyr Cys Ile Gly Leu Glu Gly Cys Gly Gln Arg Ile Val Tyr Met
            115                 120                 125

Leu Gly Pro Glu Asn Gly Asp Ala Ser Ser Leu Asp Phe Glu Leu Glu
130                 135                 140

Tyr Val Ala Ser Arg Pro Gln Leu Leu Glu Lys Leu Asn Ala Trp Phe
145                 150                 155                 160

Ala Asn Tyr Asp Pro Asp Val Ile Ile Gly Trp Asn Val Val Gln Phe
                165                 170                 175

Asp Leu Arg Met Leu Gln Lys His Ala Glu Arg Tyr Arg Leu Pro Leu
                180                 185                 190

Arg Leu Gly Arg Asp Asn Ser Glu Leu Glu Trp Arg Glu His Gly Phe
            195                 200                 205

Lys Asn Gly Val Phe Phe Ala Gln Ala Lys Gly Arg Leu Ile Ile Asp
210                 215                 220

Gly Ile Glu Ala Leu Lys Ser Ala Phe Trp Asn Phe Ser Ser Phe Ser
225                 230                 235                 240

Leu Glu Thr Val Ala Gln Glu Leu Leu Gly Glu Gly Lys Ser Ile Asp
                245                 250                 255

Asn Pro Trp Asp Arg Met Asp Glu Ile Asp Arg Arg Phe Ala Glu Asp
                260                 265                 270

Lys Pro Ala Leu Ala Thr Tyr Asn Leu Lys Asp Cys Glu Leu Val Thr
            275                 280                 285
```

```
Gln Ile Phe His Lys Thr Glu Ile Met Pro Phe Leu Glu Arg Ala
    290                 295                 300

Thr Val Asn Gly Leu Pro Val Asp Arg His Gly Gly Ser Val Ala Ala
305                 310                 315                 320

Phe Gly His Leu Tyr Phe Pro Arg Met His Arg Ala Gly Tyr Val Ala
                325                 330                 335

Pro Asn Leu Gly Glu Val Pro Pro His Ala Ser Pro Gly Gly Tyr Val
                340                 345                 350

Met Asp Ser Arg Pro Gly Leu Tyr Asp Ser Val Leu Val Leu Asp Tyr
                355                 360                 365

Lys Ser Leu Tyr Pro Ser Ile Ile Arg Thr Phe Leu Ile Asp Pro Val
370                 375                 380

Gly Leu Val Glu Gly Met Ala Gln Pro Asp Pro Glu His Ser Thr Glu
385                 390                 395                 400

Gly Phe Leu Asp Ala Trp Phe Ser Arg Glu Lys His Cys Leu Pro Glu
                405                 410                 415

Ile Val Thr Asn Ile Trp His Gly Arg Asp Glu Ala Lys Arg Gln Gly
                420                 425                 430

Asn Lys Pro Leu Ser Gln Ala Leu Lys Ile Ile Met Asn Ala Phe Tyr
                435                 440                 445

Gly Val Leu Gly Thr Thr Ala Cys Arg Phe Phe Asp Pro Arg Leu Ala
450                 455                 460

Ser Ser Ile Thr Met Arg Gly His Gln Ile Met Arg Gln Thr Lys Ala
465                 470                 475                 480

Leu Ile Glu Ala Gln Gly Tyr Asp Val Ile Tyr Gly Asp Thr Asp Ser
                485                 490                 495

Thr Phe Val Trp Leu Lys Gly Ala His Ser Glu Glu Ala Ala Lys
                500                 505                 510

Ile Gly Arg Ala Leu Val Gln His Val Asn Ala Trp Trp Ala Glu Thr
                515                 520                 525

Leu Gln Lys Gln Arg Leu Thr Ser Ala Leu Glu Leu Glu Tyr Glu Thr
530                 535                 540

His Phe Cys Arg Phe Leu Met Pro Thr Ile Arg Gly Ala Asp Thr Gly
545                 550                 555                 560

Ser Lys Lys Arg Tyr Ala Gly Leu Ile Gln Glu Gly Asp Lys Gln Arg
                565                 570                 575

Met Val Phe Lys Gly Leu Glu Thr Val Arg Thr Asp Trp Thr Pro Leu
                580                 585                 590

Ala Gln Gln Phe Gln Gln Glu Leu Tyr Leu Arg Ile Phe Arg Asn Glu
                595                 600                 605

Pro Tyr Gln Glu Tyr Val Arg Glu Thr Ile Asp Lys Leu Met Ala Gly
            610                 615                 620

Glu Leu Asp Ala Arg Leu Val Tyr Arg Lys Arg Leu Arg Arg Pro Leu
625                 630                 635                 640

Ser Glu Tyr Gln Arg Asn Val Pro Pro His Val Arg Ala Ala Arg Leu
                645                 650                 655

Ala Asp Glu Glu Asn Gln Lys Arg Gly Arg Pro Leu Gln Tyr Gln Asn
                660                 665                 670

Arg Gly Thr Ile Lys Tyr Val Trp Thr Thr Asn Gly Pro Glu Pro Leu
                675                 680                 685

Asp Tyr Gln Arg Ser Pro Leu Asp Tyr Glu His Tyr Leu Thr Arg Gln
            690                 695                 700

Leu Gln Pro Val Ala Glu Gly Ile Leu Pro Phe Ile Glu Asp Asn
```

<210> SEQ ID NO 35
<211> LENGTH: 773
<212> TYPE: PRT
<213> ORGANISM: Desilforococcus strain Tok

<400> SEQUENCE: 35

```
Met Ile Leu Asp Ala Asp Tyr Ile Thr Glu Asp Gly Lys Pro Val Ile
  1               5                  10                  15
Arg Val Phe Lys Lys Glu Lys Gly Glu Phe Lys Ile Asp Tyr Asp Arg
                 20                  25                  30
Asp Phe Glu Pro Tyr Ile Tyr Ala Leu Leu Lys Asp Asp Ser Ala Ile
             35                  40                  45
Glu Asp Ile Lys Lys Ile Thr Ala Glu Arg His Gly Thr Thr Val Arg
 50                  55                  60
Val Thr Arg Ala Glu Arg Val Lys Lys Phe Leu Gly Arg Pro Val
 65                  70                  75                  80
Glu Val Trp Lys Leu Tyr Phe Thr His Pro Gln Asp Val Pro Ala Ile
                 85                  90                  95
Arg Asp Lys Ile Arg Glu His Pro Ala Val Val Asp Ile Tyr Glu Tyr
                100                 105                 110
Asp Ile Pro Phe Ala Lys Arg Tyr Leu Ile Asp Arg Gly Leu Ile Pro
            115                 120                 125
Met Glu Gly Asp Glu Glu Leu Arg Met Leu Ala Phe Asp Ile Glu Thr
130                 135                 140
Leu Tyr His Glu Gly Glu Glu Phe Gly Glu Gly Pro Ile Leu Met Ile
145                 150                 155                 160
Ser Tyr Ala Asp Glu Glu Gly Ala Arg Val Ile Thr Trp Lys Asn Ile
                165                 170                 175
Asp Leu Pro Tyr Val Glu Ser Val Ser Thr Glu Lys Glu Met Ile Lys
            180                 185                 190
Arg Phe Leu Lys Val Ile Gln Glu Lys Asp Pro Asp Val Leu Ile Thr
        195                 200                 205
Tyr Asn Gly Asp Asn Phe Asp Phe Ala Tyr Leu Lys Lys Arg Ser Glu
210                 215                 220
Met Leu Gly Val Lys Phe Ile Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Thr Val Tyr Glu Pro Val Phe Gly Gln Pro Lys Glu
        275                 280                 285
Lys Val Tyr Ala Glu Glu Ile Ala Arg Ala Trp Glu Ser Gly Glu Gly
        290                 295                 300
Leu Glu Arg Val Ala Arg Tyr Ser Met Glu Asp Ala Lys Ala Thr Tyr
305                 310                 315                 320
Glu Leu Gly Lys Glu Phe Phe Pro Met Glu Ala Gln Leu Ser Arg Leu
                325                 330                 335
Val Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Asp Val Ala
        355                 360                 365
```

-continued

```
Pro Asn Lys Pro Asp Glu Arg Glu Leu Ala Arg Arg Thr Glu Ser Tyr
    370                 375                 380
Ala Gly Gly Tyr Val Lys Glu Pro Glu Lys Gly Leu Trp Glu Asn Ile
385                 390                 395                 400
Val Tyr Leu Asp Tyr Lys Ser Leu Tyr Pro Ser Ile Ile Ile Thr His
                405                 410                 415
Asn Val Ser Pro Asp Thr Leu Asn Arg Glu Gly Cys Arg Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Val Lys
    450                 455                 460
Lys Lys Met Lys Ala Thr Val Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Ala Tyr Ala Asn Ala Arg Trp Tyr Cys Arg Glu Cys Ala Glu Ser
            500                 505                 510
Val Thr Ala Trp Gly Arg Gln Tyr Ile Glu Thr Met Arg Glu Ile
        515                 520                 525
Glu Glu Lys Phe Gly Phe Lys Val Leu Tyr Ala Asp Thr Asp Gly Phe
    530                 535                 540
Phe Ala Thr Ile Pro Gly Ala Asp Ala Glu Thr Val Lys Asn Lys Ala
545                 550                 555                 560
Lys Glu Phe Leu Asn Tyr Ile Asn Pro Arg Leu Pro Gly Leu Leu Glu
                565                 570                 575
Leu Glu Tyr Glu Gly Phe Tyr Arg Arg Gly Phe Phe Val Thr Lys Lys
            580                 585                 590
Lys Tyr Ala Val Ile Asp Glu Glu Asp Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Arg His Glu Val Pro
                645                 650                 655
Pro Glu Lys Leu Val Ile Tyr Glu Gln Ile Thr Arg Asp Leu Arg Ser
            660                 665                 670
Tyr Arg Ala Thr Gly Pro His Val Ala Val Ala Lys Arg Leu Ala Ala
        675                 680                 685
Arg Gly Ile Lys Ile Arg Pro Gly Thr Val Ile Ser Tyr Ile Val Leu
    690                 695                 700
Lys Gly Pro Gly Arg Val Gly Asp Arg Ala Ile Pro Phe Asp Glu Phe
705                 710                 715                 720
Asp Pro Ala Lys His Arg Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Lys Gln Ala Gly Leu Gly Ala Trp
        755                 760                 765
Leu Lys Pro Lys Thr
    770
```

-continued

```
<210> SEQ ID NO 36
<211> LENGTH: 871
<212> TYPE: PRT
<213> ORGANISM: Bacteriophage RM378

<400> SEQUENCE: 36
```

| | | | | | | | | | | | | | | | |
|---|---|---|---|---|---|---|---|---|---|---|---|---|---|---|---|
| Met | Lys | Ile | Thr | Leu | Ser | Ala | Ser | Val | Tyr | Pro | Arg | Ser | Met | Lys | Ile |
| 1 | | | | 5 | | | | | 10 | | | | | 15 | |
| Tyr | Gly | Val | Glu | Leu | Ile | Glu | Gly | Lys | Lys | His | Leu | Phe | Gln | Ser | Pro |
| | | | 20 | | | | | 25 | | | | | 30 | | |
| Val | Pro | Pro | His | Leu | Lys | Arg | Ile | Ala | Gln | Gln | Asn | Arg | Gly | Lys | Ile |
| | | | 35 | | | | 40 | | | | | 45 | | | |
| Glu | Ala | Glu | Ala | Ile | Ser | Tyr | Tyr | Ile | Arg | Glu | Gln | Lys | Ser | His | Ile |
| | 50 | | | | | 55 | | | | | 60 | | | | |
| Thr | Pro | Glu | Ala | Leu | Ser | Gln | Cys | Val | Phe | Ile | Asp | Ile | Glu | Thr | Ile |
| 65 | | | | | 70 | | | | | 75 | | | | | 80 |
| Ser | Pro | Lys | Lys | Ser | Phe | Pro | Asp | Pro | Trp | Arg | Asp | Pro | Val | Tyr | Ser |
| | | | | 85 | | | | | 90 | | | | | 95 | |
| Ile | Ser | Ile | Lys | Pro | Tyr | Gly | Lys | Pro | Val | Val | Val | Leu | Leu | Leu | |
| | | | 100 | | | | | 105 | | | | | 110 | | |
| Ile | Thr | Asn | Pro | Glu | Ala | His | Ile | Asp | Asn | Phe | Asn | Lys | Phe | Thr | Thr |
| | | | 115 | | | | 120 | | | | | 125 | | | |
| Ser | Val | Gly | Asp | Asn | Thr | Phe | Glu | Ile | His | Tyr | Arg | Thr | Phe | Leu | Ser |
| | 130 | | | | | 135 | | | | | 140 | | | | |
| Glu | Lys | Arg | Leu | Leu | Glu | Tyr | Phe | Trp | Asn | Val | Leu | Lys | Pro | Lys | Phe |
| 145 | | | | | 150 | | | | | 155 | | | | | 160 |
| Thr | Phe | Met | Leu | Ala | Trp | Asn | Gly | Tyr | Gln | Phe | Asp | Tyr | Pro | Tyr | Leu |
| | | | | 165 | | | | | 170 | | | | | 175 | |
| Leu | Ile | Arg | Ser | His | Ile | His | Glu | Val | Asn | Val | Ile | Ser | Asp | Lys | Leu |
| | | | 180 | | | | | 185 | | | | | 190 | | |
| Leu | Pro | Asp | Trp | Lys | Leu | Val | Arg | Lys | Ile | Ser | Asp | Arg | Asn | Leu | Pro |
| | | | 195 | | | | | 200 | | | | | 205 | | |
| Phe | Tyr | Phe | Asn | Pro | Arg | Thr | Pro | Val | Glu | Phe | Val | Phe | Phe | Asp | Tyr |
| | 210 | | | | | 215 | | | | | 220 | | | | |
| Met | Arg | Leu | Tyr | Arg | Ser | Phe | Val | Ala | Tyr | Lys | Glu | Leu | Glu | Ser | Tyr |
| 225 | | | | | 230 | | | | | 235 | | | | | 240 |
| Arg | Leu | Asp | Tyr | Ile | Ala | Arg | Glu | Glu | Ile | Gly | Glu | Gly | Lys | Val | Asp |
| | | | | 245 | | | | | 250 | | | | | 255 | |
| Phe | Asp | Val | Arg | Phe | Tyr | His | Glu | Ile | Pro | Val | Tyr | Pro | Asp | Lys | Lys |
| | | | 260 | | | | | 265 | | | | | 270 | | |
| Leu | Val | Glu | Tyr | Asn | Ala | Val | Asp | Ala | Ile | Leu | Met | Glu | Glu | Ile | Glu |
| | | | 275 | | | | | 280 | | | | | 285 | | |
| Asn | Lys | Asn | His | Ile | Leu | Pro | Thr | Leu | Phe | Glu | Ile | Ala | Arg | Leu | Ser |
| | 290 | | | | | 295 | | | | | 300 | | | | |
| Asn | Leu | Thr | Pro | Ala | Leu | Ala | Leu | Asn | Ala | Ser | Asn | Ile | Leu | Ile | Gly |
| 305 | | | | | 310 | | | | | 315 | | | | | 320 |
| Asn | Val | Thr | Gly | Lys | Leu | Gly | Val | Lys | Phe | Val | Asp | Tyr | Ile | Lys | Lys |
| | | | | 325 | | | | | 330 | | | | | 335 | |
| Ile | Asp | Thr | Ile | Asn | Thr | Met | Phe | Lys | Lys | Ile | Pro | Glu | Met | Asn | Ile |
| | | | 340 | | | | | 345 | | | | | 350 | | |
| Asn | Lys | Tyr | Arg | Tyr | Arg | Gly | Ala | Tyr | Ile | Glu | Leu | Thr | Asn | Pro | Asp |
| | | | 355 | | | | | 360 | | | | | 365 | | |
| Ile | Tyr | Phe | Asn | Val | Phe | Asp | Leu | Asp | Phe | Thr | Ser | Leu | Tyr | Pro | Ser |
| | 370 | | | | | 375 | | | | | 380 | | | | |

-continued

```
Val Ile Ser Lys Phe Asn Ile Asp Pro Ala Thr Phe Val Thr Glu Phe
385                 390                 395                 400

Tyr Gly Cys Met Arg Val Glu Asn Lys Val Ile Pro Val Asp Gln Glu
            405                 410                 415

Glu Pro Glu Phe Gly Phe Pro Leu Tyr Ile Phe Asp Ser Gly Met Asn
            420                 425                 430

Pro Ser Tyr Arg Ser Glu Pro Leu Phe Val Ile Asn Ser Phe Glu Glu
        435                 440                 445

Leu Arg Gln Phe Leu Lys Ser Arg Asn Ile Ile Met Val Pro Asn Pro
    450                 455                 460

Ser Gly Ile Cys Trp Phe Tyr Arg Lys Glu Pro Val Gly Val Leu Pro
465                 470                 475                 480

Ser Ile Ile Arg Glu Ile Phe Thr Arg Lys Glu Arg Lys Leu
                485                 490                 495

Phe Lys Glu Thr Gly Asn Met Glu His His Phe Arg Gln Trp Ala Leu
            500                 505                 510

Lys Ile Met Met Asn Ser Met Tyr Gly Ile Phe Gly Asn Arg Ser Val
        515                 520                 525

Tyr Met Gly Cys Leu Pro Ile Ala Glu Ser Val Thr Ala Ala Gly Arg
    530                 535                 540

Met Ser Ile Arg Ser Val Ile Ser Gln Ile Arg Asp Arg Phe Ile Tyr
545                 550                 555                 560

Ser His Thr Asp Ser Ile Phe Val Lys Ala Phe Thr Asp Asp Pro Val
                565                 570                 575

Ala Glu Ala Gly Glu Leu Gln Glu His Leu Asn Ser Phe Ile Asn Asp
            580                 585                 590

Tyr Met Glu Asn Asn Phe Asn Ala Arg Glu Asp Phe Lys Leu Glu Leu
        595                 600                 605

Lys Gln Glu Phe Val Phe Lys Ser Ile Leu Ile Lys Glu Ile Asn Arg
    610                 615                 620

Tyr Phe Ala Val Thr Val Asp Gly Lys Glu Glu Met Lys Gly Ile Glu
625                 630                 635                 640

Val Ile Asn Ser Ser Val Pro Glu Ile Val Lys Lys Tyr Phe Arg Gly
                645                 650                 655

Tyr Leu Lys Tyr Ile Ser Gln Pro Asp Ile Asp Val Ile Ser Ala Thr
            660                 665                 670

Ile Ala Phe Tyr Asn Asn Phe Val Ser Gln Lys Asn Phe Trp Ser Ile
        675                 680                 685

Glu Asp Leu Tyr His Lys Met Lys Ile Ser Ser Asp Ser Ala Glu
    690                 695                 700

Arg Tyr Val Glu Tyr Val Glu Glu Val Met Lys Met Lys Lys Glu Asn
705                 710                 715                 720

Val Pro Ile Ser Glu Ile Phe Ile Lys Met Tyr Asp His Thr Leu Pro
                725                 730                 735

Ile His Tyr Lys Gly Ala Leu Phe Ala Ser Ile Gly Cys Lys Pro
            740                 745                 750

Pro Gln Met Gly Asp Lys Ile Tyr Trp Phe Tyr Cys Thr Met Leu Asp
        755                 760                 765

Pro Ser Arg Thr Asn Leu Pro Leu Ser Leu Glu Glu Val Asn Pro Glu
    770                 775                 780

His Gly Ser Gly Val Trp Asp Ile Leu Lys Ala Gly Lys Lys Thr His
785                 790                 795                 800

Ile Asn Arg Leu Arg Asn Ile His Ala Leu Ser Ile Arg Glu Asp Asp
```

-continued

```
                    805                 810                 815
Glu Glu Gly Leu Glu Ile Val Lys Lys Tyr Ile Asp Arg Asp Lys Tyr
            820                 825                 830

Cys Gln Ile Ile Ser Glu Lys Thr Ile Asp Leu Leu Lys Ser Leu Gly
            835                 840                 845

Tyr Val Glu Asn Thr Thr Lys Ile Lys Thr Val Glu Asp Leu Ile Arg
            850                 855                 860

Phe Leu Val Glu Ser Glu Asn
865                 870

<210> SEQ ID NO 37
<211> LENGTH: 898
<212> TYPE: PRT
<213> ORGANISM: Bacteriophage RB69

<400> SEQUENCE: 37

Met Lys Glu Phe Tyr Leu Thr Val Glu Gln Ile Gly Asp Ser Ile Phe
 1               5                  10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Asp Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300
```

-continued

```
Tyr Asp Gly Pro Ile Ser Lys Leu Arg Glu Ser Asn His Gln Arg Tyr
305                 310                 315                 320

Ile Ser Tyr Asn Ile Ile Asp Val Tyr Arg Val Leu Gln Ile Asp Ala
            325                 330                 335

Lys Arg Gln Phe Ile Asn Leu Ser Leu Asp Met Gly Tyr Tyr Ala Lys
            340                 345                 350

Ile Gln Ile Gln Ser Val Phe Ser Pro Ile Lys Thr Trp Asp Ala Ile
            355                 360                 365

Ile Phe Asn Ser Leu Lys Glu Gln Asn Lys Val Ile Pro Gln Gly Arg
    370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
            405                 410                 415

Pro Ser Ile Ile Arg Gln Val Asn Ile Ser Pro Glu Thr Ile Ala Gly
            420                 425                 430

Thr Phe Lys Val Ala Pro Leu His Asp Tyr Ile Asn Ala Val Ala Glu
            435                 440                 445

Arg Pro Ser Asp Val Tyr Ser Cys Ser Pro Asn Gly Met Met Tyr Tyr
    450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
            485                 490                 495

Glu Ile Ile Lys Glu Ala Leu His Asn Pro Asn Leu Ser Val Asp Glu
            500                 505                 510

Pro Leu Asp Val Asp Tyr Arg Phe Asp Phe Ser Asp Glu Ile Lys Glu
            515                 520                 525

Lys Ile Lys Lys Leu Ser Ala Lys Ser Leu Asn Glu Met Leu Phe Arg
530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
            565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
            595                 600                 605

Cys Gly Thr Glu Gly Glu Ala Phe Val Leu Tyr Gly Asp Thr Asp Ser
            610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
            645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
            675                 680                 685

Ala Gly Pro Pro Leu Gly Ser Lys Gly Ile Gly Gly Phe Trp Thr Gly
            690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
```

```
                    725                 730                 735
Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
            755                 760                 765

Lys Glu Phe Arg Gln Leu Asn Tyr Ile Ser Ile Ala Ser Val Ser Ser
            770                 775                 780

Ala Asn Asn Ile Ala Lys Tyr Asp Val Gly Phe Pro Gly Pro Lys
785                 790                 795                 800

Cys Pro Phe His Ile Arg Gly Ile Leu Thr Tyr Asn Arg Ala Ile Lys
            805                 810                 815

Gly Asn Ile Asp Ala Pro Gln Val Val Glu Gly Glu Lys Val Tyr Val
            820                 825                 830

Leu Pro Leu Arg Glu Gly Asn Pro Phe Gly Asp Lys Cys Ile Ala Trp
            835                 840                 845

Pro Ser Gly Thr Glu Ile Thr Asp Leu Ile Lys Asp Val Leu His
            850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
            885                 890                 895

Leu Phe

<210> SEQ ID NO 38
<211> LENGTH: 394
<212> TYPE: PRT
<213> ORGANISM: Autographa californica nucleopolynedrovirus

<400> SEQUENCE: 38

Met Leu His Val Ser Arg Leu Leu Ala Asn Gly Gly Val Lys Asn Leu
1               5                   10                  15

Cys Asp Lys Phe Lys Val Lys Ile Lys Asn Tyr Thr Glu His Asp Leu
            20                  25                  30

Met Val Leu Asn Tyr Glu Ser Phe Glu Arg Asp Arg Asp His Pro Val
        35                  40                  45

Val Val Glu Cys Arg Gly Leu Ile Leu Asn Ser Arg Thr Tyr Ala Val
    50                  55                  60

Val Ser Arg Ser Phe Asp Arg Phe Phe Asn Phe Gln Glu Leu Leu Gln
65              70                  75                  80

Asn Ile Gly Gly Glu Asp Ala His His Lys Leu Phe Gln Ser Lys Glu
                85                  90                  95

Asn Phe Lys Phe Tyr Glu Lys Ile Asp Gly Ser Leu Ile Lys Ile Tyr
            100                 105                 110

Lys Tyr Asn Gly Glu Trp His Ala Ser Thr Arg Gly Ser Ala Phe Ala
        115                 120                 125

Glu Asn Leu Cys Val Ser Asp Val Thr Phe Lys Arg Leu Val Leu Gln
130                 135                 140

Ala Leu Gln Leu Asp Glu Ala His Asn Gln Phe Gln Ala Leu Cys Asn
145                 150                 155                 160

Glu Tyr Leu Asp Cys Ala Ser Thr His Met Phe Glu Leu Thr Ser Lys
                165                 170                 175

His Asn Arg Ile Val Thr Val Tyr Asp Glu Gln Pro Thr Leu Trp Tyr
            180                 185                 190

Leu Ala Ser Arg Asn Asn Glu Thr Gly Asp Tyr Phe Tyr Cys Ser Asn
```

```
                195                 200                 205
Leu Pro Phe Cys Lys Tyr Pro Lys Cys Tyr Glu Phe Thr Ser Val Gln
    210                 215                 220

Glu Cys Val Glu His Ala Ala Gln Leu Lys Asn Leu Glu Glu Gly Phe
225                 230                 235                 240

Val Val Tyr Asp Lys Asn Asn Ala Pro Leu Cys Lys Ile Lys Ser Asp
                245                 250                 255

Val Tyr Leu Asn Met His Lys Asn Gln Ser Arg Ala Glu Asn Pro Thr
            260                 265                 270

Lys Leu Ala Gln Leu Val Ile Asn Gly Glu His Asp Asp Phe Leu Ala
        275                 280                 285

Leu Phe Pro His Leu Lys Ser Val Ile Lys Pro Tyr Val Asp Ala Arg
    290                 295                 300

Asn Thr Phe Thr Asn Glu Ser Thr Ile Asn Ile Met Val Ser Gly Leu
305                 310                 315                 320

Thr Leu Asn Gln Gln Arg Phe Asn Glu Leu Val Gln Thr Leu Pro Trp
                325                 330                 335

Lys Cys Leu Ala Tyr Arg Cys Arg Lys Ala Gln Thr Ile Asp Val Glu
            340                 345                 350

Ser Glu Phe Leu Lys Leu Thr Glu Pro Glu Lys Ile Lys Met Ile Lys
        355                 360                 365

Asn Ile Ile Lys Phe Val Ser Thr Lys Gln Ala Leu Asn Asn Lys Leu
    370                 375                 380

Ala Pro Thr Ile Lys Leu Pro Ser Ser Lys
385                 390

<210> SEQ ID NO 39
<211> LENGTH: 374
<212> TYPE: PRT
<213> ORGANISM: Bacteriophage T4

<400> SEQUENCE: 39

Met Gln Glu Leu Phe Asn Asn Leu Met Glu Leu Cys Lys Asp Ser Gln
1               5                   10                  15

Arg Lys Phe Phe Tyr Ser Asp Asp Val Ser Ala Ser Gly Arg Thr Tyr
            20                  25                  30

Arg Ile Phe Ser Tyr Asn Tyr Ala Ser Tyr Ser Asp Trp Leu Leu Pro
        35                  40                  45

Asp Ala Leu Glu Cys Arg Gly Ile Met Phe Glu Met Asp Gly Glu Lys
    50                  55                  60

Pro Val Arg Ile Ala Ser Arg Pro Met Glu Lys Phe Phe Asn Leu Asn
65                  70                  75                  80

Glu Asn Pro Phe Thr Met Asn Ile Asp Leu Asn Asp Val Asp Tyr Ile
                85                  90                  95

Leu Thr Lys Glu Asp Gly Ser Leu Val Ser Thr Tyr Leu Asp Gly Asp
            100                 105                 110

Glu Ile Leu Phe Lys Ser Lys Gly Ser Ile Lys Ser Glu Gln Ala Leu
        115                 120                 125

Met Ala Asn Gly Ile Leu Met Asn Ile Asn His His Arg Leu Arg Asp
    130                 135                 140

Arg Leu Lys Glu Leu Ala Glu Asp Gly Phe Thr Ala Asn Phe Glu Phe
145                 150                 155                 160

Val Ala Pro Thr Asn Arg Ile Val Leu Ala Tyr Gln Glu Met Lys Ile
                165                 170                 175
```

-continued

```
Ile Leu Leu Asn Val Arg Glu Asn Glu Thr Gly Glu Tyr Ile Ser Tyr
            180                 185                 190

Asp Asp Ile Tyr Lys Asp Ala Thr Leu Arg Pro Tyr Leu Val Glu Arg
            195                 200                 205

Tyr Glu Ile Asp Ser Pro Lys Trp Ile Glu Ala Lys Asn Ala Glu
    210                 215                 220

Asn Ile Glu Gly Tyr Val Ala Val Met Lys Asp Gly Ser His Phe Lys
225                 230                 235                 240

Ile Lys Ser Asp Trp Tyr Val Ser Leu His Ser Thr Lys Ser Ser Leu
                245                 250                 255

Asp Asn Pro Glu Lys Leu Phe Lys Thr Ile Ile Asp Gly Ala Ser Asp
            260                 265                 270

Asp Leu Lys Ala Met Tyr Ala Asp Asp Glu Tyr Ser Tyr Arg Lys Ile
            275                 280                 285

Glu Ala Phe Glu Thr Thr Tyr Leu Lys Tyr Leu Asp Arg Ala Leu Phe
    290                 295                 300

Leu Val Leu Asp Cys His Asn Lys His Cys Gly Lys Asp Arg Lys Thr
305                 310                 315                 320

Tyr Ala Met Glu Ala Gln Gly Val Ala Lys Gly Ala Gly Met Asp His
                325                 330                 335

Leu Phe Gly Ile Ile Met Ser Leu Tyr Gln Gly Tyr Asp Ser Gln Glu
            340                 345                 350

Lys Val Met Cys Glu Ile Glu Gln Asn Phe Leu Lys Asn Tyr Lys Lys
            355                 360                 365

Phe Ile Pro Glu Gly Tyr
    370
```

<210> SEQ ID NO 40
<211> LENGTH: 437
<212> TYPE: PRT
<213> ORGANISM: Bacteriophage RM378

<400> SEQUENCE: 40

```
Met Ser Met Asn Val Lys Tyr Pro Val Glu Tyr Leu Ile Glu His Leu
1               5                   10                  15

Asn Ser Phe Glu Ser Pro Glu Val Ala Val Glu Ser Leu Arg Lys Glu
            20                  25                  30

Gly Ile Met Cys Lys Asn Arg Gly Asp Leu Tyr Met Phe Lys Tyr His
            35                  40                  45

Leu Gly Cys Lys Phe Asp Lys Ile Tyr His Leu Ala Cys Arg Gly Ala
    50                  55                  60

Ile Leu Arg Lys Thr Asp Ser Gly Trp Lys Val Leu Ser Tyr Pro Phe
65                  70                  75                  80

Asp Lys Phe Phe Asn Trp Gly Glu Glu Leu Gln Pro Glu Ile Val Asn
                85                  90                  95

Tyr Tyr Gln Thr Leu Arg Tyr Ala Ser Pro Leu Asn Glu Lys Arg Lys
            100                 105                 110

Ala Gly Phe Met Phe Lys Leu Pro Met Lys Leu Val Glu Lys Leu Asp
            115                 120                 125

Gly Thr Cys Val Val Leu Tyr Tyr Asp Glu Gly Trp Lys Ile His Thr
    130                 135                 140

Leu Gly Ser Ile Asp Ala Asn Gly Ser Ile Val Lys Asn Gly Met Val
145                 150                 155                 160

Thr Thr His Met Asp Lys Thr Tyr Arg Glu Leu Phe Trp Glu Thr Phe
                165                 170                 175
```

-continued

```
Glu Lys Lys Tyr Pro Pro Tyr Leu Leu Tyr His Leu Asn Ser Ser Tyr
            180                 185                 190

Cys Tyr Ile Phe Glu Met Val His Pro Asp Ala Arg Val Val Pro
        195                 200                 205

Tyr Glu Glu Pro Asn Ile Ile Leu Ile Gly Val Arg Ser Val Asp Pro
        210                 215                 220

Glu Lys Gly Tyr Phe Glu Val Gly Pro Ser Glu Ala Val Arg Ile
225                 230                 235                 240

Phe Asn Glu Ser Gly Gly Lys Ile Asn Leu Lys Leu Pro Ala Val Leu
                245                 250                 255

Ser Gln Glu Gln Asn Tyr Thr Leu Phe Arg Ala Asn Arg Leu Gln Glu
            260                 265                 270

Leu Phe Glu Glu Val Thr Pro Leu Phe Lys Ser Leu Arg Asp Gly Tyr
        275                 280                 285

Glu Val Val Tyr Glu Gly Phe Val Ala Val Gln Glu Ile Ala Pro Arg
        290                 295                 300

Val Tyr Tyr Arg Thr Lys Ile Lys His Pro Val Tyr Leu Glu Leu His
305                 310                 315                 320

Arg Ile Lys Thr Thr Ile Thr Pro Glu Lys Leu Ala Asp Leu Phe Leu
                325                 330                 335

Glu Asn Lys Leu Asp Asp Phe Val Leu Thr Pro Asp Glu Gln Glu Thr
            340                 345                 350

Val Met Lys Leu Lys Glu Ile Tyr Thr Asp Met Arg Asn Gln Leu Glu
            355                 360                 365

Ser Ser Phe Asp Thr Ile Tyr Lys Glu Ile Ser Glu Gln Val Ser Pro
370                 375                 380

Glu Glu Asn Pro Gly Glu Phe Arg Lys Arg Phe Ala Leu Arg Leu Met
385                 390                 395                 400

Asp Tyr His Asp Lys Ser Trp Phe Phe Ala Arg Leu Asp Gly Asp Glu
                405                 410                 415

Glu Lys Met Gln Lys Ser Glu Lys Lys Leu Leu Thr Glu Arg Ile Glu
            420                 425                 430

Lys Gly Leu Phe Lys
            435

<210> SEQ ID NO 41
<211> LENGTH: 300
<212> TYPE: PRT
<213> ORGANISM: Escherichia coli

<400> SEQUENCE: 41

Met Val Gln Ile Pro Gln Asn Pro Leu Ile Leu Val Asp Gly Ser Ser
  1               5                  10                  15

Tyr Leu Tyr Arg Ala Tyr His Ala Phe Pro Pro Leu Thr Asn Ser Ala
            20                  25                  30

Gly Glu Pro Thr Gly Ala Met Tyr Gly Val Leu Asn Met Leu Arg Ser
        35                  40                  45

Leu Ile Met Gln Tyr Lys Pro Thr His Ala Ala Val Val Phe Asp Ala
    50                  55                  60

Lys Gly Lys Thr Phe Arg Asp Glu Leu Phe Glu His Tyr Lys Ser His
65                  70                  75                  80

Arg Pro Pro Met Pro Asp Asp Leu Arg Ala Gln Ile Glu Pro Leu His
                85                  90                  95

Ala Met Val Lys Ala Met Gly Leu Pro Leu Leu Ala Val Ser Gly Val
```

```
                    100                 105                 110
Glu Ala Asp Asp Val Ile Gly Thr Leu Ala Arg Glu Ala Glu Lys Ala
            115                 120                 125

Gly Arg Pro Val Leu Ile Ser Thr Gly Asp Lys Asp Met Ala Gln Leu
        130                 135                 140

Val Thr Pro Asn Ile Thr Leu Ile Asn Thr Met Thr Asn Thr Ile Leu
145                 150                 155                 160

Gly Pro Glu Glu Val Val Asn Lys Tyr Gly Val Pro Glu Leu Ile
                165                 170                 175

Ile Asp Phe Leu Ala Leu Met Gly Asp Ser Ser Asp Asn Ile Pro Gly
            180                 185                 190

Val Pro Gly Val Gly Glu Lys Thr Ala Gln Ala Leu Leu Gln Gly Leu
        195                 200                 205

Gly Gly Leu Asp Thr Leu Tyr Ala Glu Pro Glu Lys Ile Ala Gly Leu
    210                 215                 220

Ser Phe Arg Gly Ala Lys Thr Met Ala Ala Lys Leu Glu Gln Asn Lys
225                 230                 235                 240

Glu Val Ala Tyr Leu Ser Tyr Gln Leu Ala Thr Ile Lys Thr Asp Val
                245                 250                 255

Glu Leu Glu Leu Thr Cys Glu Gln Leu Glu Val Gln Gln Pro Ala Ala
            260                 265                 270

Glu Glu Leu Leu Gly Leu Phe Lys Lys Tyr Glu Phe Lys Arg Trp Thr
        275                 280                 285

Ala Asp Val Glu Ala Gly Lys Trp Leu Gln Ala Lys
    290                 295                 300

<210> SEQ ID NO 42
<211> LENGTH: 300
<212> TYPE: PRT
<213> ORGANISM: Thermus aquaticaus

<400> SEQUENCE: 42

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175
```

```
Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
                275                 280                 285

Glu Ser Pro Lys Ala Leu Glu Glu Ala Pro Trp Pro
    290                 295                 300

<210> SEQ ID NO 43
<211> LENGTH: 318
<212> TYPE: PRT
<213> ORGANISM: Bacteriophage RM378

<400> SEQUENCE: 43

Met Lys Arg Leu Arg Asn Met Val Asn Leu Ile Asp Leu Lys Asn Gln
1               5                   10                  15

Tyr Tyr Ala Tyr Ser Phe Lys Phe Phe Asp Ser Tyr Gln Ile Ser Trp
            20                  25                  30

Asp Asn Tyr Pro His Leu Lys Glu Phe Val Ile Glu Asn Tyr Pro Gly
        35                  40                  45

Thr Tyr Phe Ser Cys Tyr Ala Pro Gly Ile Leu Tyr Lys Leu Phe Leu
    50                  55                  60

Lys Trp Lys Arg Gly Met Ile Ile Asp Asp Tyr Asp Arg His Pro Leu
65                  70                  75                  80

Arg Lys Lys Leu Leu Pro Gln Tyr Lys Glu His Arg Tyr Glu Tyr Ile
                85                  90                  95

Glu Gly Lys Tyr Gly Val Val Pro Phe Pro Gly Phe Leu Lys Tyr Leu
            100                 105                 110

Lys Phe His Phe Glu Asp Leu Arg Phe Lys Met Arg Asp Leu Gly Ile
        115                 120                 125

Thr Asp Phe Lys Tyr Ala Leu Ala Ile Ser Leu Phe Tyr Asn Arg Val
    130                 135                 140

Met Leu Arg Asp Phe Leu Lys Asn Phe Thr Cys Tyr Tyr Ile Ala Glu
145                 150                 155                 160

Tyr Glu Ala Asp Asp Val Ile Ala His Leu Ala Arg Glu Ile Ala Arg
                165                 170                 175

Ser Asn Ile Asp Val Asn Ile Val Ser Thr Asp Lys Asp Tyr Tyr Gln
            180                 185                 190

Leu Trp Asp Glu Glu Asp Ile Arg Glu Arg Val Tyr Ile Asn Ser Leu
        195                 200                 205

Ser Cys Ser Asp Val Lys Thr Pro Arg Tyr Gly Phe Leu Thr Ile Lys
    210                 215                 220

Ala Leu Leu Gly Asp Lys Ser Asp Asn Ile Pro Lys Ser Leu Glu Lys
225                 230                 235                 240

Gly Lys Gly Glu Lys Tyr Leu Glu Lys Lys Gly Phe Ala Glu Glu Asp
                245                 250                 255
```

Tyr Asp Lys Glu Leu Phe Glu Asn Asn Leu Lys Val Ile Arg Phe Gly
                260                 265                 270

Asp Glu Tyr Leu Gly Glu Arg Asp Lys Ser Phe Ile Glu Asn Phe Ser
            275                 280                 285

Thr Gly Asp Thr Leu Trp Asn Phe Tyr Glu Phe Phe Tyr Tyr Asp Pro
        290                 295                 300

Leu His Glu Leu Phe Leu Arg Asn Ile Arg Lys Arg Leu
305                 310                 315

<210> SEQ ID NO 44
<211> LENGTH: 305
<212> TYPE: PRT
<213> ORGANISM: Bacteriophage T4

<400> SEQUENCE: 44

Met Asp Leu Glu Met Met Leu Asp Glu Asp Tyr Lys Glu Gly Ile Cys
1               5                   10                  15

Leu Ile Asp Phe Ser Gln Ile Ala Leu Ser Thr Ala Leu Val Asn Phe
                20                  25                  30

Pro Asp Lys Glu Lys Ile Asn Leu Ser Met Val Arg His Leu Ile Leu
            35                  40                  45

Asn Ser Ile Lys Phe Asn Val Lys Lys Ala Lys Thr Leu Gly Tyr Thr
50                  55                  60

Lys Ile Val Leu Cys Ile Asp Asn Ala Lys Ser Gly Tyr Trp Arg Arg
65                  70                  75                  80

Asp Phe Ala Tyr Tyr Lys Lys Asn Arg Gly Lys Ala Arg Glu Glu
                85                  90                  95

Ser Thr Trp Asp Trp Glu Gly Tyr Phe Glu Ser Ser His Lys Val Ile
                100                 105                 110

Asp Glu Leu Lys Ala Tyr Met Pro Tyr Ile Val Met Asp Ile Asp Lys
            115                 120                 125

Tyr Glu Ala Asp Asp His Ile Ala Val Leu Val Lys Lys Phe Ser Leu
130                 135                 140

Glu Gly His Lys Ile Leu Ile Ile Ser Ser Asp Gly Asp Phe Thr Gln
145                 150                 155                 160

Leu His Lys Tyr Pro Asn Val Lys Gln Trp Ser Pro Met His Lys Lys
                165                 170                 175

Trp Val Lys Ile Lys Ser Gly Ser Ala Glu Ile Asp Cys Met Thr Lys
            180                 185                 190

Ile Leu Lys Gly Asp Lys Lys Asp Asn Val Ala Ser Val Lys Val Arg
            195                 200                 205

Ser Asp Phe Trp Phe Thr Arg Val Glu Gly Arg Thr Pro Ser Met
210                 215                 220

Lys Thr Ser Ile Val Glu Ala Ile Ala Asn Asp Arg Glu Gln Ala Lys
225                 230                 235                 240

Val Leu Leu Thr Glu Ser Glu Tyr Asn Arg Tyr Lys Glu Asn Leu Val
                245                 250                 255

Leu Ile Asp Phe Asp Tyr Ile Pro Asp Asn Ile Ala Ser Asn Ile Val
            260                 265                 270

Asn Tyr Tyr Asn Ser Tyr Lys Leu Pro Pro Arg Gly Lys Ile Tyr Ser
                275                 280                 285

Tyr Phe Val Lys Ala Gly Leu Ser Lys Leu Thr Asn Ser Ile Asn Glu
    290                 295                 300

Phe

-continued

<210> SEQ ID NO 45
<211> LENGTH: 300
<212> TYPE: PRT
<213> ORGANISM: Bacteriophage T7

<400> SEQUENCE: 45

Met Ala Leu Leu Asp Leu Lys Gln Phe Tyr Glu Leu Arg Glu Gly Cys
1               5                   10                  15

Asp Asp Lys Gly Ile Leu Val Met Asp Gly Asp Trp Leu Val Phe Gln
            20                  25                  30

Ala Met Ser Ala Ala Glu Phe Asp Ala Ser Trp Glu Glu Ile Trp
        35                  40                  45

His Arg Cys Cys Asp His Ala Lys Ala Arg Gln Ile Leu Glu Asp Ser
    50                  55                  60

Ile Lys Ser Tyr Glu Thr Arg Lys Lys Ala Trp Ala Gly Ala Pro Ile
65                  70                  75                  80

Val Leu Ala Phe Thr Asp Ser Val Asn Trp Arg Lys Glu Leu Val Asp
                85                  90                  95

Pro Asn Tyr Lys Ala Asn Arg Lys Ala Val Lys Lys Pro Val Gly Tyr
            100                 105                 110

Phe Glu Phe Leu Asp Ala Leu Phe Glu Arg Glu Phe Tyr Cys Ile
        115                 120                 125

Arg Glu Pro Met Leu Glu Gly Asp Asp Val Met Gly Val Ile Ala Ser
130                 135                 140

Asn Pro Ser Ala Phe Gly Ala Arg Lys Ala Val Ile Ile Ser Cys Asp
145                 150                 155                 160

Lys Asp Phe Lys Thr Ile Pro Asn Cys Asp Phe Leu Trp Cys Thr Thr
                165                 170                 175

Gly Asn Ile Leu Thr Gln Thr Glu Glu Ser Ala Asp Trp Trp His Leu
            180                 185                 190

Phe Gln Thr Ile Lys Gly Asp Ile Thr Asp Gly Tyr Ser Gly Ile Ala
        195                 200                 205

Gly Trp Gly Asp Thr Ala Glu Asp Phe Leu Asn Asn Pro Phe Ile Thr
210                 215                 220

Glu Pro Lys Thr Ser Val Leu Lys Ser Gly Lys Asn Lys Gly Gln Glu
225                 230                 235                 240

Val Thr Lys Trp Val Lys Arg Asp Pro Glu Pro His Glu Thr Leu Trp
                245                 250                 255

Asp Cys Ile Lys Ser Ile Gly Ala Lys Ala Gly Met Thr Glu Glu Asp
            260                 265                 270

Ile Ile Lys Gln Gly Gln Met Ala Arg Ile Leu Arg Phe Asn Glu Tyr
        275                 280                 285

Asn Phe Ile Asp Lys Glu Ile Tyr Leu Trp Arg Pro
    290                 295                 300

<210> SEQ ID NO 46
<211> LENGTH: 287
<212> TYPE: PRT
<213> ORGANISM: Escherichia coli

<400> SEQUENCE: 46

Val Leu Asp Ala Thr Val Ala Arg Ile Glu Gln Leu Phe Gln Gln Pro
1               5                   10                  15

His Asp Gly Val Thr Gly Val Asn Thr Gly Tyr Asp Asp Leu Asn Lys

-continued

```
            20                  25                  30
Lys Thr Ala Gly Leu Gln Pro Ser Asp Leu Ile Ile Val Ala Ala Arg
            35                  40                  45

Pro Ser Met Gly Lys Thr Thr Phe Ala Met Asn Leu Val Glu Asn Ala
 50                  55                  60

Ala Met Leu Gln Asp Lys Pro Val Leu Ile Phe Ser Leu Glu Met Pro
65                  70                  75                  80

Ser Glu Gln Ile Met Met Arg Ser Leu Ala Ser Leu Ser Arg Val Asp
                    85                  90                  95

Gln Thr Lys Ile Arg Thr Gly Gln Leu Asp Asp Glu Asp Trp Ala Arg
                100                 105                 110

Ile Ser Gly Thr Met Gly Ile Leu Leu Glu Lys Arg Asn Ile Tyr Ile
                115                 120                 125

Asp Asp Ser Ser Gly Leu Thr Pro Thr Glu Val Arg Ser Arg Ala Arg
            130                 135                 140

Arg Ile Ala Arg Glu His Gly Gly Ile Gly Leu Ile Met Ile Asp Tyr
145                 150                 155                 160

Leu Gln Leu Met Arg Val Pro Ala Leu Ser Asp Asn Arg Thr Leu Glu
                165                 170                 175

Ile Ala Glu Ile Ser Arg Ser Leu Lys Ala Leu Ala Lys Glu Leu Asn
                180                 185                 190

Val Pro Val Val Ala Leu Ser Gln Leu Asn Arg Ser Leu Glu Gln Arg
                195                 200                 205

Ala Asp Lys Arg Pro Val Asn Ser Asp Leu Arg Glu Ser Gly Ser Ile
            210                 215                 220

Glu Gln Asp Ala Asp Leu Ile Met Phe Ile Tyr Arg Asp Glu Val Tyr
225                 230                 235                 240

His Glu Asn Ser Asp Leu Lys Gly Ile Ala Glu Ile Ile Gly Lys
                245                 250                 255

Gln Arg Asn Gly Pro Ile Gly Thr Val Arg Leu Thr Phe Asn Gly Gln
                260                 265                 270

Trp Ser Arg Phe Asp Asn Tyr Ala Gly Pro Gln Tyr Asp Asp Glu
            275                 280                 285

<210> SEQ ID NO 47
<211> LENGTH: 291
<212> TYPE: PRT
<213> ORGANISM: Haemophilus influenza

<400> SEQUENCE: 47

Val Leu Glu Ser Thr Ile Glu Lys Ile Asp Ile Leu Ser Lys Leu Glu
 1                   5                  10                  15

Asn His Ser Gly Val Thr Gly Val Thr Thr Gly Phe Thr Asp Leu Asp
                    20                  25                  30

Lys Lys Thr Ala Gly Leu Gln Pro Ser Asp Leu Ile Ile Val Ala Ala
            35                  40                  45

Arg Pro Ser Met Gly Lys Thr Thr Phe Ala Met Asn Leu Cys Glu Asn
 50                  55                  60

Ala Ala Met Ala Ser Glu Lys Pro Val Leu Val Phe Ser Leu Glu Met
65                  70                  75                  80

Pro Ala Glu Gln Ile Met Met Arg Met Ile Ala Ser Leu Ala Arg Val
                    85                  90                  95

Asp Gln Thr Lys Ile Arg Thr Gly Gln Asn Leu Asp Glu Ile Glu Trp
                100                 105                 110
```

-continued

```
Asn Lys Ile Ala Ser Val Val Gly Met Phe Lys Gln Lys Asn Asn Leu
        115                 120                 125

Phe Ile Asp Asp Ser Ser Gly Leu Thr Pro Thr Asp Val Arg Ser Arg
    130                 135                 140

Ala Arg Arg Val Tyr Arg Glu Asn Gly Gly Leu Ser Met Ile Met Val
145                 150                 155                 160

Asp Tyr Leu Gln Leu Met Arg Ala Pro Ala Phe Ser Asp Asn Arg Thr
                165                 170                 175

Leu Glu Ile Ala Glu Ile Ser Arg Ser Leu Lys Ala Leu Ala Lys Glu
            180                 185                 190

Leu Gln Val Pro Val Ala Leu Ser Gln Leu Asn Arg Thr Leu Glu
        195                 200                 205

Gln Arg Gly Asp Lys Arg Pro Val Asn Ser Asp Leu Arg Glu Ser Gly
    210                 215                 220

Ser Ile Glu Gln Asp Ala Asp Leu Ile Met Phe Ile Tyr Arg Asp Glu
225                 230                 235                 240

Val Tyr Asn Asp Asn Ser Glu Asp Lys Gly Val Ala Glu Ile Ile Ile
                245                 250                 255

Gly Lys Gln Arg Asn Gly Pro Ile Gly Arg Val Arg Leu Lys Phe Asn
            260                 265                 270

Gly Gln Phe Ser Arg Phe Asp Asn Leu Ala Glu Gln Arg Glu Tyr Arg
        275                 280                 285

Asp Asp Tyr
    290

<210> SEQ ID NO 48
<211> LENGTH: 287
<212> TYPE: PRT
<213> ORGANISM: Chlamydomonas trachomatis

<400> SEQUENCE: 48

Ala Leu Gln Glu Arg Gln Glu Ala Phe Gln Ala Ser Ala His Asp Ser
1               5                   10                  15

Ser Ser Pro Met Leu Ser Gly Phe Pro Thr His Phe Leu Asp Leu Asp
            20                  25                  30

Lys Met Ile Ser Gly Phe Ser Pro Ser Asn Leu Ile Ile Leu Ala Ala
        35                  40                  45

Arg Pro Ala Met Gly Lys Thr Ala Leu Ala Leu Asn Ile Val Glu Asn
    50                  55                  60

Phe Cys Phe Asp Ser Arg Leu Pro Val Gly Ile Phe Ser Leu Glu Met
65                  70                  75                  80

Thr Val Asp Gln Leu Ile His Arg Ile Ile Cys Ser Arg Ser Glu Val
                85                  90                  95

Glu Ala Lys Lys Ile Ser Val Gly Asp Ile Ser Gly Arg Asp Phe Gln
            100                 105                 110

Arg Val Val Ser Val Val Arg Glu Met Glu Glu His Thr Leu Leu Ile
        115                 120                 125

Asp Asp Tyr Pro Gly Leu Lys Ile Thr Asp Leu Arg Ala Arg Ala Arg
    130                 135                 140

Arg Met Lys Glu Ser Tyr Asp Ile Gln Phe Leu Val Ile Asp Tyr Leu
145                 150                 155                 160

Gln Leu Ile Ser Ser Ser Gly Asn Leu Arg Asn Ser Asp Ser Arg Asn
                165                 170                 175

Gln Glu Ile Ser Glu Ile Ser Arg Met Leu Lys Asn Leu Ala Arg Glu
            180                 185                 190
```

```
Leu Asn Ile Pro Ile Leu Cys Leu Ser Gln Leu Ser Arg Lys Val Glu
        195                 200                 205

Asp Arg Ala Asn His Arg Pro Leu Met Ser Asp Leu Arg Glu Ser Gly
        210                 215                 220

Ser Ile Glu Gln Asp Ala Asp Gln Ile Met Phe Leu Leu Arg Arg Glu
225                 230                 235                 240

Tyr Tyr Asp Pro Asn Asp Lys Pro Gly Thr Ala Glu Leu Ile Val Ala
            245                 250                 255

Lys Asn Arg His Gly Ser Ile Gly Ser Val Gln Leu Val Phe Glu Lys
        260                 265                 270

Asp Phe Ala Arg Phe Arg Asn Tyr Ala Gly Cys Glu Phe Pro Gly
        275                 280                 285

<210> SEQ ID NO 49
<211> LENGTH: 290
<212> TYPE: PRT
<213> ORGANISM: Bacillus stearothermophilus

<400> SEQUENCE: 49

Ile Leu Val Gln Thr Tyr Asp Asn Ile Glu Met Leu His Asn Arg Asp
1               5                   10                  15

Gly Glu Ile Thr Gly Ile Pro Thr Gly Phe Thr Glu Leu Asp Arg Met
            20                  25                  30

Thr Ser Gly Phe Gln Arg Ser Asp Leu Ile Ile Val Ala Ala Arg Pro
        35                  40                  45

Ser Val Gly Lys Thr Ala Phe Ala Leu Asn Ile Ala Gln Asn Val Ala
    50                  55                  60

Thr Lys Thr Asn Glu Asn Val Ala Ile Phe Ser Leu Glu Met Ser Ala
65                  70                  75                  80

Gln Gln Leu Val Met Arg Met Leu Cys Ala Glu Gly Asn Ile Asn Ala
                85                  90                  95

Gln Asn Leu Arg Thr Gly Lys Leu Thr Pro Glu Asp Trp Gly Lys Leu
            100                 105                 110

Thr Met Ala Met Gly Ser Leu Ser Asn Ala Gly Ile Tyr Ile Asp Asp
        115                 120                 125

Thr Pro Ser Ile Arg Val Ser Asp Ile Arg Ala Lys Cys Arg Arg Leu
    130                 135                 140

Lys Gln Glu Ser Gly Leu Gly Met Ile Val Ile Asp Tyr Leu Gln Leu
145                 150                 155                 160

Ile Gln Gly Ser Gly Arg Ser Lys Glu Asn Arg Gln Gln Glu Val Ser
                165                 170                 175

Glu Ile Ser Arg Ser Leu Lys Ala Leu Ala Arg Glu Leu Glu Val Pro
            180                 185                 190

Val Ile Ala Leu Ser Gln Leu Ser Arg Ser Val Glu Gln Arg Gln Asp
        195                 200                 205

Lys Arg Pro Met Met Ser Asp Ile Arg Glu Ser Gly Ser Ile Glu Gln
    210                 215                 220

Asp Ala Asp Ile Val Ala Phe Leu Tyr Arg Asp Tyr Tyr Asn Lys
225                 230                 235                 240

Asp Ser Glu Asn Lys Asn Ile Ile Glu Ile Ile Ala Lys Gln Arg
            245                 250                 255

Asn Gly Pro Val Gly Thr Val Gln Leu Ala Phe Ile Lys Glu Tyr Asn
        260                 265                 270

Lys Phe Val Asn Leu Glu Arg Arg Phe Asp Glu Ala Gln Ile Pro Pro
```

Gly Ala
    290

<210> SEQ ID NO 50
<211> LENGTH: 332
<212> TYPE: PRT
<213> ORGANISM: Halobacter pylori

<400> SEQUENCE: 50

Val Leu Glu Ser Ala Met Asp Leu Ile Thr Glu Asn Gln Arg Lys Gly
 1               5                  10                  15

Ser Leu Glu Val Thr Gly Ile Pro Thr Gly Phe Val Gln Leu Asp Asn
            20                  25                  30

Tyr Thr Ser Gly Phe Asn Lys Gly Ser Leu Val Ile Gly Ala Arg
        35                  40                  45

Pro Ser Met Gly Lys Thr Ser Leu Met Met Asn Met Val Leu Ser Ala
    50                  55                  60

Leu Asn Asp Asp Arg Gly Val Ala Val Phe Ser Leu Glu Met Ser Ala
65                  70                  75                  80

Glu Gln Leu Ala Leu Arg Ala Leu Ser Asp Leu Thr Ser Ile Asn Met
                85                  90                  95

His Asp Leu Glu Ser Gly Arg Leu Asp Asp Gln Trp Glu Asn Leu
            100                 105                 110

Ala Lys Cys Phe Asp His Leu Ser Gln Lys Lys Leu Phe Phe Tyr Asp
        115                 120                 125

Lys Ser Tyr Val Arg Ile Glu Gln Ile Arg Leu Gln Leu Arg Lys Leu
    130                 135                 140

Lys Ser Gln His Lys Glu Leu Gly Ile Ala Phe Ile Asp Tyr Leu Gln
145                 150                 155                 160

Leu Met Ser Gly Ser Lys Ala Thr Lys Glu Arg His Glu Gln Ile Ala
                165                 170                 175

Glu Ile Ser Arg Glu Leu Lys Thr Leu Ala Arg Glu Leu Glu Ile Pro
            180                 185                 190

Ile Ile Ala Leu Val Gln Leu Asn Arg Ser Leu Glu Asn Arg Asp Asp
        195                 200                 205

Lys Arg Pro Ile Leu Ser Asp Ile Lys Asp Ser Gly Gly Ile Glu Gln
    210                 215                 220

Asp Ala Asp Ile Val Leu Phe Leu Tyr Arg Gly Tyr Ile Tyr Gln Met
225                 230                 235                 240

Arg Ala Glu Asp Asn Lys Ile Asp Lys Leu Lys Lys Glu Gly Lys Ile
                245                 250                 255

Glu Glu Ala Gln Glu Leu Tyr Leu Lys Val Asn Glu Glu Arg Arg Ile
            260                 265                 270

His Lys Gln Asn Gly Ser Ile Glu Glu Ala Glu Ile Ile Val Ala Lys
        275                 280                 285

Asn Arg Asn Gly Ala Thr Gly Thr Val Tyr Thr Arg Phe Asn Ala Pro
    290                 295                 300

Phe Thr Arg Tyr Glu Asp Met Pro Ile Asp Ser His Leu Glu Glu Gly
305                 310                 315                 320

Gln Glu Thr Lys Val Asp Tyr Asp Ile Val Thr Thr
                325                 330

<210> SEQ ID NO 51
<211> LENGTH: 295

```
<212> TYPE: PRT
<213> ORGANISM: Mycolplasma genitalium

<400> SEQUENCE: 51

Glu Ile Ala Asn Gln Glu Ala Leu Ile Lys Lys Val His Arg Gly
 1               5                  10                  15

Glu Leu Ile Ile Ser Gly Leu Ser Ser Gly Phe Leu Lys Leu Asp Gln
             20                  25                  30

Leu Thr Ser Gly Trp Lys Pro Gly Glu Leu Ile Val Ile Ala Ala Arg
         35                  40                  45

Pro Gly Arg Gly Lys Thr Ala Leu Leu Ile Asn Phe Met Ala Ser Ala
     50                  55                  60

Ala Lys Gln Ile Asp Pro Lys Thr Asp Val Val Leu Phe Phe Ser Leu
 65                  70                  75                  80

Glu Met Arg Asn Arg Glu Ile Tyr Gln Arg His Leu Met His Glu Ser
                 85                  90                  95

Gln Thr Ser Tyr Thr Leu Thr Asn Arg Gln Arg Ile Asn Asn Val Phe
            100                 105                 110

Glu Glu Leu Met Glu Ala Ser Ser Arg Ile Lys Asn Leu Pro Ile Lys
        115                 120                 125

Leu Phe Asp Tyr Ser Ser Leu Thr Leu Gln Glu Ile Arg Asn Gln Ile
    130                 135                 140

Thr Glu Val Ser Lys Thr Ser Asn Val Arg Leu Val Ile Ile Asp Tyr
145                 150                 155                 160

Leu Gln Leu Val Asn Ala Leu Lys Asn Asn Tyr Gly Leu Thr Arg Gln
                165                 170                 175

Gln Glu Val Thr Met Ile Ser Gln Ser Leu Lys Ala Phe Ala Lys Glu
            180                 185                 190

Phe Asn Thr Pro Ile Ile Ala Ala Gln Leu Ser Arg Arg Ile Glu
        195                 200                 205

Glu Arg Lys Asp Ser Arg Pro Ile Leu Ser Asp Leu Arg Glu Ser Gly
    210                 215                 220

Ser Ile Glu Gln Asp Ala Asp Met Val Leu Phe Ile His Arg Thr Asn
225                 230                 235                 240

Asp Asp Lys Lys Glu Gln Glu Glu Asn Thr Asn Leu Phe Glu Val
                245                 250                 255

Glu Leu Ile Leu Glu Lys Asn Arg Asn Gly Pro Asn Gly Lys Val Lys
            260                 265                 270

Leu Asn Phe Arg Ser Asp Thr Ser Ser Phe Ile Ser Gln Tyr Ser Pro
        275                 280                 285

Ser Phe Asp Asp Gln Tyr Ser
    290                 295

<210> SEQ ID NO 52
<211> LENGTH: 283
<212> TYPE: PRT
<213> ORGANISM: Borrelia burgdorferi

<400> SEQUENCE: 52

Ile Ala Glu Arg Val His Asn Glu Ile Tyr Glu Arg Ser Met Lys Lys
 1               5                  10                  15

Lys Glu Ala Asn Phe Gly Ile Pro Ser Gly Phe Arg Lys Val Asp Ser
            20                  25                  30

Leu Ile Gly Gly Phe Arg Asn Ser Asp Phe Ile Ile Val Gly Ala Arg
        35                  40                  45
```

-continued

```
Pro Ser Ile Gly Lys Thr Ala Phe Ala Leu Asn Ile Ala Ser Tyr Ile
 50                  55                  60

Ala Leu Arg Lys Glu Glu Lys Lys Val Gly Phe Phe Ser Leu Glu
 65                  70                  75                  80

Met Thr Ala Asp Ala Leu Ile Lys Arg Ile Ile Ser Ser Gln Ser Cys
                 85                  90                  95

Ile Asp Ser Phe Lys Val Gln Asn Ser Ile Leu Ser Gly Gln Glu Ile
                100                 105                 110

Lys Ser Leu Asn Asp Ile Ile Asn Glu Ile Ser Asp Ser Glu Leu Tyr
                115                 120                 125

Ile Glu Asp Thr Pro Asn Ile Ser Leu Leu Thr Leu Ala Thr Gln Ala
130                 135                 140

Arg Lys Leu Lys Arg Phe Tyr Gly Ile Asp Ile Phe Val Asp Tyr
145                 150                 155                 160

Ile Ser Leu Ile Ser Phe Glu Thr Lys Asn Leu Pro Arg His Glu Gln
                165                 170                 175

Val Ala Ser Ile Ser Lys Ser Leu Lys Glu Leu Ala Arg Glu Leu Glu
                180                 185                 190

Ile Pro Ile Val Ala Leu Ser Gln Leu Thr Arg Asp Thr Glu Gly Arg
                195                 200                 205

Glu Pro Asn Leu Ala Ser Leu Arg Glu Ser Gly Ala Leu Glu Gln Asp
210                 215                 220

Ala Asp Ile Val Ile Leu Leu His Arg Asp Lys Asp Phe Lys Phe Glu
225                 230                 235                 240

Ser Ser Ala Glu Ile Glu Pro Ile Glu Thr Lys Val Ile Val Ala Lys
                245                 250                 255

His Arg Asn Gly Pro Thr Gly Arg Ala Asp Ile Leu Phe Leu Pro His
                260                 265                 270

Ile Thr Lys Phe Val Asn Lys Asp His Gln Tyr
                275                 280
```

<210> SEQ ID NO 53
<211> LENGTH: 327
<212> TYPE: PRT
<213> ORGANISM: Bacteriophage T4

<400> SEQUENCE: 53

```
Tyr Val Gly His Asp Trp Met Asp Asp Tyr Glu Ala Arg Trp Leu Ser
  1               5                  10                  15

Tyr Met Asn Lys Ala Arg Lys Val Pro Phe Lys Leu Arg Ile Leu Asn
                 20                  25                  30

Lys Ile Thr Lys Gly Gly Ala Glu Thr Gly Thr Leu Asn Val Leu Met
                 35                  40                  45

Ala Gly Val Asn Val Gly Lys Ser Leu Gly Leu Cys Ser Leu Ala Ala
 50                  55                  60

Asp Tyr Leu Gln Leu Gly His Asn Val Leu Tyr Ile Ser Met Glu Met
 65                  70                  75                  80

Ala Glu Glu Val Cys Ala Lys Arg Ile Asp Ala Asn Met Leu Asp Val
                 85                  90                  95

Ser Leu Asp Asp Ile Asp Asp Gly His Ile Ser Tyr Ala Glu Tyr Lys
                100                 105                 110

Gly Lys Met Glu Lys Trp Arg Glu Lys Ser Thr Leu Gly Arg Leu Ile
                115                 120                 125

Val Lys Gln Tyr Pro Thr Gly Gly Ala Asp Ala Asn Thr Phe Arg Ser
130                 135                 140
```

-continued

```
Leu Leu Asn Glu Leu Lys Leu Lys Lys Asn Phe Val Pro Thr Ile Ile
145                 150                 155                 160

Ile Val Asp Tyr Leu Gly Ile Cys Lys Ser Cys Arg Ile Arg Val Tyr
                165                 170                 175

Ser Glu Asn Ser Tyr Thr Thr Val Lys Ala Ile Ala Glu Glu Leu Arg
            180                 185                 190

Ala Leu Ala Val Glu Thr Glu Thr Val Leu Trp Thr Ala Ala Gln Val
        195                 200                 205

Gly Lys Gln Ala Trp Asp Ser Ser Asp Val Asn Met Ser Asp Ile Ala
    210                 215                 220

Glu Ser Ala Gly Leu Pro Ala Thr Ala Asp Phe Met Leu Ala Val Ile
225                 230                 235                 240

Glu Thr Glu Glu Leu Ala Ala Ala Glu Gln Gln Leu Ile Lys Gln Ile
                245                 250                 255

Lys Ser Arg Tyr Gly Asp Lys Asn Lys Trp Asn Lys Phe Leu Met Gly
                260                 265                 270

Val Gln Lys Gly Asn Gln Lys Trp Val Glu Ile Glu Gln Asp Ser Thr
            275                 280                 285

Pro Thr Glu Val Asn Glu Val Ala Gly Ser Gln Gln Ile Gln Ala Glu
        290                 295                 300

Gln Asn Arg Tyr Gln Arg Asn Glu Ser Thr Arg Ala Gln Leu Asp Ala
305                 310                 315                 320

Leu Ala Asn Glu Leu Lys Phe
                325

<210> SEQ ID NO 54
<211> LENGTH: 302
<212> TYPE: PRT
<213> ORGANISM: Bacteriophage T7

<400> SEQUENCE: 54

Val Val Ser Ala Leu Ser Leu Arg Glu Arg Ile Arg Glu His Leu Ser
 1               5                  10                  15

Ser Glu Glu Ser Val Gly Leu Leu Phe Ser Gly Cys Thr Gly Ile Asn
            20                  25                  30

Asp Lys Thr Leu Gly Ala Arg Gly Gly Glu Val Ile Met Val Thr Ser
        35                  40                  45

Gly Ser Gly Met Gly Lys Ser Thr Phe Val Arg Gln Gln Ala Leu Gln
    50                  55                  60

Trp Gly Thr Ala Met Gly Lys Lys Val Gly Leu Ala Met Leu Glu Glu
65                  70                  75                  80

Ser Val Glu Glu Thr Ala Glu Asp Leu Ile Gly Leu His Asn Arg Val
                85                  90                  95

Arg Leu Arg Gln Ser Asp Ser Leu Lys Arg Glu Ile Ile Glu Asn Gly
            100                 105                 110

Lys Phe Asp Gln Trp Phe Asp Glu Leu Phe Gly Asn Asp Thr Phe His
        115                 120                 125

Leu Tyr Asp Ser Phe Ala Glu Ala Thr Asp Arg Leu Leu Ala Lys
    130                 135                 140

Leu Ala Tyr Met Arg Ser Gly Leu Gly Cys Asp Val Ile Ile Leu Asp
145                 150                 155                 160

His Ile Ser Ile Val Val Ser Ala Ser Gly Glu Ser Asp Glu Arg Lys
                165                 170                 175

Met Ile Asp Asn Leu Met Thr Lys Leu Lys Gly Phe Ala Lys Ser Thr
```

```
                  180                 185                 190
Gly Val Val Leu Val Ile Cys His Leu Lys Asn Pro Asp Lys Gly
            195                 200                 205
Lys Ala His Glu Glu Gly Arg Pro Val Ser Ile Thr Asp Leu Arg Gly
210                 215                 220
Ser Gly Ala Leu Arg Gln Leu Ser Asp Thr Ile Ile Ala Leu Glu Arg
225                 230                 235                 240
Asn Gln Gln Gly Asp Met Pro Asn Leu Val Leu Val Arg Ile Leu Lys
                245                 250                 255
Cys Arg Phe Thr Gly Asp Thr Gly Ile Ala Gly Tyr Met Glu Tyr Asn
            260                 265                 270
Lys Glu Thr Gly Trp Leu Glu Pro Ser Ser Tyr Ser Gly Glu Glu Glu
                275                 280                 285
Ser His Ser Glu Ser Thr Asp Trp Ser Asn Asp Thr Asp Phe
            290                 295                 300

<210> SEQ ID NO 55
<211> LENGTH: 270
<212> TYPE: PRT
<213> ORGANISM: Bacteriophage RM378

<400> SEQUENCE: 55

Val Ser Leu Val Glu Glu Phe Asp Leu Ala Thr Ser Glu Phe Asn Glu
1               5                   10                  15
Leu Phe Val Lys Glu Glu Arg Ile Pro Thr Pro Trp Glu Ser Val Asn
                20                  25                  30
Lys Asn Met Ala Gly Gly Leu Gly Arg Gly Glu Leu Gly Ile Val Met
            35                  40                  45
Leu Pro Ser Gly Trp Gly Lys Ser Trp Phe Leu Val Ser Leu Gly Leu
        50                  55                  60
His Ala Phe Arg Thr Gly Lys Arg Val Ile Tyr Phe Thr Leu Glu Leu
65                  70                  75                  80
Asp Gln Lys Tyr Val Met Lys Arg Phe Leu Lys Met Phe Ala Pro Tyr
                85                  90                  95
Cys Lys Gly Arg Ala Ser Ser Tyr Arg Asp Val Tyr Gln Ile Met Lys
            100                 105                 110
Glu Leu Met Phe Ser Gln Asp Asn Leu Leu Lys Ile Val Phe Cys Asn
        115                 120                 125
Ala Met Glu Asp Ile Glu His Tyr Ile Ala Leu Tyr Asn Pro Asp Val
        130                 135                 140
Val Leu Ile Asp Tyr Ala Asp Leu Ile Tyr Asp Val Glu Thr Asp Lys
145                 150                 155                 160
Glu Lys Asn Tyr Leu Leu Leu Gln Lys Ile Tyr Arg Lys Leu Arg Leu
                165                 170                 175
Ile Ala Lys Val Tyr Asn Thr Ala Val Trp Ser Ala Ser Gln Leu Asn
            180                 185                 190
Arg Gly Ser Leu Ser Lys Gln Ala Asp Val Asp Phe Ile Glu Lys Tyr
        195                 200                 205
Ile Ala Asp Ser Phe Ala Lys Val Val Glu Ile Asp Phe Gly Met Ala
        210                 215                 220
Phe Ile Pro Asp Ser Glu Asn Ser Thr Pro Asp Ile His Val Gly Phe
225                 230                 235                 240
Gly Lys Ile Phe Lys Asn Arg Met Gly Ala Val Arg Lys Leu Glu Tyr
                245                 250                 255
```

-continued

```
             Thr Ile Asn Phe Glu Asn Tyr Thr Val Asp Val Ala Val Lys
                         260                 265                 270

<210> SEQ ID NO 56
<211> LENGTH: 1197
<212> TYPE: DNA
<213> ORGANISM: Bacteriophage RM378
<220> FEATURE:
<221> NAME/KEY: CDS
<222> LOCATION: (112)...(1158)

<400> SEQUENCE: 56
attttctgtt ttttcacagg caagtattcg acatgctcga aacccgcgaa gcttattatc         60
agttgcttca atcgttaaac gatttcctcg aagaagacct gaaggagaat t atg aag        117
                                                         Met Lys
                                                           1 atc acg cta agc gca agc gta tac ccc cga tcg atg aaa att tac gga         165
Ile Thr Leu Ser Ala Ser Val Tyr Pro Arg Ser Met Lys Ile Tyr Gly
        5                  10                  15 gtg gag cta atc gag ggg aaa aaa cac tta ttt caa tca ccc gta ccc         213
Val Glu Leu Ile Glu Gly Lys Lys His Leu Phe Gln Ser Pro Val Pro
 20                  25                  30 cca cat ttg aag cgc atc gct cag cag aat cga ggg aag att gag gct         261
Pro His Leu Lys Arg Ile Ala Gln Gln Asn Arg Gly Lys Ile Glu Ala
 35                  40                  45                  50 gag gct ata tcc tat tac atc aga gaa caa aaa agc cac atc acg ccg         309
Glu Ala Ile Ser Tyr Tyr Ile Arg Glu Gln Lys Ser His Ile Thr Pro
                 55                  60                  65 gaa gct ttg tct cag tgc gtc ttt atc gat att gag acg att tcc ccg         357
Glu Ala Leu Ser Gln Cys Val Phe Ile Asp Ile Glu Thr Ile Ser Pro
             70                  75                  80 aaa aaa agc ttt ccc gac ccg tgg aga gac cca gtt tat tcc att tcc         405
Lys Lys Ser Phe Pro Asp Pro Trp Arg Asp Pro Val Tyr Ser Ile Ser
         85                  90                  95 atc aaa ccg tat gga aaa ccg gtg gtg gta gtg ctt ctc ctt atc acc         453
Ile Lys Pro Tyr Gly Lys Pro Val Val Val Val Leu Leu Leu Ile Thr
    100                 105                 110 aac ccg gag gct cat atc gat aac ttt aac aaa ttt acc acc agc gta         501
Asn Pro Glu Ala His Ile Asp Asn Phe Asn Lys Phe Thr Thr Ser Val
115                 120                 125                 130 ggg gat aac aca ttt gaa att cat tac aga aca ttc ctt tcg gaa aaa         549
Gly Asp Asn Thr Phe Glu Ile His Tyr Arg Thr Phe Leu Ser Glu Lys
                135                 140                 145 aga ttg ctc gag tat ttc tgg aat gtg ctg aaa cca aaa ttt act ttc         597
Arg Leu Leu Glu Tyr Phe Trp Asn Val Leu Lys Pro Lys Phe Thr Phe
            150                 155                 160 atg ctc gca tgg aac ggt tat cag ttc gat tat ccc tac ctg ctc att         645
Met Leu Ala Trp Asn Gly Tyr Gln Phe Asp Tyr Pro Tyr Leu Leu Ile
        165                 170                 175 cgt agt cat atc cat gag gtg aat gtc att agt gat aag ttg ctt ccg         693
Arg Ser His Ile His Glu Val Asn Val Ile Ser Asp Lys Leu Leu Pro
    180                 185                 190 gac tgg aag ctg gtg cgg aaa att tcc gat cga aac cta cca ttc tat         741
Asp Trp Lys Leu Val Arg Lys Ile Ser Asp Arg Asn Leu Pro Phe Tyr
195                 200                 205                 210 ttc aat ccc cgt acc cct gta gaa ttt gtg ttt ttt gat tac atg cgg         789
Phe Asn Pro Arg Thr Pro Val Glu Phe Val Phe Phe Asp Tyr Met Arg
                215                 220                 225 ctt tat cgc tcc ttt gtg gca tac aaa gag ttg gag tcc tac cgg ctc         837
Leu Tyr Arg Ser Phe Val Ala Tyr Lys Glu Leu Glu Ser Tyr Arg Leu
            230                 235                 240
```

```
gac tat att gcg cga gag gaa ata gga gaa ggt aag gtg gat ttc gac       885
Asp Tyr Ile Ala Arg Glu Glu Ile Gly Glu Gly Lys Val Asp Phe Asp
        245                 250                 255 gta aga ttc tat cat gag att cct gtc tac ccg gat aaa aag ttg gtg       933
Val Arg Phe Tyr His Glu Ile Pro Val Tyr Pro Asp Lys Lys Leu Val
260                 265                 270 gaa tac aac gcc gta gac gcc att ttg atg gaa gaa atc gaa aat aaa       981
Glu Tyr Asn Ala Val Asp Ala Ile Leu Met Glu Glu Ile Glu Asn Lys
275                 280                 285                 290 aac cat att ctc ccg acg ctg ttt gaa att gca aga ctt tca aat ctg      1029
Asn His Ile Leu Pro Thr Leu Phe Glu Ile Ala Arg Leu Ser Asn Leu
            295                 300                 305 act ccc gca ctg gca ttg aac gct tcc aat att ctt atc gga aat gtt      1077
Thr Pro Ala Leu Ala Leu Asn Ala Ser Asn Ile Leu Ile Gly Asn Val
        310                 315                 320 aca gga aaa ctt ggt gtc aaa ttc gtt gat tac atc aag aaa atc gac      1125
Thr Gly Lys Leu Gly Val Lys Phe Val Asp Tyr Ile Lys Lys Ile Asp
    325                 330                 335 acc att aat aca atg ttc aaa aaa ata cct gag taaactatga atatgcagac    1178
Thr Ile Asn Thr Met Phe Lys Lys Ile Pro Glu
340                 345 cattgacgaa acgctttat                                                  1197

<210> SEQ ID NO 57
<211> LENGTH: 349
<212> TYPE: PRT
<213> ORGANISM: Bacteriophage RM378

<400> SEQUENCE: 57

Met Lys Ile Thr Leu Ser Ala Ser Val Tyr Pro Arg Ser Met Lys Ile
1               5                   10                  15

Tyr Gly Val Glu Leu Ile Glu Gly Lys Lys His Leu Phe Gln Ser Pro
            20                  25                  30

Val Pro Pro His Leu Lys Arg Ile Ala Gln Gln Asn Arg Gly Lys Ile
        35                  40                  45

Glu Ala Glu Ala Ile Ser Tyr Tyr Ile Arg Glu Gln Lys Ser His Ile
    50                  55                  60

Thr Pro Glu Ala Leu Ser Gln Cys Val Phe Ile Asp Ile Glu Thr Ile
65                  70                  75                  80

Ser Pro Lys Lys Ser Phe Pro Asp Pro Trp Arg Asp Pro Val Tyr Ser
                85                  90                  95

Ile Ser Ile Lys Pro Tyr Gly Lys Pro Val Val Val Leu Leu Leu
            100                 105                 110

Ile Thr Asn Pro Glu Ala His Ile Asp Asn Phe Asn Lys Phe Thr Thr
        115                 120                 125

Ser Val Gly Asp Asn Thr Phe Glu Ile His Tyr Arg Thr Phe Leu Ser
    130                 135                 140

Glu Lys Arg Leu Leu Glu Tyr Phe Trp Asn Val Leu Lys Pro Lys Phe
145                 150                 155                 160

Thr Phe Met Leu Ala Trp Asn Gly Tyr Gln Phe Asp Tyr Pro Tyr Leu
                165                 170                 175

Leu Ile Arg Ser His Ile His Glu Val Asn Val Ile Ser Asp Lys Leu
            180                 185                 190

Leu Pro Asp Trp Lys Leu Val Arg Lys Ile Ser Asp Arg Asn Leu Pro
        195                 200                 205

Phe Tyr Phe Asn Pro Arg Thr Pro Val Glu Phe Val Phe Phe Asp Tyr
```

-continued

```
              210                 215                 220
Met Arg Leu Tyr Arg Ser Phe Val Ala Tyr Lys Glu Leu Glu Ser Tyr
225                 230                 235                 240

Arg Leu Asp Tyr Ile Ala Arg Glu Glu Ile Gly Glu Gly Lys Val Asp
                245                 250                 255

Phe Asp Val Arg Phe Tyr His Glu Ile Pro Val Tyr Pro Asp Lys Lys
            260                 265                 270

Leu Val Glu Tyr Asn Ala Val Asp Ala Ile Leu Met Glu Glu Ile Glu
        275                 280                 285

Asn Lys Asn His Ile Leu Pro Thr Leu Phe Glu Ile Ala Arg Leu Ser
    290                 295                 300

Asn Leu Thr Pro Ala Leu Ala Leu Asn Ala Ser Asn Ile Leu Ile Gly
305                 310                 315                 320

Asn Val Thr Gly Lys Leu Gly Val Lys Phe Val Asp Tyr Ile Lys Lys
                325                 330                 335

Ile Asp Thr Ile Asn Thr Met Phe Lys Lys Ile Pro Glu
            340                 345

<210> SEQ ID NO 58
<211> LENGTH: 1764
<212> TYPE: DNA
<213> ORGANISM: Bacteriophage RM378
<220> FEATURE:
<221> NAME/KEY: CDS
<222> LOCATION: (142)...(1707)

<400> SEQUENCE: 58
ctatacggat gaagttttga gaattattga tctttctcca ctcgatggcg tattatacaa      60
atgtgattta aaagacacct acttatcga ggtgaaagat acccattttg atcccgcaat     120
gtaaaacaaa cgtattctgc t atg aac atc aac aag tat cgt tat cgc ggt      171
                        Met Asn Ile Asn Lys Tyr Arg Tyr Arg Gly
                          1               5                  10 gct tac att gaa ctt acc aac ccc gat att tac ttc aac gta ttc gat      219
Ala Tyr Ile Glu Leu Thr Asn Pro Asp Ile Tyr Phe Asn Val Phe Asp
                15                  20                  25 ctt gat ttt aca tcg ctg tac ccc tct gta atc agc aaa ttc aat atc      267
Leu Asp Phe Thr Ser Leu Tyr Pro Ser Val Ile Ser Lys Phe Asn Ile
            30                  35                  40 gat ccc gct acg ttc gta acg gag ttt tac ggg tgt atg cgg gtg gag      315
Asp Pro Ala Thr Phe Val Thr Glu Phe Tyr Gly Cys Met Arg Val Glu
        45                  50                  55 aac aaa gtg att ccg gta gat cag gaa gaa ccg gaa ttc ggg ttt ccc      363
Asn Lys Val Ile Pro Val Asp Gln Glu Glu Pro Glu Phe Gly Phe Pro
    60                  65                  70 ctc tac atc ttc gat tca ggg atg aac cct tct tac cgg agt gaa ccc      411
Leu Tyr Ile Phe Asp Ser Gly Met Asn Pro Ser Tyr Arg Ser Glu Pro
75                  80                  85                  90 ctc ttt gtc atc aac agc ttt gag gaa ctc cgg caa ttt tta aaa agt      459
Leu Phe Val Ile Asn Ser Phe Glu Glu Leu Arg Gln Phe Leu Lys Ser
                95                 100                 105 cga aat atc att atg gtg ccc aac ccg tcg ggt atc tgc tgg ttt tac      507
Arg Asn Ile Ile Met Val Pro Asn Pro Ser Gly Ile Cys Trp Phe Tyr
            110                 115                 120 agg aaa gag ccg gtt ggc gtg ctt cct tct atc att cgg gag att ttc      555
Arg Lys Glu Pro Val Gly Val Leu Pro Ser Ile Ile Arg Glu Ile Phe
        125                 130                 135 acc cga cgt aag gaa gaa cgt aag ctt ttc aaa gaa act ggc aac atg      603
Thr Arg Arg Lys Glu Glu Arg Lys Leu Phe Lys Glu Thr Gly Asn Met
```

-continued

| | | | | | | | | | | | | | | | | |
|---|---|---|---|---|---|---|---|---|---|---|---|---|---|---|---|---|
| | | 140 | | | | | 145 | | | | | 150 | | | | |
| gaa | cac | cat | ttc | cgt | caa | tgg | gca | ctt | aaa | att | atg | atg | aac | tcc | atg | 651 |
| Glu | His | His | Phe | Arg | Gln | Trp | Ala | Leu | Lys | Ile | Met | Met | Asn | Ser | Met | |
| 155 | | | | | 160 | | | | | 165 | | | | | 170 | |
| tac | ggt | atc | ttc | gga | aac | cgt | tcg | gtg | tac | atg | ggg | tgc | ctt | ccc | att | 699 |
| Tyr | Gly | Ile | Phe | Gly | Asn | Arg | Ser | Val | Tyr | Met | Gly | Cys | Leu | Pro | Ile | |
| | | | | 175 | | | | | 180 | | | | | 185 | | |
| gcg | gaa | agt | gta | acc | gcc | gcc | ggg | cgc | atg | tct | att | cgc | tcc | gtg | att | 747 |
| Ala | Glu | Ser | Val | Thr | Ala | Ala | Gly | Arg | Met | Ser | Ile | Arg | Ser | Val | Ile | |
| | | | | 190 | | | | | 195 | | | | | 200 | | |
| tct | cag | att | cgc | gat | cgc | ttc | att | tat | tcg | cat | acc | gac | tcc | att | ttc | 795 |
| Ser | Gln | Ile | Arg | Asp | Arg | Phe | Ile | Tyr | Ser | His | Thr | Asp | Ser | Ile | Phe | |
| | | 205 | | | | | 210 | | | | | 215 | | | | |
| gtc | aaa | gct | ttt | acg | gat | gat | ccg | gtg | gcg | gaa | gcc | ggt | gag | ctt | caa | 843 |
| Val | Lys | Ala | Phe | Thr | Asp | Asp | Pro | Val | Ala | Glu | Ala | Gly | Glu | Leu | Gln | |
| | 220 | | | | | 225 | | | | | 230 | | | | | |
| gaa | cat | ctc | aac | tct | ttt | atc | aat | gac | tat | atg | gaa | aat | aac | ttt | aat | 891 |
| Glu | His | Leu | Asn | Ser | Phe | Ile | Asn | Asp | Tyr | Met | Glu | Asn | Asn | Phe | Asn | |
| 235 | | | | | 240 | | | | | 245 | | | | | 250 | |
| gca | aga | gaa | gat | ttc | aag | ctg | gag | tta | aag | cag | gag | ttc | gtg | ttc | aaa | 939 |
| Ala | Arg | Glu | Asp | Phe | Lys | Leu | Glu | Leu | Lys | Gln | Glu | Phe | Val | Phe | Lys | |
| | | | | 255 | | | | | 260 | | | | | 265 | | |
| tcc | att | ctt | atc | aaa | gaa | atc | aac | cgc | tac | ttt | gcg | gtt | act | gta | gac | 987 |
| Ser | Ile | Leu | Ile | Lys | Glu | Ile | Asn | Arg | Tyr | Phe | Ala | Val | Thr | Val | Asp | |
| | | | 270 | | | | | 275 | | | | | 280 | | | |
| ggt | aaa | gaa | gag | atg | aag | gga | atc | gaa | gtg | atc | aac | tct | tcg | gtg | cct | 1035 |
| Gly | Lys | Glu | Glu | Met | Lys | Gly | Ile | Glu | Val | Ile | Asn | Ser | Ser | Val | Pro | |
| | | 285 | | | | | 290 | | | | | 295 | | | | |
| gaa | att | gtc | aag | aag | tat | ttc | agg | ggt | tac | ctg | aag | tat | atc | agc | caa | 1083 |
| Glu | Ile | Val | Lys | Lys | Tyr | Phe | Arg | Gly | Tyr | Leu | Lys | Tyr | Ile | Ser | Gln | |
| | 300 | | | | | 305 | | | | | 310 | | | | | |
| ccc | gac | atc | gat | gtc | att | tcc | gcc | acc | ata | gcg | ttc | tac | aat | aac | ttt | 1131 |
| Pro | Asp | Ile | Asp | Val | Ile | Ser | Ala | Thr | Ile | Ala | Phe | Tyr | Asn | Asn | Phe | |
| 315 | | | | | 320 | | | | | 325 | | | | | 330 | |
| gtg | tct | caa | aag | aat | ttc | tgg | tct | att | gaa | gat | ctc | tat | cac | aaa | atg | 1179 |
| Val | Ser | Gln | Lys | Asn | Phe | Trp | Ser | Ile | Glu | Asp | Leu | Tyr | His | Lys | Met | |
| | | | | 335 | | | | | 340 | | | | | 345 | | |
| aaa | ata | tct | tcg | tct | gac | agc | gcc | gaa | aga | tat | gtg | gag | tat | gta | gag | 1227 |
| Lys | Ile | Ser | Ser | Ser | Asp | Ser | Ala | Glu | Arg | Tyr | Val | Glu | Tyr | Val | Glu | |
| | | | 350 | | | | | 355 | | | | | 360 | | | |
| gaa | gtt | atg | aag | atg | aaa | aag | gag | aat | gtc | cca | atc | tct | gag | ata | ttc | 1275 |
| Glu | Val | Met | Lys | Met | Lys | Lys | Glu | Asn | Val | Pro | Ile | Ser | Glu | Ile | Phe | |
| | | 365 | | | | | 370 | | | | | 375 | | | | |
| ata | aaa | atg | tat | gac | cat | aca | ctt | ccc | att | cat | tat | aag | gga | gcg | ctt | 1323 |
| Ile | Lys | Met | Tyr | Asp | His | Thr | Leu | Pro | Ile | His | Tyr | Lys | Gly | Ala | Leu | |
| | 380 | | | | | 385 | | | | | 390 | | | | | |
| ttc | gct | tcc | att | ata | gga | tgc | aaa | ccc | ccg | caa | atg | gga | gac | aag | atc | 1371 |
| Phe | Ala | Ser | Ile | Ile | Gly | Cys | Lys | Pro | Pro | Gln | Met | Gly | Asp | Lys | Ile | |
| 395 | | | | | 400 | | | | | 405 | | | | | 410 | |
| tac | tgg | ttc | tac | tgc | acc | atg | ctg | gat | cct | tcc | aga | acc | aat | ctc | ccg | 1419 |
| Tyr | Trp | Phe | Tyr | Cys | Thr | Met | Leu | Asp | Pro | Ser | Arg | Thr | Asn | Leu | Pro | |
| | | | | 415 | | | | | 420 | | | | | 425 | | |
| ctt | tct | ctg | gaa | gaa | gtt | aac | ccc | gaa | cat | ggg | agc | ggc | gtg | tgg | gat | 1467 |
| Leu | Ser | Leu | Glu | Glu | Val | Asn | Pro | Glu | His | Gly | Ser | Gly | Val | Trp | Asp | |
| | | | 430 | | | | | 435 | | | | | 440 | | | |
| att | ctg | aaa | gcg | gga | aag | aaa | acg | cat | atc | aac | agg | ctc | cgc | aat | atc | 1515 |
| Ile | Leu | Lys | Ala | Gly | Lys | Lys | Thr | His | Ile | Asn | Arg | Leu | Arg | Asn | Ile | |
| | | | | 445 | | | | | 450 | | | | | 455 | | |
| cac | gca | ctt | agc | ata | cgt | gag | gat | gat | gag | gag | ggt | ctt | gaa | atc | gtt | 1563 |

```
                His Ala Leu Ser Ile Arg Glu Asp Asp Glu Glu Gly Leu Glu Ile Val
                    460                 465                 470 aaa aaa tac ata gat aga gac aaa tac tgt cag atc att tca gag aaa    1611
Lys Lys Tyr Ile Asp Arg Asp Lys Tyr Cys Gln Ile Ile Ser Glu Lys
475                 480                 485                 490 aca att gat ctg ctg aaa agt ctc ggg tat gtt gaa aat act aca aag    1659
Thr Ile Asp Leu Leu Lys Ser Leu Gly Tyr Val Glu Asn Thr Thr Lys
                495                 500                 505 ata aaa acc gtt gag gat ctt att cgt ttt ctt gta gag agt gaa aac    1707
Ile Lys Thr Val Glu Asp Leu Ile Arg Phe Leu Val Glu Ser Glu Asn
                510                 515                 520 taaacccatt agcgccatga ttctcaaatt cgacactgaa ggcattgttc gtatcct     1764
```

<210> SEQ ID NO 59
<211> LENGTH: 522
<212> TYPE: PRT
<213> ORGANISM: Bacteriophage RM378

<400> SEQUENCE: 59

```
Met Asn Ile Asn Lys Tyr Arg Tyr Arg Gly Ala Tyr Ile Glu Leu Thr
1               5                   10                  15

Asn Pro Asp Ile Tyr Phe Asn Val Phe Asp Leu Asp Phe Thr Ser Leu
                20                  25                  30

Tyr Pro Ser Val Ile Ser Lys Phe Asn Ile Asp Pro Ala Thr Phe Val
                35                  40                  45

Thr Glu Phe Tyr Gly Cys Met Arg Val Glu Asn Lys Val Ile Pro Val
                50                  55                  60

Asp Gln Glu Glu Pro Glu Phe Gly Phe Pro Leu Tyr Ile Phe Asp Ser
65                  70                  75                  80

Gly Met Asn Pro Ser Tyr Arg Ser Glu Pro Leu Phe Val Ile Asn Ser
                85                  90                  95

Phe Glu Glu Leu Arg Gln Phe Leu Lys Ser Arg Asn Ile Ile Met Val
                100                 105                 110

Pro Asn Pro Ser Gly Ile Cys Trp Phe Tyr Arg Lys Glu Pro Val Gly
                115                 120                 125

Val Leu Pro Ser Ile Ile Arg Glu Ile Phe Thr Arg Arg Lys Glu Glu
                130                 135                 140

Arg Lys Leu Phe Lys Glu Thr Gly Asn Met Glu His His Phe Arg Gln
145                 150                 155                 160

Trp Ala Leu Lys Ile Met Met Asn Ser Met Tyr Gly Ile Phe Gly Asn
                165                 170                 175

Arg Ser Val Tyr Met Gly Cys Leu Pro Ile Ala Glu Ser Val Thr Ala
                180                 185                 190

Ala Gly Arg Met Ser Ile Arg Ser Val Ile Ser Gln Ile Arg Asp Arg
                195                 200                 205

Phe Ile Tyr Ser His Thr Asp Ser Ile Phe Val Lys Ala Phe Thr Asp
                210                 215                 220

Asp Pro Val Ala Glu Ala Gly Glu Leu Gln Glu His Leu Asn Ser Phe
225                 230                 235                 240

Ile Asn Asp Tyr Met Glu Asn Asn Phe Asn Ala Arg Glu Asp Phe Lys
                245                 250                 255

Leu Glu Leu Lys Gln Glu Phe Val Phe Lys Ser Ile Leu Ile Lys Glu
                260                 265                 270

Ile Asn Arg Tyr Phe Ala Val Thr Val Asp Gly Lys Glu Glu Met Lys
                275                 280                 285
```

-continued

```
Gly Ile Glu Val Ile Asn Ser Ser Val Pro Glu Ile Val Lys Lys Tyr
            290                 295                 300

Phe Arg Gly Tyr Leu Lys Tyr Ile Ser Gln Pro Asp Ile Asp Val Ile
305                 310                 315                 320

Ser Ala Thr Ile Ala Phe Tyr Asn Asn Phe Val Ser Gln Lys Asn Phe
                325                 330                 335

Trp Ser Ile Glu Asp Leu Tyr His Lys Met Lys Ile Ser Ser Ser Asp
            340                 345                 350

Ser Ala Glu Arg Tyr Val Glu Tyr Val Glu Glu Val Met Lys Met Lys
        355                 360                 365

Lys Glu Asn Val Pro Ile Ser Glu Ile Phe Ile Lys Met Tyr Asp His
370                 375                 380

Thr Leu Pro Ile His Tyr Lys Gly Ala Leu Phe Ala Ser Ile Ile Gly
385                 390                 395                 400

Cys Lys Pro Pro Gln Met Gly Asp Lys Ile Tyr Trp Phe Tyr Cys Thr
                405                 410                 415

Met Leu Asp Pro Ser Arg Thr Asn Leu Pro Leu Ser Leu Glu Glu Val
            420                 425                 430

Asn Pro Glu His Gly Ser Gly Val Trp Asp Ile Leu Lys Ala Gly Lys
        435                 440                 445

Lys Thr His Ile Asn Arg Leu Arg Asn Ile His Ala Leu Ser Ile Arg
450                 455                 460

Glu Asp Asp Glu Glu Gly Leu Glu Ile Val Lys Lys Tyr Ile Asp Arg
465                 470                 475                 480

Asp Lys Tyr Cys Gln Ile Ile Ser Glu Lys Thr Ile Asp Leu Leu Lys
                485                 490                 495

Ser Leu Gly Tyr Val Glu Asn Thr Thr Lys Ile Lys Thr Val Glu Asp
            500                 505                 510

Leu Ile Arg Phe Leu Val Glu Ser Glu Asn
515                 520
```

<210> SEQ ID NO 60
<211> LENGTH: 1619
<212> TYPE: DNA
<213> ORGANISM: Bacteriophage RM378

<400> SEQUENCE: 60

```
ccggtttgat acccgtattg gtcatttcct tgtggaaacc ccggttgaaa agtggagtaa      60
caaaatgttg cgcgtagctg aaaaacttgt aaccaattcc cgtaaacaga tttacgaagg     120
aggtgtgtga ttgctacggt ttcctatccg gaaactatga agttgtagac gaactccctg     180
atcaaccgac gcttccgaaa actcaaaaca agacttatag tacgctatgg aatcgatgaa     240
cgtaaaatac ccggttgagt accttatcga acacctgaac tcttttgagt ctccggaagt     300
agccgtcgaa tcccttcgca aggaggggat tatgtgcaaa accggggtg atctatacat      360
gttcaaatat caccttggtt gtaagtttga taagatatat caccttgcct gtcgcggggc     420
gattctccgc aaaacggata gtggttgaa agttctgtct tatccctttg acaaattttt      480
caactggggg gaagaactcc agccggaaat cgtaaactat tatcagacgc ttcgttacgc     540
gtctcccctg aatgaaaagc gcaaagccgg tttcatgttc aaacttccca tgaaactggt     600
tgaaaagctg gatggtactt gtgtggtttt atattatgat gaagggtgga aaattcacac     660
tcttgggagt attgacgcaa atggatccat tgtcaaaaac ggaatggtta ccactcatat     720
ggataaaaca tatcgagaat tgttctggga aaccttgaa aagaaatatc cgccttacct      780
```

-continued

```
tctctatcat ttgaactcct catactgtta catatttgaa atggttcatc cggacgcgcg      840
agtggtggtt cctatgagg agccaaatat cattctgatc ggtgtgcgtt cggtggatcc       900
ggagaaggga tatttcgagg tgggtccctc cgaagaagcc gtacgcattt tcaacgaaag      960
tggcggaaaa ataaatctta agctaccggc tgttctgtct caagagcaaa actatactct     1020
ttttcgtgcc aatcgccttc aggaactatt tgaggaagtt acaccgcttt tcaaaagcct     1080
gagagacggt tatgaggtgg tatatgaagg atttgtagcc gtacaggaaa ttgccccgcg     1140
tgtttattac cgcacaaaga tcaagcaccc ggtatatctg gagctccacc ggattaaaac     1200
tacaatcact cctgagaagc tcgccgatct ttttcttgaa acaaacttg  atgattttgt     1260 acttaccccg gatgaacagg aaaccgtgat gaaactcaaa gaaatttata ccgatatgcg     1320
aaatcagctt gagtcatctt ttgatacgat ttataaagag atttccgaac aggtttctcc     1380
ggaagaaaac cccggagagt ttcgcaaaag gttcgctctt cgacttatgg attatcatga     1440
taaaagttgg ttttttgccc gccttgacgg cgacgaagag aaaatgcaaa agtcggaaaa     1500
gaagcttcta acggagagaa ttgaaaaggg gttatttaaa taaaaatgat aaaaaagcgt     1560
aatcctcttt tctggggaag acgggaactc aatcttcttc agcattttgc ccttgaagc      1619
```

<210> SEQ ID NO 61
<211> LENGTH: 1440
<212> TYPE: DNA
<213> ORGANISM: Bacteriophage RM378

<400> SEQUENCE: 61

```
gcttcgtcaa aactcacgtc tatagtatct atgtcgtagg gttcgaggtt ggaggcaatc       60
aggttgaaca gttcatcata atcataattc tcgaaaagaa tgttgcgaat accgatccct      120
cttttctgga t cgtagggata ttcccccggc tcgatgaaaa gcaggagttt tatcttatcg     180
atcaggagtt ttaccgggtc atcaggaaat ctgaaattcg gtgcagtgtc gttcagatag      240
aacatttcat ttttgtttaa ataaatcctc gaggaatctt caaataaaga ggggcgttaa      300
tggatgaaaa gactgaggaa tatggtcaat cttatcgatc tcaaaaatca gtattatgct      360
tactctttca gtttttcga ctcctatcag atcagctggg ataattaccc gcatcttaaa       420
gagttcgtca ttgaaaacta tcccggcact tattttttcat gctacgctcc ggggattctg      480
tacaagcttt tcctcaaatg gaagcggggt atgatcattg acgactatga ccgacacccg      540
ctccgaaaga agttacttcc tcagtacaaa gagcaccgct atgaatacat tgagggaaaa      600
tacggtgtgg ttccttttccc cgggtttctg aaatatctga agttccactt tgaggacttg     660
cggtttaaaa tgcgcgatct tggaatcacc gatttcaaat atgcacttgc catttctctt     720
ttttacaacc gggtaatgct cagagatttt ctgaaaaact ttacctgtta ttacattgcc      780
gaatatgaag ctgacgatgt aatcgcacat ctggcgcgtg agattgcacg aagcaatatc      840
gacgtaaaca tcgtctcaac ggataaagat tattaccagc tatgggatga agaggatata      900
agagaaaggg tttatatcaa ttctctttca tgtagtgatg tgaagacacc ccgctacgga     960
tttcttacca ttaaagcact tcttggagac aaaagcgata acattcccaa atctctggaa    1020
aaaggaaaag gcgaaaagta tcttgaaaag aaaggatttg cggaggaaga ttacgataag    1080
gaactattcg agaataatct gaaggtgatc aggtttggag acgaatatct ggagaaaggg    1140
gataaaagct ttatagaaaa ttttttctacg ggggatactc tgtggaactt ttatgaattt    1200 tttactatg acccttttgca tgaacttttc ctcagaaata taagaaagag gagactatga    1260
aagtactcgc atttaccgat gcacctacgt ttcccacggg ggtgggtcat cagcttcaca    1320
```

-continued

```
acattatcaa ttacgggttt gacgcaaccg atcgctgggt tgtggtgcac ccgccccggt    1380
cgccaagggc tggagagact aaaaacgtcg ttattggaaa cactccagtc aagcttatca    1440
```

<210> SEQ ID NO 62
<211> LENGTH: 1508
<212> TYPE: DNA
<213> ORGANISM: Bacteriophage RM378

<400> SEQUENCE: 62

```
acttcccaaa tgctatgtgg aggtggatga tagaaagcgt attgttaatg aagaggcggt      60
caagtctttt ctccataagc atgttaccga actgctgaag aattatcagt aacccaaacc     120
taaacccgaa aaatatatgg aaacgattgt aatttcccaa acaatacga cggagatgac      180 ggaaccccccc cagaacattt ccgattcggt taaaagcggg tttatctatc ttatcgaaaa    240
gtctcatttc cttgaaaaga aaacttcct taaaatcata tcgaacatgg accccgccg       300 catttccaat ccggaggtgc gcgtggtggc ggagtacata tatgattatt tcaaaagtca    360
tagtaatttc ccttctaaaa gaaatctttg ccatcacttt gagtggagcg aagatctgga    420
aggagacccc gccgattatc agcgtatcat tcagtatctc aaatcttctt acattcgatc    480
ctctataaca aaaacgcttt catatcttga aaggatgac ctttccgcgt tgaaagaaat      540
tgtcagagcc attcgggtgg tggaggatag tggggtgtcg ctggtggagg aattcgatct    600
tgcaaccagc gagtttaatg aactttttgt taaagaagaa cgcattccca ccccctggga    660
gagtgtaaac aaaaatatgg cggcggtct tggtcgggga gagcttggaa tcgttatgct     720
tccttcgggg tggggtaagt catggttcct tgtttcactt ggtcttcatg cctttcgaac    780
gggtaagcgc gtgatttatt tcactctgga gcttgaccaa aaatatgtga tgaagcggtt    840
tttaaagatg tttgcacctt attgcaaagg acgcgcttct tcctatcgcg acgtttatca    900
aataatgaaa gagcttatgt tttctcagga taatcttttg ragattgttt tctgtaatgc    960
gatggaagat attgagcact atattgcgct gtataacccc gacgttgtgc tgattgacta    1020
tgccgatctt atttatgatg tggaaaccga caaagagaaa aattatctgc ttttgcaaaa    1080
aatttatagg aaacttcgtc tcattgcaaa ggtatataat acagcagtat ggagcgcctc    1140
tcagcttaat cgcggttccc tttcaaagca agccgacgtc gatttcattg agaaatacat    1200
tgccgattca tttgcaaaag ttkttgaaat cgacttcggg atggcgttta ttccggatag    1260
cgagaactca accccgata ttcacgtcgg attcggtaaa atcttcaaaa accgtatggg     1320
tgcggtaaga aagctggaat atacaattaa ctttgaaaac tatacggtag acgttgctgt    1380
taaatgacac aagttaagac aaaagggctt aaagacatca gaataggtag aaaggagggt    1440
aagttcacac atgtaaatac aacaaagaaa ggaaagaata agaaatattt cagggcggaa    1500
catgaacg                                                             1508
```

<210> SEQ ID NO 63
<211> LENGTH: 8
<212> TYPE: PRT
<213> ORGANISM: Artificial Sequence
<220> FEATURE:
<223> OTHER INFORMATION: Peptide
<220> FEATURE:
<221> NAME/KEY: VARIANT
<222> LOCATION: (0)...(0)
<223> OTHER INFORMATION: Xaa = Any amino acid

<400> SEQUENCE: 63

```
Asp Xaa Xaa Ser Leu Tyr Pro Ser
 1               5
```

<210> SEQ ID NO 64
<211> LENGTH: 33
<212> TYPE: DNA
<213> ORGANISM: Artificial Sequence
<220> FEATURE:
<223> OTHER INFORMATION: Nucleic acid

<400> SEQUENCE: 64
cacgagctca tgaagatcac gctaagcgca agc        33

<210> SEQ ID NO 65
<211> LENGTH: 33
<212> TYPE: DNA
<213> ORGANISM: Artificial Sequence
<220> FEATURE:
<223> OTHER INFORMATION: Nucleic acid

<400> SEQUENCE: 65
acaggtacct tactcaggta ttttttgaa cat        33

<210> SEQ ID NO 66
<211> LENGTH: 33
<212> TYPE: DNA
<213> ORGANISM: Artificial Sequence
<220> FEATURE:
<223> OTHER INFORMATION: Nucleic acid

<400> SEQUENCE: 66
cacgagctca tgaacatcaa caagtatcgt tat        33

<210> SEQ ID NO 67
<211> LENGTH: 30
<212> TYPE: DNA
<213> ORGANISM: Artificial Sequence
<220> FEATURE:
<223> OTHER INFORMATION: Nucleic acid

<400> SEQUENCE: 67
acaggtacct tagttttcac tctctacaag        30

<210> SEQ ID NO 68
<211> LENGTH: 28
<212> TYPE: DNA
<213> ORGANISM: Artificial Sequence
<220> FEATURE:
<223> OTHER INFORMATION: Nucleic acid

<400> SEQUENCE: 68
gggaattctt atgaacgtaa aatacccg        28

<210> SEQ ID NO 69
<211> LENGTH: 28
<212> TYPE: DNA
<213> ORGANISM: Artificial Sequence
<220> FEATURE:
<223> OTHER INFORMATION: Nucleic acid

<400> SEQUENCE: 69
ggagatctta tttaaataac ccctttc        28

<210> SEQ ID NO 70
<211> LENGTH: 30
<212> TYPE: DNA

```
<213> ORGANISM: Artificial Sequence
<220> FEATURE:
<223> OTHER INFORMATION: Nucleic acid

<400> SEQUENCE: 70
gggaattctt atgaaaagac tgaggaatat                                       30

<210> SEQ ID NO 71
<211> LENGTH: 26
<212> TYPE: DNA
<213> ORGANISM: Artificial Sequence
<220> FEATURE:
<223> OTHER INFORMATION: Nucleic acid

<400> SEQUENCE: 71
ggagatctca tagtctcctc tttctt                                           26

<210> SEQ ID NO 72
<211> LENGTH: 31
<212> TYPE: DNA
<213> ORGANISM: Artificial Sequence
<220> FEATURE:
<223> OTHER INFORMATION: Nucleic acid

<400> SEQUENCE: 72
gggcaattgt tatggaaacg attgtaattt c                                     31

<210> SEQ ID NO 73
<211> LENGTH: 26
<212> TYPE: DNA
<213> ORGANISM: Artificial Sequence
<220> FEATURE:
<223> OTHER INFORMATION: Nucleic acid

<400> SEQUENCE: 73
cgggatcctc atttaacagc aacgtc                                           26
```